US008956845B2

(12) United States Patent
Zhang et al.

(10) Patent No.: US 8,956,845 B2
(45) Date of Patent: Feb. 17, 2015

(54) β-GLUCOSIDASE VARIANTS

(71) Applicant: Codexis, Inc., Redwood City, CA (US)

(72) Inventors: Xiyun Zhang, Fremont, CA (US); Jie Yang, Foster City, CA (US); Dipnath Baidyaroy, Fremont, CA (US); Sally R. Postlethwaite, Redwood City, CA (US); Attila Andor, Budapest (HU); Louis A. Clark, San Francisco, CA (US); Lisa Marie Newman, San Jose, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 14/289,021

(22) Filed: May 28, 2014

(65) Prior Publication Data

US 2014/0256018 A1   Sep. 11, 2014

Related U.S. Application Data

(62) Division of application No. 13/375,189, filed as application No. PCT/US2010/038902 on Jun. 16, 2010, now Pat. No. 8,772,010.

(60) Provisional application No. 61/187,565, filed on Jun. 16, 2009, provisional application No. 61/218,020, filed on Jun. 17, 2009, provisional application No. 61/264,605, filed on Nov. 25, 2009, provisional application No. 61/264,608, filed on Nov. 25, 2009.

(51) Int. Cl.
*C12N 9/24* (2006.01)
*C12N 9/14* (2006.01)
*C12N 9/00* (2006.01)
*C12P 21/06* (2006.01)

(52) U.S. Cl.
CPC ..................................... *C12N 9/2482* (2013.01)
USPC ........... 435/200; 435/69.1; 435/183; 435/195

(58) Field of Classification Search
None
See application file for complete search history.

(56) References Cited

U.S. PATENT DOCUMENTS

| | | | |
|---|---|---|---|
| 4,486,553 A | 12/1984 | Wesch | |
| 4,683,202 A | 7/1987 | Mullis | |
| 5,426,039 A | 6/1995 | Wallace et al. | |
| 5,811,381 A | 9/1998 | Emalfarb et al. | |
| 6,015,707 A | 1/2000 | Emalfarb et al. | |
| 6,117,679 A | 9/2000 | Stemmer | |
| 6,376,246 B1 | 4/2002 | Crameri et al. | |
| 6,573,086 B1 | 6/2003 | Emalfrab et al. | |
| 6,586,182 B1 | 7/2003 | Patten et al. | |
| 7,696,411 B2 | 4/2010 | Sticklen et al. | |
| 7,883,872 B2 | 2/2011 | Gusakov et al. | |
| 8,017,361 B2 | 9/2011 | Scott et al. | |
| 8,017,373 B2 | 9/2011 | Hill et al. | |
| 2004/0253702 A1 | 12/2004 | Fidantsef et al. | |
| 2008/0194005 A1 | 8/2008 | Emalfarb et al. | |
| 2008/0220990 A1 | 9/2008 | Fox | |
| 2009/0099079 A1 | 4/2009 | Emalfarb et al. | |
| 2009/0209009 A1 | 8/2009 | Tolan et al. | |
| 2009/0280105 A1 | 11/2009 | Gusakov et al. | |
| 2009/0312196 A1 | 12/2009 | Colbeck et al. | |
| 2010/0093560 A1 | 4/2010 | Colbeck et al. | |

FOREIGN PATENT DOCUMENTS

| | | |
|---|---|---|
| EP | 0137280 B1 | 3/1992 |
| WO | 98/15633 A1 | 4/1998 |
| WO | 99/09834 A2 | 3/1999 |
| WO | 2004/099228 A2 | 11/2004 |
| WO | 2007/075899 A2 | 7/2007 |
| WO | 2008/042876 A2 | 4/2008 |
| WO | 2008/073914 A2 | 6/2008 |

OTHER PUBLICATIONS

Adams, S.P., et al., "Hindered dialkylarnino nucleoside phosphite reagents in the synthesis of two DNA 51-mers," J. Am. Chem. Soc., 105:661 (1983).
Altschul, S.F., et al., "Gapped BLAST and PSI-BLAST: a new generation of protein database search programs," Nucleic Acids Res., 25(17):3389-3402 (1997).
Arnheim, N., et al., "Polymerase Chain Reaction," C&EN, pp. 36-47 (1990).
Barringer, K.J., et al., "Blunt-end and single-strand ligations by *Escherichia coli* ligase: influence on an in vitro amplification scheme," Gene, 89:117-122 (1990).
Beaucage, S.L., et al., "Deoxynucleoside phosphoamidites—A new class of key intermediates for deoxypolynucleotide synthesis," Tetrahedron Letters, 22(20):1859-62 (1981).
Boel, E., et al., "Two different types of intervening sequences in the glucoamylase gene from *Aspergillus niger*," EMBO J., 3(7):1581-1585 (1984).
Botstein, D., et al., "Strategies and applications of in vitro mutagenesis," Science, 229(4719):1193-1201 (1985).
Brigham. J.S., et al., "Hemicellulases: Diversity and Applications," in Handbook on Bioethanol (C. Wyman ed.) pp. 119-141, Taylor and Francis, Washington DC, (1995).
Cantarel B.L., et al., "The Cabohydrate-Active EnZymes database (CAZy): an expert resource for Glycogenomics," Nucleic Acids Research, 37:D233-D238 (2009).
Carter, P., "Site-directed mutagenesis," Biochem. J., 237:1-7 (1986).
Caruthers, M.H., et al., "Chemical Synthesis and Biological Studies on Mutated Gene-control Regions," Cold Harbor Symp. Quant. Biol., 47:411-418 (1982).
Case, M.E. et al., "Efficient transformation of *Neurospora crassa* by utilizing hybrid plasmid DNA," Proc. Natl. Acad. Sci. USA, 76(10):5259-5263 (1979).

(Continued)

Primary Examiner — Suzanne M Noakes
Assistant Examiner — Jae W Lee
(74) Attorney, Agent, or Firm — Codexis, Inc.

(57) ABSTRACT

The invention relates to recombinantly produced β-glucosidase variants with enhanced thermoactivity compared to naturally occurring proteins. The invention also provides methods for producing a variant β-glucosidase polypeptide with improved thermoactivity by identifying performance sensitive positions in a target β-glucosidase polypeptide and substituting the residue at that position with a thermoactivity enhancing residue.

11 Claims, No Drawings

(56) References Cited

OTHER PUBLICATIONS

Dale, S.J., et al., "Oligonucleotide-directed random mutagenesis using the phosphorothioate method," Methods Mol. Biol., 57:369-74 (1996).

Davies, G., et al., "Structures and mechanisms of glycosyl hydrolases," Structure, 3:853-859 (1995).

Dayhoff, M.O., et al., "A model of evolutionary change in proteins" in "Atlas of Protein Sequence and Structure," vol. 5, Suppl. 3, pp. 345-352, Natl. Biomed. Res. Round., Washington, D.C. (1978).

Dodd, D., et al., "Functional Diversity of Four Glycoside Hydrolase Family 3 Enzymes from the Rumen Bacterium *Prevotella bryantii* B14," J Bacteriol., 192:2335-45 (2001).

Finn, R.D., et al., "The Pfam protein families database," Nucleic Acids Research, 38:D211-D222 (2010).

Garg. A.K., "An addition to the genus *Chrysosporium corda*," Mycopathologia, 30(3-4):221-224 (1966).

Gonzalez-Blasco, G., et al., "Directed Evolution of Beta-Glucosidase A from *Paenibacillus polymyxa* to Thermal Resistance," J. Bio. Chem., 275(18):13708-13712 (2000).

Guatelli, J.C., et al., "Isothermal, in vitro amplification of nucleic acids by a multienzyme reaction modeled after retroviral replication," Proc. Natl. Acad. Sci. USA, 87:1874-1878 (1990).

Heanut, A., et al., "Analysis and predictions from *Escherichia coli* sequences, or *E. coli* in silico," in *Escherichia coli* and *Salmonella*, ASM Pres, Washington D.C., pp. 2047-2066 (1987).

Henikoff, S., et al. "Amino acid substitution matrices from protein blocks," Proc. Natl. Acad. Sci. USA, 89:10915-10919 (1992).

Henriksen, A.L.S., et al., "Study of the glucoamylase promoter in *Aspergilllus niger* using green fluorescent protein," Microbiol., 145:729-34 [1999].

Henrissat, B., "A classification of glycosyl hydrolases based on amino acid sequence similarities," Biochem. J., 280:309-316 (1991).

Henrissat, B., et al., "New families in the classification of glycosyl hydrolases based on amino acid sequence similarities," Biochem. J., 293:781-788 (1993).

Henrissat, B., et al., "Structural and sequence-based classification of glycoside hydrolases," Curr Opinion Struct Biology, 7:637-644 (1997).

Henrissat, B., et al., "Updating the sequence-based classification of glycosyl hydrolases," Biochem. J., 316:695-696 (1996).

Johnstone, I.L., et al., "Cloning an *Aspergillus nidulans* developmental gene by transformation," EMBO J., 4 (5):1307-1311 (1985).

Kelly, J.M., et al., "Transformation of *Asoergillus niger* by the amdS gene of *Aspergillus nidulans*," EMBO J., 4 (2):475-479 (1985).

Kinsey, J. A., et al., "Transformation of *Neurospora crassa* with the Cloned am (Glutamate Dehydrogenase) Gene", Molecular and Cellular Biology, 4:117-122 (1984).

Kwoh, D.Y., et al., "Transcription-based amplification system and detection of amplified human immunodeficiency virus type 1 with a bead-based sandwich hybridization format," Proc., Natl. Acad. Sci. USA, 86:1173-1177 (1989).

Ladisch, M.R., et al., "Process considerations in the enzymatic hydrolysis of biomass," Enzyme Microb. Technol., 5:82 (1983).

Landegren, U., et al., "A Ligase-Mediated Gene Detection Technique," Science, 241:1077-1080 (1988).

Limon, C., et al., "Primary structure and expression pattern of the 33-kDa chitinase gene from the nucoparasitic fungus *Trichocherma harzianum*," Curr. Genet., 28:478-83 [1995].

Ling, M.M., et al., "Approaches to DNA mutagenesis: an overview," Anal. Biochem., 254(2):157-78 (1997).

Lomeli, H., et al., "Quantitative Assays Based on the Use of Replicatable Hybridization Probes," J. Clin. Chem, 35 (9): 1826-1831 (1989).

Lopez-Camacho, C., et al., "Amino acid substitutions enhancing thermostability of *Bacillus polymyxa* beta-glucosidase A," Biochem J., 314:833-838 (1996).

Matthes H.W.D., et al., "Simutaneous rapid chemical synthesis of over one hundred oligonucletides on a microscale," EMBO J., 3(4):801-05 (1984).

Minshull, J., et al., "Protein evolution by molecular breeding," Current Opinion in Chemical Biology, 3:284-290 (1999).

Notredame, C., et al., "T-Coffee: A Novel Method for Fast and Accurate Multiple Sequence Alignment," J. Mol. Bio., 302:205-17 (2000).

Nunberg, J.H., et al., "Molecular Cloning and Characterization of the Glucoamylase Gene of *Aspergillus awamori*," Mol. Cell Biol., 4(11):2306-2315 (1984).

Punt, P.J., et al., "Intracellular and extracellular production of proteins in *Aspergillus* under the control of expression signals of the highly expressed *Aspergillus nidulans* gpdA gene," L. Biotechnol., 17:19-33 [1991].

Ricciardelli, C., et al.,"Development and characterization of primary cultures of smooth muscle cells from the fibromuscular stroma of the guinea pig prostate," In vitro Cell Dev. Biol., 25:1016-1024 (1989).

Robert, "Amplification of the nucleic acid sequence: The choices multiply," The Journal Of NIH Research, 3:81-94 (1991).

Romanos, M.A., et al., "Foreign gene expesson in yeast: a review," Yeast 8:423-488 [1992].

Sheir-Neiss, G., et al., "Characterization of the secreted cellulases of *Trichoderma reesei* wild type and mutants during controlled fermentations," Appl. Microbiol. Biotechnol., 20:46-53 (1984).

Simonen, M., et al., "Protein Secretion in *Bacillus* Species," Microbiological Reviews, 57:109-137 (1993).

Sooknanan, R., et al., "NASBRA: A detection and amplification system uniquely suited for RNA," Biotechnology, 13:508-564 (1995).

SwissProt Accession No. P00724, INV2-YEAST, created Jul. 21, 1986, 8 pages, downloaded from www.ncbi.nlm.nih.gov/ on Mar. 2, 2012.

Taussig, R., et al., "Nucleotide sequence of the yeast SUC2 gene for invertase," Nucl. Acids Res., 11(6):1943-54 [1983].

Tilburn, J., et al., "Transformation by integration in *Asperfillus nidulans*," Gene, 26:205-221 [1982].

Van Brunt, J., "Amplifying Genes: PCR and its alternatives," Biotechnology, 8:291-294 [1990].

Viikari, L., et al., "Thermostable enzymes in lignocellulose hydrolysis," Adv. Biochem. Eng. Biotechnol., 108:121-45 [2007].

Wells J.A. et al., "Cassette mutagenesis: an efficient method for generation of multiple mutations at defined sites," Gene, 34:315-323 [1985].

Wright, A., et al., "Diverse Plasmid DNA Vectors by Directed Molecular Evolution of Cytomegalovirus Promoters," Hum. Gene Ther., 16:881-892 [2005].

Yelton, M.M., et al., "Transformation of *Aspergillus nidulans* by using a trpC plasmid," Proc. Natl. Acad. Sci. USA, 81:1470-1474 [1984].

Zhu, T., et al., "Construction of two Gateway vectors for gene expression in fungi," Plasmid, 62:128-33 [2009].

Turner, P., et al., "Potential and utilization of thermophiles and thermostable enzymes in biorefining," Microb Cell Fact, 6(9):1-23 [2007].

Zanoelo, F.F., et al., "Beta-Glucosidase activity from the thermophilic fungus *Scytalidium thermophilum* is stimulated by glucose and xylose," FEMS Microbiology Letters, 240:137-143 [2004].

SEQUENCE LISTING

```
<160> NUMBER OF SEQ ID NOS: 82

<210> SEQ ID NO 1
<211> LENGTH: 851
<212> TYPE: PRT
<213> ORGANISM: Chrysosporium lucknowense C1

<400> SEQUENCE: 1

Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Asp Gly Trp Ala Glu
            20                  25                  30

Ala Tyr Ala Gln Ala Lys Ser Phe Val Ser Gln Met Thr Leu Leu Glu
        35                  40                  45

Lys Val Asn Leu Thr Thr Gly Val Gly Trp Gly Ala Glu Gln Cys Val
    50                  55                  60

Gly Gln Val Gly Ala Ile Pro Arg Leu Gly Leu Arg Ser Leu Cys Met
65                  70                  75                  80

His Asp Ser Pro Leu Gly Ile Arg Gly Ala Asp Tyr Asn Ser Ala Phe
                85                  90                  95

Pro Ser Gly Gln Thr Val Ala Ala Thr Trp Asp Arg Gly Leu Met Tyr
            100                 105                 110

Arg Arg Gly Tyr Ala Met Gly Gln Glu Ala Lys Gly Lys Gly Ile Asn
        115                 120                 125

Val Leu Leu Gly Pro Val Ala Gly Pro Leu Gly Arg Met Pro Glu Gly
    130                 135                 140
```

```
Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
            165                 170                 175

Cys Ala Lys His Phe Ile Gly Asn Glu Gln Glu His Phe Arg Gln Val
            180                 185                 190

Pro Glu Ala Gln Gly Tyr Gly Tyr Asn Ile Ser Glu Thr Leu Ser Ser
            195                 200                 205

Asn Ile Asp Asp Lys Thr Met His Glu Leu Tyr Leu Trp Pro Phe Ala
210                 215                 220

Asp Ala Val Arg Ala Gly Val Gly Ser Val Met Cys Ser Tyr Gln Gln
225                 230                 235                 240

Val Asn Asn Ser Tyr Ala Cys Gln Asn Ser Lys Leu Leu Asn Asp Leu
            245                 250                 255

Leu Lys Asn Glu Leu Gly Phe Gln Gly Phe Val Met Ser Asp Trp Gln
            260                 265                 270

Ala Gln His Thr Gly Ala Ala Ser Ala Val Ala Gly Leu Asp Met Ser
            275                 280                 285

Met Pro Gly Asp Thr Gln Phe Asn Thr Gly Val Ser Phe Trp Gly Ala
290                 295                 300

Asn Leu Thr Leu Ala Val Leu Asn Gly Thr Val Pro Ala Tyr Arg Leu
305                 310                 315                 320

Asp Asp Met Ala Met Arg Ile Met Ala Ala Leu Phe Lys Val Thr Lys
            325                 330                 335

Thr Thr Asp Leu Glu Pro Ile Asn Phe Ser Phe Trp Thr Asp Asp Thr
            340                 345                 350

Tyr Gly Pro Ile His Trp Ala Ala Lys Gln Gly Tyr Gln Glu Ile Asn
            355                 360                 365

Ser His Val Asp Val Arg Ala Asp His Gly Asn Leu Ile Arg Glu Ile
            370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Ser Ser
            405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
            435                 440                 445

Ser Pro Asp Ala Ala Leu Gln Ala Arg Ala Ile Gln Asp Gly Thr Arg
450                 455                 460

Tyr Glu Ser Val Leu Ser Asn Tyr Ala Glu Glu Lys Thr Lys Ala Leu
465                 470                 475                 480

Val Ser Gln Ala Asn Ala Thr Ala Ile Val Phe Val Asn Ala Asp Ser
            485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
            515                 520                 525

Trp Cys Ser Asn Thr Ile Val Ile His Ser Val Gly Pro Val Leu
            530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
```

```
              565                 570                 575
Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
        595                 600                 605

Gly Ala Pro Gln Gln Asp Phe Thr Glu Gly Val Phe Ile Asp Tyr Arg
    610                 615                 620

Tyr Phe Asp Lys Val Asp Asp Ser Val Ile Tyr Glu Phe Gly His
625                 630                 635                 640

Gly Leu Ser Tyr Thr Thr Phe Glu Tyr Ser Asn Ile Arg Val Val Lys
            645                 650                 655

Ser Asn Val Ser Glu Tyr Arg Pro Thr Thr Gly Thr Thr Ala Gln Ala
            660                 665                 670

Pro Thr Phe Gly Asn Phe Ser Thr Asp Leu Glu Asp Tyr Leu Phe Pro
        675                 680                 685

Lys Asp Glu Phe Pro Tyr Ile Tyr Gln Tyr Ile Tyr Pro Tyr Leu Asn
    690                 695                 700

Thr Thr Asp Pro Arg Arg Ala Ser Ala Asp Pro His Tyr Gly Gln Thr
705                 710                 715                 720

Ala Glu Glu Phe Leu Pro Pro His Ala Thr Asp Asp Pro Gln Pro
            725                 730                 735

Leu Leu Arg Ser Ser Gly Gly Asn Ser Pro Gly Gly Asn Arg Gln Leu
            740                 745                 750

Tyr Asp Ile Val Tyr Thr Ile Thr Ala Asp Ile Thr Asn Thr Gly Ser
            755                 760                 765

Val Val Gly Glu Glu Val Pro Gln Leu Tyr Val Ser Leu Gly Gly Pro
    770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Arg Asp Leu
            805                 810                 815

Ser Asn Trp Asp Val Thr Val Gln Asp Trp Val Ile Ser Arg Tyr Pro
            820                 825                 830

Lys Thr Ala Tyr Val Gly Arg Ser Arg Lys Leu Asp Leu Lys Ile
            835                 840                 845

Glu Leu Pro
    850

<210> SEQ ID NO 2
<211> LENGTH: 842
<212> TYPE: PRT
<213> ORGANISM: Thermoascus aurantiacus

<400> SEQUENCE: 2

Lys Asp Asp Leu Ala Tyr Ser Pro Pro Phe Tyr Pro Ser Pro Trp Met
1               5                   10                  15

Asp Gly Asn Gly Glu Trp Ala Glu Ala Tyr Arg Arg Ala Val Asp Phe
            20                  25                  30

Val Ser Gln Leu Thr Leu Ala Glu Lys Val Asn Leu Thr Thr Gly Val
        35                  40                  45

Gly Trp Met Gln Glu Lys Cys Val Gly Glu Thr Gly Ser Ile Pro Arg
    50                  55                  60

Leu Gly Phe Arg Gly Leu Cys Leu Gln Asp Ser Pro Leu Gly Val Arg
65                  70                  75                  80
```

-continued

```
Phe Ala Asp Tyr Val Ser Ala Phe Pro Ala Gly Val Asn Val Ala Ala
                 85                  90                  95

Thr Trp Asp Lys Asn Leu Ala Tyr Leu Arg Gly Lys Ala Met Gly Glu
            100                 105                 110

Glu His Arg Gly Lys Gly Val Asp Val Gln Leu Gly Pro Val Ala Gly
        115                 120                 125

Pro Leu Gly Arg His Pro Asp Gly Gly Arg Asn Trp Glu Gly Phe Ser
    130                 135                 140

Pro Asp Pro Val Leu Thr Gly Val Leu Met Ala Glu Thr Ile Lys Gly
145                 150                 155                 160

Ile Gln Asp Ala Gly Val Ile Ala Cys Ala Lys His Phe Ile Gly Asn
                165                 170                 175

Glu Met Glu His Phe Arg Gln Ala Ser Glu Ala Val Gly Tyr Gly Phe
            180                 185                 190

Asp Ile Thr Glu Ser Val Ser Ser Asn Ile Asp Asp Lys Thr Leu His
        195                 200                 205

Glu Leu Tyr Leu Trp Pro Phe Ala Asp Ala Val Arg Ala Gly Val Gly
    210                 215                 220

Ser Phe Met Cys Ser Tyr Asn Gln Val Asn Asn Ser Tyr Ser Cys Ser
225                 230                 235                 240

Asn Ser Tyr Leu Leu Asn Lys Leu Leu Lys Ser Glu Leu Asp Phe Gln
                245                 250                 255

Gly Phe Val Met Ser Asp Trp Gly Ala His His Ser Gly Val Gly Ala
            260                 265                 270

Ala Leu Ala Gly Leu Asp Met Ser Met Pro Gly Asp Thr Ala Phe Gly
        275                 280                 285

Thr Gly Lys Ser Phe Trp Gly Thr Asn Leu Thr Ile Ala Val Leu Asn
    290                 295                 300

Gly Thr Val Pro Glu Trp Arg Val Asp Asp Met Ala Val Arg Ile Met
305                 310                 315                 320

Ala Ala Phe Tyr Lys Val Gly Arg Asp Arg Tyr Gln Val Pro Val Asn
                325                 330                 335

Phe Asp Ser Trp Thr Lys Asp Glu Tyr Gly Tyr Glu His Ala Leu Val
            340                 345                 350

Gly Gln Asn Tyr Val Lys Val Asn Asp Lys Val Asp Val Arg Ala Asp
        355                 360                 365

His Ala Asp Ile Ile Arg Gln Ile Gly Ser Ala Ser Val Val Leu Leu
    370                 375                 380

Lys Asn Asp Gly Gly Leu Pro Leu Thr Gly Tyr Glu Lys Phe Thr Gly
385                 390                 395                 400

Val Phe Gly Glu Asp Ala Gly Ser Asn Arg Trp Gly Ala Asp Gly Cys
                405                 410                 415

Ser Asp Arg Gly Cys Asp Asn Gly Thr Leu Ala Met Gly Trp Gly Ser
            420                 425                 430

Gly Thr Ala Asp Phe Pro Tyr Leu Val Thr Pro Glu Gln Ala Ile Gln
        435                 440                 445

Asn Glu Ile Leu Ser Lys Gly Lys Gly Leu Val Ser Ala Val Thr Asp
    450                 455                 460

Asn Gly Ala Leu Asp Gln Met Glu Gln Val Ala Ser Gln Ala Ser Val
465                 470                 475                 480

Ser Ile Val Phe Val Asn Ala Asp Ser Gly Glu Gly Tyr Ile Asn Val
                485                 490                 495

Asp Gly Asn Glu Gly Asp Arg Lys Asn Leu Thr Leu Trp Lys Gly Gly
```

```
                500             505             510
Glu Glu Val Ile Lys Thr Val Ala Ala Asn Cys Asn Asn Thr Ile Val
            515                 520                 525

Val Met His Thr Val Gly Pro Val Leu Ile Asp Glu Trp Tyr Asp Asn
        530                 535                 540

Pro Asn Val Thr Ala Ile Val Trp Ala Gly Leu Pro Gly Gln Glu Ser
545                 550                 555                 560

Gly Asn Ser Leu Val Asp Val Leu Tyr Gly Arg Val Ser Pro Gly Gly
                565                 570                 575

Lys Thr Pro Phe Thr Trp Gly Lys Thr Arg Glu Ser Tyr Gly Ala Pro
            580                 585                 590

Leu Leu Thr Lys Pro Asn Asn Gly Lys Gly Ala Pro Gln Asp Asp Phe
        595                 600                 605

Thr Glu Gly Val Phe Ile Asp Tyr Arg Arg Phe Asp Lys Tyr Asn Glu
        610                 615                 620

Thr Pro Ile Tyr Glu Phe Gly Phe Gly Leu Ser Tyr Thr Thr Phe Glu
625                 630                 635                 640

Tyr Ser Asp Ile Tyr Val Gln Pro Leu Asn Ala Arg Pro Tyr Thr Pro
                645                 650                 655

Ala Ser Gly Ser Thr Lys Ala Ala Pro Thr Phe Gly Asn Ile Ser Thr
            660                 665                 670

Asp Tyr Ala Asp Tyr Leu Tyr Pro Glu Asp Ile His Lys Val Pro Leu
        675                 680                 685

Tyr Ile Tyr Pro Trp Leu Asn Thr Thr Asp Pro Lys Lys Ser Ser Gly
        690                 695                 700

Asp Pro Asp Tyr Gly Met Lys Ala Glu Asp Tyr Ile Pro Ser Gly Ala
705                 710                 715                 720

Thr Asp Gly Ser Pro Gln Pro Ile Leu Pro Ala Gly Ala Pro Gly
                725                 730                 735

Gly Asn Pro Gly Leu Tyr Asp Glu Met Tyr Arg Val Ser Ala Ile Ile
            740                 745                 750

Thr Asn Thr Gly Asn Val Val Gly Asp Glu Val Pro Gln Leu Tyr Val
        755                 760                 765

Ser Leu Gly Gly Pro Asp Asp Pro Lys Val Val Leu Arg Asn Phe Asp
        770                 775                 780

Arg Ile Thr Leu His Pro Gly Gln Gln Thr Met Trp Thr Thr Thr Leu
785                 790                 795                 800

Thr Arg Arg Asp Ile Ser Asn Trp Asp Pro Ala Ser Gln Asn Trp Val
                805                 810                 815

Val Thr Lys Tyr Pro Lys Thr Val Tyr Ile Gly Ser Ser Arg Lys
            820                 825                 830

Leu His Leu Gln Ala Pro Leu Pro Pro Tyr
        835                 840

<210> SEQ ID NO 3
<211> LENGTH: 658
<212> TYPE: PRT
<213> ORGANISM: Azospirillum irakense

<400> SEQUENCE: 3

Gln Glu Gly Ala Ala Pro Ala Ala Ile Leu His Pro Glu Lys Trp Pro
1               5                   10                  15

Arg Pro Ala Thr Gln Arg Leu Ile Asp Pro Ala Val Glu Lys Arg Val
            20                  25                  30
```

```
Asp Ala Leu Leu Lys Gln Leu Ser Val Glu Lys Val Gly Gln Val
             35                  40                  45
Ile Gln Gly Asp Ile Gly Thr Ile Thr Pro Glu Asp Leu Arg Lys Tyr
 50                  55                  60
Pro Leu Gly Ser Ile Leu Ala Gly Gly Asn Ser Gly Pro Asn Gly Asp
 65                  70                  75                  80
Asp Arg Ala Pro Pro Lys Glu Trp Leu Asp Leu Ala Asp Ala Phe Tyr
                 85                  90                  95
Arg Val Ser Leu Glu Lys Arg Pro Gly His Thr Pro Ile Pro Val Leu
            100                 105                 110
Phe Gly Ile Asp Ala Val His Gly His Gly Asn Ile Gly Ser Ala Thr
            115                 120                 125
Ile Phe Pro His Asn Ile Ala Leu Gly Ala Thr His Asp Pro Glu Leu
        130                 135                 140
Leu Arg Arg Ile Gly Glu Val Thr Ala Val Glu Met Ala Ala Thr Gly
145                 150                 155                 160
Ile Asp Trp Thr Phe Ala Pro Ala Leu Ser Val Val Arg Asp Asp Arg
                165                 170                 175
Trp Gly Arg Thr Tyr Glu Gly Phe Ser Glu Asp Pro Glu Ile Val Ala
            180                 185                 190
Ala Tyr Ser Ala Ala Ile Val Glu Gly Val Gln Gly Lys Phe Gly Ser
            195                 200                 205
Lys Asp Phe Met Ala Pro Gly Arg Ile Val Ala Ser Ala Lys His Phe
        210                 215                 220
Leu Ala Asp Gly Gly Thr Asp Gln Gly Arg Asp Gln Gly Asp Ala Arg
225                 230                 235                 240
Ile Ser Glu Asp Glu Leu Ile Arg Ile His Asn Ala Gly Tyr Pro Pro
                245                 250                 255
Ala Ile Asp Ala Gly Val Leu Thr Val Met Ala Ser Phe Ser Ser Trp
            260                 265                 270
Gln Gly Ile Lys His His Gly His Lys Gln Leu Leu Thr Asp Val Leu
            275                 280                 285
Lys Gly Gln Met Gly Phe Asn Gly Phe Ile Val Gly Asp Trp Asn Ala
        290                 295                 300
His Asp Gln Val Pro Gly Cys Thr Lys Phe Asn Cys Pro Thr Ser Leu
305                 310                 315                 320
Ile Ala Gly Leu Asp Met Tyr Met Ala Ala Asp Ser Trp Lys Gln Leu
                325                 330                 335
Tyr Glu Asn Thr Leu Ala Gln Val Lys Asp Gly Thr Ile Pro Met Ala
            340                 345                 350
Arg Leu Asp Asp Ala Val Arg Arg Ile Leu Arg Val Lys Val Leu Ala
        355                 360                 365
Gly Leu Phe Glu Lys Pro Ala Pro Lys Asp Arg Pro Gly Leu Pro Gly
370                 375                 380
Leu Glu Thr Leu Gly Ser Pro Glu His Arg Ala Val Gly Arg Glu Ala
385                 390                 395                 400
Val Arg Lys Ser Leu Val Leu Leu Lys Asn Asp Lys Gly Thr Leu Pro
                405                 410                 415
Leu Ser Pro Lys Ala Arg Val Leu Val Ala Gly Asp Gly Ala Asp Asn
            420                 425                 430
Ile Gly Lys Gln Ser Gly Gly Trp Thr Ile Ser Trp Gln Gly Thr Gly
        435                 440                 445
Asn Arg Asn Asp Glu Phe Pro Gly Ala Thr Ser Ile Leu Gly Gly Ile
```

```
                450             455             460
Arg Asp Ala Val Ala Asp Ala Gly Gly Ser Val Glu Phe Asp Val Ala
465                 470                 475                 480

Gly Gln Tyr Lys Thr Lys Pro Asp Val Ala Ile Val Val Phe Gly Glu
                485                 490                 495

Glu Pro Tyr Ala Glu Phe Gln Gly Asp Val Glu Thr Leu Glu Tyr Gln
                500                 505                 510

Pro Asp Gln Lys Gln Asp Leu Ala Leu Leu Lys Lys Leu Lys Asp Gln
            515                 520                 525

Gly Ile Pro Val Val Ala Val Phe Leu Ser Gly Arg Pro Met Trp Val
530                 535                 540

Asn Pro Glu Leu Asn Ala Ser Asp Ala Phe Val Ala Ala Trp Leu Pro
545                 550                 555                 560

Gly Thr Glu Gly Gly Val Ala Asp Val Leu Phe Thr Asp Lys Ala
                565                 570                 575

Gly Lys Val Gln His Asp Phe Ala Gly Lys Leu Ser Tyr Ser Trp Pro
            580                 585                 590

Arg Thr Ala Ala Gln Thr Thr Val Asn Arg Gly Asp Ala Asp Tyr Asn
            595                 600                 605

Pro Leu Phe Ala Tyr Gly Tyr Gly Leu Thr Tyr Lys Asp Lys Ser Lys
610                 615                 620

Val Gly Thr Leu Pro Glu Glu Ser Gly Val Pro Ala Glu Ala Arg Gln
625                 630                 635                 640

Asn Ala Gly Ile Tyr Phe Arg Ala Gly Ala Leu Arg Leu Pro Gly Arg
                645                 650                 655

Phe Leu

<210> SEQ ID NO 4
<211> LENGTH: 754
<212> TYPE: PRT
<213> ORGANISM: Clostridium thermocellum DSM 1237

<400> SEQUENCE: 4

Met Ala Val Asp Ile Lys Lys Ile Ile Lys Gln Met Thr Leu Glu Glu
1               5                   10                  15

Lys Ala Gly Leu Cys Ser Gly Leu Asp Phe Trp His Thr Lys Pro Val
                20                  25                  30

Glu Arg Leu Gly Ile Pro Ser Ile Met Met Thr Asp Gly Pro His Gly
            35                  40                  45

Leu Arg Lys Gln Arg Glu Asp Ala Glu Ile Ala Asp Ile Asn Asn Ser
        50                  55                  60

Val Pro Ala Thr Cys Phe Pro Ser Ala Ala Gly Leu Ala Cys Ser Trp
65                  70                  75                  80

Asp Arg Glu Leu Val Glu Arg Val Gly Ala Ala Leu Gly Glu Glu Cys
                85                  90                  95

Gln Ala Glu Asn Val Ser Ile Leu Leu Gly Pro Gly Ala Asn Ile Lys
                100                 105                 110

Arg Ser Pro Leu Cys Gly Arg Asn Phe Glu Tyr Phe Pro Glu Asp Pro
            115                 120                 125

Tyr Leu Ser Ser Glu Leu Ala Ser His Ile Lys Gly Val Gln Ser
        130                 135                 140

Gln Gly Val Gly Ala Cys Leu Lys His Phe Ala Ala Asn Asn Gln Glu
145                 150                 155                 160

His Arg Arg Met Thr Val Asp Thr Ile Val Asp Glu Arg Thr Leu Arg
```

```
              165                 170                 175
Glu Ile Tyr Phe Ala Ser Phe Glu Asn Ala Val Lys Lys Ala Arg Pro
            180                 185                 190

Trp Val Val Met Cys Ala Tyr Asn Lys Leu Asn Gly Glu Tyr Cys Ser
            195                 200                 205

Glu Asn Arg Tyr Leu Leu Thr Glu Val Leu Lys Asn Glu Trp Met His
            210                 215                 220

Asp Gly Phe Val Val Ser Asp Trp Gly Ala Val Asn Asp Arg Val Ser
225                 230                 235                 240

Gly Leu Asp Ala Gly Leu Asp Leu Glu Met Pro Thr Ser His Gly Ile
                245                 250                 255

Thr Asp Lys Lys Ile Val Glu Ala Val Lys Ser Gly Lys Leu Ser Glu
            260                 265                 270

Asn Ile Leu Asn Arg Ala Val Glu Arg Ile Leu Lys Val Ile Ile Met
            275                 280                 285

Ala Leu Glu Asn Lys Lys Glu Asn Ala Gln Tyr Glu Gln Asp Ala His
            290                 295                 300

His Arg Leu Ala Arg Gln Ala Ala Glu Ser Met Val Leu Leu Lys
305                 310                 315                 320

Asn Glu Asp Asp Val Leu Pro Leu Lys Lys Ser Gly Thr Ile Ala Leu
                325                 330                 335

Ile Gly Ala Phe Val Lys Lys Pro Arg Tyr Gln Gly Ser Gly Ser Ser
            340                 345                 350

His Ile Thr Pro Thr Arg Leu Asp Asp Ile Tyr Glu Glu Ile Lys Lys
            355                 360                 365

Ala Gly Ala Asp Lys Val Asn Leu Val Tyr Ser Glu Gly Tyr Arg Leu
            370                 375                 380

Glu Asn Asp Gly Ile Asp Glu Glu Leu Ile Asn Glu Ala Lys Lys Ala
385                 390                 395                 400

Ala Ser Ser Ser Asp Val Ala Val Phe Ala Gly Leu Pro Asp Glu
                405                 410                 415

Tyr Glu Ser Glu Gly Phe Asp Arg Thr His Met Ser Ile Pro Glu Asn
            420                 425                 430

Gln Asn Arg Leu Ile Glu Ala Val Ala Glu Val Gln Ser Asn Ile Val
            435                 440                 445

Val Val Leu Leu Asn Gly Ser Pro Val Glu Met Pro Trp Ile Asp Lys
450                 455                 460

Val Lys Ser Val Leu Glu Ala Tyr Leu Gly Gly Gln Ala Leu Gly Gly
465                 470                 475                 480

Arg Trp Arg Met Cys Tyr Ser Val Lys Ser Ile Val Gly Lys Leu Ala
                485                 490                 495

Glu Thr Phe Pro Val Lys Leu Ser His Asn Pro Ser Tyr Leu Asn Phe
            500                 505                 510

Pro Gly Glu Asp Asp Arg Val Glu Tyr Lys Glu Gly Leu Phe Val Gly
            515                 520                 525

Tyr Arg Tyr Tyr Asp Thr Lys Gly Ile Glu Pro Leu Phe Pro Phe Gly
            530                 535                 540

His Gly Leu Ser Tyr Thr Lys Phe Glu Tyr Ser Asp Ile Ser Val Asp
545                 550                 555                 560

Lys Lys Asp Val Ser Asp Asn Ser Ile Ile Asn Val Ser Val Lys Val
                565                 570                 575

Lys Asn Val Gly Lys Met Ala Gly Lys Glu Ile Val Gln Leu Tyr Val
            580                 585                 590
```

-continued

```
Lys Asp Val Lys Ser Ser Val Arg Arg Pro Glu Lys Glu Leu Lys Gly
            595                 600                 605

Phe Glu Lys Val Phe Leu Asn Pro Gly Glu Glu Lys Thr Val Thr Phe
    610                 615                 620

Thr Leu Asp Lys Arg Ala Phe Ala Tyr Tyr Asn Thr Gln Ile Lys Asp
625                 630                 635                 640

Trp His Val Glu Ser Gly Glu Phe Leu Ile Leu Ile Gly Arg Ser Ser
                645                 650                 655

Arg Asp Ile Val Leu Lys Glu Ser Val Arg Val Asn Ser Thr Val Lys
            660                 665                 670

Ile Arg Lys Arg Phe Thr Val Asn Ser Ala Val Glu Asp Val Met Ser
        675                 680                 685

Asp Ser Ser Ala Ala Val Leu Gly Pro Val Leu Lys Glu Ile Thr
    690                 695                 700

Asp Ala Leu Gln Ile Asp Met Asp Asn Ala His Asp Met Met Ala Ala
705                 710                 715                 720

Asn Ile Lys Asn Met Pro Leu Arg Ser Leu Val Gly Tyr Ser Gln Gly
                725                 730                 735

Arg Leu Ser Glu Glu Met Leu Glu Leu Val Asp Lys Ile Asn Asn
            740                 745                 750

Val Glu

<210> SEQ ID NO 5
<211> LENGTH: 730
<212> TYPE: PRT
<213> ORGANISM: Thermoanaerobacter brockii

<400> SEQUENCE: 5

Met Ser Tyr Gly Ile Gly Gln Ile Thr Arg Leu Gly Gly Ala Ser Asn
1               5                   10                  15

Leu Ser Pro Arg Glu Thr Val Arg Ile Ala Asn Gln Ile Gln Lys Phe
            20                  25                  30

Leu Ile Glu Asn Thr Arg Leu Gly Ile Pro Ala Leu Ile His Glu Glu
        35                  40                  45

Ser Cys Ser Gly Tyr Met Ala Lys Gly Ala Thr Ile Phe Pro Gln Thr
    50                  55                  60

Ile Gly Val Ala Ser Thr Trp Asn Asn Glu Ile Val Glu Lys Met Ala
65                  70                  75                  80

Ser Val Ile Arg Glu Gln Met Lys Ala Val Gly Ala Arg Gln Ala Leu
                85                  90                  95

Ala Pro Leu Leu Asp Ile Thr Arg Asp Pro Arg Trp Gly Arg Thr Glu
            100                 105                 110

Glu Thr Phe Gly Glu Asp Pro Tyr Leu Val Met Arg Met Gly Val Ser
        115                 120                 125

Tyr Ile Arg Gly Leu Gln Thr Glu Ser Leu Lys Glu Gly Ile Val Ala
    130                 135                 140

Thr Gly Lys His Phe Val Gly Tyr Gly Asn Ser Glu Gly Gly Met Asn
145                 150                 155                 160

Trp Ala Pro Ala His Ile Pro Gly Arg Glu Leu Arg Glu Val Phe Leu
                165                 170                 175

Tyr Pro Phe Glu Ala Ala Val Lys Glu Ala Lys Leu Ser Ser Ile Met
            180                 185                 190

Pro Gly Tyr His Glu Leu Asp Gly Val Pro Cys His Lys Ser Lys Lys
        195                 200                 205
```

```
Leu Leu Asn Asp Ile Leu Arg Lys Asp Trp Gly Phe Glu Gly Ile Val
        210                 215                 220

Val Ser Asp Tyr Phe Ala Ile Ser Gln Leu Tyr Glu Tyr His His Val
225                 230                 235                 240

Thr Ser Asp Lys Lys Gly Ala Ala Lys Leu Ala Leu Glu Ala Gly Val
            245                 250                 255

Asp Val Glu Leu Pro Ser Thr Asp Tyr Tyr Gly Leu Pro Leu Arg Glu
                260                 265                 270

Leu Ile Glu Ser Gly Glu Ile Asp Ile Asp Phe Val Asn Glu Ala Val
            275                 280                 285

Lys Arg Val Leu Lys Ile Lys Phe Glu Leu Gly Leu Phe Glu Asn Pro
290                 295                 300

Tyr Ile Asn Glu Glu Lys Ala Val Glu Ile Phe Asp Thr Asn Glu Gln
305                 310                 315                 320

Arg Glu Leu Ala Tyr Lys Ile Ala Gln Glu Ser Ile Val Leu Leu Lys
                325                 330                 335

Asn Glu Asn Asn Leu Leu Pro Leu Lys Lys Asp Leu Lys Ser Ile Ala
            340                 345                 350

Val Ile Gly Pro Asn Ala Asp Ser Ile Arg Asn Met Ile Gly Asp Tyr
            355                 360                 365

Ala Tyr Pro Cys His Ile Glu Ser Leu Leu Glu Met Arg Glu Thr Asp
370                 375                 380

Asn Val Phe Asn Thr Pro Leu Pro Glu Ser Leu Glu Ala Lys Asp Ile
385                 390                 395                 400

Tyr Val Pro Ile Val Thr Val Leu Gln Gly Ile Lys Ala Lys Val Ser
                405                 410                 415

Ser Asn Thr Glu Val Leu Tyr Ala Lys Gly Cys Asp Val Leu Asn Asn
            420                 425                 430

Ser Lys Asp Gly Phe Lys Glu Ala Val Glu Ile Ala Lys Gln Ala Asp
            435                 440                 445

Val Ala Val Val Val Gly Asp Lys Ser Gly Leu Thr Asp Gly Cys
450                 455                 460

Thr Ser Gly Glu Ser Arg Asp Arg Ala Asp Leu Asn Leu Pro Gly Val
465                 470                 475                 480

Gln Glu Glu Leu Ile Lys Ala Ile Tyr Glu Thr Gly Thr Pro Val Ile
                485                 490                 495

Val Val Leu Ile Asn Gly Arg Pro Met Ser Ile Ser Trp Ile Ala Glu
            500                 505                 510

Lys Ile Pro Ala Ile Ile Glu Ala Trp Leu Pro Gly Glu Glu Gly Gly
            515                 520                 525

Arg Ala Val Ala Asp Val Ile Phe Gly Asp Tyr Asn Pro Gly Gly Lys
530                 535                 540

Leu Pro Ile Ser Ile Pro Gln Ser Val Gly Gln Leu Pro Val Tyr Tyr
545                 550                 555                 560

Tyr His Lys Pro Ser Gly Gly Arg Ser His Trp Lys Gly Asp Tyr Val
                565                 570                 575

Glu Leu Ser Thr Lys Pro Leu Tyr Pro Phe Gly Tyr Gly Leu Ser Tyr
            580                 585                 590

Thr Glu Phe Ser Tyr Thr Asn Leu Asn Ile Ser Asn Arg Lys Val Ser
            595                 600                 605

Leu Arg Asp Arg Met Val Glu Ile Ser Val Asp Ile Lys Asn Thr Gly
610                 615                 620
```

```
Thr Leu Lys Gly Asp Glu Val Val Gln Leu Tyr Ile His Gln Glu Ala
625                 630                 635                 640

Leu Ser Val Thr Arg Pro Val Lys Glu Leu Lys Gly Phe Lys Arg Ile
            645                 650                 655

Thr Leu Asp Ala Gly Glu Glu Lys Thr Val Ile Phe Lys Leu Ser Ile
        660                 665                 670

Glu Gln Leu Gly Phe Tyr Asp Glu Asn Met Glu Tyr Val Val Glu Pro
            675                 680                 685

Gly Arg Val Asp Val Met Ile Gly Ser Ser Ser Glu Asp Ile Arg Leu
        690                 695                 700

Arg Asp Tyr Phe Glu Ile Val Gly Glu Lys Lys Val Ala Lys Lys
705                 710                 715                 720

Phe Ile Thr Glu Val Arg Val Glu Asn Lys
            725                 730

<210> SEQ ID NO 6
<211> LENGTH: 721
<212> TYPE: PRT
<213> ORGANISM: Thermotoga maritima MSB8

<400> SEQUENCE: 6

Met Glu Arg Ile Asp Glu Ile Leu Ser Gln Leu Thr Thr Glu Glu Lys
1               5                   10                  15

Val Lys Leu Val Val Gly Val Gly Leu Pro Gly Leu Phe Gly Asn Pro
            20                  25                  30

His Ser Arg Val Ala Gly Ala Ala Gly Glu Thr His Pro Val Pro Arg
        35                  40                  45

Leu Gly Ile Pro Ala Phe Val Leu Ala Asp Gly Pro Ala Gly Leu Arg
    50                  55                  60

Ile Asn Pro Thr Arg Glu Asn Asp Glu Asn Thr Tyr Tyr Thr Thr Ala
65              70                  75                  80

Phe Pro Val Glu Ile Met Leu Ala Ser Thr Trp Asn Arg Asp Leu Leu
            85                  90                  95

Glu Glu Val Gly Lys Ala Met Gly Glu Glu Val Arg Glu Tyr Gly Val
            100                 105                 110

Asp Val Leu Leu Ala Pro Ala Met Asn Ile His Arg Asn Pro Leu Cys
        115                 120                 125

Gly Arg Asn Phe Glu Tyr Tyr Ser Glu Asp Pro Val Leu Ser Gly Glu
    130                 135                 140

Met Ala Ser Ala Phe Val Lys Gly Val Gln Ser Gln Gly Val Gly Ala
145                 150                 155                 160

Cys Ile Lys His Phe Val Ala Asn Asn Gln Glu Thr Asn Arg Met Val
            165                 170                 175

Val Asp Thr Ile Val Ser Glu Arg Ala Leu Arg Glu Ile Tyr Leu Lys
        180                 185                 190

Gly Phe Glu Ile Ala Val Lys Lys Ala Arg Pro Trp Thr Val Met Ser
    195                 200                 205

Ala Tyr Asn Lys Leu Asn Gly Lys Tyr Cys Ser Gln Asn Glu Trp Leu
    210                 215                 220

Leu Lys Lys Val Leu Arg Glu Glu Trp Gly Phe Asp Gly Phe Val Met
225                 230                 235                 240

Ser Asp Trp Tyr Ala Gly Asp Asn Pro Val Glu Gln Leu Lys Ala Gly
            245                 250                 255

Asn Asp Met Ile Met Pro Gly Lys Ala Tyr Gln Val Asn Thr Glu Arg
            260                 265                 270
```

```
Arg Asp Glu Ile Glu Ile Met Glu Ala Leu Lys Glu Gly Lys Leu
    275                 280                 285

Ser Glu Glu Val Leu Asp Glu Cys Val Arg Asn Ile Leu Lys Val Leu
290                 295                 300

Val Asn Ala Pro Ser Phe Lys Gly Tyr Arg Tyr Ser Asn Lys Pro Asp
305                 310                 315                 320

Leu Glu Ser His Ala Glu Val Ala Tyr Glu Ala Gly Ala Glu Gly Val
                325                 330                 335

Val Leu Leu Glu Asn Asn Gly Val Leu Pro Phe Asp Glu Asn Thr His
                340                 345                 350

Val Ala Val Phe Gly Thr Gly Gln Ile Glu Thr Ile Lys Gly Gly Thr
                355                 360                 365

Gly Ser Gly Asp Thr His Pro Arg Tyr Thr Ile Ser Ile Leu Glu Gly
    370                 375                 380

Ile Lys Glu Arg Asn Met Lys Phe Asp Glu Glu Leu Ala Ser Thr Tyr
385                 390                 395                 400

Glu Glu Tyr Ile Lys Lys Met Arg Glu Thr Glu Tyr Lys Pro Arg
                405                 410                 415

Thr Asp Ser Trp Gly Thr Val Ile Lys Pro Lys Leu Pro Glu Asn Phe
    420                 425                 430

Leu Ser Glu Lys Glu Ile Lys Lys Ala Ala Lys Lys Asn Asp Val Ala
    435                 440                 445

Val Val Val Ile Ser Arg Ile Ser Gly Glu Gly Tyr Asp Arg Lys Pro
    450                 455                 460

Val Lys Gly Asp Phe Tyr Leu Ser Asp Asp Glu Leu Glu Leu Ile Lys
465                 470                 475                 480

Thr Val Ser Lys Glu Phe His Asp Gln Gly Lys Lys Val Val Val Leu
                485                 490                 495

Leu Asn Ile Gly Ser Pro Ile Glu Val Ala Ser Trp Arg Asp Leu Val
                500                 505                 510

Asp Gly Ile Leu Leu Val Trp Gln Ala Gly Gln Glu Met Gly Arg Ile
    515                 520                 525

Val Ala Asp Val Leu Val Gly Lys Ile Asn Pro Ser Gly Lys Leu Pro
    530                 535                 540

Thr Thr Phe Pro Lys Asp Tyr Ser Asp Val Pro Ser Trp Thr Phe Pro
545                 550                 555                 560

Gly Glu Pro Lys Asp Asn Pro Gln Arg Val Val Tyr Glu Glu Asp Ile
                565                 570                 575

Tyr Val Gly Tyr Arg Tyr Tyr Asp Thr Phe Gly Val Glu Pro Ala Tyr
                580                 585                 590

Glu Phe Gly Tyr Gly Leu Ser Tyr Thr Lys Phe Glu Tyr Lys Asp Leu
    595                 600                 605

Lys Ile Ala Ile Asp Gly Glu Thr Leu Arg Val Ser Tyr Thr Ile Thr
    610                 615                 620

Asn Thr Gly Asp Arg Ala Gly Lys Glu Val Ser Gln Val Tyr Ile Lys
625                 630                 635                 640

Ala Pro Lys Gly Lys Ile Asp Lys Pro Phe Gln Glu Leu Lys Ala Phe
                645                 650                 655

His Lys Thr Lys Leu Leu Asn Pro Gly Glu Ser Glu Glu Ile Ser Leu
                660                 665                 670

Glu Ile Pro Leu Arg Asp Leu Ala Ser Phe Asp Gly Lys Glu Trp Val
    675                 680                 685
```

```
Val Glu Ser Gly Glu Tyr Glu Val Arg Val Gly Ala Ser Ser Arg Asp
    690             695                 700

Ile Arg Leu Arg Asp Ile Phe Leu Val Glu Gly Glu Lys Arg Phe Lys
705             710                 715                 720

Pro

<210> SEQ ID NO 7
<211> LENGTH: 721
<212> TYPE: PRT
<213> ORGANISM: Thermotoga neapolitana DSM 4359

<400> SEQUENCE: 7

Met Glu Lys Val Asn Glu Ile Leu Ser Gln Leu Thr Leu Glu Glu Lys
1               5                   10                  15

Val Lys Leu Val Gly Val Gly Leu Pro Gly Leu Phe Gly Asn Pro
            20                  25                  30

His Ser Arg Val Ala Gly Ala Ala Gly Glu Thr His Pro Val Pro Arg
            35                  40                  45

Val Gly Leu Pro Ala Phe Val Leu Ala Asp Gly Pro Ala Gly Leu Arg
        50                  55                  60

Ile Asn Pro Thr Arg Glu Asn Asp Glu Asn Thr Tyr Tyr Thr Thr Ala
65                  70                  75                  80

Phe Pro Val Glu Ile Met Leu Ala Ser Thr Trp Asn Arg Glu Leu Leu
                85                  90                  95

Glu Glu Val Gly Lys Ala Met Gly Glu Val Arg Glu Tyr Gly Val
            100                 105                 110

Asp Val Leu Leu Ala Pro Ala Met Asn Ile His Arg Asn Pro Leu Cys
        115                 120                 125

Gly Arg Asn Phe Glu Tyr Tyr Ser Glu Asp Pro Val Leu Ser Gly Glu
    130                 135                 140

Met Ala Ser Ser Phe Val Lys Gly Val Gln Ser Gln Gly Val Gly Ala
145                 150                 155                 160

Cys Ile Lys His Phe Val Ala Asn Asn Gln Glu Thr Asn Arg Met Val
                165                 170                 175

Val Asp Thr Ile Val Ser Glu Arg Ala Leu Arg Glu Ile Tyr Leu Arg
            180                 185                 190

Gly Phe Glu Ile Ala Val Lys Lys Ser Lys Pro Trp Ser Val Met Ser
        195                 200                 205

Ala Tyr Asn Lys Leu Asn Gly Lys Tyr Cys Ser Gln Asn Glu Trp Leu
    210                 215                 220

Leu Lys Lys Val Leu Arg Glu Trp Gly Phe Glu Gly Phe Val Met
225                 230                 235                 240

Ser Asp Trp Tyr Ala Gly Asp Asn Pro Val Glu Gln Leu Lys Ala Gly
                245                 250                 255

Asn Asp Leu Ile Met Pro Gly Lys Ala Tyr Gln Val Asn Thr Glu Arg
            260                 265                 270

Arg Asp Glu Ile Glu Glu Ile Met Glu Ala Leu Lys Glu Gly Lys Leu
        275                 280                 285

Ser Glu Glu Val Leu Asp Glu Cys Val Arg Asn Ile Leu Lys Val Leu
    290                 295                 300

Val Asn Ala Pro Ser Phe Lys Asn Tyr Arg Tyr Ser Asn Lys Pro Asp
305                 310                 315                 320

Leu Glu Lys His Ala Lys Val Ala Tyr Glu Ala Gly Ala Glu Gly Val
                325                 330                 335
```

```
Val Leu Leu Arg Asn Glu Glu Ala Leu Pro Leu Ser Glu Asn Ser Lys
            340                 345                 350

Ile Ala Leu Phe Gly Thr Gly Gln Ile Glu Thr Ile Lys Gly Gly Thr
    355                 360                 365

Gly Ser Gly Asp Thr His Pro Arg Tyr Ala Ile Ser Ile Leu Glu Gly
370                 375                 380

Ile Lys Glu Arg Gly Leu Asn Phe Asp Glu Glu Leu Ala Lys Thr Tyr
385                 390                 395                 400

Glu Asp Tyr Ile Lys Lys Met Arg Glu Thr Glu Tyr Lys Pro Arg
            405                 410                 415

Arg Asp Ser Trp Gly Thr Ile Ile Lys Pro Lys Leu Pro Glu Asn Phe
            420                 425                 430

Leu Ser Glu Lys Glu Ile His Lys Leu Ala Lys Lys Asn Asp Val Ala
            435                 440                 445

Val Ile Val Ile Ser Arg Ile Ser Gly Glu Gly Tyr Asp Arg Lys Pro
            450                 455                 460

Val Lys Gly Asp Phe Tyr Leu Ser Asp Asp Glu Thr Asp Leu Ile Lys
465                 470                 475                 480

Thr Val Ser Arg Glu Phe His Glu Gln Gly Lys Lys Val Ile Val Leu
            485                 490                 495

Leu Asn Ile Gly Ser Pro Val Glu Val Val Ser Trp Arg Asp Leu Val
            500                 505                 510

Asp Gly Ile Leu Leu Val Trp Gln Ala Gly Gln Glu Thr Gly Arg Ile
            515                 520                 525

Val Ala Asp Val Leu Thr Gly Arg Ile Asn Pro Ser Gly Lys Leu Pro
            530                 535                 540

Thr Thr Phe Pro Arg Asp Tyr Ser Asp Val Pro Ser Trp Thr Phe Pro
545                 550                 555                 560

Gly Glu Pro Lys Asp Asn Pro Gln Lys Val Val Tyr Glu Glu Asp Ile
                565                 570                 575

Tyr Val Gly Tyr Arg Tyr Tyr Asp Thr Phe Gly Val Glu Pro Ala Tyr
            580                 585                 590

Glu Phe Gly Tyr Gly Leu Ser Tyr Thr Thr Phe Glu Tyr Ser Asp Leu
    595                 600                 605

Asn Val Ser Phe Asp Gly Glu Thr Leu Arg Val Gln Tyr Arg Ile Glu
    610                 615                 620

Asn Thr Gly Gly Arg Ala Gly Lys Glu Val Ser Gln Val Tyr Ile Lys
625                 630                 635                 640

Ala Pro Lys Gly Lys Ile Asp Lys Pro Phe Gln Glu Leu Lys Ala Phe
                645                 650                 655

His Lys Thr Arg Leu Leu Asn Pro Gly Glu Ser Glu Glu Val Val Leu
            660                 665                 670

Glu Ile Pro Val Arg Asp Leu Ala Ser Phe Asn Gly Glu Glu Trp Val
            675                 680                 685

Val Glu Ala Gly Glu Tyr Glu Val Arg Val Gly Ala Ser Ser Arg Asn
690                 695                 700

Ile Lys Leu Lys Gly Thr Phe Ser Val Gly Glu Glu Arg Arg Phe Lys
705                 710                 715                 720

Pro
```

<210> SEQ ID NO 8
<211> LENGTH: 720
<212> TYPE: PRT
<213> ORGANISM: Thermotoga neapolitana Z2706-MC24

<400> SEQUENCE: 8

```
Met Glu Lys Val Asn Glu Ile Leu Ser Gln Leu Thr Leu Glu Lys
1               5                   10                  15

Ser Glu Thr Cys Ser Gly Gly Trp Thr Ser Gly Val Val Trp Lys Ser
                20                  25                  30

His Ser Gly Trp Arg Cys Arg Gly Glu Thr His Pro Val Pro Arg Val
            35                  40                  45

Gly Leu Pro Ala Phe Val Leu Ala Asp Gly Pro Ala Gly Leu Arg Ile
        50                  55                  60

Asn Pro Thr Arg Glu Asn Asp Glu Asn Thr Tyr Tyr Thr Thr Ala Phe
65                  70                  75                  80

Pro Val Glu Ile Met Leu Ala Ser Thr Trp Asn Arg Glu Leu Leu Glu
                85                  90                  95

Glu Val Gly Lys Ala Met Gly Glu Glu Val Arg Glu Tyr Gly Val Asp
                100                 105                 110

Val Leu Leu Gly Pro Ala Met Asn Ile His Arg Asn Pro Leu Cys Gly
            115                 120                 125

Arg Asn Phe Glu Tyr Tyr Ser Glu Asp Pro Val Leu Ser Gly Glu Met
    130                 135                 140

Ala Ser Ser Phe Val Lys Gly Val Gln Ser Gln Gly Val Gly Ala Cys
145                 150                 155                 160

Ile Lys His Phe Val Ala Asn Asn Gln Glu Thr Asn Arg Met Val Val
                165                 170                 175

Asp Thr Ile Val Ile Glu Arg Ala Leu Arg Glu Ile Tyr Leu Arg Gly
            180                 185                 190

Phe Glu Ile Ala Val Lys Lys Ser Lys Pro Trp Ser Val Met Ser Ala
    195                 200                 205

Tyr Asn Lys Leu Asn Gly Lys Tyr Cys Ser Gln Asn Glu Trp Leu Leu
210                 215                 220

Lys Lys Val Leu Arg Glu Glu Trp Gly Phe Glu Gly Phe Val Met Ser
225                 230                 235                 240

Asp Trp Tyr Ala Gly Asp Asn Pro Val Glu Gln Leu Lys Ala Gly Asn
                245                 250                 255

Asp Leu Ile Met Pro Gly Lys Ala Tyr Gln Val Asn Thr Glu Arg Arg
            260                 265                 270

Asp Glu Ile Glu Glu Ile Met Glu Ala Leu Lys Glu Gly Lys Leu Ser
        275                 280                 285

Glu Glu Val Leu Asp Glu Cys Val Arg Asn Ile Leu Lys Val Leu Val
    290                 295                 300

Asn Ala Pro Ser Phe Lys Asn Tyr Arg Tyr Ser Asn Lys Pro Asp Leu
305                 310                 315                 320

Glu Lys His Ala Lys Val Ala Tyr Glu Ala Gly Ala Glu Gly Val Val
                325                 330                 335

Leu Leu Lys Asn Glu Glu Ala Leu Pro Leu Ser Glu Asn Ser Lys Ile
            340                 345                 350

Ala Leu Phe Gly Thr Gly Gln Ile Glu Thr Ile Lys Gly Gly Thr Gly
        355                 360                 365

Ser Gly Asp Thr His Pro Arg Tyr Ala Ile Ser Ile Leu Glu Gly Ile
    370                 375                 380

Lys Glu Arg Gly Leu Asn Phe Asp Glu Glu Leu Ala Lys Ile Tyr Glu
385                 390                 395                 400

Asp Tyr Ile Lys Lys Met Arg Glu Thr Glu Glu Tyr Lys Pro Arg Arg
```

```
            405                 410                 415
Asp Ser Trp Gly Thr Ile Ile Lys Pro Lys Leu Ser Glu Asn Phe Leu
        420                 425                 430

Ser Glu Lys Glu Val His Lys Leu Ala Lys Lys Asn Asp Val Ala Val
        435                 440                 445

Ile Val Ile Ser Arg Ile Ser Gly Glu Gly Tyr Asp Arg Lys Pro Val
        450                 455                 460

Lys Gly Asp Phe Tyr Leu Ser Asp Glu Thr Asp Leu Ile Lys Thr
465                 470                 475                 480

Val Ser Arg Glu Phe His Glu Gln Gly Lys Lys Val Ile Val Leu Leu
        485                 490                 495

Asn Ile Gly Ser Pro Val Glu Val Val Ser Trp Arg Asp Leu Val Asp
        500                 505                 510

Gly Ile Leu Leu Val Trp Gln Ala Gly Gln Thr Gly Arg Ile Val
        515                 520                 525

Ala Asp Val Leu Thr Gly Arg Ile Asn Pro Ser Gly Lys Leu Pro Thr
        530                 535                 540

Thr Phe Pro Arg Asp Tyr Ser Asp Val Pro Ser Trp Thr Phe Pro Gly
545                 550                 555                 560

Glu Pro Lys Asp Asn Pro Gln Lys Val Tyr Glu Asp Ile Tyr
                565                 570                 575

Val Gly Tyr Arg Tyr Tyr Asp Thr Phe Gly Val Glu Pro Ala Tyr Glu
        580                 585                 590

Phe Gly Tyr Gly Leu Ser Tyr Thr Thr Phe Glu Tyr Ser Asp Leu Asn
        595                 600                 605

Val Ser Phe Asp Gly Glu Thr Leu Arg Val Gln Tyr Arg Ile Glu Asn
        610                 615                 620

Thr Gly Gly Arg Ala Gly Lys Glu Val Ser Gln Val Tyr Ile Lys Ala
625                 630                 635                 640

Pro Lys Gly Lys Ile Asp Lys Pro Phe Gln Glu Leu Lys Ala Phe His
                645                 650                 655

Lys Thr Arg Leu Leu Asn Pro Gly Glu Ser Glu Glu Val Val Leu Glu
        660                 665                 670

Ile Pro Val Arg Asp Leu Ala Ser Phe Asn Gly Glu Glu Trp Val Val
        675                 680                 685

Glu Ala Gly Glu Tyr Glu Val Arg Val Gly Ala Ser Ser Arg Asn Ile
        690                 695                 700

Lys Leu Lys Gly Thr Phe Ser Val Gly Glu Glu Arg Arg Phe Lys Pro
705                 710                 715                 720

<210> SEQ ID NO 9
<211> LENGTH: 857
<212> TYPE: PRT
<213> ORGANISM: Talaromyces emersonii

<400> SEQUENCE: 9

Met Arg Asn Gly Leu Leu Lys Val Ala Ala Leu Ala Ala Ala Ser Ala
1               5                   10                  15

Val Asn Gly Glu Asn Leu Ala Tyr Ser Pro Pro Phe Tyr Pro Ser Pro
            20                  25                  30

Trp Ala Asn Gly Gln Gly Asp Trp Ala Glu Ala Tyr Gln Lys Ala Val
        35                  40                  45

Gln Phe Val Ser Gln Leu Thr Leu Ala Glu Lys Val Asn Leu Thr Thr
    50                  55                  60
```

Gly Thr Gly Trp Glu Gln Asp Arg Cys Val Gly Gln Val Gly Ser Ile
65                  70                  75                  80

Pro Arg Leu Gly Phe Pro Gly Leu Cys Met Gln Asp Ser Pro Leu Gly
                85                  90                  95

Val Arg Asp Thr Asp Tyr Asn Ser Ala Phe Pro Ala Gly Val Asn Val
            100                 105                 110

Ala Ala Thr Trp Asp Arg Asn Leu Ala Tyr Arg Arg Gly Val Ala Met
        115                 120                 125

Gly Glu Glu His Arg Gly Lys Gly Val Asp Val Gln Leu Gly Pro Val
    130                 135                 140

Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
                165                 170                 175

Gln Gly Ile Gln Asp Ala Gly Val Ile Ala Cys Ala Lys His Phe Ile
            180                 185                 190

Leu Tyr Glu Gln Glu His Phe Arg Gln Gly Ala Gln Asp Gly Tyr Asp
        195                 200                 205

Ile Ser Asp Ser Ile Ser Ala Asn Ala Asp Asp Lys Thr Met His Glu
    210                 215                 220

Leu Tyr Leu Trp Pro Phe Ala Asp Ala Val Arg Ala Gly Val Gly Ser
225                 230                 235                 240

Val Met Cys Ser Tyr Asn Gln Val Asn Asn Ser Tyr Ala Cys Ser Asn
                245                 250                 255

Ser Tyr Thr Met Asn Lys Leu Leu Lys Ser Glu Leu Gly Phe Gln Gly
            260                 265                 270

Phe Val Met Thr Asp Trp Gly His His Ser Gly Val Gly Ser Ala
        275                 280                 285

Leu Ala Gly Leu Asp Met Ser Met Pro Gly Asp Ile Ala Phe Asp Ser
    290                 295                 300

Gly Thr Ser Phe Trp Gly Thr Asn Leu Thr Val Ala Val Leu Asn Gly
305                 310                 315                 320

Ser Ile Pro Glu Trp Arg Val Asp Asp Met Ala Val Arg Ile Met Ser
                325                 330                 335

Ala Tyr Tyr Lys Val Gly Arg Asp Arg Tyr Ser Val Pro Ile Asn Phe
            340                 345                 350

Asp Ser Trp Thr Leu Asp Thr Tyr Gly Pro Glu His Tyr Ala Val Gly
        355                 360                 365

Gln Gly Gln Thr Lys Ile Asn Glu His Val Asp Val Arg Gly Asn His
    370                 375                 380

Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
                405                 410                 415

Phe Gly Lys Asp Ala Gly Ser Asn Pro Trp Gly Val Asn Gly Cys Ser
            420                 425                 430

Asp Arg Gly Cys Asp Asn Gly Thr Leu Ala Met Gly Trp Gly Ser Gly
        435                 440                 445

Thr Ala Asn Phe Pro Tyr Leu Val Thr Pro Glu Gln Ala Ile Gln Arg
    450                 455                 460

Glu Val Leu Ser Arg Asn Gly Thr Phe Thr Gly Ile Thr Asp Asn Gly
465                 470                 475                 480

Ala Leu Ala Glu Met Ala Ala Ala Ala Ser Gln Ala Asp Thr Cys Leu

```
            485                 490                 495
Val Phe Ala Asn Ala Asp Ser Gly Glu Gly Tyr Ile Thr Val Asp Gly
            500                 505                 510

Asn Glu Gly Asp Arg Lys Asn Leu Thr Leu Trp Gln Gly Ala Asp Gln
            515                 520                 525

Val Ile His Asn Val Ser Ala Asn Cys Asn Asn Thr Val Val Val Leu
            530                 535                 540

His Thr Val Gly Pro Val Leu Ile Asp Asp Trp Tyr Asp His Pro Asn
545                 550                 555                 560

Val Thr Ala Ile Leu Trp Ala Gly Leu Pro Gly Gln Glu Ser Gly Asn
                565                 570                 575

Ser Leu Val Asp Val Leu Tyr Gly Arg Val Asn Pro Gly Lys Thr Pro
            580                 585                 590

Phe Thr Trp Gly Arg Ala Arg Asp Asp Tyr Gly Ala Pro Leu Ile Val
            595                 600                 605

Lys Pro Asn Asn Gly Lys Gly Ala Pro Gln Gln Asp Phe Thr Glu Gly
            610                 615                 620

Ile Phe Ile Asp Tyr Arg Arg Phe Asp Lys Tyr Asn Ile Thr Pro Ile
625                 630                 635                 640

Tyr Glu Phe Gly Phe Gly Leu Ser Tyr Thr Thr Phe Glu Phe Ser Gln
                645                 650                 655

Leu Asn Val Gln Pro Ile Asn Ala Pro Pro Tyr Thr Pro Ala Ser Gly
            660                 665                 670

Phe Thr Lys Ala Ala Gln Ser Phe Gly Gln Pro Ser Asn Ala Ser Asp
            675                 680                 685

Asn Leu Tyr Pro Ser Asp Ile Glu Arg Val Pro Leu Tyr Ile Tyr Pro
            690                 695                 700

Trp Leu Asn Ser Thr Asp Leu Lys Ala Ser Ala Asn Asp Pro Asp Tyr
705                 710                 715                 720

Gly Leu Pro Thr Glu Lys Tyr Val Pro Pro Asn Ala Thr Asn Gly Asp
                725                 730                 735

Pro Gln Pro Ile Asp Pro Ala Gly Gly Ala Pro Gly Gly Asn Pro Ser
            740                 745                 750

Leu Tyr Glu Pro Val Ala Arg Val Thr Thr Ile Ile Thr Asn Thr Gly
            755                 760                 765

Lys Val Thr Gly Asp Glu Val Pro Gln Leu Tyr Val Ser Leu Gly Gly
            770                 775                 780

Pro Asp Asp Ala Pro Lys Val Leu Arg Gly Phe Asp Arg Ile Thr Leu
785                 790                 795                 800

Ala Pro Gly Gln Gln Tyr Leu Trp Thr Thr Thr Leu Thr Arg Arg Asp
                805                 810                 815

Ile Ser Asn Trp Asp Pro Val Thr Gln Asn Trp Val Val Thr Asn Tyr
            820                 825                 830

Thr Lys Thr Ile Tyr Val Gly Asn Ser Ser Arg Asn Leu Pro Leu Gln
            835                 840                 845

Ala Pro Leu Lys Pro Tyr Pro Gly Ile
850                 855

<210> SEQ ID NO 10
<211> LENGTH: 825
<212> TYPE: PRT
<213> ORGANISM: Wickerhamomyces anomalus var. acetaetherius

<400> SEQUENCE: 10
```

-continued

```
Met Leu Leu Pro Leu Tyr Gly Leu Ala Ser Phe Leu Val Leu Ser Gln
1               5                   10                  15

Ala Ala Leu Val Asn Thr Ser Ala Pro Gln Ala Ser Asn Asp Asp Pro
            20                  25                  30

Phe Asn His Ser Pro Ser Phe Tyr Pro Thr Pro Gln Gly Gly Arg Ile
            35                  40                  45

Asn Asp Gly Lys Trp Gln Ala Ala Phe Tyr Arg Ala Arg Glu Leu Val
50                  55                  60

Asp Gln Met Ser Ile Ala Glu Lys Val Asn Leu Thr Thr Gly Val Gly
65                  70                  75                  80

Ser Ala Ser Gly Pro Cys Ser Gly Asn Thr Gly Ser Val Pro Arg Leu
                85                  90                  95

Asn Ile Ser Ser Ile Cys Val Gln Asp Gly Pro Leu Ser Val Arg Ala
            100                 105                 110

Ala Asp Leu Thr Asp Val Phe Pro Cys Gly Met Ala Ala Ser Ser Ser
            115                 120                 125

Phe Asn Lys Gln Leu Ile Tyr Asp Arg Ala Val Ala Ile Gly Ser Glu
130                 135                 140

Phe Lys Gly Lys Gly Ala Asp Ala Ile Leu Gly Pro Val Tyr Gly Pro
145                 150                 155                 160

Met Gly Val Lys Ala Ala Gly Arg Gly Trp Glu Gly His Gly Pro
                165                 170                 175

Asp Pro Tyr Leu Glu Gly Val Ile Ala Tyr Leu Gln Thr Ile Gly Ile
            180                 185                 190

Gln Ser Gln Gly Val Val Ser Thr Ala Lys His Leu Ile Gly Asn Glu
    195                 200                 205

Gln Glu His Phe Arg Phe Ala Lys Lys Asp Lys His Ala Gly Lys Ile
    210                 215                 220

Asp Pro Gly Met Phe Asn Thr Ser Ser Ser Leu Ser Ser Glu Ile Asp
225                 230                 235                 240

Asp Arg Ala Met His Glu Ile Tyr Leu Trp Pro Phe Ala Glu Ala Val
            245                 250                 255

Arg Gly Gly Val Ser Ser Ile Met Cys Ser Tyr Asn Lys Leu Asn Gly
            260                 265                 270

Ser His Ala Cys Gln Asn Ser Tyr Leu Leu Asn Tyr Leu Leu Lys Glu
    275                 280                 285

Glu Leu Gly Phe Gln Gly Phe Val Met Thr Asp Trp Gly Ala Leu Tyr
    290                 295                 300

Ser Gly Ile Asp Ala Ala Asn Ala Gly Leu Asp Met Asp Met Pro Cys
305                 310                 315                 320

Glu Ala Gln Tyr Phe Gly Gly Asn Leu Thr Thr Ala Val Leu Asn Gly
            325                 330                 335

Thr Leu Pro Gln Asp Arg Leu Asp Asp Met Ala Thr Arg Ile Leu Ser
            340                 345                 350

Ala Leu Ile Tyr Ser Gly Val His Asn Pro Asp Gly Pro Asn Tyr Asn
            355                 360                 365

Ala Gln Thr Phe Leu Thr Glu Gly His Glu Tyr Phe Lys Gln Gln Glu
    370                 375                 380

Gly Asp Ile Val Val Leu Asn Lys His Val Asp Val Arg Ser Asp Ile
385                 390                 395                 400

Asn Arg Ala Val Ala Leu Arg Ser Ala Val Glu Gly Val Val Leu Leu
            405                 410                 415

Lys Asn Glu His Glu Thr Leu Pro Leu Gly Arg Glu Lys Val Lys Arg
```

```
                420             425             430
Ile Ser Ile Leu Gly Gln Ala Ala Gly Asp Asp Ser Lys Gly Thr Ser
            435             440             445
Cys Ser Leu Arg Gly Cys Gly Ser Gly Ala Ile Gly Thr Gly Tyr Gly
450             455             460
Ser Gly Ala Gly Thr Phe Ser Tyr Phe Val Thr Pro Ala Asp Gly Ile
465             470             475             480
Gly Ala Arg Ala Gln Gln Glu Lys Ile Ser Tyr Glu Phe Ile Gly Asp
                485             490             495
Ser Trp Asn Gln Ala Ala Met Asp Ser Ala Leu Tyr Ala Asp Ala
            500             505             510
Ala Ile Glu Val Ala Asn Ser Val Ala Gly Glu Ile Gly Asp Val
            515             520             525
Asp Gly Asn Tyr Gly Asp Leu Asn Asn Leu Thr Leu Trp His Asn Ala
            530             535             540
Val Pro Leu Ile Lys Asn Ile Ser Ser Ile Asn Asn Thr Ile Val
545             550             555             560
Ile Val Thr Ser Gly Gln Gln Ile Asp Leu Glu Pro Phe Ile Asp Asn
                565             570             575
Glu Asn Val Thr Ala Val Ile Tyr Ser Ser Tyr Leu Gly Gln Asp Phe
            580             585             590
Gly Thr Val Leu Ala Lys Val Leu Phe Gly Asp Glu Asn Pro Ser Gly
            595             600             605
Lys Leu Pro Phe Thr Ile Ala Lys Asp Val Asn Asp Tyr Ile Pro Val
            610             615             620
Ile Glu Lys Val Asp Val Pro Asp Pro Val Asp Lys Phe Thr Glu Ser
625             630             635             640
Ile Tyr Val Asp Tyr Arg Tyr Phe Asp Lys Tyr Asn Lys Pro Val Arg
                645             650             655
Tyr Glu Phe Gly Tyr Gly Leu Ser Tyr Ser Asn Phe Ser Leu Ser Asp
                660             665             670
Ile Glu Ile Gln Thr Leu Gln Pro Phe Ser Glu Asn Ala Glu Pro Ala
            675             680             685
Ala Asn Tyr Ser Glu Thr Tyr Gln Tyr Lys Gln Ser Asn Met Asp Pro
            690             695             700
Ser Glu Tyr Thr Val Pro Glu Gly Phe Lys Glu Leu Ala Asn Tyr Thr
705             710             715             720
Tyr Pro Tyr Ile His Asp Ala Ser Ser Ile Lys Ala Asn Ser Ser Tyr
                725             730             735
Asp Tyr Pro Glu Gly Tyr Ser Thr Glu Gln Leu Asp Gly Pro Lys Ser
            740             745             750
Leu Ala Ala Gly Gly Leu Gly Gly Asn His Thr Cys Gly Met Leu Val
            755             760             765
Thr Leu Ser Leu Leu Lys Ser Gln Ile Lys Val Leu Met Leu Val Gly
            770             775             780
Leu His Leu Asn Cys Met Leu Asp Ile Gln Ile Met Met Asn Ser Gln
785             790             795             800
His Leu Gln Cys Asn Tyr Val Asp Leu Lys Arg Cys Phe Trp Ile Lys
                805             810             815
Ile Ile Leu Lys Leu Phe Leu Leu Asn
            820             825

<210> SEQ ID NO 11
```

```
<211> LENGTH: 649
<212> TYPE: PRT
<213> ORGANISM: Azospirillum irakense KBC1

<400> SEQUENCE: 11

Met Arg Arg Leu Pro His Leu Ser Leu Leu Ala Leu Met Leu Tyr Ser
1               5                   10                  15

Gly Thr Ala Leu Ala Ala Pro Gln Gln Pro Ala Leu Pro Glu Gly Gln
            20                  25                  30

Pro Leu Leu Thr Val Glu Gly Leu Ser Phe Arg Asp Leu Asn Arg Asp
        35                  40                  45

Gly Thr Leu Asn Pro Tyr Glu Asp Trp Arg Leu Ser Pro Glu Val Arg
50                  55                  60

Ala Ala Asp Leu Val Ala Arg Met Thr Leu Ala Glu Lys Ala Gly Ala
65                  70                  75                  80

Gly Val His Gly Thr Ala Pro Ile Gln Gly Gly Pro Met Ala Ser Gly
                85                  90                  95

Pro Ala Tyr Asp Met Thr Ala Ala Gln Ala Ile Ile Arg Asp Gln His
            100                 105                 110

Leu Asn Ser Leu Ile Thr Arg Met Ala Ile Ala Pro Ala Asp Phe Ala
        115                 120                 125

Ala Glu Asn Asn Arg Leu Gln Gly Ile Ala Ala Gly Thr Arg Leu Gly
130                 135                 140

Ile Pro Leu Thr Ile Ser Thr Asp Pro Arg Asn His Phe Gln Val Leu
145                 150                 155                 160

Gly Gly Ala Ser Val Ala Ala Ser Gly Phe Ser Gln Trp Pro Glu Thr
                165                 170                 175

Leu Gly Phe Gly Ala Leu Asn Asp Pro Ala Leu Thr Arg Arg Phe Ala
            180                 185                 190

Asp Leu Val Arg Ala Glu Tyr Arg Ala Val Gly Ile Gln Met Ala Leu
        195                 200                 205

Ser Pro Gln Ala Asp Leu Ala Thr Glu Pro Arg Trp Ser Arg Ile Asn
210                 215                 220

Gly Thr Phe Gly Glu Asp Pro Ala Arg Val Ser Ala Gln Val Lys Ala
225                 230                 235                 240

Tyr Val Gln Gly Met Gln Gly Ala Asp Thr Gly Leu Ala Pro Gly Gly
                245                 250                 255

Val Ala Thr Val Val Lys His Trp Val Gly Tyr Gly Ala Gln Ile Asp
            260                 265                 270

Gly Tyr Asp Gly His Asn Tyr Tyr Gly Arg Phe Thr Asp Phe Thr Lys
        275                 280                 285

Gly Gly Phe Asp Arg His Val Ala Ala Phe Gln Gly Ala Phe Glu Ala
290                 295                 300

Gly Ala Thr Gly Ile Met Pro Thr Tyr Thr Ile Gln Lys Gly Leu Ser
305                 310                 315                 320

Leu Glu Gly Lys Pro Val Glu Pro Val Ser Gly Tyr Asn Lys Gln
                325                 330                 335

Met Leu Ile Asp Leu Leu Arg Gly Thr His Lys Phe Lys Gly Leu Ile
            340                 345                 350

Leu Ser Asp Trp Ala Ile Thr Asn Asp Cys Asn Glu Ser Cys Arg Thr
        355                 360                 365

Gly Asn Pro Pro Gln Gln Pro Lys Asp Ile Ala Thr Pro Trp Gly Val
370                 375                 380

Glu Asp Leu Thr Gln Pro Gln Arg Phe Ala Lys Gly Met Leu Ala Gly
```

```
            385                 390                 395                 400
        Ile Asp Gln Phe Gly Gly Val Asn Asp Gly Leu Pro Leu Leu Ala Ala
                        405                 410                 415
        Val Glu Gln Lys Leu Pro Glu Ala Arg Leu Asn Glu Ala Val Ala
                        420                 425                 430
        Thr Ile Met Thr Leu Lys Phe Glu Gln Gly Leu Phe Glu Asn Pro Phe
                        435                 440                 445
        Val Asp Pro Ala Ala Ala Thr Ile Val Gly Arg Ala Asp Val Val
            450                 455                 460
        Ala Glu Gly Arg Ala Thr Gln Ala Lys Ser Leu Val Met Leu Glu Asn
        465                 470                 475                 480
        Arg Leu Gly Pro Ala Pro Leu Pro Ala Gly Gly Lys Arg Leu Phe
                        485                 490                 495
        Ile Tyr Gly Val Asp Ala Ala Asn Ala Lys Ala Ala Gly Phe Thr Ile
                        500                 505                 510
        Ala Ala Ser Leu Asp Glu Ala Asp Ile Ala Leu Ile Arg Leu Lys Ala
                        515                 520                 525
        Pro Phe Gln Thr Leu His Pro Gly Phe Phe Gly Arg Met Gln His
            530                 535                 540
        Glu Gly Asp Leu Asp Phe Lys Glu Gly Asp Ala Gly Leu Thr Leu Val
        545                 550                 555                 560
        Arg Gln Ala Ala Ala Lys Val Pro Val Ile Leu Thr Ile Tyr Leu Asp
                        565                 570                 575
        Arg Pro Ala Ile Leu Thr Asn Ile Lys Pro His Ala Ala Thr Leu Ile
                        580                 585                 590
        Gly Glu Phe Gly Ile Thr Asp Ala Ala Leu Phe Asp Ala Leu Thr Gly
                        595                 600                 605
        Lys Val Ala Pro Met Gly Lys Leu Pro Phe Glu Leu Pro Ala Thr Met
                        610                 615                 620
        Ala Ala Val Arg Ala Gln Ser Pro Ala Leu Pro His Asp Ser Ala Asp
        625                 630                 635                 640
        Pro Leu Tyr Pro Val Gly Phe Gly Arg
                        645

<210> SEQ ID NO 12
<211> LENGTH: 732
<212> TYPE: PRT
<213> ORGANISM: Azospirillum irakense KBC1

<400> SEQUENCE: 12

Met Lys Val His Gln Leu Phe Lys Ala Ala Leu Ala Thr Ser Leu Cys
        1               5                   10                  15
        Leu Thr Ala Phe Ala Gly Gly Ala Met Ala Gln Ala Lys Gly Ala Trp
                        20                  25                  30
        Gln Asn Thr Ser Leu Ser Pro Asp Glu Arg Ala Arg Leu Leu Asp Ala
                        35                  40                  45
        Glu Leu Thr Leu Asp Glu Arg Ile Ser Leu Leu His Gly Pro Met Pro
            50                  55                  60
        Leu Pro Phe Pro Gly Ser Pro Ile Pro Glu Gly Pro Ser Leu Val
        65                  70                  75                  80
        Pro Val Ile Phe Pro Gly Val Pro Arg Leu Gly Ile Pro Ala Leu Lys
                        85                  90                  95
        Glu Thr Asp Ala Ser Leu Gly Val Thr Asn Pro Met Asn Val Arg Pro
                        100                 105                 110
```

```
Gly Asp Thr Ala Thr Ala Leu Pro Ser Gly Leu Ala Leu Ala Ser Thr
            115                 120                 125

Phe Asn Pro Lys Leu Ser Tyr Asp Gly Gly Ala Ala Ile Ala Lys Glu
    130                 135                 140

Ala Ala Ser Lys Gly Phe Asn Val Leu Leu Ala Gly Gly Ala Asn Leu
145                 150                 155                 160

Ala Arg Asp Pro Arg Asn Gly Arg Asn Phe Glu Tyr Leu Gly Glu Asp
                165                 170                 175

Pro Leu Leu Ala Gly Ile Leu Ala Gly Glu Ser Ile Arg Gly Ile Gln
                180                 185                 190

Ser Gln Asn Ile Ile Ser Thr Val Lys His Phe Ser Leu Asn Gly Gln
            195                 200                 205

Glu Thr Asn Arg His Trp Gly Asn Ser Val Ile Asp Glu Ala Ala His
    210                 215                 220

Arg Glu Ser Asp Leu Leu Ala Phe Gln Ile Ala Ile Glu Arg Gly Gln
225                 230                 235                 240

Pro Gly Ser Val Met Cys Ala Tyr Asn Leu Val Asn Gly Ala Tyr Ser
                245                 250                 255

Cys Gly Asn Asp His Leu Leu Asn Lys Val Leu Lys Gly Asp Trp Gly
                260                 265                 270

Tyr Lys Gly Trp Val Met Ser Asp Trp Gly Ala Val Pro Ala Thr Asp
    275                 280                 285

Phe Ala Leu Lys Gly Leu Asp Gln Gln Ser Gly Gln Gln Leu Asp Glu
    290                 295                 300

Lys Ile Trp Phe Gly Asp Leu Leu Lys Glu Ala Ala Ala Gly Thr
305                 310                 315                 320

Ile Pro Ala Glu Arg Leu Ser Asp Met Ser Arg Arg Ile Leu Arg Ser
                325                 330                 335

Met Phe Ala Ala Gly Phe Phe Asp Gly Lys Pro Gly Lys Pro Val Val
                340                 345                 350

Asp Leu Asp Ala His Ala Ala Ile Ala Lys Gln Val Ala Asp Glu Gly
                355                 360                 365

Ile Val Leu Leu Ala Asn Asp Lys Gly Leu Leu Pro Leu Ala Ala Gly
    370                 375                 380

Ser Gln Lys Ile Ala Val Ile Gly Gly Phe Ala Asp Gln Gly Val Leu
385                 390                 395                 400

Ser Gly Ala Gly Ser Ser Gln Val Thr Ser Val Gly Gly Asn Pro Val
                405                 410                 415

Val Ile Pro Val Gly Gly Glu Gly Met Leu Ala Ala Phe Leu Arg Gln
                420                 425                 430

Ala Tyr His Asn Ser Ser Pro Leu Lys Ala Leu Lys Glu Arg Leu Pro
    435                 440                 445

Asn Ala Thr Ile Arg Phe Asn Asp Gly Arg Tyr Ser Ala Ala Ala Ala
    450                 455                 460

Ala Leu Ala Arg Gln Ser Asp Ile Val Ile Leu Phe Ala Asn Gln Trp
465                 470                 475                 480

Met Ser Glu Gly Met Asp Ala Tyr Asp Leu Lys Leu Pro Gln Gly Gln
                485                 490                 495

Asp Ala Leu Ile Glu Ala Val Ala Glu Ala Asn Pro Asn Ala Val Ile
                500                 505                 510

Val Leu Gln Thr Gly Gly Pro Val Leu Met Pro Trp Lys Asp Lys Val
    515                 520                 525

Gly Ala Ile Val Ser Ala Trp Tyr Ser Gly Gln Lys Gly Gly Glu Ala
```

```
            530             535             540
Ile Ala Asp Ile Leu Val Gly Lys Thr Asn Pro Ser Gly Arg Leu Pro
545                 550                 555                 560

Ser Thr Phe Pro Ala Ser Ala Asp Gln Tyr Pro His Pro Glu Val Pro
                565                 570                 575

Gly Trp Asn Leu Pro Glu Lys Gln Gln Phe Asp Val Val Tyr Glu Glu
                580                 585                 590

Gly Ser Asp Val Gly Tyr Arg Arg Phe Ala Ala Lys Gly Met Lys Pro
                595                 600                 605

Leu Phe Pro Phe Gly His Gly Leu Ser Tyr Thr Thr Phe Ala Tyr Asp
                610                 615                 620

Lys Leu Lys Val Lys Gly Glu Thr Leu Glu Val Ser Phe Gln Val
625                 630                 635                 640

Thr Asn Thr Gly Lys Leu Gln Gly Lys Asp Ala Pro Gln Ile Tyr Leu
                645                 650                 655

Ala Gly Ala Asn Gly Gln Lys Leu Gln Arg Leu Ile Gly Phe Glu Lys
                660                 665                 670

Ile Asp Leu Lys Pro Gly Glu Arg Arg Thr Val Thr Ile Lys Ala Asp
                675                 680                 685

Pro Arg Leu Leu Ala Arg Phe Asp Glu Gln Gly His Gln Trp Arg Ile
                690                 695                 700

Asp Gly Gly Asp Tyr Asp Val Val Val Gly Arg Ser Ala Thr Met Thr
705                 710                 715                 720

Val Leu Ser Gly Lys Ala Ala Ser Ala Ser Val Pro
                725                 730

<210> SEQ ID NO 13
<211> LENGTH: 828
<212> TYPE: PRT
<213> ORGANISM: Cellulomonas biazotea

<400> SEQUENCE: 13

Met Thr Ser Gln Thr Ala Leu Asp Pro Ala Ala Leu Val Ala Ser Leu
1               5                   10                  15

Pro Leu Glu Thr Lys Val Arg Leu Leu Thr Gly Ala Thr Ala Phe Thr
                20                  25                  30

Leu Ala Pro Glu Glu Ser Ile Gly Leu Gly Glu Val Arg Leu Ser Asp
                35                  40                  45

Gly Pro Thr Gly Val Arg Gly Leu Lys Phe Ser Gly Gly Arg Thr Val
            50                  55                  60

Ala Leu Phe Pro Asn Ala Thr Leu Leu Ala Ser Ala Trp Ser Glu Glu
65                  70                  75                  80

Ser Thr Thr Glu Val Gly Arg Leu Leu Ala Glu Glu Ala Leu Ala Gln
                85                  90                  95

Gln Ile His Val Val Leu Gly Pro Thr Ile Asn Leu His Arg Ser Val
                100                 105                 110

Leu Gly Gly Arg Leu Phe Glu Ala Tyr Ser Glu Asp Pro Leu Leu Thr
                115                 120                 125

Gly Arg Leu Ala Ala Ala Tyr Val Arg Gly Leu Gln Asp Leu Gly Val
            130                 135                 140

Gly Ala Cys Leu Lys His Leu Val Ala Asn Glu Ser Glu Thr Glu Arg
145                 150                 155                 160

Asn Thr Met Asn Ser Val Val Asp Pro Ala Thr Leu Arg Glu Leu Tyr
                165                 170                 175
```

```
Leu Leu Pro Phe Glu Ile Ala Val Asp Glu Ser Asp Pro Trp Ser Val
            180                 185                 190

Met Ala Ala Tyr Asn Asp Val Asn Gly Val Pro Ala Thr Glu His His
        195                 200                 205

His Val Val Asn Glu Val Leu Lys Gly Glu Trp Gly Tyr Thr Gly Leu
    210                 215                 220

Val Met Ser Asp Trp Phe Ala Thr Arg Thr Ala Ala Pro Ala Ala Ala
225                 230                 235                 240

Gly Gly Leu Asp Leu Val Met Pro Gly Pro Asp Gly Pro Trp Gly Asp
                245                 250                 255

Ala Leu Val Ala Ala Val Arg Ser Gly Glu Leu Asp Glu Ser Val Val
            260                 265                 270

Asp Asp His Leu Arg Arg Leu Leu Val Leu Ala Ala Arg Val Gly Ala
        275                 280                 285

Leu Gly Asp Leu Arg Asp Tyr Pro Asp Asp Leu Pro Ala Pro Asp Ser
    290                 295                 300

Ala Val Arg Arg Glu Gln Leu Thr Arg Leu Ala Ala Gly Met Thr
305                 310                 315                 320

Val Leu Thr Asn Ala Asp Asp Thr Leu Pro Leu Ala Arg Gly Thr Arg
                325                 330                 335

Val Ala Leu Val Gly Arg His Ala Leu Glu Thr Ile Asp Met Gly Gly
            340                 345                 350

Gly Ser Ala Thr Val Asn Pro Pro Tyr Gln Val Ser Val Ala Glu Gly
        355                 360                 365

Leu Thr Ala Leu Leu Gly Asp Ala Val Asp Val Val Asp Gly Val Glu
    370                 375                 380

Val Arg Thr Arg Pro Val Pro Ala Arg Pro Gly Phe Val Val Asp Pro
385                 390                 395                 400

Asp Thr Gly Arg Pro Gly Leu His Leu Thr Leu Leu Ala Ala Asp Gly
                405                 410                 415

Thr Val Leu Asp Glu Arg His Asp Ala Pro Ser Thr Val Met Val Gly
            420                 425                 430

Phe Asp Asp Asp Phe Pro Gln Ala Val Ala Arg Val Arg Phe Arg Ala
        435                 440                 445

Arg Val Ala Gly Glu Gly Ala Leu Glu Val Gly Ala Ile Gly Val Gly
    450                 455                 460

Arg Trp Gln Val Thr Ala Gly Gly Thr Glu Leu Ala Trp Thr Leu Ala
465                 470                 475                 480

Thr Ser Gly Thr Gly Phe Ala Glu Glu Met Leu Ala Pro Pro Thr Arg
                485                 490                 495

Thr Asp Gln Val His Val Gly Ser Asp Ala Val Val Asp Ala Thr Val
            500                 505                 510

Val Leu Arg Ser Ser Thr Arg Ser Val Thr Val Gly Asp Ala Asp Pro
        515                 520                 525

Gly Thr Asp Ala Gly Ala Ala Glu Pro Leu Ala Gly Val Gly Leu
    530                 535                 540

Phe Gly Leu Val Ala Arg Pro Ala Pro Glu Ala Glu Asp Val Ile
545                 550                 555                 560

Thr Arg Ala Ala Ala Ala Ala Gln Ala Asp Val Ala Val Val
                565                 570                 575

Val Gly Leu Thr Glu Glu Glu Thr Glu Ser Val Asp Lys Ser Thr
            580                 585                 590

Ile Ala Leu Pro Gly Ala Gln Asp Ala Leu Val Arg Ala Val Ala Ala
```

```
                      595                 600                 605
Ala Ala Arg Arg Thr Val Val Val Asn Ala Ala Thr Pro Val Leu
    610                 615                 620
Met Pro Trp Leu Asp Asp Val Asp Ala Val Leu Trp Ala Gly Leu Pro
625                 630                 635                 640
Gly Gln Glu Gly Gly His Ala Val Ala Ala Leu Leu Gly Asp Gln
                    645                 650                 655
Glu Pro Thr Gly Arg Leu Val Thr Thr Phe Pro Ala Ala Asp Gly Ala
                660                 665                 670
Ala Pro Ala Trp Ser Val Thr Pro Val Asp Gly Asp Leu Glu Tyr Thr
            675                 680                 685
Glu Gly Arg Phe Val Gly Tyr Arg Gly His Trp Ala Asp Arg Ala Pro
        690                 695                 700
Ala Pro Ala Phe Trp Leu Gly His Gly Leu Gly Tyr Ala Thr Trp Glu
705                 710                 715                 720
Tyr Ala Asp Ala Thr Leu Asp Thr Asp Gly Asp Ala Pro Ala Val Thr
                    725                 730                 735
Val Thr Val Thr Asn Thr Gly Ala Arg Thr Ser Arg Glu Val Val Gln
                740                 745                 750
Val Tyr Leu Glu Pro Ala Ser Ser Asp Glu Pro Val Arg Leu Val Gly
            755                 760                 765
Trp Ala Asp Ala Thr Val Asp Ala Gly Ala Ser Ala Arg Val Thr Val
        770                 775                 780
Thr Ala Asp Ala Arg Met Trp Arg Arg Trp Asp Glu Ala Ala Gly Gly
785                 790                 795                 800
Trp Ser Arg Leu Ala Asp Gly Gly Arg Leu Leu Val Ala Arg Gly Leu
                    805                 810                 815
Gly Asp Val Arg Ala Thr Leu Ala Leu Pro Thr Ala
                820                 825

<210> SEQ ID NO 14
<211> LENGTH: 726
<212> TYPE: PRT
<213> ORGANISM: Elizabethkingia meningoseptica

<400> SEQUENCE: 14

Met Thr Leu Asp Glu Lys Ile Gly Gln Leu Asn Leu Pro Ser Ser Gly
1               5                   10                  15
Asp Phe Thr Thr Gly Gln Ala Gln Ser Ser Asp Ile Gly Lys Lys Ile
                20                  25                  30
Glu Gln Gly Leu Val Gly Gly Leu Phe Asn Ile Lys Gly Val Asn Lys
            35                  40                  45
Ile Lys Ala Val Gln Lys Val Ala Ile Glu Lys Ser Arg Leu Lys Ile
        50                  55                  60
Pro Met Ile Phe Gly Met Asp Val Ile His Gly Tyr Glu Thr Thr Phe
65                  70                  75                  80
Pro Ile Pro Leu Gly Leu Ala Ser Ser Trp Asp Met Asp Leu Ile Gln
                85                  90                  95
Arg Ser Ala Gln Ile Ala Ala Lys Glu Ala Ser Ala Asp Gly Ile Asn
                100                 105                 110
Trp Thr Phe Ser Pro Met Val Asp Val Ser Arg Glu Pro Arg Trp Gly
            115                 120                 125
Arg Val Ser Glu Gly Ser Gly Glu Asp Pro Tyr Leu Gly Ser Glu Ile
        130                 135                 140
```

```
Ala Lys Ala Met Val Tyr Gly Tyr Gln Gly Lys Asp Leu Ser Leu Lys
145                 150                 155                 160

Asn Thr Ile Leu Ala Cys Val Lys His Phe Ala Leu Tyr Gly Ala Pro
            165                 170                 175

Glu Gly Gly Arg Asp Tyr Asn Thr Val Asp Met Ser His Ile Arg Met
        180                 185                 190

Phe Asn Glu Tyr Phe Pro Pro Tyr Lys Ala Ala Val Asp Ala Gly Val
    195                 200                 205

Gly Ser Val Met Ala Ser Phe Asn Glu Val Asp Gly Val Pro Ala Thr
210                 215                 220

Gly Asn Lys Trp Leu Met Asp Asp Val Leu Arg Lys Gln Trp Gly Phe
225                 230                 235                 240

Asn Gly Phe Ile Val Thr Asp Tyr Thr Gly Ile Asn Glu Met Ile Gln
                245                 250                 255

His Gly Met Gly Asp Leu Gln Gln Val Ser Ala Leu Ala Leu Asn Ala
            260                 265                 270

Gly Val Asp Met Asp Met Val Gly Glu Gly Phe Leu Thr Thr Leu Lys
            275                 280                 285

Lys Ser Leu Ser Glu Gly Lys Val Thr Glu Gln Ile Thr Leu Ala
290                 295                 300

Ala Arg Arg Ile Leu Glu Ala Lys Tyr Asp Leu Gly Leu Phe Asp Asp
305                 310                 315                 320

Pro Tyr Arg Tyr Thr Asp Glu Lys Arg Ala Lys Ala Glu Val Phe Ser
                325                 330                 335

Lys Pro His Arg Glu Glu Ala Arg Asn Ile Ala Ala Gln Ser Met Val
            340                 345                 350

Leu Leu Lys Asn Asp Lys Gln Thr Leu Pro Leu Lys Ala Gly Gly Thr
            355                 360                 365

Val Ala Val Ile Gly Pro Leu Ala Asn Asn Asn Glu Asn Met Thr Gly
            370                 375                 380

Thr Trp Ser Val Ala Ser Arg Met Lys Asp Ala Val Ser Ile Met Thr
385                 390                 395                 400

Gly Leu Lys Glu Thr Val Lys Gly Val Asn Phe Ile Tyr Ala Lys Gly
                405                 410                 415

Ser Asn Val Phe Tyr Asp Ala Lys Met Glu Glu Lys Ala Thr Met Phe
            420                 425                 430

Gly Lys Thr Ala Asn Arg Asp Ser Arg Ser Lys Glu Glu Leu Leu Lys
            435                 440                 445

Glu Ala Val Ala Thr Ala Asn Lys Ala Asp Val Val Leu Ala Ile
450                 455                 460

Gly Glu Thr Ala Glu Leu Ser Gly Glu Ser Ser Arg Ala Asn Ile
465                 470                 475                 480

Glu Ile Pro Gln Ala Gln Lys Asp Leu Leu Thr Glu Leu Lys Lys Thr
            485                 490                 495

Gly Lys Pro Ile Val Met Val Leu Phe Thr Gly Arg Pro Leu Val Leu
            500                 505                 510

Asn Asp Glu Asn Lys Gln Ala Asp Ala Ile Val Asn Ala Trp Phe Ala
            515                 520                 525

Gly Ser Glu Ala Gly Tyr Ala Ile Ala Asp Val Leu Tyr Gly Lys Val
            530                 535                 540

Asn Pro Ser Gly Lys Leu Pro Met Thr Phe Pro Arg Ser Val Gly Gln
545                 550                 555                 560

Val Pro Ile Tyr Tyr Asn Ala Lys Asn Thr Gly Arg Pro Leu Ser Asp
```

```
                    565                 570                 575

Glu Arg Ser Asp Lys Cys Glu Phe Glu Lys Phe Arg Ser Asn Tyr Ile
                580                 585                 590

Asp Glu Cys Asn Thr Pro Leu Phe Pro Phe Gly Tyr Gly Leu Ser Tyr
                595                 600                 605

Thr Thr Phe Asn Tyr Ser Asp Ile Gln Leu Asn Lys Thr Gln Leu Ser
                610                 615                 620

Gly Asn Asp Gln Leu Thr Ala Ser Val Thr Leu Thr Asn Asn Gly Lys
625                 630                 635                 640

Tyr Asp Gly Asn Glu Val Val Gln Leu Tyr Ile Arg Asp Met Val Gly
                645                 650                 655

Ser Val Thr Arg Pro Val Lys Glu Leu Lys Gly Phe Gln Lys Val Phe
                660                 665                 670

Leu Lys Ala Gly Glu Ser Lys Ile Val Thr Phe Asn Ile Thr Pro Glu
                675                 680                 685

Asp Leu Lys Phe Tyr Asn Ser Ala Leu Lys Tyr Asp Trp Glu Pro Gly
                690                 695                 700

Glu Phe Asp Ile Met Ile Gly Thr Asn Ser His Asp Val Lys His Ala
705                 710                 715                 720

Lys Ile Asn Trp Asn Lys
                725

<210> SEQ ID NO 15
<211> LENGTH: 654
<212> TYPE: PRT
<213> ORGANISM: Erwinia chrysanthemi D1

<400> SEQUENCE: 15

Met Glu Lys Ser Ala Thr Arg Gln Lys Ala Leu Leu Ile Ala Leu Pro
1               5                   10                  15

Leu Leu Phe Ser Pro Leu Ala Ser Ala Val Gln Gln Ala Val Leu Asp
                20                  25                  30

Thr Arg Gly Ala Pro Leu Ile Thr Val Asn Gly Leu Thr Phe Lys Asp
            35                  40                  45

Leu Asn Arg Asp Gly Lys Leu Asn Pro Tyr Glu Asp Trp Arg Leu Pro
        50                  55                  60

Ala Ala Glu Arg Ala Ala Asp Leu Val Ser Arg Met Thr Leu Ala Glu
65                  70                  75                  80

Lys Ala Gly Val Met Met His Gly Ser Ala Pro Thr Ala Gly Ser Val
                85                  90                  95

Thr Gly Ala Gly Thr Gln Tyr Asp Leu Asn Ala Ala Lys Thr Met Ile
            100                 105                 110

Ala Asp Arg Tyr Val Asn Ser Phe Ile Thr Arg Leu Ser Gly Asp Asn
        115                 120                 125

Pro Ala Gln Met Ala Glu Glu Asn Asn Lys Leu Gln Gln Leu Ala Glu
    130                 135                 140

Ala Thr Arg Leu Gly Ile Pro Leu Thr Ile Ser Thr Asp Pro Arg Ser
145                 150                 155                 160

Ser Phe Gln Ser Leu Val Gly Val Ser Val Ser Val Gly Lys Phe Ser
                165                 170                 175

Lys Trp Pro Glu Thr Leu Gly Leu Ala Ala Ile Gly Asp Glu Glu Leu
            180                 185                 190

Val Arg Arg Phe Ala Asp Ile Val Arg Gln Glu Tyr Arg Ala Val Gly
        195                 200                 205
```

```
Ile Thr Glu Ala Leu Ser Pro Gln Ala Asp Leu Ala Thr Glu Pro Arg
    210                 215                 220

Trp Pro Arg Ile Asp Gly Thr Phe Gly Glu Asp Pro Asp Leu Thr Lys
225                 230                 235                 240

Lys Met Val Arg Gly Tyr Val Thr Gly Met Gln Asn Gly Lys Asn Gly
                245                 250                 255

Leu Asn Ala Gln Ser Val Ile Ser Ile Val Lys His Trp Val Gly Tyr
            260                 265                 270

Gly Ala Ala Lys Asp Gly Trp Asp Ser His Asn Val Tyr Gly Lys Tyr
                275                 280                 285

Ala Gln Phe Arg Gln Asn Asn Leu Gln Trp His Ile Asp Pro Phe Thr
290                 295                 300

Gly Ala Phe Glu Ala His Ala Ala Gly Ile Met Pro Thr Tyr Ser Ile
305                 310                 315                 320

Leu Arg Asn Ala Ser Trp His Gly Lys Pro Ile Glu Gln Val Gly Ala
                325                 330                 335

Gly Phe Asn Arg Phe Leu Leu Thr Asp Leu Leu Arg Gly Gln Tyr Gly
                340                 345                 350

Phe Asp Gly Val Ile Leu Ser Asp Trp Leu Ile Thr Asn Asp Cys Lys
                355                 360                 365

Gly Asp Cys Leu Thr Gly Val Lys Pro Gly Glu Lys Pro Val Pro Arg
370                 375                 380

Gly Met Pro Trp Gly Val Glu Lys Leu Thr Pro Ala Glu Arg Phe Val
385                 390                 395                 400

Lys Ala Val Asn Ala Gly Val Asp Gln Phe Gly Gly Val Thr Asp Ser
                405                 410                 415

Ala Leu Leu Val Gln Ala Val Gln Asp Gly Lys Leu Thr Glu Ala Arg
                420                 425                 430

Leu Asp Thr Ser Val Asn Arg Ile Leu Lys Gln Lys Phe Gln Thr Gly
            435                 440                 445

Leu Phe Glu Arg Pro Tyr Val Asn Ala Thr Gln Ala Asn Asp Ile Val
450                 455                 460

Gly Arg Ala Asp Trp Gln Gln Leu Ala Asp Asp Thr Gln Ala Arg Ser
465                 470                 475                 480

Leu Val Leu Leu Gln Asn Asn Asn Leu Leu Pro Leu Arg Lys Gly Ser
                485                 490                 495

Arg Val Trp Leu His Gly Ile Ala Ala Asn Ala Ala Gln Glu Val Gly
                500                 505                 510

Phe Ile Val Val Asn Thr Pro Glu Gln Ala Asp Val Ala Leu Ile Arg
                515                 520                 525

Thr His Thr Pro Tyr Glu Gln Pro His Lys Asn Phe Phe Gly Ser
            530                 535                 540

Arg His His Glu Gly Ser Leu Ala Phe Arg Asn Asp Asn Pro Asp Tyr
545                 550                 555                 560

Gln Ala Ile Val Arg Ala Ser Ala Lys Val Pro Thr Leu Val Thr Val
                565                 570                 575

Tyr Met Glu Arg Pro Ala Ile Leu Thr Asn Val Val Asp Lys Thr Arg
                580                 585                 590

Ala Val Val Ala Asn Phe Gly Val Ser Asp Ser Val Leu Leu Asn Arg
                595                 600                 605

Leu Met Ser Gly Ala Ala Tyr Thr Ala Lys Leu Pro Phe Glu Leu Pro
610                 615                 620

Ser Ser Met Ser Ala Val Arg Asn Gln Gln Pro Asp Leu Pro Tyr Asp
```

Ser Ala Lys Pro Leu Phe Pro Phe Gly Tyr Gly Leu Pro His
       625                 630                 635                 640
                    645                 650

<210> SEQ ID NO 16
<211> LENGTH: 789
<212> TYPE: PRT
<213> ORGANISM: Escherichia coli K-12 MG1655

<400> SEQUENCE: 16

Met Leu Met Ala Asn Tyr Gly Phe Cys Thr Ile Phe Ala Ala Thr Ser
1               5                   10                  15

Gly Asn Lys Gly Arg Lys Ile His Met Lys Trp Leu Cys Ser Val Gly
            20                  25                  30

Ile Ala Val Ser Leu Ala Leu Gln Pro Ala Leu Ala Asp Asp Leu Phe
        35                  40                  45

Gly Asn His Pro Leu Thr Pro Glu Ala Arg Asp Ala Phe Val Thr Glu
    50                  55                  60

Leu Leu Lys Lys Met Thr Val Asp Glu Lys Ile Gly Gln Leu Arg Leu
65                  70                  75                  80

Ile Ser Val Gly Pro Asp Asn Pro Lys Glu Ala Ile Arg Glu Met Ile
                85                  90                  95

Lys Asp Gly Gln Val Gly Ala Ile Phe Asn Thr Val Thr Arg Gln Asp
            100                 105                 110

Ile Arg Ala Met Gln Asp Gln Val Met Glu Leu Ser Arg Leu Lys Ile
        115                 120                 125

Pro Leu Phe Phe Ala Tyr Asp Val Leu His Gly Gln Arg Thr Val Phe
    130                 135                 140

Pro Ile Ser Leu Gly Leu Ala Ser Ser Phe Asn Leu Asp Ala Val Lys
145                 150                 155                 160

Thr Val Gly Arg Val Ser Ala Tyr Glu Ala Ala Asp Asp Gly Leu Asn
                165                 170                 175

Met Thr Trp Ala Pro Met Val Asp Val Ser Arg Asp Pro Arg Trp Gly
            180                 185                 190

Arg Ala Ser Glu Gly Phe Gly Glu Asp Thr Tyr Leu Thr Ser Thr Met
        195                 200                 205

Gly Lys Thr Met Val Glu Ala Met Gln Gly Lys Ser Pro Ala Asp Arg
    210                 215                 220

Tyr Ser Val Met Thr Ser Val Lys His Phe Ala Ala Tyr Gly Ala Val
225                 230                 235                 240

Glu Gly Gly Lys Glu Tyr Asn Thr Val Asp Met Ser Pro Gln Arg Leu
                245                 250                 255

Phe Asn Asp Tyr Met Pro Pro Tyr Lys Ala Gly Leu Ala Gly Ser
            260                 265                 270

Gly Ala Val Met Val Ala Leu Asn Ser Leu Asn Gly Thr Pro Ala Thr
        275                 280                 285

Ser Asp Ser Trp Leu Leu Lys Asp Val Leu Arg Asp Gln Trp Gly Phe
    290                 295                 300

Lys Gly Ile Thr Val Ser Asp His Gly Ala Ile Lys Glu Leu Ile Lys
305                 310                 315                 320

His Gly Thr Ala Ala Asp Pro Glu Asp Ala Val Arg Val Ala Leu Lys
                325                 330                 335

Ser Gly Ile Asn Met Ser Met Ser Asp Glu Tyr Tyr Ser Lys Tyr Leu
            340                 345                 350

```
Pro Gly Leu Ile Lys Ser Gly Lys Val Thr Met Ala Glu Leu Asp Asp
            355                 360                 365

Ala Ala Arg His Val Leu Asn Val Lys Tyr Asp Met Gly Leu Phe Asn
370                 375                 380

Asp Pro Tyr Ser His Leu Gly Pro Lys Glu Ser Asp Pro Val Asp Thr
385                 390                 395                 400

Asn Ala Glu Ser Arg Leu His Arg Lys Glu Ala Arg Glu Val Ala Arg
                405                 410                 415

Glu Ser Leu Val Leu Leu Lys Asn Arg Leu Glu Thr Leu Pro Leu Lys
            420                 425                 430

Lys Ser Ala Thr Ile Ala Val Val Gly Pro Leu Ala Asp Ser Lys Arg
            435                 440                 445

Asp Val Met Gly Ser Trp Ser Ala Ala Gly Val Ala Asp Gln Ser Val
        450                 455                 460

Thr Val Leu Thr Gly Ile Lys Asn Ala Val Gly Glu Asn Gly Lys Val
465                 470                 475                 480

Leu Tyr Ala Lys Gly Ala Asn Val Thr Ser Asp Lys Gly Ile Ile Asp
                485                 490                 495

Phe Leu Asn Gln Tyr Glu Glu Ala Val Lys Val Asp Pro Arg Ser Pro
            500                 505                 510

Gln Glu Met Ile Asp Glu Ala Val Gln Thr Ala Lys Gln Ser Asp Val
        515                 520                 525

Val Val Ala Val Val Gly Glu Ala Gln Gly Met Ala His Glu Ala Ser
530                 535                 540

Ser Arg Thr Asp Ile Thr Ile Pro Gln Ser Gln Arg Asp Leu Ile Ala
545                 550                 555                 560

Ala Leu Lys Ala Thr Gly Lys Pro Leu Val Leu Val Leu Met Asn Gly
                565                 570                 575

Arg Pro Leu Ala Leu Val Lys Glu Asp Gln Gln Ala Asp Ala Ile Leu
            580                 585                 590

Glu Thr Trp Phe Ala Gly Thr Glu Gly Gly Asn Ala Ile Ala Asp Val
        595                 600                 605

Leu Phe Gly Asp Tyr Asn Pro Ser Gly Lys Leu Pro Met Ser Phe Pro
610                 615                 620

Arg Ser Val Gly Gln Ile Pro Val Tyr Tyr Ser His Leu Asn Thr Gly
625                 630                 635                 640

Arg Pro Tyr Asn Ala Asp Lys Pro Asn Lys Tyr Thr Ser Arg Tyr Phe
                645                 650                 655

Asp Glu Ala Asn Gly Ala Leu Tyr Pro Phe Gly Tyr Gly Leu Ser Tyr
            660                 665                 670

Thr Thr Phe Thr Val Ser Asp Val Lys Leu Ser Ala Pro Thr Met Lys
        675                 680                 685

Arg Asp Gly Lys Val Thr Ala Ser Val Gln Val Thr Asn Thr Gly Lys
690                 695                 700

Arg Glu Gly Ala Thr Val Val Gln Met Tyr Leu Gln Asp Val Thr Ala
705                 710                 715                 720

Ser Met Ser Arg Pro Val Lys Gln Leu Lys Gly Phe Glu Lys Ile Thr
                725                 730                 735

Leu Lys Pro Gly Glu Thr Gln Thr Val Ser Phe Pro Ile Asp Ile Glu
            740                 745                 750

Ala Leu Lys Phe Trp Asn Gln Gln Met Lys Tyr Asp Ala Glu Pro Gly
        755                 760                 765

Lys Phe Asn Val Phe Ile Gly Thr Asp Ser Ala Arg Val Lys Lys Gly
```

```
                 770                 775                 780

Glu Phe Glu Leu Leu
785

<210> SEQ ID NO 17
<211> LENGTH: 735
<212> TYPE: PRT
<213> ORGANISM: Gluconacetobacter xylinus BPR2001

<400> SEQUENCE: 17

Met Arg Leu Ser Arg Lys Ile Phe Leu Leu Ser Ala Val Ala Cys Gly
1               5                   10                  15

Met Ala Leu Ala Gln Ala Pro Ala Phe Ala Arg His Ala His Asp Gly
            20                  25                  30

Gly Gly Asp Gln Ala Asp Ala Arg Ala Arg Gln Val Leu Ala Ser Met
        35                  40                  45

Ser Leu Glu Asp Lys Met Ser Leu Leu Phe Ser Val Asp Gly Gly Gly
    50                  55                  60

Phe Asn Gly Ser Val Ala Pro Pro Gly Gly Leu Gly Ser Ala Ala Tyr
65                  70                  75                  80

Leu Arg Ala Pro Gln Gly Ser Gly Leu Pro Asp Leu Gln Ile Ser Asp
                85                  90                  95

Ala Gly Leu Gly Val Arg Asn Pro Ala His Ile Arg Arg Asn Gly Glu
            100                 105                 110

Ala Val Ser Leu Pro Ser Gly Gln Ser Thr Ala Ser Thr Trp Asp Met
        115                 120                 125

Asp Met Ala Arg Gln Ala Gly Val Met Ile Gly Arg Glu Ala Trp Gln
    130                 135                 140

Ser Gly Phe Asn Ile Leu Leu Gly Gly Gly Ala Asp Leu Thr Arg Asp
145                 150                 155                 160

Pro Arg Gly Gly Arg Asn Phe Glu Tyr Ala Gly Glu Asp Pro Leu Gln
                165                 170                 175

Thr Gly Arg Met Val Gly Ser Thr Ile Ala Gly Val Gln Ser Gln His
            180                 185                 190

Val Ile Ser Thr Leu Lys His Tyr Ala Met Asn Asp Leu Glu Thr Ser
        195                 200                 205

Arg Met Thr Met Ser Ala Asp Ile Asp Pro Val Ala Met Arg Glu Ser
    210                 215                 220

Asp Leu Leu Gly Phe Glu Ile Ala Leu Glu Thr Gly His Pro Gly Ala
225                 230                 235                 240

Val Met Cys Ser Tyr Asn Arg Val Asn Asp Leu Tyr Ala Cys Glu Asn
                245                 250                 255

Pro Tyr Leu Leu Asn Lys Thr Leu Lys Gln Asp Trp His Tyr Pro Gly
            260                 265                 270

Phe Val Met Ser Asp Trp Gly Ala Thr His Ser Ser Ala Arg Ala Ala
        275                 280                 285

Leu Ala Gly Leu Asp Gln Glu Ser Ala Gly Asp His Thr Asp Ala Arg
    290                 295                 300

Pro Tyr Phe Arg Thr Leu Leu Ala Ala Asp Val Lys Ala Gly Arg Val
305                 310                 315                 320

Pro Glu Ala Arg Ile Asn Asp Met Ala Glu Arg Val Val Arg Ala Leu
                325                 330                 335

Phe Ala Ala Gly Leu Val Asp His Pro Ala Gln Arg Gly Pro Leu Asp
            340                 345                 350
```

```
Val Val Thr Asp Thr Leu Val Ala Gln Lys Asp Glu Glu Gly Ala
            355                 360                 365

Val Leu Leu Arg Asn Gln Gly Asn Ile Leu Pro Leu Ser Pro Thr Ala
    370                 375                 380

Arg Ile Ala Val Ile Gly Gly His Ala Asp Ala Gly Val Ile Ser Gly
385                 390                 395                 400

Gly Gly Ser Ser Gln Val Asp Pro Ile Gly Gly Glu Ala Val Lys Gly
                405                 410                 415

Pro Gly Lys Lys Glu Trp Pro Gly Asp Pro Val Tyr Phe Pro Ser Ser
                420                 425                 430

Pro Leu Lys Ala Met Gln Ala Glu Ala Pro Gly Ala Arg Ile Thr Tyr
            435                 440                 445

Asp Pro Gly Thr Ser Ile Ala Ser Ala Val Arg Ala Ala Arg Ala Ala
            450                 455                 460

Asp Val Val Val Val Tyr Ala Thr Gln Phe Thr Phe Glu Gly Met Asp
465                 470                 475                 480

Ala Pro Ser Met His Leu Asp Asp Asn Ala Asp Ala Leu Ile Thr Ala
                485                 490                 495

Val Ala Ala Ala Asn Pro Arg Thr Val Val Val Met Glu Thr Gly Asp
            500                 505                 510

Pro Val Leu Met Pro Trp Asn Ser Ser Val Ala Gly Val Leu Glu Ala
            515                 520                 525

Trp Phe Pro Gly Ser Gly Gly Pro Ala Ile Ala Arg Leu Leu Phe
            530                 535                 540

Gly Lys Val Ala Pro Ser Gly His Leu Thr Met Thr Phe Pro Gln Ala
545                 550                 555                 560

Glu Ser Gln Leu Ala His Pro Asp Ile Ala Gly Val Thr Ala Asp Asn
                565                 570                 575

Val Phe Glu Met Gln Phe His Thr Asp Gln Glu Leu Val Tyr Asp Glu
            580                 585                 590

Gly Ser Asp Val Gly Tyr Arg Trp Phe Asp Arg Asn His Phe Lys Pro
            595                 600                 605

Leu Tyr Pro Phe Gly Tyr Gly Leu Thr Tyr Thr Thr Phe Ser Thr Asp
            610                 615                 620

Gly Leu Lys Val Thr Glu Arg His Gly Gln Val Thr Ala Thr Phe Asn
625                 630                 635                 640

Val His Asn Thr Gly Thr Arg Ala Gly Val Asp Val Pro Gln Val Tyr
                645                 650                 655

Val Gly Leu Pro Asp Gly Gly Ala Arg Arg Leu Ala Gly Trp Gln Arg
            660                 665                 670

Ile Ser Leu Ala Pro Gly Glu Ser Arg Gln Val Ser Val Gln Leu Glu
            675                 680                 685

Pro Arg Leu Leu Ala His Phe Asp Gly Lys His Asp Arg Trp Ser Val
            690                 695                 700

Pro Ser Gly Thr Phe Arg Val Trp Leu Ala Ser Cys Ala Thr Asp Asp
705                 710                 715                 720

Ser Gln Gln Thr Thr Met His Leu His Gly Arg Thr Met Ala Pro
                725                 730                 735

<210> SEQ ID NO 18
<211> LENGTH: 756
<212> TYPE: PRT
<213> ORGANISM: Paenibacillus sp. C7

<400> SEQUENCE: 18
```

```
Met Asn Asn Lys Trp Val Glu Thr Asn Val Lys Ala Ile Thr Tyr Val
1               5                   10                  15

Thr Asn Glu Gly Gly Pro Thr Leu Gly Tyr Ala Asp Ala Ser Gly Val
            20                  25                  30

Asn Ile Ile Phe Asp Asp Gly Tyr Ala Phe Lys Asp Leu Asn Lys Asp
        35                  40                  45

Gly Lys Leu Asp Lys Tyr Glu Asp Trp Arg Leu Pro Val Asp Ile Arg
50                  55                  60

Ala Lys Asp Leu Ala Ser Lys Met Ser Ile Glu Gln Ile Ala Gly Leu
65                  70                  75                  80

Met Leu Tyr Ser Arg His Gln Ala Val Pro Ala Ser Asn Gly Phe Phe
            85                  90                  95

Pro Ala Thr Tyr Asn Gly Glu Ser Tyr Thr Glu Ser Gly Val Lys Pro
            100                 105                 110

Tyr Asp Leu Ser Asp Glu Gln Ile Glu Phe Leu Thr Lys Asp His Leu
        115                 120                 125

Arg His Val Leu Leu Thr Thr Val Glu Ser Pro Glu Ile Ala Ala Cys
    130                 135                 140

Trp Asn Asn Val Gln Ala Leu Ala Glu Ser Ile Gly Leu Gly Ile
145                 150                 155                 160

Pro Val Asn Asn Ser Ser Asp Pro Arg His Gly Ser Asp Ala Ser Lys
                165                 170                 175

Glu Tyr Asn Ala Gly Ala Gly Gly Ser Ile Ser Met Trp Pro Glu Ser
            180                 185                 190

Leu Gly Leu Ala Ala Ser Phe Asp Pro Glu Leu Val Gln Arg Tyr Gly
        195                 200                 205

Glu Ile Ala Ser Lys Glu Tyr Arg Ala Leu Gly Ile Ala Thr Ala Leu
    210                 215                 220

Ser Pro Gln Ile Asp Ile Ala Thr Asp Pro Arg Trp Ser Arg Phe Asp
225                 230                 235                 240

Gly Thr Phe Gly Glu Asp Ser Lys Leu Ser Val Asp Leu Thr Arg Ala
            245                 250                 255

Tyr Ile Asp Gly Phe Gln Thr Ser Phe Gly Arg Leu Val Thr Asp
        260                 265                 270

Gly Trp Gly Cys Asp Ser Val Asn Ala Met Val Lys His Trp Pro Gly
    275                 280                 285

Gly Gly Ser Gly Glu Gly Gly Arg Asp Ala His Phe Gly Tyr Gly Lys
    290                 295                 300

Tyr Ala Val Tyr Pro Gly Asn Asn Phe Glu Glu His Leu Ile Pro Phe
305                 310                 315                 320

Leu Glu Gly Ala Phe Gln Leu Lys Gly Gly Thr Glu Lys Ala Ser Ala
            325                 330                 335

Ile Met Pro Tyr Tyr Thr Ile Ser Tyr Asn His Asp Gln Val Asn Gly
            340                 345                 350

Glu Asn Val Gly Asn Ser Tyr Asn Ala His Ile Ile Gly Asp Leu Leu
        355                 360                 365

Arg Asp Lys Tyr Gly Tyr Asp Gly Val Val Cys Thr Asp Trp Gly Ile
    370                 375                 380

Thr Asp Asp Glu Gly Ser Asp Ile Ser Arg Leu Phe Pro Gly Gly Arg
385                 390                 395                 400

Ser Trp Gly Val Glu Glu Gly Tyr Thr Val Ala Asp Arg His Tyr Lys
            405                 410                 415
```

Ala Leu Met Ala Gly Val Asp Gln Phe Gly Asn Asn Asp Gly
            420                 425                 430

Pro Val Leu Glu Ala Tyr Arg Ile Gly Val Ala Glu His Gly Glu Ala
            435                 440                 445

Tyr Met Arg Gln Arg Phe Glu Gln Ser Ala Val Arg Leu Leu Lys Asn
450                 455                 460

Met Phe Arg Val Gly Leu Phe Glu Asn Pro Tyr Cys Gln Thr Glu Glu
465                 470                 475                 480

Thr Val Arg Ile Val Gly Asn Ala Glu Tyr Met Ala Ala Gly Tyr Glu
                485                 490                 495

Ala Gln Leu Lys Ser Leu Val Leu Lys Asn Lys Asp Gln Val Leu
            500                 505                 510

Pro Leu Gln Lys Met Lys Thr Val Tyr Ile Pro Lys Arg Tyr Arg Pro
            515                 520                 525

Ala Gly Thr Asn Trp Ile Gly Phe Pro Thr Pro Glu Val Asp Gly Tyr
            530                 535                 540

Pro Val Asn Met Asp Val Ile Arg Lys Tyr Phe Asn Phe Thr Asp Glu
545                 550                 555                 560

Pro Glu Thr Ala Asp Phe Ala Ile Val Phe Ile Thr Gly Ala Asp Ser
                565                 570                 575

Gly Ser Gly Tyr Ser Lys Gly Asp Val Glu Ala Gly Gly Asn Gly Tyr
            580                 585                 590

Val Pro Ile Ser Leu Gln Tyr Ala Pro Tyr Thr Ala Glu His Ala Arg
            595                 600                 605

Glu Lys Ser Ile Ala Gly Asp Glu Arg Asp Ile Val Asn Arg Ser Tyr
610                 615                 620

Lys Gly Lys Met Ile Ser Ala Thr Asn Ala Ser Asp Leu Asp Ala Val
625                 630                 635                 640

Leu Lys Ala Lys Ala Leu Met Lys Gly Lys Pro Val Ile Val Ser Leu
                645                 650                 655

Gln Leu Ser Lys Pro Ser Ile Val Ala Glu Phe Glu Ala Val Ala Asp
            660                 665                 670

Ala Val Val Ala Thr Phe Gly Val Gln Asp Gln Ala Phe Leu Asp Ile
            675                 680                 685

Leu Ile Gly Glu Ala Glu Pro Ser Gly Leu Leu Pro Met Gln Ile Pro
690                 695                 700

Ala Asn Met Lys Thr Val Glu Glu Gln Leu Glu Asp Val Pro His Asp
705                 710                 715                 720

Met Glu Val His Val Asp Ser Glu Gly Asn Ala Tyr Asp Phe Ala Tyr
                725                 730                 735

Gly Leu Asn Trp Ser Gly Val Ile Ser Asp Glu Arg Thr Lys Arg Tyr
            740                 745                 750

Gly Lys Lys Lys
            755

<210> SEQ ID NO 19
<211> LENGTH: 781
<212> TYPE: PRT
<213> ORGANISM: Prevotella albensis M384

<400> SEQUENCE: 19

Met Lys His Arg Lys Leu Ser Leu Thr Leu Ala Val Gly Leu Leu Ser
1               5                   10                  15

Thr Thr Met Thr Ala Gln Lys Ala Leu Gln Leu Asn Lys Lys Asn Ile
            20                  25                  30

-continued

```
Asp Glu Val Ile Ala Ala Met Thr Leu Glu Glu Lys Ala Gln Leu Leu
         35                  40                  45

Val Gly Val Gly His Gln Asp Phe Val Gly Ser Gly Thr Met Leu Gly
 50                  55                  60

Gln His Ser Arg Leu Val Ala Gly Ala Gly Gln Thr Ala Glu Ile
 65                  70                  75                  80

Ser Arg Leu Gly Ile Pro Ala Thr Val Ala Asp Gly Pro Ala Gly
                     85                  90                  95

Val His Ile Asn Pro Thr Arg Pro Gly Thr Asn Gln Thr Phe Tyr Ala
                    100                 105                 110

Thr Gly Phe Pro Ile Gly Thr Cys Leu Ala Ser Thr Trp Asn Thr Asp
                115                 120                 125

Leu Val Tyr His Val Gly Lys Ala Ile Gly Asn Glu Thr Leu Glu Tyr
            130                 135                 140

Gly Ile Asp Val Ile Leu Gly Pro Gly Met Asn Leu His Arg Ser Pro
145                 150                 155                 160

Leu Cys Gly Arg Asn Phe Glu Tyr Tyr Ser Glu Asp Pro Ile Val Thr
                165                 170                 175

Gly Leu Ile Gly Ser Ala Met Val Lys Gly Ile Gln Ser Gln Gly Val
                180                 185                 190

Gly Val Ser Ala Lys His Phe Ala Ala Asn Ser Gln Glu Ser Asp Arg
            195                 200                 205

Thr Arg Val Asp Glu Arg Ile Ser Gln Arg Ala Leu Arg Glu Leu Tyr
210                 215                 220

Leu Lys Gly Phe Glu Ile Met Val Arg Asp Ser Lys Pro Trp Thr Leu
225                 230                 235                 240

Met Ser Ser Tyr Asn Lys Ile Asn Gly Thr Tyr Thr Gln Gly Ser Lys
                245                 250                 255

Asp Leu Leu Thr Asn Ile Leu Arg Lys Asp Trp Gly Tyr Gln Gly Ile
                260                 265                 270

Val Met Thr Asp Trp Ile Gly Glu Arg Ala Asp Leu Pro Val Glu Thr
            275                 280                 285

Glu Val Glu Ala Gly Asn Asp Phe Met Met Pro Gly Asn Ala Asp Arg
290                 295                 300

Ala Lys His Ile Val Lys Ala Val Lys Ala Gly Arg Leu Asp Ile Lys
305                 310                 315                 320

Asp Val Ala Arg Asn Ile Lys Asn Met Leu Glu Tyr Ile Leu Lys Thr
                325                 330                 335

Pro Arg Tyr Lys Lys Tyr Lys Tyr Thr Asn Gln Pro Asp Leu Lys Ala
                340                 345                 350

His Ala Gln Ile Thr Arg Gln Ala Ser Thr Glu Gly Met Val Leu Leu
            355                 360                 365

Lys Asn Asp Asn Asn Val Leu Pro Val Lys Asn Met Lys Lys Val Ala
370                 375                 380

Leu Phe Gly Val Asn Ser Tyr Asp Phe Leu Ser Gly Gly Leu Gly Ser
385                 390                 395                 400

Gly Cys Val Asn Val Pro Tyr Val Val Asp Met Val His Gly Leu Gln
                405                 410                 415

Asn Ala Gly Ile Ala Thr Thr Lys Gln Leu Thr Glu Ile Tyr Glu Asn
            420                 425                 430

Tyr Val Lys Tyr Ala Lys Ala Lys Leu Gln Ala Asp Lys Asn Pro Glu
435                 440                 445
```

```
Met Trp Phe Leu Asp Gln Gly Gln Pro Lys Leu Asp Glu Ile Glu Ile
450                 455                 460

Thr Gln Arg Cys Val Glu His Glu Val Gly Asp Ala Asp Ala Ala Ile
465                 470                 475                 480

Ile Thr Ile Ala Arg Gln Ala Gly Glu Gly Met Asp Arg Ser Ile Glu
                485                 490                 495

Gly Glu Phe Asn Leu Thr Asp His Glu Lys Ala Met Ile Ser Arg Val
            500                 505                 510

Ser Asp Val Phe His Ala Asn Lys Pro Val Ile Val Ile Asn
        515                 520                 525

Ser Gly Ser Val Met Glu Thr Ala Ser Trp Arg Asp Arg Val Asp Ala
530                 535                 540

Ile Leu Val Ala Trp Gln Pro Gly Glu Gly Gly Asn Ser Val Ala
545                 550                 555                 560

Asp Val Leu Ile Gly Lys Ala Asn Pro Ser Gly His Leu Thr Ser Thr
                565                 570                 575

Trp Pro Ile Ser Ala Ala Asp Val Pro Ser Thr Lys Asn Phe Pro Gln
            580                 585                 590

Gln Pro Ala Tyr Tyr Asn Leu Ser Asp Lys Leu Tyr Ser Asn Asn Met
        595                 600                 605

Lys Gly Val Asn Tyr Thr Asn His Glu Glu Asp Ile Tyr Val Gly Tyr
    610                 615                 620

Arg Tyr Phe Asp Thr Phe Asn Lys Lys Val Ala Tyr Pro Phe Gly Tyr
625                 630                 635                 640

Gly Leu Ser Tyr Thr Thr Phe Glu Phe Gly Lys Pro Ser Val Ser Leu
                645                 650                 655

Asn Gly Asp Lys Ile Thr Val Thr Val Ser Val Lys Asn Ile Gly Lys
            660                 665                 670

Val Ala Gly Lys Gln Val Ala Gln Val Tyr Val Lys Ala Pro Lys Gly
        675                 680                 685

Ala Tyr Glu Lys Pro Ser Cys Glu Leu Lys Ala Phe Ala Lys Thr Lys
    690                 695                 700

Asn Leu Lys Pro Gly Gln Ser Glu Thr Leu Lys Met Ile Ile Ala Lys
705                 710                 715                 720

Arg Asp Leu Ala Ser Phe Asp Glu Ala Asn Ser Gln Trp Lys Val Asp
                725                 730                 735

Ala Gly Lys Tyr Glu Phe Cys Val Gly Asp Asn Val Glu Ser Ile Lys
            740                 745                 750

Gly Thr Ala Ser Leu Asn Leu Ser Glu Tyr Thr Glu Lys Thr Thr Asn
        755                 760                 765

Ser Leu Pro Leu Asn Thr Lys Met Asn Leu Leu His Gln
    770                 775                 780

<210> SEQ ID NO 20
<211> LENGTH: 689
<212> TYPE: PRT
<213> ORGANISM: Rhizobium leguminosarum bv. Trifolii

<400> SEQUENCE: 20

Met Thr Asp Gly Thr Tyr Gly Val Arg Tyr Gln Pro Asp Leu Ile Asp
1               5                   10                  15

Gly Val Asn Asp Asp Arg Ala Asn Leu Glu Gln Phe Leu Ala Val Val
            20                  25                  30

Asn Arg Arg Thr Glu His Thr Ile Glu Gly Asp Phe Ser Gly Thr Ser
        35                  40                  45
```

```
Pro Ala Thr Cys Phe Pro Asn Gly Ser Ser Phe Ala Cys Ser Trp Asp
    50                  55                  60
Leu Asp Leu Ala Phe Gln Leu Gly Thr Ala Leu Ala Ala Glu Cys Gln
65                  70                  75                  80
Ala Leu Gly Val Asn Leu Leu Leu Gly Pro Gly Ile Asn Ile Arg Arg
                85                  90                  95
Met Pro Leu Gly Gly Arg Gly Tyr Glu Tyr Tyr Ser Glu Asp Pro Val
                100                 105                 110
Leu Thr Gly Tyr Ile Arg Pro Ala Val Ile Trp Glu Leu Lys Gly Ser
            115                 120                 125
Gly Val Gly Ala Ser Leu Lys His Phe Ala Cys Asn Asn Ser Glu Val
    130                 135                 140
Gln Arg Thr Thr Met Ser Ser Asp Val Asp Glu Arg Ala Leu Arg Glu
145                 150                 155                 160
Ile Tyr Leu Ala Gly Phe Glu Arg Ala Ile Arg Lys Gly Asn Pro Trp
                165                 170                 175
Thr Val Met Ser Ser Tyr Asn Arg Leu Asn Gly Val Gln Ala Ala Glu
                180                 185                 190
Asn Lys Trp Leu Leu Thr Thr Val Leu Arg Asp Glu Trp His Tyr Asp
            195                 200                 205
Gly Val Val Ser Asp Trp His Gly Ile Lys Asp Arg Ala Ala Ala
    210                 215                 220
Ala Lys Ala Gly Asn Asp Leu Asp Met Pro Ala Ser Lys Ser Arg Lys
225                 230                 235                 240
Lys Gln Leu Leu Ala Val Glu Asn Gly Thr Val Pro Leu Ala Thr
                245                 250                 255
Ile Asp Gln Ser Cys Leu Arg Met Leu Gln Leu Val Arg Arg Val Lys
                260                 265                 270
Ala Gly Glu Arg Arg Asp Ala Thr Trp Asp Leu Arg Glu Asn His Thr
            275                 280                 285
Leu Ala Arg Gln Met Ala Ala Glu Ser Ile Val Leu Leu Lys Asn Glu
    290                 295                 300
Gly Asn Leu Leu Pro Leu Glu Met Met Ala Gly Arg Ile Ala Ile Ile
305                 310                 315                 320
Gly Asp Thr Ala Met Asp Pro Ile Phe Gln Gly Trp Gly Cys Ala Thr
                325                 330                 335
Thr His Pro Ser Met Val Asp Ile Pro Leu Asp Glu Ile Arg Ala Phe
                340                 345                 350
Ala Ala Pro Gly Val Glu Val Gln His Phe Pro Leu Gly Gly Asp
            355                 360                 365
Lys Leu Lys Leu Ala Glu Ala Ile Ala Gly Ala Ala Ser Ala Asp
370                 375                 380
Val Val Leu Phe Phe Ala Asn Thr Glu Asn Gly Tyr Asp Gly Glu Gly
385                 390                 395                 400
Ser Asp Arg Leu His Leu Gly Leu Ala Asp Gly Gln Asp Ala Leu Ile
                405                 410                 415
Ala Arg Ile Ala Thr Ala Asn Pro Arg Thr Ile Val Ile Val Ala Ser
                420                 425                 430
Pro Asp Ala Val Glu Met Pro Trp Leu Ala Glu Val Pro Ser Val Leu
            435                 440                 445
Ala Thr Phe Phe Ala Gly Gln Gly Met Gly His Ala Val Ala Ser Ile
    450                 455                 460
```

```
Leu Phe Gly Arg Thr Asn Pro Ser Gly Lys Leu Thr Val Thr Phe Pro
465                 470                 475                 480

Lys Arg Leu Gln Asp Val Ala Ala Tyr Leu His Tyr Pro Gly Glu Asn
                485                 490                 495

Asp Arg His Ala Tyr Ser Glu Ala Ile Tyr Val Gly Tyr Arg Tyr Tyr
            500                 505                 510

Asp Arg Arg Glu Leu Ser Pro Leu Phe Pro Phe Arg Phe Gly Leu Ser
            515                 520                 525

Phe Thr Glu Phe Arg Tyr Ser Asp Leu Glu Leu Asp Arg Val Val Leu
        530                 535                 540

Lys Asp Gly Glu Thr Leu Thr Ala Thr Phe Ser Leu Thr Asn Thr Gly
545                 550                 555                 560

Arg Met Thr Gly Lys Glu Ile Cys Gln Leu Tyr Gly Arg Pro Val Lys
                565                 570                 575

Thr Arg Leu His Arg Pro Val Arg Glu Leu Lys Gly Phe Thr Lys Val
            580                 585                 590

Gly Leu Lys Pro Gly Thr Lys Arg Val Ser Ile Val Phe Glu Ala
        595                 600                 605

Arg Asp Thr Arg Tyr Phe Asp Pro Glu Leu Gly Gln Trp Leu Thr Asp
610                 615                 620

Gly Gly Ala Tyr Gly Ile Asp Val Gly Ala Ser Ser Arg Asp Ile Arg
625                 630                 635                 640

Leu Ser Ala Glu Val Thr Cys Glu Thr Pro Gln Leu Thr Pro Arg Arg
                645                 650                 655

Leu Thr Leu Glu Thr Gln Pro Phe Leu Leu Phe Glu Thr Pro Val Gly
            660                 665                 670

Arg Glu Arg Leu Ala Ala Phe Phe Arg Glu Arg Leu Gly Leu Asp Gly
        675                 680                 685

Val

<210> SEQ ID NO 21
<211> LENGTH: 772
<212> TYPE: PRT
<213> ORGANISM: Ruminococcus albus 7

<400> SEQUENCE: 21

Met Ile Ile Asn Leu Leu Lys Arg Arg Ile Lys Val Met Asp Ile Ala
1               5                   10                  15

His Ile Met Glu Ile Met Thr Leu Glu Glu Lys Ala Ser Leu Cys Ser
                20                  25                  30

Gly Ala Asp Phe Trp His Thr Lys Ala Ile Glu Arg Leu Asp Ile Pro
            35                  40                  45

Gln Ile Met Val Ser Asp Gly Pro His Gly Leu Arg Lys Asn Val Asp
        50                  55                  60

Gly Ser Asn Asp Pro Asn Glu Ala Ile Glu Ala Val Cys Phe Pro Thr
65                  70                  75                  80

Ala Ala Ala Leu Ala Cys Ser Tyr Asp Arg Glu Leu Leu Lys Asp Ile
                85                  90                  95

Gly Lys Ala Leu Gly Glu Glu Cys Gln Ser Glu Lys Val Ser Val Ile
            100                 105                 110

Leu Gly Pro Gly Cys Asn Ile Lys Arg Ser Pro Leu Cys Gly Arg Asn
        115                 120                 125

Phe Glu Tyr Phe Ser Glu Asp Pro Tyr Leu Ala Ser Gln Met Ala Ile
    130                 135                 140
```

-continued

Ser His Ile Lys Gly Val Gln Ser Lys Gly Ala Gly Thr Ser Leu Lys
145                 150                 155                 160

His Phe Ala Ala Asn Asn Gln Glu His Arg Arg Met Ser Val Ser Ala
            165                 170                 175

Glu Ile Asp Glu Arg Thr Leu His Glu Ile Tyr Leu Ala Ala Phe Glu
        180                 185                 190

Ser Val Ile Lys Glu Ala Lys Pro Trp Thr Val Met Cys Ser Tyr Asn
    195                 200                 205

Lys Ile Asn Gly Glu Tyr Ser Ser Gln Asn Lys Ser Leu Leu Thr Asp
210                 215                 220

Thr Leu Arg Glu Lys Trp Gly Phe Asp Gly Leu Val Met Ser Asp Trp
225                 230                 235                 240

Gly Ala Val Asp Asp Arg Val Lys Gly Ile Glu Ala Gly Leu Asp Leu
                245                 250                 255

Glu Met Pro Gly Ser Met Cys Lys Asn Asp Lys Met Ile Leu Lys Ala
            260                 265                 270

Val Glu Asp Gly Lys Leu Ser Val Glu Ala Leu Asp Lys Cys Val Lys
        275                 280                 285

Arg Ile Leu Glu Leu Ile Asp Lys Ser Leu Glu Cys Arg Thr Glu Met
    290                 295                 300

Asp Trp Asp Lys Glu Arg His His Gln Leu Ala Gln Lys Ala Ala Glu
305                 310                 315                 320

Lys Ser Ala Val Leu Leu Lys Asn Asp Asp His Ile Leu Pro Leu Ser
                325                 330                 335

Lys Asn Glu Lys Ile Ala Phe Ile Gly Ala Phe Ala Glu Gln Pro Arg
            340                 345                 350

Tyr Gln Gly Gly Gly Ser Ser His Ile Asn Ser Phe Arg Thr Val Ser
        355                 360                 365

Ala Leu Glu Ala Val Asp Gly Trp Glu Asn Ile Thr Tyr Ala Lys Gly
    370                 375                 380

Phe Ser Leu Asp Asn Asp Glu Ile Asn Thr Glu Leu Glu Gln Gln Ala
385                 390                 395                 400

Val Glu Ala Ala Met Asn Ala Asp Lys Val Val Phe Ala Gly Leu
                405                 410                 415

Pro Asp Ser Phe Glu Ser Glu Gly Phe Asp Arg Lys His Met Gln Leu
            420                 425                 430

Pro Gln Cys Gln Ile Asp Leu Ile Asp Lys Leu Ser Glu Val Asn Pro
        435                 440                 445

Asn Ile Val Val Leu His Asn Gly Ala Pro Val Glu Met Pro Phe
    450                 455                 460

Ala Asn Gly Asp Glu Asp Ser Asn Ser Val Lys Ala Ile Leu Glu Met
465                 470                 475                 480

Tyr Leu Ser Gly Gln Ala Ala Gly Glu Ala Val Val Arg Ile Leu Phe
                485                 490                 495

Gly Glu Val Asn Pro Ser Gly Lys Leu Ala Glu Thr Phe Pro Leu Arg
            500                 505                 510

Leu Glu Asp Asn Pro Ser Tyr Leu Asn Phe Pro Gly Glu Ala Asp Ile
        515                 520                 525

Val Lys Tyr Ser Glu Gly Ile Phe Val Gly Tyr Arg Tyr Tyr Glu Lys
    530                 535                 540

Lys Asn Met Glu Val Leu Tyr Pro Phe Gly His Gly Leu Ser Tyr Thr
545                 550                 555                 560

Glu Phe Glu Tyr Ser Asp Ile Lys Ile Ser Ser Tyr Glu Ile Ser Asp

```
                       565                 570                 575
Lys Lys Ala Phe Thr Val Glu Met Thr Val Thr Asn Ser Gly Ser Arg
                580                 585                 590

Asp Gly Glu Glu Ile Ile Gln Leu Tyr Ile Glu Pro Leu Thr Pro Thr
            595                 600                 605

Val Ile Arg Pro Ile Lys Glu Leu Lys Gly Phe Glu Lys Val Phe Leu
        610                 615                 620

Lys Ala Gly Glu Ser Lys Arg Val Val Phe Arg Leu Asp Ser Ser Ala
625                 630                 635                 640

Phe Ala Tyr Tyr Ser Asp Lys Ile His Asp Trp Leu Ser Glu Ser Gly
                645                 650                 655

Tyr Tyr Asn Ile Leu Ile Gly Lys Ser Ser Ala Asp Ile Cys Leu Glu
            660                 665                 670

Glu Gln Val His Phe Asn Ser Ser Val Arg Ile Pro Ile Leu Phe Thr
        675                 680                 685

Leu Asp Asn Thr Val Ser Asp Ile Asn Ser Thr Ala Glu Gly Lys Lys
    690                 695                 700

Leu Phe Lys Asp Met Met Ser Thr Val Phe Ala Thr Ala Asn Gly Gly
705                 710                 715                 720

Ala Asp Gln Leu Gly Asp Ser Ala Arg Glu Met Glu Met Ala Ile Ala
                725                 730                 735

Asn Asp Leu Pro Leu His Ala Met Val Ser Phe Thr Asn Pro Asp
            740                 745                 750

Ile Thr Arg Glu Lys Leu Gln Met Met Leu Asp Lys Leu Asn Val Ile
        755                 760                 765

Ile Asn Ser Lys
    770

<210> SEQ ID NO 22
<211> LENGTH: 765
<212> TYPE: PRT
<213> ORGANISM: Salmonella typhimurium LT2 SGSC 1412

<400> SEQUENCE: 22

Met Lys Trp Leu Cys Ser Val Gly Val Ala Val Ser Leu Ala Met Gln
1               5                   10                  15

Pro Ala Leu Ala Glu Asn Leu Phe Gly Asn His Pro Leu Thr Pro Glu
            20                  25                  30

Ala Arg Asp Ala Phe Val Thr Asp Leu Leu Lys Met Thr Val Asp
        35                  40                  45

Glu Lys Ile Gly Gln Leu Arg Leu Ile Ser Val Gly Pro Asp Asn Pro
    50                  55                  60

Lys Glu Ala Ile Arg Glu Met Ile Lys Asp Gly Gln Val Gly Ala Ile
65                  70                  75                  80

Phe Asn Thr Val Thr Arg Gln Asp Ile Arg Gln Met Gln Asp Gln Val
                85                  90                  95

Met Ala Leu Ser Arg Leu Lys Ile Pro Leu Phe Ala Tyr Asp Val
            100                 105                 110

Val His Gly Gln Arg Thr Val Phe Pro Ile Ser Leu Gly Leu Ala Ser
        115                 120                 125

Ser Phe Asn Leu Asp Ala Val Arg Thr Val Gly Arg Val Ser Ala Tyr
    130                 135                 140

Glu Ala Ala Asp Asp Gly Leu Asn Met Thr Trp Ala Pro Met Val Asp
145                 150                 155                 160
```

```
Val Ser Arg Asp Pro Arg Trp Gly Arg Ala Ser Glu Gly Phe Gly Glu
            165                 170                 175

Asp Thr Tyr Leu Thr Ser Ile Met Gly Glu Thr Met Val Lys Ala Met
        180                 185                 190

Gln Gly Lys Ser Pro Ala Asp Arg Tyr Ser Val Met Thr Ser Val Lys
        195                 200                 205

His Phe Ala Ala Tyr Gly Ala Val Glu Gly Gly Lys Glu Tyr Asn Thr
    210                 215                 220

Val Asp Met Ser Ser Gln Arg Leu Phe Asn Asp Tyr Met Pro Pro Tyr
225                 230                 235                 240

Lys Ala Gly Leu Asp Ala Gly Ser Gly Ala Val Met Val Ala Leu Asn
                245                 250                 255

Ser Leu Asn Gly Thr Pro Ala Thr Ser Asp Ser Trp Leu Leu Lys Asp
            260                 265                 270

Val Leu Arg Asp Glu Trp Gly Phe Lys Gly Ile Thr Val Ser Asp His
        275                 280                 285

Gly Ala Ile Lys Glu Leu Ile Lys His Gly Thr Ala Ala Asp Pro Glu
    290                 295                 300

Asp Ala Val Arg Val Ala Leu Lys Ala Gly Val Asp Met Ser Met Ala
305                 310                 315                 320

Asp Glu Tyr Tyr Ser Lys Tyr Leu Pro Gly Leu Ile Lys Ser Gly Lys
                325                 330                 335

Val Thr Met Ala Glu Leu Asp Asp Ala Thr Arg His Val Leu Asn Val
            340                 345                 350

Lys Tyr Asp Met Gly Leu Phe Asn Asp Pro Tyr Ser His Leu Gly Pro
        355                 360                 365

Lys Glu Ser Asp Pro Val Asp Thr Asn Ala Glu Ser Arg Leu His Arg
    370                 375                 380

Lys Glu Ala Arg Glu Val Ala Arg Glu Ser Val Val Leu Leu Lys Asn
385                 390                 395                 400

Arg Leu Glu Thr Leu Pro Leu Lys Lys Ser Gly Thr Ile Ala Val Val
                405                 410                 415

Gly Pro Leu Ala Asp Ser Gln Arg Asp Val Met Gly Ser Trp Ser Ala
            420                 425                 430

Ala Gly Val Ala Asn Gln Ser Val Thr Val Leu Ala Gly Ile Gln Asn
        435                 440                 445

Ala Val Gly Asp Gly Ala Lys Ile Leu Tyr Ala Lys Gly Ala Asn Ile
    450                 455                 460

Thr Asn Asp Lys Gly Ile Val Asp Phe Leu Asn Leu Tyr Glu Glu Ala
465                 470                 475                 480

Val Lys Ile Asp Pro Arg Ser Pro Gln Ala Met Ile Asp Glu Ala Val
                485                 490                 495

Gln Ala Ala Lys Gln Ala Asp Val Val Val Ala Val Val Gly Glu Ser
            500                 505                 510

Gln Gly Met Ala His Glu Ala Ser Ser Arg Thr Asn Ile Thr Ile Pro
        515                 520                 525

Gln Ser Gln Arg Asp Leu Ile Thr Ala Leu Lys Ala Thr Gly Lys Pro
    530                 535                 540

Leu Val Leu Val Leu Met Asn Gly Arg Pro Leu Ala Leu Val Lys Glu
545                 550                 555                 560

Asp Gln Gln Ala Asp Ala Ile Leu Glu Thr Trp Phe Ala Gly Thr Glu
                565                 570                 575

Gly Gly Asn Ala Ile Ala Asp Val Leu Phe Gly Asp Tyr Asn Pro Ser
```

```
                    580                 585                 590
Gly Lys Leu Pro Ile Ser Phe Pro Arg Ser Val Gly Gln Ile Pro Val
            595                 600                 605

Tyr Tyr Ser His Leu Asn Thr Gly Arg Pro Tyr Asn Pro Glu Lys Pro
        610                 615                 620

Asn Lys Tyr Thr Ser Arg Tyr Phe Asp Glu Ala Asn Gly Pro Leu Tyr
625                 630                 635                 640

Pro Phe Gly Tyr Gly Leu Ser Tyr Thr Thr Phe Thr Val Ser Asp Val
                645                 650                 655

Thr Leu Ser Ser Pro Thr Met Gln Arg Asp Gly Lys Val Thr Ala Ser
            660                 665                 670

Val Glu Val Thr Asn Thr Gly Lys Arg Glu Gly Ala Thr Val Ile Gln
        675                 680                 685

Met Tyr Leu Gln Asp Val Thr Ala Ser Met Ser Arg Pro Val Lys Gln
    690                 695                 700

Leu Lys Gly Phe Glu Lys Ile Thr Leu Lys Pro Gly Glu Arg Lys Thr
705                 710                 715                 720

Val Ser Phe Pro Ile Asp Ile Glu Ala Leu Lys Phe Trp Asn Gln Gln
                725                 730                 735

Met Lys Tyr Asp Ala Glu Pro Gly Lys Phe Asn Val Phe Ile Gly Val
            740                 745                 750

Asp Ser Ala Arg Val Lys Gln Gly Ser Phe Glu Leu Leu
        755                 760                 765

<210> SEQ ID NO 23
<211> LENGTH: 745
<212> TYPE: PRT
<213> ORGANISM: Unknown
<220> FEATURE:
<223> OTHER INFORMATION: Uncultured bacterium, beta-glucosidase thereof

<400> SEQUENCE: 23

Met Lys His Ile Leu Asn Leu Cys Leu Leu Ala Val Leu Cys Ala Val
1               5                   10                  15

Leu Ser Cys Gln Glu Gln Lys Pro Ser Thr Val Gly Ala Thr Ala Glu
            20                  25                  30

Val Glu Ser Arg Val Glu Ala Leu Leu Ser Arg Met Thr Leu Ala Glu
        35                  40                  45

Lys Ile Gly Gln Met Asn Gln Val Ser Ala Gly Gly Asp Val Ser Asn
    50                  55                  60

Tyr Ala Glu Ser Ile Arg Lys Gly Gln Val Gly Ser Ile Leu Asn Glu
65                  70                  75                  80

Val Asp Pro Val Lys Ile Asn Ala Phe Gln Arg Leu Ala Val Glu Glu
                85                  90                  95

Ser Arg Leu Gly Ile Pro Leu Leu Val Gly Arg Asp Val Ile His Gly
            100                 105                 110

Phe His Thr Val Phe Pro Ile Pro Leu Gly Leu Ala Ala Thr Phe Asp
        115                 120                 125

Pro Asp Leu Val Glu Glu Gly Ala Arg Val Ala Ala Val Glu Ala Thr
    130                 135                 140

Ser Gln Gly Val Arg Trp Thr Phe Ser Pro Met Leu Asp Ile Ala Arg
145                 150                 155                 160

Asp Pro Arg Trp Gly Arg Ile Ala Glu Gly Ser Gly Glu Asp Thr Tyr
                165                 170                 175

Leu Asp Thr Arg Met Ala Glu Ala Met Val Tyr Gly Tyr Gln Gly Arg
```

```
            180                 185                 190
Thr Ala Asp Ser Thr Ser Met Ala Ala Cys Ile Lys His Phe Val Gly
            195                 200                 205

Tyr Gly Ala Ala Glu Gly Gly Arg Asp Tyr Asn Ser Thr Tyr Leu Thr
        210                 215                 220

Glu Arg Gln Leu Arg Asn Val Tyr Leu Pro Phe Glu Ala Ala Val
225                 230                 235                 240

Lys Ala Gly Ala Met Thr Leu Met Thr Ser Phe Asn Asp Asn Asp Gly
                245                 250                 255

Val Pro Ser Thr Gly Asn Thr Phe Val Val Lys Asp Val Leu Arg Gly
            260                 265                 270

Glu Trp Gly Phe Asp Gly Leu Val Thr Asp Trp Asp Ser Met Gly
        275                 280                 285

Glu Met Ile Ala His Gly Phe Gly Val Asp Arg Lys Asp Val Ala Glu
        290                 295                 300

Lys Ala Ala Asn Ala Gly Val Asp Met Asp Met Met Thr Phe Gly Phe
305                 310                 315                 320

Leu Ser His Leu Glu Glu Leu Val Lys Ser Gly Ala Val Lys Gln Asn
                325                 330                 335

Thr Ile Asp Asn Ala Val Arg Asn Ile Leu Arg Val Lys Phe Met Leu
                340                 345                 350

Gly Leu Phe Glu Asn Pro Tyr Val Asn Val Glu Ala Ser Gln Ala Val
            355                 360                 365

Gln Tyr Ala Pro Glu His Leu Ala Ala Gln Lys Thr Ala Glu Glu
        370                 375                 380

Ser Ala Ile Leu Leu Lys Asn Asp Gly Val Leu Pro Leu Lys Ala Gly
385                 390                 395                 400

Val Arg Ile Leu Val Thr Gly Pro Met Ala Asp Ala Pro His Asp Gln
                405                 410                 415

Leu Gly Thr Trp Ala Phe Asp Gly Gln Lys Ala His Thr Val Thr Pro
                420                 425                 430

Leu Lys Ala Leu Gln Ala Arg Phe Pro Gly Leu Val Asp Tyr Val Pro
        435                 440                 445

Gly Leu Thr Tyr Ser Arg Glu Lys Arg Ser Gly Phe Ser Asp Val Val
        450                 455                 460

Ala Ala Ala Arg Ser Ala Asp Val Val Leu Ala Phe Leu Gly Glu Glu
465                 470                 475                 480

Ala Ile Leu Ser Gly Glu Ala His Ser Leu Ala Asp Leu Asn Leu Met
                485                 490                 495

Gly Ser Gln Ser Glu Leu Leu Glu Ala Leu Lys Thr Ala Gly Lys Pro
                500                 505                 510

Val Val Ala Thr Val Met Ala Gly Arg Pro Leu Thr Ile Glu Arg Asp
            515                 520                 525

Leu Pro Asn Val Asn Ala Met Leu Tyr Ser Phe His Pro Gly Thr Met
                530                 535                 540

Gly Gly Pro Ala Leu Ala Asn Leu Leu Phe Gly Asp Val Asn Pro Ser
545                 550                 555                 560

Gly Lys Thr Pro Ile Thr Phe Leu Arg Thr Val Gly Gln Ala Pro Leu
                565                 570                 575

Tyr Tyr Ser His Asn Met Thr Gly Arg Pro Tyr Lys Gly Glu Thr Leu
                580                 585                 590

Leu Asp Asp Ile Pro Ala Glu Ala Gly Gln Thr Ser Leu Gly Asn Thr
            595                 600                 605
```

```
Ser Tyr Tyr Leu Asp Tyr Gly Ala Tyr Pro Leu Phe Pro Phe Gly Phe
        610                 615                 620

Gly Leu Ser Tyr Thr Ser Phe Ala Tyr Ser Asp Ile Ala Leu Asp Lys
625                 630                 635                 640

Glu Ser Tyr Ala Ala Asp Asp Val Leu His Val Ser Phe Asn Leu Ala
                645                 650                 655

Asn Thr Gly Thr Phe Asp Gly Thr Glu Val Ala Gln Val Tyr Ile Arg
            660                 665                 670

Asp Leu Val Gly Ser Val Thr Arg Pro Val Lys Glu Leu Lys Ala Phe
        675                 680                 685

Arg Arg Val Ser Leu Lys Ala Gly Glu Ser Arg Leu Thr Leu Asp
690                 695                 700

Ile Pro Val Ser Glu Leu Ala Phe Tyr Gly Leu Asp Met Gln Lys Lys
705                 710                 715                 720

Val Glu Pro Gly Gln Phe Gln Leu Trp Val Ala Gly Asp Ser Ser
                725                 730                 735

Gly Glu Ala Leu Thr Phe Ser Val Arg
            740                 745

<210> SEQ ID NO 24
<211> LENGTH: 793
<212> TYPE: PRT
<213> ORGANISM: Unknown
<220> FEATURE:
<223> OTHER INFORMATION: Uncultured bacterium, beta-glucosidase thereof

<400> SEQUENCE: 24

Met Ser Ile Thr Thr Lys Leu Lys Ala Val Ser Leu Gly Val Ser Leu
1               5                   10                  15

Ala Leu Ala Gly Leu Leu Val Gly Cys Asn Gln Asn Asp Ser Asp Pro
            20                  25                  30

Leu Ile Lys Asp Asp Ala Tyr Tyr Arg Gly Gln Ala Glu Ala Met Val
        35                  40                  45

Ala Arg Leu Thr Leu Gly Glu Lys Leu Asp Leu Leu Ser Gly Pro Gly
    50                  55                  60

Tyr Gly Ser Ala Asn Gly Ala Ile Asn Val Lys Gln Asp Val Pro Gly
65                  70                  75                  80

Val Ala Gly Tyr Ile Asn Gly Val Leu Arg Ser Ala Asp Gly Ile Asp
                85                  90                  95

Ile Pro Ala Leu Lys Leu Ala Asp Gly Pro Ala Gly Val Arg Ile Asn
            100                 105                 110

Ala Asn Arg Asp Gly Asp Ser Ala Ser Tyr Tyr Ala Thr Ala Trp Pro
        115                 120                 125

Ile Gly Ser Leu Leu Ala Ser Ser Trp Asp Val Lys Leu Val Lys Ala
    130                 135                 140

Val Gly Glu Ala Met Gly Asp Glu Val Arg Gln Tyr Gly Val Asp Ile
145                 150                 155                 160

Leu Leu Ala Pro Gly Met Asn Ile Gln Arg Asn Pro Leu Asn Gly Arg
                165                 170                 175

Asn Phe Glu Tyr Tyr Ser Glu Asp Pro Leu Thr Gly Lys Ile Gly
            180                 185                 190

Ala Ala Met Val Asn Gly Val Glu Ser Asn Gly Val Gly Thr Thr Ile
        195                 200                 205

Lys His Tyr Phe Gly Asn Asn Ser Glu Thr Asn Arg Asn Gln Ile Asn
    210                 215                 220
```

```
Asp Ile Gly Glu Pro Arg Thr Phe Arg Glu Ile Tyr Leu Arg Gly Phe
225                 230                 235                 240

Gln Ile Ala Val Asp Glu Ala Gln Pro Trp Ala Val Met Thr Ser Tyr
            245                 250                 255

Asn Lys Val Asn Gly Thr Tyr Val Asn Glu Arg Arg Asp Ala Val Thr
            260                 265                 270

Asp Leu Leu Arg Gly Glu Trp Lys Phe Asp Gly Leu Val Met Ser Asp
        275                 280                 285

Trp Phe Ala Gly Asp Val Ala Asn Asn Ala Tyr Lys Gln Val Leu Ala
290                 295                 300

Gly Gln Asp Leu Ile Glu Pro Gly Asn Val Lys Glu Gln Leu Gln Gln
305                 310                 315                 320

Ser Ile Glu Gln Gly Asp Leu Asp Glu Ala Lys Val Asn Glu Ala Ala
            325                 330                 335

Ile His Ile Leu Thr Gln Val Met Lys Ser Pro Ser Tyr Asn Gln Leu
            340                 345                 350

Ala Ile Ser Asn Ser Pro Asp Leu Thr Ala His Ser Lys Leu Ala Arg
        355                 360                 365

Gln Ala Gly Ala Glu Ser Met Val Leu Leu Arg Asn Glu Ala Ala Ala
370                 375                 380

Leu Pro Leu Ala Ala Ser Ser Ala Leu Ala Ser Phe Gly Ile Asn Gln
385                 390                 395                 400

Ile Asn Thr Tyr Lys Gly Gly Thr Gly Ser Gly Asp Val Asn Ala Ala
            405                 410                 415

Ser Thr Ala Thr Ile Ala Gln Gly Leu Ala Ala Arg Phe Pro Val Asn
        420                 425                 430

Glu Ala Leu Gln Ser Tyr Tyr Arg Asp Phe Tyr Glu Asn Asn Lys Val
        435                 440                 445

Tyr His Glu Gly Gln Phe Gly Ala Lys Gly Tyr Tyr Thr Cys Ala Glu
    450                 455                 460

Ala Pro Ile Ser Gly Glu Leu Ala Ala Leu Ile Ala Asn Ala Ala Ala
465                 470                 475                 480

Thr Gln Gln Ala Ala Val Ile Ser Ile Gly Arg Gln Ala Gly Glu Gly
            485                 490                 495

Ala Asp Arg Ser Ser Gly Lys Gly Asp Tyr Leu Leu Gly Asp Asp Glu
        500                 505                 510

Arg Ala Leu Ile Asp Ala Val Ser Ser Ala Phe His Thr Gln Gly Lys
    515                 520                 525

Lys Val Val Val Val Leu Asn Val Asn Gly Val Ile Asp Thr Ala Gln
530                 535                 540

Trp Gly Asp Lys Val Asp Gly Ile Leu Leu Ala Tyr Met Ala Gly Gln
545                 550                 555                 560

Glu Thr Gly His Ala Val Ala Asp Val Leu Ser Gly Ala Val Asn Pro
            565                 570                 575

Ser Gly Lys Leu Ala Gln Ser Phe Pro His Ser Tyr Ala Ser Val Pro
        580                 585                 590

Ser Ala Gly Thr Phe Pro Gly Glu Asp Thr Asp Gly Asp Gly Glu Pro
    595                 600                 605

Asp Asp Leu Tyr Tyr Asn Glu Gly Ile Tyr Val Gly Tyr Arg Tyr Tyr
        610                 615                 620

Ser Thr Phe Glu Gln Ala Val Ser Tyr Pro Phe Gly Phe Gly Leu Ser
625                 630                 635                 640
```

```
Tyr Thr Ser Phe Ser Tyr Thr Ser Pro Ala Ile Ala Ser Asn Thr Leu
                645                 650                 655

Glu Gly Gly Ser Ala Gly Asn Leu Val Leu Thr Ala Thr Ile Thr Asn
            660                 665                 670

Thr Gly Ala Val Ala Gly Lys Glu Ala Ala Gln Val Tyr Val Thr Ala
        675                 680                 685

Pro Glu Val Lys Leu Lys Pro Leu Ile Glu Leu Lys Ala Phe Ala
    690                 695                 700

Lys Thr Ala Gln Leu Ala Pro Gly Ala Ser Glu Gln Leu Ser Phe Thr
705                 710                 715                 720

Ile Pro Ala Ser Ile Leu Ala Ser Phe Asp Glu Ala Ser Asn Gln Trp
                725                 730                 735

Ile Val Glu Pro Gly Arg Tyr Ser Ala Tyr Ile Ser Pro Ser Ser Asp
            740                 745                 750

Val Ser Ala Ile Thr Pro Val Ser Phe Thr Val Ser Lys Glu Ile Val
        755                 760                 765

Val Ser Asn Thr Thr Pro Gly Ala Leu Ala Leu Pro Ala Gly Val Asp
    770                 775                 780

Pro Ala Ser Val Thr Thr Ile Thr Arg
785                 790

<210> SEQ ID NO 25
<211> LENGTH: 860
<212> TYPE: PRT
<213> ORGANISM: Aspergillus aculeatus F-50

<400> SEQUENCE: 25

Met Lys Leu Ser Trp Leu Glu Ala Ala Leu Thr Ala Ala Ser Val
1               5                   10                  15

Val Ser Ala Asp Glu Leu Ala Phe Ser Pro Pro Phe Tyr Pro Ser Pro
                20                  25                  30

Trp Ala Asn Gly Gln Gly Glu Trp Ala Glu Ala Tyr Gln Arg Ala Val
            35                  40                  45

Ala Ile Val Ser Gln Met Thr Leu Asp Glu Lys Val Asn Leu Thr Thr
    50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
    115                 120                 125

Gly Gln Glu Phe Ser Asp Lys Gly Ile Asp Val Gln Leu Gly Pro Ala
130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
            180                 185                 190

Leu Asn Glu Gln Glu His Phe Arg Gln Val Ala Glu Ala Ala Gly Tyr
    195                 200                 205

Gly Phe Asn Ile Ser Asp Thr Ile Ser Ser Asn Val Asp Asp Lys Thr
210                 215                 220
```

```
Ile His Glu Met Tyr Leu Trp Pro Phe Ala Asp Ala Val Arg Ala Gly
225                 230                 235                 240

Val Gly Ala Ile Met Cys Ser Tyr Asn Gln Ile Asn Asn Ser Tyr Gly
            245                 250                 255

Cys Gln Asn Ser Tyr Thr Leu Asn Lys Leu Leu Lys Ala Glu Leu Gly
        260                 265                 270

Phe Gln Gly Phe Val Met Ser Asp Trp Gly Ala His His Ser Gly Val
    275                 280                 285

Gly Ser Ala Leu Ala Gly Leu Asp Met Ser Met Pro Gly Asp Ile Thr
290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
            340                 345                 350

Pro Asn Phe Ser Ser Trp Thr Arg Asp Glu Tyr Gly Phe Lys Tyr Phe
        355                 360                 365

Tyr Pro Gln Glu Gly Pro Tyr Glu Lys Val Asn His Phe Val Asn Val
    370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
            420                 425                 430

Asn Gly Cys Ser Asp Arg Gly Cys Asp Asn Gly Thr Leu Ala Met Ala
        435                 440                 445

Trp Gly Ser Gly Thr Ala Glu Phe Pro Tyr Leu Val Thr Pro Glu Gln
450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile
            500                 505                 510

Ser Val Asp Gly Asn Glu Gly Asp Arg Asn Asn Leu Thr Leu Trp Lys
        515                 520                 525

Asn Gly Asp Asn Leu Ile Lys Ala Ala Ala Asn Cys Asn Asn Thr
530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
    610                 615                 620

Asp Phe Ser Glu Gly Val Phe Ile Asp Tyr Arg Gly Phe Asp Lys Arg
625                 630                 635                 640
```

-continued

```
Asn Glu Thr Pro Ile Tyr Glu Phe Gly His Gly Leu Ser Tyr Thr Thr
                645                 650                 655

Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
    690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
    770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Ala Leu Pro Lys Val Gln
    850                 855                 860

<210> SEQ ID NO 26
<211> LENGTH: 769
<212> TYPE: PRT
<213> ORGANISM: Aspergillus fumigatus Af293

<400> SEQUENCE: 26

Met His Ser Asn Val Gly Leu Ala Gly Leu Ala Gly Leu Leu Ala Thr
1               5                   10                  15

Ala Ser Val Cys Leu Ser Ala Pro Ala Asp Gln Asn Ile Thr Ser Asp
            20                  25                  30

Thr Tyr Phe Tyr Gly Gln Ser Pro Pro Val Tyr Pro Ser Pro Glu Gly
        35                  40                  45

Thr Gly Thr Gly Ser Trp Ala Ala Ala Tyr Lys Ala Lys Lys Phe
    50                  55                  60

Val Ala Gln Leu Thr Pro Glu Glu Lys Val Asn Leu Thr Ala Gly Thr
65                  70                  75                  80

Asp Ala Asn Asn Gly Cys Ser Gly Asn Ile Ala Ala Ile Pro Arg Leu
                85                  90                  95

Asn Phe Pro Gly Leu Cys Val Ser Asp Ala Gly Asn Gly Leu Arg Gly
            100                 105                 110

Thr Asp Tyr Val Ser Ser Trp Pro Ser Gly Leu His Val Gly Ala Ser
        115                 120                 125

Trp Asn Lys Ala Leu Ala Arg Gln Arg Ala Val Gln Met Ala Thr Glu
    130                 135                 140

Phe Arg Lys Lys Gly Val Asn Val Leu Leu Gly Pro Val Val Gly Pro
145                 150                 155                 160
```

```
Leu Gly Arg Val Ala Glu Ala Gly Arg Asn Trp Gly Phe Ser Asn
            165                 170                 175

Asp Pro Tyr Leu Ser Gly Ala Leu Val Tyr Glu Thr Val Asp Gly Ala
        180                 185                 190

Gln Ser Val Gly Val Ala Thr Cys Thr Lys His Tyr Ile Leu Asn Glu
            195                 200                 205

Gln Glu Thr Asn Arg Asn Pro Gly Met Glu Asp Gly Val Glu Val Ala
        210                 215                 220

Ala Val Ser Ser Asn Ile Asp Asp Lys Thr Met His Glu Leu Tyr Leu
225                 230                 235                 240

Trp Pro Phe Gln Asp Ala Val Leu Ala Gly Ser Ala Ser Ile Met Cys
            245                 250                 255

Ser Tyr Asn Arg Val Asn Asn Ser Tyr Gly Cys Gln Asn Ser Lys Thr
            260                 265                 270

Leu Asn Gly Leu Leu Lys Thr Glu Leu Gly Phe Gln Gly Tyr Val Met
            275                 280                 285

Thr Asp Trp Gly Ala Gln His Ala Gly Ile Ala Gly Ala Asn Ala Gly
            290                 295                 300

Leu Asp Met Val Met Pro Ser Thr Glu Thr Trp Gly Ala Asn Leu Thr
305                 310                 315                 320

Thr Ala Ile Ser Asn Gly Thr Met Asp Ala Ser Arg Leu Asp Asp Met
                325                 330                 335

Ala Thr Arg Ile Ile Ala Ser Trp Tyr Gln Met Asn Gln Asp Ser Asp
            340                 345                 350

Phe Pro Ser Pro Gly Ala Gly Met Pro Ser Asp Met Tyr Ala Pro His
            355                 360                 365

Gln Arg Val Ile Gly Arg Asp Ala Ser Ser Lys Gln Thr Leu Leu Arg
        370                 375                 380

Gly Ala Ile Glu Gly His Val Leu Val Lys Asn Asn His Ser Ala Leu
385                 390                 395                 400

Pro Leu Lys Ser Pro Gln Leu Leu Ser Val Phe Gly Tyr Asp Ala Lys
            405                 410                 415

Gly Pro Asn Ala Leu Lys Gln Asn Phe Asn Trp Leu Ser Tyr Ser Pro
            420                 425                 430

Ala Ile Gln Glu Asn His Thr Leu Trp Val Gly Gly Ser Gly Ala
        435                 440                 445

Asn Asn Ala Ala Tyr Ile Asp Ala Pro Ile Asp Ala Ile Gln Arg Gln
450                 455                 460

Ala Tyr Glu Asp Gly Thr Ser Val Leu Tyr Asp Ile Ser Ser Glu Asp
465                 470                 475                 480

Pro Glu Val Asp Pro Thr Thr Asp Ala Cys Leu Val Phe Ile Asn Ser
            485                 490                 495

Tyr Ala Thr Glu Gly Trp Asp Arg Pro Gly Leu Ala Asp Asn Ser Ser
                500                 505                 510

Asp Thr Leu Val Lys Asn Val Ala Arg Lys Cys Ala Asn Thr Ile Val
            515                 520                 525

Thr Ile His Asn Ala Gly Ile Arg Val Val Gly Glu Trp Ile Asp His
            530                 535                 540

Glu Asn Val Thr Ala Val Ile Phe Ala His Leu Pro Gly Gln Asp Ser
545                 550                 555                 560

Gly Arg Ala Leu Val Glu Leu Leu Tyr Gly Arg Ala Asn Pro Ser Gly
            565                 570                 575
```

```
Lys Leu Pro Tyr Thr Val Ala Lys Lys Val Glu Asp Tyr Gly Ser Leu
                580                 585                 590

Leu His Pro Ser Leu Pro Glu Thr Pro Tyr Gly Leu Phe Pro Gln Ser
            595                 600                 605

Asp Phe Asp Glu Gly Val Tyr Ile Asp Tyr Arg Ala Phe Asp Arg Ala
610                 615                 620

Asn Ile Thr Ala Gln Phe Glu Phe Gly Phe Gly Leu Ser Tyr Thr Ser
625                 630                 635                 640

Phe Asp Tyr Ser Gly Leu Gln Ile Ser Asn Pro Lys Gln Ser Pro Gln
            645                 650                 655

Tyr Pro Pro Ser Ala Ala Ile Gln Gln Gly Gly Asn Pro His Leu Trp
            660                 665                 670

Asp Asn Ile Val Thr Val Ser Ala Glu Ile Lys Asn Thr Gly Arg Val
            675                 680                 685

Ala Gly Ala Glu Val Ala Gln Leu Tyr Ile Gly Ile Pro Asn Gly Pro
690                 695                 700

Val Arg Gln Leu Arg Gly Phe Glu Lys Val Asp Val Ser Ala Gly Glu
705                 710                 715                 720

Thr Thr Gln Val Gln Phe Ala Leu Asn Arg Arg Asp Leu Ser Thr Trp
                725                 730                 735

Asp Val Glu Ala Gln Gln Trp Ser Leu Gln Arg Gly Thr Tyr Arg Val
            740                 745                 750

Tyr Val Gly Arg Ser Ser Arg Asp Leu Pro Leu Thr Gly Ser Phe Thr
            755                 760                 765

Leu

<210> SEQ ID NO 27
<211> LENGTH: 863
<212> TYPE: PRT
<213> ORGANISM: Aspergillus fumigatus Af293

<400> SEQUENCE: 27

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175
```

```
Ile Lys Gly Ile Gln Asp Ala Gly Val Ile Ala Thr Ala Lys His Tyr
                180                 185                 190

Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
        210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
        290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
        370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
        450                 455                 460

Gln Ala Ile Gln Arg Glu Val Ile Ser Asn Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
        530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
```

```
            595                 600                 605
Gly Ala Pro Leu Leu Thr Glu Pro Asn Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
    690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
    770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
    850                 855                 860

<210> SEQ ID NO 28
<211> LENGTH: 860
<212> TYPE: PRT
<213> ORGANISM: Aspergillus kawachii IFO4308

<400> SEQUENCE: 28

Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Ala Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ser Gly Met Asn Val
            100                 105                 110
```

-continued

Ala Ala Thr Trp Asp Lys Asn Leu Ala Tyr Leu Arg Gly Lys Ala Met
            115                 120                 125

Gly Gln Glu Phe Ser Asp Lys Gly Ala Asp Ile Gln Leu Gly Pro Ala
130                 135                 140

Ala Gly Pro Leu Gly Arg Ser Pro Asp Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
            195                 200                 205

Gly Phe Asn Ile Ser Glu Ser Gly Ser Ala Asn Leu Asp Asp Lys Thr
210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
            275                 280                 285

Ser Gly Ala Leu Ala Gly Leu Asp Met Ser Met Pro Gly Asp Val Asp
            290                 295                 300

Tyr Asp Ser Gly Thr Ser Tyr Trp Gly Thr Asn Leu Thr Val Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
            355                 360                 365

Tyr Val Ser Glu Gly Pro Tyr Glu Lys Val Asn His Tyr Val Asn Val
            370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
450                 455                 460

Ala Ile Ser Asn Glu Val Leu Lys Asn Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Lys Asn Leu Thr Leu Trp Arg
            515                 520                 525

Asn Gly Asp Asn Val Ile Lys Ala Ala Ala Ser Asn Cys Asn Asn Thr

```
              530                 535                 540
Ile Val Ile Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
                580                 585                 590

Gly Ala Lys Ser Pro Phe Thr Trp Gly Lys Thr Arg Glu Ala Tyr Gln
                595                 600                 605

Asp Tyr Leu Val Thr Glu Pro Asn Asn Gly Asn Gly Ala Pro Gln Glu
                610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
                660                 665                 670

Glu Pro Ala Ser Gly Glu Thr Glu Ala Ala Pro Thr Phe Gly Glu Val
                675                 680                 685

Gly Asn Ala Ser Asn Tyr Leu Tyr Pro Asp Gly Leu Gln Lys Ile Thr
                690                 695                 700

Lys Phe Ile Tyr Pro Trp Leu Asn Ser Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
                740                 745                 750

Gly Gly Asn Pro Arg Leu Tyr Asp Glu Leu Ile Arg Val Ser Val Thr
                755                 760                 765

Ile Lys Asn Thr Gly Lys Val Ala Gly Asp Glu Val Pro Gln Leu Tyr
770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Thr Lys Trp Ser Thr Thr
                805                 810                 815

Leu Thr Arg Arg Asp Leu Ala Asn Trp Asn Val Glu Lys Gln Asp Trp
                820                 825                 830

Glu Ile Thr Ser Tyr Pro Lys Met Val Phe Val Gly Ser Ser Ser Arg
                835                 840                 845

Lys Pro Pro Leu Arg Ala Ser Leu Pro Thr Val His
850                 855                 860

<210> SEQ ID NO 29
<211> LENGTH: 618
<212> TYPE: PRT
<213> ORGANISM: Aspergillus nidulans FGSC A4

<400> SEQUENCE: 29

Met Arg Val Asp Ser Thr Val Leu Ala Leu Val Ala Leu Ala Thr Asp
1               5                   10                  15

Cys Leu Gly Leu Ala Ile Lys Ser Asn Glu Pro Glu Leu Leu Arg Arg
                20                  25                  30

Asp Ala Leu Pro Ile Tyr Lys Asn Ala Ser Tyr Cys Val Asp Glu Arg
            35                  40                  45
```

Val Arg Asp Leu Leu Ser Arg Met Thr Leu Glu Glu Lys Ala Gly Gln
 50                  55                  60

Leu Phe His Lys Gln Leu Ser Glu Gly Pro Leu Asp Asp Ser Ser
 65                  70                  75                  80

Gly Asn Ser Thr Glu Thr Met Ile Gly Lys Lys His Met Thr His Phe
                 85                  90                  95

Asn Leu Ala Ser Asp Ile Thr Asn Ala Thr Gln Thr Ala Glu Phe Ile
            100                 105                 110

Asn Leu Ile Gln Lys Arg Ala Leu Gln Thr Arg Leu Gly Ile Pro Ile
        115                 120                 125

Thr Ile Ser Thr Asp Pro Arg His Ser Phe Thr Glu Asn Val Gly Thr
130                 135                 140

Gly Phe Gln Ala Gly Val Phe Ser Gln Trp Pro Glu Ser Leu Gly Leu
145                 150                 155                 160

Ala Ala Leu Arg Asp Pro Gln Leu Val Arg Glu Phe Ala Glu Val Ala
                165                 170                 175

Arg Glu Glu Tyr Leu Ala Val Gly Ile Arg Ala Ala Leu His Pro Gln
            180                 185                 190

Val Asp Leu Ser Thr Glu Pro Arg Trp Ala Arg Ile Ser Gly Thr Trp
        195                 200                 205

Gly Glu Asn Ser Thr Leu Thr Ser Glu Leu Ile Val Glu Tyr Ile Lys
210                 215                 220

Gly Phe Gln Gly Glu Gly Lys Leu Gly Pro Lys Ser Val Lys Thr Val
225                 230                 235                 240

Thr Lys His Phe Pro Gly Gly Pro Met Glu Asn Gly Glu Asp Ser
                245                 250                 255

His Phe Tyr Tyr Gly Lys Asn Gln Thr Tyr Pro Gly Asn Asn Ile Asp
            260                 265                 270

Glu His Leu Ile Pro Phe Lys Ala Ala Leu Ala Ala Gly Ala Thr Glu
        275                 280                 285

Ile Met Pro Tyr Tyr Ser Arg Pro Ile Gly Thr Asn Trp Glu Ala Val
290                 295                 300

Gly Phe Ser Phe Asn Lys Glu Ile Val Thr Asp Leu Leu Arg Gly Glu
305                 310                 315                 320

Leu Gly Phe Asp Gly Ile Val Leu Thr Asp Trp Gly Leu Ile Thr Asp
                325                 330                 335

Thr Tyr Ile Gly Asn Gln Tyr Met Pro Ala Arg Ala Trp Gly Val Glu
            340                 345                 350

Tyr Leu Ser Glu Leu Gln Arg Ala Ala Arg Ile Leu Asp Ala Gly Cys
        355                 360                 365

Asp Gln Phe Gly Gly Glu Glu Arg Pro Glu Leu Ile Val Gln Leu Val
370                 375                 380

Arg Glu Gly Thr Ile Ser Glu Asp Arg Ile Asp Val Ser Val Ala Arg
385                 390                 395                 400

Leu Leu Lys Glu Lys Phe Leu Leu Gly Leu Phe Asp Asn Pro Phe Val
                405                 410                 415

Asn Ala Ser Ala Ala Asn Asn Ile Val Gly Asn Glu His Phe Val Asn
            420                 425                 430

Leu Gly Arg Asp Ala Gln Arg Arg Ser Tyr Thr Leu Leu Thr Asn Asn
        435                 440                 445

Gln Thr Ile Leu Pro Leu Ala Lys Pro Gly Glu Gly Thr Arg Phe Tyr
450                 455                 460

Ile Glu Gly Phe Asp Ser Ala Phe Met Ser Ala Arg Asn Tyr Thr Val

```
            465                 470                 475                 480

Val Asn Thr Thr Glu Glu Ala Asp Phe Ala Leu Leu Arg Tyr Asn Ala
                    485                 490                 495

Pro Tyr Glu Pro Arg Asn Gly Thr Phe Glu Ala Asn Phe His Ala Gly
                500                 505                 510

Ser Leu Ala Phe Asn Ala Thr Glu Lys Ala Arg Gln Ala Lys Ile Tyr
                515                 520                 525

Ser Ser Leu Pro Thr Ile Val Asp Ile Ile Leu Asp Arg Pro Ala Val
            530                 535                 540

Ile Pro Glu Val Val Glu Gln Ala Gln Ala Val Leu Ala Ser Tyr Gly
545                 550                 555                 560

Ser Asp Ser Glu Ala Phe Leu Asp Val Val Phe Gly Val Ser Lys Pro
                565                 570                 575

Glu Gly Lys Leu Pro Phe Asp Leu Pro Arg Ser Met Asp Ala Val Glu
                580                 585                 590

Ala Gln Ala Glu Asp Leu Pro Phe Asp Thr Glu Asn Pro Val Phe Arg
                595                 600                 605

Tyr Gly His Gly Leu Glu Tyr Glu Asp Asn
610                 615

<210> SEQ ID NO 30
<211> LENGTH: 840
<212> TYPE: PRT
<213> ORGANISM: Aspergillus oryzae

<400> SEQUENCE: 30

Met Lys Leu Gly Trp Ile Glu Val Ala Ala Leu Ala Ala Ser Val
1               5                   10                  15

Val Ser Ala Lys Asp Asp Leu Ala Tyr Ser Pro Pro Phe Tyr Pro Ser
                20                  25                  30

Pro Trp Ala Asp Gly Gln Gly Glu Trp Ala Glu Val Tyr Lys Arg Ala
            35                  40                  45

Val Asp Ile Val Ser Gln Met Thr Leu Thr Glu Lys Val Asn Leu Thr
50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
                100                 105                 110

Val Ala Ala Thr Trp Asp Lys Thr Leu Ala Tyr Leu Arg Gly Gln Ala
            115                 120                 125

Met Gly Glu Glu Phe Ser Asp Lys Gly Ile Asp Val Gln Leu Gly Pro
            130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
            195                 200                 205

Tyr Gly Phe Asn Val Ser Asp Ser Leu Ser Ser Asn Val Asp Asp Lys
        210                 215                 220
```

```
Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
                260                 265                 270

Gly Phe Gln Gly Phe Val Met Ser Asp Trp Thr Ala His His Ser Gly
            275                 280                 285

Val Gly Ala Ala Leu Ala Gly Leu Asp Met Ser Met Pro Gly Asp Val
        290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
                340                 345                 350

Pro Pro Asn Phe Ser Ser Trp Thr Arg Asp Glu Tyr Gly Phe Ala His
                355                 360                 365

Asn His Val Ser Glu Gly Ala Tyr Glu Arg Val Asn Glu Phe Val Asp
        370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
                420                 425                 430

Ala Asn Gly Cys Asp Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
        450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
                485                 490                 495

Ala Ser Val Ser Leu Val Phe Val Asn Ser Asp Ser Gly Glu Ser Tyr
                500                 505                 510

Leu Ser Val Asp Gly Asn Glu Gly Asp Arg Asn Asn Ile Thr Leu Trp
            515                 520                 525

Lys Asn Gly Asp Asn Val Val Lys Thr Ala Ala Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
            595                 600                 605

Gly Ser Pro Leu Val Lys Asp Ala Asn Asn Gly Asn Gly Ala Pro Gln
            610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
```

645                 650                 655
Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
        675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
        755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys
        835                 840

<210> SEQ ID NO 31
<211> LENGTH: 840
<212> TYPE: PRT
<213> ORGANISM: Aspergillus oryzae RIB40

<400> SEQUENCE: 31

Met Ala Ala Phe Pro Ala Tyr Leu Ala Leu Leu Ser Tyr Leu Val Pro
1               5                   10                  15

Gly Ala Leu Ser His Pro Glu Ala Lys Thr Leu Thr Ser Arg Ala Ser
            20                  25                  30

Thr Glu Ala Tyr Ser Pro Pro Tyr Pro Ala Pro Asn Gly Gly Trp
        35                  40                  45

Ile Ser Glu Trp Ala Ser Ala Tyr Glu Lys Ala His Arg Val Val Ser
    50                  55                  60

Asn Met Thr Leu Ala Glu Lys Val Asn Leu Thr Ser Gly Thr Gly Ile
65                  70                  75                  80

Tyr Met Gly Pro Cys Ala Gly Gln Thr Gly Ser Val Pro Arg Phe Gly
                85                  90                  95

Ile Pro Asn Leu Cys Leu His Asp Ser Pro Leu Gly Val Arg Asn Ser
            100                 105                 110

Asp His Asn Thr Ala Phe Pro Ala Gly Ile Thr Val Gly Ala Thr Phe
        115                 120                 125

Asp Lys Asp Leu Met Tyr Glu Arg Gly Val Gly Leu Gly Glu Glu Ala
    130                 135                 140

Arg Gly Lys Gly Ile Asn Val Leu Leu Gly Pro Ser Val Gly Pro Ile
145                 150                 155                 160

Gly Arg Lys Pro Arg Gly Gly Arg Asn Trp Glu Gly Phe Gly Ala Asp
                165                 170                 175

```
Pro Ser Leu Gln Ala Phe Gly Gly Ser Leu Thr Ile Lys Gly Met Gln
            180                 185                 190
Ser Thr Gly Ala Ile Ala Ser Leu Lys His Leu Ile Gly Asn Glu Gln
        195                 200                 205
Glu Gln His Arg Met Ser Ser Val Ile Thr Gln Gly Tyr Ser Ser Asn
    210                 215                 220
Ile Asp Asp Arg Thr Leu His Glu Leu Tyr Leu Trp Pro Phe Ala Glu
225                 230                 235                 240
Ser Val Arg Ala Gly Ala Gly Ser Val Met Ile Ala Tyr Asn Asp Val
                245                 250                 255
Asn Arg Ser Ala Cys Ser Gln Asn Ser Lys Leu Ile Asn Gly Ile Leu
            260                 265                 270
Lys Asp Glu Leu Gly Phe Gln Gly Phe Val Val Thr Asp Trp Leu Ala
        275                 280                 285
His Ile Gly Gly Val Ser Ser Ala Leu Ala Gly Leu Asp Met Ser Met
    290                 295                 300
Pro Gly Asp Gly Ala Ile Pro Leu Leu Gly Thr Ser Tyr Trp Ser Trp
305                 310                 315                 320
Glu Leu Ser Arg Ser Val Leu Asn Gly Ser Val Pro Val Glu Arg Leu
                325                 330                 335
Asn Asp Met Val Thr Arg Ile Val Ala Thr Trp Tyr Lys Met Gly Gln
            340                 345                 350
Asp Lys Asp Tyr Pro Leu Pro Asn Phe Ser Ser Asn Thr Glu Asp Glu
        355                 360                 365
Thr Gly Pro Leu Tyr Pro Gly Ala Leu Phe Ser Pro Ser Gly Ile Val
    370                 375                 380
Asn Gln Tyr Val Asn Val Gln Gly Asn His Asn Val Thr Ala Arg Ala
385                 390                 395                 400
Ile Ala Arg Asp Ala Ile Thr Leu Leu Lys Asn Asn Glu Asn Val Leu
                405                 410                 415
Pro Leu Lys Arg Asn Asp Thr Leu Lys Ile Phe Gly Thr Asp Ala Gly
            420                 425                 430
Thr Asn Ser Asp Gly Ile Asn Ser Cys Thr Asp Lys Gly Cys Asn Lys
        435                 440                 445
Gly Val Leu Thr Met Gly Trp Gly Ser Gly Thr Ser Arg Leu Pro Tyr
    450                 455                 460
Leu Ile Thr Pro Gln Glu Ala Ile Ala Asn Ile Ser Ser Asn Ala Glu
465                 470                 475                 480
Phe His Ile Thr Asp Thr Phe Pro Leu Gly Val Thr Ala Gly Pro Asp
                485                 490                 495
Asp Ile Ala Ile Val Phe Ile Asn Ser Asp Ser Gly Glu Asn Tyr Ile
            500                 505                 510
Thr Val Asp Gly Asn Pro Gly Asp Arg Thr Leu Ala Gly Leu His Ala
        515                 520                 525
Trp His Asn Gly Asp Asn Leu Val Lys Ala Ala Glu Lys Phe Ser
    530                 535                 540
Asn Val Val Val Val His Thr Val Gly Pro Ile Leu Met Glu Glu
545                 550                 555                 560
Trp Ile Asp Leu Asp Ser Val Lys Ala Val Leu Val Ala His Leu Pro
                565                 570                 575
Gly Gln Glu Ala Gly Trp Ser Leu Thr Asp Ile Leu Phe Gly Asp Tyr
            580                 585                 590
Ser Pro Ser Gly His Leu Pro Tyr Thr Ile Pro His Ser Glu Ser Asp
```

```
                595                 600                 605
Tyr Pro Glu Ser Val Gly Leu Ile Ala Gln Pro Phe Gly Gln Ile Gln
    610                 615                 620
Asp Asp Tyr Thr Glu Gly Leu Tyr Ile Asp Tyr Arg His Phe Leu Lys
625                 630                 635                 640
Ala Asn Ile Thr Pro Arg Tyr Pro Phe Gly His Gly Leu Ser Tyr Thr
                645                 650                 655
Thr Phe Asn Phe Thr Glu Pro Asn Leu Ser Ile Ile Lys Ala Leu Asp
            660                 665                 670
Thr Ala Tyr Pro Ala Ala Arg Pro Pro Lys Gly Ser Thr Pro Thr Tyr
            675                 680                 685
Pro Thr Ala Lys Pro Asp Ala Ser Glu Val Ala Trp Pro Lys Asn Phe
690                 695                 700
Asn Arg Ile Trp Arg Tyr Leu Tyr Pro Tyr Leu Asp Asn Pro Glu Gly
705                 710                 715                 720
Ala Ala Ala Asn Ser Ser Lys Thr Tyr Pro Tyr Pro Asp Gly Tyr Thr
                725                 730                 735
Thr Glu Pro Lys Pro Ala Pro Arg Ala Gly Ala Glu Gly Gly Asn
            740                 745                 750
Pro Ala Leu Trp Asp Val Thr Phe Ser Val Gln Val Lys Val Thr Asn
            755                 760                 765
Thr Gly Ser Arg Asp Gly Arg Ala Val Ala Gln Leu Tyr Val Glu Leu
    770                 775                 780
Pro Ser Ser Leu Gly Leu Asp Thr Pro Ser Arg Gln Leu Arg Gln Phe
785                 790                 795                 800
Glu Lys Thr Lys Ile Leu Ala Ala Gly Glu Ser Val Leu Thr Leu
                805                 810                 815
Asp Val Thr Arg Lys Asp Leu Ser Val Trp Asp Val Val Gln Asp
                820                 825                 830
Trp Lys Ala Pro Val Asn Gly Glu
        835                 840

<210> SEQ ID NO 32
<211> LENGTH: 856
<212> TYPE: PRT
<213> ORGANISM: Aspergillus oryzae RIB40

<400> SEQUENCE: 32

Met Leu Thr Ser Pro Thr Ala Arg Thr Ser Val Arg Ile Ser Arg Pro
1               5                   10                  15
Ala Thr Thr Glu Arg Pro Asn Thr Val Leu Thr Ser Gly Ser Leu Asp
                20                  25                  30
Ile Ala Met Val Gln Val Val Ser Arg Thr Leu Thr Pro Pro Thr Ser
            35                  40                  45
Asn Met Lys Leu Ser Ala Ala Leu Ser Thr Leu Ala Ala Leu Gln Pro
        50                  55                  60
Ala Val Gly Ala Ala Val Gln Asn Arg Ala Ser Asp Val Ala Asp Leu
65                  70                  75                  80
Glu His Tyr Trp Ser Tyr Gly His Ser Glu Pro Val Tyr Pro Thr Pro
                85                  90                  95
Glu Thr Lys Gly Leu Gly Asp Trp Glu Glu Ala Phe Thr Lys Ala Arg
                100                 105                 110
Ser Leu Val Ala Gln Met Thr Asp Lys Glu Lys Asn Asn Ile Thr Tyr
            115                 120                 125
```

```
Gly Tyr Ser Ser Thr Ala Asn Gly Cys Gly Thr Ser Gly Gly Val
    130                 135                 140

Pro Arg Leu Gly Phe Pro Gly Ile Cys Leu Gln Asp Ala Gly Asn Gly
145                 150                 155                 160

Val Arg Gly Thr Asp Met Val Asn Ser Tyr Ala Ser Gly Val His Val
                165                 170                 175

Gly Ala Ser Trp Asn Arg Asp Leu Thr Tyr Ser Arg Ala Gln Tyr Met
            180                 185                 190

Gly Ala Glu Phe Lys Arg Lys Gly Val Asn Val Ala Leu Gly Pro Val
        195                 200                 205

Ala Gly Pro Ile Gly Arg Ile Ala Arg Gly Gly Arg Asn Trp Glu Gly
    210                 215                 220

Phe Ser Asn Asp Pro Tyr Leu Ser Gly Ala Leu Thr Gly Asp Thr Val
225                 230                 235                 240

Arg Gly Leu Gln Glu Ser Val Ile Ala Cys Val Lys His Leu Ile Gly
                245                 250                 255

Asn Glu Gln Glu Thr His Arg Ser Thr Pro Ser Met Leu Ala Asn Ser
            260                 265                 270

Arg Asn Gln Ser Ser Ser Ser Asn Leu Asp Asp Lys Thr Met His Glu
        275                 280                 285

Leu Tyr Leu Trp Pro Phe Gln Asp Ala Val Lys Ala Gly Ala Gly Ser
    290                 295                 300

Val Met Cys Ser Tyr Asn Arg Ile Asn Asn Ser Tyr Gly Cys Gln Asn
305                 310                 315                 320

Ser Lys Ala Met Asn Gly Leu Leu Lys Gly Glu Leu Gly Phe Gln Gly
                325                 330                 335

Phe Val Val Ser Asp Trp Gly Ala Gln His Thr Gly Ile Ala Ser Ala
            340                 345                 350

Ala Ala Gly Leu Asp Met Ala Met Pro Ser Ser Tyr Trp Glu Asn
        355                 360                 365

Gly Thr Leu Ala Leu Ala Val Lys Asn Glu Ser Leu Pro Ser Thr Arg
    370                 375                 380

Leu Asp Asp Met Ala Thr Arg Ile Val Ala Thr Trp Tyr Lys Tyr Ala
385                 390                 395                 400

Glu Ile Glu Asn Pro Gly His Gly Leu Pro Tyr Ser Leu Leu Ala Pro
                405                 410                 415

His Asn Leu Thr Asp Ala Arg Asp Pro Lys Ser Lys Ser Thr Ile Leu
            420                 425                 430

Gln Gly Ala Val Glu Gly His Val Leu Val Lys Asn Thr Asn Asn Ala
        435                 440                 445

Leu Pro Leu Lys Lys Pro Gln Phe Leu Ser Leu Phe Gly Tyr Asp Ala
    450                 455                 460

Val Ala Ala Arg Asn Thr Met Asp Asp Leu Asp Trp Asn Met Trp
465                 470                 475                 480

Ser Met Gly Tyr Asp Asn Ser Leu Thr Tyr Pro Asn Gly Ser Ala Val
                485                 490                 495

Asp Ala Met Met Leu Lys Tyr Ile Phe Leu Ser Ser Ala Asn Pro Ser
            500                 505                 510

Ala Phe Gly Pro Gly Val Ala Leu Asn Ala Thr Ile Thr Gly Gly
        515                 520                 525

Gly Ser Gly Ala Ser Thr Ala Ser Tyr Ile Asp Ala Pro Phe Asn Ala
    530                 535                 540

Phe Gln Arg Gln Ala Tyr Asp Asp Asp Thr Phe Leu Ala Trp Asp Phe
```

-continued

```
545                 550                 555                 560
Ala Ser Gln Asn Pro Leu Val Asn Pro Ala Ser Asp Ala Cys Ile Val
                565                 570                 575

Phe Ile Asn Glu Gln Ser Ser Glu Gly Trp Asp Arg Pro Tyr Leu Ala
            580                 585                 590

Asp Pro Tyr Ser Asp Thr Leu Val Gln Asn Val Ala Ser Gln Cys Ser
        595                 600                 605

Asn Thr Met Val Val Ile His Asn Ala Gly Val Arg Leu Val Asp Arg
    610                 615                 620

Trp Ile Glu Asn Asp Asn Ile Thr Ala Val Ile Tyr Ala His Leu Pro
625                 630                 635                 640

Gly Gln Asp Ser Gly Arg Ala Leu Val Glu Val Met Tyr Gly Lys Gln
                645                 650                 655

Ser Pro Ser Gly Arg Leu Pro Tyr Thr Val Ala Lys Asn Glu Ser Asp
            660                 665                 670

Tyr Gly Ser Leu Leu Asn Pro Val Ile Gln Ser Gly Thr Asp Asp Ile
        675                 680                 685

Tyr Tyr Pro Gln Asp Asn Phe Thr Glu Gly Val Tyr Ile Asp Tyr Lys
    690                 695                 700

Ala Phe Val Ala Ala Asn Ile Thr Pro Arg Tyr Glu Phe Gly Tyr Gly
705                 710                 715                 720

Leu Thr Tyr Ser Thr Phe Asp Tyr Ser Asp Leu Lys Val Ser Thr Ser
                725                 730                 735

Ser Asn Val Ser Thr Ser Tyr Leu Ala Pro Gly Thr Thr Val Ala Glu
            740                 745                 750

Gly Gly Leu Pro Ser Val Trp Asp Ile Ile Ala Thr Val Thr Cys Thr
        755                 760                 765

Val Ser Asn Thr Gly Ser Val Ala Ala Ala Glu Val Ala Gln Leu Tyr
    770                 775                 780

Ile Gly Ile Pro Gly Gly Pro Ala Lys Val Leu Arg Gly Phe Glu Lys
785                 790                 795                 800

Gln Leu Ile Glu Pro Gly Gln Gln Val Gln Val Thr Phe Asp Leu Thr
                805                 810                 815

Arg Arg Asp Leu Ser Thr Trp Asp Thr Glu Lys Gln Asn Trp Gly Leu
            820                 825                 830

Gln Ala Gly Ser Tyr Ala Leu Tyr Val Gly Lys Ser Val Leu Asp Ile
        835                 840                 845

Gln Leu Thr Gly Ser Leu Ser Leu
    850                 855

<210> SEQ ID NO 33
<211> LENGTH: 870
<212> TYPE: PRT
<213> ORGANISM: Coccidioides posadasii

<400> SEQUENCE: 33

Met Ser Pro Thr Ile Trp Ile Ala Thr Leu Leu Tyr Trp Phe Ala Phe
1               5                   10                  15

Gln Ala Arg Lys Ser Val Ala Ala Pro Pro Gly Val Gly Ala Leu Asp
            20                  25                  30

Asp Arg Ala Glu Leu Pro Asp Gly Phe His Ser Pro Gln Tyr Tyr Pro
        35                  40                  45

Ala Pro Arg Gly Leu Gly Ala Gly Met Glu Glu Ala Tyr Ser Lys Ala
    50                  55                  60
```

```
His Thr Val Val Ser Lys Met Thr Leu Ala Gly Lys Val Asn Leu Thr
 65                  70                  75                  80

Thr Gly Thr Gly Phe Leu Met Ala Leu Val Gly Gln Thr Gly Ser Ala
                 85                  90                  95

Leu Arg Phe Gly Ile Pro Arg Leu Cys Leu Gln Asp Gly Pro Leu Gly
            100                 105                 110

Leu Arg Asn Thr Asp His Asn Thr Ala Phe Pro Ala Gly Ile Ser Val
        115                 120                 125

Gly Ala Thr Phe Asp Lys Lys Leu Met Tyr Glu Arg Gly Cys Ala Met
130                 135                 140

Gly Glu Glu Phe Arg Gly Lys Gly Ala Asn Val His Leu Gly Pro Ser
145                 150                 155                 160

Val Gly Pro Leu Gly Arg Lys Pro Arg Gly Gly Arg Asn Trp Glu Gly
                165                 170                 175

Phe Gly Ser Asp Pro Ser Leu Gln Ala Ile Ala Ala Val Glu Thr Ile
            180                 185                 190

Lys Gly Val Gln Ser Lys Gly Val Ile Ala Thr Ile Lys His Leu Val
        195                 200                 205

Gly Asn Glu Gln Glu Met Tyr Arg Met Thr Asn Ile Val Gln Arg Ala
210                 215                 220

Tyr Ser Ala Asn Ile Asp Asp Arg Thr Met His Glu Leu Tyr Leu Trp
225                 230                 235                 240

Pro Phe Ala Glu Ser Val Arg Ala Gly Val Gly Ala Val Met Met Ala
                245                 250                 255

Tyr Asn Asp Val Asn Gly Ser Ala Ser Cys Gln Asn Ser Lys Leu Ile
            260                 265                 270

Asn Gly Ile Leu Lys Asp Glu Leu Gly Phe Gln Gly Phe Val Met Thr
        275                 280                 285

Asp Trp Tyr Ala Gln Ile Gly Gly Val Ser Ser Ala Leu Ala Gly Leu
290                 295                 300

Asp Met Ser Met Pro Gly Asp Gly Ser Val Pro Leu Ser Gly Thr Ser
305                 310                 315                 320

Phe Trp Ala Ser Glu Leu Ser Arg Ser Ile Leu Asn Gly Thr Val Ala
                325                 330                 335

Leu Asp Arg Leu Asn Asp Met Val Thr Arg Ile Val Ala Thr Trp Phe
            340                 345                 350

Lys Phe Gly Gln Asp Lys Asp Phe Pro Leu Pro Asn Phe Ser Ser Tyr
        355                 360                 365

Thr Gln Asn Ala Lys Gly Leu Leu Tyr Pro Gly Ala Leu Phe Ser Pro
370                 375                 380

Leu Gly Val Val Asn Gln Phe Val Asn Val Gln Ala Asp His His Lys
385                 390                 395                 400

Leu Ala Arg Val Ile Ala Arg Glu Ser Ile Thr Leu Leu Lys Asn Glu
                405                 410                 415

Asp Asn Leu Leu Pro Leu Asp Pro Asn Arg Ala Ile Lys Tyr Ser Glu
            420                 425                 430

Gln Met Pro Gly Thr Asn Pro Arg Gly Ile Asn Ala Cys Pro Asp Lys
        435                 440                 445

Gly Cys Asn Lys Gly Val Leu Thr Met Gly Trp Gly Ser Gly Thr Ser
450                 455                 460

Asn Leu Pro Tyr Leu Val Thr Pro Glu Asp Ala Ile Arg Asn Ile Ser
465                 470                 475                 480

Lys Asn Thr Glu Phe His Ile Thr Asp Lys Phe Pro Asn Asn Val Gln
```

```
                485                 490                 495
Pro Gly Pro Asp Asp Val Ala Ile Val Phe Val Asn Ala Asp Ser Gly
            500                 505                 510
Glu Asn Tyr Ile Ile Val Glu Ser Asn Pro Gly Asp Arg Thr Val Ala
            515                 520                 525
Gln Met Lys Leu Trp His Asn Gly Asp Glu Leu Ile Glu Ser Ala Ala
            530                 535                 540
Lys Lys Phe Ser Asn Val Val Val Val His Thr Val Gly Pro
545                 550                 555                 560
Ile Ile Met Glu Lys Trp Ile Asp Leu Leu Arg Ser Arg Val Ser Cys
                565                 570                 575
Leu Pro Asp Phe Gln Asp Lys Lys Leu Glu Ile Leu Leu Ile Ser
            580                 585                 590
Cys Ser Glu Thr Ser Val Arg Val Ala Ala Ser Ile Tyr Asp Thr Glu
            595                 600                 605
Ser Arg Ile Gly Leu Ser Asp Ser Val Ser Leu Ile Asn Gln Arg Phe
            610                 615                 620
Gly Gln Ile Gln Asp Thr Phe Thr Glu Gly Leu Phe Ile Asp Tyr Arg
625                 630                 635                 640
His Phe Gln Lys Glu Asn Ile Thr Pro Arg Tyr His Phe Gly Tyr Gly
                645                 650                 655
Leu Ser Tyr Thr Thr Phe Asn Phe Thr Glu Pro Arg Leu Glu Ser Val
            660                 665                 670
Thr Thr Leu Ser Glu Tyr Pro Pro Ala Arg Lys Pro Lys Ala Gly Asp
            675                 680                 685
Arg His Thr Pro Thr Ile Ser His Leu Leu Gln Lys Trp Pro Gly Pro
            690                 695                 700
Lys Thr Leu Thr Gly Ser Gly Ala Tyr Leu Tyr Pro Tyr Leu Asp Asn
705                 710                 715                 720
Pro Ser Ala Ile Lys Pro Lys Pro Gly Tyr Pro Tyr Pro Glu Ala Ile
                725                 730                 735
Gln Pro Asn Leu Asn Leu Asn Pro Arg Ala Gly Gly Ser Glu Ala Val
            740                 745                 750
Thr Arg Arg Tyr Gly Met Leu Arg Ser Arg Phe Pro Leu Lys Leu Leu
            755                 760                 765
Ile Leu Glu Arg Asn Pro Val Arg Ala Val Ala Gln Leu Tyr Val Glu
            770                 775                 780
Leu Pro Thr Asp Asp Glu His Pro Thr Pro Lys Leu Gln Leu Arg Gln
785                 790                 795                 800
Phe Glu Lys Thr Ala Thr Leu Glu Pro Gly Gln Ser Glu Val Leu Lys
                805                 810                 815
Met Glu Ile Thr Arg Lys Asp Val Ser Ile Trp Asp Thr Met Val Gln
                820                 825                 830
Asp Trp Lys Val Pro Ala Thr Gly Lys Gly Ile Lys Leu Trp Ile Gly
                835                 840                 845
Ala Ser Val Gly Asp Leu Lys Ala Val Cys Glu Thr Gly Lys Gly Lys
            850                 855                 860
Ser Cys His Val Leu Asn
865                 870

<210> SEQ ID NO 34
<211> LENGTH: 858
<212> TYPE: PRT
<213> ORGANISM: Coccidioides posadasii
```

<400> SEQUENCE: 34

```
Met Trp Leu Gly Trp Leu Pro Ala Val Phe Val Leu Val Ala Gly Gly
1               5                   10                  15

Ala Ala Glu Lys Glu Trp Ala Phe Ser Pro Pro Tyr Tyr Pro Ser Pro
            20                  25                  30

Trp Ala Ser Gly Gln Gly Glu Trp Ser Glu Ala Tyr Asn Lys Ala Arg
        35                  40                  45

Glu Phe Val Ser Gln Leu Thr Leu Thr Glu Lys Val Asn Leu Thr Thr
    50                  55                  60

Gly Val Gly Trp Met Gln Glu Ala Cys Val Gly Asn Val Gly Ser Ile
65                  70                  75                  80

Pro Arg Leu Gly Phe Arg Ser Leu Cys Met Gln Asp Gly Pro Leu Gly
                85                  90                  95

Ile Arg Phe Ala Asp His Val Ser Ala Phe Pro Ala Gly Ile Asn Val
            100                 105                 110

Gly Ala Thr Trp Ser Lys Ser Leu Ala Tyr Leu Arg Gly Lys Ala Met
        115                 120                 125

Gly Glu Glu His Arg Asp Lys Gly Val Asp Val Gln Leu Gly Pro Ala
130                 135                 140

Val Gly Pro Leu Gly Arg Ser Pro Asp Gly Gly Arg Asn Trp Glu Gly
145                 150                 155                 160

Phe Ser Pro Asp Pro Val Leu Ser Gly Tyr Leu Val Ala Glu Thr Ile
                165                 170                 175

Lys Gly Ile Gln Asp Ala Gly Val Ile Ala Cys Val Lys His Phe Ile
            180                 185                 190

Val Asn Glu Gln Glu Arg Phe Arg Gln Ala Pro Glu Ala Gln Gly Tyr
        195                 200                 205

Gly Phe Asn Ile Ser Glu Ser Ser Ser Asn Val Asp Asp Val Thr
    210                 215                 220

Met His Glu Leu Tyr Leu Trp Pro Phe Ala Asp Ala Val Arg Ala Gly
225                 230                 235                 240

Val Gly Ser Val Met Cys Ser Tyr Asn Gln Ile Asn Asn Ser Tyr Gly
                245                 250                 255

Cys Ser Asn Ser Tyr Thr Gln Asn Lys Leu Leu Lys Gly Glu Leu Gly
            260                 265                 270

Phe Gln Gly Phe Ile Met Ser Asp Trp Gln Ala His Ser Gly Val
        275                 280                 285

Gly Asp Asp Leu Ala Gly Leu Asp Met Ser Met Pro Gly Asp Thr Leu
290                 295                 300

Phe Leu Thr Gly Lys Ser Tyr Trp Gly Pro Asn Leu Thr Ile Ala Val
305                 310                 315                 320

Thr Asn Gly Thr Ile Pro Gln Trp Arg Leu Asp Asp Met Ala Val Arg
                325                 330                 335

Ile Met Ala Ala Tyr Tyr Lys Val Arg Arg Asp Gln Thr Gln Val Pro
            340                 345                 350

Ile Asn Phe Asn Ser Trp Thr Arg Asp Glu Phe Gly Tyr Leu His Ala
        355                 360                 365

Gly Gly Gln Glu Gly Tyr Gly Arg Val Asn Gln Met Val Asn Val Arg
    370                 375                 380

Gly Arg His Ala Val Ile Ala Arg Lys Val Ala Ser Ala Ser Thr Val
385                 390                 395                 400

Leu Leu Lys Asn Arg Gly Val Leu Pro Leu Lys Gly Lys Glu Lys Leu
```

-continued

```
                405                 410                 415
Thr Ala Val Ile Gly Glu Asp Ala Gly Pro Asn Leu Trp Gly Pro Asn
            420                 425                 430
Gly Cys Pro Asp Arg Gly Cys Ala Asn Gly Thr Leu Ala Met Gly Trp
            435                 440                 445
Gly Ser Gly Thr Ala Asp Phe Pro Tyr Leu Val Thr Pro Ala Gln Ala
        450                 455                 460
Ile Glu Asn Glu Val Ile Thr Lys Gly Val Gly Glu Ala Met Ser Val
465                 470                 475                 480
Phe Asp Asn Tyr Ala Thr Ser Gln Ile Glu Ser Val Val Ser Gln Ala
                485                 490                 495
Thr Val Ser Leu Val Phe Val Asn Ala Gly Ala Gly Glu Gly Phe Ile
            500                 505                 510
Ser Val Asp Gly Asn Glu Gly Asp Arg Lys Asn Leu Thr Leu Trp Lys
            515                 520                 525
Asn Gly Asp Glu Leu Ile Lys Thr Val Ala Ser Met Cys Asn Asn Thr
        530                 535                 540
Val Val Met His Thr Ala Gly Pro Val Leu Val Asn Lys Trp Tyr
545                 550                 555                 560
Asp His Pro Asn Val Thr Ala Ile Leu Trp Ala Gly Leu Pro Gly Gln
                565                 570                 575
Glu Ser Gly Asn Ala Leu Gly Asp Val Ile Tyr Gly Arg Val Asn Pro
            580                 585                 590
Gly Ala Lys Ser Pro Phe Thr Trp Ala Ala Thr Ser Glu Asp Tyr Gly
            595                 600                 605
Val Ser Ile Leu Lys Glu Pro Asn Ala Ala Thr Lys Ala Pro Gln Ile
        610                 615                 620
Asp Phe Glu Glu Gly Ile Phe Ile Asp Tyr Arg Ala Phe Asp Lys Ser
625                 630                 635                 640
Asn Thr Lys Pro Ile Tyr Glu Phe Gly Phe Gly Leu Ser Tyr Thr Thr
                645                 650                 655
Phe Thr Phe Ser Asp Leu Glu Val Gln Pro Leu Arg Ala Asn Pro Tyr
            660                 665                 670
Val Pro Thr Ser Gly Phe Thr Asp Ser Ala Pro Val Phe Gly Asn Ser
            675                 680                 685
Thr Asp His Leu Gln Phe Pro Ala Gly Phe Asp Pro Val His Leu Tyr
        690                 695                 700
Ile Tyr Pro Trp Leu Asn Ser Thr Asp Leu Lys Glu Ser Ser Met Asp
705                 710                 715                 720
Arg Asp Tyr Gly Leu Pro Thr Glu Lys Tyr Val Pro Pro Gly Ala Thr
                725                 730                 735
Asp Gly Gly Pro Gln Ala Leu Leu Pro Ala Gly Gly Pro Gly Gly
            740                 745                 750
Asn Pro Gly Leu Tyr Glu Glu Leu Tyr Arg Val Ser Val Thr Ile Thr
            755                 760                 765
Asn Thr Gly Ser Val Thr Gly Asp Glu Val Pro Gln Leu Tyr Leu Ser
        770                 775                 780
Leu Gly Gly Pro Asn Asp Ala Lys Ile Val Leu Arg Gly Phe Asp Arg
785                 790                 795                 800
Val Thr Leu Arg Pro Gly Glu Asn Thr Val Trp Gln Thr Thr Leu Thr
                805                 810                 815
Arg Arg Asp Ile Ser Asn Trp Asp Pro Val Thr Gln Asn Trp Val Val
            820                 825                 830
```

```
Thr Ser His Pro Lys Met Ile Tyr Val Gly Asn Ser Ser Arg Asn Gln
        835                 840                 845

Pro Leu Ser Ala Pro Leu Ala Pro Ser Ser
        850                 855

<210> SEQ ID NO 35
<211> LENGTH: 820
<212> TYPE: PRT
<213> ORGANISM: Dictyostelium discoideum AX3

<400> SEQUENCE: 35

Met Lys Thr Ile Lys Ser Leu Phe Leu Leu Ser Leu Leu Ile Val Asn
1               5                   10                  15

Leu Leu Ile Ser Ser Thr Tyr Gly Ser Ser Ile Arg Val Ser Ile Val
            20                  25                  30

Gly Gly Glu Glu Ala Glu Val Ile Glu Lys Pro Arg Thr Phe Gly Asn
        35                  40                  45

Lys Arg Glu Leu Lys Leu Glu Tyr Ser Gln Ile Tyr Pro Lys Lys Gln
    50                  55                  60

Leu Asn Gln Glu Asn Ile Asn Phe Met Ser Ala Arg Asp Thr Phe Val
65                  70                  75                  80

Asp Asn Leu Met Ser Lys Met Ser Ile Thr Glu Lys Ile Gly Gln Met
                85                  90                  95

Thr Gln Leu Asp Ile Thr Thr Leu Thr Ser Pro Asn Thr Ile Thr Ile
            100                 105                 110

Asn Glu Thr Thr Leu Ala Tyr Tyr Ala Lys Thr Tyr Tyr Ile Gly Ser
        115                 120                 125

Tyr Leu Asn Ser Pro Val Ser Gly Gly Leu Ala Gly Asp Ile His His
    130                 135                 140

Ile Asn Ser Ser Val Trp Leu Asp Met Ile Asn Thr Ile Gln Thr Ile
145                 150                 155                 160

Val Ile Glu Gly Ser Pro Asn Lys Ile Pro Met Ile Tyr Gly Leu Asp
                165                 170                 175

Ser Val His Gly Ala Asn Tyr Val His Lys Ala Thr Leu Phe Pro His
            180                 185                 190

Asn Thr Gly Leu Ala Ala Thr Phe Asn Ile Glu His Ala Thr Thr Ala
        195                 200                 205

Ala Gln Ile Thr Ser Lys Asp Thr Val Ala Val Gly Ile Pro Trp Val
    210                 215                 220

Phe Ala Pro Val Leu Gly Ile Gly Val Gln Pro Leu Trp Ser Arg Ile
225                 230                 235                 240

Tyr Glu Thr Phe Gly Glu Asp Pro Tyr Val Ala Ser Met Met Gly Ala
                245                 250                 255

Ala Ala Val Arg Gly Phe Gln Gly Gly Asn Asn Ser Phe Asp Gly Pro
            260                 265                 270

Ile Asn Ala Pro Ser Ala Val Cys Thr Ala Lys His Tyr Phe Gly Tyr
        275                 280                 285

Ser Asn Pro Thr Ser Gly Lys Asp Arg Thr Ala Ala Trp Ile Pro Glu
    290                 295                 300

Arg Met Leu Arg Arg Tyr Phe Leu Pro Ser Phe Ala Glu Ala Ile Thr
305                 310                 315                 320

Gly Ala Gly Ala Gly Thr Ile Met Ile Asn Ser Gly Glu Val Asn Gly
                325                 330                 335

Val Pro Met His Thr Ser Tyr Lys Tyr Leu Thr Glu Val Leu Arg Gly
```

```
                340             345             350
Glu Leu Gln Phe Glu Gly Val Ala Val Thr Asp Trp Gln Asp Ile Glu
                355                 360                 365
Lys Leu Val Tyr Phe His His Thr Ala Gly Ser Ala Glu Glu Ala Ile
            370                 375                 380
Leu Gln Ala Leu Asp Ala Gly Ile Ile Cys Leu Cys His Asp Leu Leu
385                 390                 395                 400
Ser Gln Leu Phe Ser Leu Glu Ile Leu Ala Ala Gly Thr Val Pro Glu
                405                 410                 415
Ser Arg Leu Asp Leu Ser Val Arg Arg Ile Leu Asn Leu Lys Tyr Ala
            420                 425                 430
Leu Gly Leu Phe Ser Asn Pro Tyr Pro Asn Pro Asn Ala Ala Ile Val
                435                 440                 445
Asp Thr Ile Gly Gln Val Gln Asp Arg Glu Ala Ala Ala Thr Ala
            450                 455                 460
Glu Glu Ser Ile Thr Leu Leu Leu Phe Lys Asn Asn Ile Leu Pro Leu
465                 470                 475                 480
Asn Thr Asn Thr Ile Lys Asn Val Leu Leu Thr Gly Pro Ser Ala Asp
                485                 490                 495
Ser Ile Arg Asn Leu Asn Gly Gly Trp Ser Val His Trp Gln Gly Ala
            500                 505                 510
Tyr Glu Asp Ser Glu Phe Pro Phe Gly Thr Ser Ile Leu Thr Gly Leu
                515                 520                 525
Arg Glu Ile Thr Asn Asp Thr Ala Asp Phe Asn Ile Gln Tyr Thr Ile
            530                 535                 540
Gly His Glu Ile Gly Val Pro Thr Asn Gln Thr Ser Ile Asp Glu Ala
545                 550                 555                 560
Val Glu Leu Ala Gln Ser Ser Asp Val Val Val Val Ile Gly Glu
                565                 570                 575
Leu Pro Glu Ala Glu Thr Pro Gly Asp Ile Tyr Asp Leu Ser Met Asp
            580                 585                 590
Pro Asn Glu Val Leu Leu Gln Gln Leu Val Asp Thr Gly Lys Pro
                595                 600                 605
Val Val Leu Ile Leu Val Glu Ala Arg Pro Arg Ile Leu Pro Pro Asp
            610                 615                 620
Leu Val Tyr Ser Cys Ala Ala Val Leu Met Ala Tyr Leu Pro Gly Ser
625                 630                 635                 640
Glu Gly Gly Lys Pro Ile Ala Asn Ile Leu Met Gly Asn Val Asn Pro
                645                 650                 655
Ser Gly Arg Leu Pro Leu Thr Tyr Pro Gly Thr Thr Asp Ile Gly
            660                 665                 670
Val Pro Tyr Tyr His Lys Tyr Ser Glu Asn Gly Val Thr Thr Pro Leu
                675                 680                 685
Phe Gln Phe Gly Asp Gly Leu Ser Tyr Thr Thr Phe Asn Tyr Thr Asn
            690                 695                 700
Leu Ala Cys Ser Asn Cys Lys Pro Ile Ser Gly Gln Ser Gly Asn Tyr
705                 710                 715                 720
Thr Gly Leu Gly Gln Ser Tyr Thr Phe Thr Val Thr Val Thr
                725                 730                 735
Asn Asn Gly Asn Val Gln Gly Lys Asp Ser Val Leu Leu Tyr Leu Ser
            740                 745                 750
Asp Leu Trp Ala Gln Val Thr Pro Glu Val Lys Met Leu Arg Gly Phe
                755                 760                 765
```

```
Gln Lys Val Asp Leu Met Pro Ala Lys Ser Gln Gln Ile Ser Phe Thr
        770                 775                 780

Leu Asn Ala Tyr Glu Phe Ser Phe Ile Gly Val Asp Asn Lys Ile Thr
785                 790                 795                 800

Leu Glu Ser Gly Pro Phe Ile Ile Met Val Gly Asn Gln Gln Leu Gly
                805                 810                 815

Leu Tyr Leu Gln
        820

<210> SEQ ID NO 36
<211> LENGTH: 744
<212> TYPE: PRT
<213> ORGANISM: Hypocrea jecorina QM9414

<400> SEQUENCE: 36

Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
                35                  40                  45

Ala Ala Leu Ala Lys Leu Asn Leu Gln Asp Lys Val Gly Ile Val Ser
50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
                100                 105                 110

Ala Ser Thr Trp Asp Val Asn Leu Ile Arg Glu Arg Gly Gln Phe Ile
            115                 120                 125

Gly Glu Glu Val Lys Ala Ser Gly Ile His Val Ile Leu Gly Pro Val
        130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
                180                 185                 190

Leu Asn Glu Gln Glu Leu Asn Arg Glu Thr Ile Ser Ser Asn Pro Asp
            195                 200                 205

Asp Arg Thr Leu His Glu Leu Tyr Thr Trp Pro Phe Ala Asp Ala Val
        210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
                260                 265                 270

Thr Thr Val Gln Ser Ala Asn Ser Gly Leu Asp Met Ser Met Pro Gly
            275                 280                 285

Thr Asp Phe Asn Gly Asn Asn Arg Leu Trp Gly Pro Ala Leu Thr Asn
        290                 295                 300

Ala Val Asn Ser Asn Gln Val Pro Thr Ser Arg Val Asp Asp Met Val
```

-continued

```
            305                 310                 315                 320
        Thr Arg Ile Leu Ala Ala Trp Tyr Leu Thr Gly Gln Asp Gln Ala Gly
                        325                 330                 335
        Tyr Pro Ser Phe Asn Ile Ser Arg Asn Val Gln Gly Asn His Lys Thr
                        340                 345                 350
        Asn Val Arg Ala Ile Ala Arg Asp Gly Ile Val Leu Leu Lys Asn Asp
                        355                 360                 365
        Ala Asn Ile Leu Pro Leu Lys Lys Pro Ala Ser Ile Ala Val Val Gly
                370                 375                 380
        Ser Ala Ala Ile Ile Gly Asn His Ala Arg Asn Ser Pro Ser Cys Asn
        385                 390                 395                 400
        Asp Lys Gly Cys Asp Asp Gly Ala Leu Gly Met Gly Trp Gly Ser Gly
                        405                 410                 415
        Ala Val Asn Tyr Pro Tyr Phe Val Ala Pro Tyr Asp Ala Ile Asn Thr
                        420                 425                 430
        Arg Ala Ser Ser Gln Gly Thr Gln Val Thr Leu Ser Asn Thr Asp Asn
                        435                 440                 445
        Thr Ser Ser Gly Ala Ser Ala Ala Arg Gly Lys Asp Val Ala Ile Val
                450                 455                 460
        Phe Ile Thr Ala Asp Ser Gly Glu Gly Tyr Ile Thr Val Glu Gly Asn
        465                 470                 475                 480
        Ala Gly Asp Arg Asn Asn Leu Asp Pro Trp His Asn Gly Asn Ala Leu
                        485                 490                 495
        Val Gln Ala Val Ala Gly Ala Asn Ser Asn Val Ile Val Val His Ser
                        500                 505                 510
        Val Gly Ala Ile Ile Leu Glu Gln Ile Leu Ala Leu Pro Gln Val
                        515                 520                 525
        Lys Ala Val Val Trp Ala Gly Leu Pro Ser Gln Glu Ser Gly Asn Ala
                530                 535                 540
        Leu Val Asp Val Leu Trp Gly Asp Val Ser Pro Ser Gly Lys Leu Val
        545                 550                 555                 560
        Tyr Thr Ile Ala Lys Ser Pro Asn Asp Tyr Asn Thr Arg Ile Val Ser
                        565                 570                 575
        Gly Gly Ser Asp Ser Phe Ser Glu Gly Leu Phe Ile Asp Tyr Lys His
                        580                 585                 590
        Phe Asp Asp Ala Asn Ile Thr Pro Arg Tyr Glu Phe Gly Tyr Gly Leu
                        595                 600                 605
        Ser Tyr Thr Lys Phe Asn Tyr Ser Arg Leu Ser Val Leu Ser Thr Ala
                610                 615                 620
        Lys Ser Gly Pro Ala Thr Gly Ala Val Val Pro Gly Gly Pro Ser Asp
        625                 630                 635                 640
        Leu Phe Gln Asn Val Ala Thr Val Thr Val Asp Ile Ala Asn Ser Gly
                        645                 650                 655
        Gln Val Thr Gly Ala Glu Val Ala Gln Leu Tyr Ile Thr Tyr Pro Ser
                        660                 665                 670
        Ser Ala Pro Arg Thr Pro Pro Lys Gln Leu Arg Gly Phe Ala Lys Leu
                        675                 680                 685
        Asn Leu Thr Pro Gly Gln Ser Gly Thr Ala Thr Phe Asn Ile Arg Arg
                        690                 695                 700
        Arg Asp Leu Ser Tyr Trp Asp Thr Ala Ser Gln Lys Trp Val Val Pro
        705                 710                 715                 720
        Ser Gly Ser Phe Gly Ile Ser Val Gly Ala Ser Ser Arg Asp Ile Arg
                        725                 730                 735
```

Leu Thr Ser Thr Leu Ser Val Ala
            740

<210> SEQ ID NO 37
<211> LENGTH: 763
<212> TYPE: PRT
<213> ORGANISM: Kuraishia capsulata 35M5N

<400> SEQUENCE: 37

Met Lys Ser Thr Ile Ile Ile Leu Ser Val Leu Ala Ala Ala Thr Ala
1               5                   10                  15

Lys Asn Ile Ser Lys Ala Glu Met Glu Asn Leu Glu His Trp Trp Ser
            20                  25                  30

Tyr Gly Arg Ser Asp Pro Val Tyr Pro Ser Glu Ile Ser Gly Leu
        35                  40                  45

Gly Asp Trp Gln Phe Ala Tyr Gln Arg Ala Arg Glu Ile Val Ala Leu
    50                  55                  60

Met Thr Asn Glu Glu Lys Thr Asn Leu Thr Phe Gly Ser Ser Gly Asp
65                  70                  75                  80

Thr Gly Cys Ser Gly Met Ile Ser Asp Val Pro Asp Val Asp Phe Pro
                85                  90                  95

Gly Leu Cys Leu Gln Asp Ala Gly Asn Gly Val Arg Gly Thr Asp Met
            100                 105                 110

Val Asn Ala Tyr Ala Ser Gly Leu His Val Gly Ala Ser Trp Asn Arg
        115                 120                 125

Gln Leu Ala Tyr Asp Arg Ala Val Tyr Met Gly Ala Glu Phe Arg His
    130                 135                 140

Lys Gly Val Asn Val Leu Leu Gly Pro Val Val Gly Pro Ile Gly Arg
145                 150                 155                 160

Val Ala Thr Gly Gly Arg Asn Trp Glu Gly Phe Thr Asn Asp Pro Tyr
                165                 170                 175

Leu Ala Gly Ala Leu Val Tyr Glu Thr Thr Lys Gly Ile Gln Glu Asn
            180                 185                 190

Val Ile Ala Cys Thr Lys His Phe Ile Gly Asn Glu Gln Glu Thr Asn
        195                 200                 205

Arg Asn Pro Ser Gly Thr Tyr Asn Gln Ser Val Ser Ala Asn Ile Asp
    210                 215                 220

Asp Lys Thr Met His Glu Leu Tyr Leu Trp Pro Phe Gln Asp Ser Val
225                 230                 235                 240

Arg Ala Gly Leu Gly Ser Ile Met Gly Ser Tyr Asn Arg Val Asn Asn
                245                 250                 255

Ser Tyr Ala Cys Lys Asn Ser Lys Val Leu Asn Gly Leu Leu Lys Ser
            260                 265                 270

Glu Leu Gly Phe Gln Gly Phe Val Val Ser Asp Trp Gly Gly Gln His
        275                 280                 285

Thr Gly Ile Ala Ser Ala Asn Ala Gly Leu Asp Met Ala Met Pro Ser
    290                 295                 300

Ser Thr Tyr Trp Glu Glu Gly Leu Ile Glu Ala Val Lys Asn Gly Thr
305                 310                 315                 320

Val Asp Gln Ser Arg Leu Asp Asp Met Ala Thr Arg Ile Ile Ala Ala
                325                 330                 335

Trp Tyr Lys Tyr Ala Arg Leu Asp Asp Pro Gly Phe Gly Met Pro Val
            340                 345                 350

Ser Leu Ala Glu Asp His Glu Leu Val Asp Ala Arg Asp Pro Ala Ala

```
          355                 360                 365
Ala Ser Thr Ile Phe Gln Gly Ala Val Glu Gly His Val Leu Val Lys
    370                 375                 380

Asn Glu Asn Ala Leu Pro Leu Lys Lys Pro Lys Tyr Ile Ser Leu Phe
385                 390                 395                 400

Gly Tyr Asp Gly Val Ser Asp Val Asn Thr Val Gly Gly Phe
                    405                 410                 415

Ser Phe Phe Ser Phe Asp Val Lys Ala Ile Glu Asn Lys Thr Leu Ile
                420                 425                 430

Ser Gly Gly Gly Ser Gly Thr Asn Thr Pro Ser Tyr Val Asp Ala Pro
            435                 440                 445

Phe Asn Ala Phe Val Ala Lys Ala Arg Glu Asp Asn Thr Phe Leu Ser
        450                 455                 460

Trp Asp Phe Thr Ser Ala Glu Pro Val Ala Asn Pro Ala Ser Asp Ala
465                 470                 475                 480

Cys Ile Asp Phe Ile Asn Ala Ala Ala Ser Glu Gly Tyr Asp Arg Pro
                485                 490                 495

Asn Leu Ala Asp Lys Tyr Ser Asp Lys Leu Val Glu Ala Val Ala Ser
                500                 505                 510

Gln Cys Ser Asn Thr Ile Val Val Ile His Asn Ala Gly Ile Arg Leu
            515                 520                 525

Val Asp Asn Trp Ile Glu His Glu Asn Val Thr Gly Val Ile Leu Ala
530                 535                 540

His Leu Pro Gly Gln Asp Thr Gly Thr Ser Leu Ile Glu Val Leu Tyr
545                 550                 555                 560

Gly Asn Gln Ser Pro Ser Gly Arg Leu Pro Tyr Thr Val Ala Lys Lys
                565                 570                 575

Ala Ser Asp Tyr Gly Gly Leu Leu Trp Pro Thr Glu Pro Glu Gly Asp
                580                 585                 590

Leu Asp Leu Tyr Phe Pro Gln Ser Asn Phe Thr Glu Gly Val Tyr Ile
            595                 600                 605

Asp Tyr Lys Tyr Phe Ile Gln Lys Asn Ile Thr Pro Arg Tyr Glu Phe
        610                 615                 620

Gly Tyr Gly Leu Thr Tyr Thr Thr Phe Asp Tyr Ser Glu Leu Glu Val
625                 630                 635                 640

Asp Ala Ile Thr Asn Gln Ser Tyr Leu Pro Pro Asp Cys Thr Ile Glu
                645                 650                 655

Glu Gly Gly Ala Lys Ser Leu Trp Asp Ile Val Ala Thr Val Lys Phe
                660                 665                 670

Thr Val Thr Asn Thr Gly Asp Val Ala Ala Glu Val Pro Gln Leu
            675                 680                 685

Tyr Val Gly Ile Pro Asn Gly Pro Pro Lys Val Leu Arg Gly Phe Asp
        690                 695                 700

Lys Lys Leu Ile His Pro Gly Gln Ser Glu Glu Phe Val Phe Glu Leu
705                 710                 715                 720

Thr Arg Arg Asp Leu Ser Thr Trp Asp Val Val Ala Gln Asn Trp Gly
                725                 730                 735

Leu Gln Ala Gly Thr Tyr Gln Phe Tyr Val Gly Arg Ser Val Phe Asp
                740                 745                 750

Val Pro Leu Thr Ser Ala Leu Val Phe Thr Asn
            755                 760

<210> SEQ ID NO 38
```

-continued

<211> LENGTH: 628
<212> TYPE: PRT
<213> ORGANISM: Nicotiana tabacum

<400> SEQUENCE: 38

Met Gly Arg Met Ser Ile Pro Met Met Gly Phe Val Val Leu Cys Leu
1               5                   10                  15

Trp Ala Val Val Ala Glu Gly Glu Tyr Val Lys Tyr Lys Asp Pro Lys
            20                  25                  30

Gln Pro Val Gly Ala Arg Ile Lys Asp Leu Met Lys Arg Met Thr Leu
        35                  40                  45

Glu Glu Lys Ile Gly Gln Met Thr Gln Ile Glu Arg Lys Val Ala Thr
    50                  55                  60

Ala Asp Val Met Lys Gln Asn Phe Ile Gly Ser Val Leu Ser Gly Gly
65                  70                  75                  80

Gly Ser Val Pro Ala Pro Lys Ala Ser Ala Gln Val Trp Thr Asn Met
                85                  90                  95

Val Asp Glu Ile Gln Lys Gly Ser Leu Ser Thr Arg Leu Gly Ile Pro
            100                 105                 110

Met Ile Tyr Gly Ile Asp Ala Val His Gly His Asn Asn Val Tyr Gly
        115                 120                 125

Ala Thr Ile Phe Pro His Asn Val Gly Leu Gly Val Thr Arg Asp Pro
    130                 135                 140

Asp Leu Val Lys Arg Ile Gly Ala Ala Thr Ala Leu Glu Val Arg Ala
145                 150                 155                 160

Thr Gly Ile Pro Tyr Ala Phe Ala Pro Cys Ile Ala Val Cys Arg Asn
                165                 170                 175

Pro Arg Trp Gly Arg Cys Tyr Glu Ser Tyr Ser Glu Asp His Arg Ile
            180                 185                 190

Val Arg Ser Met Thr Glu Ile Ile Pro Gly Leu Gln Gly Asp Leu Pro
        195                 200                 205

Ala Lys Ser Lys Asn Gly Val Pro Tyr Val Gly Lys Thr Lys Val
    210                 215                 220

Ala Ala Cys Ala Lys His Phe Val Gly Asp Gly Gly Thr Leu His Gly
225                 230                 235                 240

Val Asp Glu Ser Asn Thr Val Ile Ser Ser Asn Ser Leu Phe Ser Ile
                245                 250                 255

His Met Pro Ala Tyr Tyr Asp Ser Leu Arg Lys Gly Val Ala Thr Val
            260                 265                 270

Met Val Ser Tyr Ser Ser Trp Asn Gly Arg Lys Met His Ala Asn Arg
        275                 280                 285

Asp Leu Val Thr Gly Phe Leu Lys Asp Lys Leu Lys Phe Arg Gly Phe
    290                 295                 300

Val Ile Ser Asp Trp Gln Gly Ile Asp Arg Ile Thr Asp Pro Pro His
305                 310                 315                 320

Ala Asn Tyr Ser Tyr Ser Val Gln Ala Gly Ile Met Ala Gly Ile Asp
                325                 330                 335

Met Ile Met Val Pro Glu Asn Tyr Arg Glu Phe Ile Asp Thr Leu Thr
            340                 345                 350

Ser Gln Val Lys Ala Asn Ile Ile Pro Met Ser Arg Ile Asp Asp Ala
        355                 360                 365

Val Lys Arg Ile Leu Arg Val Lys Phe Val Met Gly Leu Phe Glu Asn
    370                 375                 380

Pro Met Ser Asp Pro Ser Leu Ala Asn Gln Leu Gly Ser Gln Glu His

```
                385                 390                 395                 400
Arg Glu Leu Ala Arg Glu Ala Val Arg Lys Ser Leu Val Leu Leu Lys
                    405                 410                 415

Asn Gly Lys Thr Pro Ser Gln Pro Leu Leu Pro Leu Pro Lys Lys Ala
                420                 425                 430

Pro Lys Ile Leu Val Ala Gly Thr His Ala Asp Asn Leu Gly Tyr Gln
            435                 440                 445

Cys Gly Gly Trp Thr Ile Glu Trp Gln Gly Val Ala Gly Asn Asp Leu
        450                 455                 460

Thr Ile Gly Thr Thr Ile Leu Thr Ala Ile Lys Lys Thr Val Asp Pro
465                 470                 475                 480

Ser Thr Gln Val Val Tyr Gln Gln Asn Pro Asp Ala Asn Phe Val Lys
                    485                 490                 495

Ser Asn Lys Phe Ser Tyr Ala Ile Val Val Gly Glu Val Pro Tyr
                500                 505                 510

Ala Glu Met Phe Gly Asp Ser Ser Asn Leu Thr Ile Ala Glu Pro Gly
            515                 520                 525

Pro Ser Thr Ile Ser Asn Ile Cys Gly Ser Val Lys Cys Val Val Val
        530                 535                 540

Val Val Ser Gly Arg Pro Val Val Leu Glu Pro Tyr Val Ser Lys Met
545                 550                 555                 560

Asp Ala Leu Val Ala Ala Trp Leu Pro Gly Thr Glu Gly Gln Gly Val
                    565                 570                 575

Ala Asp Ala Leu Phe Gly Asp Tyr Gly Phe Thr Gly Lys Leu Ala Arg
                580                 585                 590

Thr Trp Phe Lys Arg Val Asp Gln Leu Pro Met Asn Phe Asp Asp Ala
            595                 600                 605

His Val Asp Pro Leu Phe Pro Phe Gly Phe Gly Ile Thr Thr Lys Pro
        610                 615                 620

Val Lys Gly Tyr
625

<210> SEQ ID NO 39
<211> LENGTH: 878
<212> TYPE: PRT
<213> ORGANISM: Penicillium brasilianum IBT 20888

<400> SEQUENCE: 39

Met Gln Gly Ser Thr Ile Phe Leu Ala Phe Ala Ser Trp Ala Ser Gln
1               5                   10                  15

Val Ala Ala Ile Ala Gln Pro Ile Gln Lys His Glu Pro Gly Phe Leu
                20                  25                  30

His Gly Pro Gln Ala Ile Glu Ser Phe Ser Glu Pro Phe Tyr Pro Ser
            35                  40                  45

Pro Trp Met Asn Pro His Ala Glu Gly Trp Glu Ala Ala Tyr Gln Lys
        50                  55                  60

Ala Gln Asp Phe Val Ser Gln Leu Thr Ile Leu Glu Lys Ile Asn Leu
65                  70                  75                  80

Thr Thr Gly Val Gly Trp Glu Asn Gly Pro Cys Val Gly Asn Thr Gly
                85                  90                  95

Ser Ile Pro Arg Leu Gly Phe Lys Gly Phe Cys Thr Gln Asp Ser Pro
            100                 105                 110

Gln Gly Val Arg Phe Ala Asp Tyr Ser Ser Ala Phe Thr Ser Ser Gln
        115                 120                 125
```

```
Met Ala Ala Thr Phe Asp Arg Ser Ile Leu Tyr Gln Arg Gly Gln
    130                 135                 140

Ala Met Ala Gln Glu His Lys Ala Lys Gly Ile Thr Ile Gln Leu Gly
145                 150                 155                 160

Pro Val Ala Gly Pro Leu Gly Arg Ile Pro Glu Gly Gly Arg Asn Trp
                165                 170                 175

Glu Gly Phe Ser Pro Asp Pro Val Leu Thr Gly Ile Ala Met Ala Glu
                180                 185                 190

Thr Ile Lys Gly Met Gln Asp Thr Gly Val Ile Ala Cys Ala Lys His
        195                 200                 205

Tyr Ile Gly Asn Glu Gln Glu His Phe Arg Gln Val Gly Glu Ala Ala
210                 215                 220

Gly His Gly Tyr Thr Ile Ser Asp Thr Ile Ser Ser Asn Ile Asp Asp
225                 230                 235                 240

Arg Ala Met His Glu Leu Tyr Leu Trp Pro Phe Ala Asp Ala Val Arg
                245                 250                 255

Ala Gly Val Gly Ser Phe Met Cys Ser Tyr Ser Gln Ile Asn Asn Ser
                260                 265                 270

Tyr Gly Cys Gln Asn Ser Gln Thr Leu Asn Lys Leu Leu Lys Ser Glu
        275                 280                 285

Leu Gly Phe Gln Gly Phe Val Met Ser Asp Trp Gly Ala His His Ser
290                 295                 300

Gly Val Ser Ser Ala Leu Ala Gly Leu Asp Met Ser Met Pro Gly Asp
305                 310                 315                 320

Thr Glu Phe Asp Ser Gly Leu Ser Phe Trp Gly Ser Asn Leu Thr Ile
                325                 330                 335

Ala Ile Leu Asn Gly Thr Val Pro Glu Trp Arg Leu Asp Asp Met Ala
                340                 345                 350

Met Arg Ile Met Ala Ala Tyr Phe Lys Val Gly Leu Thr Ile Glu Asp
        355                 360                 365

Gln Pro Asp Val Asn Phe Asn Ala Trp Thr His Asp Thr Tyr Gly Tyr
370                 375                 380

Lys Tyr Ala Tyr Ser Lys Glu Asp Tyr Glu Gln Val Asn Trp His Val
385                 390                 395                 400

Asp Val Arg Ser Asp His Asn Lys Leu Ile Arg Glu Thr Ala Ala Lys
                405                 410                 415

Gly Thr Val Leu Leu Lys Asn Asn Phe His Ala Leu Pro Leu Lys Gln
                420                 425                 430

Pro Arg Phe Val Ala Val Gly Gln Asp Ala Gly Pro Asn Pro Lys
        435                 440                 445

Gly Pro Asn Gly Cys Ala Asp Arg Gly Cys Asp Gln Gly Thr Leu Ala
450                 455                 460

Met Gly Trp Gly Ser Gly Ser Thr Glu Phe Pro Tyr Leu Val Thr Pro
465                 470                 475                 480

Asp Thr Ala Ile Gln Ser Lys Val Leu Glu Tyr Gly Gly Arg Tyr Glu
                485                 490                 495

Ser Ile Phe Asp Asn Tyr Asp Asn Ala Ile Leu Ser Leu Val Ser
                500                 505                 510

Gln Pro Asp Ala Thr Cys Ile Val Phe Ala Asn Ala Asp Ser Gly Glu
        515                 520                 525

Gly Tyr Ile Thr Val Asp Asn Asn Trp Gly Asp Arg Asn Asn Leu Thr
530                 535                 540

Leu Trp Gln Asn Ala Asp Gln Val Ile Ser Thr Val Ser Ser Arg Cys
```

```
            545                 550                 555                 560
Asn Asn Thr Ile Val Val Leu His Ser Val Gly Pro Val Leu Leu Asn
                565                 570                 575
Gly Ile Tyr Glu His Pro Asn Ile Thr Ala Ile Val Trp Ala Gly Met
                580                 585                 590
Pro Gly Glu Glu Ser Gly Asn Ala Leu Val Asp Ile Leu Trp Gly Asn
                595                 600                 605
Val Asn Pro Ala Gly Arg Thr Pro Phe Thr Trp Ala Lys Ser Arg Glu
                610                 615                 620
Asp Tyr Gly Thr Asp Ile Met Tyr Glu Pro Asn Asn Gly Gln Arg Ala
625                 630                 635                 640
Pro Gln Gln Asp Phe Thr Glu Ser Ile Tyr Leu Asp Tyr Arg His Phe
                645                 650                 655
Asp Lys Ala Gly Ile Glu Pro Ile Tyr Glu Phe Gly Phe Gly Leu Ser
                660                 665                 670
Tyr Thr Thr Phe Glu Tyr Ser Asp Leu Arg Val Val Lys Lys Tyr Val
                675                 680                 685
Gln Pro Tyr Ser Pro Thr Thr Gly Thr Gly Ala Gln Ala Pro Ser Ile
                690                 695                 700
Gly Gln Pro Pro Ser Gln Asn Leu Asp Thr Tyr Lys Phe Pro Ala Thr
705                 710                 715                 720
Tyr Lys Tyr Ile Lys Thr Phe Ile Tyr Pro Tyr Leu Asn Ser Thr Val
                725                 730                 735
Ser Leu Arg Ala Ala Ser Lys Asp Pro Glu Tyr Gly Arg Thr Asp Phe
                740                 745                 750
Ile Pro Pro His Ala Arg Asp Gly Ser Pro Gln Pro Leu Asn Pro Ala
                755                 760                 765
Gly Asp Pro Val Ala Ser Gly Asn Asn Met Leu Tyr Asp Glu Leu
                770                 775                 780
Tyr Glu Val Thr Ala Gln Ile Lys Asn Thr Gly Asp Val Ala Gly Asp
785                 790                 795                 800
Glu Val Val Gln Leu Tyr Val Asp Leu Gly Gly Asp Asn Pro Pro Arg
                805                 810                 815
Gln Leu Arg Asn Phe Asp Arg Phe Tyr Leu Leu Pro Gly Gln Ser Ser
                820                 825                 830
Thr Phe Arg Ala Thr Leu Thr Arg Arg Asp Leu Ser Asn Trp Asp Ile
                835                 840                 845
Glu Ala Gln Asn Trp Arg Val Thr Glu Ser Pro Lys Arg Val Tyr Val
                850                 855                 860
Gly Arg Ser Ser Arg Asp Leu Pro Leu Ser Ser Gln Leu Glu
865                 870                 875

<210> SEQ ID NO 40
<211> LENGTH: 861
<212> TYPE: PRT
<213> ORGANISM: Penicillium decumbens JU-A10

<400> SEQUENCE: 40

Met Lys Leu Glu Trp Leu Glu Ala Thr Val Leu Ala Ala Ala Thr Val
1               5                   10                  15

Ala Ser Ala Lys Asp Leu Ala Tyr Ser Pro Pro Phe Tyr Pro Ser Pro
                20                  25                  30

Trp Ala Thr Gly Glu Gly Glu Trp Ala Glu Ala Tyr Lys Lys Ala Val
                35                  40                  45
```

```
Asp Phe Val Ser Gly Leu Thr Leu Ala Glu Lys Val Asn Ile Thr Thr
 50                  55                  60

Gly Ala Gly Trp Glu Gln Glu Arg Cys Val Gly Glu Thr Gly Gly Val
 65                  70                  75                  80

Pro Arg Leu Gly Met Trp Gly Met Cys Met Gln Asp Ser Pro Leu Gly
                 85                  90                  95

Val Arg Asn Ala Asp Tyr Ser Ser Ala Phe Pro Ala Gly Val Asn Val
            100                 105                 110

Ala Ala Thr Trp Asp Arg Arg Leu Ala Tyr Gln Arg Gly Thr Ala Met
        115                 120                 125

Gly Glu Glu His Arg Asp Lys Gly Val Asp Val Gln Leu Gly Pro Val
130                 135                 140

Ala Gly Pro Leu Gly Lys Asn Pro Asp Gly Arg Gly Trp Glu Gly
145                 150                 155                 160

Phe Ser Pro Asp Pro Val Leu Thr Gly Val Met Met Ala Glu Thr Ile
                165                 170                 175

Lys Gly Ile Gln Asp Ala Gly Val Ile Ala Cys Ala Lys His Phe Ile
            180                 185                 190

Met Asn Glu Gln Glu His Phe Arg Gln Ala Gly Glu Ala Gln Gly Tyr
        195                 200                 205

Gly Phe Asn Ile Ser Gln Ser Leu Ser Ser Asn Val Asp Asp Lys Thr
210                 215                 220

Met His Glu Leu Tyr Leu Trp Pro Phe Val Asp Ser Val Arg Ala Gly
225                 230                 235                 240

Val Gly Ser Val Met Cys Ser Tyr Asn Gln Ile Asn Asn Ser Tyr Gly
                245                 250                 255

Cys Ser Asn Ser Tyr Thr Leu Asn Lys Leu Leu Lys Gly Glu Leu Gly
            260                 265                 270

Phe Gln Gly Phe Val Met Ser Asp Trp Gly Ala His His Ser Gly Val
        275                 280                 285

Gly Asp Ala Leu Ala Gly Leu Asp Met Ser Met Pro Gly Asp Val Ile
290                 295                 300

Leu Gly Ser Pro Tyr Ser Phe Trp Gly Thr Asn Leu Thr Val Ser Val
305                 310                 315                 320

Leu Asn Ser Thr Ile Pro Glu Trp Arg Leu Asp Asp Met Ala Val Arg
                325                 330                 335

Ile Met Ala Ala Tyr Tyr Lys Val Gly Arg Asp Arg His Arg Thr Pro
            340                 345                 350

Pro Asn Phe Ser Ser Trp Thr Arg Asp Glu Tyr Gly Tyr Glu His Phe
        355                 360                 365

Ile Val Gln Glu Asn Tyr Val Lys Leu Asn Glu Arg Val Asn Val Gln
370                 375                 380

Arg Asp His Ala Asn Val Ile Arg Lys Ile Gly Ser Asp Ser Ile Val
385                 390                 395                 400

Met Leu Lys Asn Asn Gly Gly Leu Pro Leu Thr His Gln Glu Arg Leu
                405                 410                 415

Val Ala Ile Leu Gly Glu Asp Ala Gly Ser Asn Ala Tyr Gly Ala Asn
            420                 425                 430

Gly Cys Ser Asp Arg Gly Cys Asp Asn Gly Thr Leu Ala Met Gly Trp
        435                 440                 445

Gly Ser Gly Thr Ala Asn Phe Pro Tyr Leu Ile Thr Pro Glu Gln Ala
450                 455                 460

Ile Gln Asn Glu Val Leu Asn Tyr Gly Asn Gly Asp Thr Asn Val Phe
```

```
            465                 470                 475                 480
        Ala Val Thr Asp Asn Gly Ala Leu Gly Gln Met Ala Ala Leu Ala Ser
                        485                 490                 495
        Thr Ala Ser Val Ala Leu Val Phe Val Asn Ala Asp Ser Gly Glu Gly
                    500                 505                 510
        Tyr Ile Ser Val Asp Gly Asn Glu Gly Asp Arg Lys Asn Met Thr Leu
                    515                 520                 525
        Trp Lys Asn Gly Glu Glu Leu Ile Lys Thr Ala Thr Ala Asn Cys Asn
                530                 535                 540
        Asn Thr Ile Val Ile Met His Thr Pro Asn Ala Val Leu Val Asp Ser
        545                 550                 555                 560
        Trp Tyr Asp Asn Glu Asn Ile Thr Ala Ile Leu Trp Ala Gly Met Pro
                        565                 570                 575
        Gly Gln Glu Ser Gly Arg Ser Leu Val Asp Val Leu Tyr Gly Arg Thr
                    580                 585                 590
        Asn Pro Gly Gly Lys Thr Pro Phe Thr Trp Gly Lys Glu Arg Lys Asp
                    595                 600                 605
        Trp Gly Ser Pro Leu Leu Thr Lys Pro Asn Asn Gly His Gly Ala Pro
        610                 615                 620
        Gln Asp Asp Phe Thr Asp Val Leu Ile Asp Tyr Arg Arg Phe Asp Lys
        625                 630                 635                 640
        Asp Asn Val Glu Pro Ile Phe Glu Phe Gly Phe Gly Leu Ser Tyr Thr
                        645                 650                 655
        Lys Phe Glu Phe Ser Asp Ile Gln Val Lys Ala Leu Asn His Gly Glu
                    660                 665                 670
        Tyr Asn Ala Thr Val Gly Lys Thr Lys Pro Ala Pro Ser Leu Gly Lys
                    675                 680                 685
        Pro Gly Asn Ala Ser Asp His Leu Phe Pro Ser Asn Ile Asn Arg Val
                690                 695                 700
        Arg Gln Tyr Leu Tyr Pro Tyr Leu Asn Ser Thr Asp Leu Lys Ala Ser
        705                 710                 715                 720
        Ala Asn Asp Pro Asp Tyr Gly Met Asn Ala Ser Ala Tyr Ile Pro Pro
                        725                 730                 735
        His Ala Thr Asp Ser Asp Pro Gln Asp Leu Leu Pro Ala Ser Gly Pro
                    740                 745                 750
        Ser Gly Gly Asn Pro Gly Leu Phe Glu Asp Leu Ile Glu Val Thr Ala
                    755                 760                 765
        Thr Val Thr Asn Thr Gly Ser Val Thr Gly Asp Glu Val Pro Gln Leu
                770                 775                 780
        Tyr Val Ser Leu Gly Gly Ala Asp Asp Pro Val Lys Val Leu Arg Ala
        785                 790                 795                 800
        Phe Asp Arg Val Thr Ile Ala Pro Gly Gln Lys Leu Arg Trp Thr Ala
                        805                 810                 815
        Thr Leu Asn Arg Arg Asp Leu Ser Asn Trp Asp Val Pro Ser Gln Asn
                    820                 825                 830
        Trp Ile Ile Ser Asp Ala Pro Lys Lys Val Trp Val Gly Asn Ser Ser
                    835                 840                 845
        Arg Lys Leu Pro Leu Ser Ala Asp Leu Pro Lys Val Gln
                850                 855                 860

<210> SEQ ID NO 41
<211> LENGTH: 856
<212> TYPE: PRT
<213> ORGANISM: Penicillium purpurogenum KJS506
```

<400> SEQUENCE: 41

| | | | | | | | | | | | | | | |
|---|---|---|---|---|---|---|---|---|---|---|---|---|---|---|
| Met | Arg | Asn | Ser | Leu | Leu | Ile | Ser | Leu | Ala | Val | Ala | Ala | Leu | Ala | Glu |
| 1 | | | | 5 | | | | | 10 | | | | | 15 | |

| Gly | Lys | Ala | Tyr | Ser | Pro | Pro | Ala | Tyr | Pro | Thr | Pro | Trp | Ala | Ser | Gly |
|---|---|---|---|---|---|---|---|---|---|---|---|---|---|---|---|
| | | | 20 | | | | | 25 | | | | | 30 | | |

| Ala | Gly | Glu | Trp | Ala | Gln | Ala | His | Glu | Arg | Ala | Val | Glu | Phe | Val | Ser |
|---|---|---|---|---|---|---|---|---|---|---|---|---|---|---|---|
| | | 35 | | | | | 40 | | | | | 45 | | | |

| Gln | Leu | Thr | Leu | Ala | Glu | Lys | Ile | Asn | Leu | Thr | Thr | Gly | Ala | Gly | Trp |
|---|---|---|---|---|---|---|---|---|---|---|---|---|---|---|---|
| | 50 | | | | | 55 | | | | | 60 | | | | |

| Glu | Gly | Gly | Gln | Cys | Val | Gly | Asn | Thr | Gly | Ser | Ile | Pro | Arg | Leu | Gly |
|---|---|---|---|---|---|---|---|---|---|---|---|---|---|---|---|
| 65 | | | | | 70 | | | | | 75 | | | | | 80 |

| Phe | Arg | Ser | Leu | Cys | Met | Gln | Asp | Ser | Pro | Leu | Gly | Val | Arg | Asp | Thr |
|---|---|---|---|---|---|---|---|---|---|---|---|---|---|---|---|
| | | | | 85 | | | | | 90 | | | | | 95 | |

| Asp | Tyr | Asn | Thr | Ala | Phe | Pro | Ala | Gly | Val | Asn | Val | Ala | Ala | Thr | Trp |
|---|---|---|---|---|---|---|---|---|---|---|---|---|---|---|---|
| | | | 100 | | | | | 105 | | | | | 110 | | |

| Asp | Leu | Asp | Leu | Ala | Tyr | Arg | Arg | Gly | Ile | Ala | Met | Ala | Glu | Glu | His |
|---|---|---|---|---|---|---|---|---|---|---|---|---|---|---|---|
| | | | 115 | | | | | 120 | | | | | 125 | | |

| Arg | Gly | Lys | Gly | Val | Asp | Val | Gln | Leu | Gly | Pro | Val | Ala | Gly | Pro | Leu |
|---|---|---|---|---|---|---|---|---|---|---|---|---|---|---|---|
| 130 | | | | | 135 | | | | | 140 | | | | | |

| Gly | Arg | Val | Pro | Glu | Gly | Gly | Arg | Asn | Trp | Glu | Gly | Phe | Ala | Pro | Asp |
|---|---|---|---|---|---|---|---|---|---|---|---|---|---|---|---|
| 145 | | | | | 150 | | | | | 155 | | | | | 160 |

| Pro | Val | Leu | Thr | Gly | Gln | Met | Met | Ala | Ser | Thr | Ile | Gln | Gly | Met | Gln |
|---|---|---|---|---|---|---|---|---|---|---|---|---|---|---|---|
| | | | | 165 | | | | | 170 | | | | | 175 | |

| Asp | Thr | Gly | Val | Ile | Ala | Cys | Ala | Lys | His | Tyr | Ile | Gly | Asn | Glu | Gln |
|---|---|---|---|---|---|---|---|---|---|---|---|---|---|---|---|
| | | | 180 | | | | | 185 | | | | | 190 | | |

| Glu | His | Phe | Arg | Gln | Gly | Ser | Gln | Glu | Asn | Phe | Thr | Val | Ala | Asp | Ala |
|---|---|---|---|---|---|---|---|---|---|---|---|---|---|---|---|
| | | 195 | | | | | 200 | | | | | 205 | | | |

| Ile | Ser | Ser | Asn | Ile | Asp | Asp | Val | Thr | Leu | His | Glu | Leu | Tyr | Leu | Trp |
|---|---|---|---|---|---|---|---|---|---|---|---|---|---|---|---|
| | 210 | | | | | 215 | | | | | 220 | | | | |

| Pro | Phe | Ala | Asp | Ala | Val | Arg | Ala | Gly | Val | Gly | Ser | Ile | Met | Cys | Ser |
|---|---|---|---|---|---|---|---|---|---|---|---|---|---|---|---|
| 225 | | | | | 230 | | | | | 235 | | | | | 240 |

| Tyr | Asn | Gln | Leu | Asn | Asn | Ser | Tyr | Ser | Cys | Gly | Asn | Ser | Tyr | Ser | Leu |
|---|---|---|---|---|---|---|---|---|---|---|---|---|---|---|---|
| | | | | 245 | | | | | 250 | | | | | 255 | |

| Asn | His | Ile | Leu | Lys | Gly | Glu | Leu | Asp | Phe | Gln | Gly | Phe | Val | Met | Thr |
|---|---|---|---|---|---|---|---|---|---|---|---|---|---|---|---|
| | | | 260 | | | | | 265 | | | | | 270 | | |

| Asp | Trp | Gly | Ala | Gln | His | Ser | Gly | Val | Gly | Asp | Ala | Leu | Ala | Gly | Ala |
|---|---|---|---|---|---|---|---|---|---|---|---|---|---|---|---|
| | | 275 | | | | | 280 | | | | | 285 | | | |

| Asp | Met | Asp | Met | Pro | Gly | Asp | Val | Ala | Phe | Asp | Ser | Gly | Thr | Ala | Phe |
|---|---|---|---|---|---|---|---|---|---|---|---|---|---|---|---|
| | 290 | | | | | 295 | | | | | 300 | | | | |

| Trp | Gly | Thr | Asn | Leu | Thr | Ile | Ala | Val | Leu | Asn | Gly | Thr | Val | Pro | Glu |
|---|---|---|---|---|---|---|---|---|---|---|---|---|---|---|---|
| 305 | | | | | 310 | | | | | 315 | | | | | 320 |

| Trp | Arg | Ile | Asp | Asp | Met | Ala | Val | Arg | Ile | Met | Ser | Ala | Phe | Tyr | Lys |
|---|---|---|---|---|---|---|---|---|---|---|---|---|---|---|---|
| | | | | 325 | | | | | 330 | | | | | 335 | |

| Val | Gly | Arg | Asp | Arg | Thr | Gln | Val | Pro | Ile | Asn | Phe | Ala | Ser | Trp | Thr |
|---|---|---|---|---|---|---|---|---|---|---|---|---|---|---|---|
| | | | 340 | | | | | 345 | | | | | 350 | | |

| Leu | Asp | Thr | Tyr | Gly | Asn | Glu | Tyr | Tyr | Tyr | Ala | Gly | Glu | Gly | Tyr | Lys |
|---|---|---|---|---|---|---|---|---|---|---|---|---|---|---|---|
| | | | 355 | | | | | 360 | | | | | 365 | | |

| Glu | Ile | Asn | Gln | His | Val | Asp | Val | Arg | Gly | Asp | His | Ala | Glu | Val | Val |
|---|---|---|---|---|---|---|---|---|---|---|---|---|---|---|---|
| | | 370 | | | | | 375 | | | | | 380 | | | |

| Arg | Glu | Ile | Gly | Ser | Ala | Ser | Ile | Val | Leu | Leu | Lys | Asn | Val | Asp | Asp |
|---|---|---|---|---|---|---|---|---|---|---|---|---|---|---|---|
| 385 | | | | | 390 | | | | | 395 | | | | | 400 |

| Ala | Leu | Pro | Leu | Thr | Gly | Ser | Glu | Arg | Phe | Val | Ala | Val | Phe | Gly | Glu |
|---|---|---|---|---|---|---|---|---|---|---|---|---|---|---|---|

```
                405                 410                 415
Asp Ala Gly Ser Asn Pro Asp Gly Val Asn Gly Cys Ser Asp Arg Gly
            420                 425                 430

Cys Asp Asn Gly Thr Leu Ala Met Gly Trp Gly Ser Gly Thr Ala Asn
            435                 440                 445

Phe Pro Tyr Leu Val Thr Pro Glu Gln Ala Ile Gln Ala Glu Val Val
450                 455                 460

Lys Asn Gly Gly Met Phe Thr Ala Ile Thr Asp Ser Gly Ala Thr Asn
465                 470                 475                 480

Thr Thr Ala Asn Thr Val Ala Ala Gln Ala Ser Ala Cys Leu Val Phe
                485                 490                 495

Ala Asn Ala Asp Ser Gly Glu Gly Tyr Ile Thr Val Asp Gly Asn Val
            500                 505                 510

Gly Asp Arg Lys Asn Leu Thr Leu Trp Gln Asn Gly Glu Ala Met Ile
            515                 520                 525

Ser Ala Val Ala Gly Asn Cys Asn Asn Thr Ile Val Ile Leu His Thr
530                 535                 540

Val Gly Pro Val Leu Ile Glu Asp Trp Val Asn His Pro Asn Ile Thr
545                 550                 555                 560

Ala Val Leu Trp Ala Gly Leu Pro Gly Glu Gln Ser Gly Asn Ser Leu
                565                 570                 575

Val Asp Val Leu Tyr Gly Ser Val Asn Pro Gly Gly Lys Thr Pro Phe
            580                 585                 590

Thr Trp Gly Lys Gln Arg Ser Asp Trp Gly Val Asp Val Ile Tyr Glu
            595                 600                 605

Pro Ser Asn Gly Asp Gly Ala Pro Gln Gln Asp Phe Thr Glu Gly Ile
610                 615                 620

Phe Ile Asp Tyr Arg His Phe Asp Lys Tyr Asn Ile Thr Pro Thr Tyr
625                 630                 635                 640

Glu Phe Gly Tyr Gly Leu Ser Tyr Ser Thr Phe Ser Phe Ser Asp Leu
                645                 650                 655

Lys Val Thr Pro Leu Ala Ala Ser Pro Tyr Gln Pro Ala Lys Gly Gln
            660                 665                 670

Ser Gly Pro Ala Pro Val Leu Gly Lys Val Leu Asn Ala Thr Ala Tyr
            675                 680                 685

Leu Phe Pro Asp Tyr Ile Lys Arg Ile Glu Ala Phe Ile Tyr Pro Trp
690                 695                 700

Leu Asn Ser Thr Asp Leu Lys Thr Ser Ser Gly Asp Pro Asn Tyr Gly
705                 710                 715                 720

Trp Ser Thr Ser Lys Tyr Val Pro Asp Gly Ala Gln Asp Gly Ser Pro
                725                 730                 735

Gln Pro Val Asn Pro Ala Gly Gly Ala Pro Gly Gly Asn Pro Ala Leu
            740                 745                 750

Tyr Asp Pro Val Ala Glu Ile Thr Val Thr Val Lys Asn Thr Gly Glu
            755                 760                 765

Val Ala Gly Val Glu Val Pro Gln Leu Tyr Val Ser Leu Gly Gly Pro
770                 775                 780

Ser Asp Ala Pro Lys Val Leu Arg Gly Phe Gly Arg Leu Pro Leu Ala
785                 790                 795                 800

Pro Val Asn Glu Thr Gln Trp Thr Ala Thr Leu Thr Arg Arg Asp Val
                805                 810                 815

Ser Asn Trp Asp Thr Val Ser Gln Asn Trp Val Val Thr Asp Tyr Thr
            820                 825                 830
```

```
Lys Thr Val Tyr Val Gly Asn Ser Ser Arg Asn Leu Pro Leu Gln Gln
        835                 840                 845

Thr Leu Ala Leu Asn Ile Gly Lys
        850                 855

<210> SEQ ID NO 42
<211> LENGTH: 866
<212> TYPE: PRT
<213> ORGANISM: Periconia sp. BCC 2871

<400> SEQUENCE: 42

Met Ala Ser Trp Leu Ala Pro Ala Leu Leu Ala Val Gly Leu Ala Ser
1               5                   10                  15

Ala Gln Ala Pro Phe Pro Asn Gly Ser Ser Pro Leu Asn Asp Ile Thr
            20                  25                  30

Ser Pro Pro Phe Tyr Pro Ser Pro Trp Met Asp Pro Ser Ala Ala Gly
        35                  40                  45

Trp Ala Glu Ala Tyr Thr Lys Ala Gln Ala Phe Val Arg Gln Leu Thr
    50                  55                  60

Leu Leu Glu Lys Val Asn Leu Thr Thr Gly Val Gly Trp Glu Gly Glu
65                  70                  75                  80

Ala Cys Val Gly Asn Thr Gly Ser Ile Pro Arg Leu Gly Phe Pro Gly
                85                  90                  95

Phe Cys Thr Gln Asp Ser Pro Leu Gly Val Arg Phe Ala Asp Tyr Val
            100                 105                 110

Ser Ala Phe Thr Ala Gly Gly Thr Ile Ala Ala Ser Trp Asp Arg Ser
        115                 120                 125

Glu Phe Tyr Arg Arg Gly Tyr Gln Met Gly Val Glu His Arg Gly Lys
    130                 135                 140

Gly Val Asp Val Gln Leu Gly Pro Val Val Gly Pro Ile Gly Arg His
145                 150                 155                 160

Pro Lys Gly Gly Arg Asn Trp Glu Gly Phe Ser Pro Asp Pro Val Leu
                165                 170                 175

Ser Gly Ile Ala Val Ala Glu Thr Val Lys Gly Ile Gln Asp Ala Gly
            180                 185                 190

Val Ile Ala Cys Thr Lys His Phe Ile Leu Asn Glu Gln Glu His Phe
        195                 200                 205

Arg Gln Pro Gly Asn Val Gly Asp Phe Gly Phe Val Asp Ala Val Ser
    210                 215                 220

Ala Asn Leu Ala Asp Lys Thr Leu His Glu Leu Tyr Leu Trp Pro Phe
225                 230                 235                 240

Ala Asp Ala Val Arg Ala Gly Thr Gly Ser Ile Met Cys Ser Tyr Asn
                245                 250                 255

Lys Ala Asn Asn Ser Gln Val Cys Gln Asn Ser Tyr Leu Gln Asn Tyr
            260                 265                 270

Ile Leu Lys Gly Glu Leu Gly Phe Gln Gly Phe Thr Met Ser Asp Trp
        275                 280                 285

Asp Ala Gln His Ser Gly Val Ala Ser Thr Leu Ala Gly Leu Asp Met
    290                 295                 300

Asn Met Pro Gly Asp Thr Asp Phe Asp Ser Gly Phe Ser Phe Trp Gly
305                 310                 315                 320

Pro Asn Met Thr Leu Ser Ile Ile Asn Gly Thr Val Pro Glu Trp Arg
                325                 330                 335

Leu Asp Asp Ala Ala Thr Arg Ile Met Ala Ala Tyr Tyr Leu Val Gly
```

```
                340                 345                 350
Arg Asp Arg His Ala Val Pro Val Asn Phe Asn Ser Trp Ser Lys Asp
            355                 360                 365

Thr Tyr Gly Tyr Gln His Ala Tyr Ala Lys Val Gly Tyr Gly Leu Ile
370                 375                 380

Asn Gln His Val Asp Val Arg Ala Asp His Phe Lys Ser Ile Arg Thr
385                 390                 395                 400

Ala Ala Ala Lys Ser Thr Val Leu Leu Lys Asn Asn Gly Val Leu Pro
            405                 410                 415

Leu Lys Gly Thr Glu Lys Tyr Thr Ala Val Phe Gly Asn Asp Ala Gly
            420                 425                 430

Glu Ala Gln Tyr Gly Pro Asn Gly Cys Ala Asp His Gly Cys Asp Asn
            435                 440                 445

Gly Thr Leu Ala Met Gly Trp Gly Ser Gly Thr Ala Asp Tyr Pro Tyr
            450                 455                 460

Leu Val Thr Pro Leu Glu Ala Ile Lys Arg Thr Val Gly Asp His Gly
465                 470                 475                 480

Gly Val Ile Ala Ser Val Thr Asp Asn Tyr Ala Phe Ser Gln Ile Met
                485                 490                 495

Ala Leu Ala Lys Gln Ala Thr His Ala Ile Val Phe Val Asn Ala Asp
            500                 505                 510

Ser Gly Glu Gly Tyr Ile Thr Val Asp Gly Asn Glu Gly Asp Arg Asn
            515                 520                 525

Asn Leu Thr Leu Trp Gln Asn Gly Glu Glu Leu Val Arg Asn Val Ser
            530                 535                 540

Gly Tyr Cys Asn Asn Thr Ile Val Val Ile His Ser Val Gly Pro Val
545                 550                 555                 560

Leu Val Asp Ser Phe Asn Asn Ser Pro Asn Val Ser Ala Ile Leu Trp
                565                 570                 575

Ala Gly Leu Pro Gly Gln Glu Ser Gly Asn Ala Ile Thr Asp Val Leu
            580                 585                 590

Tyr Gly Arg Val Asn Pro Gly Gly Lys Leu Pro Phe Thr Ile Gly Lys
            595                 600                 605

Ser Ala Glu Glu Tyr Gly Pro Asp Ile Ile Tyr Glu Pro Thr Ala Gly
            610                 615                 620

His Gly Ser Pro Gln Ala Asn Phe Glu Glu Gly Val Phe Ile Asp Tyr
625                 630                 635                 640

Arg Ser Phe Asp Lys Lys Asn Ile Thr Pro Val Tyr Glu Phe Gly Phe
                645                 650                 655

Gly Leu Ser Tyr Thr Asn Phe Ser Tyr Ser Asn Leu Val Val Thr Arg
            660                 665                 670

Val Asn Ala Pro Ala Tyr Val Pro Thr Thr Gly Asn Thr Thr Ala Ala
            675                 680                 685

Pro Thr Leu Gly Asn Ser Ser Lys Asp Ala Ser Asp Tyr Gln Trp Pro
            690                 695                 700

Ala Asn Leu Thr Tyr Val Asn Lys Tyr Ile Tyr Pro Tyr Leu Asn Ser
705                 710                 715                 720

Thr Asp Leu Lys Glu Ala Ser Asn Asp Pro Gly Tyr Gly Ile Glu His
                725                 730                 735

Glu Tyr Pro Glu Gly Ala Thr Asp Gly Ser Pro Gln Pro Arg Ile Ala
            740                 745                 750

Ala Gly Gly Gly Pro Gly Gly Asn Pro Gln Leu Trp Asp Val Leu Tyr
            755                 760                 765
```

```
Lys Val Thr Ala Thr Val Thr Asn Asn Gly Ala Val Ala Gly Asp Glu
        770                 775                 780

Val Ala Gln Leu Tyr Val Ser Leu Gly Gly Pro Glu Asp Pro Pro Val
785                 790                 795                 800

Val Leu Arg Asn Phe Asp Arg Leu Thr Ile Ala Pro Gly Gln Ser Val
            805                 810                 815

Glu Phe Thr Ala Asp Ile Thr Arg Arg Asp Val Ser Asn Trp Asp Thr
                820                 825                 830

Val Ser Gln Asn Trp Val Ile Ser Asn Ser Thr Lys Thr Val Tyr Val
        835                 840                 845

Gly Ala Ser Ser Arg Lys Leu Pro Leu Lys Ala Thr Leu Pro Ser Ser
850                 855                 860

Ser Tyr
865

<210> SEQ ID NO 43
<211> LENGTH: 871
<212> TYPE: PRT
<213> ORGANISM: Phaeosphaeria avenaria WAC1293

<400> SEQUENCE: 43

Met Ala Leu Ala Val Ala Phe Phe Val Thr Gln Val Leu Ala Gln Gln
1               5                   10                  15

Tyr Pro Thr Ser Asn Thr Ser Ser Pro Ala Ala Asn Ser Ser Ser Pro
            20                  25                  30

Leu Asp Asn Ala Val Ser Pro Pro Phe Tyr Pro Ser Pro Trp Ile Glu
        35                  40                  45

Gly Leu Gly Asp Trp Glu Ala Ala Tyr Gln Lys Ala Gln Ala Phe Val
    50                  55                  60

Ser Gln Leu Thr Leu Leu Glu Lys Val Asn Leu Thr Thr Gly Thr Gly
65                  70                  75                  80

Trp Gln Ser Asp His Cys Val Gly Asn Thr Gly Val Pro Arg Leu
                85                  90                  95

Asn Phe Thr Gly Ile Cys Asn Gln Asp Ala Pro Leu Gly Val Arg Phe
            100                 105                 110

Ala Asp Tyr Val Ser Ala Phe Pro Ser Gly Gly Thr Ile Ala Ala Ala
        115                 120                 125

Trp Asp Arg Gly Glu Trp Tyr Leu Arg Gly Tyr Gln Met Gly Ser Glu
130                 135                 140

His Arg Ser Lys Gly Val Asp Val Gln Leu Gly Pro Val Val Gly Pro
145                 150                 155                 160

Leu Gly Arg Asn Pro Lys Gly Gly Arg Asn Trp Glu Gly Phe Ser Pro
            165                 170                 175

Asp Pro Tyr Leu Ser Gly Ile Ala Ser Ala Glu Ser Val Arg Gly Ile
        180                 185                 190

Gln Asp Ala Gly Val Ile Ala Cys Thr Lys His Tyr Ile Met Asn Glu
    195                 200                 205

Gln Glu His Phe Arg Gln Pro Gly Asn Phe Glu Asp Gln Gly Phe Val
210                 215                 220

Asp Ala Leu Ser Ser Asn Leu Asp Lys Thr Leu His Glu Leu Tyr
225                 230                 235                 240

Leu Trp Pro Phe Ala Asp Ala Val Arg Ala Gly Thr Gly Ser Ile Met
            245                 250                 255

Cys Ser Tyr Asn Lys Val Asn Asn Ser Gln Ala Cys Gln Asn Ser Tyr
```

```
            260                 265                 270
Leu Gln Asn Tyr Ile Leu Lys Gly Glu Leu Gly Phe Gln Gly Phe Ile
            275                 280                 285
Met Ser Asp Trp Asp Ala Gln His Ser Gly Val Ala Ser Thr Phe Ala
        290                 295                 300
Gly Leu Asp Met Thr Met Pro Gly Asp Thr Asp Phe Asn Ser Gly Lys
305                 310                 315                 320
Thr Phe Trp Gly Thr Asn Phe Thr Thr Ser Ile Leu Asn Gly Thr Val
                325                 330                 335
Pro Gln Trp Arg Leu Asp Asp Ala Val Thr Arg Ile Met Ala Ala Phe
                340                 345                 350
Tyr Tyr Val Gly Arg Asp Lys Ala Arg Ile Pro Val Asn Phe Asp Ser
        355                 360                 365
Trp Ser Arg Asp Thr Tyr Gly Phe Asp His Tyr Gly Lys Ala Gly
        370                 375                 380
Tyr Ser Gln Ile Asn Ser His Val Asp Val Arg Ala Asp His Phe Arg
385                 390                 395                 400
Ser Ile Arg Arg Thr Ala Ala Met Ser Thr Val Leu Leu Lys Asn Glu
                405                 410                 415
Gly Ala Leu Pro Leu Thr Gly Ser Glu Lys Trp Thr Ala Val Phe Gly
                420                 425                 430
Asp Asp Ala Gly Glu Gly Gln Leu Gly Pro Asn Gly Phe Pro Asp His
        435                 440                 445
Gly Gly Asn Asn Gly Thr Leu Ala Met Gly Trp Gly Ser Gly Thr Ser
        450                 455                 460
Asp Tyr Pro Tyr Leu Val Thr Pro Leu Glu Ser Ile Lys Ala Thr Val
465                 470                 475                 480
Ala Gln Asn Gly Gly Ile Val Thr Ser Val Thr Asp Asn Trp Ala Tyr
                485                 490                 495
Thr Gln Ile Gln Thr Leu Ala Lys Gln Ala Ser Val Ala Ile Val Phe
                500                 505                 510
Val Asn Ala Asp Ser Gly Glu Gly Tyr Ile Thr Val Asp Gly Asn Ala
                515                 520                 525
Gly Asp Arg Asn Asn Leu Thr Leu Trp Gln Asp Gly Asp Thr Leu Ile
        530                 535                 540
Lys Asn Val Ser Ser Leu Cys Asn Asn Thr Ile Val Ile His Ser
545                 550                 555                 560
Val Gly Pro Val Leu Val Asn Ser Phe Tyr Asp Ser Glu Asn Val Thr
                565                 570                 575
Ala Ile Leu Trp Ala Gly Leu Pro Gly Gln Glu Ser Gly Asn Ala Ile
                580                 585                 590
Ala Asp Ile Leu Tyr Gly Arg His Asn Pro Gly Gly Lys Leu Pro Phe
        595                 600                 605
Thr Ile Gly Ser Asp Ala Ala Glu Tyr Gly Pro Asp Leu Ile Tyr Glu
        610                 615                 620
Pro Thr Asn Asn Ser Ser Ser Pro Gln Asp Asn Phe Glu Glu Gly Val
625                 630                 635                 640
Phe Ile Asp Tyr Arg Ala Phe Asp Lys Gln Asn Val Thr Pro Ile Tyr
                645                 650                 655
Glu Phe Gly Phe Gly Leu Ser Tyr Thr Lys Phe Ser Tyr Ser Asn Leu
                660                 665                 670
Thr Val Lys Lys Ala Asn Ala Gly Ala Tyr Thr Pro Ala Thr Gly Gln
                675                 680                 685
```

```
Ser Lys Ala Pro Thr Leu Gly Asn Phe Ser Thr Asp Ala Ser Gln
    690                 695                 700

Tyr Gln Trp Pro Ser Asp Phe Thr Tyr Ile Asp Thr Phe Ile Tyr Pro
705                 710                 715                 720

Tyr Leu Asn Ser Thr Asp Leu Lys Thr Ala Ser Gln Asp Pro Glu Tyr
                725                 730                 735

Gly Leu Asn Tyr Thr Trp Pro Ala Gly Ala Thr Asp Gly Thr Pro Gln
                740                 745                 750

Ala Arg Ile Pro Ala Gly Gly Ala Pro Gly Gly Asn Pro Gln Leu Trp
                755                 760                 765

Asp Val Leu Phe Ser Val Glu Ala Thr Ile Thr Asn Asn Gly Thr Val
                770                 775                 780

Pro Gly Asp Glu Val Val Gln Leu Tyr Val Ser Leu Gly Asn Pro Asp
785                 790                 795                 800

Asp Pro Lys Ile Val Leu Arg Gly Phe Asp Arg Leu Ser Ile Gln Pro
                805                 810                 815

Gly Lys Thr Ala Thr Phe His Ala Asp Ile Thr Arg Arg Asp Val Ser
                820                 825                 830

Asn Trp Asp Val Ala Ser Gln Asn Trp Val Ile Thr Ser Ala Pro Lys
                835                 840                 845

Thr Val Tyr Val Gly Ala Ser Ser Arg Lys Leu Pro Leu Thr Ala Thr
                850                 855                 860

Leu Asp Thr Ser Asp Phe Gln
865                 870

<210> SEQ ID NO 44
<211> LENGTH: 717
<212> TYPE: PRT
<213> ORGANISM: Rhizomucor miehei NRRL 5282

<400> SEQUENCE: 44

Met Phe Ala Lys Thr Ala Leu Ala Leu Leu Thr Ala Trp Ser Ala Met
1               5                   10                  15

Gln Gly Val Ala Gly Gly Ile Asn Phe Arg Ser Trp Asp Glu Ala His
                20                  25                  30

Glu Leu Ala Lys Ala Val Thr Asp Gln Met Ser Leu Glu Gln Trp Val
            35                  40                  45

Asn Ile Thr Thr Gly Thr Gly Trp Met Lys Ser Glu Cys Val Gly Asn
        50                  55                  60

Thr Arg Pro Thr Lys Asn Pro Asp Phe Pro Ser Leu Cys Leu Glu Asp
65                  70                  75                  80

Gly Pro Pro Gly Ile Arg Phe Gly Asp Asn Val Thr Ala Gly Val Ser
                85                  90                  95

Gly Ile Thr Ala Ala Ala Ser Phe Asp Lys Glu Gln Leu Leu Lys Arg
                100                 105                 110

Gly Gln Tyr Met Gly Lys Glu Phe Arg Gly Lys Gly Ile His Phe Ala
            115                 120                 125

Leu Gly Pro Cys Val Asp Ile Met Arg Ala Pro Gln Thr Gly Arg Gly
        130                 135                 140

Trp Glu Gly Phe Gly Glu Asp Pro Tyr Leu Ala Gly Val Ala Gly Ala
145                 150                 155                 160

Leu Thr Val Glu Gly Ile Gln Ser Gln Gly Val Ile Ala Thr Ala Lys
                165                 170                 175

His Tyr Ile Gly Asn Asn Gln Glu Thr Asn Arg Lys Asn Ser Thr Ser
```

```
            180                 185                 190
Asn Ile Ser Arg Arg Ala Leu His Glu Ile Trp Thr Trp Pro Tyr Ala
            195                 200                 205
Arg Met Ile Glu Ala Gly Ile Gly Ala Ile Met Cys Ser Tyr Asn Gln
            210                 215                 220
Leu His Gly Thr Trp Ala Cys Glu Asp Glu Tyr Thr Leu Asn Thr Ile
225                 230                 235                 240
Leu Lys Gln Glu Tyr Asn Phe Arg Gly Leu Ile Met Ser Asp Trp Gly
            245                 250                 255
Ala Thr His Ser Thr Ala Pro Ala Ile Asn Ser Gly Leu Asp Met Thr
            260                 265                 270
Met Pro Gly Asp Leu Glu Met Gly Asp Asn Tyr Thr Tyr Phe Gly Val
            275                 280                 285
Asn Met Thr Lys Ala Val Arg Asn Gly Glu Val Thr Glu Glu Arg Ala
            290                 295                 300
Gln Glu Met Ala Thr Arg Ile Ile Ala Ala Tyr Tyr Lys Leu Gly Gln
305                 310                 315                 320
Asp Glu Gly Phe Pro Glu Met Ala Ile Arg Ala Phe Gln Arg Asp Glu
            325                 330                 335
Ala Pro Tyr Val Pro Val Gln Glu Asp His Gly Lys Leu Val Arg Glu
            340                 345                 350
Met Gly Ala Ala Ala Cys Thr Leu Leu Lys Asn Glu Asp Lys Val Leu
            355                 360                 365
Pro Ile Ser Ser Ser Val Lys Lys Ile Ala Ile Gly Ser Asp Ala
            370                 375                 380
Gly Pro Asn Pro Asp Gly Leu His Asp Pro Asp Cys Val Asp Gln Gly
385                 390                 395                 400
Cys Ala Lys Gly Thr Thr Ala Met Gly Trp Gly Ser Gly Thr Val Asp
            405                 410                 415
Phe Pro Tyr Leu Val Thr Pro Leu Asp Gly Ile Thr Ala Arg Ala Gly
            420                 425                 430
Asp Asp Val Glu Val Val His Thr Phe Asp Asp Trp Asp Glu Glu Gly
            435                 440                 445
Ala Ala Glu Leu Ala Lys Asp Ala Asp Ile Ala Phe Val Phe Ser Met
            450                 455                 460
Thr Lys Ala Gly Glu Glu Tyr Ile Val Val Asp Gly Asn His Asp Arg
465                 470                 475                 480
Lys Asn Leu Ser Leu Trp Asn Asn Gly Asp Asn Leu Ile Arg Ala Val
            485                 490                 495
Ala Asp Ala Asn Glu Asn Thr Val Val Val Ile His Ser Val Gly Pro
            500                 505                 510
Val Asp Met Pro Trp Ile Asp His Pro Asn Ile Lys Ala Val Val Trp
            515                 520                 525
Pro His Leu Pro Gly Gln Glu Thr Gly Asn Ser Leu Ala Asp Val Leu
            530                 535                 540
Phe Gly Asp Val Asn Pro Ser Gly Pro Ser Ser Ile Ala Pro Leu Ala
545                 550                 555                 560
Gly Leu Gln Arg Thr Thr Leu Leu Ile Glu Tyr Thr Glu Glu Leu Asn
            565                 570                 575
Val Gly Tyr Arg His Phe Asp Ala Asn Asn Ile Glu Pro Leu Phe Pro
            580                 585                 590
Phe Gly His Gly Leu Ser Tyr Thr Thr Phe Glu Tyr Asn Lys Leu Lys
            595                 600                 605
```

```
Val Lys Lys Gly Arg Lys Lys Asp Asn Ser Leu Ile Arg Ala Thr Ile
610                 615                 620

Tyr Ile Arg Asn Thr Gly Glu Val Asp Gly Ala Glu Ile Pro Gln Ala
625                 630                 635                 640

Tyr Ile Ser Phe Pro Ala Cys Glu Pro Pro Lys Val Leu Arg Gly Phe
                645                 650                 655

Glu Lys Val Phe Leu Lys Ala Gly Lys His Ala Lys Val Glu Phe Asn
                660                 665                 670

Phe Gly Glu Thr Glu Leu Ser Ile Trp Asp Pro Glu Thr Glu Glu Trp
            675                 680                 685

Thr Val Pro Ser Gly Glu Tyr Thr Leu His Ile Gly Ala Ser Ser Arg
        690                 695                 700

Asp Ile Arg Gln Thr Ala Lys Phe Arg Leu Tyr Leu Tyr
705                 710                 715

<210> SEQ ID NO 45
<211> LENGTH: 876
<212> TYPE: PRT
<213> ORGANISM: Saccharomycopsis fibuligera

<400> SEQUENCE: 45

Met Leu Met Ile Val Gln Leu Leu Val Phe Ala Leu Gly Leu Ala Val
1               5                   10                  15

Ala Val Pro Ile Gln Asn Tyr Thr Gln Ser Pro Ser Gln Arg Asp Glu
            20                  25                  30

Ser Ser Gln Trp Val Ser Pro His Tyr Tyr Pro Thr Pro Gln Gly Gly
        35                  40                  45

Arg Leu Gln Asp Val Trp Gln Glu Ala Tyr Ala Arg Ala Lys Ala Ile
    50                  55                  60

Val Gly Gln Met Thr Ile Val Glu Lys Val Asn Leu Thr Thr Gly Thr
65                  70                  75                  80

Gly Trp Gln Leu Asp Pro Cys Val Gly Asn Thr Gly Ser Val Pro Arg
                85                  90                  95

Phe Gly Ile Pro Asn Leu Cys Leu Gln Asp Gly Pro Leu Gly Val Arg
            100                 105                 110

Phe Ala Asp Phe Val Thr Gly Tyr Pro Ser Gly Leu Ala Thr Gly Ala
        115                 120                 125

Thr Phe Asn Lys Asp Leu Phe Leu Gln Arg Gly Gln Ala Leu Gly His
    130                 135                 140

Glu Phe Asn Ser Lys Gly Val His Ile Ala Leu Gly Pro Ala Val Gly
145                 150                 155                 160

Pro Leu Gly Val Lys Ala Arg Gly Gly Arg Asn Phe Glu Ala Phe Gly
                165                 170                 175

Ser Asp Pro Tyr Leu Gln Gly Thr Ala Ala Ala Thr Ile Lys Gly
            180                 185                 190

Leu Gln Glu Asn Asn Val Met Ala Cys Val Lys His Phe Ile Gly Asn
        195                 200                 205

Glu Gln Glu Lys Tyr Arg Gln Pro Asp Asp Ile Asn Pro Ala Thr Asn
    210                 215                 220

Gln Thr Thr Lys Glu Ala Ile Ser Ala Asn Ile Pro Asp Arg Ala Met
225                 230                 235                 240

His Ala Leu Tyr Leu Trp Pro Phe Ala Asp Ser Val Arg Ala Gly Val
                245                 250                 255

Gly Ser Val Met Cys Ser Tyr Asn Arg Val Asn Asn Thr Tyr Ala Cys
```

```
                260                265                270
Glu Asn Ser Tyr Met Met Asn His Leu Leu Lys Glu Glu Leu Gly Phe
                275                280                285
Gln Gly Phe Val Val Ser Asp Trp Gly Ala Gln Leu Ser Gly Val Tyr
                290                295                300
Ser Ala Ile Ser Gly Leu Asp Met Ser Met Pro Gly Glu Val Tyr Gly
305                310                315                320
Gly Trp Asn Thr Gly Thr Ser Phe Trp Gly Gln Asn Leu Thr Lys Ala
                325                330                335
Ile Tyr Asn Glu Thr Val Pro Ile Glu Arg Leu Asp Asp Met Ala Thr
                340                345                350
Arg Ile Leu Ala Ala Leu Tyr Ala Thr Asn Ser Phe Pro Thr Glu Asp
                355                360                365
His Leu Pro Asn Phe Ser Ser Trp Thr Thr Lys Glu Tyr Gly Asn Lys
                370                375                380
Tyr Tyr Ala Asp Asn Thr Thr Glu Ile Val Lys Val Asn Tyr Asn Val
385                390                395                400
Asp Pro Ser Asn Asp Phe Thr Glu Asp Thr Ala Leu Lys Val Ala Glu
                405                410                415
Glu Ser Ile Val Leu Leu Lys Asn Glu Asn Asn Thr Leu Pro Ile Ser
                420                425                430
Pro Glu Lys Ala Lys Arg Leu Leu Leu Ser Gly Ile Ala Ala Gly Pro
                435                440                445
Asp Pro Ile Gly Tyr Gln Cys Glu Asp Gln Ser Cys Thr Asn Gly Ala
                450                455                460
Leu Phe Gln Gly Trp Gly Ser Gly Ser Val Gly Ser Pro Lys Tyr Gln
465                470                475                480
Val Thr Pro Phe Glu Glu Ile Ser Tyr Leu Ala Arg Lys Asn Lys Met
                485                490                495
Gln Phe Asp Tyr Ile Arg Glu Ser Tyr Asp Leu Ala Gln Val Thr Lys
                500                505                510
Val Ala Ser Asp Ala His Leu Ser Ile Val Val Ser Ala Ala Ser
                515                520                525
Gly Glu Gly Tyr Ile Thr Val Asp Gly Asn Gln Gly Asp Arg Lys Asn
                530                535                540
Leu Thr Leu Trp Asn Asn Gly Asp Lys Leu Ile Glu Thr Val Ala Glu
545                550                555                560
Asn Cys Ala Asn Thr Val Val Val Thr Ser Thr Gly Gln Ile Asn
                565                570                575
Phe Glu Gly Phe Ala Asp His Pro Asn Val Thr Ala Ile Val Trp Ala
                580                585                590
Gly Pro Leu Gly Asp Arg Ser Gly Thr Ala Ile Ala Asn Ile Leu Phe
                595                600                605
Gly Lys Ala Asn Pro Ser Gly His Leu Pro Phe Thr Ile Ala Lys Thr
                610                615                620
Asp Asp Asp Tyr Ile Pro Ile Glu Thr Tyr Ser Pro Ser Ser Gly Glu
625                630                635                640
Pro Glu Asp Asn His Leu Val Glu Asn Asp Leu Leu Val Asp Tyr Arg
                645                650                655
Tyr Phe Glu Glu Lys Asn Ile Glu Pro Arg Tyr Ala Phe Gly Tyr Gly
                660                665                670
Leu Ser Tyr Asn Glu Tyr Glu Val Ser Asn Ala Lys Val Ser Ala Ala
                675                680                685
```

```
Lys Lys Val Asp Glu Leu Pro Glu Pro Ala Thr Tyr Leu Ser Glu
    690                 695                 700

Phe Ser Tyr Gln Asn Ala Lys Asp Ser Lys Asn Pro Ser Asp Ala Phe
705                 710                 715                 720

Ala Pro Ala Asp Leu Asn Arg Val Asn Glu Tyr Leu Tyr Pro Tyr Leu
                725                 730                 735

Asp Ser Asn Val Thr Leu Lys Asp Gly Asn Tyr Glu Tyr Pro Asp Gly
            740                 745                 750

Tyr Ser Thr Glu Gln Arg Thr Thr Pro Asn Gln Pro Gly Gly Gly Leu
        755                 760                 765

Gly Gly Asn Asp Ala Leu Trp Glu Val Ala Tyr Asn Ser Thr Asp Lys
    770                 775                 780

Phe Val Pro Gln Gly Asn Ser Thr Asp Lys Phe Val Pro Gln Leu Tyr
785                 790                 795                 800

Leu Lys His Pro Glu Asp Gly Lys Phe Glu Thr Pro Ile Gln Leu Arg
                805                 810                 815

Gly Phe Glu Lys Val Glu Leu Ser Pro Gly Glu Lys Lys Thr Val Asp
            820                 825                 830

Leu Arg Leu Leu Arg Arg Asp Leu Ser Val Trp Asp Thr Thr Arg Gln
        835                 840                 845

Ser Trp Ile Val Glu Ser Gly Thr Tyr Glu Ala Leu Ile Gly Val Ala
    850                 855                 860

Val Asn Asp Ile Lys Thr Ser Val Leu Phe Thr Ile
865                 870                 875

<210> SEQ ID NO 46
<211> LENGTH: 880
<212> TYPE: PRT
<213> ORGANISM: Saccharomycopsis fibuligera

<400> SEQUENCE: 46

Met Leu Leu Ile Leu Glu Leu Leu Val Leu Ile Ile Gly Leu Gly Val
1               5                   10                  15

Ala Leu Pro Val Gln Thr His Asn Leu Thr Asp Asn Gln Gly Phe Asp
                20                  25                  30

Glu Glu Ser Ser Gln Trp Ile Ser Pro His Tyr Tyr Pro Thr Pro Gln
            35                  40                  45

Gly Gly Arg Leu Gln Gly Val Trp Gln Asp Ala Tyr Thr Lys Ala Lys
        50                  55                  60

Ala Leu Val Ser Gln Met Thr Ile Val Glu Lys Val Asn Leu Thr Thr
65                  70                  75                  80

Gly Thr Gly Trp Gln Leu Gly Pro Cys Val Gly Asn Thr Gly Ser Val
                85                  90                  95

Pro Arg Phe Gly Ile Pro Asn Leu Cys Leu Gln Asp Gly Pro Leu Gly
                100                 105                 110

Val Arg Leu Thr Asp Phe Ser Thr Gly Tyr Pro Ser Gly Met Ala Thr
            115                 120                 125

Gly Ala Thr Phe Asn Lys Asp Leu Phe Leu Gln Arg Gly Gln Ala Leu
        130                 135                 140

Gly His Glu Phe Asn Ser Lys Gly Val His Ile Ala Leu Gly Pro Ala
145                 150                 155                 160

Val Gly Pro Leu Gly Val Lys Ala Arg Gly Gly Arg Asn Phe Glu Ala
                165                 170                 175

Phe Gly Ser Asp Pro Tyr Leu Gln Gly Ile Ala Ala Ala Ala Thr Ile
```

```
            180                 185                 190
Lys Gly Leu Gln Glu Asn Asn Val Met Ala Cys Val Lys His Phe Ile
            195                 200                 205

Gly Asn Glu Gln Asp Ile Tyr Arg Gln Pro Ser Asn Ser Lys Val Asp
            210                 215                 220

Pro Glu Tyr Asp Pro Ala Thr Lys Glu Ser Ile Ser Ala Asn Ile Pro
225                 230                 235                 240

Asp Arg Ala Met His Glu Leu Tyr Leu Trp Pro Phe Ala Asp Ser Ile
                    245                 250                 255

Arg Ala Gly Val Gly Ser Val Met Cys Ser Tyr Asn Arg Val Asn Asn
                260                 265                 270

Thr Tyr Ser Cys Glu Asn Ser Tyr Met Ile Asn His Leu Leu Lys Glu
            275                 280                 285

Glu Leu Gly Phe Gln Gly Phe Val Val Ser Asp Trp Ala Ala Gln Met
            290                 295                 300

Ser Gly Ala Tyr Ser Ala Ile Ser Gly Leu Asp Met Ser Met Pro Gly
305                 310                 315                 320

Glu Leu Leu Gly Gly Trp Asn Thr Gly Lys Ser Tyr Trp Gly Gln Asn
                325                 330                 335

Leu Thr Lys Ala Val Tyr Asn Glu Thr Val Pro Ile Glu Arg Leu Asp
                340                 345                 350

Asp Met Ala Thr Arg Ile Leu Ala Ala Leu Tyr Ala Thr Asn Ser Phe
            355                 360                 365

Pro Thr Lys Asp Arg Leu Pro Asn Phe Ser Ser Phe Thr Thr Lys Glu
        370                 375                 380

Tyr Gly Asn Glu Phe Phe Val Asp Lys Thr Ser Pro Val Val Lys Val
385                 390                 395                 400

Asn His Phe Val Asp Pro Ser Asn Asp Phe Thr Glu Thr Ala Leu
                    405                 410                 415

Lys Val Ala Glu Glu Ser Ile Val Leu Leu Lys Asn Glu Lys Asn Thr
                420                 425                 430

Leu Pro Ile Ser Pro Asn Lys Val Arg Lys Leu Leu Leu Ser Gly Ile
            435                 440                 445

Ala Ala Gly Pro Asp Pro Lys Gly Tyr Glu Cys Ser Asp Gln Ser Cys
        450                 455                 460

Val Asp Gly Ala Leu Phe Glu Gly Trp Gly Ser Gly Ser Val Gly Tyr
465                 470                 475                 480

Pro Lys Tyr Gln Val Thr Pro Phe Glu Glu Ile Ser Ala Asn Ala Arg
                485                 490                 495

Lys Asn Lys Met Gln Phe Asp Tyr Ile Arg Glu Ser Phe Asp Leu Thr
            500                 505                 510

Gln Val Ser Thr Val Ala Ser Asp Ala His Met Ser Ile Val Val Val
            515                 520                 525

Ser Ala Val Ser Gly Glu Gly Tyr Leu Ile Ile Asp Gly Asn Arg Gly
        530                 535                 540

Asp Lys Asn Asn Val Thr Leu Trp His Asn Ser Asp Asn Leu Ile Lys
545                 550                 555                 560

Ala Val Ala Glu Asn Cys Ala Asn Thr Val Val Ile Thr Ser Thr
                    565                 570                 575

Gly Gln Val Asp Val Glu Ser Phe Ala Asp His Pro Asn Val Thr Ala
            580                 585                 590

Ile Val Trp Ala Gly Pro Leu Gly Asp Arg Ser Gly Thr Ala Ile Ala
            595                 600                 605
```

```
Asn Ile Leu Phe Gly Asn Ala Asn Pro Ser Gly His Leu Pro Phe Thr
            610                 615                 620

Val Ala Lys Ser Asn Asp Asp Tyr Ile Pro Ile Val Thr Tyr Asn Pro
625                 630                 635                 640

Pro Asn Gly Glu Pro Glu Asp Asn Thr Leu Ala Glu His Asp Leu Leu
                645                 650                 655

Val Asp Tyr Arg Tyr Phe Glu Glu Lys Asn Ile Glu Pro Arg Tyr Ala
                660                 665                 670

Phe Gly Tyr Gly Leu Ser Tyr Asn Glu Tyr Lys Val Ser Asn Ala Lys
                675                 680                 685

Val Ser Ala Ala Lys Lys Val Asp Glu Glu Leu Pro Gln Pro Lys Leu
690                 695                 700

Tyr Leu Ala Glu Tyr Ser Tyr Asn Lys Thr Glu Glu Ile Asn Asn Pro
705                 710                 715                 720

Glu Asp Ala Phe Phe Pro Ser Asn Ala Arg Arg Ile Gln Glu Phe Leu
                725                 730                 735

Tyr Pro Tyr Leu Asp Ser Asn Val Thr Leu Lys Asp Gly Asn Tyr Glu
                740                 745                 750

Tyr Pro Asp Gly Tyr Ser Thr Glu Gln Arg Thr Thr Pro Ile Gln Pro
                755                 760                 765

Gly Gly Gly Leu Gly Gly Asn Asp Ala Leu Trp Glu Val Ala Tyr Lys
770                 775                 780

Val Glu Val Asp Val Gln Asn Leu Gly Asn Ser Thr Asp Lys Phe Val
785                 790                 795                 800

Pro Gln Leu Tyr Leu Lys His Pro Glu Asp Gly Lys Phe Glu Thr Pro
                805                 810                 815

Val Gln Leu Arg Gly Phe Glu Lys Val Glu Leu Ser Pro Gly Glu Lys
                820                 825                 830

Lys Thr Val Glu Phe Glu Leu Leu Arg Arg Asp Leu Ser Val Trp Asp
                835                 840                 845

Thr Thr Arg Gln Ser Trp Ile Val Glu Ser Gly Thr Tyr Glu Ala Leu
                850                 855                 860

Ile Gly Val Ala Val Asn Asp Ile Lys Thr Ser Val Leu Phe Thr Ile
865                 870                 875                 880

<210> SEQ ID NO 47
<211> LENGTH: 780
<212> TYPE: PRT
<213> ORGANISM: Septoria lycopersici

<400> SEQUENCE: 47

Met Val Ser Ser Leu Phe Asn Ile Ala Ala Leu Ala Gly Ala Val Ile
1               5                   10                  15

Ala Leu Ser His Glu Asp Gln Ser Lys His Phe Thr Thr Ile Pro Thr
                20                  25                  30

Phe Pro Thr Pro Asp Ser Thr Gly Glu Gly Trp Lys Ala Ala Phe Glu
            35                  40                  45

Lys Ala Ala Asp Ala Val Ser Arg Leu Asn Leu Thr Gln Lys Val Ala
        50                  55                  60

Leu Thr Thr Gly Thr Thr Ala Gly Leu Ser Cys Asn Gly Asn Ile Ala
65                  70                  75                  80

Pro Ile Pro Glu Ile Asn Phe Ser Gly Leu Cys Leu Ala Asp Gly Pro
                85                  90                  95

Val Ser Val Arg Ile Ala Asp Leu Ala Thr Val Phe Pro Ala Gly Leu
```

```
                    100                 105                 110
Thr Ala Ala Thr Trp Asp Arg Gln Leu Ile Tyr Glu Arg Ala Arg
                115                 120                 125

Ala Leu Gly Ser Glu Phe Arg Gly Lys Gly Ser Gln Val His Leu Gly
            130                 135                 140

Pro Ala Ser Gly Ala Leu Gly Arg His Pro Leu Gly Gly Arg Asn Trp
145                 150                 155                 160

Glu Ser Phe Ser Pro Asp Pro Tyr Leu Ser Gly Val Ala Met Asp Phe
                165                 170                 175

Ser Ile Arg Gly Ile Gln Glu Met Gly Val Gln Ala Asn Arg Lys His
            180                 185                 190

Phe Ile Gly Asn Glu Gln Glu Thr Gln Arg Ser Asn Thr Phe Thr Asp
            195                 200                 205

Asp Gly Thr Glu Ile Gln Ala Ile Ser Ser Asn Ile Asp Asp Arg Thr
        210                 215                 220

Met His Glu Leu Tyr Leu Trp Pro Phe Ala Asn Ala Val Arg Ser Gly
225                 230                 235                 240

Val Ala Ser Val Met Cys Ser Tyr Asn Arg Leu Asn Gln Thr Tyr Ala
                245                 250                 255

Cys Glu Asn Ser Lys Leu Met Asn Gly Ile Leu Lys Gly Glu Leu Gly
            260                 265                 270

Phe Gln Gly Tyr Val Val Ser Asp Trp Tyr Ala Thr His Ser Gly Val
        275                 280                 285

Glu Ser Val Asn Ala Gly Leu Asp Met Thr Met Pro Gly Pro Leu Asp
        290                 295                 300

Ser Pro Ser Thr Ala Leu Arg Pro Pro Ser Tyr Leu Gly Gly Asn
305                 310                 315                 320

Leu Thr Glu Ala Val Leu Asn Gly Thr Ile Pro Glu Ala Arg Val Asp
                325                 330                 335

Asp Met Ala Arg Arg Ile Leu Met Pro Tyr Phe Phe Leu Gly Gln Asp
            340                 345                 350

Thr Asp Phe Pro Thr Val Asp Pro Ser Thr Gly Phe Val Phe Ala Arg
            355                 360                 365

Thr Tyr Asn Tyr Pro Asp Glu Tyr Leu Thr Leu Gly Gly Leu Asp Pro
        370                 375                 380

Tyr Asn Pro Pro Ala Arg Asp Val Arg Gly Asn His Ser Asp Ile
385                 390                 395                 400

Val Arg Lys Val Ala Ala Ala Gly Thr Val Leu Leu Lys Asn Val Asn
                405                 410                 415

Asn Val Leu Pro Leu Lys Glu Pro Lys Ser Val Gly Ile Phe Gly Asn
            420                 425                 430

Gly Ala Ala Asp Val Thr Glu Gly Leu Thr Phe Thr Gly Asp Asp Ser
            435                 440                 445

Gly Pro Trp Gly Ala Asp Ile Gly Ala Leu Ser Val Gly Gly Gly Ser
            450                 455                 460

Gly Ala Gly Arg His Thr His Leu Val Ser Pro Leu Ala Ala Ile Arg
465                 470                 475                 480

Lys Arg Thr Glu Ser Val Gly Gly Arg Val Gln Tyr Leu Leu Ser Asn
                485                 490                 495

Ser Arg Ile Val Asn Asp Asp Phe Thr Ser Ile Tyr Pro Thr Pro Glu
            500                 505                 510

Val Cys Leu Val Phe Leu Lys Thr Trp Ala Arg Glu Gly Thr Asp Arg
            515                 520                 525
```

Leu Ser Tyr Glu Asn Asp Trp Asn Ser Thr Ala Val Val Asn Val
530                 535                 540

Ala Arg Arg Cys Pro Asn Thr Ile Val Val Thr His Ser Gly Gly Ile
545                 550                 555                 560

Asn Thr Met Pro Trp Ala Asp Asn Ala Asn Val Thr Ala Ile Leu Ala
                565                 570                 575

Ala His Tyr Pro Gly Gln Glu Asn Gly Asn Ser Ile Met Asp Ile Leu
                580                 585                 590

Tyr Gly Asp Val Asn Pro Ser Gly Arg Leu Pro Tyr Thr Ile Pro Lys
            595                 600                 605

Leu Ala Thr Asp Tyr Asp Phe Pro Val Val Asn Ile Thr Asn Glu Ala
610                 615                 620

Gln Asp Pro Tyr Val Trp Gln Ala Asp Phe Thr Glu Gly Leu Leu Ile
625                 630                 635                 640

Asp Tyr Arg His Phe Asp Ala Arg Asn Ile Thr Pro Leu Tyr Glu Phe
                645                 650                 655

Gly Tyr Gly Leu Ser Tyr Thr Thr Phe Glu Ile Glu Gly Val Ala Asn
                660                 665                 670

Leu Val Ala Lys Ser Ala Lys Leu Ser Ala Phe Pro Ala Ser Thr Asp
            675                 680                 685

Ile Ser His Pro Gly Gly Asn Pro Asp Leu Trp Glu Glu Val Val Ser
690                 695                 700

Val Thr Ala Ala Val Lys Asn Thr Gly Ser Val Ser Gly Ser Gln Val
705                 710                 715                 720

Val Gln Leu Tyr Ile Ser Leu Pro Ala Asp Gly Ile Pro Glu Asn Ser
                725                 730                 735

Pro Met Gln Val Leu Arg Gly Phe Glu Lys Val Asp Leu Gln Pro Gly
                740                 745                 750

Gln Ser Lys Ser Val Glu Phe Ser Ile Met Arg Arg Asp Leu Ser Phe
            755                 760                 765

Trp Asn Thr Thr Ala Gln Asp Trp Glu Ile Pro Asn
770                 775                 780

<210> SEQ ID NO 48
<211> LENGTH: 654
<212> TYPE: PRT
<213> ORGANISM: Tropaeolum majus

<400> SEQUENCE: 48

Met Gly Arg Phe Leu Leu Pro Ile Leu Gly Trp Phe Leu Leu Leu Ser
1               5                   10                  15

Cys Leu Ser Ala Phe Thr Glu Ala Glu Tyr Met Arg Tyr Lys Asp Pro
                20                  25                  30

Lys Lys Pro Leu Asn Val Arg Ile Lys Asp Leu Met Ser Arg Met Thr
            35                  40                  45

Leu Ala Glu Lys Ile Gly Gln Met Thr Gln Ile Glu Arg Lys Glu Ala
        50                  55                  60

Thr Pro Asp Val Ile Ser Lys Tyr Phe Ile Gly Ser Val Leu Ser Gly
65                  70                  75                  80

Gly Gly Ser Val Pro Ala Pro Lys Ala Ser Pro Glu Ala Trp Val Asp
                85                  90                  95

Leu Val Asn Gly Met Gln Lys Ala Leu Ser Thr Arg Leu Gly Ile
                100                 105                 110

Pro Met Ile Tyr Gly Ile Asp Ala Val His Gly His Asn Asn Val Tyr

```
            115                 120                 125
Asn Ala Thr Ile Phe Pro His Asn Val Gly Leu Gly Val Thr Arg Asp
130                 135                 140

Pro Ala Leu Ile Lys Arg Ile Gly Glu Ala Thr Ala Leu Glu Cys Arg
145                 150                 155                 160

Ala Thr Gly Ile Pro Tyr Ala Phe Ala Pro Cys Ile Ala Val Cys Arg
                165                 170                 175

Asp Pro Arg Trp Gly Arg Cys Tyr Glu Ser Tyr Ser Glu Asp His Thr
            180                 185                 190

Ile Val Gln Ala Met Thr Glu Ile Ile Pro Gly Leu Gln Gly Asp Val
        195                 200                 205

Pro Pro Asp Val Lys Lys Gly Val Pro Phe Val Gly Gly Lys Thr Lys
210                 215                 220

Val Ala Ala Cys Ala Lys His Phe Val Gly Asp Gly Gly Thr Thr Lys
225                 230                 235                 240

Gly Ile Asp Glu Asn Asn Thr Val Ile Asp Ser Arg Gly Leu Phe Ser
                245                 250                 255

Ile His Met Pro Ala Tyr His Asp Ser Ile Lys Lys Gly Val Ala Thr
            260                 265                 270

Val Met Val Ser Tyr Ser Ser Trp Asn Gly Leu Arg Met His Ala Asn
        275                 280                 285

Arg Asp Leu Val Thr Gly Tyr Leu Lys Asn Lys Leu Lys Phe Arg Gly
290                 295                 300

Phe Val Ile Ser Asp Trp Glu Gly Ile Asp Arg Ile Thr Asp Pro Pro
305                 310                 315                 320

Gly Arg Asn Tyr Ser Tyr Ser Val Glu Ala Val Gly Ala Gly Ile
                325                 330                 335

Asp Met Ile Met Val Pro Glu Asp Phe Thr Lys Phe Leu Asn Glu Leu
            340                 345                 350

Thr Ser Gln Val Lys Lys Asn Ile Ile Pro Met Ser Arg Ile Asp Asp
        355                 360                 365

Ala Val Lys Arg Ile Leu Arg Val Lys Phe Val Met Gly Leu Phe Glu
370                 375                 380

Ser Pro Leu Ala Asp Tyr Ser Leu Ala Asn Gln Leu Gly Ser Gln Glu
385                 390                 395                 400

His Arg Asp Leu Ala Arg Glu Ala Val Arg Lys Ser Leu Val Leu Leu
                405                 410                 415

Lys Asn Gly Glu Ser Ala Asp Lys Pro Phe Val Pro Leu Pro Lys Asn
            420                 425                 430

Ala Lys Lys Ile Leu Val Ala Gly Ser His Ala Asp Asn Leu Gly Arg
        435                 440                 445

Gln Cys Gly Gly Trp Thr Ile Glu Trp Gln Gly Val Asn Gly Asn Asp
450                 455                 460

Leu Thr Thr Gly Thr Thr Ile Leu Asn Ala Ile Lys Lys Thr Val Asp
465                 470                 475                 480

Pro Thr Thr Gln Val Ile Tyr Asn Glu Asn Pro Asp Ser Asn Tyr Val
                485                 490                 495

Lys Thr Asn Ser Phe Asp Tyr Ala Ile Val Val Gly Glu Pro Pro
            500                 505                 510

Tyr Ala Glu Met Gln Gly Asp Ser Phe Asn Leu Thr Ile Pro Glu Pro
        515                 520                 525

Gly Pro Thr Thr Ile Ser Ser Val Cys Gly Ala Val Lys Cys Val Val
530                 535                 540
```

```
Val Val Ile Ser Gly Arg Pro Val Val Leu Gln Pro Tyr Val Ser Tyr
545                 550                 555                 560

Met Asp Ala Leu Val Ala Ala Trp Leu Pro Gly Thr Glu Gly Gln Gly
                565                 570                 575

Val Thr Asp Val Leu Phe Gly Asp Tyr Gly Phe Thr Gly Lys Leu Ala
            580                 585                 590

Arg Thr Trp Phe Lys Thr Val Asp Gln Leu Pro Met Asn Val Gly Asp
        595                 600                 605

Lys His Tyr Asp Pro Leu Phe Pro Phe Gly Phe Gly Leu Thr Thr Lys
    610                 615                 620

Pro Ser Asn Arg Thr Glu Phe Ile Gly Leu Ile Phe Gly Asp Leu Glu
625                 630                 635                 640

Met Phe Ser Arg Tyr Tyr Val Glu Gly Cys Lys Asp Gly Val
                645                 650

<210> SEQ ID NO 49
<211> LENGTH: 843
<212> TYPE: PRT
<213> ORGANISM: Uromyces viciae-fabae

<400> SEQUENCE: 49

Met Lys Thr Pro Leu Gly Ile Gly Ser Thr Ala Ala Val Leu Tyr Ile
1               5                   10                  15

Leu Ser Asn Ile Ser His Val Gln Leu Ala Thr Thr Ser Pro Ser Glu
                20                  25                  30

Asn Gln Asn Gln Ser Tyr Asn Pro Gln Ile Glu Gly Leu Thr Val Gln
            35                  40                  45

Pro Ser Thr Val Ala Asn Gly Leu Arg Ile Asn Ser Asn Ser Leu Ile
        50                  55                  60

Ser Asn Phe Asp Phe Glu Ile Ile Gln Pro Pro Gly Tyr Glu Glu
65                  70                  75                  80

Trp Thr Ser Pro Val Val Leu Pro Ala Pro Val Gln Ser Gly Leu Ser
                85                  90                  95

Pro Trp Ser Glu Ser Ile Val Arg Ala Arg Ala Phe Val Ala Gln Leu
            100                 105                 110

Thr Ile Glu Glu Lys Val Asn Leu Thr Thr Gly Ala Gly Thr Gln Gly
        115                 120                 125

Arg Cys Val Gly Glu Thr Gly Thr Val Pro Arg Leu Gly Phe Asn Gln
    130                 135                 140

Pro Ile Cys Leu Gln Asp Gly Pro Val Gly Ile Arg Tyr Thr Asp Phe
145                 150                 155                 160

Asn Ser Val Phe Pro Ala Ala Ile Asn Val Ala Ala Thr Phe Asp Lys
                165                 170                 175

Gln Leu Met Phe Lys Arg Ala Gln Ala Met Ala Glu Glu Phe Arg Gly
            180                 185                 190

Lys Gly Ala Asn Val Val Leu Ala Pro Met Thr Asn Leu Met Arg Thr
        195                 200                 205

Pro Gln Ala Gly Arg Ala Trp Glu Gly Tyr Gly Ser Asp Pro Tyr Leu
    210                 215                 220

Ser Gly Val Ala Thr Val Gln Ser Val Leu Gly Ile Gln Ser Thr Arg
225                 230                 235                 240

Ala Ser Ala Cys Val Lys His Tyr Ile Gly Asn Glu Gln Glu His Tyr
                245                 250                 255

Arg Gly Gly Ser Gly Ala Thr Ala Ser Ser Ser Asn Ile Asp Asp Arg
```

```
                260                 265                 270
Thr Leu Arg Glu Leu Tyr Glu Trp Pro Phe Ala Glu Ala Ile His Ala
            275                 280                 285
Gly Val Asp Tyr Ile Met Cys Ser Tyr Asn Arg Val Asn Gln Thr Tyr
        290                 295                 300
Ala Cys Glu Asn Ser Lys Leu Ile Asn Gly Ile Ala Lys Gly Glu His
305                 310                 315                 320
Lys Phe Gln Gly Val Met Val Thr Asp Trp Ala Ala Ala Glu Ser Gly
                325                 330                 335
Val Arg Thr Ala Leu Ala Gly Thr Asp Met Asn Met Pro Gly Phe Met
            340                 345                 350
Ala Tyr Gly Gln Pro Ser Glu Pro Asn Pro Ser Thr Ala Asn Gly Ser
        355                 360                 365
Tyr Trp Gly Leu Arg Met Ile Glu Ala Val Lys Asn Gly Thr Val Pro
    370                 375                 380
Met Glu Arg Leu Asp Asp Met Val Thr Arg Val Ile Ser Thr Tyr Tyr
385                 390                 395                 400
Lys Gln Gly Gln Asp Lys Ser Asp Tyr Pro Lys Leu Asn Phe Met Ser
                405                 410                 415
Met Gly Gln Gly Thr Pro Ala Glu Gln Ala Val Ser Asn His His Val
            420                 425                 430
Asn Val Gln Lys Asp His Tyr Leu Ile Ile Arg Gln Ile Ala Thr Ala
        435                 440                 445
Ser Thr Ile Leu Leu Lys Asn Val Asn His Thr Leu Pro Leu Lys Ser
    450                 455                 460
Pro Asp Lys Met Arg Ser Val Val Val Gly Ser Asp Ala Gly Asp
465                 470                 475                 480
Asn Pro Gln Gly Pro Asn Ser Cys Val Asp Arg Gly Cys Asn Arg Gly
                485                 490                 495
Ile Leu Ala Ile Gly Trp Gly Ser Gly Thr Ala Asn Phe Ala His Leu
            500                 505                 510
Thr Ala Pro Ala Thr Ser Ile Gln Asn Tyr Leu Leu Gln Ser Asn Pro
        515                 520                 525
Thr Ile Thr Tyr Arg Ser Ile Phe Asp Asp Tyr Ala Tyr Asp Glu Ile
    530                 535                 540
Ala Lys Ala Ala Ser Thr Ala Asp Val Ser Ile Val His Val Ser Ser
545                 550                 555                 560
Asp Ser Gly Glu Gly Tyr Leu Thr Val Glu Gly Asn Gln Gly Asp Arg
                565                 570                 575
Ser Asn Thr Ser Leu Trp Asn Lys Gly Asp Glu Leu Ile Leu Lys Ala
            580                 585                 590
Ala Glu Ala Cys Asn Asn Val Val Val Ile His Ser Val Gly Pro
        595                 600                 605
Val Asp Met Glu Ala Trp Ile Asn His Pro Asn Val Thr Ala Val Leu
    610                 615                 620
Leu Ala Gly Leu Pro Gly Gln Glu Ala Gly Ser Ala Glu Val Asp Val
625                 630                 635                 640
Leu Trp Gly Ser Thr Asn Pro Ser Gly Arg Leu Pro Tyr Thr Ile Ala
                645                 650                 655
Lys Lys Pro Ser Asp Tyr Pro Ala Glu Leu Leu Tyr Glu Ser Asn Met
            660                 665                 670
Thr Val Pro Gln Ile Asn Tyr Ser Glu Arg Leu Asn Ile Asp Tyr Arg
        675                 680                 685
```

```
His Phe Asp Thr Tyr Asn Ile Glu Pro Arg Phe Glu Phe Gly Phe Gly
            690                 695                 700

Leu Ser Tyr Thr Thr Phe Ala Trp Asn Ser Leu Lys Phe Ser Ser Ser
705                 710                 715                 720

Phe Gln Leu Gln Lys Thr Ser Pro Val Ile Val Pro Pro Asn Leu Asp
                725                 730                 735

Leu Tyr Gln Asp Val Ile Glu Phe Glu Phe Gln Val Thr Asn Ser Gly
            740                 745                 750

Pro Phe Asp Gly Ser Glu Val Ala Gln Leu Tyr Val Asp Phe Pro Asn
            755                 760                 765

Gln Val Asn Glu Pro Pro Lys Val Leu Arg Gly Phe Glu Arg Ala Tyr
770                 775                 780

Ile Pro Ser Lys Gln Ser Lys Thr Ile Glu Ile Lys Leu Arg Val Lys
785                 790                 795                 800

Asp Leu Ser Phe Trp Asp Val Ile Thr Gln Ser Trp Gln Ile Pro Asp
                805                 810                 815

Gly Lys Phe Asn Phe Met Ile Gly Ser Ser Ser Arg Lys Ile Ile Phe
                820                 825                 830

Thr Gln Glu Ile Ser Leu Gln His Ser His Met
            835                 840

<210> SEQ ID NO 50
<211> LENGTH: 740
<212> TYPE: PRT
<213> ORGANISM: Unknown
<220> FEATURE:
<223> OTHER INFORMATION: Uncultured microorganism, beta-glucosidase
      thereof

<400> SEQUENCE: 50

Met Lys Arg Leu Ile Pro Phe Cys Ala Leu Val Leu Leu Ala Ala Cys
1               5                   10                  15

Gly Pro Arg Trp Thr Glu Thr Glu Ala Asp Gly Tyr Arg Leu Ile Thr
            20                  25                  30

Gln Arg Asn Gly Ala Thr Leu Gly Val Thr Ser Ala Pro Leu Leu Asp
        35                  40                  45

Leu Asn Gly His Ile Phe Lys Asp Leu Asn Arg Asn Gly Arg Val Asp
50                  55                  60

Pro Tyr Glu Asp Trp Arg Leu Pro Ala Leu Thr Arg Ala Gln Asp Leu
65                  70                  75                  80

Ala Ala Gln Leu Ser Ile Glu Glu Ile Ala Gly Leu Met Leu Tyr Ser
                85                  90                  95

Ala His Gln Ser Val Pro Thr Pro Glu Ile Thr Glu Arg Gln Lys Lys
            100                 105                 110

Phe Leu Glu Glu Asp Asn Leu Arg Ala Val Leu Val Thr Thr Val Gly
        115                 120                 125

Ser Pro Glu Ile Ala Ala Arg Trp Asn Asn Val Gln Ala Phe Val
    130                 135                 140

Glu Ala Leu Gly His Gly Ile Pro Ala Asn Asn Ser Ser Asp Pro Arg
145                 150                 155                 160

Asn Glu Cys Ser Ala Thr Ala Glu Phe Asn Leu Gly Ser Gly Gly Gln
                165                 170                 175

Ile Ser Leu Trp Pro Thr Pro Leu Gly Leu Ala Ala Thr Phe Asp Pro
            180                 185                 190

Ala Leu Val Glu Gln Phe Gly Arg Ile Ala Ser Ala Glu Tyr Arg Ala
```

```
              195                 200                 205
Leu Gly Ile Ala Thr Ala Leu Ser Pro Gln Ile Asp Leu Ala Thr Glu
    210                 215                 220

Pro Arg Trp Ser Arg Phe Asn Gly Thr Phe Gly Glu Asp Pro Glu Leu
225                 230                 235                 240

Asp Val Ala Leu Ala Arg Ala Tyr Val Asp Gly Phe Gln Thr Thr Glu
                245                 250                 255

Asp Ala Pro Asp Gly Trp Gly Ala Gln Ser Val Asn Ala Met Val Lys
            260                 265                 270

His Trp Pro Ser Gly Pro Glu Glu Gly Arg Asp Ala His Phe
        275                 280                 285

Asn Tyr Gly Lys Tyr Ala Val Tyr Pro Gly Gly Asn Phe Ala Thr His
    290                 295                 300

Leu Arg Pro Phe Thr Glu Gly Ala Phe Arg Leu Asp Gly Gly Thr Lys
305                 310                 315                 320

Ser Ala Ser Ala Val Met Pro Tyr Tyr Thr Ile Ser Tyr Gly Val Asp
                325                 330                 335

Pro Ser Gly Lys Asn Ala Gly Asn Ser Tyr Asn Glu Tyr Ile Ile Gly
            340                 345                 350

Asp Leu Leu Arg Gly Glu Tyr Gly Phe Asp Gly Val Cys Thr Asp
        355                 360                 365

Trp Gly Ile Thr Ala Asp Asn Ala Ala Val Ser Ser Phe Asp Gly Lys
    370                 375                 380

Cys Trp Gly Met Glu Glu Leu Ser Val Ala Glu Arg His Tyr Ala Val
385                 390                 395                 400

Ile Lys Ala Gly Val Asp Gln Phe Gly Gly Asn Asn Asp Lys Gly Pro
                405                 410                 415

Val Leu Glu Ala Tyr Lys Met Trp Val Ala Glu Phe Gly Glu Glu Ser
            420                 425                 430

Ala Arg Ala Arg Phe Glu Gln Ser Ala Val Arg Leu Leu Met Asn Ser
        435                 440                 445

Phe Arg Thr Gly Leu Phe Glu Asn Pro Tyr Thr Asp Pro Ala Ala Ala
    450                 455                 460

Ala Ala Val Val Gly Asn Pro Glu Tyr Met Glu Ala Gly Phe Gln Ala
465                 470                 475                 480

Gln Arg Lys Ser Ile Val Met Leu Lys Asn His Gly Gly Val Leu Pro
                485                 490                 495

Asn Asp Ser Ala Arg Val Tyr Val Pro Gln Arg Leu Tyr Pro Gln Thr
            500                 505                 510

Pro Gly Met Phe Gly Leu Ser Met Gly Pro Ala Ala His Trp Asp Tyr
        515                 520                 525

Pro Ile Asp Lys Glu Leu Val Gly Lys Tyr Phe Gln Trp Thr Glu Asp
    530                 535                 540

Pro Glu Ala Ala Asp Phe Ala Leu Val Met Ile Gln Glu Pro Phe Pro
545                 550                 555                 560

Gly Ala Gly Tyr Asp Val Asn Asp Arg Lys Arg Gly Gly Asn Gly Tyr
                565                 570                 575

Val Pro Ile Ser Leu Gln Tyr Arg Pro Tyr Lys Ala Glu Tyr Ala Arg
            580                 585                 590

Pro Val Ser Ile Ala Gly Gly Asp Pro Lys Glu Thr Phe Thr Asn Arg
        595                 600                 605

Ser Tyr Arg Gly Lys Lys Val Thr Tyr Asn Glu Ser Asp Leu Asp
    610                 615                 620
```

```
Leu Val Ile Glu Thr Lys Arg Arg Met Gly Asp Lys Pro Val Val
625                 630                 635                 640

Val Ile Gly Val Ser Arg Pro Leu Val Leu Ala Glu Leu Glu Pro Tyr
            645                 650                 655

Ala Asp Ala Ile Leu Leu Thr Phe Gly Val Gln Asn Gln Ala Val Leu
            660                 665                 670

Asp Ile Leu Ser Gly Ala Ala Glu Pro Ser Gly Leu Leu Pro Met Gln
            675                 680                 685

Leu Pro Ala Asp Met Arg Thr Val Glu Glu Gln Ala Glu Asp Val Pro
690                 695                 700

Arg Asp Met Arg Val Tyr Val Asp Ala Asp Gly His Ala Tyr Asp Phe
705                 710                 715                 720

Ala Tyr Gly Leu Gly Trp Asp Gly Val Ile Asn Asp Ala Arg Val Ser
            725                 730                 735

Ile Tyr Arg Arg
            740

<210> SEQ ID NO 51
<211> LENGTH: 756
<212> TYPE: PRT
<213> ORGANISM: Bacillus sp. GL1

<400> SEQUENCE: 51

Met Glu Asn Ala Ala Arg Gln Ala Ser Val Arg Tyr Ala Gln Asn Gly
1               5                   10                  15

Gln Gly Pro Leu Leu Gly Tyr Asp Glu Ser Ser Gly Val Arg Ile Leu
            20                  25                  30

Arg Val Asp Gly His Ala Phe Lys Asp Leu Asn Lys Asp Gly Lys Leu
            35                  40                  45

Asp Pro Tyr Glu Asp Trp Arg Leu Pro Pro Glu Glu Arg Ala Arg Asp
        50                  55                  60

Leu Ala Ser Lys Met Thr Ile Glu Gln Ile Ala Gly Leu Met Leu Tyr
65                  70                  75                  80

Ser Ser His Gln Ala Ile Pro Gly Asn Met Gly Trp Phe Pro Ala Thr
                85                  90                  95

Tyr Ala Gly Gly Lys Ala Phe Pro Asp Ser Gly Ala Ala Pro Ser Asp
            100                 105                 110

Leu Ser Asp Gln Gln Leu Asp Phe Leu Ser Asn Asp His Ile Arg His
            115                 120                 125

Ile Leu Val Thr Arg Val Gln Ser Pro Glu Val Ala Ala Asn Trp Asn
130                 135                 140

Asn Asn Val Gln Ala Tyr Ala Glu Arg Leu Gly Leu Gly Ile Pro Ala
145                 150                 155                 160

Asn Asn Ser Ser Asp Pro Arg His Gly Ser Asp Thr Ser Lys Glu Phe
                165                 170                 175

Asn Ala Gly Ala Gly Gly Ala Ile Ser Met Trp Pro Glu Ser Met Gly
            180                 185                 190

Leu Ala Ala Thr Phe Asp Pro Ala Val Ala Arg Glu Phe Gly Glu Ile
            195                 200                 205

Ala Ser Arg Glu Tyr Arg Ala Leu Gly Leu Ser Thr Ala Leu Ser Pro
        210                 215                 220

Gln Val Asp Leu Ala Thr Asp Pro Arg Trp Phe Arg Phe Gly Met Thr
225                 230                 235                 240

Phe Gly Glu Asp Pro Arg Leu Ala Thr Asp Met Ala Arg Ala Tyr Ile
```

-continued

```
                245                 250                 255
Asp Gly Phe Gln Thr Ser Glu Gly Asp Ala Glu Ile Ala Asp Gly Trp
            260                 265                 270
Gly Ser Asp Ser Val Asn Ala Met Val Lys His Trp Pro Gly Gly Gly
        275                 280                 285
Ser Gly Glu Ala Gly Arg Asp Ala His Phe Gly Tyr Gly Lys Tyr Ala
    290                 295                 300
Val Tyr Pro Gly Asn Asn Phe Glu Glu His Leu Arg Pro Phe Thr Glu
305                 310                 315                 320
Gly Ala Phe Arg Leu Ala Gly Lys Thr Gly Glu Ala Ser Ala Val Met
                325                 330                 335
Pro Tyr Tyr Thr Ile Ser Val Gly Gln Asp Pro Val Asn Gly Glu Asn
            340                 345                 350
Val Gly Asn Ala Tyr Asn Ala Tyr Leu Ile Arg Asp Leu Leu Arg Gly
        355                 360                 365
Lys Tyr Gly Tyr Asp Gly Val Val Cys Thr Asp Trp Gly Ile Thr Ala
    370                 375                 380
Asp Glu Gly Pro Asp Ile Glu Arg Leu Phe Pro Gly Gly Arg Cys Trp
385                 390                 395                 400
Gly Val Glu Glu Asn His Thr Val Ala Gln Arg His Tyr Lys Leu Leu
                405                 410                 415
Met Ala Gly Val Asp Gln Phe Gly Gly Asn Asp Ala Gly Pro Val
            420                 425                 430
Ile Glu Ala Tyr Arg Ile Gly Val Glu Ala His Gly Glu Pro Phe Met
        435                 440                 445
Arg Ala Arg Phe Glu Gln Ser Ala Val Arg Leu Leu Lys Asn Met Phe
    450                 455                 460
Arg Leu Gly Leu Phe Glu Asn Pro Tyr Leu Asn Pro Gly Lys Ser Ala
465                 470                 475                 480
Ala Leu Val Gly Asn Pro Ala Phe Met Glu Ala Gly Tyr Arg Ala Gln
                485                 490                 495
Leu Arg Ser Val Val Met Leu Lys Asn Glu Gly Ile Leu Pro Leu Pro
            500                 505                 510
Lys Arg Gln Thr Val Tyr Ile Pro Lys Arg Lys Leu Pro Ala Asp Ala
        515                 520                 525
Asp Trp Met Gly Asn Pro Val Pro Pro Ser Glu Thr Tyr Pro Ile Asn
    530                 535                 540
Leu Asp Val Val Arg Lys Tyr Phe Asp Val Thr Asp Arg Pro Ala Asp
545                 550                 555                 560
Ala Asp Phe Ala Leu Val Cys Ile Glu Ser Pro Arg Ser Thr Lys Gly
                565                 570                 575
Tyr Ser Lys Ala Asp Ala Glu Ala Gly Gly Asn Gly Tyr Val Pro Ile
            580                 585                 590
Ser Leu Gln Tyr Arg Pro Tyr Thr Ala Asp His Ala Arg Glu Thr Ser
        595                 600                 605
Leu Ala Gly Asp Pro Arg Asp Val Leu Asn Arg Ser Tyr Lys Gly Lys
    610                 615                 620
Thr Ala Val Ala Asn Glu Gly Asp Leu Asp Ala Val Leu Glu Thr
625                 630                 635                 640
Lys Arg Leu Met Asn Gly Lys Pro Val Val Ser Ile Ala Leu Ser
                645                 650                 655
Asn Pro Ala Val Ala Ala Glu Phe Glu Pro Ala Ala Asp Ala Ile Leu
            660                 665                 670
```

```
Ala His Phe Gly Val Gln Asp Gln Ala Ile Leu Asp Ile Leu Thr Gly
            675                 680                 685

Ala Phe Glu Pro Gln Ala Leu Leu Pro Phe Arg Met Pro Ala Asp Met
690                 695                 700

Thr Thr Val Glu Lys Gln Leu Glu Asp Val Pro His Asp Met Asp Val
705                 710                 715                 720

Tyr Val Asp Ser Ala Gly His Ala Tyr Asp Phe Ala Phe Gly Leu Asn
                725                 730                 735

Trp Ser Gly Val Ile Ala Asp Ala Arg Thr Ser Arg Tyr Ala Asn Lys
                740                 745                 750

Arg Arg Thr Leu
            755

<210> SEQ ID NO 52
<211> LENGTH: 762
<212> TYPE: PRT
<213> ORGANISM: Streptomyces coelicolor A3(2)

<400> SEQUENCE: 52

Met Thr Leu Pro Leu Tyr Arg Asp Pro Ala Ala Pro Val Pro Asp Arg
1               5                   10                  15

Val Arg Asp Leu Leu Gly Arg Met Thr Leu Ala Glu Lys Val Gly Gln
                20                  25                  30

Val Asn Gln Arg Met Tyr Gly Trp Asp Ala Tyr Glu Arg Ala Gly Asp
                35                  40                  45

Gly His Arg Leu Thr Asp Ala Phe Arg Ala Glu Val Ala Ala Phe Asp
            50                  55                  60

Gly Met Gly Ala Leu Tyr Gly Leu Gln Arg Ala Asp Ala Trp Ser Gly
65              70                  75                  80

Val Gly Phe Ala Asp Gly Leu Asp Ala Arg Asp Gly Ala Arg Thr Ala
                85                  90                  95

Ala Ala Val Gln Arg Tyr Val Met Asp His Thr Arg Leu Gly Ile Pro
            100                 105                 110

Val Leu Leu Val Glu Glu Met Pro His Gly His Gln Ala Leu Asp Gly
            115                 120                 125

Thr Val Leu Pro Val Asn Leu Ala Val Gly Ala Thr Trp Asp Pro Asp
130                 135                 140

Leu Tyr Ala Asp Ala Val Ala Gly Ala Ala Ala Glu Leu Arg Ala Arg
145                 150                 155                 160

Gly Ala His Ile Ala Leu Val Ser Ala Leu Asp Leu Val Arg Asp Pro
                165                 170                 175

Arg Trp Gly Arg Ser Glu Glu Cys Phe Ser Glu Asp Pro Tyr Leu Ala
                180                 185                 190

Ala Arg Met Thr Glu Ala Leu Val Glu Gly Ala Arg Arg Ala Gly Val
            195                 200                 205

Ala Val Val Leu Lys His Phe Ala Gly Gln Gly Ala Thr Val Gly Gly
            210                 215                 220

Arg Asn Ser Ala Ala Thr Glu Leu Gly Pro Arg Glu Leu His Glu Val
225                 230                 235                 240

His Leu Ala Ala Ala Arg Ala Gly Val Ala Ala Gly Ala Ala Gly Val
                245                 250                 255

Met Ala Ala Tyr Asn Glu Phe Asp Gly Leu Pro Cys Val Ala Asn Arg
                260                 265                 270

Tyr Leu Leu Thr Asp Leu Leu Arg Thr Glu Trp Gly Phe Glu Gly Val
```

```
                275                 280                 285
Val Met Ala Asp Gly Thr Ala Val Asp Arg Leu Val Arg Leu Thr Gly
290                 295                 300
Asp Pro Val Ser Ala Gly Ala Leu Ala Leu Asp Ala Gly Cys Asp Leu
305                 310                 315                 320
Ser Leu Trp Asp Ala Ser Phe Thr Arg Leu Gly Glu Ala Val Glu Arg
                325                 330                 335
Gly Leu Val Ser Glu Ser Ala Leu Asp Ala Val Ala Arg Val Leu
                340                 345                 350
Thr Leu Lys Phe Arg Leu Gly Leu Phe Glu Gln Pro Leu Pro Pro Ala
                355                 360                 365
Arg Ser Glu Thr Val Glu Leu Pro Asp Pro Ala Glu Leu Gly Glu Arg
                370                 375                 380
Ile Ala Arg Ala Ser Val Thr Leu Leu Ala His Glu Gly Gly Val Leu
385                 390                 395                 400
Pro Leu Ser Arg Ala Val Arg Arg Ile Ala Val Leu Gly Pro Asn Ala
                405                 410                 415
Asp Ser Val Ala Gln Gln Ile Gly Asp Tyr Thr Ala Pro Gln Arg Pro
                420                 425                 430
Gly Gly Gly Ile Thr Val Leu Glu Gly Ile Arg Ala Ala Val Ala Ala
                435                 440                 445
Gly Thr Glu Val Val His Asp Arg Gly Cys Ala Leu Val Gly Asp Asp
450                 455                 460
Val Ser Gly Val Pro Ala Ala Val Ala Leu Ala Ala Gly Ser Asp Val
465                 470                 475                 480
Ala Val Leu Val Leu Gly Gly Ser Ser Ala Arg Ser Pro Asp Thr Val
                485                 490                 495
Phe Asp Ala Asn Gly Ala Ala Val Thr Gly Thr Gly Thr Pro Ser Gly
                500                 505                 510
Met Thr Cys Gly Glu Gly Val Asp Leu Ala Asp Leu Ala Leu Pro Pro
                515                 520                 525
Gly Gln Arg Ala Leu Leu Thr Ala Val Ser Ala Thr Gly Thr Pro Val
                530                 535                 540
Val Val Leu Val Gln Gly Arg Pro His Ala Leu Thr Glu Leu Asp
545                 550                 555                 560
Ala Pro Ala Ala Ala Val Leu Ser Ala Trp Tyr Pro Gly Pro Arg Gly
                565                 570                 575
Gly Arg Ala Val Ala Glu Val Leu Phe Gly Asp Ala Glu Pro Arg Gly
                580                 585                 590
Arg Leu Pro Val Ser Val Pro Arg Ser Ala Ala Gln Leu Pro Val Tyr
                595                 600                 605
Tyr Asn Gly Lys Asp His Arg Tyr Arg Gly Tyr Ala Asp Gln Ser Ala
                610                 615                 620
Gly Pro Leu His Ala Phe Gly His Gly Leu Ser Tyr Thr Ser Val Val
                625                 630                 635                 640
Tyr Gly Ala Pro Arg Leu Ser Gln Ala Arg Val Gly Thr Arg Ala Pro
                645                 650                 655
Arg Leu Thr Cys Arg Val Thr Val Arg Asn Thr Gly Ser Arg Pro Ala
                660                 665                 670
Glu Glu Thr Val Gln Leu Tyr Val Arg Leu Ser Gly Gly Ser Ser
                675                 680                 685
Trp Pro Arg Val Arg Glu Leu Arg Gly Phe Val Arg Leu Thr Ile Ala
                690                 695                 700
```

```
Pro Gly Glu Glu Ala Glu Ala Val Phe Glu Val Asp Arg Asp Thr Leu
705                 710                 715                 720

Ala Ser Val Gly Arg Asp Leu Arg Leu Ala Val Glu Pro Gly Leu Val
            725                 730                 735

Glu Leu Glu Thr Gly Pro Ala Ser Asp Arg Thr Thr Gly Val Arg Leu
            740                 745                 750

Glu Ile Thr Asp Ser Glu Ser Asn Ala Thr
            755                 760
```

<210> SEQ ID NO 53
<211> LENGTH: 226
<212> TYPE: PRT
<213> ORGANISM: Artificial
<220> FEATURE:
<223> OTHER INFORMATION: Synthetic polypeptide of GH3 domain consensus
      sequence

<400> SEQUENCE: 53

```
Ala Glu Lys Pro Arg Leu Gly Ile Pro Leu Leu Val Val Val Asp Ala
1               5                   10                  15

Glu His Gly Val Arg Gln Arg Asp Lys Glu Glu Ala Thr Ala Phe Pro
            20                  25                  30

Ser Ala Leu Ala Leu Ala Ala Thr Trp Asp Lys Glu Leu Ile Lys Glu
        35                  40                  45

Val Gly Lys Ala Ile Gly Glu Glu Leu Arg Ala Lys Gly Ile Asp Val
    50                  55                  60

Leu Leu Ala Pro Val Val Asp Leu Lys Arg Ser Pro Arg Trp Gly Arg
65                  70                  75                  80

Asn Phe Glu Ser Phe Ser Glu Asp Pro Tyr Leu Val Gly Ala Leu Ala
                85                  90                  95

Ala Ala Thr Ile Lys Gly Leu Gln Ser Ala Gly Val Ala Ala Thr Ala
            100                 105                 110

Lys His Phe Ala Gly Asn Gly Gln Glu Thr Ala Arg Ser Lys Glu Thr
        115                 120                 125

Val Ser Ala Glu Ile Asp Glu Arg Ala Leu Arg Glu Ile Tyr Leu Leu
    130                 135                 140

Pro Phe Glu Ala Ala Val Lys Glu Ala Gly Val Gly Ser Val Met Cys
145                 150                 155                 160

Ser Tyr Asn Lys Val Asn Gly Leu Pro Ala Thr Glu Asn Ser Lys Leu
                165                 170                 175

Leu Thr Lys Leu Leu Arg Glu Glu Leu Gly Phe Gln Gly Phe Val Val
            180                 185                 190

Ser Asp Trp Leu Ala Val Lys Ser Gly Val Ala Ser Asp Ala Ala Asn
        195                 200                 205

Glu Ser Glu Ala Ala Ala Ala Leu Lys Ala Gly Leu Asp Ile Glu
    210                 215                 220

Met Pro
225
```

<210> SEQ ID NO 54
<211> LENGTH: 211
<212> TYPE: PRT
<213> ORGANISM: Artificial
<220> FEATURE:
<223> OTHER INFORMATION: Synthetic polypeptide of GH3-C domain consensus
      sequence

<400> SEQUENCE: 54

```
Ile Val Leu Leu Lys Asn Glu Gly Asn Leu Leu Pro Leu Lys Lys Lys
1               5                   10                  15

Lys Lys Lys Ile Ala Val Ile Gly Pro Asn Ala Asp Gly Thr Val Lys
            20                  25                  30

Ser Gly Gly Gly Ser Gly Ala Val Asn Pro Ser Tyr Leu Val Ser Pro
        35                  40                  45

Leu Glu Gly Ile Arg Lys Arg Leu Ser Lys Ala Lys Val Val Val Glu
    50                  55                  60

Glu Gly Ser Glu Asp Asp Glu Glu Ile Ala Glu Ala Val Ala Ala Ala
65                  70                  75                  80

Lys Lys Ala Asp Val Ala Val Val Val Val Gly Glu Trp Glu Gly Glu
                85                  90                  95

Gly Glu Ser Glu Glu Gly Asp Arg Thr Asp Leu Ala Leu Pro Glu Asn
            100                 105                 110

Gln Asp Glu Leu Ile Glu Ala Val Ala Ala Ala Asn Lys Pro Val Val
        115                 120                 125

Val Val Leu His Ser Gly Gly Pro Val Asp Met Glu Pro Trp Ala Glu
    130                 135                 140

Lys Val Lys Ala Ile Leu Ala Ala Trp Tyr Pro Gly Gln Glu Gly Gly
145                 150                 155                 160

Asn Ala Ile Ala Asp Val Leu Phe Gly Asp Val Asn Pro Ser Gly Lys
                165                 170                 175

Leu Pro Val Thr Phe Pro Lys Ser Leu Glu Asp Leu Pro Ala Tyr Tyr
            180                 185                 190

Arg Tyr Lys Ser Glu Asp Pro Leu Tyr Pro Phe Gly Glu Gly Leu Ser
        195                 200                 205

Val Gly Tyr
    210

<210> SEQ ID NO 55
<211> LENGTH: 870
<212> TYPE: PRT
<213> ORGANISM: Chrysosporium lucknowense C1

<400> SEQUENCE: 55

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
```

```
                145                 150                 155                 160
        Pro Glu Gly Gly Arg Asn Trp Glu Gly Phe Ala Pro Asp Pro Val Leu
                        165                 170                 175

Thr Gly Ile Gly Met Ser Glu Thr Ile Lys Gly Ile Gln Asp Ala Gly
                        180                 185                 190

Val Ile Ala Cys Ala Lys His Phe Ile Gly Asn Glu Gln Glu His Phe
                        195                 200                 205

Arg Gln Val Pro Glu Ala Gln Gly Tyr Gly Tyr Asn Ile Ser Glu Thr
                210                 215                 220

Leu Ser Ser Asn Ile Asp Asp Lys Thr Met His Glu Leu Tyr Leu Trp
        225                 230                 235                 240

Pro Phe Ala Asp Ala Val Arg Ala Gly Val Gly Ser Val Met Cys Ser
                        245                 250                 255

Tyr Gln Gln Val Asn Asn Ser Tyr Ala Cys Gln Asn Ser Lys Leu Leu
                        260                 265                 270

Asn Asp Leu Leu Lys Asn Glu Leu Gly Phe Gln Gly Phe Val Met Ser
                        275                 280                 285

Asp Trp Gln Ala Gln His Thr Gly Ala Ala Ser Ala Val Ala Gly Leu
                290                 295                 300

Asp Met Ser Met Pro Gly Asp Thr Gln Phe Asn Thr Gly Val Ser Phe
        305                 310                 315                 320

Trp Gly Ala Asn Leu Thr Leu Ala Val Leu Asn Gly Thr Val Pro Ala
                        325                 330                 335

Tyr Arg Leu Asp Asp Met Ala Met Arg Ile Met Ala Ala Leu Phe Lys
                        340                 345                 350

Val Thr Lys Thr Thr Asp Leu Glu Pro Ile Asn Phe Ser Phe Trp Thr
                        355                 360                 365

Asp Asp Thr Tyr Gly Pro Ile His Trp Ala Ala Lys Gln Gly Tyr Gln
                370                 375                 380

Glu Ile Asn Ser His Val Asp Val Arg Ala Asp His Gly Asn Leu Ile
        385                 390                 395                 400

Arg Glu Ile Ala Ala Lys Gly Thr Val Leu Leu Lys Asn Thr Gly Ser
                        405                 410                 415

Leu Pro Leu Asn Lys Pro Lys Phe Val Ala Val Ile Gly Glu Asp Ala
                        420                 425                 430

Gly Ser Ser Pro Asn Gly Pro Asn Gly Cys Ser Asp Arg Gly Cys Asn
                        435                 440                 445

Glu Gly Thr Leu Ala Met Gly Trp Gly Ser Gly Thr Ala Asn Tyr Pro
                450                 455                 460

Tyr Leu Val Ser Pro Asp Ala Ala Leu Gln Ala Arg Ala Ile Gln Asp
        465                 470                 475                 480

Gly Thr Arg Tyr Glu Ser Val Leu Ser Asn Tyr Ala Glu Glu Lys Thr
                        485                 490                 495

Lys Ala Leu Val Ser Gln Ala Asn Ala Thr Ala Ile Val Phe Val Asn
                        500                 505                 510

Ala Asp Ser Gly Glu Gly Tyr Ile Asn Val Asp Gly Asn Glu Gly Asp
                        515                 520                 525

Arg Lys Asn Leu Thr Leu Trp Asn Asn Gly Asp Thr Leu Val Lys Asn
                530                 535                 540

Val Ser Ser Trp Cys Ser Asn Thr Ile Val Ile His Ser Val Gly
        545                 550                 555                 560

Pro Val Leu Leu Thr Asp Trp Tyr Asp Asn Pro Asn Ile Thr Ala Ile
                        565                 570                 575
```

-continued

```
Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
        595                 600                 605

Gly Lys Thr Arg Glu Ser Tyr Gly Ala Asp Val Leu Tyr Lys Pro Asn
    610                 615                 620

Asn Gly Asn Gly Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
            645                 650                 655

Phe Gly His Gly Leu Ser Tyr Thr Thr Phe Glu Tyr Ser Asn Ile Arg
            660                 665                 670

Val Val Lys Ser Asn Val Ser Glu Tyr Arg Pro Thr Thr Gly Thr Thr
        675                 680                 685

Ala Gln Ala Pro Thr Phe Gly Asn Phe Ser Thr Asp Leu Glu Asp Tyr
    690                 695                 700

Leu Phe Pro Lys Asp Glu Phe Pro Tyr Ile Tyr Gln Tyr Ile Tyr Pro
705                 710                 715                 720

Tyr Leu Asn Thr Thr Asp Pro Arg Arg Ala Ser Ala Asp Pro His Tyr
            725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Gly Asn Ser Pro Gly Gly Asn
        755                 760                 765

Arg Gln Leu Tyr Asp Ile Val Tyr Thr Ile Thr Ala Asp Ile Thr Asn
    770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
            805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
        835                 840                 845

Arg Tyr Pro Lys Thr Ala Tyr Val Gly Arg Ser Ser Arg Lys Leu Asp
    850                 855                 860

Leu Lys Ile Glu Leu Pro
865                 870

<210> SEQ ID NO 56
<211> LENGTH: 843
<212> TYPE: PRT
<213> ORGANISM: Artificial
<220> FEATURE:
<223> OTHER INFORMATION: Synthetic polypeptide with N-terminal
      methionine residue and sequence of T. aurantiacus Bgl protein from
      a synthetic nucleotide sequence based on codon selection from a
      merged S. cerevisiae and P. pastoris codon bias table

<400> SEQUENCE: 56

Met Lys Asp Asp Leu Ala Tyr Ser Pro Pro Phe Tyr Pro Ser Pro Trp
1               5                   10                  15

Met Asp Gly Asn Gly Glu Trp Ala Glu Ala Tyr Arg Arg Ala Val Asp
            20                  25                  30

Phe Val Ser Gln Leu Thr Leu Ala Glu Lys Val Asn Leu Thr Thr Gly
        35                  40                  45
```

```
Val Gly Trp Met Gln Glu Lys Cys Val Gly Glu Thr Gly Ser Ile Pro
 50                  55                  60

Arg Leu Gly Phe Arg Gly Leu Cys Leu Gln Asp Ser Pro Leu Gly Val
 65                  70                  75                  80

Arg Phe Ala Asp Tyr Val Ser Ala Phe Pro Ala Gly Val Asn Val Ala
                 85                  90                  95

Ala Thr Trp Asp Lys Asn Leu Ala Tyr Leu Arg Gly Lys Ala Met Gly
                100                 105                 110

Glu Glu His Arg Gly Lys Gly Val Asp Val Gln Leu Gly Pro Val Ala
            115                 120                 125

Gly Pro Leu Gly Arg His Pro Asp Gly Arg Asn Trp Glu Gly Phe
            130                 135                 140

Ser Pro Asp Pro Val Leu Thr Gly Val Leu Met Ala Glu Thr Ile Lys
145                 150                 155                 160

Gly Ile Gln Asp Ala Gly Val Ile Ala Cys Ala Lys His Phe Ile Gly
                165                 170                 175

Asn Glu Met Glu His Phe Arg Gln Ala Ser Glu Ala Val Gly Tyr Gly
                180                 185                 190

Phe Asp Ile Thr Glu Ser Val Ser Ser Asn Ile Asp Asp Lys Thr Leu
            195                 200                 205

His Glu Leu Tyr Leu Trp Pro Phe Ala Asp Ala Val Arg Ala Gly Val
            210                 215                 220

Gly Ser Phe Met Cys Ser Tyr Asn Gln Val Asn Asn Ser Tyr Ser Cys
225                 230                 235                 240

Ser Asn Ser Tyr Leu Leu Asn Lys Leu Leu Lys Ser Glu Leu Asp Phe
                245                 250                 255

Gln Gly Phe Val Met Ser Asp Trp Gly Ala His His Ser Gly Val Gly
                260                 265                 270

Ala Ala Leu Ala Gly Leu Asp Met Ser Met Pro Gly Asp Thr Ala Phe
            275                 280                 285

Gly Thr Gly Lys Ser Phe Trp Gly Thr Asn Leu Thr Ile Ala Val Leu
            290                 295                 300

Asn Gly Thr Val Pro Glu Trp Arg Val Asp Asp Met Ala Val Arg Ile
305                 310                 315                 320

Met Ala Ala Phe Tyr Lys Val Gly Arg Asp Arg Tyr Gln Val Pro Val
                325                 330                 335

Asn Phe Asp Ser Trp Thr Lys Asp Glu Tyr Gly Tyr Glu His Ala Leu
                340                 345                 350

Val Gly Gln Asn Tyr Val Lys Val Asn Asp Lys Val Asp Val Arg Ala
            355                 360                 365

Asp His Ala Asp Ile Ile Arg Gln Ile Gly Ser Ala Ser Val Val Leu
            370                 375                 380

Leu Lys Asn Asp Gly Gly Leu Pro Leu Thr Gly Tyr Glu Lys Phe Thr
385                 390                 395                 400

Gly Val Phe Gly Glu Asp Ala Gly Ser Asn Arg Trp Gly Ala Asp Gly
                405                 410                 415

Cys Ser Asp Arg Gly Cys Asp Asn Gly Thr Leu Ala Met Gly Trp Gly
                420                 425                 430

Ser Gly Thr Ala Asp Phe Pro Tyr Leu Val Thr Pro Glu Gln Ala Ile
            435                 440                 445

Gln Asn Glu Ile Leu Ser Lys Gly Lys Gly Leu Val Ser Ala Val Thr
450                 455                 460
```

Asp Asn Gly Ala Leu Asp Gln Met Glu Gln Val Ala Ser Gln Ala Ser
465                 470                 475                 480

Val Ser Ile Val Phe Val Asn Ala Asp Ser Gly Glu Gly Tyr Ile Asn
                485                 490                 495

Val Asp Gly Asn Glu Gly Asp Arg Lys Asn Leu Thr Leu Trp Lys Gly
            500                 505                 510

Gly Glu Glu Val Ile Lys Thr Val Ala Ala Asn Cys Asn Asn Thr Ile
        515                 520                 525

Val Val Met His Thr Val Gly Pro Val Leu Ile Asp Glu Trp Tyr Asp
    530                 535                 540

Asn Pro Asn Val Thr Ala Ile Val Trp Ala Gly Leu Pro Gly Gln Glu
545                 550                 555                 560

Ser Gly Asn Ser Leu Val Asp Val Leu Tyr Gly Arg Val Ser Pro Gly
                565                 570                 575

Gly Lys Thr Pro Phe Thr Trp Gly Lys Thr Arg Glu Ser Tyr Gly Ala
            580                 585                 590

Pro Leu Leu Thr Lys Pro Asn Asn Gly Lys Gly Ala Pro Gln Asp Asp
        595                 600                 605

Phe Thr Glu Gly Val Phe Ile Asp Tyr Arg Arg Phe Asp Lys Tyr Asn
610                 615                 620

Glu Thr Pro Ile Tyr Glu Phe Gly Phe Gly Leu Ser Tyr Thr Thr Phe
625                 630                 635                 640

Glu Tyr Ser Asp Ile Tyr Val Gln Pro Leu Asn Ala Arg Pro Tyr Thr
                645                 650                 655

Pro Ala Ser Gly Ser Thr Lys Ala Ala Pro Thr Phe Gly Asn Ile Ser
            660                 665                 670

Thr Asp Tyr Ala Asp Tyr Leu Tyr Pro Glu Asp Ile His Lys Val Pro
        675                 680                 685

Leu Tyr Ile Tyr Pro Trp Leu Asn Thr Thr Asp Pro Lys Lys Ser Ser
    690                 695                 700

Gly Asp Pro Asp Tyr Gly Met Lys Ala Glu Asp Tyr Ile Pro Ser Gly
705                 710                 715                 720

Ala Thr Asp Gly Ser Pro Gln Pro Ile Leu Pro Ala Gly Gly Ala Pro
                725                 730                 735

Gly Gly Asn Pro Gly Leu Tyr Asp Glu Met Tyr Arg Val Ser Ala Ile
            740                 745                 750

Ile Thr Asn Thr Gly Asn Val Val Gly Asp Glu Val Pro Gln Leu Tyr
        755                 760                 765

Val Ser Leu Gly Gly Pro Asp Asp Pro Lys Val Val Leu Arg Asn Phe
    770                 775                 780

Asp Arg Ile Thr Leu His Pro Gly Gln Gln Thr Met Trp Thr Thr Thr
785                 790                 795                 800

Leu Thr Arg Arg Asp Ile Ser Asn Trp Asp Pro Ala Ser Gln Asn Trp
                805                 810                 815

Val Val Thr Lys Tyr Pro Lys Thr Val Tyr Ile Gly Ser Ser Ser Arg
            820                 825                 830

Lys Leu His Leu Gln Ala Pro Leu Pro Pro Tyr
        835                 840

<210> SEQ ID NO 57
<211> LENGTH: 663
<212> TYPE: PRT
<213> ORGANISM: Artificial
<220> FEATURE:
<223> OTHER INFORMATION: Synthetic polypeptide coded by a gene for A.

irakense CelA codon optimized for expression in B. megaterium and
E.coli and cloned behind a nucleotide sequence encoding the
Bacillus megaterium penicillin G acylase signal peptide plus a
spacer region

<400> SEQUENCE: 57

```
Ser Thr Ala Ile Ala Gln Glu Gly Ala Ala Pro Ala Ala Ile Leu His
1               5                   10                  15

Pro Glu Lys Trp Pro Arg Pro Ala Thr Gln Arg Leu Ile Asp Pro Ala
            20                  25                  30

Val Glu Lys Arg Val Asp Ala Leu Leu Lys Gln Leu Ser Val Glu Glu
        35                  40                  45

Lys Val Gly Gln Val Ile Gln Gly Asp Ile Gly Thr Ile Thr Pro Glu
    50                  55                  60

Asp Leu Arg Lys Tyr Pro Leu Gly Ser Ile Leu Ala Gly Gly Asn Ser
65                  70                  75                  80

Gly Pro Asn Gly Asp Asp Arg Ala Pro Pro Lys Glu Trp Leu Asp Leu
                85                  90                  95

Ala Asp Ala Phe Tyr Arg Val Ser Leu Glu Lys Arg Pro Gly His Thr
            100                 105                 110

Pro Ile Pro Val Leu Phe Gly Ile Asp Ala Val His Gly His Gly Asn
        115                 120                 125

Ile Gly Ser Ala Thr Ile Phe Pro His Asn Ile Ala Leu Gly Ala Thr
    130                 135                 140

His Asp Pro Glu Leu Leu Arg Arg Ile Gly Glu Val Thr Ala Val Glu
145                 150                 155                 160

Met Ala Ala Thr Gly Ile Asp Trp Thr Phe Ala Pro Ala Leu Ser Val
                165                 170                 175

Val Arg Asp Asp Arg Trp Gly Arg Thr Tyr Glu Gly Phe Ser Glu Asp
            180                 185                 190

Pro Glu Ile Val Ala Ala Tyr Ser Ala Ala Ile Val Glu Gly Val Gln
        195                 200                 205

Gly Lys Phe Gly Ser Lys Asp Phe Met Ala Pro Gly Arg Ile Val Ala
    210                 215                 220

Ser Ala Lys His Phe Leu Ala Asp Gly Gly Thr Asp Gln Gly Arg Asp
225                 230                 235                 240

Gln Gly Asp Ala Arg Ile Ser Glu Asp Glu Leu Ile Arg Ile His Asn
                245                 250                 255

Ala Gly Tyr Pro Pro Ala Ile Asp Ala Gly Val Leu Thr Val Met Ala
            260                 265                 270

Ser Phe Ser Ser Trp Gln Gly Ile Lys His Gly His Lys Gln Leu
        275                 280                 285

Leu Thr Asp Val Leu Lys Gly Gln Met Gly Phe Asn Gly Phe Ile Val
    290                 295                 300

Gly Asp Trp Asn Ala His Asp Gln Val Pro Gly Cys Thr Lys Phe Asn
305                 310                 315                 320

Cys Pro Thr Ser Leu Ile Ala Gly Leu Asp Met Tyr Met Ala Ala Asp
                325                 330                 335

Ser Trp Lys Gln Leu Tyr Glu Asn Thr Leu Ala Gln Val Lys Asp Gly
            340                 345                 350

Thr Ile Pro Met Ala Arg Leu Asp Asp Ala Val Arg Arg Ile Leu Arg
        355                 360                 365

Val Lys Val Leu Ala Gly Leu Phe Glu Lys Pro Ala Pro Lys Asp Arg
    370                 375                 380
```

```
Pro Gly Leu Pro Gly Leu Glu Thr Leu Gly Ser Pro Glu His Arg Ala
385                 390                 395                 400

Val Gly Arg Glu Ala Val Arg Lys Ser Leu Val Leu Leu Lys Asn Asp
            405                 410                 415

Lys Gly Thr Leu Pro Leu Ser Pro Lys Ala Arg Val Leu Val Ala Gly
            420                 425                 430

Asp Gly Ala Asp Asn Ile Gly Lys Gln Ser Gly Gly Trp Thr Ile Ser
            435                 440                 445

Trp Gln Gly Thr Gly Asn Arg Asn Asp Glu Phe Pro Gly Ala Thr Ser
        450                 455                 460

Ile Leu Gly Gly Ile Arg Asp Ala Val Ala Asp Ala Gly Gly Ser Val
465                 470                 475                 480

Glu Phe Asp Val Ala Gly Gln Tyr Lys Thr Lys Pro Asp Val Ala Ile
            485                 490                 495

Val Val Phe Gly Glu Glu Pro Tyr Ala Glu Phe Gln Gly Asp Val Glu
            500                 505                 510

Thr Leu Glu Tyr Gln Pro Asp Gln Lys Gln Asp Leu Ala Leu Leu Lys
            515                 520                 525

Lys Leu Lys Asp Gln Gly Ile Pro Val Ala Val Phe Leu Ser Gly
            530                 535                 540

Arg Pro Met Trp Val Asn Pro Glu Leu Asn Ala Ser Asp Ala Phe Val
545                 550                 555                 560

Ala Ala Trp Leu Pro Gly Thr Glu Gly Gly Val Ala Asp Val Leu
            565                 570                 575

Phe Thr Asp Lys Ala Gly Lys Val Gln His Asp Phe Ala Gly Lys Leu
            580                 585                 590

Ser Tyr Ser Trp Pro Arg Thr Ala Ala Gln Thr Thr Val Asn Arg Gly
            595                 600                 605

Asp Ala Asp Tyr Asn Pro Leu Phe Ala Tyr Gly Tyr Gly Leu Thr Tyr
            610                 615                 620

Lys Asp Lys Ser Lys Val Gly Thr Leu Pro Glu Glu Ser Gly Val Pro
625                 630                 635                 640

Ala Glu Ala Arg Gln Asn Ala Gly Ile Tyr Phe Arg Ala Gly Ala Leu
            645                 650                 655

Arg Leu Pro Gly Arg Phe Leu
            660

<210> SEQ ID NO 58
<211> LENGTH: 754
<212> TYPE: PRT
<213> ORGANISM: Sulfolobus solfataricus P2

<400> SEQUENCE: 58

Met Thr Ala Ile Lys Ser Leu Leu Asn Gln Met Ser Ile Glu Glu Lys
1               5                   10                  15

Ile Ala Gln Leu Gln Ala Ile Pro Ile Asp Ala Leu Met Glu Gly Lys
            20                  25                  30

Glu Phe Ser Glu Glu Lys Ala Arg Lys Tyr Leu Lys Leu Gly Ile Gly
        35                  40                  45

Gln Ile Thr Arg Val Ala Gly Ser Arg Leu Gly Leu Lys Pro Lys Glu
    50                  55                  60

Val Val Lys Leu Val Asn Lys Val Gln Lys Phe Leu Val Glu Asn Thr
65                  70                  75                  80

Arg Leu Lys Ile Pro Ala Ile Ile His Glu Glu Cys Leu Ser Gly Leu
            85                  90                  95
```

```
Met Gly Tyr Ser Ser Thr Ala Phe Pro Gln Ala Ile Gly Leu Ala Ser
            100                 105                 110

Thr Trp Asn Pro Glu Leu Leu Thr Asn Val Ala Ser Thr Ile Arg Ser
            115                 120                 125

Gln Gly Arg Leu Ile Gly Val Asn Gln Cys Leu Ser Pro Val Leu Asp
            130                 135                 140

Val Cys Arg Asp Pro Arg Trp Gly Arg Cys Glu Glu Thr Tyr Gly Glu
145                 150                 155                 160

Asp Pro Tyr Leu Val Ala Ser Met Gly Leu Ala Tyr Ile Thr Gly Leu
                165                 170                 175

Gln Gly Glu Thr Gln Leu Val Ala Thr Ala Lys His Phe Ala Ala His
            180                 185                 190

Gly Phe Pro Glu Gly Gly Arg Asn Ile Ala Gln Val His Val Gly Asn
            195                 200                 205

Arg Glu Leu Arg Glu Thr Phe Leu Phe Pro Phe Glu Val Ala Val Lys
            210                 215                 220

Ile Gly Lys Val Met Ser Ile Met Pro Ala Tyr His Glu Ile Asp Gly
225                 230                 235                 240

Val Pro Cys His Gly Asn Pro Gln Leu Leu Thr Asn Ile Leu Arg Gln
                245                 250                 255

Glu Trp Gly Phe Asp Gly Ile Val Val Ser Asp Tyr Asp Gly Ile Arg
            260                 265                 270

Gln Leu Glu Ala Ile His Lys Val Ala Ser Asn Lys Met Glu Ala Ala
            275                 280                 285

Ile Leu Ala Leu Glu Ser Gly Val Asp Ile Glu Phe Pro Thr Ile Asp
            290                 295                 300

Cys Tyr Gly Glu Pro Leu Val Thr Ala Ile Lys Glu Gly Leu Val Ser
305                 310                 315                 320

Glu Ala Ile Ile Asp Arg Ala Val Glu Arg Val Leu Arg Ile Lys Glu
                325                 330                 335

Arg Leu Gly Leu Leu Asp Asn Pro Phe Val Asp Glu Ser Ala Val Pro
            340                 345                 350

Glu Arg Leu Asp Asp Arg Lys Ser Arg Glu Leu Ala Leu Lys Ala Ala
            355                 360                 365

Arg Glu Ser Ile Val Leu Leu Lys Asn Glu Asn Asn Met Leu Pro Leu
            370                 375                 380

Ser Lys Asn Ile Asn Lys Ile Ala Val Ile Gly Pro Asn Ala Asn Asp
385                 390                 395                 400

Pro Arg Asn Met Leu Gly Asp Tyr Thr Tyr Thr Gly His Leu Asn Ile
                405                 410                 415

Asp Ser Gly Ile Glu Ile Val Thr Val Leu Gln Gly Ile Ala Lys Lys
            420                 425                 430

Val Gly Glu Gly Lys Val Leu Tyr Ala Lys Gly Cys Asp Ile Ala Gly
            435                 440                 445

Glu Ser Lys Glu Gly Phe Ser Glu Ala Ile Glu Ile Ala Lys Gln Ala
            450                 455                 460

Asp Val Ile Ile Ala Val Met Gly Glu Lys Ser Gly Leu Pro Leu Ser
465                 470                 475                 480

Trp Thr Asp Ile Pro Ser Glu Glu Phe Lys Lys Tyr Gln Ala Val
                485                 490                 495

Thr Gly Glu Gly Asn Asp Arg Ala Ser Leu Arg Leu Leu Gly Val Gln
            500                 505                 510
```

Glu Glu Leu Leu Lys Glu Leu Tyr Lys Thr Gly Lys Pro Ile Ile Leu
515                 520                 525

Val Leu Ile Asn Gly Arg Pro Leu Val Leu Ser Pro Ile Ile Asn Tyr
530                 535                 540

Val Lys Ala Ile Ile Glu Ala Trp Phe Pro Gly Glu Glu Gly Gly Asn
545                 550                 555                 560

Ala Ile Ala Asp Ile Ile Phe Gly Asp Tyr Asn Pro Ser Gly Arg Leu
            565                 570                 575

Pro Ile Thr Phe Pro Met Asp Thr Gly Gln Ile Pro Leu Tyr Tyr Ser
            580                 585                 590

Arg Lys Pro Ser Ser Phe Arg Pro Tyr Val Met Leu His Ser Ser Pro
            595                 600                 605

Leu Phe Thr Phe Gly Tyr Gly Leu Ser Tyr Thr Gln Phe Glu Tyr Ser
            610                 615                 620

Asn Leu Glu Val Thr Pro Lys Glu Val Gly Pro Leu Ser Tyr Ile Thr
625                 630                 635                 640

Ile Leu Leu Asp Val Lys Asn Val Gly Asn Met Glu Gly Asp Glu Val
            645                 650                 655

Val Gln Leu Tyr Ile Ser Lys Ser Phe Ser Ser Val Ala Arg Pro Val
            660                 665                 670

Lys Glu Leu Lys Gly Phe Ala Lys Val His Leu Lys Pro Gly Glu Lys
            675                 680                 685

Arg Arg Val Lys Phe Ala Leu Pro Met Glu Ala Leu Ala Phe Tyr Asp
            690                 695                 700

Asn Phe Met Arg Leu Val Val Glu Lys Gly Glu Tyr Gln Ile Leu Ile
705                 710                 715                 720

Gly Asn Ser Ser Glu Asn Ile Ile Leu Lys Asp Thr Phe Arg Ile Lys
            725                 730                 735

Glu Thr Lys Pro Ile Met Glu Arg Arg Ile Phe Leu Ser Asn Val Gln
            740                 745                 750

Ile Glu

<210> SEQ ID NO 59
<211> LENGTH: 715
<212> TYPE: PRT
<213> ORGANISM: Clostridium stercorarium

<400> SEQUENCE: 59

Met Glu Asn Lys Pro Val Tyr Leu Asp Pro Ser Tyr Ser Phe Glu Glu
1               5                   10                  15

Arg Ala Lys Asp Leu Val Ser Arg Met Thr Ile Glu Glu Lys Val Ser
                20                  25                  30

Gln Met Leu Tyr Asn Ser Pro Ala Ile Glu Arg Leu Gly Ile Pro Ala
            35                  40                  45

Tyr Asn Trp Trp Asn Glu Ala Leu His Gly Val Ala Arg Ala Gly Thr
        50                  55                  60

Ala Thr Met Phe Pro Gln Ala Ile Gly Met Ala Ala Thr Phe Asp Glu
65                  70                  75                  80

Glu Leu Ile Tyr Lys Val Ala Asp Val Ile Ser Thr Glu Gly Arg Ala
                85                  90                  95

Lys Tyr His Ala Ser Ser Lys Lys Gly Asp Arg Gly Ile Tyr Lys Gly
            100                 105                 110

Leu Thr Phe Trp Ser Pro Asn Ile Asn Ile Phe Arg Asp Pro Arg Trp
        115                 120                 125

```
Gly Arg Gly Gln Glu Thr Tyr Gly Glu Asp Pro Tyr Leu Thr Ala Arg
    130                 135                 140
Leu Gly Val Ala Phe Val Lys Gly Leu Gln Gly Asn His Pro Lys Tyr
145                 150                 155                 160
Leu Lys Ala Gly Gly Met Cys Lys Asn Ile Leu Pro Phe Thr Val Val
                165                 170                 175
Pro Glu Ser Leu Arg His Glu Phe Asn Ala Val Val Ser Lys Lys Asp
            180                 185                 190
Leu Tyr Glu Thr Tyr Leu Pro Ala Phe Lys Ala Leu Val Gln Glu Ala
        195                 200                 205
Lys Val Glu Ser Val Met Gly Ala Tyr Asn Arg Thr Asn Gly Glu Pro
210                 215                 220
Cys Cys Gly Ser Lys Thr Leu Leu Ser Asp Ile Leu Arg Gly Glu Trp
225                 230                 235                 240
Gly Phe Lys Gly His Val Val Ser Asp Cys Trp Ala Ile Arg Asp Phe
                245                 250                 255
His Met His His His Val Thr Ala Thr Pro Glu Ser Ala Ala Leu
        260                 265                 270
Ala Val Arg Asn Gly Cys Asp Leu Asn Cys Gly Asn Met Phe Gly Asn
        275                 280                 285
Leu Leu Ile Ala Leu Lys Glu Gly Leu Ile Thr Glu Glu Ile Asp
290                 295                 300
Arg Ala Val Thr Arg Leu Met Ile Thr Arg Met Lys Leu Gly Met Phe
305                 310                 315                 320
Asp Pro Glu Asp Gln Val Pro Tyr Ala Ser Ile Ser Ser Phe Val Asp
                325                 330                 335
Cys Lys Glu His Arg Glu Leu Ala Leu Asp Val Ala Lys Lys Ser Ile
            340                 345                 350
Val Leu Leu Lys Asn Asp Gly Leu Leu Pro Leu Asp Arg Lys Lys Ile
        355                 360                 365
Arg Ser Ile Ala Val Ile Gly Pro Asn Ala Asp Ser Arg Gln Ala Leu
370                 375                 380
Ile Gly Asn Tyr Glu Gly Thr Ala Ser Glu Tyr Val Thr Val Leu Asp
385                 390                 395                 400
Gly Ile Arg Glu Met Ala Gly Asp Asp Val Arg Ile Tyr Tyr Ser Val
                405                 410                 415
Gly Cys His Leu Tyr Lys Asp Arg Val Glu Asn Leu Gly Glu Pro Gly
            420                 425                 430
Asp Arg Ile Ala Glu Ala Val Thr Cys Ala Glu His Ala Asp Val Val
        435                 440                 445
Ile Met Cys Leu Gly Leu Asp Ser Thr Ile Glu Gly Glu Glu Met His
450                 455                 460
Glu Ser Asn Ile Tyr Gly Ser Gly Asp Lys Pro Asp Leu Asn Leu Pro
465                 470                 475                 480
Gly Gln Gln Gln Glu Leu Leu Glu Ala Val Tyr Ala Thr Gly Lys Pro
                485                 490                 495
Ile Val Leu Val Leu Leu Thr Gly Ser Ala Leu Ala Val Thr Trp Ala
            500                 505                 510
Asp Glu His Ile Pro Ala Ile Leu Asn Ala Trp Tyr Pro Gly Ala Leu
        515                 520                 525
Gly Gly Arg Ala Ile Ala Ser Val Leu Phe Gly Glu Thr Asn Pro Ser
530                 535                 540
Gly Lys Leu Pro Val Thr Phe Tyr Arg Thr Thr Glu Glu Leu Pro Asp
```

```
545                 550                 555                 560
Phe Thr Asp Tyr Ser Met Glu Asn Arg Thr Tyr Arg Phe Met Lys Asn
                565                 570                 575

Glu Ala Leu Tyr Pro Phe Gly Phe Gly Leu Ser Tyr Thr Thr Phe Asp
                580                 585                 590

Tyr Ser Asp Leu Lys Leu Ser Lys Asp Thr Ile Arg Ala Gly Glu Gly
                595                 600                 605

Phe Asn Val Ser Val Lys Val Thr Asn Thr Gly Lys Met Ala Gly Glu
                610                 615                 620

Glu Val Val Gln Val Tyr Ile Lys Asp Leu Glu Ala Ser Trp Arg Val
625                 630                 635                 640

Pro Asn Trp Gln Leu Ser Gly Met Lys Arg Val Arg Leu Glu Ser Gly
                645                 650                 655

Glu Thr Ala Glu Ile Thr Phe Glu Ile Arg Pro Glu Gln Leu Ala Val
                660                 665                 670

Val Thr Asp Glu Gly Lys Ser Val Ile Glu Pro Gly Glu Phe Glu Ile
                675                 680                 685

Tyr Val Gly Gly Ser Gln Pro Asp Ala Arg Ser Val Arg Leu Met Gly
                690                 695                 700

Lys Ala Pro Leu Lys Ala Val Leu Arg Val Gln
705                 710                 715
```

<210> SEQ ID NO 60
<211> LENGTH: 861
<212> TYPE: PRT
<213> ORGANISM: Prevotella ruminicola

<400> SEQUENCE: 60

```
Met Lys Tyr Gln Leu Phe Leu Ser Leu Ala Leu Cys Val Gly Leu Gly
1               5                   10                  15

Ala Ser Ala Gln Thr Leu Pro Tyr Gln Asn Pro Asn Leu Ser Ala Lys
                20                  25                  30

Glu Arg Ala Val Asp Leu Cys Ser Arg Leu Thr Leu Glu Glu Lys Ala
            35                  40                  45

Met Leu Met Leu Asp Glu Ser Pro Ala Ile Pro Arg Leu Gly Ile Lys
        50                  55                  60

Lys Phe Phe Trp Trp Ser Glu Ala Leu His Gly Ala Ala Asn Met Gly
65                  70                  75                  80

Asn Val Thr Asn Phe Pro Glu Pro Val Gly Met Ala Ala Ser Phe Asn
                85                  90                  95

Pro His Leu Leu Phe Lys Val Phe Asp Ile Ala Ser Thr Glu Phe Arg
                100                 105                 110

Ala Gln Tyr Asn His Arg Met Tyr Asp Leu Asn Gly Glu Asp Met Lys
            115                 120                 125

Met Arg Ser Leu Ser Val Trp Thr Pro Asn Val Asn Ile Phe Arg Asp
        130                 135                 140

Pro Arg Trp Gly Arg Gly Gln Glu Thr Tyr Gly Glu Asp Pro Tyr Leu
145                 150                 155                 160

Thr Ser Val Met Gly Val Gln Val Val Lys Gly Leu Gln Gly Pro Glu
                165                 170                 175

Asp Ala Arg Tyr Arg Lys Leu Trp Ala Cys Ala Lys His Tyr Ala Val
                180                 185                 190

His Ser Gly Pro Glu Tyr Thr Arg His Thr Ala Asn Leu Thr Asp Val
            195                 200                 205
```

```
Ser Ala Arg Asp Phe Trp Glu Thr Tyr Met Pro Ala Phe Lys Thr Leu
210                 215                 220
Val Lys Asp Ala Lys Val Arg Glu Val Met Cys Ala Tyr Gln Arg Leu
225                 230                 235                 240
Asp Asp Asp Pro Cys Cys Gly Ser Thr Arg Leu Leu Gln Gln Ile Leu
                245                 250                 255
Arg Asp Glu Trp Gly Phe Glu Tyr Leu Val Val Ser Asp Cys Gly Ala
            260                 265                 270
Val Ser Asp Phe Tyr Glu Asn His Lys Ser Ser Asp Ala Val His
        275                 280                 285
Gly Thr Ser Lys Ala Val Leu Ala Gly Thr Asp Val Glu Cys Gly Phe
290                 295                 300
Asn Tyr Ala Tyr Lys Ser Leu Pro Glu Ala Val Arg Lys Gly Leu Leu
305                 310                 315                 320
Ser Glu Lys Glu Val Asp Lys His Val Ile Arg Leu Leu Glu Gly Arg
                325                 330                 335
Phe Asp Leu Gly Glu Met Asp Asp Pro Ser Leu Val Glu Trp Ser Lys
            340                 345                 350
Ile Pro Tyr Ser Ala Met Ser Thr Lys Ala Ser Ala Asn Val Ala Leu
        355                 360                 365
Asp Met Ala Arg Gln Thr Ile Val Leu Leu Gln Asn Lys Asn Asn Ile
370                 375                 380
Leu Pro Leu Lys Lys Asn Ala Glu Lys Ile Ala Ile Ile Gly Pro Asn
385                 390                 395                 400
Ala His Asn Glu Pro Met Met Trp Gly Asn Tyr Asn Gly Thr Pro Asn
                405                 410                 415
His Thr Val Thr Ile Leu Asp Gly Val Lys Ala Lys Gln Lys Lys Leu
            420                 425                 430
Val Tyr Ile Pro Gly Cys Asp Leu Thr Asn Asp Lys Val Met Glu Cys
        435                 440                 445
His Leu Ala Thr Asp Cys Val Thr Pro Asp Gly Lys Lys Gly Leu Lys
450                 455                 460
Gly Thr Phe Trp Asn Asn Thr Glu Met Ala Gly Lys Pro Phe Thr Thr
465                 470                 475                 480
Glu Tyr Tyr Thr Lys Pro Val Asn Val Thr Thr Ala Gly Met His Val
                485                 490                 495
Phe Ala Pro Asn Leu Pro Ile Glu Asp Phe Ser Ala Lys Tyr Glu Thr
            500                 505                 510
Thr Phe Thr Ala Lys Glu Ala Gly Glu Tyr Val Val Asn Val Glu Ser
        515                 520                 525
Thr Gly His Phe Glu Leu Tyr Val Asn Gly Lys Gln Gln Phe Val Asn
530                 535                 540
His Ile Trp Arg Ala Thr Pro Thr Arg Thr Val Leu Lys Ala Glu Lys
545                 550                 555                 560
Gly Gln Lys Phe Asp Ile Glu Val Arg Phe Gln Thr Val Lys Thr Trp
                565                 570                 575
Gly Ala Ser Met Lys Ile Asp Val Ala Arg Glu Leu Asn Ile Asp Tyr
            580                 585                 590
Gln Glu Thr Ile Ala Gln Leu Lys Gly Ile Asn Lys Val Ile Phe Cys
        595                 600                 605
Gly Gly Ile Ala Pro Ser Leu Glu Gly Glu Met Pro Val Asn Ile
610                 615                 620
Glu Gly Phe Lys Gly Gly Asp Arg Thr Ser Ile Glu Leu Pro Lys Val
```

```
                        625                 630                 635                 640
            Gln Arg Glu Phe Leu Lys Ala Leu Lys Ala Ala Gly Lys Gln Val Ile
                                645                 650                 655

Tyr Val Asn Cys Ser Gly Ser Ala Ile Ala Leu Gln Pro Glu Thr Glu
                                660                 665                 670

Ser Cys Asp Ala Ile Val Gln Ala Trp Tyr Pro Gly Gln Glu Gly
                                675                 680                 685

Thr Ala Val Ala Asp Val Leu Phe Gly Asp Tyr Asn Pro Gly Gly Lys
                690                 695                 700

Leu Ser Val Thr Phe Tyr Lys Asn Asp Gln Gln Leu Pro Asp Tyr Glu
            705                 710                 715                 720

Asp Tyr Ser Met Lys Gly Arg Thr Tyr Arg Tyr Phe Asp Ala Leu
                                725                 730                 735

Phe Pro Phe Gly Tyr Gly Leu Ser Tyr Thr Thr Phe Glu Val Gly Glu
                                740                 745                 750

Ala Lys Val Glu Ala Ala Thr Asp Gly Ala Leu Tyr Asn Val Gln Ile
                                755                 760                 765

Pro Val Thr Asn Thr Gly Thr Lys Asn Gly Ser Glu Thr Ile Gln Leu
                770                 775                 780

Tyr Ile Arg Asn Leu Gln Asp Pro Asp Gly Pro Leu Lys Ser Leu Arg
            785                 790                 795                 800

Gly Phe Glu Arg Leu Asp Ile Lys Ala Gly Lys Thr Ala Thr Ala Asn
                                805                 810                 815

Leu Lys Leu Thr Lys Glu Ser Leu Glu Phe Trp Asp Ala Glu Thr Asn
                                820                 825                 830

Thr Met Arg Thr Lys Pro Gly Lys Tyr Glu Ile Leu Tyr Gly Thr Ser
                                835                 840                 845

Ser Leu Asp Lys Asp Leu Lys Lys Leu Thr Ile Thr Leu
                850                 855                 860

<210> SEQ ID NO 61
<211> LENGTH: 861
<212> TYPE: PRT
<213> ORGANISM: Streptomyces lividans

<400> SEQUENCE: 61

Met Thr Ala Asp Val Ala Val Glu Thr Thr Pro Glu Ile Pro Leu Trp
            1               5                   10                  15

Asn Asp Pro Asn His Pro Val Ala Ser Arg Val Asp Ala Leu Val Ala
                                20                  25                  30

Ala Met Thr Leu Glu Glu Lys Ile Ala Gln Leu Tyr Gly Val Trp Val
                                35                  40                  45

Gly Ala Ser Asp Gln Gly Gly Glu Val Ala Pro Ile Ser Thr Thr Trp
                50                  55                  60

Arg Arg Pro Ser Thr Ser Thr Arg Ser Cys Pro Pro Gly Ser Val Ser
            65                  70                  75                  80

Ser Pro Gly Pro Ser Ala Pro Ser Arg Ser Thr Pro Arg Ser Ala Pro
                                85                  90                  95

Ser Arg Ser Cys Ala Arg Arg Pro Arg Ile Thr Ser Ala Gly Arg Phe
                                100                 105                 110

Gly Ile Pro Ala Val Ala His Glu Glu Cys Leu Ala Gly Phe Ala Pro
                                115                 120                 125

Trp Gly Ala Thr Ala Tyr Pro Val Pro Leu Ser Trp Gly Ala Thr Phe
                130                 135                 140
```

```
Asp Pro Asp Ala Val Arg Arg Met Ala Ala Ala Ile Gly Arg Asp Met
145                 150                 155                 160
Arg Ser Val Gly Ile His Gln Gly Leu Ala Pro Val Leu Asp Val Val
            165                 170                 175
Arg Asp Gly Arg Trp Gly Arg Val Glu Glu Thr Ile Gly Glu Asp Pro
        180                 185                 190
Tyr Leu Val Gly Thr Ile Gly Thr Ala Tyr Val Gln Gly Leu Glu Ser
        195                 200                 205
Ala Gly Ile Val Ala Thr Leu Lys His Phe Val Gly Tyr Ser Ala Ser
210                 215                 220
Arg Ala Gly Arg Asn Leu Gly Pro Ser Ser Val Gly Thr Arg Glu Arg
225                 230                 235                 240
Thr Asp Val Leu Leu Pro Pro Phe Glu Met Ala Val Arg Glu Gly Gly
            245                 250                 255
Ser Arg Ser Val Met Ser Ala Tyr Thr Asp Ile Asp Gly Val Pro Ala
            260                 265                 270
Ala Ala Asp Glu Ala Leu Leu Thr Gly Ala Val Arg Asp Thr Trp Gly
        275                 280                 285
Phe Glu Gly Thr Val Val Ala Asp Tyr Phe Gly Ile Ala Phe Leu Lys
        290                 295                 300
Thr Leu His Gly Ile Thr Ala Asp Trp Ala Asp Ala Gly Ala Ala
305                 310                 315                 320
Leu Lys Ala Gly Leu Asp Val Glu Leu Pro Thr Val Gln Asp Phe Gly
            325                 330                 335
Thr Pro Leu Val Asp Ala Val Thr Asp Gly Arg Val Pro Glu Ala Leu
            340                 345                 350
Ile Asp Arg Ala Ala Pro Arg Pro Gly Thr Glu Gly Gly Ala Arg Thr
        355                 360                 365
Ala Arg Pro Gly Leu Glu Pro Gly Pro Ala Ala Leu Asp Gly Val Asp
        370                 375                 380
Leu Ser His Pro Glu Ala Leu Arg Gly Arg Ile Asp Leu Asp Arg Pro
385                 390                 395                 400
Glu Asn Arg Glu Leu Ala Arg Glu Ile Ala Glu Lys Ala Val Val Leu
            405                 410                 415
Leu Thr Asn Asp Gly Thr Leu Pro Leu Ala Arg Pro Arg Ile Ala
            420                 425                 430
Leu Ile Gly Pro Asn Ala Ala Glu Ala Thr Ala Val Leu Gly Cys Tyr
        435                 440                 445
Ser Phe Pro Arg His Val Gly Val Gln His Pro Glu Val Pro Val Gly
450                 455                 460
Leu Asp Leu Pro Thr Leu Tyr Asp Thr Leu Thr Ala Glu Phe Pro Asp
465                 470                 475                 480
Ala Asp Ile Ala Leu Ala Arg Gly Thr Gly Val Asp Asp Gly Glu Val
            485                 490                 495
Ser Gly Ile Gly Glu Ala Val Asp Ala Ala Arg Ala Ala Asp Val Val
            500                 505                 510
Val Ala Val Leu Gly Asp Arg Ala Gly Leu Phe Gly Arg Gly Thr Ser
        515                 520                 525
Gly Glu Gly Cys Asp Ala Glu Ser Leu Thr Leu Pro Gly Ala Gln Gln
        530                 535                 540
Arg Leu Leu Asp Ala Leu Leu Asp Ser Gly Thr Pro Val Val Thr Val
545                 550                 555                 560
Leu Leu Ala Gly Arg Pro Tyr Ala Leu Gly Arg Ala Arg Gln Ser Ala
```

```
                565                 570                 575
Ala Ile Val Gln Ser Phe Phe Pro Gly Glu Glu Gly Thr Ala Ala Leu
                580                 585                 590

Ala Gly Val Leu Ser Gly Arg Thr Ser Pro Thr Gly Arg Leu Pro Val
                595                 600                 605

Ser Val Pro Gly Ser Ala Ala Gln Pro Thr Thr Tyr Leu Gly Ala Arg
    610                 615                 620

Leu Ala Gln Ala Ser Glu Val Ser Asn Ile Asp Pro Thr Pro Ala Phe
625                 630                 635                 640

Gly Phe Gly His Gly Leu Thr Tyr Thr Thr Phe Ala Trp Ser Asp Leu
                645                 650                 655

Val Ala His Thr Lys Glu Ala Pro Thr Asp Gly Ala Phe Ser Leu Glu
                660                 665                 670

Leu Thr Val Arg Asn Thr Gly Glu Arg His Gly Thr Glu Val Val Gln
                675                 680                 685

Leu Tyr Leu His Asp Pro Val Ala Ser Val Val Gln Pro Val Gln Arg
            690                 695                 700

Leu Ile Gly Tyr Thr Arg Val Pro Leu Arg Pro Gly Glu Ala Arg Arg
705                 710                 715                 720

Val Arg Val Glu Val Pro Ala Asp Leu Ala Ser Phe Asn Arg Arg Asp
                725                 730                 735

Gly Arg Arg Ile Val Glu Pro Gly Asp Leu Glu Leu Arg Phe Ala Ala
                740                 745                 750

Ser Ser Thr Glu Pro Arg Leu Thr Ala Thr Val Ala Leu Thr Gly Pro
            755                 760                 765

Glu Arg Arg Val Asp Gln His Pro Ala Thr Ala Arg Arg Leu Arg Ala
770                 775                 780

Gly Asp Arg Gly Arg Arg Gly Arg Gly Arg Leu Ser Gly Pro Trp Glu
785                 790                 795                 800

Ala Pro Val Val Pro Ala Thr Thr Ala Arg Arg Ala Val Gln Arg Thr
                805                 810                 815

Thr Ser Lys Thr Phe Phe Trp Met Pro Leu Ala Tyr Thr Ser Cys Ser
                820                 825                 830

Thr Ser Leu Ser Phe Arg Ala Ser Leu Ser Val Ser Leu Asn Ser Arg
            835                 840                 845

Leu Pro Ala Pro Ser Ser Gly Lys Thr Ser Arg Trp
    850                 855                 860

<210> SEQ ID NO 62
<211> LENGTH: 778
<212> TYPE: PRT
<213> ORGANISM: Thermotoga neapolitana

<400> SEQUENCE: 62

Met Glu Leu Tyr Arg Asp Pro Ser Gln Pro Val Glu Val Arg Val Lys
1               5                   10                  15

Asp Leu Leu Ser Arg Met Thr Leu Glu Glu Lys Ile Ala Gln Leu Gly
                20                  25                  30

Ser Val Trp Gly Tyr Glu Leu Ile Asp Glu Arg Gly Lys Phe Lys Arg
            35                  40                  45

Glu Lys Ala Lys Asp Leu Leu Lys Asn Gly Ile Gly Gln Ile Thr Arg
        50                  55                  60

Pro Gly Gly Ser Thr Asn Leu Glu Pro Gln Glu Ala Ala Glu Leu Val
65                  70                  75                  80
```

-continued

```
Asn Glu Ile Gln Arg Phe Leu Val Glu Glu Thr Arg Leu Gly Ile Pro
             85                  90                  95
Ala Met Ile His Glu Glu Cys Leu Thr Gly Tyr Met Gly Leu Gly Gly
            100                 105                 110
Thr Asn Phe Pro Gln Ala Ile Ala Met Ala Ser Thr Trp Asp Pro Asp
        115                 120                 125
Leu Ile Glu Lys Met Thr Ala Ala Ile Arg Glu Asp Met Arg Lys Leu
    130                 135                 140
Gly Ala His Gln Gly Leu Ala Pro Val Leu Asp Val Ala Arg Asp Pro
145                 150                 155                 160
Arg Trp Gly Arg Thr Glu Glu Thr Phe Gly Glu Ser Pro Tyr Leu Val
                165                 170                 175
Ala Arg Met Gly Val Ser Tyr Val Lys Gly Leu Gln Gly Glu Asn Ile
            180                 185                 190
Lys Glu Gly Val Val Ala Thr Val Lys His Phe Ala Gly Tyr Ser Ala
        195                 200                 205
Ser Glu Gly Gly Lys Asn Trp Ala Pro Thr Asn Ile Pro Glu Arg Glu
    210                 215                 220
Phe Arg Glu Val Phe Leu Phe Pro Phe Glu Ala Ala Val Lys Glu Ala
225                 230                 235                 240
Arg Val Leu Ser Val Met Asn Ser Tyr Ser Glu Ile Asp Gly Val Pro
                245                 250                 255
Cys Ala Ala Asn Arg Arg Leu Leu Thr Asp Ile Leu Arg Lys Asp Trp
            260                 265                 270
Gly Phe Glu Gly Ile Val Val Ser Asp Tyr Phe Ala Val Asn Met Leu
        275                 280                 285
Gly Glu Tyr His Arg Ile Ala Lys Asp Lys Ser Glu Ser Ala Arg Leu
    290                 295                 300
Ala Leu Glu Ala Gly Ile Asp Val Glu Leu Pro Lys Thr Asp Cys Tyr
305                 310                 315                 320
Gln His Leu Lys Asp Leu Val Glu Lys Gly Ile Val Pro Glu Ser Leu
                325                 330                 335
Ile Asp Glu Ala Val Ser Arg Val Leu Lys Leu Lys Phe Met Leu Gly
            340                 345                 350
Leu Phe Glu Asn Pro Tyr Val Asp Val Glu Lys Ala Lys Ile Glu Ser
        355                 360                 365
His Arg Asp Leu Ala Leu Glu Ile Ala Arg Lys Ser Ile Ile Leu Leu
    370                 375                 380
Lys Asn Asp Gly Thr Leu Pro Leu Gln Lys Asn Lys Val Ala Leu
385                 390                 395                 400
Ile Gly Pro Asn Ala Gly Glu Val Arg Asn Leu Leu Gly Asp Tyr Met
                405                 410                 415
Tyr Leu Ala His Ile Arg Ala Leu Leu Asp Asn Ile Asp Asp Val Phe
            420                 425                 430
Gly Asn Pro Gln Ile Pro Arg Glu Asn Tyr Glu Arg Leu Lys Lys Ser
        435                 440                 445
Ile Glu Glu His Met Lys Ser Ile Pro Ser Val Leu Asp Ala Phe Lys
    450                 455                 460
Glu Glu Gly Ile Asp Phe Glu Tyr Ala Lys Gly Cys Glu Val Thr Gly
465                 470                 475                 480
Glu Asp Arg Ser Gly Phe Lys Glu Ala Ile Glu Val Ala Lys Arg Ser
                485                 490                 495
Asp Val Ala Ile Val Val Val Gly Asp Arg Ser Gly Leu Thr Leu Asp
```

-continued

```
                500             505             510
Cys Thr Thr Gly Glu Ser Arg Asp Met Ala Asn Leu Lys Leu Pro Gly
            515                 520                 525
Val Gln Glu Glu Leu Val Leu Glu Ile Ala Lys Thr Gly Lys Pro Val
            530                 535                 540
Val Leu Val Leu Ile Thr Gly Arg Pro Tyr Ser Lys Asn Leu Val
545                 550                 555                 560
Asp Arg Val Asn Ala Ile Leu Gln Val Trp Leu Pro Gly Glu Ala Gly
            565                 570                 575
Gly Arg Ala Ile Val Asp Val Ile Tyr Gly Lys Val Asn Pro Ser Gly
            580                 585                 590
Lys Leu Pro Ile Ser Phe Pro Arg Ser Ala Gly Gln Ile Pro Val Phe
            595                 600                 605
His Tyr Val Lys Pro Ser Gly Arg Ser His Trp His Gly Asp Tyr
            610                 615                 620
Val Asp Glu Ser Thr Lys Pro Leu Phe Pro Phe Gly His Gly Leu Ser
625                 630                 635                 640
Tyr Thr Arg Phe Glu Tyr Ser Asn Leu Arg Ile Glu Pro Lys Glu Val
                    645                 650                 655
Pro Ser Ala Gly Glu Val Val Ile Lys Val Asp Val Glu Asn Val Gly
                    660                 665                 670
Asp Met Asp Gly Asp Glu Val Val Gln Leu Tyr Ile Gly Arg Glu Phe
                675                 680                 685
Ala Ser Val Thr Arg Pro Val Lys Glu Leu Lys Gly Phe Lys Arg Val
            690                 695                 700
Ser Leu Lys Ala Lys Glu Lys Lys Thr Val Val Phe Arg Leu His Thr
705                 710                 715                 720
Asp Val Leu Ala Tyr Tyr Asp Arg Asp Met Lys Leu Val Val Glu Pro
                    725                 730                 735
Gly Glu Phe Arg Val Met Val Gly Ser Ser Ser Glu Asp Ile Arg Leu
                740                 745                 750
Thr Gly Ser Phe Ser Val Thr Gly Ser Lys Arg Glu Val Val Gly Lys
            755                 760                 765
Arg Lys Phe Phe Thr Glu Val Tyr Glu Glu
            770                 775

<210> SEQ ID NO 63
<211> LENGTH: 761
<212> TYPE: PRT
<213> ORGANISM: Unknown
<220> FEATURE:
<223> OTHER INFORMATION: Uncultured rumen bacterium, beta-xylosidase
      thereof

<400> SEQUENCE: 63

Met Met Asn Leu Arg Leu Cys Phe Arg Ala Ala Leu Ala Ala Ala Cys
1               5                   10                  15
Met Met Ala Ala Phe Ala Ser Cys Ala Pro Gln Glu Ile Ser Tyr Thr
            20                  25                  30
Asp Lys Ser Gln Pro Ala Glu Leu Arg Ala Lys Ala Leu Leu Pro Lys
        35                  40                  45
Leu Ser Leu Glu Glu Lys Ala Gly Leu Val Gln Tyr Asn Ser Pro Ala
    50                  55                  60
Val Glu Arg Leu Gly Ile Lys Ala Tyr Asn Trp Trp Ser Glu Ala Leu
65                  70                  75                  80
```

His Gly Val Ala Arg Asn Gly Ser Ala Thr Val Phe Pro Gln Pro Ile
            85                  90                  95
Gly Met Ala Ala Ser Phe Asp Val Glu Lys Ile Glu Thr Val Phe Thr
        100                 105                 110
Ala Val Ser Asp Glu Ala Arg Val Lys Asn Arg Ile Ala Ala Glu Asp
    115                 120                 125
Gly Arg Val Tyr Gln Tyr Ala Gly Leu Ser Phe Trp Thr Pro Asn Ile
130                 135                 140
Asn Ile Phe Arg Asp Pro Arg Trp Gly Arg Gly Met Glu Thr Tyr Gly
145                 150                 155                 160
Glu Asp Pro Tyr Leu Met Gly Gln Leu Gly Met Ala Val Val Arg Gly
            165                 170                 175
Leu Gln Gly Asp Pro Asp Ala Asp Val Leu Lys Thr His Ala Cys Ala
        180                 185                 190
Lys His Tyr Ala Val His Ser Gly Leu Glu Ser Asn Arg His Arg Phe
    195                 200                 205
Asp Ala Gln Val Ser Glu Arg Asp Leu Arg Glu Thr Tyr Leu Pro Ala
210                 215                 220
Phe Lys Asp Leu Val Thr Lys Ala Gly Val Lys Glu Val Met Thr Ala
225                 230                 235                 240
Tyr Asn Arg Phe Arg Gly Tyr Pro Cys Ala Ala Ser Glu Tyr Leu Val
            245                 250                 255
Gln Lys Ile Leu Arg Glu Glu Trp Gly Tyr Lys Gly Leu Val Val Ser
        260                 265                 270
Asp Cys Trp Ala Ile Pro Asp Phe Phe Glu Pro Gly Arg His Gly Phe
    275                 280                 285
Val Ala Thr Gly Glu Glu Ala Ala Leu Ala Val Ala Asn Gly Leu
290                 295                 300
Asp Val Glu Cys Gly Ser Thr Phe Ser Lys Ile Pro Ala Ala Ile Asp
305                 310                 315                 320
Gln Gly Leu Leu Lys Glu Glu Asp Leu Asp Arg Asn Leu Leu Arg Val
            325                 330                 335
Leu Thr Glu Arg Phe Arg Leu Gly Glu Met Asp Gly Glu Ser Pro Trp
        340                 345                 350
Asp Asp Leu Asp Pro Ala Ile Val Glu Gly Pro Glu His Arg Ala Leu
    355                 360                 365
Ser Leu Asp Ile Ala Arg Glu Thr Met Val Leu Leu Arg Asn Asn Gly
370                 375                 380
Val Leu Pro Leu Lys Ala Gly Glu Lys Ile Ala Leu Ile Gly Pro Asn
385                 390                 395                 400
Ala Asp Asp Ala Gln Met Gln Trp Gly Asn Tyr Asn Pro Val Pro Lys
            405                 410                 415
Ser Thr Ile Thr Leu Leu Gln Ala Met Gln Ala Arg Val Pro Gly Leu
        420                 425                 430
Val Tyr Asp Arg Ala Cys Gly Ile Leu Asp Ala Glu Tyr Ala Pro Gln
    435                 440                 445
Gly Ser Ala Tyr Ala Asn Leu Ile Gly Ala Ser Glu Ala Gln Leu Glu
450                 455                 460
Ala Ala Ala Arg Arg Tyr Ala Val Ser Val Asn Asp Ile Lys Asn Tyr
465                 470                 475                 480
Ile Arg Arg Asp Glu Glu Gln Arg Arg Ser Phe Met Pro Ala Leu Asp
            485                 490                 495
Glu Ala Ala Val Leu Lys Lys Leu Glu Gly Val Asp Val Val Val Phe

```
            500                 505                 510
Ala Gly Gly Ile Ser Pro Arg Leu Glu Gly Glu Met Arg Val Gln
        515                 520                 525
Val Pro Gly Phe Ser Gly Gly Asp Arg Thr Asp Ile Glu Leu Pro Gly
        530                 535                 540
Val Gln Arg Arg Leu Leu Lys Ala Leu His Asp Ala Gly Lys Lys Val
545                 550                 555                 560
Val Leu Val Asn Phe Ser Gly Cys Ala Ile Gly Leu Val Pro Glu Thr
                565                 570                 575
Glu Ser Cys Asp Ala Ile Leu Gln Ala Trp Tyr Pro Gly Gln Glu Gly
            580                 585                 590
Gly Thr Ala Ile Ala Asp Val Leu Phe Gly Asp Val Asn Pro Ser Gly
        595                 600                 605
Lys Leu Pro Val Thr Phe Tyr Lys Asn Val Asp Gln Leu Pro Asp Val
        610                 615                 620
Glu Asp Tyr Asn Met Glu Gly His Thr Tyr Arg Tyr Phe Arg Gly Glu
625                 630                 635                 640
Pro Leu Tyr Pro Phe Gly Tyr Gly Leu Ser Tyr Thr Ser Phe Ala Phe
                645                 650                 655
Gly Glu Pro Lys Val Lys Gly Lys Asn Leu Glu Ile Asp Val Thr Asn
            660                 665                 670
Thr Gly Ser Val Ala Gly Thr Glu Val Val Gln Leu Tyr Val Arg Lys
        675                 680                 685
Pro Asp Asp Thr Ala Gly Pro Val Lys Thr Leu Arg Ala Phe Arg Arg
        690                 695                 700
Val Ser Val Pro Ala Gly Gln Thr Val Lys Val Ser Ile Pro Leu Asp
705                 710                 715                 720
Lys Glu Thr Phe Leu Trp Trp Ser Glu Lys Asp Gln Asp Met Val Pro
                725                 730                 735
Val Arg Gly Arg Tyr Glu Leu Leu Cys Gly Gly Ser Ser Ala Ala Ser
            740                 745                 750
Asp Leu Lys Ser Val Ser Tyr Lys Phe
        755                 760

<210> SEQ ID NO 64
<211> LENGTH: 784
<212> TYPE: PRT
<213> ORGANISM: Arabidopsis thaliana

<400> SEQUENCE: 64

Met Gly Ser Ser Ser Pro Leu Thr Arg Arg Asn Arg Ala Pro Pro Ser
1               5                   10                  15
Ser Val Ser Ser Val Tyr Leu Ile Phe Leu Cys Phe Phe Leu Tyr Phe
                20                  25                  30
Leu Asn Phe Ser Asn Ala Gln Ser Ser Pro Val Phe Ala Cys Asp Val
            35                  40                  45
Ala Ala Asn Pro Ser Leu Ala Ala Tyr Gly Phe Cys Asn Thr Val Leu
        50                  55                  60
Lys Ile Glu Tyr Arg Val Ala Asp Leu Val Ala Arg Leu Thr Leu Gln
65                  70                  75                  80
Glu Lys Ile Gly Phe Leu Val Ser Lys Ala Asn Gly Val Thr Arg Leu
                85                  90                  95
Gly Ile Pro Thr Tyr Glu Trp Trp Ser Glu Ala Leu His Gly Val Ser
            100                 105                 110
```

Tyr Ile Gly Pro Gly Thr His Phe Ser Ser Gln Val Pro Gly Ala Thr
            115                 120                 125

Ser Phe Pro Gln Val Ile Leu Thr Ala Ala Ser Phe Asn Val Ser Leu
130                 135                 140

Phe Gln Ala Ile Gly Lys Val Val Ser Thr Glu Ala Arg Ala Met Tyr
145                 150                 155                 160

Asn Val Gly Leu Ala Gly Leu Thr Tyr Trp Ser Pro Asn Val Asn Ile
                165                 170                 175

Phe Arg Asp Pro Arg Trp Gly Arg Gly Gln Thr Pro Gly Glu Asp
            180                 185                 190

Pro Leu Leu Ala Ser Lys Tyr Ala Ser Gly Tyr Val Lys Gly Leu Gln
                195                 200                 205

Glu Thr Asp Gly Gly Asp Ser Asn Arg Leu Lys Val Ala Ala Cys Cys
            210                 215                 220

Lys His Tyr Thr Ala Tyr Asp Val Asp Asn Trp Lys Gly Val Glu Arg
225                 230                 235                 240

Tyr Ser Phe Asn Ala Val Val Thr Gln Gln Asp Met Asp Asp Thr Tyr
                245                 250                 255

Gln Pro Pro Phe Lys Ser Cys Val Val Asp Gly Asn Val Ala Ser Val
            260                 265                 270

Met Cys Ser Tyr Asn Gln Val Asn Gly Lys Pro Thr Cys Ala Asp Pro
            275                 280                 285

Asp Leu Leu Ser Gly Val Ile Arg Gly Glu Trp Lys Leu Asn Gly Tyr
            290                 295                 300

Ile Val Ser Asp Cys Asp Ser Val Asp Val Leu Tyr Lys Asn Gln His
305                 310                 315                 320

Tyr Thr Lys Thr Pro Ala Glu Ala Ala Ile Ser Ile Leu Ala Gly
                325                 330                 335

Leu Asp Leu Asn Cys Gly Ser Phe Leu Gly Gln His Thr Glu Glu Ala
            340                 345                 350

Val Lys Ser Gly Leu Val Asn Glu Ala Ala Ile Asp Lys Ala Ile Ser
            355                 360                 365

Asn Asn Phe Leu Thr Leu Met Arg Leu Gly Phe Phe Asp Gly Asn Pro
370                 375                 380

Lys Asn Gln Ile Tyr Gly Gly Leu Gly Pro Thr Asp Val Cys Thr Ser
385                 390                 395                 400

Ala Asn Gln Glu Leu Ala Ala Asp Ala Ala Arg Gln Gly Ile Val Leu
                405                 410                 415

Leu Lys Asn Thr Gly Cys Leu Pro Leu Ser Pro Lys Ser Ile Lys Thr
            420                 425                 430

Leu Ala Val Ile Gly Pro Asn Ala Asn Val Thr Lys Thr Met Ile Gly
            435                 440                 445

Asn Tyr Glu Gly Thr Pro Cys Lys Tyr Thr Thr Pro Leu Gln Gly Leu
            450                 455                 460

Ala Gly Thr Val Ser Thr Thr Tyr Leu Pro Gly Cys Ser Asn Val Ala
465                 470                 475                 480

Cys Ala Val Ala Asp Val Ala Gly Ala Thr Lys Leu Ala Ala Thr Ala
                485                 490                 495

Asp Val Ser Val Leu Val Ile Gly Ala Asp Gln Ser Ile Glu Ala Glu
            500                 505                 510

Ser Arg Asp Arg Val Asp Leu His Leu Pro Gly Gln Gln Gln Glu Leu
            515                 520                 525

Val Ile Gln Val Ala Lys Ala Ala Lys Gly Pro Val Leu Leu Val Ile

```
                530             535             540
Met Ser Gly Gly Gly Phe Asp Ile Thr Phe Ala Lys Asn Asp Pro Lys
545                 550                 555                 560

Ile Ala Gly Ile Leu Trp Val Gly Tyr Pro Gly Glu Ala Gly Gly Ile
                565                 570                 575

Ala Ile Ala Asp Ile Ile Phe Gly Arg Tyr Asn Pro Ser Gly Lys Leu
            580                 585                 590

Pro Met Thr Trp Tyr Pro Gln Ser Tyr Val Glu Lys Val Pro Met Thr
        595                 600                 605

Ile Met Asn Met Arg Pro Asp Lys Ala Ser Gly Tyr Pro Gly Arg Thr
    610                 615                 620

Tyr Arg Phe Tyr Thr Gly Glu Thr Val Tyr Ala Phe Gly Asp Gly Leu
625                 630                 635                 640

Ser Tyr Thr Lys Phe Ser His Thr Leu Val Lys Ala Pro Ser Leu Val
                645                 650                 655

Ser Leu Gly Leu Glu Glu Asn His Val Cys Arg Ser Ser Glu Cys Gln
                660                 665                 670

Ser Leu Asp Ala Ile Gly Pro His Cys Glu Asn Ala Val Ser Gly Gly
            675                 680                 685

Gly Ser Ala Phe Glu Val His Ile Lys Val Arg Asn Gly Gly Asp Arg
        690                 695                 700

Glu Gly Ile His Thr Val Phe Leu Phe Thr Thr Pro Ala Ile His
705                 710                 715                 720

Gly Ser Pro Arg Lys His Leu Val Gly Phe Glu Lys Ile Arg Leu Gly
                725                 730                 735

Lys Arg Glu Glu Ala Val Val Arg Phe Lys Val Glu Ile Cys Lys Asp
                740                 745                 750

Leu Ser Val Val Asp Glu Ile Gly Lys Arg Lys Ile Gly Leu Gly Lys
            755                 760                 765

His Leu Leu His Val Gly Asp Leu Lys His Ser Leu Ser Ile Arg Ile
        770                 775                 780

<210> SEQ ID NO 65
<211> LENGTH: 774
<212> TYPE: PRT
<213> ORGANISM: Arabidopsis thaliana

<400> SEQUENCE: 65

Met Ser Cys Tyr Asn Lys Ala Leu Leu Ile Gly Asn Lys Val Val
1               5                   10                  15

Ile Leu Val Phe Leu Leu Cys Leu Val His Ser Ser Glu Ser Leu Arg
                20                  25                  30

Pro Leu Phe Ala Cys Asp Pro Ala Asn Gly Leu Thr Arg Thr Leu Arg
            35                  40                  45

Phe Cys Arg Ala Asn Val Pro Ile His Val Arg Val Gln Asp Leu Leu
        50                  55                  60

Gly Arg Leu Thr Leu Gln Glu Lys Ile Arg Asn Leu Val Asn Asn Ala
65                  70                  75                  80

Ala Ala Val Pro Arg Leu Gly Ile Gly Gly Tyr Glu Trp Trp Ser Glu
                85                  90                  95

Ala Leu His Gly Ile Ser Asp Val Gly Pro Gly Ala Lys Phe Gly Gly
                100                 105                 110

Ala Phe Pro Gly Ala Thr Ser Phe Pro Gln Val Ile Thr Thr Ala Ala
            115                 120                 125
```

```
Ser Phe Asn Gln Ser Leu Trp Glu Glu Ile Gly Arg Val Val Ser Asp
130                 135                 140

Glu Ala Arg Ala Met Tyr Asn Gly Gly Val Ala Gly Leu Thr Tyr Trp
145                 150                 155                 160

Ser Pro Asn Val Asn Ile Leu Arg Asp Pro Arg Trp Gly Arg Gly Gln
                165                 170                 175

Glu Thr Pro Gly Glu Asp Pro Ile Val Ala Ala Lys Tyr Ala Ala Ser
                180                 185                 190

Tyr Val Arg Gly Leu Gln Gly Thr Ala Ala Gly Asn Arg Leu Lys Val
                195                 200                 205

Ala Ala Cys Cys Lys His Tyr Thr Ala Tyr Asp Leu Asp Asn Trp Asn
210                 215                 220

Gly Val Asp Arg Phe His Phe Asn Ala Lys Val Thr Gln Gln Asp Leu
225                 230                 235                 240

Glu Asp Thr Tyr Asn Val Pro Phe Lys Ser Cys Val Tyr Glu Gly Lys
                245                 250                 255

Val Ala Ser Val Met Cys Ser Tyr Asn Gln Val Asn Gly Lys Pro Thr
                260                 265                 270

Cys Ala Asp Glu Asn Leu Leu Lys Asn Thr Ile Arg Gly Gln Trp Arg
                275                 280                 285

Leu Asn Gly Tyr Ile Val Ser Asp Cys Asp Ser Val Asp Val Phe Phe
290                 295                 300

Asn Gln Gln His Tyr Thr Ser Thr Pro Glu Glu Ala Ala Ala Arg Ser
305                 310                 315                 320

Ile Lys Ala Gly Leu Asp Leu Asp Cys Gly Pro Phe Leu Ala Ile Phe
                325                 330                 335

Thr Glu Gly Ala Val Lys Lys Gly Leu Leu Thr Glu Asn Asp Ile Asn
                340                 345                 350

Leu Ala Leu Ala Asn Thr Leu Thr Val Gln Met Arg Leu Gly Met Phe
                355                 360                 365

Asp Gly Asn Leu Gly Pro Tyr Ala Asn Leu Gly Pro Arg Asp Val Cys
370                 375                 380

Thr Pro Ala His Lys His Leu Ala Leu Glu Ala Ala His Gln Gly Ile
385                 390                 395                 400

Val Leu Leu Lys Asn Ser Ala Arg Ser Leu Pro Leu Ser Pro Arg Arg
                405                 410                 415

His Arg Thr Val Ala Val Ile Gly Pro Asn Ser Asp Val Thr Glu Thr
                420                 425                 430

Met Ile Gly Asn Tyr Ala Gly Lys Ala Cys Ala Tyr Thr Ser Pro Leu
                435                 440                 445

Gln Gly Ile Ser Arg Tyr Ala Arg Thr Leu His Gln Ala Gly Cys Ala
                450                 455                 460

Gly Val Ala Cys Lys Gly Asn Gln Gly Phe Gly Ala Ala Glu Ala Ala
465                 470                 475                 480

Ala Arg Glu Ala Asp Ala Thr Val Leu Val Met Gly Leu Asp Gln Ser
                485                 490                 495

Ile Glu Ala Glu Thr Arg Asp Arg Thr Gly Leu Leu Leu Pro Gly Tyr
                500                 505                 510

Gln Gln Asp Leu Val Thr Arg Val Ala Gln Ala Ser Arg Gly Pro Val
                515                 520                 525

Ile Leu Val Leu Met Ser Gly Gly Pro Ile Asp Val Thr Phe Ala Lys
530                 535                 540

Asn Asp Pro Arg Val Ala Ala Ile Ile Trp Ala Gly Tyr Pro Gly Gln
```

```
                    545                 550                 555                 560
Ala Gly Gly Ala Ala Ile Ala Asn Ile Ile Phe Gly Ala Ala Asn Pro
                565                 570                 575

Gly Gly Lys Leu Pro Met Thr Trp Tyr Pro Gln Asp Tyr Val Ala Lys
                580                 585                 590

Val Pro Met Thr Val Met Ala Met Arg Ala Ser Gly Asn Tyr Pro Gly
                595                 600                 605

Arg Thr Tyr Arg Phe Tyr Lys Gly Pro Val Val Phe Pro Phe Gly Phe
                610                 615                 620

Gly Leu Ser Tyr Thr Thr Phe Thr His Ser Leu Ala Lys Ser Pro Leu
625                 630                 635                 640

Ala Gln Leu Ser Val Ser Leu Ser Asn Leu Asn Ser Ala Asn Thr Ile
                645                 650                 655

Leu Asn Ser Ser Ser His Ser Ile Lys Val Ser His Thr Asn Cys Asn
                660                 665                 670

Ser Phe Pro Lys Met Pro Leu His Val Glu Val Ser Asn Thr Gly Glu
                675                 680                 685

Phe Asp Gly Thr His Thr Val Phe Val Phe Ala Glu Pro Pro Ile Asn
                690                 695                 700

Gly Ile Lys Gly Leu Gly Val Asn Lys Gln Leu Ile Ala Phe Glu Lys
705                 710                 715                 720

Val His Val Met Ala Gly Ala Lys Gln Thr Val Gln Val Asp Val Asp
                725                 730                 735

Ala Cys Lys His Leu Gly Val Val Asp Glu Tyr Gly Lys Arg Arg Ile
                740                 745                 750

Pro Met Gly Glu His Lys Leu His Ile Gly Asp Leu Lys His Thr Ile
                755                 760                 765

Leu Val Gln Pro Gln Leu
        770

<210> SEQ ID NO 66
<211> LENGTH: 773
<212> TYPE: PRT
<213> ORGANISM: Arabidopsis thaliana

<400> SEQUENCE: 66

Met Ala Ser Arg Asn Arg Ala Leu Phe Ser Val Ser Thr Leu Phe Leu
1               5                   10                  15

Cys Phe Ile Val Cys Ile Ser Glu Gln Ser Asn Asn Gln Ser Ser Pro
                20                  25                  30

Val Phe Ala Cys Asp Val Thr Gly Asn Pro Ser Leu Ala Gly Leu Arg
                35                  40                  45

Phe Cys Asn Ala Gly Leu Ser Ile Lys Ala Arg Val Thr Asp Leu Val
        50                  55                  60

Gly Arg Leu Thr Leu Glu Glu Lys Ile Gly Phe Leu Thr Ser Lys Ala
65              70                  75                  80

Ile Gly Val Ser Arg Leu Gly Ile Pro Ser Tyr Lys Trp Trp Ser Glu
                85                  90                  95

Ala Leu His Gly Val Ser Asn Val Gly Gly Gly Ser Arg Phe Thr Gly
                100                 105                 110

Gln Val Pro Gly Ala Thr Ser Phe Pro Gln Val Ile Leu Thr Ala Ala
                115                 120                 125

Ser Phe Asn Val Ser Leu Phe Gln Ala Ile Gly Lys Val Val Ser Thr
        130                 135                 140
```

```
Glu Ala Arg Ala Met Tyr Asn Val Gly Ser Ala Gly Leu Thr Phe Trp
145                 150                 155                 160

Ser Pro Asn Val Asn Ile Phe Arg Asp Pro Arg Trp Gly Arg Gly Gln
                165                 170                 175

Glu Thr Pro Gly Glu Asp Pro Thr Leu Ser Ser Lys Tyr Ala Val Ala
            180                 185                 190

Tyr Val Lys Gly Leu Gln Glu Thr Asp Gly Asp Pro Asn Arg Leu
        195                 200                 205

Lys Val Ala Ala Cys Cys Lys His Tyr Thr Ala Tyr Asp Ile Asp Asn
    210                 215                 220

Trp Arg Asn Val Asn Arg Leu Thr Phe Asn Ala Val Asn Gln Gln
225                 230                 235                 240

Asp Leu Ala Asp Thr Phe Gln Pro Pro Phe Lys Ser Cys Val Val Asp
                245                 250                 255

Gly His Val Ala Ser Val Met Cys Ser Tyr Asn Gln Val Asn Gly Lys
                260                 265                 270

Pro Thr Cys Ala Asp Pro Asp Leu Leu Ser Gly Val Ile Arg Gly Gln
            275                 280                 285

Trp Gln Leu Asn Gly Tyr Ile Val Ser Asp Cys Asp Ser Val Asp Val
290                 295                 300

Leu Phe Arg Lys Gln His Tyr Ala Lys Thr Pro Glu Glu Ala Val Ala
305                 310                 315                 320

Lys Ser Leu Leu Ala Gly Leu Asp Leu Asn Cys Asp His Phe Asn Gly
                325                 330                 335

Gln His Ala Met Gly Ala Val Lys Ala Gly Leu Val Asn Glu Thr Ala
            340                 345                 350

Ile Asp Lys Ala Ile Ser Asn Asn Phe Ala Thr Leu Met Arg Leu Gly
                355                 360                 365

Phe Phe Asp Gly Asp Pro Lys Lys Gln Leu Tyr Gly Gly Leu Gly Pro
                370                 375                 380

Lys Asp Val Cys Thr Ala Asp Asn Gln Glu Leu Ala Arg Asp Gly Ala
385                 390                 395                 400

Arg Gln Gly Ile Val Leu Leu Lys Asn Ser Ala Gly Ser Leu Pro Leu
                405                 410                 415

Ser Pro Ser Ala Ile Lys Thr Leu Ala Val Ile Gly Pro Asn Ala Asn
            420                 425                 430

Ala Thr Glu Thr Met Ile Gly Asn Tyr His Gly Val Pro Cys Lys Tyr
            435                 440                 445

Thr Thr Pro Leu Gln Gly Leu Ala Glu Thr Val Ser Ser Thr Tyr Gln
            450                 455                 460

Leu Gly Cys Asn Val Ala Cys Val Asp Ala Asp Ile Gly Ser Ala Val
465                 470                 475                 480

Asp Leu Ala Ala Ser Ala Asp Ala Val Val Leu Val Val Gly Ala Asp
                485                 490                 495

Gln Ser Ile Glu Arg Glu Gly His Asp Arg Val Asp Leu Tyr Leu Pro
            500                 505                 510

Gly Lys Gln Gln Glu Leu Val Thr Arg Val Ala Met Ala Ala Arg Gly
            515                 520                 525

Pro Val Val Leu Val Ile Met Ser Gly Gly Phe Asp Ile Thr Phe
            530                 535                 540

Ala Lys Asn Asp Lys Lys Ile Thr Ser Ile Met Trp Val Gly Tyr Pro
545                 550                 555                 560

Gly Glu Ala Gly Gly Leu Ala Ile Ala Asp Val Ile Phe Gly Arg His
```

```
                    565                 570                 575
Asn Pro Ser Gly Asn Leu Pro Met Thr Trp Tyr Pro Gln Ser Tyr Val
                580                 585                 590

Glu Lys Val Pro Met Ser Asn Met Asn Met Arg Pro Asp Lys Ser Lys
                595                 600                 605

Gly Tyr Pro Gly Arg Ser Tyr Arg Phe Tyr Thr Gly Glu Thr Val Tyr
                610                 615                 620

Ala Phe Ala Asp Ala Leu Thr Tyr Thr Lys Phe Asp His Gln Leu Ile
625                 630                 635                 640

Lys Ala Pro Arg Leu Val Ser Leu Ser Leu Asp Glu Asn His Pro Cys
                645                 650                 655

Arg Ser Ser Glu Cys Gln Ser Leu Asp Ala Ile Gly Pro His Cys Glu
                660                 665                 670

Asn Ala Val Glu Gly Gly Ser Asp Phe Glu Val His Leu Asn Val Lys
                675                 680                 685

Asn Thr Gly Asp Arg Ala Gly Ser His Thr Val Phe Leu Phe Thr Thr
                690                 695                 700

Ser Pro Gln Val His Gly Ser Pro Ile Lys Gln Leu Leu Gly Phe Glu
705                 710                 715                 720

Lys Ile Arg Leu Gly Lys Ser Glu Glu Ala Val Val Arg Phe Asn Val
                725                 730                 735

Asn Val Cys Lys Asp Leu Ser Val Val Asp Glu Thr Gly Lys Arg Lys
                740                 745                 750

Ile Ala Leu Gly His His Leu Leu His Val Gly Ser Leu Lys His Ser
                755                 760                 765

Leu Asn Ile Ser Val
                770

<210> SEQ ID NO 67
<211> LENGTH: 804
<212> TYPE: PRT
<213> ORGANISM: Aspergillus awamori

<400> SEQUENCE: 67

Met Ala His Ser Met Ser Arg Pro Val Ala Thr Ala Ala Ala Leu Leu
1               5                   10                  15

Leu Ala Leu Ala Leu Pro Gln Ala Leu Ala Gln Ala Asn Thr Ser Tyr
                20                  25                  30

Val Asp Tyr Asn Ile Glu Ala Asn Pro Asp Leu Tyr Pro Leu Cys Ile
                35                  40                  45

Glu Thr Ile Pro Leu Ser Phe Pro Asp Cys Gln Asn Gly Pro Leu Arg
50                  55                  60

Ser His Leu Ile Cys Asp Glu Thr Ala Thr Pro Tyr Asp Arg Ala Ala
65                  70                  75                  80

Ser Leu Ile Ser Leu Phe Thr Leu Asp Glu Leu Ile Ala Asn Thr Gly
                85                  90                  95

Asn Thr Gly Leu Gly Val Ser Arg Gly Leu Pro Ala Tyr Gln Val
                100                 105                 110

Trp Ser Glu Ala Leu His Gly Leu Asp Arg Ala Asn Phe Ser Asp Ser
                115                 120                 125

Gly Ala Tyr Asn Trp Ala Thr Ser Phe Pro Gln Pro Ile Leu Thr Thr
                130                 135                 140

Ala Ala Leu Asn Arg Thr Leu Ile His Gln Ile Ala Ser Ile Ile Ser
145                 150                 155                 160
```

```
Thr Gln Gly Arg Ala Phe Asn Asn Ala Gly Arg Tyr Gly Leu Asp Val
            165                 170                 175

Tyr Ala Pro Asn Ile Asn Thr Phe Arg His Pro Val Trp Gly Arg Gly
            180                 185                 190

Gln Glu Thr Pro Gly Glu Asp Val Ser Leu Ala Ala Val Tyr Ala Tyr
            195                 200                 205

Glu Tyr Ile Thr Gly Ile Gln Gly Pro Asp Pro Glu Ser Asn Leu Lys
            210                 215                 220

Leu Ala Ala Thr Ala Lys His Tyr Ala Gly Tyr Asp Ile Glu Asn Trp
225                 230                 235                 240

His Asn His Ser Arg Leu Gly Asn Asp Met Asn Ile Thr Gln Gln Asp
            245                 250                 255

Leu Ser Glu Tyr Tyr Thr Pro Gln Phe His Val Ala Ala Arg Asp Ala
            260                 265                 270

Lys Val Gln Ser Val Met Cys Ala Tyr Asn Ala Val Asn Gly Val Pro
            275                 280                 285

Ala Cys Ala Asp Ser Tyr Phe Leu Gln Thr Leu Leu Arg Asp Thr Phe
            290                 295                 300

Gly Phe Val Asp His Gly Tyr Val Ser Ser Asp Cys Asp Ala Ala Tyr
305                 310                 315                 320

Asn Ile Tyr Asn Pro His Gly Tyr Ala Ser Ser Gln Ala Ala Ala Ala
            325                 330                 335

Ala Glu Ala Ile Leu Ala Gly Thr Asp Ile Asp Cys Gly Thr Thr Tyr
            340                 345                 350

Gln Trp His Leu Asn Glu Ser Ile Thr Ala Gly Asp Leu Ser Arg Asp
            355                 360                 365

Asp Ile Glu Gln Gly Val Ile Arg Leu Tyr Thr Thr Leu Val Gln Ala
            370                 375                 380

Gly Tyr Phe Asp Ser Asn Thr Thr Lys Ala Asn Asn Pro Tyr Arg Asp
385                 390                 395                 400

Leu Ser Trp Ser Asp Val Leu Glu Thr Asp Ala Trp Asn Ile Ser Tyr
            405                 410                 415

Gln Ala Ala Thr Gln Gly Ile Val Leu Leu Lys Asn Ser Asn Asn Val
            420                 425                 430

Leu Pro Leu Thr Glu Lys Ala Tyr Pro Pro Ser Asn Thr Thr Val Ala
            435                 440                 445

Leu Ile Gly Pro Trp Ala Asn Ala Thr Thr Gln Leu Leu Gly Asn Tyr
            450                 455                 460

Tyr Gly Asn Ala Pro Tyr Met Ile Ser Pro Arg Ala Ala Phe Glu Glu
465                 470                 475                 480

Ala Gly Tyr Lys Val Asn Phe Ala Glu Gly Thr Gly Ile Ser Ser Thr
            485                 490                 495

Ser Thr Ser Gly Phe Ala Ala Ala Leu Ser Ala Ala Gln Ser Ala Asp
            500                 505                 510

Val Ile Ile Tyr Ala Gly Gly Ile Asp Asn Thr Leu Glu Ala Glu Ala
            515                 520                 525

Leu Asp Arg Glu Ser Ile Ala Trp Pro Gly Asn Gln Leu Asp Leu Ile
            530                 535                 540

Gln Lys Leu Ala Ser Ala Ala Gly Lys Lys Pro Leu Ile Val Leu Gln
545                 550                 555                 560

Met Gly Gly Gly Gln Val Asp Ser Ser Ser Leu Lys Asn Asn Thr Lys
            565                 570                 575

Val Ser Ala Leu Leu Trp Gly Gly Tyr Pro Gly Gln Ser Gly Gly Phe
```

```
                580              585                 590
Ala Leu Arg Asp Ile Ile Thr Gly Lys Lys Asn Pro Ala Gly Arg Leu
            595                 600                 605

Val Thr Thr Gln Tyr Pro Ala Ser Tyr Ala Glu Glu Phe Pro Ala Thr
    610                 615                 620

Asp Met Asn Leu Arg Pro Glu Gly Asp Asn Pro Gly Gln Thr Tyr Lys
625                 630                 635                 640

Trp Tyr Thr Gly Glu Ala Val Tyr Glu Phe Gly His Gly Leu Phe Tyr
                645                 650                 655

Thr Thr Phe Ala Glu Ser Ser Ser Asn Thr Thr Lys Glu Val Lys
            660                 665                 670

Leu Asn Ile Gln Asp Ile Leu Ser Arg Thr His Glu Glu Leu Ala Ser
            675                 680                 685

Ile Thr Gln Leu Pro Val Leu Asn Phe Thr Ala Asn Ile Arg Asn Thr
            690                 695                 700

Gly Lys Leu Glu Ser Asp Tyr Thr Ala Met Val Phe Ala Asn Thr Ser
705                 710                 715                 720

Asp Ala Gly Pro Ala Pro Tyr Pro Lys Lys Trp Leu Val Gly Trp Asp
                725                 730                 735

Arg Leu Gly Glu Val Lys Val Gly Glu Thr Arg Glu Leu Arg Val Pro
                740                 745                 750

Val Glu Val Gly Ser Phe Ala Arg Val Asn Glu Asp Gly Asp Trp Val
            755                 760                 765

Leu Phe Pro Gly Thr Phe Glu Leu Ala Leu Asn Leu Glu Arg Lys Val
    770                 775                 780

Arg Val Lys Val Val Leu Gly Gly Glu Glu Val Val Leu Lys Trp
785                 790                 795                 800

Pro Gly Lys Glu

<210> SEQ ID NO 68
<211> LENGTH: 792
<212> TYPE: PRT
<213> ORGANISM: Aspergillus fumigatus

<400> SEQUENCE: 68

Met Ala Val Ala Lys Ser Ile Ala Ala Val Val Ala Leu Leu Pro
1               5                   10                  15

Gly Ala Leu Ala Gln Ala Asn Thr Ser Tyr Val Asp Tyr Asn Val Glu
                20                  25                  30

Ala Asn Pro Asp Leu Thr Pro Gln Ser Val Ala Thr Ile Asp Leu Ser
            35                  40                  45

Phe Pro Asp Cys Glu Asn Gly Pro Leu Ser Lys Thr Leu Val Cys Asp
    50                  55                  60

Thr Ser Ala Arg Pro His Asp Arg Ala Ala Ala Leu Val Ser Met Phe
65                  70                  75                  80

Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
                100                 105                 110

Gly Leu Asp Arg Ala Asn Phe Thr Asp Glu Gly Glu Tyr Ser Trp Ala
            115                 120                 125

Thr Ser Phe Pro Met Pro Ile Leu Thr Met Ser Ala Leu Asn Arg Thr
    130                 135                 140

Leu Ile Asn Gln Ile Ala Thr Ile Ile Ala Thr Gln Gly Arg Ala Phe
```

```
              145                 150                 155                 160
Asn Asn Val Gly Arg Tyr Gly Leu Asp Val Tyr Ala Pro Asn Ile Asn
                    165                 170                 175
Ala Phe Arg Ser Ala Met Trp Gly Arg Gly Gln Glu Thr Pro Gly Glu
                    180                 185                 190
Asp Ala Tyr Cys Leu Ala Ser Ala Tyr Ala Tyr Glu Tyr Ile Thr Gly
                    195                 200                 205
Ile Gln Gly Gly Val Asp Pro Glu His Leu Lys Leu Val Ala Thr Ala
        210                 215                 220
Lys His Tyr Ala Gly Tyr Asp Leu Glu Asn Trp Asp Gly His Ser Arg
225                 230                 235                 240
Leu Gly Asn Asp Met Asn Ile Thr Gln Gln Glu Leu Ser Glu Tyr Tyr
                    245                 250                 255
Thr Pro Gln Phe Leu Val Ala Ala Arg Asp Ala Lys Val His Ser Val
                    260                 265                 270
Met Cys Ser Tyr Asn Ala Val Asn Gly Val Pro Ser Cys Ala Asn Ser
                    275                 280                 285
Phe Phe Leu Gln Thr Leu Leu Arg Asp Thr Phe Gly Phe Val Glu Asp
        290                 295                 300
Gly Tyr Val Ser Ser Asp Cys Asp Ser Ala Tyr Asn Val Trp Asn Pro
305                 310                 315                 320
His Glu Phe Ala Ala Asn Ile Thr Gly Ala Ala Asp Ser Ile Arg
                    325                 330                 335
Ala Gly Thr Asp Ile Asp Cys Gly Thr Thr Tyr Gln Tyr Tyr Phe Gly
                    340                 345                 350
Glu Ala Phe Asp Glu Gln Glu Val Thr Arg Ala Glu Ile Glu Arg Gly
                    355                 360                 365
Val Ile Arg Leu Tyr Ser Asn Leu Val Arg Leu Gly Tyr Phe Asp Gly
        370                 375                 380
Asn Gly Ser Val Tyr Arg Asp Leu Thr Trp Asn Asp Val Val Thr Thr
385                 390                 395                 400
Asp Ala Trp Asn Ile Ser Tyr Glu Ala Ala Val Glu Gly Ile Val Leu
                    405                 410                 415
Leu Lys Asn Asp Gly Thr Leu Pro Leu Ala Lys Ser Val Arg Ser Val
                    420                 425                 430
Ala Leu Ile Gly Pro Trp Met Asn Val Thr Thr Gln Leu Gln Gly Asn
                    435                 440                 445
Tyr Phe Gly Pro Ala Pro Tyr Leu Ile Ser Pro Leu Asn Ala Phe Gln
        450                 455                 460
Asn Ser Asp Phe Asp Val Asn Tyr Ala Phe Gly Thr Asn Ile Ser Ser
465                 470                 475                 480
His Ser Thr Asp Gly Phe Ser Glu Ala Leu Ser Ala Lys Lys Ser
                    485                 490                 495
Asp Val Ile Ile Phe Ala Gly Gly Ile Asp Asn Thr Leu Glu Ala Glu
                    500                 505                 510
Ala Met Asp Arg Met Asn Ile Thr Trp Pro Gly Asn Gln Leu Gln Leu
                    515                 520                 525
Ile Asp Gln Leu Ser Gln Leu Gly Lys Pro Leu Ile Val Leu Gln Met
        530                 535                 540
Gly Gly Gly Gln Val Asp Ser Ser Ser Leu Lys Ser Asn Lys Asn Val
545                 550                 555                 560
Asn Ser Leu Ile Trp Gly Gly Tyr Pro Gly Gln Ser Gly Gly Gln Ala
                    565                 570                 575
```

```
Leu Leu Asp Ile Ile Thr Gly Lys Arg Ala Pro Ala Gly Arg Leu Val
            580                 585                 590

Val Thr Gln Tyr Pro Ala Glu Tyr Ala Thr Gln Phe Pro Ala Thr Asp
        595                 600                 605

Met Ser Leu Arg Pro His Gly Asn Asn Pro Gly Gln Thr Tyr Met Trp
610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
            660                 665                 670

Glu Gln Met Pro Leu Leu Asn Phe Thr Val Thr Ile Thr Asn Thr Gly
        675                 680                 685

Lys Val Ala Ser Asp Tyr Thr Ala Met Leu Phe Ala Asn Thr Thr Ala
690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
            740                 745                 750

Pro Gly Lys Tyr Glu Leu Ala Leu Asn Asn Glu Arg Ser Val Val Leu
        755                 760                 765

Gln Phe Val Leu Thr Gly Arg Glu Ala Val Val Phe Lys Trp Pro Val
770                 775                 780

Glu Gln Gln Gln Ile Ser Ser Ala
785                 790

<210> SEQ ID NO 69
<211> LENGTH: 780
<212> TYPE: PRT
<213> ORGANISM: Aspergillus japonicus

<400> SEQUENCE: 69

Met Ala Val Ala Ala Leu Ala Leu Leu Ala Leu Pro Gln Ala Leu
1               5                   10                  15

Gly Gln His Asn Ser Ser Tyr Val Asp Tyr Asn Val Glu Ala Asn Pro
            20                  25                  30

Asp Leu Phe Pro Gln Cys Leu Asp Thr Ile Ser Leu Ser Phe Pro Asp
        35                  40                  45

Cys Gln Ser Gly Pro Leu Ser Lys Asn Leu Val Cys Asp Ser Thr Ala
    50                  55                  60

Ser Pro Tyr Asp Arg Ala Ala Ala Leu Val Ser Leu Phe Thr Leu Glu
65                  70                  75                  80

Glu Leu Ile Ala Asn Thr Gly Asn Thr Ser Pro Gly Val Pro Arg Leu
                85                  90                  95

Gly Leu Pro Pro Tyr Gln Val Trp Ser Glu Ala Leu His Gly Leu Ala
            100                 105                 110

Arg Ala Asn Phe Thr Asp Asn Gly Ala Tyr Ser Trp Ala Thr Ser Phe
        115                 120                 125

Pro Ser Pro Ile Leu Ser Ala Ala Phe Asn Arg Thr Leu Ile Asn
    130                 135                 140

Gln Ile Ala Ser Ile Ile Ser Thr Gln Gly Arg Ala Phe Asn Asn Ala
```

```
               145                 150                 155                 160
          Gly Arg Phe Gly Leu Asp Val Tyr Ser Pro Asn Ile Asn Thr Phe Arg
                           165                 170                 175

His Pro Val Trp Gly Arg Gly Gln Glu Thr Pro Gly Glu Asp Ala Tyr
                           180                 185                 190

Thr Leu Thr Ala Ala Tyr Ala Tyr Glu Tyr Ile Thr Gly Ile Gln Gly
                           195                 200                 205

Gly Val Asn Pro Glu His Leu Lys Leu Ala Ala Thr Ala Lys His Phe
              210                 215                 220

Ala Gly Tyr Asp Ile Glu Asn Trp Asp Asn His Ser Arg Leu Gly Asn
          225                 230                 235                 240

Asp Val Asn Ile Thr Gln Gln Asp Leu Ala Glu Tyr Tyr Thr Pro Gln
                           245                 250                 255

Phe Leu Val Ala Ala Arg Asp Ala His Val His Ser Phe Met Cys Ser
                           260                 265                 270

Tyr Asn Ala Val Asn Gly Val Pro Ser Cys Ser Asn Thr Phe Phe Leu
                           275                 280                 285

Gln Thr Leu Leu Arg Asp Thr Phe Ser Phe Val Asp His Gly Tyr Val
                           290                 295                 300

Ser Gly Asp Cys Gly Ala Val Tyr Gly Val Phe Asn Pro His Gly Tyr
          305                 310                 315                 320

Ala Ala Asn Glu Pro Ser Ala Ala Asp Ala Ile Leu Ala Gly Thr
                           325                 330                 335

Asp Ile Asp Cys Gly Thr Ser Tyr Gln Tyr His Phe Asn Glu Ser Ile
                           340                 345                 350

Thr Thr Gly Ala Val Ala Arg Asp Ile Glu Arg Gly Phe Ile Arg
                           355                 360                 365

Leu Tyr Ala Asn Leu Val Glu Leu Gly Tyr Phe Asp Gly Asn Ser Ser
                           370                 375                 380

Ser Ser Asn Pro Tyr Arg Ser Leu Gly Trp Pro Asp Val Gln Lys Thr
          385                 390                 395                 400

Asp Ala Trp Asn Ile Ser Tyr Glu Ala Ala Val Glu Gly Ile Val Leu
                           405                 410                 415

Leu Lys Asn Asp Gly Thr Leu Pro Leu Ala Ser Pro Ser Glu Gly Lys
                           420                 425                 430

Asn Lys Ser Ile Ala Leu Ile Gly Pro Trp Ala Asn Ala Thr Thr Gln
                           435                 440                 445

Leu Gln Gly Asn Tyr Tyr Gly Asp Ala Pro Tyr Leu Ile Ser Pro Val
              450                 455                 460

Asp Ala Phe Thr Ala Ala Gly Tyr Thr Val His Tyr Ala Pro Gly Thr
          465                 470                 475                 480

Glu Ile Ser Thr Asn Ser Thr Ala Asn Phe Ser Ala Ala Leu Ser Ala
                           485                 490                 495

Ala Arg Ala Ala Asp Thr Ile Val Phe Leu Gly Gly Ile Asp Asn Thr
                           500                 505                 510

Ile Glu Ala Glu Ala Gln Asp Arg Ser Ser Ile Ala Trp Pro Gly Asn
                           515                 520                 525

Gln Leu Glu Leu Ile Ser Gln Leu Ala Ala Gln Lys Ser Asp Asp Gln
              530                 535                 540

Pro Leu Val Val Tyr Gln Met Gly Gly Gly Gln Val Asp Ser Ser Ala
          545                 550                 555                 560

Leu Lys Ser Asn Ala Lys Val Asn Ala Leu Leu Trp Gly Gly Tyr Pro
                           565                 570                 575
```

Gly Gln Ser Gly Gly Leu Ala Leu Arg Asp Ile Leu Thr Gly Ala Arg
            580                 585                 590

Ala Pro Ala Gly Arg Leu Thr Thr Thr Gln Tyr Pro Ala Ala Tyr Ala
        595                 600                 605

Glu Ser Phe Ser Ala Leu Asp Met Asn Leu Arg Pro Asn Glu Thr Thr
    610                 615                 620

Gln Asn Pro Gly Gln Thr Tyr Met Trp Tyr Thr Gly Glu Pro Val Tyr
625                 630                 635                 640

Ala Phe Gly His Gly Leu Phe Tyr Thr Thr Phe Asn Ala Ser Ser Ala
                645                 650                 655

Gln Ala Ala Lys Thr Lys Tyr Thr Phe Asn Ile Thr Asp Leu Thr Ser
            660                 665                 670

Ala Ala His Pro Asp Thr Thr Thr Val Gly Gln Arg Thr Leu Phe Asn
        675                 680                 685

Phe Thr Ala Ser Ile Thr Asn Ser Gly Gln Arg Asp Ser Asp Tyr Thr
    690                 695                 700

Ala Leu Val Tyr Ala Asn Thr Ser Thr Ala Gly Pro Ser Pro Tyr Pro
705                 710                 715                 720

Asn Lys Trp Leu Val Gly Phe Asp Arg Leu Ala Ala Val Ala Lys Glu
                725                 730                 735

Gly Gly Thr Ala Glu Leu Asn Val Pro Val Ala Val Asp Arg Leu Ala
            740                 745                 750

Arg Val Asp Glu Ala Gly Asn Thr Val Leu Phe Pro Gly Arg Tyr Glu
        755                 760                 765

Val Ala Leu Asn Asn Glu Arg Glu Val Val Val Glu
    770                 775                 780

<210> SEQ ID NO 70
<211> LENGTH: 803
<212> TYPE: PRT
<213> ORGANISM: Artificial
<220> FEATURE:
<223> OTHER INFORMATION: Synthetic polypeptide with sequence of
      hypothetical protein AN2359.2 of Aspergillus nidulans FGSC A4

<400> SEQUENCE: 70

Met Arg Ser Leu Ile Ser Val Ala Val Leu Ser Ala Leu Pro Thr Ala
1               5                   10                  15

Phe Ser Gln Ala Asn Thr Ser Tyr Thr Asp Tyr Asn Val Glu Ala Asn
            20                  25                  30

Pro Asp Leu Phe Pro Leu Cys Leu Gln His Leu Asn Ala Ser Phe Pro
        35                  40                  45

Asp Cys Ala Ser Gly Pro Leu Ser Leu Thr Pro Val Cys Asp Arg Ser
    50                  55                  60

Leu Ser Pro Lys Asp Arg Ala Thr Ala Leu Val Ser Leu Phe Thr Phe
65                  70                  75                  80

Asp Glu Leu Val Asn Asn Thr Gly Asn Thr Gly Leu Gly Val Ser Arg
                85                  90                  95

Leu Gly Leu Pro Asn Tyr Gln Val Trp Gly Glu Ala Leu His Gly Val
            100                 105                 110

Gly Arg Ala Asn Phe Val Glu Ser Gly Asn Phe Ser Trp Ala Thr Ser
        115                 120                 125

Phe Pro Met Pro Ile Thr Met Met Ala Ala Leu Asn Lys Thr Leu Ile
    130                 135                 140

His Gln Ile Gly Thr Ile Val Ser Thr Gln Leu Arg Ala Phe Ser Asn

-continued

```
            145                 150                 155                 160
        Ala Gly Leu Gly Gly Val Asp Val Tyr Ser Pro Asn Ile Asn Thr Phe
                        165                 170                 175
        Arg His Pro Val Trp Arg Gly Gln Glu Thr Pro Gly Glu Asp Ala
                        180                 185                 190
        Phe Leu Thr Ser Val Tyr Gly Tyr Glu Tyr Ile Thr Ala Leu Gln Gly
                        195                 200                 205
        Gly Val Asp Pro Glu Thr Leu Lys Ile Ile Ala Thr Ala Lys His Tyr
                210                 215                 220
        Ala Gly Tyr Asp Ile Glu Ser Trp Asn Asn His Ser Arg Leu Gly Asn
        225                 230                 235                 240
        Asp Met Gln Ile Thr Gln Gln Glu Leu Ser Glu Tyr Tyr Thr Pro Pro
                        245                 250                 255
        Phe Ile Val Ala Ser Arg Asp Ala Lys Val Arg Ser Val Met Cys Ser
                        260                 265                 270
        Tyr Asn Ala Val Asn Gly Val Pro Ser Cys Ala Asn Lys Phe Phe Leu
                        275                 280                 285
        Gln Thr Leu Leu Arg Asp Thr Phe Glu Phe Ser Glu Asp Gly Tyr Val
                        290                 295                 300
        Ser Gly Asp Cys Gly Ala Val Tyr Asn Val Trp Asn Pro His Gly Tyr
        305                 310                 315                 320
        Ala Ser Asn Glu Ala Ala Ser Ala Asp Ser Ile Leu Ala Gly Thr
                        325                 330                 335
        Asp Ile Asp Cys Gly Thr Ser Tyr Gln Trp His Ser Glu Asp Ala Phe
                        340                 345                 350
        Glu Asp Ser Leu Val Ser Arg Ser Asp Ile Glu Arg Gly Val Ile Arg
                        355                 360                 365
        Leu Tyr Ser Asn Leu Val Gln Ala Gly Tyr Phe Asp Gly Glu Asp Ala
                        370                 375                 380
        Pro Tyr Arg Asp Ile Thr Trp Asp Asp Val Leu Ser Thr Asp Ala Trp
        385                 390                 395                 400
        Asn Ile Ala Tyr Glu Ala Ala Val Glu Gly Ile Val Leu Leu Lys Asn
                        405                 410                 415
        Asp Glu Thr Leu Pro Leu Ser Lys Asp Ile Lys Ser Val Ala Val Ile
                        420                 425                 430
        Gly Pro Trp Ala Asn Val Thr Glu Glu Leu Gln Gly Asn Tyr Phe Gly
                        435                 440                 445
        Pro Ala Pro Tyr Leu Ile Ser Pro Leu Thr Gly Phe Arg Asp Ser Gly
                        450                 455                 460
        Leu Asp Val His Tyr Ala Leu Gly Thr Asn Leu Thr Ser His Ser Thr
        465                 470                 475                 480
        Ser Gly Phe Glu Glu Ala Leu Thr Ala Ala Lys Gln Ala Asp Ala Ile
                        485                 490                 495
        Ile Phe Ala Gly Gly Ile Asp Asn Thr Ile Glu Ala Glu Ala Met Asp
                        500                 505                 510
        Arg Glu Asn Ile Thr Trp Pro Gly Asn Gln Leu Asp Leu Ile Ser Lys
                        515                 520                 525
        Leu Ser Glu Leu Gly Lys Pro Leu Val Val Leu Gln Met Gly Gly Gly
                        530                 535                 540
        Gln Val Asp Ser Ser Ser Leu Lys Asp Asn Asp Asn Val Asn Ala Leu
        545                 550                 555                 560
        Ile Trp Gly Gly Tyr Pro Gly Gln Ser Gly Gly His Ala Leu Ala Asp
                        565                 570                 575
```

Ile Ile Thr Gly Lys Arg Ala Pro Ala Gly Arg Leu Val Thr Thr Gln
            580                 585                 590

Tyr Pro Ala Glu Tyr Ala Glu Val Phe Pro Ala Ile Asp Met Asn Leu
        595                 600                 605

Arg Pro Asn Glu Thr Ser Gly Asn Pro Gly Gln Thr Tyr Met Trp Tyr
    610                 615                 620

Thr Gly Thr Pro Val Tyr Glu Phe Gly His Gly Leu Phe Tyr Thr Thr
625                 630                 635                 640

Phe Glu Glu Ser Thr Glu Thr Thr Asp Ala Gly Ser Phe Asn Ile Gln
                645                 650                 655

Thr Val Leu Thr Thr Pro His Ser Gly Tyr Glu His Ala Gln Gln Lys
            660                 665                 670

Thr Leu Leu Asn Phe Thr Ala Thr Val Lys Asn Thr Gly Glu Arg Glu
        675                 680                 685

Ser Asp Tyr Thr Ala Leu Val Tyr Val Asn Thr Thr Ala Gly Pro Ala
    690                 695                 700

Pro Tyr Pro Lys Lys Trp Val Val Gly Phe Asp Arg Leu Gly Gly Leu
705                 710                 715                 720

Glu Pro Gly Asp Ser Gln Thr Leu Thr Val Pro Val Thr Val Glu Ser
                725                 730                 735

Val Ala Arg Thr Asp Glu Gln Gly Asn Arg Val Leu Tyr Pro Gly Ser
            740                 745                 750

Tyr Glu Leu Ala Leu Asn Asn Glu Arg Ser Val Val Lys Phe Glu
        755                 760                 765

Leu Lys Gly Glu Glu Ala Val Ile Leu Ser Trp Pro Glu Asp Thr Thr
    770                 775                 780

Ser Asp Phe Val Ser Ser Ile Asp Gly Gly Leu Asp Arg Lys Gln Asp
785                 790                 795                 800

Val Ile Ala

<210> SEQ ID NO 71
<211> LENGTH: 763
<212> TYPE: PRT
<213> ORGANISM: Artificial
<220> FEATURE:
<223> OTHER INFORMATION: Synthetic polypeptide with sequence of
      hypothetical protein AN8401.2 of Aspergillus nidulans FGSC A4

<400> SEQUENCE: 71

Met Ala Val Phe Lys Ser Trp Asn Leu Ala Leu Leu Ser Ser Leu Phe
1               5                   10                  15

Ile Pro Ala Leu Cys Gln Ser Asn Tyr Pro Asp Cys Thr Thr Gly Pro
            20                  25                  30

Leu Ser Glu Leu Pro Ile Cys Asp Thr Ser Leu Ser Pro Leu Glu Arg
        35                  40                  45

Ala Lys Ser Leu Val Ser Ala Leu Thr Leu Glu Glu Lys Ile Asn Asn
    50                  55                  60

Thr Gly His Glu Ala Ala Gly Ser Ser Arg Leu Gly Leu Pro Ala Tyr
65                  70                  75                  80

Asn Trp Trp Asn Glu Ala Leu His Gly Val Ala Glu Lys His Gly Val
                85                  90                  95

Ser Phe Glu Glu Ser Gly Asp Phe Ser Tyr Ala Thr Ser Phe Pro Ala
            100                 105                 110

Pro Ile Val Leu Gly Ala Ala Phe Asn Asp Ala Leu Ile Arg Arg Val
        115                 120                 125

```
Ala Glu Ile Ile Ser Thr Glu Ala Arg Ala Phe Ser Asn Ser Asp His
    130                 135                 140
Ala Gly Ile Asp Tyr Trp Thr Pro Asn Val Asn Pro Phe Lys Asp Pro
145                 150                 155                 160
Arg Trp Gly Arg Gly Gln Glu Thr Pro Gly Glu Asp Pro Leu His Cys
                165                 170                 175
Ser Arg Tyr Val Lys Glu Phe Val Gly Gly Leu Gln Gly Asp Asp Pro
            180                 185                 190
Glu Lys Pro Lys Val Val Ala Thr Cys Lys His Leu Ala Ala Tyr Asp
                195                 200                 205
Leu Glu Glu Trp Gly Gly Val Ser Arg Phe Glu Phe Asp Ala Lys Val
    210                 215                 220
Ser Ala Val Asp Leu Leu Glu Tyr Tyr Leu Pro Pro Phe Lys Thr Cys
225                 230                 235                 240
Ala Val Asp Ala Ser Val Gly Ala Phe Met Cys Ser Tyr Asn Ala Leu
                245                 250                 255
Asn Gly Val Pro Ala Cys Ala Asp Arg Tyr Leu Leu Gln Thr Val Leu
            260                 265                 270
Arg Glu His Trp Gly Trp Glu Gly Pro Gly His Trp Val Thr Gly Asp
                275                 280                 285
Cys Gly Ala Val Glu Arg Ile Gln Thr Tyr His His Tyr Val Glu Ser
    290                 295                 300
Gly Pro Glu Ala Ala Ala Ala Leu Asn Ala Gly Val Asp Leu Asp
305                 310                 315                 320
Cys Gly Thr Trp Leu Pro Ser Tyr Leu Gly Glu Ala Glu Arg Gln Gly
                325                 330                 335
Leu Ile Ser Asn Glu Thr Leu Asp Ala Ala Leu Thr Arg Leu Tyr Thr
            340                 345                 350
Ser Leu Val Gln Leu Gly Tyr Phe Asp Pro Ala Glu Gly Gln Pro Leu
                355                 360                 365
Arg Ser Leu Gly Trp Asp Asp Val Ala Thr Ser Glu Ala Glu Glu Leu
    370                 375                 380
Ala Lys Thr Val Ala Ile Gln Gly Thr Val Leu Leu Lys Asn Ile Asp
385                 390                 395                 400
Trp Thr Leu Pro Leu Lys Ala Asn Gly Thr Leu Ala Leu Ile Gly Pro
                405                 410                 415
Phe Ile Asn Phe Thr Thr Glu Leu Gln Ser Asn Tyr Ala Gly Pro Ala
            420                 425                 430
Lys His Ile Pro Thr Met Ile Glu Ala Ala Glu Arg Leu Gly Tyr Asn
                435                 440                 445
Val Leu Thr Ala Pro Gly Thr Glu Val Asn Ser Thr Ser Thr Asp Gly
    450                 455                 460
Phe Asp Asp Ala Leu Ala Ile Ala Ala Glu Ala Asp Ala Leu Ile Phe
465                 470                 475                 480
Phe Gly Gly Ile Asp Asn Thr Val Glu Glu Ser Leu Asp Arg Thr
                485                 490                 495
Arg Ile Asp Trp Pro Gly Asn Gln Glu Glu Leu Ile Leu Glu Leu Ala
            500                 505                 510
Glu Leu Gly Arg Pro Leu Thr Val Val Gln Phe Gly Gly Gly Gln Val
                515                 520                 525
Asp Asp Ser Ala Leu Leu Ala Ser Ala Gly Val Gly Ala Ile Val Trp
530                 535                 540
```

Ala Gly Tyr Pro Ser Gln Ala Gly Ala Gly Val Phe Asp Val Leu
545                 550                 555                 560

Thr Gly Lys Ala Ala Pro Ala Gly Arg Leu Pro Ile Thr Gln Tyr Pro
                565                 570                 575

Lys Ser Tyr Val Asp Glu Val Pro Met Thr Asp Met Asn Leu Gln Pro
                580                 585                 590

Gly Thr Asp Asn Pro Gly Arg Thr Tyr Arg Trp Tyr Glu Asp Ala Val
            595                 600                 605

Leu Pro Phe Gly Phe Gly Leu His Tyr Thr Thr Phe Asn Val Ser Trp
610                 615                 620

Ala Lys Lys Ala Phe Gly Pro Tyr Asp Ala Ala Thr Leu Ala Arg Gly
625                 630                 635                 640

Lys Asn Pro Ser Ser Asn Ile Val Asp Thr Phe Ser Leu Ala Val Thr
                645                 650                 655

Asn Thr Gly Asp Val Ala Ser Asp Tyr Val Ala Leu Val Phe Ala Ser
            660                 665                 670

Ala Pro Glu Leu Gly Ala Gln Pro Ala Pro Ile Lys Thr Leu Val Gly
        675                 680                 685

Tyr Ser Arg Ala Ser Leu Ile Lys Pro Gly Glu Thr Arg Lys Val Asp
690                 695                 700

Val Glu Val Thr Val Ala Pro Leu Thr Arg Ala Thr Glu Asp Gly Arg
705                 710                 715                 720

Val Val Leu Tyr Pro Gly Glu Tyr Thr Leu Leu Val Asp Val Asn Asp
                725                 730                 735

Glu Tyr Pro Thr Ala Lys Phe Gly Ile Lys Gly Asp Val Gln Val Leu
            740                 745                 750

Glu Lys Phe Pro Leu Ser Gly Asn Asp Ser Asp
        755                 760

<210> SEQ ID NO 72
<211> LENGTH: 798
<212> TYPE: PRT
<213> ORGANISM: Aspergillus oryzae

<400> SEQUENCE: 72

Met Pro Gly Ala Ala Ser Ile Val Ala Val Leu Ala Ala Leu Leu Pro
1               5                   10                  15

Thr Ala Leu Gly Gln Ala Asn Gln Ser Tyr Val Asp Tyr Asn Ser Glu
            20                  25                  30

Ala Asn Pro Asp Leu Phe Ser Glu Cys Leu Glu Thr Gly Gly Thr Ser
        35                  40                  45

Phe Pro Asp Cys Glu Ser Gly Pro Leu Ser Lys Thr Leu Val Cys Asp
50                  55                  60

Thr Ser Ala Lys Pro His Asp Arg Ala Ala Ala Leu Val Ser Leu Leu
65                  70                  75                  80

Thr Phe Glu Glu Leu Val Asn Asn Thr Ala Asn Thr Gly His Gly Ala
                85                  90                  95

Pro Arg Ile Gly Leu Pro Ala Tyr Gln Val Trp Asn Glu Ala Leu His
            100                 105                 110

Gly Val Ala His Ala Asp Phe Ser Asp Ala Gly Asp Phe Ser Trp Ser
        115                 120                 125

Thr Ser Phe Pro Gln Pro Ile Ser Thr Met Ala Ala Leu Asn Arg Thr
    130                 135                 140

Leu Ile His Gln Ile Ala Thr Ile Ile Ser Thr Gln Gly Arg Ala Phe
145                 150                 155                 160

```
Met Asn Ala Gly Arg Tyr Gly Leu Asp Val Tyr Ser Pro Asn Ile Asn
                165                 170                 175

Thr Phe Arg His Pro Val Trp Gly Arg Gly Gln Glu Thr Pro Gly Glu
            180                 185                 190

Asp Ala Tyr Cys Leu Ala Ser Thr Tyr Ala Tyr Glu Tyr Ile Thr Gly
        195                 200                 205

Ile Gln Gly Gly Val Asp Ala Asn Pro Leu Lys Leu Ile Ala Thr Ala
    210                 215                 220

Lys His Tyr Ala Gly Tyr Asp Ile Glu Asn Trp Asp Asn His Ser Arg
225                 230                 235                 240

Leu Gly Asn Asp Met Gln Ile Thr Gln Gln Asp Leu Ala Glu Tyr Tyr
                245                 250                 255

Thr Pro Gln Phe Leu Val Ala Ser Arg Asp Ala Lys Val His Ser Val
            260                 265                 270

Met Cys Ser Tyr Asn Ala Val Asn Gly Val Pro Ser Cys Ser Asn Ser
        275                 280                 285

Phe Phe Leu Gln Thr Leu Leu Arg Asp Thr Phe Asp Phe Val Glu Asp
    290                 295                 300

Gly Tyr Val Ser Gly Asp Cys Gly Ala Val Tyr Asn Val Phe Asn Pro
305                 310                 315                 320

His Gly Tyr Ala Thr Asn Glu Ser Ser Ala Ala Asp Ser Ile Arg
                325                 330                 335

Ala Gly Thr Asp Ile Asp Cys Gly Val Ser Tyr Pro Arg His Phe Gln
                340                 345                 350

Glu Ser Phe His Asp Gln Glu Val Ser Arg Gln Asp Leu Glu Arg Gly
            355                 360                 365

Val Ile Arg Leu Tyr Ala Ser Leu Ile Arg Ala Gly Tyr Phe Asp Gly
        370                 375                 380

Lys Thr Ser Pro Tyr Arg Asn Ile Thr Trp Ser Asp Val Val Ser Thr
385                 390                 395                 400

Asn Ala Gln Asn Leu Ser Tyr Glu Ala Ala Ala Gln Ser Ile Val Leu
                405                 410                 415

Leu Lys Asn Asp Gly Ile Leu Pro Leu Thr Ser Thr Ser Ser Ser Thr
            420                 425                 430

Lys Thr Ile Ala Leu Ile Gly Pro Trp Ala Asn Ala Thr Thr Gln Met
        435                 440                 445

Leu Gly Asn Tyr Tyr Gly Pro Ala Pro Tyr Leu Ile Ser Pro Leu Gln
    450                 455                 460

Ala Phe Gln Asp Ser Glu Tyr Lys Ile Thr Tyr Thr Ile Gly Thr Asn
465                 470                 475                 480

Thr Thr Thr Asp Pro Asp Ser Thr Ser Gln Ser Thr Ala Leu Thr Thr
                485                 490                 495

Ala Lys Glu Ala Asp Leu Ile Ile Phe Ala Gly Gly Ile Asp Asn Thr
            500                 505                 510

Leu Glu Thr Glu Ala Gln Asp Arg Ser Asn Ile Thr Trp Pro Ser Asn
        515                 520                 525

Gln Leu Ser Leu Ile Thr Lys Leu Ala Asp Leu Gly Lys Pro Leu Ile
    530                 535                 540

Val Leu Gln Met Gly Gly Gly Gln Val Asp Ser Ser Ala Leu Lys Asn
545                 550                 555                 560

Asn Lys Asn Val Asn Ala Leu Ile Trp Gly Gly Tyr Pro Gly Gln Ser
                565                 570                 575
```

```
Gly Gly Gln Ala Leu Ala Asp Ile Ile Thr Gly Lys Arg Ala Pro Ala
            580                 585                 590

Ala Arg Leu Val Thr Thr Gln Tyr Pro Ala Glu Tyr Ala Glu Val Phe
        595                 600                 605

Pro Ala Ile Asp Met Asn Leu Arg Pro Asn Gly Ser Asn Pro Gly Gln
610                 615                 620

Thr Tyr Met Trp Tyr Thr Gly Thr Pro Val Tyr Glu Phe Gly His Gly
625                 630                 635                 640

Leu Phe Tyr Thr Asn Phe Thr Ala Ser Ala Ser Ala Gly Ser Gly Thr
                645                 650                 655

Lys Asn Arg Thr Ser Phe Asn Ile Asp Glu Val Leu Gly Arg Pro His
            660                 665                 670

Pro Gly Tyr Lys Leu Val Glu Gln Met Pro Leu Leu Asn Phe Thr Val
        675                 680                 685

Asp Val Lys Asn Thr Gly Asp Arg Val Ser Asp Tyr Thr Ala Met Ala
690                 695                 700

Phe Val Asn Thr Thr Ala Gly Pro Ala Pro His Pro Asn Lys Trp Leu
705                 710                 715                 720

Val Gly Phe Asp Arg Leu Ser Ala Val Glu Pro Gly Ser Ala Lys Thr
                725                 730                 735

Met Val Ile Pro Val Thr Val Asp Ser Leu Ala Arg Thr Asp Glu Glu
            740                 745                 750

Gly Asn Arg Val Leu Tyr Pro Gly Arg Tyr Glu Val Ala Leu Asn Asn
        755                 760                 765

Glu Arg Glu Val Val Leu Gly Phe Thr Leu Thr Gly Glu Lys Ala Val
770                 775                 780

Leu Phe Lys Trp Pro Lys Glu Glu Gln Leu Ile Ala Pro Gln
785                 790                 795

<210> SEQ ID NO 73
<211> LENGTH: 802
<212> TYPE: PRT
<213> ORGANISM: Emericella nidulans

<400> SEQUENCE: 73

Met Arg Ser Leu Ile Ser Val Ala Val Leu Ser Ala Leu Ala Ala Phe
1               5                   10                  15

Ser Gln Ala Asn Thr Ser Tyr Thr Asp Tyr Asn Val Glu Ala Asn Pro
            20                  25                  30

Asp Leu Phe Pro Leu Cys Leu Gln His Leu Asn Ala Ser Phe Pro Asp
        35                  40                  45

Cys Ala Thr Gly Pro Leu Ser Leu Thr Pro Val Cys Asp Arg Ser Leu
50                  55                  60

Ser Pro Lys Asp Arg Ala Thr Ala Leu Val Leu Phe Thr Phe Asp
65                  70                  75                  80

Glu Leu Val Asn Asn Thr Gly Asn Thr Gly Leu Gly Val Ser Arg Leu
                85                  90                  95

Gly Leu Pro Asn Tyr Gln Val Trp Gly Glu Ala Leu His Gly Val Gly
            100                 105                 110

Arg Ala Asn Phe Val Glu Ser Gly Asn Phe Ser Trp Ala Thr Ser Phe
        115                 120                 125

Pro Met Pro Ile Thr Met Met Ala Ala Leu Asn Lys Thr Leu Ile His
130                 135                 140

Gln Ile Gly Thr Ile Val Ser Thr Gln Leu Arg Ala Phe Ser Asn Ala
145                 150                 155                 160
```

```
Gly Leu Gly Gly Val Asp Val Tyr Ser Pro Asn Ile Asn Thr Phe Arg
                165                 170                 175

His Pro Val Trp Gly Arg Gly Gln Glu Thr Pro Gly Glu Asp Ala Phe
            180                 185                 190

Leu Thr Ser Val Tyr Gly Tyr Glu Tyr Ile Thr Ala Leu Gln Gly Ala
        195                 200                 205

Val Asp Pro Glu Thr Ser Lys Ile Ile Ala Thr Ala Lys His Tyr Ala
    210                 215                 220

Gly Tyr Asp Ile Glu Ser Trp Asn Asn His Ser Arg Leu Gly Asn Asp
225                 230                 235                 240

Met Gln Ile Thr Gln Gln Glu Leu Ser Glu Tyr Tyr Thr Pro Pro Phe
                245                 250                 255

Ile Val Ala Ser Arg Asp Ala Lys Val Arg Ser Val Met Cys Ser Tyr
            260                 265                 270

Asn Ala Val Asn Gly Val Pro Ser Cys Ala Asn Lys Phe Phe Leu Gln
        275                 280                 285

Thr Leu Leu Arg Asp Thr Phe Glu Phe Ser Glu Asp Gly Tyr Val Ser
    290                 295                 300

Gly Asp Cys Gly Ala Val Tyr Asn Val Trp Asn Pro His Gly Tyr Ala
305                 310                 315                 320

Ser Asn Glu Ala Ala Ala Ser Ala Asp Ser Ile Leu Ala Gly Thr Asp
                325                 330                 335

Ile Asp Cys Gly Thr Ser Tyr Gln Trp His Ser Glu Asp Ala Phe Glu
            340                 345                 350

Asp Ser Leu Val Ser Arg Ser Asp Ile Glu Arg Gly Val Ile Arg Leu
        355                 360                 365

Tyr Ser Asn Leu Val Gln Ala Gly Tyr Phe Asp Gly Glu Asp Ala Pro
    370                 375                 380

Tyr Arg Asp Ile Thr Trp Asp Asp Val Leu Ser Thr Asp Ala Trp Asn
385                 390                 395                 400

Ile Ala Tyr Glu Ala Ala Val Glu Gly Ile Val Leu Leu Lys Asn Asp
                405                 410                 415

Glu Thr Leu Pro Leu Ser Lys Asp Ile Lys Ser Val Ala Val Ile Gly
            420                 425                 430

Pro Trp Ala Asn Val Thr Glu Glu Leu Gln Gly Asn Tyr Phe Gly Pro
        435                 440                 445

Ala Pro Tyr Leu Ile Ser Pro Leu Thr Gly Phe Arg Asp Ser Gly Leu
    450                 455                 460

Asp Val His Tyr Ala Leu Gly Thr Asn Leu Thr Ser His Ser Thr Ser
465                 470                 475                 480

Gly Phe Glu Glu Ala Leu Thr Ala Ala Lys Gln Ala Asp Ala Ile Ile
                485                 490                 495

Phe Ala Gly Gly Ile Asp Asn Thr Ile Glu Ala Glu Ala Met Asp Arg
            500                 505                 510

Glu Asn Ile Thr Trp Pro Gly Asn Gln Leu Asp Leu Ile Ser Lys Leu
        515                 520                 525

Ser Glu Leu Gly Lys Pro Leu Val Val Leu Gln Met Gly Gly Gly Gln
    530                 535                 540

Val Asp Ser Ser Ser Leu Lys Asp Asn Asp Asn Val Asn Ala Leu Ile
545                 550                 555                 560

Trp Gly Gly Tyr Pro Gly Gln Ser Gly Gly His Ala Leu Ala Asp Ile
                565                 570                 575
```

```
Ile Thr Gly Lys Arg Ala Pro Ala Gly Arg Leu Val Thr Thr Gln Tyr
            580                 585                 590

Pro Ala Glu Tyr Ala Glu Val Phe Pro Ala Ile Asp Met Asn Leu Arg
        595                 600                 605

Pro Asn Glu Thr Ser Gly Asn Pro Gly Gln Thr Tyr Met Trp Tyr Thr
    610                 615                 620

Gly Thr Pro Val Tyr Glu Phe Gly His Gly Leu Phe Tyr Thr Thr Phe
625                 630                 635                 640

Glu Glu Ser Thr Glu Thr Thr Asp Ala Gly Ser Phe Asn Ile Gln Thr
                645                 650                 655

Val Leu Thr Thr Pro His Ser Gly Tyr Glu His Ala Gln Gln Lys Thr
            660                 665                 670

Leu Leu Asn Phe Thr Ala Thr Val Lys Asn Thr Gly Glu Arg Glu Ser
        675                 680                 685

Asp Tyr Thr Ala Leu Val Tyr Val Asn Thr Thr Ala Gly Pro Ala Pro
    690                 695                 700

Tyr Pro Lys Lys Trp Val Val Gly Phe Asp Arg Leu Gly Gly Leu Glu
705                 710                 715                 720

Pro Gly Asp Ser Gln Thr Leu Thr Val Pro Val Thr Val Glu Ser Val
                725                 730                 735

Ala Arg Thr Asp Glu Gln Gly Asn Arg Val Leu Tyr Pro Gly Ser Tyr
            740                 745                 750

Asp Val Ala Leu Asn Asn Glu Arg Ser Val Val Lys Phe Glu Leu
        755                 760                 765

Lys Gly Glu Glu Ala Val Ile Leu Ser Trp Pro Glu Asp Thr Thr Ser
770                 775                 780

Asp Phe Val Ser Ser Ile Asp Gly Gly Leu Asp Arg Lys Gln Asp Val
785                 790                 795                 800

Ile Ala

<210> SEQ ID NO 74
<211> LENGTH: 772
<212> TYPE: PRT
<213> ORGANISM: Fragaria x ananassa

<400> SEQUENCE: 74

Met Ala Ser Gly Tyr Asn Asn Lys Leu Ser Leu Ile Ala Leu Val Leu
1               5                   10                  15

Cys Val Ser Ala Leu Leu Phe Asn Leu Val His Ala Arg Pro Pro Phe
            20                  25                  30

Ala Cys Asp Pro Arg Asn Pro Leu Thr Arg Gly Phe Lys Phe Cys Arg
        35                  40                  45

Thr Arg Val Pro Val His Val Arg Val Gln Asp Leu Ile Gly Arg Leu
    50                  55                  60

Thr Leu Gln Glu Lys Ile Arg Leu Leu Val Asn Asn Ala Ile Ala Val
65                  70                  75                  80

Pro Arg Leu Gly Ile Gln Gly Tyr Glu Trp Trp Ser Glu Ala Leu His
                85                  90                  95

Gly Val Ser Asn Val Gly Pro Gly Thr Lys Phe Gly Gly Ala Phe Pro
            100                 105                 110

Gly Ala Thr Ser Phe Pro Gln Val Ile Thr Thr Ala Ala Ser Phe Asn
        115                 120                 125

Gln Ser Leu Trp Gln Glu Ile Gly Gln Val Val Ser Asp Glu Ala Arg
    130                 135                 140
```

```
Ala Met Tyr Asn Gly Gly Gln Ala Gly Leu Thr Tyr Trp Ser Pro Asn
145                 150                 155                 160

Val Asn Ile Phe Arg Asp Pro Arg Trp Gly Arg Gln Glu Thr Pro
            165                 170                 175

Gly Glu Asp Pro Val Leu Ser Ala Lys Tyr Ala Ala Ser Tyr Val Lys
            180                 185                 190

Gly Leu Gln Gly Asp Gly Ala Gly Asn Arg Leu Lys Val Ala Ala Cys
            195                 200                 205

Cys Lys His Tyr Thr Ala Tyr Asp Leu Asp Asn Trp Asn Gly Val Asp
            210                 215                 220

Arg Phe His Phe Asn Ala Arg Val Ser Lys Gln Asp Leu Ala Asp Thr
225                 230                 235                 240

Tyr Asp Val Pro Phe Arg Gly Cys Val Leu Glu Gly Lys Val Ala Ser
            245                 250                 255

Val Met Cys Ser Tyr Asn Gln Val Asn Gly Lys Pro Thr Cys Ala Asp
            260                 265                 270

Pro Asp Leu Leu Lys Asn Thr Ile Arg Gly Glu Trp Lys Leu Asn Gly
            275                 280                 285

Tyr Ile Val Ser Asp Cys Asp Ser Val Gly Val Phe Tyr Asp Gln Gln
290                 295                 300

His Tyr Thr Arg Thr Pro Glu Glu Ala Ala Ala Glu Ala Ile Lys Ala
305                 310                 315                 320

Gly Leu Asp Leu Asp Cys Gly Pro Phe Leu Ala Ile His Thr Glu Gly
            325                 330                 335

Ala Ile Lys Ala Gly Leu Leu Pro Glu Ile Asp Val Asp Tyr Ala Leu
            340                 345                 350

Ala Asn Thr Leu Thr Val Gln Met Arg Leu Gly Met Phe Asp Gly Glu
            355                 360                 365

Pro Ser Ala Gln Gln Tyr Gly Asn Leu Gly Pro Arg Asp Val Cys Thr
370                 375                 380

Pro Ala His Gln Glu Leu Ala Leu Glu Ala Ser Arg Gln Gly Ile Val
385                 390                 395                 400

Leu Leu Gln Asn Asn Gly His Thr Leu Pro Leu Ser Thr Val Arg His
            405                 410                 415

Arg Thr Val Ala Val Val Gly Pro Asn Ser Asp Val Thr Glu Thr Met
            420                 425                 430

Ile Gly Asn Tyr Ala Gly Val Ala Cys Gly Tyr Thr Thr Pro Leu Gln
            435                 440                 445

Gly Ile Gly Arg Tyr Thr Lys Thr Ile His Gln Gln Gly Cys Thr Asn
            450                 455                 460

Val Ala Cys Thr Thr Asn Gln Leu Phe Gly Ala Ala Glu Ala Ala
465                 470                 475                 480

Arg Gln Ala Asp Ala Thr Val Leu Val Met Gly Leu Asp Gln Ser Ile
            485                 490                 495

Glu Ala Glu Phe Arg Asp Arg Thr Asp Leu Val Met Pro Gly His Gln
            500                 505                 510

Gln Glu Leu Val Ser Arg Val Ala Arg Ala Ser Arg Gly Pro Thr Val
            515                 520                 525

Leu Val Leu Met Ser Gly Gly Pro Ile Asp Val Ser Phe Ala Lys Asn
            530                 535                 540

Asp Pro Lys Ile Gly Ala Ile Ile Trp Val Gly Tyr Pro Gly Gln Ala
545                 550                 555                 560

Gly Gly Thr Ala Met Ala Asp Val Leu Phe Gly Thr Thr Asn Pro Ser
```

```
                565                 570                 575
Gly Lys Leu Pro Met Thr Trp Tyr Pro Gln Asp Tyr Val Ser Lys Val
            580                 585                 590

Pro Met Thr Asn Met Ala Met Arg Ala Gly Arg Gly Tyr Pro Gly Arg
            595                 600                 605

Thr Tyr Arg Phe Tyr Lys Gly Pro Val Val Phe Pro Phe Gly Leu Gly
            610                 615                 620

Leu Ser Tyr Thr Thr Phe Ala His Ser Leu Ala Gln Val Pro Thr Ser
625                 630                 635                 640

Val Ser Val Pro Leu Thr Ser Leu Ser Ala Thr Thr Asn Ser Thr Met
            645                 650                 655

Leu Ser Ser Ala Val Arg Val Ser His Thr Asn Cys Asn Pro Leu Ser
            660                 665                 670

Leu Ala Leu His Val Val Lys Asn Thr Gly Ala Arg Asp Gly Thr
            675                 680                 685

His Thr Leu Leu Val Phe Ser Ser Pro Pro Ser Gly Lys Trp Ala Ala
            690                 695                 700

Asn Lys Gln Leu Val Gly Phe His Lys Val His Ile Val Ala Gly Ser
705                 710                 715                 720

His Lys Arg Val Lys Val Asp Val His Val Cys Lys His Leu Ser Val
            725                 730                 735

Val Asp Gln Phe Gly Ile Arg Arg Ile Pro Ile Gly Glu His Lys Leu
            740                 745                 750

Gln Ile Gly Asp Leu Glu His His Ile Ser Val Glu Ala Asn Val Gly
            755                 760                 765

Glu Ile Arg Ser
            770

<210> SEQ ID NO 75
<211> LENGTH: 777
<212> TYPE: PRT
<213> ORGANISM: Hordeum vulgare

<400> SEQUENCE: 75

Met Ala Thr Ala Ala Arg Pro Pro Phe Leu Ala Met Ala Ala Ala Ala
1               5                   10                  15

Leu Leu Val Ala Ala Trp Trp Gly Gly Asn Ala Gly Ala Ala Glu Ala
            20                  25                  30

Gln Ala Gln Ala Pro Val Phe Ala Cys Asp Ala Ser Asn Ala Thr Leu
            35                  40                  45

Ala Ala Tyr Gly Phe Cys Asn Arg Lys Ala Thr Ala Ser Ala Arg Ala
            50                  55                  60

Arg Asp Leu Val Ser Arg Leu Thr Leu Ala Glu Lys Val Gly Phe Leu
65                  70                  75                  80

Val Asn Lys Gln Pro Ala Leu Gly Arg Leu Gly Ile Pro Ala Tyr Glu
            85                  90                  95

Trp Trp Ser Glu Ala Leu His Gly Val Ser Tyr Val Gly Pro Gly Thr
            100                 105                 110

Arg Phe Ser Pro Leu Val Pro Gly Ala Thr Ser Phe Pro Gln Pro Ile
            115                 120                 125

Leu Thr Ala Ala Ser Phe Asn Ala Ser Leu Phe Arg Ala Ile Gly Glu
            130                 135                 140

Val Val Ser Thr Glu Ala Arg Ala Met His Asn Val Gly Leu Ala Gly
145                 150                 155                 160
```

-continued

```
Leu Thr Phe Trp Ser Pro Asn Ile Asn Ile Phe Arg Asp Pro Arg Trp
                165                 170                 175
Gly Arg Gly Gln Glu Thr Pro Gly Glu Asp Pro Leu Leu Ala Ser Lys
            180                 185                 190
Tyr Ala Val Gly Tyr Val Thr Gly Leu Gln Asp Ala Gly Ala Gly Gly
        195                 200                 205
Val Thr Asp Gly Ala Leu Lys Val Ala Cys Cys Lys His Tyr Thr
    210                 215                 220
Ala Tyr Asp Val Asp Asn Trp Lys Gly Val Arg Tyr Thr Phe Asp
225                 230                 235                 240
Ala Lys Val Ser Gln Gln Asp Leu Asp Asp Thr Phe Gln Pro Pro Phe
                245                 250                 255
Lys Ser Cys Val Leu Asp Gly Asn Val Ala Ser Val Met Cys Ser Tyr
            260                 265                 270
Asn Lys Val Asn Gly Lys Pro Thr Cys Ala Asp Lys Asp Leu Leu Glu
        275                 280                 285
Gly Val Ile Arg Gly Asp Trp Lys Leu Asn Gly Tyr Ile Val Ser Asp
    290                 295                 300
Cys Asp Ser Val Asp Val Leu Tyr Thr Gln Gln His Tyr Thr Lys Thr
305                 310                 315                 320
Pro Glu Glu Ala Ala Ala Ile Thr Ile Lys Ser Gly Val Asp Leu Asn
                325                 330                 335
Cys Gly Asn Phe Leu Ala Gln His Thr Val Ala Val Gln Ala Gly
            340                 345                 350
Glu Leu Ser Glu Glu Asp Val Asp Arg Ala Ile Thr Asn Asn Phe Ile
        355                 360                 365
Met Leu Met Arg Leu Gly Phe Phe Asp Gly Asp Pro Arg Gln Leu Ala
    370                 375                 380
Phe Gly Ser Leu Gly Pro Lys Asp Val Cys Thr Ser Ser Asn Arg Glu
385                 390                 395                 400
Leu Ala Arg Glu Thr Ala Arg Gln Gly Ile Val Leu Leu Lys Asn Ser
                405                 410                 415
Gly Ala Leu Pro Leu Ser Ala Lys Ser Ile Lys Ser Met Ala Val Ile
            420                 425                 430
Gly Pro Asn Ala Asn Ala Ser Phe Thr Met Ile Gly Asn Tyr Glu Gly
        435                 440                 445
Thr Pro Cys Lys Tyr Thr Thr Pro Leu Gln Gly Leu Gly Ala Lys Val
    450                 455                 460
Asn Thr Val Tyr Gln Pro Gly Cys Thr Asn Val Gly Cys Ser Gly Asn
465                 470                 475                 480
Ser Leu Gln Leu Ser Thr Ala Val Ala Ala Ala Ser Ala Asp Val
                485                 490                 495
Thr Val Leu Val Val Gly Ala Asp Gln Ser Ile Glu Arg Glu Ser Leu
            500                 505                 510
Asp Arg Thr Ser Leu Leu Pro Gly Gln Gln Thr Gln Leu Val Ser
        515                 520                 525
Ala Val Ala Asn Ala Ser Ser Gly Pro Val Ile Leu Val Met Ser
    530                 535                 540
Gly Gly Pro Phe Asp Ile Ser Phe Ala Lys Ala Ser Asp Lys Ile Ala
545                 550                 555                 560
Ala Thr Leu Trp Val Gly Tyr Pro Gly Glu Ala Gly Gly Ala Ala Leu
                565                 570                 575
Asp Asp Thr Leu Phe Gly Ser His Asn Pro Ser Gly Arg Leu Pro Val
```

```
                      580             585             590
Thr Trp Tyr Pro Ala Ser Tyr Ala Asp Thr Val Thr Met Thr Asp Met
                595             600             605

Arg Met Arg Pro Asp Thr Ser Thr Gly Tyr Pro Gly Arg Thr Tyr Arg
610             615             620

Phe Tyr Thr Gly Asp Thr Val Phe Ala Phe Gly Asp Gly Leu Ser Tyr
625             630             635             640

Thr Lys Met Ser His Ser Leu Val Ser Ala Pro Pro Ser Tyr Val Ser
                645             650             655

Met Arg Leu Ala Glu Asp His Leu Cys Arg Ala Glu Cys Ala Ser
                660             665             670

Val Glu Ala Ala Gly Asp His Cys Asp Asp Leu Ala Leu Asp Val Lys
                675             680             685

Leu Gln Val Arg Asn Ala Gly Glu Val Ala Gly Ala His Ser Val Leu
                690             695             700

Leu Phe Ser Ser Pro Pro Ala His Asn Ala Pro Ala Lys His Leu
705             710             715             720

Val Gly Phe Glu Lys Val Ser Leu Ala Pro Gly Glu Ala Gly Thr Val
                725             730             735

Ala Phe Arg Val Asp Val Cys Arg Asp Leu Ser Val Val Asp Glu Leu
                740             745             750

Gly Gly Arg Lys Val Ala Leu Gly Gly His Thr Leu His Asp Gly Asp
                755             760             765

Leu Lys His Thr Val Glu Leu Arg Val
                770             775

<210> SEQ ID NO 76
<211> LENGTH: 777
<212> TYPE: PRT
<213> ORGANISM: Hordeum vulgare

<400> SEQUENCE: 76

Met Gly Arg Arg Thr His Val Val Leu Ala Ala Ala Val Pro Ala Leu
1               5               10              15

Leu Leu Val Leu Leu Arg Leu His Ala Ala Val Ala Ala Asp Pro
                20              25              30

Pro Phe Ser Cys Gly Ala Pro Ser Ser Ala Ala Phe Cys Asp Arg Arg
                35              40              45

Leu Pro Ile Glu Gln Arg Ala Ala Asp Leu Val Ser Lys Leu Thr Leu
                50              55              60

Glu Glu Lys Ile Ser Gln Leu Gly Asp Glu Ser Pro Ala Val Asp Arg
65              70              75              80

Leu Gly Val Pro Ala Tyr Lys Trp Trp Ser Glu Ala Leu His Gly Val
                85              90              95

Ala Asn Ala Gly Arg Gly Val His Leu Asp Gly Pro Leu Arg Ala Ala
                100             105             110

Thr Ser Phe Pro Gln Val Ile Leu Thr Ala Ala Ser Phe Asn Pro His
                115             120             125

Leu Trp Tyr Arg Ile Gly Gln Val Ile Gly Thr Glu Ala Arg Gly Val
                130             135             140

Tyr Asn Asn Gly Gln Ala Glu Gly Leu Thr Phe Trp Ala Pro Asn Ile
145             150             155             160

Asn Val Phe Arg Asp Pro Arg Trp Gly Arg Gly Gln Glu Thr Pro Gly
                165             170             175
```

Glu Asp Pro Thr Met Thr Gly Lys Tyr Ala Ala Val Phe Val Arg Gly
            180                 185                 190

Val Gln Gly Tyr Gly Met Ser Gly Ala Ile Asn Ser Ser Asp Leu Glu
        195                 200                 205

Ala Ser Ala Cys Cys Lys His Phe Thr Ala Tyr Asp Leu Glu Asn Trp
    210                 215                 220

Lys Gly Val Thr Arg Phe Ala Phe Asp Ala Lys Val Thr Glu Gln Asp
225                 230                 235                 240

Leu Ala Asp Thr Tyr Asn Pro Pro Phe Lys Ser Cys Val Glu Asp Gly
                245                 250                 255

Gly Ala Ser Gly Ile Met Cys Ser Tyr Asn Arg Val Asn Gly Val Pro
            260                 265                 270

Thr Cys Ala Asp His Asn Leu Leu Ser Lys Thr Ala Arg Gly Asp Trp
        275                 280                 285

Ser Phe Asn Gly Tyr Ile Thr Ser Asp Cys Asp Ala Val Ala Ile Ile
    290                 295                 300

His Asp Val Gln Gly Tyr Ala Lys Ala Pro Glu Asp Ala Val Ala Asp
305                 310                 315                 320

Val Leu Lys Ala Gly Met Asp Val Asn Cys Gly Gly Tyr Ile Gln Thr
                325                 330                 335

His Gly Val Ser Ala Tyr Gln Gln Gly Lys Ile Thr Gly Glu Asp Ile
            340                 345                 350

Asp Arg Ala Leu Arg Asn Leu Phe Ala Ile Arg Met Arg Leu Gly Leu
        355                 360                 365

Phe Asp Gly Asn Pro Lys Tyr Asn Arg Tyr Gly Asn Ile Gly Ala Asp
    370                 375                 380

Gln Val Cys Ser Lys Glu His Gln Asp Leu Ala Leu Gln Ala Ala Arg
385                 390                 395                 400

Asp Gly Ile Val Leu Leu Lys Asn Asp Gly Ala Ala Leu Pro Leu Ser
                405                 410                 415

Lys Ser Lys Val Ser Ser Leu Ala Val Ile Gly Pro Asn Gly Asn Asn
            420                 425                 430

Ala Ser Leu Leu Leu Gly Asn Tyr Phe Gly Pro Pro Cys Ile Ser Val
        435                 440                 445

Thr Pro Leu Gln Ala Leu Gln Gly Tyr Val Lys Asp Ala Arg Phe Val
    450                 455                 460

Gln Gly Cys Asn Ala Ala Val Cys Asn Val Ser Asn Ile Gly Glu Ala
465                 470                 475                 480

Val His Ala Ala Gly Ser Ala Asp Tyr Val Val Leu Phe Met Gly Leu
                485                 490                 495

Asp Gln Asn Gln Glu Arg Glu Glu Val Asp Arg Leu Glu Leu Gly Leu
            500                 505                 510

Pro Gly Met Gln Glu Ser Leu Val Asn Ser Val Ala Asp Ala Ala Lys
        515                 520                 525

Lys Pro Val Ile Leu Val Leu Cys Gly Gly Pro Val Asp Val Thr
    530                 535                 540

Phe Ala Lys Asn Asn Pro Lys Ile Gly Ala Ile Val Trp Ala Gly Tyr
545                 550                 555                 560

Pro Gly Gln Ala Gly Gly Ile Ala Ile Ala Gln Val Leu Phe Gly Asp
                565                 570                 575

His Asn Pro Gly Gly Arg Leu Pro Val Thr Trp Tyr Pro Lys Glu Phe
            580                 585                 590

Thr Ala Val Pro Met Thr Asp Met Arg Met Arg Ala Asp Pro Ser Thr

```
                    595                 600                 605
        Gly Tyr Pro Gly Arg Thr Tyr Arg Phe Tyr Lys Gly Lys Thr Val Tyr
            610                 615                 620

Asn Phe Gly Tyr Gly Leu Ser Tyr Ser Lys Tyr Ser His Arg Phe Ala
        625                 630                 635                 640

Ser Lys Gly Thr Lys Pro Pro Ser Met Ser Gly Ile Glu Gly Leu Lys
                            645                 650                 655

Ala Thr Ala Arg Ala Ser Ala Ala Gly Thr Val Ser Tyr Asp Val Glu
                        660                 665                 670

Glu Met Gly Ala Glu Ala Cys Asp Arg Leu Arg Phe Pro Ala Val Val
                    675                 680                 685

Arg Val Gln Asn His Gly Pro Met Asp Gly Gly His Leu Val Leu Leu
                690                 695                 700

Phe Leu Arg Trp Pro Asn Ala Thr Asp Gly Arg Pro Ala Ser Gln Leu
        705                 710                 715                 720

Ile Gly Phe Gln Ser Val His Leu Arg Ala Asp Glu Ala Ala His Val
                            725                 730                 735

Glu Phe Glu Val Ser Pro Cys Lys His Leu Ser Arg Ala Ala Glu Asp
                        740                 745                 750

Gly Arg Lys Val Ile Asp Gln Gly Ser His Phe Val Arg Val Gly Asp
                    755                 760                 765

Asp Glu Phe Glu Leu Ser Phe Met Ala
                770                 775

<210> SEQ ID NO 77
<211> LENGTH: 797
<212> TYPE: PRT
<213> ORGANISM: Hypocrea jecorina

<400> SEQUENCE: 77

Met Val Asn Asn Ala Ala Leu Leu Ala Ala Leu Ser Ala Leu Leu Pro
        1               5                   10                  15

Thr Ala Leu Ala Gln Asn Asn Gln Thr Tyr Ala Asn Tyr Ser Ala Gln
                    20                  25                  30

Gly Gln Pro Asp Leu Tyr Pro Glu Thr Leu Ala Thr Leu Thr Leu Ser
                35                  40                  45

Phe Pro Asp Cys Glu His Gly Pro Leu Lys Asn Asn Leu Val Cys Asp
        50                  55                  60

Ser Ser Ala Gly Tyr Val Glu Arg Ala Gln Ala Leu Ile Ser Leu Phe
        65                  70                  75                  80

Thr Leu Glu Glu Leu Ile Leu Asn Thr Gln Asn Ser Gly Pro Gly Val
                        85                  90                  95

Pro Arg Leu Gly Leu Pro Asn Tyr Gln Val Trp Asn Glu Ala Leu His
                    100                 105                 110

Gly Leu Asp Arg Ala Asn Phe Ala Thr Lys Gly Gly Gln Phe Glu Trp
                115                 120                 125

Ala Thr Ser Phe Pro Met Pro Ile Leu Thr Thr Ala Ala Leu Asn Arg
            130                 135                 140

Thr Leu Ile His Gln Ile Ala Asp Ile Ile Ser Thr Gln Ala Arg Ala
        145                 150                 155                 160

Phe Ser Asn Ser Gly Arg Tyr Gly Leu Asp Val Tyr Ala Pro Asn Val
                        165                 170                 175

Asn Gly Phe Arg Ser Pro Leu Trp Gly Arg Gly Gln Glu Thr Pro Gly
                    180                 185                 190
```

-continued

Glu Asp Ala Phe Phe Leu Ser Ser Ala Tyr Thr Tyr Glu Tyr Ile Thr
            195                 200                 205

Gly Ile Gln Gly Gly Val Asp Pro Glu His Leu Lys Val Ala Ala Thr
210                 215                 220

Val Lys His Phe Ala Gly Tyr Asp Leu Glu Asn Trp Asn Asn Gln Ser
225                 230                 235                 240

Arg Leu Gly Phe Asp Ala Ile Ile Thr Gln Asp Leu Ser Glu Tyr
            245                 250                 255

Tyr Thr Pro Gln Phe Leu Ala Ala Arg Tyr Ala Lys Ser Arg Ser
        260                 265                 270

Leu Met Cys Ala Tyr Asn Ser Val Asn Gly Val Pro Ser Cys Ala Asn
        275                 280                 285

Ser Phe Phe Leu Gln Thr Leu Leu Arg Glu Ser Trp Gly Phe Pro Glu
    290                 295                 300

Trp Gly Tyr Val Ser Ser Asp Cys Asp Ala Val Tyr Asn Val Phe Asn
305                 310                 315                 320

Pro His Asp Tyr Ala Ser Asn Gln Ser Ser Ala Ala Ser Ser Leu
            325                 330                 335

Arg Ala Gly Thr Asp Ile Asp Cys Gly Gln Thr Tyr Pro Trp His Leu
            340                 345                 350

Asn Glu Ser Phe Val Ala Gly Glu Val Ser Arg Gly Glu Ile Glu Arg
        355                 360                 365

Ser Val Thr Arg Leu Tyr Ala Asn Leu Val Arg Leu Gly Tyr Phe Asp
    370                 375                 380

Lys Lys Asn Gln Tyr Arg Ser Leu Gly Trp Lys Asp Val Val Lys Thr
385                 390                 395                 400

Asp Ala Trp Asn Ile Ser Tyr Glu Ala Ala Val Glu Gly Ile Val Leu
            405                 410                 415

Leu Lys Asn Asp Gly Thr Leu Pro Leu Ser Lys Lys Val Arg Ser Ile
            420                 425                 430

Ala Leu Ile Gly Pro Trp Ala Asn Ala Thr Thr Gln Met Gln Gly Asn
        435                 440                 445

Tyr Tyr Gly Pro Ala Pro Tyr Leu Ile Ser Pro Leu Glu Ala Ala Lys
    450                 455                 460

Lys Ala Gly Tyr His Val Asn Phe Glu Leu Gly Thr Glu Ile Ala Gly
465                 470                 475                 480

Asn Ser Thr Thr Gly Phe Ala Lys Ala Ile Ala Ala Lys Lys Ser
            485                 490                 495

Asp Ala Ile Ile Tyr Leu Gly Gly Ile Asp Asn Thr Ile Glu Gln Glu
            500                 505                 510

Gly Ala Asp Arg Thr Asp Ile Ala Trp Pro Gly Asn Gln Leu Asp Leu
        515                 520                 525

Ile Lys Gln Leu Ser Glu Val Gly Lys Pro Leu Val Val Leu Gln Met
    530                 535                 540

Gly Gly Gly Gln Val Asp Ser Ser Leu Lys Ser Asn Lys Lys Val
545                 550                 555                 560

Asn Ser Leu Val Trp Gly Gly Tyr Pro Gly Gln Ser Gly Gly Val Ala
            565                 570                 575

Leu Phe Asp Ile Leu Ser Gly Lys Arg Ala Pro Ala Gly Arg Leu Val
            580                 585                 590

Thr Thr Gln Tyr Pro Ala Glu Tyr Val His Gln Phe Pro Gln Asn Asp
        595                 600                 605

Met Asn Leu Arg Pro Asp Gly Lys Ser Asn Pro Gly Gln Thr Tyr Ile

```
                610                 615                 620
Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
                645                 650                 655

Asn Thr Ser Ser Ile Leu Ser Ala Pro His Pro Gly Tyr Thr Tyr Ser
                660                 665                 670

Glu Gln Ile Pro Val Phe Thr Phe Glu Ala Asn Ile Lys Asn Ser Gly
                675                 680                 685

Lys Thr Glu Ser Pro Tyr Thr Ala Met Leu Phe Val Arg Thr Ser Asn
                690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
                740                 745                 750

Tyr Pro Gly Lys Tyr Glu Leu Ala Leu Asn Thr Asp Glu Ser Val Lys
                755                 760                 765

Leu Glu Phe Glu Leu Val Gly Glu Val Thr Ile Glu Asn Trp Pro
770                 775                 780

Leu Glu Glu Gln Gln Ile Lys Asp Ala Thr Pro Asp Ala
785                 790                 795

<210> SEQ ID NO 78
<211> LENGTH: 774
<212> TYPE: PRT
<213> ORGANISM: Medicago sativa subsp. x varia

<400> SEQUENCE: 78

Ala Asn Thr Lys Asn Arg Glu Pro Lys Val Ser Ser Val Phe Leu Cys
1               5                   10                  15

Phe Ser Ile Phe Tyr Val Thr Val Leu Leu Asn Cys Asn His Val Tyr
                20                  25                  30

Gly Gln Thr Ser Thr Val Phe Ala Cys Asp Val Ala Lys Asn Thr Asn
                35                  40                  45

Val Ser Ser Tyr Gly Phe Cys Asp Asn Ser Leu Ser Val Glu Asp Arg
50                  55                  60

Val Ser Asp Leu Val Lys Arg Leu Thr Leu Gln Glu Lys Ile Gly Asn
65                  70                  75                  80

Leu Gly Asn Ser Ala Val Glu Val Ser Arg Leu Gly Ile Pro Lys Tyr
                85                  90                  95

Glu Trp Trp Ser Glu Ala Leu His Gly Val Ser Asn Ile Gly Pro Gly
                100                 105                 110

Thr His Phe Ser Ser Leu Val Pro Gly Ala Thr Asn Phe Pro Met Pro
                115                 120                 125

Ile Leu Thr Ala Ala Ser Phe Asn Thr Ser Leu Phe Gln Ala Ile Gly
                130                 135                 140

Ser Val Val Ser Asn Glu Ala Arg Ala Met Tyr Asn Val Gly Leu Ala
145                 150                 155                 160

Gly Leu Thr Tyr Trp Ser Pro Asn Ile Asn Ile Phe Arg Asp Pro Arg
                165                 170                 175

Trp Gly Arg Gly Gln Glu Thr Pro Gly Glu Asp Pro Leu Leu Ser Ser
                180                 185                 190
```

-continued

```
Lys Tyr Ala Ala Gly Tyr Val Lys Gly Leu Gln Gln Thr Asp Asp Gly
            195                 200                 205

Asp Ser Asp Lys Leu Lys Val Ala Ala Cys Cys Lys His Tyr Thr Ala
210                 215                 220

Tyr Asp Val Asp Asn Trp Lys Gly Val Gln Arg Tyr Thr Phe Asp Ala
225                 230                 235                 240

Val Val Ser Gln Gln Asp Leu Asp Asp Thr Phe Gln Pro Pro Phe Lys
            245                 250                 255

Ser Cys Val Ile Asp Gly Asn Val Ala Ser Val Met Cys Ser Tyr Asn
            260                 265                 270

Lys Val Asn Gly Lys Pro Thr Cys Ala Asp Pro Asp Leu Leu Lys Gly
            275                 280                 285

Val Ile Arg Gly Lys Trp Lys Leu Asn Gly Tyr Ile Val Ser Asp Cys
            290                 295                 300

Asp Ser Val Glu Val Leu Tyr Lys Asp Gln His Tyr Thr Lys Thr Pro
305                 310                 315                 320

Glu Glu Ala Ala Lys Thr Ile Leu Ser Gly Leu Asp Leu Asp Cys
            325                 330                 335

Gly Ser Tyr Leu Gly Gln Tyr Thr Gly Gly Ala Val Lys Gln Gly Leu
            340                 345                 350

Val Asp Glu Ala Ser Ile Thr Asn Ala Val Ser Asn Asn Phe Ala Thr
            355                 360                 365

Leu Met Arg Leu Gly Phe Phe Asp Gly Asp Pro Ser Lys Gln Pro Tyr
            370                 375                 380

Gly Asn Leu Gly Pro Lys Asp Val Cys Thr Pro Glu Asn Gln Glu Leu
385                 390                 395                 400

Ala Arg Glu Ala Ala Arg Gln Gly Ile Val Leu Leu Lys Asn Ser Pro
            405                 410                 415

Arg Ser Leu Pro Leu Ser Ser Lys Ala Ile Lys Ser Leu Ala Val Ile
            420                 425                 430

Gly Pro Asn Ala Asn Ala Thr Arg Val Met Ile Gly Asn Tyr Glu Gly
            435                 440                 445

Ile Pro Cys Lys Tyr Thr Ser Pro Leu Gln Gly Leu Thr Ala Phe Val
450                 455                 460

Pro Thr Ser Tyr Ala Pro Gly Cys Pro Asp Val Gln Cys Ala Asn Ala
465                 470                 475                 480

Gln Ile Asp Asp Ala Ala Lys Ile Ala Ala Ser Ala Asp Ala Thr Ile
            485                 490                 495

Ile Val Val Gly Ala Asn Leu Ala Ile Glu Ala Glu Ser Leu Asp Arg
            500                 505                 510

Val Asn Ile Leu Leu Pro Gly Gln Gln Gln Leu Val Asn Glu Val
            515                 520                 525

Ala Asn Val Ser Lys Gly Pro Val Ile Leu Val Ile Met Ser Gly Gly
            530                 535                 540

Gly Met Asp Val Ser Phe Ala Lys Thr Asn Asp Lys Ile Thr Ser Ile
545                 550                 555                 560

Leu Trp Val Gly Tyr Pro Gly Glu Ala Gly Ala Ala Ile Ala Asp
            565                 570                 575

Val Ile Phe Gly Ser Tyr Asn Pro Ser Gly Arg Leu Pro Met Thr Trp
            580                 585                 590

Tyr Pro Gln Ser Tyr Val Glu Lys Val Pro Met Thr Asn Met Asn Met
            595                 600                 605

Arg Ala Asp Pro Ala Thr Gly Tyr Pro Gly Arg Thr Tyr Arg Phe Tyr
```

```
            610                 615                 620
Lys Gly Glu Thr Val Phe Ser Phe Gly Asp Gly Met Ser Phe Gly Thr
625                 630                 635                 640

Val Glu His Lys Ile Val Lys Ala Pro Gln Leu Val Ser Val Pro Leu
                645                 650                 655

Ala Glu Asp His Glu Cys Arg Ser Leu Glu Cys Lys Ser Leu Asp Val
                660                 665                 670

Ala Asp Lys His Cys Gln Asn Leu Ala Phe Asp Ile His Leu Ser Val
                675                 680                 685

Lys Asn Met Gly Lys Met Ser Ser Ser His Ser Val Leu Leu Phe Phe
                690                 695                 700

Thr Pro Pro Asn Val His Asn Ala Pro Gln Lys His Leu Leu Gly Phe
705                 710                 715                 720

Glu Lys Val Gln Leu Ala Gly Lys Ser Glu Gly Met Val Arg Phe Lys
                725                 730                 735

Val Asp Val Cys Asn Asp Leu Ser Val Val Asp Glu Leu Gly Asn Arg
                740                 745                 750

Lys Val Pro Leu Gly Asp His Met Leu His Val Gly Asn Leu Lys His
                755                 760                 765

Ser Leu Ser Val Arg Ile
                770

<210> SEQ ID NO 79
<211> LENGTH: 732
<212> TYPE: PRT
<213> ORGANISM: Populus alba x Populus tremula

<400> SEQUENCE: 79

Met Pro Thr Ser Phe Ile Ile Thr Leu Ser Val Leu Phe Leu Gly Val
1                   5                   10                  15

Ser Leu Gln Thr Ser Lys Ala Leu Asp Pro Phe Ala Cys Asp Pro Lys
                20                  25                  30

Asp Gly Thr Asn Arg Asp Leu Pro Phe Cys Gln Val Asn Leu Pro Ile
                35                  40                  45

His Thr Arg Val Asn Asp Leu Ile Gly Arg Met Thr Leu Gln Glu Lys
            50                  55                  60

Val Gly Leu Leu Val Asn Asn Ala Ala Ala Val Pro Arg Leu Gly Ile
65                  70                  75                  80

Lys Gly Tyr Glu Trp Trp Ser Glu Ala Leu His Gly Val Ser Asn Val
                85                  90                  95

Gly Pro Gly Thr Lys Phe Gly Gly Ala Phe Pro Val Ala Thr Ser Phe
                100                 105                 110

Pro Gln Val Ile Thr Thr Ala Ala Ser Phe Asn Ala Thr Leu Trp Glu
            115                 120                 125

Ala Ile Gly Arg Val Val Ser Asp Glu Ala Arg Ala Met Phe Asn Gly
130                 135                 140

Gly Val Ala Gly Leu Thr Tyr Trp Ser Pro Asn Val Thr Tyr Ser Val
145                 150                 155                 160

Tyr Pro Arg Trp Gly Arg Gly Gln Glu Thr Pro Gly Glu Asp Pro Val
                165                 170                 175

Val Val Gly Lys Tyr Ala Ala Ser Tyr Val Arg Gly Leu Gln Gly Ser
                180                 185                 190

Asp Gly Ile Arg Leu Lys Val Ala Ala Cys Cys Lys His Phe Thr Ala
            195                 200                 205
```

```
Tyr Asp Leu Asp Asn Trp Asn Gly Val Asp Arg Phe His Phe Asn Ala
            210                 215                 220

Lys Val Ser Lys Gln Asp Met Val Asp Thr Phe Asp Val Pro Phe Arg
225                 230                 235                 240

Met Cys Val Lys Glu Gly Lys Val Ala Ser Val Met Cys Ser Tyr Asn
                245                 250                 255

Gln Val Asn Gly Ile Pro Thr Cys Ala Asp Pro Asn Leu Leu Lys Lys
                260                 265                 270

Thr Val Arg Gly Gln Trp Arg Leu Asn Gly Tyr Ile Val Ser Asp Cys
            275                 280                 285

Asp Ser Phe Gly Val Tyr Tyr Gly Gln Gln His Phe Thr Ser Pro Arg
290                 295                 300

Arg Ser Ser Leu Gly Cys Tyr Lys Ala Gly Leu Asp Leu Asp Cys Gly
305                 310                 315                 320

Pro Phe Leu Val Thr His Arg Asp Ala Val Lys Lys Ala Ala Glu Glu
                325                 330                 335

Ala Glu Ile Asn Asn Ala Trp Leu Lys Thr Leu Thr Phe Gln Ile Ser
                340                 345                 350

Leu Gly Ile Phe Asp Gly Ser Pro Leu Gln Ala Val Gly Asp Val Val
            355                 360                 365

Pro Thr Met Gly Pro Pro Thr Asn Gln Asp Leu Ala Val Asn Ala Pro
370                 375                 380

Lys Arg Leu Phe Ile Phe Lys Asn Arg Ala Phe Leu Leu Tyr Ser Pro
385                 390                 395                 400

Arg His Ile Phe Gly Pro Val Ala Leu Phe Lys Ser Leu Pro Phe Met
                405                 410                 415

Leu Gly Asn Tyr Glu Gly Leu Pro Cys Lys Tyr Leu Phe Pro Leu Gln
            420                 425                 430

Gly Leu Ala Gly Phe Val Ser Leu Leu Tyr Leu Pro Gly Cys Ser Asn
            435                 440                 445

Val Ile Cys Ala Val Ala Asp Val Gly Ser Ala Val Asp Leu Ala Ala
        450                 455                 460

Ser Ala Asp Ala Val Val Leu Val Val Gly Ala Asp Gln Ser Ile Glu
465                 470                 475                 480

Arg Glu Gly His Asp Arg Val Asp Phe Tyr Leu Pro Gly Lys Gln Gln
                485                 490                 495

Glu Leu Val Thr Arg Val Ala Met Ala Ala Lys Gly Pro Val Leu Leu
            500                 505                 510

Val Ile Met Asp Leu Ala Ile Ser Gly Gly Cys Ser Tyr Asn Gln
        515                 520                 525

Val Asn Gly Ile Pro Ile Ser Asp Val Cys Glu Gly Ser Ser Tyr Arg
530                 535                 540

Trp Pro Ser Phe Ser Asn Cys His Gly Tyr Met Pro Trp Ile Ser Tyr
545                 550                 555                 560

Ser Arg Ala Ile Trp Glu Thr Leu Arg Phe Thr Lys Val Asn Trp Val
                565                 570                 575

Pro Thr Trp Ser Trp Asn Lys Leu His Lys Phe Gly Ser His His Ser
            580                 585                 590

Lys Cys Thr Asp Asp Gly Phe Gly Thr Pro Arg Arg Pro Pro Trp
                595                 600                 605

Leu Arg Lys Cys Asn His Phe Gln Gly Arg Gln Ser Glu Leu His Met
610                 615                 620

Leu Asp Val Ile Asp Ser Leu Leu Gly Met Gln Val Asp Val Lys Asn
```

```
            625                 630                 635                 640
Thr Gly Ser Met Asp Gly Thr His Thr Leu Leu Val Tyr Phe Arg Pro
                        645                 650                 655

Pro Ala Arg His Trp Ala Pro His Lys Gln Leu Val Ala Phe Glu Lys
                660                 665                 670

Val His Val Ala Ala Gly Thr Gln Gln Arg Val Gly Ile Asn Ile His
            675                 680                 685

Val Cys Lys Ser Leu Ser Val Val Asp Gly Ser Gly Ile Arg Arg Ile
        690                 695                 700

Pro Met Gly Glu His Ser Leu His Ile Gly Asp Val Lys His Ser Val
705                 710                 715                 720

Ser Leu Gln Ala Ser Ile Leu Gly Val Val Glu Ser
                    725                 730

<210> SEQ ID NO 80
<211> LENGTH: 780
<212> TYPE: PRT
<213> ORGANISM: Raphanus sativus

<400> SEQUENCE: 80

Met Gly Ser Ser Ser Pro Pro Thr Arg Arg Asn Arg Ala Pro Ser Ser
1               5                   10                  15

Val Phe Ser Leu Ser Leu Ile Phe Leu Cys Leu Leu Asp Ser Ser Asn
            20                  25                  30

Ala Gln Ser Thr Pro Val Phe Ala Cys Asp Val Ala Gly Asn Pro Ser
        35                  40                  45

Leu Ala Ala Tyr Gly Phe Cys Asn Thr Ala Ile Lys Ile Glu Tyr Arg
50                  55                  60

Val Ala Asp Leu Val Ala Arg Leu Thr Leu Gln Glu Lys Ile Gly Val
65                  70                  75                  80

Leu Thr Ser Lys Leu His Gly Val Ala Arg Leu Gly Ile Pro Thr Tyr
                85                  90                  95

Glu Trp Trp Ser Glu Ala Leu His Gly Val Ser Tyr Val Gly Pro Gly
            100                 105                 110

Thr Arg Phe Ser Gly Gln Val Pro Gly Ala Thr Ser Phe Pro Gln Val
        115                 120                 125

Ile Leu Thr Ala Ala Ser Phe Asn Val Ser Leu Phe Gln Ala Ile Gly
    130                 135                 140

Lys Val Val Ser Thr Glu Ala Arg Ala Met Tyr Asn Val Gly Leu Ala
145                 150                 155                 160

Gly Leu Thr Tyr Trp Ser Pro Asn Val Asn Ile Phe Arg Asp Pro Arg
                165                 170                 175

Trp Gly Arg Gly Gln Glu Thr Pro Gly Glu Asp Pro Leu Leu Ser Ser
            180                 185                 190

Lys Tyr Ala Ser Gly Tyr Val Lys Gly Leu Gln Glu Thr Asp Ser Ser
        195                 200                 205

Asp Ala Asn Arg Leu Lys Val Ala Cys Cys Lys His Tyr Thr Ala
    210                 215                 220

Tyr Asp Val Asp Asn Trp Lys Gly Val Glu Arg Tyr Ser Phe Asn Ala
225                 230                 235                 240

Val Val Asn Gln Gln Asp Leu Asp Asp Thr Tyr Gln Pro Pro Phe Lys
                245                 250                 255

Ser Cys Val Val Asp Gly Asn Val Ala Ser Val Met Cys Ser Tyr Asn
            260                 265                 270
```

-continued

```
Lys Val Asn Gly Lys Pro Thr Cys Ala Asp Pro Asp Leu Ser Gly
            275                 280                 285
Val Ile Arg Gly Glu Trp Lys Leu Asn Gly Tyr Ile Val Ser Asp Cys
290                 295                 300
Asp Ser Val Asp Val Leu Tyr Lys Asn Gln His Tyr Thr Lys Thr Pro
305                 310                 315                 320
Glu Glu Ala Ala Ala Ile Ser Ile Asn Ala Gly Leu Asp Leu Asn Cys
                    325                 330                 335
Gly Tyr Phe Leu Gly Asp His Thr Glu Ala Ala Val Lys Ala Gly Leu
            340                 345                 350
Val Lys Glu Ala Ala Ile Asp Lys Ala Ile Thr Asn Asn Phe Leu Thr
            355                 360                 365
Leu Met Arg Leu Gly Phe Phe Asp Gly Asp Pro Lys Lys Gln Ile Tyr
            370                 375                 380
Gly Gly Leu Gly Pro Lys Asp Val Cys Thr Pro Ala Asn Gln Glu Leu
385                 390                 395                 400
Ala Ala Glu Ala Ala Arg Gln Gly Ile Val Leu Leu Lys Asn Thr Gly
                    405                 410                 415
Ala Leu Pro Leu Ser Pro Lys Thr Ile Lys Thr Leu Ala Val Ile Gly
            420                 425                 430
Pro Asn Ala Asn Val Thr Lys Thr Met Ile Gly Asn Tyr Glu Gly Thr
            435                 440                 445
Pro Cys Lys Tyr Thr Thr Pro Leu Gln Gly Leu Ala Gly Thr Val His
            450                 455                 460
Thr Thr Tyr Leu Pro Gly Cys Ser Asn Val Ala Cys Ala Val Ala Asp
465                 470                 475                 480
Val Ala Gly Ser Thr Lys Leu Ala Ala Ala Ser Asp Ala Thr Val Leu
                    485                 490                 495
Val Ile Gly Ala Asp Gln Ser Ile Glu Ala Glu Ser Arg Asp Arg Val
            500                 505                 510
Asp Leu Asn Leu Pro Gly Gln Gln Gln Glu Leu Val Thr Gln Val Ala
            515                 520                 525
Lys Ala Ala Lys Gly Pro Val Phe Leu Val Ile Met Ser Gly Gly Gly
            530                 535                 540
Phe Asp Ile Thr Phe Ala Lys Asn Asp Ala Lys Ile Ala Gly Ile Leu
545                 550                 555                 560
Trp Val Gly Tyr Pro Gly Glu Ala Gly Gly Ile Ala Thr Ala Asp Val
                    565                 570                 575
Ile Phe Gly Arg Tyr Asn Pro Ser Gly Arg Leu Pro Met Thr Trp Tyr
            580                 585                 590
Pro Gln Ser Tyr Val Glu Lys Val Pro Met Thr Asn Met Asn Met Arg
            595                 600                 605
Pro Asp Lys Ser Asn Gly Tyr Pro Gly Arg Thr Tyr Arg Phe Tyr Thr
610                 615                 620
Gly Glu Thr Val Tyr Ala Phe Gly Asp Gly Leu Ser Tyr Thr Lys Phe
625                 630                 635                 640
Ser His Ser Leu Val Lys Ala Pro Arg Leu Val Ser Leu Ser Leu Glu
                    645                 650                 655
Glu Asn His Val Cys Arg Ser Ser Glu Cys Gln Ser Leu Asn Ala Ile
            660                 665                 670
Gly Pro His Cys Asp Asn Ala Val Ser Gly Thr Gly Gly Lys Ala Phe
            675                 680                 685
Glu Val His Ile Lys Val Gln Asn Gly Gly Asp Arg Glu Gly Ile His
```

```
                    690                 695                 700
Thr Val Phe Leu Phe Thr Thr Pro Pro Ala Val His Gly Ser Pro Arg
705                 710                 715                 720

Lys His Leu Leu Gly Phe Glu Lys Ile Arg Leu Gly Lys Met Glu Glu
                    725                 730                 735

Ala Val Val Lys Phe Lys Val Asp Val Cys Lys Asp Leu Ser Val Val
                740                 745                 750

Asp Glu Val Gly Lys Arg Lys Ile Gly Leu Gly Gln His Leu Leu His
            755                 760                 765

Val Gly Asp Val Lys His Ser Leu Ser Ile Arg Ile
770                 775                 780

<210> SEQ ID NO 81
<211> LENGTH: 796
<212> TYPE: PRT
<213> ORGANISM: Talaromyces emersonii

<400> SEQUENCE: 81

Met Met Thr Arg Thr Ala Ile Leu Thr Ala Leu Ala Ala Leu Leu Pro
1               5                   10                  15

Thr Ala Thr Trp Ala Gln Asp Asn Gln Thr Tyr Ala Asn Tyr Ser Ser
                20                  25                  30

Gln Ser Gln Pro Asp Leu Phe Pro Arg Thr Val Ala Thr Ile Asp Leu
            35                  40                  45

Ser Phe Pro Asp Cys Glu Asn Gly Pro Leu Ser Thr Asn Leu Val Cys
50                  55                  60

Asn Thr Ser Ala Asp Pro Trp Ala Arg Ala Glu Ala Leu Val Ser Leu
65                  70                  75                  80

Phe Thr Leu Glu Glu Leu Ile Asn Asn Thr Gln Asn Thr Ala Pro Gly
                85                  90                  95

Val Pro Arg Leu Gly Leu Pro Gln Tyr Gln Val Trp Asn Glu Ala Leu
            100                 105                 110

His Gly Leu Asp Arg Ala Asn Phe Ser Asp Ser Gly Glu Tyr Ser Trp
        115                 120                 125

Ala Thr Ser Phe Pro Met Pro Ile Leu Ser Met Ala Ser Phe Asn Arg
    130                 135                 140

Thr Leu Ile Asn Gln Ile Ala Ser Ile Ile Ala Thr Gln Ala Arg Ala
145                 150                 155                 160

Phe Asn Asn Ala Gly Arg Tyr Gly Leu Asp Ser Tyr Ala Pro Asn Ile
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Ala Tyr Glu Tyr Ile Thr
        195                 200                 205

Gly Leu Gln Gly Gly Val Asp Pro Glu His Val Lys Ile Val Ala Thr
    210                 215                 220

Ala Lys His Phe Ala Gly Tyr Asp Leu Glu Asn Trp Gly Asn Val Ser
225                 230                 235                 240

Arg Leu Gly Ser Asn Ala Ile Ile Thr Gln Gln Asp Leu Ser Glu Tyr
                245                 250                 255

Tyr Thr Pro Gln Phe Leu Ala Ser Ala Arg Tyr Ala Lys Thr Arg Ser
            260                 265                 270

Leu Met Cys Ser Tyr Asn Ala Val Asn Gly Val Pro Ser Cys Ser Asn
        275                 280                 285
```

```
Ser Phe Phe Leu Gln Thr Leu Leu Arg Glu Ser Phe Asn Phe Val Asp
    290             295                 300

Asp Gly Tyr Val Ser Ser Asp Cys Asp Ala Val Tyr Asn Val Phe Asn
305             310                 315                 320

Pro His Gly Tyr Ala Leu Asn Gln Ser Gly Ala Ala Asp Ser Leu
                325                 330                 335

Leu Ala Gly Thr Asp Ile Asp Cys Gly Gln Thr Met Pro Trp His Leu
                340                 345                 350

Asn Glu Ser Phe Tyr Glu Arg Tyr Val Ser Arg Gly Asp Ile Glu Lys
            355                 360                 365

Ser Leu Thr Arg Leu Tyr Ala Asn Leu Val Arg Leu Gly Tyr Phe Asp
370                 375                 380

Gly Asn Asn Ser Val Tyr Arg Asn Leu Asn Trp Asn Asp Val Val Thr
385                 390                 395                 400

Thr Asp Ala Trp Asn Ile Ser Tyr Glu Ala Ala Val Glu Gly Ile Thr
                405                 410                 415

Leu Leu Lys Asn Asp Gly Thr Leu Pro Leu Ser Lys Lys Val Arg Ser
            420                 425                 430

Ile Ala Leu Ile Gly Pro Trp Ala Asn Ala Thr Val Gln Met Gln Gly
        435                 440                 445

Asn Tyr Tyr Gly Thr Pro Pro Tyr Leu Ile Ser Pro Leu Glu Ala Ala
    450                 455                 460

Lys Ala Ser Gly Phe Thr Val Asn Tyr Ala Phe Gly Thr Asn Ile Ser
465                 470                 475                 480

Thr Asp Ser Thr Gln Trp Phe Ala Glu Ala Ile Ser Ala Ala Lys Lys
                485                 490                 495

Ser Asp Val Ile Ile Tyr Ala Gly Gly Ile Asp Asn Thr Ile Glu Ala
            500                 505                 510

Glu Gly Gln Asp Arg Thr Asp Leu Lys Trp Pro Gly Asn Gln Leu Asp
        515                 520                 525

Leu Ile Glu Gln Leu Ser Lys Val Gly Lys Pro Leu Val Val Leu Gln
    530                 535                 540

Met Gly Gly Gly Gln Val Asp Ser Ser Ser Leu Lys Ala Asn Lys Asn
545                 550                 555                 560

Val Asn Ala Leu Val Trp Gly Gly Tyr Pro Gly Gln Ser Gly Gly Ala
                565                 570                 575

Ala Leu Phe Asp Ile Leu Thr Gly Lys Arg Ala Pro Ala Gly Arg Leu
            580                 585                 590

Val Ser Thr Gln Tyr Pro Ala Glu Tyr Ala Thr Gln Phe Pro Ala Asn
        595                 600                 605

Asp Met Asn Leu Arg Pro Asn Gly Ser Asn Pro Gly Gln Thr Tyr Ile
    610                 615                 620

Trp Tyr Thr Gly Thr Pro Val Tyr Glu Phe Gly His Gly Leu Phe Tyr
625                 630                 635                 640

Thr Glu Phe Gln Glu Ser Ala Ala Ala Gly Thr Asn Lys Thr Ser Thr
                645                 650                 655

Leu Asp Ile Leu Asp Leu Val Pro Thr Pro His Pro Gly Tyr Glu Tyr
            660                 665                 670

Ile Glu Leu Val Pro Phe Leu Asn Val Thr Val Asp Val Lys Asn Val
        675                 680                 685

Gly His Thr Pro Ser Pro Tyr Thr Gly Leu Leu Phe Ala Asn Thr Thr
    690                 695                 700

Ala Gly Pro Lys Pro Tyr Pro Asn Lys Trp Leu Val Gly Phe Asp Arg
```

-continued

```
            705                 710                 715                 720
Leu Ala Thr Ile His Pro Ala Lys Thr Ala Gln Val Thr Phe Pro Val
                    725                 730                 735

Pro Leu Gly Ala Ile Ala Arg Ala Asp Glu Asn Gly Asn Lys Val Ile
                740                 745                 750

Phe Pro Gly Glu Tyr Glu Leu Ala Leu Asn Asn Glu Arg Ser Val Val
            755                 760                 765

Val Ser Phe Ser Leu Thr Gly Asn Ala Ala Thr Leu Glu Asn Trp Pro
770                 775                 780

Val Trp Glu Gln Ala Val Pro Gly Val Leu Gln Gln
785                 790                 795

<210> SEQ ID NO 82
<211> LENGTH: 780
<212> TYPE: PRT
<213> ORGANISM: Zea mays

<400> SEQUENCE: 82

Met Pro Leu Ala Ala Met Ala Ser Ala Ser Ser Pro Cys Ser Arg
1               5                   10                  15

His Pro Leu Ile Leu Val Val Leu Leu Cys Ala Ile Ala Ala Ile Ser
                20                  25                  30

Phe Ser Ser Ser Val Ala Ala Gly Thr Val Gly Gly Thr Gly Gly
            35                  40                  45

Leu Gly Pro Ile Ser Thr Asn Gly Lys Asn Tyr Thr Lys Val Cys Asp
    50                  55                  60

Pro Ala Arg Phe Val Ala Leu Gly Leu Asp Met Ser Arg Phe Arg Tyr
65                  70                  75                  80

Cys Asp Ala Ser Leu Pro Tyr Ala Asp Arg Val Arg Asp Leu Val Gly
                85                  90                  95

Arg Leu Ala Leu Glu Glu Lys Val Arg Asn Leu Gly Asp Gln Ala Glu
                100                 105                 110

Gly Ala Pro Arg Val Gly Leu Pro Pro Tyr Lys Trp Trp Gly Glu Ala
            115                 120                 125

Leu His Gly Val Ser Asp Val Gly Pro Gly Gly Thr Trp Phe Gly Asp
    130                 135                 140

Val Val Pro Gly Ala Thr Ser Phe Pro Leu Val Ile Asn Ser Ala Ala
145                 150                 155                 160

Ala Phe Asn Glu Ser Leu Trp Arg Ala Ile Gly Gly Val Val Ser Thr
                165                 170                 175

Glu Ile Arg Ala Met Tyr Asn Leu Gly His Ala Glu Leu Thr Tyr Trp
            180                 185                 190

Ser Pro Asn Ile Asn Val Val Arg Asp Pro Arg Trp Gly Arg Ala Ser
    195                 200                 205

Glu Thr Pro Gly Glu Asp Pro Phe Val Val Gly Arg Tyr Ala Val Asn
210                 215                 220

Phe Val Arg Gly Met Gln Asp Val Asp Arg Pro Tyr Ala Ala Ala
225                 230                 235                 240

Ala Asp Pro Phe Ser Arg Pro Ile Lys Val Ser Ser Cys Cys Lys His
                245                 250                 255

Phe Ala Ala Tyr Asp Val Asp Ala Trp Phe Lys Ala Asp Arg Leu Thr
            260                 265                 270

Phe Asp Ala Gln Val Glu Glu Arg Asp Met Val Glu Thr Phe Glu Arg
    275                 280                 285
```

```
Pro Phe Glu Met Cys Ile Arg Asp Gly Asp Ala Ser Cys Val Met Cys
    290                 295                 300

Ser Tyr Asn Arg Ile Asn Gly Ile Pro Ala Cys Ala Asp Ala Arg Leu
305                 310                 315                 320

Leu Ser Glu Thr Val Arg Ser Gln Trp Gln Leu His Gly Tyr Ile Val
                325                 330                 335

Ser Asp Cys Asp Ser Val Arg Val Met Val Arg Asp Ala Lys Trp Leu
                340                 345                 350

Asn Tyr Thr Gly Val Glu Ala Thr Ala Ala Met Lys Ala Gly Leu
            355                 360                 365

Asp Leu Asp Cys Gly Met Phe Trp Glu Gly Ala Arg Asp Phe Phe Thr
    370                 375                 380

Thr Tyr Gly Val Asp Ala Val Arg Gln Gly Lys Ile Lys Glu Gly Asp
385                 390                 395                 400

Val Asp Asn Ala Leu Ser Asn Val Tyr Thr Thr Leu Met Arg Leu Gly
                405                 410                 415

Phe Phe Asp Gly Met Pro Glu Phe Glu Ser Leu Gly Ala Ser Asn Val
            420                 425                 430

Cys Thr Asp Gly His Lys Glu Leu Ala Ala Asp Ala Ala Arg Gln Gly
        435                 440                 445

Met Val Leu Leu Lys Asn Asp Ala Arg Arg Leu Pro Leu Asp Pro Asn
    450                 455                 460

Lys Ile Asn Ser Val Ser Leu Val Gly Leu Leu Glu His Ile Asn Ala
465                 470                 475                 480

Thr Asp Val Met Leu Gly Asp Tyr Arg Gly Lys Pro Cys Arg Ile Val
                485                 490                 495

Thr Pro Tyr Asn Ala Ile Arg Asn Met Val Asn Ala Thr Tyr Val His
            500                 505                 510

Ala Cys Asp Ser Gly Ala Cys Asn Thr Ala Glu Gly Met Gly Arg Ala
        515                 520                 525

Ser Ser Thr Ala Lys Ile Ala Asp Ala Thr Ile Val Ile Ala Gly Leu
    530                 535                 540

Asn Met Ser Val Glu Arg Glu Ser Asn Asp Arg Glu Asp Leu Leu Leu
545                 550                 555                 560

Pro Trp Asn Gln Ser Ser Trp Ile Asn Ala Val Ala Met Ala Ser Pro
                565                 570                 575

Thr Pro Ile Val Leu Val Ile Met Ser Ala Gly Gly Val Asp Val Ser
            580                 585                 590

Phe Ala His Asn Asn Thr Lys Ile Gly Ala Ile Val Trp Ala Gly Tyr
        595                 600                 605

Pro Gly Glu Glu Gly Gly Thr Ala Ile Ala Asp Val Leu Phe Gly Lys
    610                 615                 620

Tyr Asn Pro Gly Gly Arg Leu Pro Leu Thr Trp Phe Lys Asn Glu Tyr
625                 630                 635                 640

Val Asn Gln Ile Pro Met Thr Ser Met Ala Leu Arg Pro Asp Ala Ala
                645                 650                 655

Leu Gly Tyr Pro Gly Arg Thr Tyr Lys Phe Tyr Gly Gly Pro Ala Val
            660                 665                 670

Leu Tyr Pro Phe Gly His Gly Leu Ser Tyr Thr Asn Phe Ser Tyr Ala
        675                 680                 685

Ser Gly Thr Thr Gly Ala Thr Val Thr Ile His Ile Gly Ala Trp Glu
    690                 695                 700

His Cys Lys Met Leu Thr Tyr Lys Met Gly Ala Pro Ser Pro Ser Pro
```

-continued

```
                705                 710                 715                 720
        Ala Cys Pro Ala Leu Asn Val Ala Ser His Met Cys Ser Glu Val Val
                        725                 730                 735

Ser Phe Ser Leu Arg Val Ala Asn Thr Gly Gly Val Gly Gly Asp His
                        740                 745                 750

Val Val Pro Val Tyr Thr Ala Pro Pro Glu Val Gly Asp Ala Pro
                        755                 760                 765

Leu Lys Gln Leu Val Ala Phe Arg Arg Val Phe Val
                        770                 775                 780
```

US 8,956,845 B2

β-GLUCOSIDASE VARIANTS

CROSS-REFERENCE TO RELATED APPLICATIONS

The present application is a Divisional of U.S. patent application Ser. No. 13/375,189 (filed Nov. 29, 2011), which claims benefit of U.S. Prov. Pat. Appln. Ser. Nos. 61/187,565 (filed Jun. 16, 2009), 61/218,020 (filed Jun. 17, 2009), 61/264,605 (filed Nov. 25, 2009), and 61/264,608 (filed Nov. 25, 2009), the entire disclosures of which are incorporated herein by reference for all purposes. The entire disclosures of commonly owned U.S. patent application Ser. No. 12/816,989 (filed Jun. 16, 2010) and U.S. Prov. Appln. Ser. No. 61/355,511 (filed Jun. 16, 2010) are also incorporated herein by reference for all purposes.

FIELD OF THE INVENTION

The invention relates to expression of recombinant β-glucosidase variants and their use in the production of soluble sugars from cellulosic biomass.

BACKGROUND OF THE INVENTION

Cellulosic biomass is a significant renewable resource for the generation of soluble sugars. These sugars can be used as reactants in various metabolic processes, including fermentation, to produce biofuels, chemical compounds, and other commercially valuable end-products. While the fermentation of simple sugars such as glucose to ethanol is relatively straightforward, the efficient conversion of cellulosic biomass to soluble sugars is challenging. See, e.g., Ladisch et al., 1983, *Enzyme Microb. Technol.* 5:82. Cellulose may be pre-treated chemically, mechanically, enzymatically or in other ways to increase the susceptibility of cellulose to hydrolysis. Such pretreatment may be followed by the enzymatic conversion of cellulose to cellobiose, cello-oligosaccharides, glucose, and other sugars and sugar polymers, using enzymes that break down the β-1-4 glycosidic bonds of cellulose. These enzymes are collectively referred to as "cellulases."

Cellulases are divided into three sub-categories of enzymes: 1,4-β-D-glucan glucanohydrolase ("endoglucanase" or "EG"); 1,4-β-D-glucan cellobiohydrolase ("exoglucanase", "cellobiohydrolase", or "CBH"); and β-D-glucoside-glucohydrolase ("β-glucosidase", "cellobiase" or "BGL"). Endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetraose. β-Glucosidases split cellobiose into glucose monomers.

Cellulases with improved properties for use in processing cellulosic biomass would reduce costs and increase the efficiency of production of biofuels and other commercially valuable compounds.

SUMMARY OF THE INVENTION

In one aspect the invention provides a method of producing a variant β-glucosidase polypeptide with improved thermoactivity, by (a) identifying a first performance sensitive position (PSP) in a target β-glucosidase polypeptide, (b) expressing a variant β-glucosidase polypeptide in which the residue at the first performance sensitive position is replaced with a thermoactivity enhancing residue, where the variant β-glucosidase polypeptide has greater thermoactivity than the target β-glucosidase polypeptide. In some embodiments the target β-glucosidase polypeptide has the sequence of a naturally occurring protein or has at least 80% sequence identity to a naturally occurring protein. In some embodiments the method includes the further steps of (c) identifying a second performance sensitive position in the target β-glucosidase polypeptide, and (d) expressing a polypeptide in which the residues at both the first and second performance sensitive positions are replaced with thermoactivity enhancing residues. In some embodiments the method includes the further steps of (c) identifying a second performance sensitive position in the variant β-glucosidase polypeptide, and (d) expressing a second variant polypeptide, in which the residues at both the first and second performance sensitive positions are replaced with thermoactivity enhancing residues.

In some embodiments the step of identifying a performance sensitive position includes (a) aligning the primary sequence of the target β-glucosidase polypeptide with one or more a β-glucosidase polypeptides in which performance sensitive positions ("PSP") have been defined and (b) identifying a position in the target β-glucosidase polypeptide that corresponds in the alignment to a PSP in the one or more a β-glucosidase polypeptides, wherein the position so identified is a PSP. In some embodiments the step of identifying a performance sensitive position includes (a) aligning the primary sequence of the target β-glucosidase polypeptide with one or both of a GH3 consensus sequence (SEQ ID NO:53) or portion thereof and a GH3-C consensus sequence (SEQ ID NO:54) or portion thereof, and (b) identifying a position in the target β-glucosidase polypeptide that corresponds in the alignment to a PSP in the one or more a β-glucosidase polypeptides, wherein the position so identified is a PSP. The invention also provides a non-naturally occurring β-glucosidase polypeptide.

In a related aspect the invention provides a recombinant or non-naturally occurring β-glucosidase protein variant with a first segment with at least 26% sequence identity to the GH3 Domain Consensus Sequence (SEQ ID NO:53) and a second segment with at least 19% sequence identity to the GH3-C Domain Consensus Sequence (SEQ ID NO:54), where the segments are in the order N-first segment-second segment-C; where the β-glucosidase comprises no more than one of the following residues: a) alanine at a position corresponding to position 104 of SEQ ID NO:1, b) leucine at a position corresponding to position 157 of SEQ ID NO:1, c) isoleucine at a position corresponding to position 210 of SEQ ID NO:1, d) alanine at a position corresponding to position 485 of SEQ ID NO:1, e) alanine at a position corresponding to position 572 of SEQ ID NO:1, and f) tyrosine at a position corresponding to position 649 of SEQ ID NO:1; wherein the β-glucosidase protein variant is catalytically active.

In a related aspect the invention provides a catalytically active recombinant β-glucosidase protein variant with a first segment with at least 26% sequence identity to the GH3 Domain Consensus Sequence (SEQ ID NO:53) and a second segment with at least 19% sequence identity to the GH3-C Domain Consensus Sequence (SEQ ID NO:54), where the protein has a sequence in the first segment that differs from SEQ ID NO:53 at one or more performance sensitive positions selected from positions 39, 43, 51, 57, 58, 65, 91, 94, 97, 98, 133 and 134 of SEQ ID NO:53, and differs from SEQ ID NO:54 at one or more performance sensitive positions selected from positions 61, 82, 83, 115 and 163 of SEQ ID NO:54, wherein the number of said positions at which the variant protein differs from SEQ ID NOs:53 and 54 is 9 or more.

In a related aspect, the invention provides a recombinant or non-naturally occurring β-glucosidase protein variant that has a sequence with at least 80% sequence identity to a naturally occurring β-glucosidase protein and comprises substitutions relative to the naturally occurring β-glucosidase protein at one or more performance sensitive positions (PSPs), where the performance sensitive positions correspond to positions in SEQ ID NO:1 selected from residues 60, 87, 104, 116, 122, 123, 130, 160, 163, 164, 210, 484, 521, 572, 211, 338, 339, 295, 299, 350, 415, 463, 485, 108, 157, and 649. In one embodiment the naturally occurring occurring β-glucosidase protein has a sequence of one of SEQ ID NO:4-52. In one embodiment the variant β-glucosidase protein has a sequence from 80% to 99% identical to one of SEQ ID NO:4-52. The variant β-glucosidase protein may be more thermoactive than the naturally occurring β-glucosidase protein.

GH3 β-xylosidases are structurally related to β-glucosidases and the invention provides variant β-xylosidase polypeptides with improved thermoactivity and methods of making such polypeptides. In one aspect the invention provides a method of producing a variant β-xylosidase polypeptide with improved thermoactivity, by (a) identifying a first performance sensitive position (PSP) in a target β-xylosidase polypeptide and (b) expressing a variant β-xylosidase polypeptide in which the residue at the first performance sensitive position is replaced with a thermoactivity enhancing residue, where the variant β-xylosidase polypeptide has greater thermoactivity than the target β-xylosidase polypeptide. In certain embodiments the target β-xylosidase polypeptide has the sequence of a naturally occurring protein or has at least 80% sequence identity to a naturally occurring protein. In some embodiments the method comprises further steps of identifying additional performance sensitive positions and expressing corresponding variant polypeptides.

The invention also provides non-naturally occurring β-xylosidase polypeptide variants produced according to the method.

In a related aspect the invention provides a recombinant or non-naturally occurring β-xylosidase protein variant that has a sequence with at least 80% sequence identity to a naturally occurring β-xylosidase protein and comprises substitutions relative to the naturally occurring β-xylosidase protein at one or more performance sensitive positions (PSPs), wherein the performance sensitive positions correspond to positions in SEQ ID NO:1 selected from the group consisting of residues 60, 87, 104, 116, 122, 123, 130, 160, 163, 164, 210, 484, 521, 572, 211, 338, 339, 295, 299, 350, 415, 463, 485, 108, 157, and 649. In one embodiment the naturally occurring occurring β-xylosidase protein has a sequence of one of SEQ ID NO:58-82.

DETAILED DESCRIPTION OF THE INVENTION

I. Definitions

The following definitions are provided to assist the reader. Unless otherwise defined, all terms of art are intended to have the meanings commonly understood by those of skill in the molecular biology and microbiology arts. In some cases, terms with commonly understood meanings are defined herein for clarity and/or for ready reference, and the inclusion of such definitions herein should not necessarily be construed to represent a substantial difference over the definition of the term as generally understood in the art.

The term "cellulase" refers to a category of enzymes capable of hydrolyzing cellulose (β-1,4-glucan or β-D-glucosidic linkages) to shorter oligosaccharides, cellobiose and/or glucose.

"Cellulolytic activity" encompasses exoglucanase activity (CBH), endoglucanase (EG) activity and/or β-glucosidase (BGL) activity.

The terms "endoglucanase" or "EG" refer to a group of cellulase enzymes classified as E.C. 3.2.1.4. These enzymes catalyze the hydrolysis of internal β-1,4 glucosidic bonds of cellulose.

The terms "cellobiohydrolase", "exoglucanase", "exo-cellobiohydrolase" or "CBH" refer to a group of cellulase enzymes classified as E.C. 3.2.1.91. These enzymes hydrolyze cellobiose from the reducing or non-reducing end of cellulose.

The terms "β-D-glucoside-glucohydrolase", "β-glucosidase", "cellobiase" or "BGL" refer to a group of cellulase enzymes classified as E.C. 3.2.1.21. These enzymes hydrolyze cellobiose to glucose.

The terms "Xylan 1,4-β-xylosidase", "β-xylosidase", "xylobiase" or "BXL" refer to a group of cellulase enzymes classified as E.C. 3.2.1.37. These enzymes hydrolyze xylobiose to xylose.

The term "wild-type" as applied to a polypeptide (protein) means a polypeptide (protein) expressed by a naturally occurring microorganism such as bacteria or filamentous fungus. As applied to a microorganism, the term "wild-type" refers to the native, non-recombinant micro-organism.

A "variant" as used herein means a β-glucosidase polypeptide comprising one or more modifications relative to a wild-type β-glucosidase protein.

The term "pre-protein" refers to a protein including an amino-terminal signal peptide (or leader sequence) region attached. The signal peptide is cleaved from the pre-protein by a signal peptidase prior to secretion to result in the "mature" or "secreted" protein.

As used herein, the term "isolated" refers to a nucleic acid, polynucleotide, polypeptide, protein, or other component that is partially or completely separated from components with which it is normally associated (other proteins, nucleic acids, cells, etc.).

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. Likewise, a polynucleotide sequence that does not appear in nature, for example a variant of a naturally occurring gene, is recombinant. A protein expressed in vitro or in vivo from a recombinant polynucleotide is an example of a recombinant polypeptide.

A β-glucosidase or β-xylosidase polypeptide with an "improved property" exhibits an improvement in any property as compared to the wild-type form. Improved properties may include increased protein expression, catalytic activity, thermostability, pH activity, pH stability, increased specific activity, substrate specificity, increased resistance to substrate or end-product inhibition, altered pH/temperature profile, and chemical stability. The phrase "improved thermoactivity" is used herein to refer to a polypeptide with increased catalytic activity and/or increased stability relative to a reference or wild-type protein under low pH and/or high temperature conditions.

A β-glucosidase variant polypeptide is "enzymatically active" or "catalytically active," or "biologically active" when it has β-glucosidase activity.

A β-xylosidase variant polypeptide is "enzymatically active" or "catalytically active," or "biologically active" when it has β-xylosidase activity.

The terms "percent identity," "% identity," "percent identical," and "% identical" are used interchangeably herein to refer to the percent amino acid sequence identity. Percent sequence identity can be calculated as the number of identical residues divided by the number of non-gap positions, multiplied by 100. While optimal alignment and scoring can be accomplished manually, the process is facilitated by the use of a computer-implemented alignment algorithm. In a preferred embodiment, the alignment can be obtained by AlignX® (AlignX Jul. 31, 2006, a component of Vector NTI advance 10.3.0 and is based on the ClustalW algorithm), followed by counting the number of identical matches in the alignment and dividing such number of identical matches by the length of the reference sequence. The following default AlignX multiple alignment parameters are used for multiple sequence alignment—DNA/Protein Gap Open Penalty: 15/10; DNA/Protein Gap Extension Penalty: 6.66/0.05; Gap separation penalty range: 8; Use end gap separation penalty; % identity for alignment delay: 40; Use residue-specific gaps; Use hydrophilic residue gap. Another useful multiple sequence alignment algorithm is ClustalW analysis (version W1.8 available from European Bioinformatics Institute, Cambridge, UK), counting the number of identical matches in the alignment and dividing such number of identical matches by the length of the reference sequence, and using the following default ClustalW parameters to achieve slow/accurate pairwise optimal alignments—DNA/Protein Gap Open Penalty: 15/10; DNA/Protein Gap Extension Penalty: 6.66/0.1; Protein weight matrix: Gonnet series; DNA weight matrix: Identity; Toggle Slow/Fast pairwise alignments=SLOW or FULL Alignment; DNA/Protein Number of K-tuple matches: 2/1; DNA/Protein number of best diagonals: 4/5; DNA/Protein Window size: 4/5. Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences Amino acid substitution matrices and their use in quantifying the similarity between two sequences are well-known in the art. See e.g., Dayhoff et al., 1978, "A model of evolutionary change in proteins"; "Atlas of Protein Sequence and Structure," Vol. 5, Suppl. 3 (Ed. M. O. Dayhoff), pp. 345-352, *Natl. Biomed. Res. Round.*, Washington, D.C.; and Henikoff et al., 1992, *Proc. Natl. Acad. Sci. USA*, 89:10915-10919, both of which are incorporated herein by reference. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. Other useful programs include gapped BLAST 2.0, described in Altschul, et al., 1997, *Nucleic Acids Res.*, 25:3389-3402 (incorporated herein by reference), and made available to the public at the National Center for Biotechnology Information Website. Optimal alignments, including multiple alignments can be prepared using readily available programs such as AlignX®, supra, PSI-BLAST, which is described by Altschul, supra. "T-Coffee" (Notredame et al., 2000, *J. Mol. Bio.*, 302:205-17). T-Coffee alignments may be carried out using default parameters (T-Coffee Technical Documentation, Version 8.01, July 2009, WorldWideWeb.tcoffee.org).

In the context of sequence identity, a reference to "at least x % sequence identity" in this specification is intended to refer to "x % sequence identity" as well as to alternative embodiments in which % sequence identity is defined by each integer from (x+1) % to 99% identity, just as if each alternative embodiment was explicitly listed. For example, reference to "at least 70% sequence identity to SEQ ID NO:2" refers to alternative embodiments with at least 71% sequence identity, at least 72% identity, at least 73% identity, at least 74% identity, at least 75% identity, at least 76% identity, at least 77% identity, at least 78% identity, at least 79% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity to SEQ ID NO:2. When used in a claim, "at least x % identity" refers to the specific range or genus recited in the claim.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an variant, that insertion will not correspond to a numbered amino acid position in the reference sequence. In the case of truncations or fusions there can be stretches of amino acids in either the reference or aligned sequence that do not correspond to any amino acid in the corresponding sequence.

The terms "culturing" or "cultivation" refer to growing a population of microbial cells under suitable conditions in a liquid or solid medium.

The term "contacting" refers to the placing of a respective enzyme in sufficiently close proximity to a respective substrate to enable the enzyme to convert the substrate to a product. Those skilled in the art will recognize that mixing solution of the enzyme with the respective substrate will effect contacting. Such contacting also includes incubating a cell secreting an enzyme in a medium containing an enzyme substrate.

As used herein, reference to a cell "metabolizing" a soluble sugar or other substrate to produce an end product means the sugar serves as a carbon source and/or energy source for a metabolic reaction in the cell. Typically the cell is a microbial cell such as a fungal cell or bacterial cell.

The term "introduced" in the context of inserting a nucleic acid sequence into a cell means transfected, transduced or transformed (collectively "transformed") or otherwise incorporated into the genome of, or maintained as an episome in, the cell.

As used herein the term "transformed" or "transformation" used in reference to a cell means a cell has a non-native nucleic acid sequence integrated into its genome or as an episomal plasmid that is maintained through multiple generations.

When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

The term "operably linked" refers herein to a configuration in which a control sequence is appropriately placed at a position relative to the coding sequence of the DNA sequence such that the control sequence influences the expression of a polypeptide.

A promoter sequence, signal peptide, or other sequence is "heterologous", when it is operably linked to a nucleic acid or protein sequence with which the promoter, signal peptide or other sequence is not associated in nature.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

As used herein, a "start codon" is the ATG codon that encodes the first amino acid residue (methionine) of a protein.

As used herein, "C1" refers to a fungal strain described by Garg, A., 1966, "An addition to the genus *Chrysosporium corda*" *Mycopathologia* 30:3-4. "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophilia*. Other C1 strains include cells deposited under accession numbers ATCC 44006, CBS (Centraalbureau voor Schimmelcultures) 122188, CBS 251.72, CBS143.77, CBS 272.77, and VKM F-3500D. Exemplary C1 derivatives include modified organisms in which one or more endogenous genes or sequences has been deleted or modified and/or one or more heterologous genes or sequences has been introduced. Derivatives include UV18#100f [Δalp1, UV18#100f [Δ]pyr5 [Δ]alp1, UV18#100.f Aalp1 Apep4 Aalp2, UV18#100.f [Δ]pyr5 Aalp1 Apep4 Aalp2 and UV18#100.f [Δ]pyr4 [Δ]pyr5 Aalp 1 Apep4 Aalp2. as described in WO2008073914, incorporated herein by reference.

The following conventions are used to describe substitutions in a variant polypeptide (or nucleic acid) sequence relative to a parent sequence: "R-#" or "R-#-V", where "#" refers to the position in a reference sequence and to corresponding residues in a variant or homologous sequence, "R" refers to the amino acid at that position in the reference sequence, and "V" refers to the amino acid at that position in the variant sequence, using the IUPAC single letter designation. For example, for a variant β-glucosidase described with reference to SEQ ID NO: 1, "D350R" indicates that in the variant protein, the residue at the position corresponding to the aspartic acid at position 350 of reference sequence SEQ ID NO:1 is replaced with arginine. As will be apparent, "R-#-(V1/V2/ . . . V$_N$)" means that the residue in the variant at position # is selected from V1, V2, . . . V$_N$. In variants comprising multiple substitutions, modifications are separated by semicolons (;) or addition marks ("+"), e.g., "I49V; E69T; S212P; K294P" or "I49V+E69T+S212P+K294P."

A "substitution," in the context of a variant polypeptide sequence, means that the residue in the variant protein is other then the residue identified in the reference sequence. For example, "A88" denotes a variant comprising an amino acid other than alanine at position 88 (i.e., one of the other 19 naturally occurring amino acids). In some embodiments, the amino acid in the variant protein is neither the wild-type residue nor a residue that is a residue commonly exchanged with the wild-type residue as defined by the following pairs: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. In some embodiments, the amino acid in the variant protein is neither the wild-type residue nor a residue that is a conservative substitute for the wild-type residue, where a conservative substitute for a residue is another residue in the same group, defined as follows: basic amino acids (arginine, lysine, histidine); acidic amino acids (glutamic acid, aspartic acid); polar amino acids (glutamine, asparagine); hydrophobic amino acids (leucine, isoleucine, valine); aromatic amino acids (phenylalanine, tryptophan, tyrosine) and small amino acids (glycine, alanine, serine, threonine, proline, cysteine, methionine).

II. Compositions and Methods

A. Introduction

β-glucosidases (BGLs) are enzymes that catalyze the hydrolysis of cellobiose to glucose. BGLs are expressed in nature by a variety of organisms, including filamentous fungi and cellulose-digesting bacteria. Recombinantly expressed BGLs find use in a variety of commercial applications. For example, BGLs and other cellulases may be used in the conversion of cellulosic biomass to soluble sugars (saccharification). The sugars may be used as carbon and energy sources for biosynthesis of ethanol and other commercially valuable products.

Commercial saccharification processes are often carried out at high temperatures (e.g., >65° C.) and low pH. High temperature is detrimental to the activity and stability of most naturally occurring β-glucosidases. Therefore, nonnaturally occurring β-glucosidase variants that are more catalytically active at elevated temperature and/or more thermostable than naturally occurring counterparts are of considerable value. The β-glucosidase variants of the invention have improved activity at elevated temperature, and optionally low pH, relative to natural occurring forms.

Improved activity can be detected using the β-glucosidase activity assays described herein. In some embodiments, improved activity can be detected by measuring residual activity. Hereinafter, except as otherwise indicated, the terms "thermoactive" or "improved thermoactivity" refer to variants that have greater catalytic activity and/or greater stability at elevated temperatures.

The present invention provides thermoactive β-glucosidase variants as well as methods for making these enzymes.

In studies carried out by the inventors, β-glucosidase variants with improved activity or thermostability relative to naturally occurring (wild-type) enzymes were identified using molecular evolution and high throughput screening (see Examples). β-glucosidase variants with improved thermoactivity were generated from wild-type enzymes from two cellulose-degrading fungi (C1 and *Thermoascus aurantiacus*) and a cellulose-degrading bacterium (*Azospirillum irakense*).

The thermoactive variants differed from the naturally occurring enzymes by substitution at one or more specific residues, referred to herein as performance sensitive residues ("PSRs"). By way of illustration, in naturally occurring C1 β-glucosidase (described hereinbelow), residue 350 is aspartic acid. Variants in which this position is substituted (to A, C, E, F, H, I, K, L, M, P, Q, R, S, T, V, or Y) had improved thermoactivity.

Surprisingly, it was discovered that many performance sensitive residues are at equivalent positions in two or all three of these β-glucosidases. This was particularly striking because the C1, *T. aurantiacus* and *A. irakense* β-glucosidases do not have high primary sequence identity, as shown below.

TABLE 1

| First enzyme | Second Enzyme | Seq Identity[1] |
|---|---|---|
| C1 BGL1 | *T. aurantiacus* BGL | 65% |
| C1 BGL1 | *A. irakense* CelA | 21% |
| *T. aurantiacus* BGL | *A. irakense* CelA | 21% |

[1]Multiple sequence alignments were made using AlignX. C1 BGL 1 = SEQ ID NO: 1; *T. aurantiacus* BGL = SEQ ID NO: 2; *A. irakense* CelA = SEQ ID NO: 3.

Residues are in "equivalent" or "corresponding" positions when they occupy the same relative position in an alignment of two or more amino acid sequences, as discussed below. By way of illustration, position 350 of C1 β-glucosidase ("C1BGL1") corresponds to position 342 of *T. aurantiacus* β-glucosidase ("TaBGL"). See Table 14.

D350 of C1 BGL1 and K342 of TaBGL each were independently identified as performance sensitive residues. That is, certain thermoactive variants of C1 BGL had a substitution at position 350 (as well as other residues), and thermoactive variants of TaBGL had a substitution at position 342 (as well as other residues). When performance sensitive residues found in corresponding positions in different β-glucosidase, those positions are called performance sensitive positions ("PSPs"). Based on this discovery, it is possible to produce novel BGL variants with increased thermoactivity by identifying a performance sensitive position in a parent β-glucosidase polypeptide and then replacing the residue at the performance sensitive position with a thermoactivity enhancing residue.

For example, position 338 of C1 BGL1, position 372 of TaBGL, and position 330 of CelA are corresponding performance sensitive positions. Guided by this disclosure, one of skill will predict that the corresponding position in other β-glucosidase are also performance sensitive positions and that substitution of a residue at a corresponding position in other β-glucosidase polypeptide will result in a β-glucosidase variant with increased thermoactivity.

Having identified a performance sensitive position in a β-glucosidase polypeptide one of skill can determine which substitutions (i.e., which of the 19 amino acids not found in, e.g., the naturally occurring form) are associated with increased thermoactivity using routine methods. Briefly, a DNA primers are synthesized encoding each of the alternative codons of interest, and are hybridized with a single-stranded DNA encoding the β-glucosidase polypeptide and sequences required for expression of the coding sequence (i.e., expression vector sequences). The single stranded fragment is extended using DNA polymerase, which copies the rest of the gene. The resulting double stranded molecule polynucleotide is introduced into a host cell and cloned. Finally, mutants are selected for desired property(s).

Thus, the invention provides variant β-glucosidase proteins that are thermoactive and which comprise substitutions relative to a naturally occurring β-glucosidase protein at one or more performance sensitive positions. The invention also provides methods for increasing thermoactivity of a β-glucosidase polypeptide by identifying a performance sensitive position in said β-glucosidase polypeptide and replacing the residue with a thermoactivity enhancing residue. These and other aspects of the invention are described in additional detail below.

B. β-Glucosidase

As used herein, "β-glucosidase" refers to glycoside hydrolase family 3 ("GH3") β-glucosidases" classified as E.C. 3.2.1.21. The term "β-glucosidase variant" is used for convenience to refer to enzymes that have amino acid substitutions relative to naturally occurring forms, but it will be recognized that the term "β-glucosidase" encompasses both natural enzymes and recombinant variants. As noted above, β-glucosidases catalyze the hydrolysis of cellobiose to glucose. β-glucosidase activity can be measured in a variety of assays, including the para-nitrophenyl-β-D-glucopyranoside (pNPG) and cellobiose assays described hereinbelow.

GH3 β-glucosidases are characterized by β-glucosidase activity and the presence of two GH3 domains, the "GH3 domain" and the "GH3-C domain." Hidden Markov Model (HMM) consensus sequences for the two domains are shown below.

TABLE 2

GH3 Domain Consensus Sequence (SEQ ID NO: 53):
AEKPRLGIPLLVVVDAEHGVRQRDKEEATAFPSALALAATWDKELIKE

VGKAIGEELRAKGIDVLLAPVVDLKRSPRWGRNFESFSEDPYLVGALA

AATIKGLQSAGVAATAKHFAGNGQETARSKETVSAEIDERALREIYLLPF

EAAVKEAGVGSVMCSYNKVNGLPATENSKLLTKLLREELGFQGFVVSD

WLAVKSGVASDAANESEAAAAALKAGLDIEMP

TABLE 3

GH3-C Domain Consensus Sequence (SEQ ID NO: 54):
IVLLKNEGNLLPLKKKKKKIAVIGPNADGTVKSGGGSGAVNPSYLVSP

LEGIRKRLSKAKVVVEEGSEDDEEIAEAVAAAKKADVAVVVVGEWEG

EGESEEGDRTDLALPENQDELIEAVAAANKPVVVVLHSGGPVDMEP

WAEKVKAILAAWYPGQEGGNAIADVLFGDVNPSGKLPVTFPKSLEDL

PAYYRYKSEDPLYPFGEGLSVGY

Those of skill in the art will recognize that EC 3.2.1.21 β-glucosidases may have one or both of the GH3 Domains. Common domain architectures include "GH3-GH3C", "GH3", "GH3C-GH3", GH3-GH3_C-CARDB, CBM_1-

GH3-GH3_C and others. In one embodiment, "β-glucosidase" of the present invention have the domain structure "GH3-GH3C." Table 4, below, lists 49 proteins (in addition to C1BGL1, TaBGL and CelA) identified as GH3-GH3C β-glucosidases using "PFAM v.24", developed by the Wellcome Trust Sanger Institute, which is available at the web address "pfam.sanger.ac.uk/about".

Structurally related GH3 β-xylosidases ("BXLs"), classified as E.C. 3.2.1.37, also have GH3 domains, including the GH3-GH3C domain structure. See Table 13 below. BXLs share many features of GH3 BGLs, as explained in Section II(I), below. In some aspects the invention provides methods and compositions related to variant BXLs.

Naturally occurring β-glucosidases and recombinant β-glucosidase variants may be grouped based on sequence similarity to the consensus sequences. (See Table 4.) For example, GH3 β-glucosidases may have a GH3 domain with at least 26% identity, at least 30% identity, at least 32% identity, or at least 45% identity to the GH3 domain consensus sequence. Similarly, GH3 β-glucosidases may have a GH3-C domain with at least 19% identity, at least 26% identity, at least 34% identity, or at least 39% identity to the GH3-C domain consensus sequence. In one embodiment the β-glucosidase has at least 26% identity to the GH3 consensus sequence and at least 19% identity to the GH3-C consensus sequence. In another embodiment the β-glucosidase has at least 32% identity to the GH3 consensus and at least 34% identity to the GH3-C consensus.

Table 4, below, shows the sequence identity of the domain consensus sequences and the corresponding domains in 52 β-glucosidase polypeptides listed in Table 5 and aligned in Table 14. Alignments were carried out using AlignX®, supra. Table 4 provides GenBank Accession numbers.

TABLE 4

| Gene | GH3-PFAM | GH3C-PFAM |
|---|---|---|
| CBGL1 | 49% | 39% |
| TABGL | 50% | 39% |
| CelA | 32% | 34% |
| ABP88968.1 | 46% | 35% |
| AAL69548.3 | 48% | 39% |
| ACD86466.1 | 45% | 35% |
| ABU35789.1 | 47% | 38% |

TABLE 4-continued

| Gene | GH3-PFAM | GH3C-PFAM |
|---|---|---|
| BAA19913.1 | 46% | 41% |
| BAA10968.1 | 47% | 44% |
| CAD67686.1 | 47% | 39% |
| AAF21242.1 | 47% | 42% |
| ACV87737.1 | 45% | 36% |
| ABX84365.1 | 43% | 44% |
| CAB82861.1 | 44% | 41% |
| AAA91297.1 | 45% | 29% |
| BAE58551.1 | 44% | 26% |
| EAL91070.1 | 43% | 29% |
| AAB08445.1 | 47% | 38% |
| CAA07070.1 | 35% | 37% |
| BAA33065.1 | 30% | 38% |
| AAL21070.1 | 33% | 44% |
| AAA60495.1 | 33% | 43% |
| AAB66561.1 | 36% | 39% |
| AAZ32298.1 | 38% | 40% |
| CAA91219.1 | 41% | 51% |
| CAB56688.1 | 39% | 38% |
| AAA74233.1 | 31% | 34% |
| AAA80156.1 | 29% | 21% |
| AAF21799.1 | 27% | 23% |
| EAA64969.1 | 29% | 24% |
| ABU68675.1 | 27% | 19% |
| BAA36161.1 | 28% | 19% |
| AAX35883.1 | 26% | 19% |
| ABI29899.1 | 48% | 35% |
| CAB01407.1 | 48% | 36% |
| AAD35119.1 | 49% | 37% |
| CAC07184.1 | 44% | 34% |
| ABE60716.1 | 41% | 35% |
| AAC05445.1 | 49% | 39% |
| CAA33665.1 | 49% | 37% |
| AAM93475.1 | 38% | 38% |
| AAC38196.1 | 41% | 39% |
| AAQ38005.1 | 41% | 43% |
| AAF21798.1 | 44% | 42% |
| AAA34314.1 | 50% | 39% |
| AAA34315.1 | 48% | 38% |
| CAA26662.1 | 44% | 36% |
| CAP58431.2 | 37% | 43% |
| CAE01320.1 | 39% | 41% |
| AAB67972.1 | 46% | 30% |
| BAE57053.1 | 46% | 40% |
| AAA18473.1 | 42% | 41% |

Table 5 corresponds organism names with the GenBank Accession numbers (preceded by the NCBI GI numbers) shown in Table 4 and Table 14.

TABLE 5

| Organism | Accession Number | Length | SEQ ID NO: |
|---|---|---|---|
| *Clostridium thermocellum* DSM 1237** | CAA33665.1 | 754 | 4 |
| *Thermoanaerobacter brockii*** | CAA91219.1 | 730 | 5 |
| *Thermotoga maritima* MSB8** | AAD35119.1 | 721 | 6 |
| *Thermotoga neapolitana* DSM 4359** | ABI29899.1 | 721 | 7 |
| *Thermotoga neapolitana* Z2706-MC24** | CAB01407.1 | 720 | 8 |
| *Talaromyces emersonii*** | AAL69548.3 | 857 | 9 |
| *Wickerhamomyces anomalus* var. *acetaetherius*** | CAA26662.1 | 825 | 10 |
| *Azospirillum irakense* KBC1 | AAF21799.1 | 649 | 11 |
| *Azospirillum irakense* KBC1 | AAF21798.1 | 732 | 12 |
| *Cellulomonas biazotea* | AAC38196.1 | 828 | 13 |
| *Elizabethkingia meningoseptica* | AAB66561.1 | 726 | 14 |
| *Erwinia chrysanthemi* D1 | AAA80156.1 | 654 | 15 |
| *Escherichia coli* K-12 MG1655 | AAA60495.1 | 789 | 16 |
| *Gluconacetobacter xylinus* BPR2001 | AAQ38005.1 | 735 | 17 |
| *Paenibacillus* sp. C7 | AAX35883.1 | 756 | 18 |
| *Prevotella albensis* M384 | CAC07184.1 | 781 | 19 |
| *Rhizobium leguminosarum* bv. *Trifolii* | AAM93475.1 | 689 | 20 |
| *Ruminococcus albus* 7 | AAC05445.1 | 772 | 21 |
| *Salmonella typhimurium* LT2 SGSC 1412; ATCC 700720 | AAL21070.1 | 765 | 22 |
| uncultured bacterium | AAZ32298.1 | 745 | 23 |
| uncultured bacterium | ABE60716.1 | 793 | 24 |

TABLE 5-continued

| Organism | Accession Number | Length | SEQ ID NO: |
|---|---|---|---|
| Aspergillus aculeatus F-50 | BAA10968.1 | 860 | 25 |
| Aspergillus fumigatus Af293 | EAL91070.1 | 769 | 26 |
| Aspergillus fumigatus Af293 | ABU35789.1 | 863 | 27 |
| Aspergillus kawachii IFO4308 | BAA19913.1 | 860 | 28 |
| Aspergillus nidulans FGSC A4 | EAA64969.1 | 618 | 29 |
| Aspergillus oryzae | CAD67686.1 | 861 | 30 |
| Aspergillus oryzae RIB40 | BAE57053.1 | 866 | 31 |
| Aspergillus oryzae RIB40 | BAE58551.1 | 856 | 32 |
| Coccidioides posadasii | AAB67972.1 | 870 | 33 |
| Coccidioides posadasii | AAF21242.1 | 858 | 34 |
| Dictyostelium discoideum AX3 | AAA74233.1 | 820 | 35 |
| Hypocrea jecorina QM9414 | AAA18473.1 | 744 | 36 |
| Kuraishia capsulata 35M5N | AAA91297.1 | 763 | 37 |
| Nicotiana tabacum | BAA33065.1 | 628 | 38 |
| Penicillium brasilianum IBT 20888 | ABP88968.1 | 878 | 39 |
| Penicillium decumbens JU-A10 | ACD86466.1 | 861 | 40 |
| Penicillium purpurogenum KJS506 (KACC 93053P) | ACV87737.1 | 856 | 41 |
| Periconia sp. BCC 2871 | ABX84365.1 | 866 | 42 |
| Phaeosphaeria avenaria WAC1293 | CAB82861.1 | 871 | 43 |
| Rhizomucor miehei NRRL 5282 | CAP58431.2 | 717 | 44 |
| Saccharomycopsis fibuligera | AAA34314.1 | 876 | 45 |
| Saccharomycopsis fibuligera | AAA34315.1 | 880 | 46 |
| Septoria lycopersici | AAB08445.1 | 803 | 47 |
| Tropaeolum majus | CAA07070.1 | 654 | 48 |
| Uromyces viciae-fabae | CAE01320.1 | 843 | 49 |
| uncultured microorganism | ABU68675.1 | 740 | 50 |
| Bacillus sp. GL1 | BAA36161.1 | 756 | 51 |
| Streptomyces coelicolor A3(2) | CAB56688.1 | 762 | 52 |

**Thermophiles

Other β-glucosidase polypeptides are known and/will be recognized by those of skill in the art. Identification of β-glucosidase polypeptides containing the GH3-GH3-C domain architecture is facilitated by using "PFAM v.24", described supra.

C. Performance Sensitive Positions in β-Glucosidase Variants

Described herein are β-glucosidase variants useful for production of soluble sugars from a cellulosic substrate (e.g., cellobiose). Preferred variants have desirable properties such as improved thermoactivity relative to naturally occurring forms.

As discussed above, β-glucosidase variants with improved thermoactivity relative to the naturally occurring (wild-type) enzymes C1 β-glucosidase 1 ("C1BGL1"; SEQ ID NO:1), *Thermoascus aurantiacus* β-glucosidase ("TaBGL"; SEQ ID NO:2) and *Azospirillum irakense* ("CelA"; SEQ ID NO:3) β-glucosidase were generated and studied and performance sensitive residues (PSRs) identified. Tables 6-9 show selected PSRs found in each of the organisms. Both the native residue and the residue(s) in thermoactive variants are shown. For example, T338ALP in Table 6 shows that at position 338 of C1BGL1 the naturally occurring residue is threonine (T) and a variant in which substitutions were made including alanine (A), leucine (L) and prolene (P) at position 338 had enhanced thermoactivity. Importantly, positions in each row correspond to each other. For example, Row 1 of Table 6 shows that position 338 of C1BGL1, position 372 of CelA and position 330 of TaBGL are corresponding positions (and are corresponding performance sensitive positions). This is illustrated in the alignment of 52 sequences in Table 14. The alignment of PSPs is consistent (except where noted) in alignments of the 52 β-glucosidase sequences, in alignments of the three experimentally tested enzymes alone, and in alignments of ten enzymes of which three were the experimentally tested enzymes and seven were thermophilic β-glucosidase proteins). Column 1 of each of Tables 6-9 provides the corresponding position in C1BGL1, which may be used as a reference numbering system.

TABLE 6

Performance Sensitive Positions Corresponding in C1Bgl, TaBGL and CelA BGL

| Corresponding position in C1BGL1 | Beneficial mutations in C1BGL1 | Beneficial mutations in CelA | Beneficial Mutations in TaBGL |
|---|---|---|---|
| 338 | T338ALP | E372D | R330K |
| 339 | D339EKN | K373R | Y331C |

TABLE 7

Performance Sensitive Positions Corresponding in C1 BGL1 and CelA BGL

| Corresponding position in C1BGL1 | C1 BGL1 | CelA BGL |
|---|---|---|
| 104 | A104N | A138IMQT |
| 116 | Y116IMQ | E150ADKMPQWS |
| 122 | A122F | M156TV |
| 123 | K123R | A157STV |
| 130 | L130QM | T164N |
| 160 | I160M | A193CDELMNQSTW |
| 163 | S163LW | A196GPS |
| 164 | E164GMQK | A197FKNPSTY |
| 210 | I210M | I241CV |
| 484 | A484E | K486R |
| 572 | T572ACR | A568SV |
| 60* | A60EGM | T55HY |

TABLE 7-continued

Performance Sensitive Positions
Corresponding in C1 BGL1 and CelA BGL

| Corresponding position in C1BGL1 | C1 BGL1 | CelA BGL |
|---|---|---|
| 87** | I87V | I109TV |
| 521*** | T521K | A520STKMG |

*Positions 55 and 60 corresponded in alignments of 52 sequences and 3 sequences.
**Positions 87 and 109 corresponded in alignments of 52 sequences and 10 sequences.
***Positions 521 and 520 corresponded in alignments of 3 sequences and 10 sequences.

TABLE 8

Performance Sensitive Positions Corresponding in C1Bgl and TaBGL

| Corresponding position in C1BGL1 | Beneficial mutations in CBGL1 | Beneficial Mutations in TaBGL |
|---|---|---|
| 295 | F295LV | F287Y |
| 299 | V299E | K291EI |
| 350 | D350ACEFHIKLMPQRVY | K342R |
| 415 | S415P | S408N |
| 463 | T463A | K456R |
| 485 | N485Y | A478V |

TABLE 9

Performance Sensitive Positions
Corresponding in TaBGL and CelA BGL

| Corresponding position in C1BGL1 | CelA | TaBGL |
|---|---|---|
| 108 | P142GIKLRTW | K100R |
| 157 | I190L | L149V |
| 211 | S242P | D203G |
| 649* | K624CR | Y641N |

*Positions 624 and 641 corresponded in alignments of 52 sequences and 7 sequences.

Notably, several of the performance sensitive positions are at positions that are conserved in naturally occurring BGL proteins. Table 10 shows 6 performance sensitive positions in which greater than 40% of the proteins listed in Table 5 share a common residue (referred to herein as a "conserved consensus residue").

TABLE 10

Performance Sensitive Positions Corresponding
in C1Bgl, TaBGL and CelA BGL

| Performance Sensitive Position (numbered according to C1BGL1) | Beneficial mutations in C1BGL1 | Beneficial mutations in CelA | Beneficial Mutations in TaBGL | Most common residue (>40%) |
|---|---|---|---|---|
| 104 | A104N | A138MIQT | | A |
| 157 | | I190L | L149V | L |
| 210 | I210M | I241CV | | I |
| 211 | | S242P | D203G | D |
| 485 | N485Y | | A478V | A |
| 572 | T572ACR | A568SV | | A |
| 649 | | K624C | Y641N | Y |

The data suggest that substitutions at these sites are less common in nature and more common in thermoactive variants. In certain embodiments β-glucosidase variants of the invention do not have a conserved consensus residue at any of these six sites. That is, the residue at a position corresponding to position 104 is not alanine, the residue at a position corresponding to position 157 is not leucine, the residue at a position corresponding to position 210 is not isoleucine, the residue at a position corresponding to position 211 is not aspartate, the residue at a position corresponding to position 485 is not alanine, the residue at a position corresponding to position 572 is not alanine, and the residue at a position corresponding to position 649 is not tyrosine. In certain embodiments β-glucosidase variants of the invention do not have a conserved consensus residue at more than six of these seven sites. In certain embodiments β-glucosidase variants of the invention do not have a conserved consensus residue at more than five of these seven sites. In certain embodiments β-glucosidase variants of the invention do not have a conserved consensus residue at more than four of these seven sites, with the proviso that the variants do not have the sequence of BGLs AAF21799.1 or CAA07070.1.

Column 2 of Table 11 shows, for several performance sensitive positions, the most common residues in the group of BGLs listed in Table 5. Column 4 of Table 11 shows the residue found in the domain consensus sequence (SEQ ID NOs:53 and 54) at several corresponding positions. It is expected that the frequently occurring and consensus residues at these performance sensitive positions will be under-represented in β-glucosidase variants with improved thermoactivity. Therefore, in certain embodiments the thermoactive β-glucosidase variants of the invention do not include these residues at PSPs.

TABLE 11

| 1 Performance Sensitive Position (numbered according to C1BGL1, SEQ ID NO: 1) | 2 Frequency Consensus Residue | 3 Domain | 4 Domain consensus residue | 5 Performance Sensitive Position (numbered according to domain, SEQ ID NOs: 53 and 54) |
|---|---|---|---|---|
| 104 | A | GH3 | A | 39 |
| 108 | R | GH3 | K | 43 |
| 116 | Q | GH3 | K | 51 |
| 122 | F | GH3 | L | 57 |
| 123 | R | GH3 | R | 58 |
| 130 | A, L | GH3 | A | 65 |
| 157 | L | GH3 | L | 91 |
| 160 | V, I | GH3 | A | 94 |
| 163 | A | GH3 | A | 97 |
| 164 | A, E | GH3 | A | 98 |
| 210 | I | GH3 | I | 133 |
| 211 | D | GH3 | D | 134 |
| 295 | F | GH3 | A | 219 |
| 299 | T | GH3 | I | 223 |
| 338 | E | linker | | |
| 339 | N | linker | | |
| 350 | R | linker | | |
| 415 | S | GH3-C | | |
| 463 | G | GH3-C | V | 61 |
| 484 | Q | GH3-C | K | 82 |
| 485 | A | GH3-C | A | 83 |
| 521 | T | GH3-C | T | 115 |
| 572 | A | GH3-C | I | 164 |
| 631 | S | | | |
| 633 | T | | | |
| 649 | Y | | | |

Guided by this disclosure, one of skill can rapidly and efficiently design and produce β-glucosidase variants with enhanced thermoactivity. Thus, in one aspect, the invention provides a method of increasing thermoactivity of a β-glucosidase polypeptide by a) identifying a performance sensitive position in the β-glucosidase polypeptide and b) replacing the residue at said position with a thermoactivity enhancing residue. In one approach, a variant β-glucosidase polypeptide with improved thermoactivity can be produced by identifying a performance sensitive position in a target β-glucosidase polypeptide and expressing a variant β-glucosidase polypeptide in which the residue at the performance sensitive position is replaced with a thermoactivity enhancing residue, where the variant β-glucosidase polypeptide has greater thermoactivity than the target β-glucosidase polypeptide. The target β-glucosidase polypeptide may have the sequence of a naturally occurring β-glucosidase (including, for example, SEQ ID NOs:4-52 and homologs thereof). Alternatively, the target polypeptide may be a non-naturally occurring protein that has been modified to improve desirable characteristics (e.g., thermoactivity).

D. Identifying Performance Sensitive Positions

Performance sensitive positions in a β-glucosidase polypeptide can be identified by reference to positions of PSPs in the C1 BGL1 sequence (i.e., positions 104; 108; 116; 122; 123; 130; 157; 160; 163; 164; 210; 211; 295; 299; 338; 339; 350; 415; 463; 484; 485; 521; 572; 60, 87 or 649 of C1). In one approach the target β-glucosidase polypeptide sequence is aligned with the C1 BGL1 sequence, and residues in the target that correspond in the alignment to the positions in C1 are identified.

Alternatively, the target β-glucosidase polypeptide sequence may be aligned with the TaBGL sequence or CelA sequence, in which PSPs have been identified that correspond to the C1 residues listed above (see Tables 6-9, supra). By way of illustration, the same three PSPs can be identified in a target β-glucosidase polypeptide sequence by aligning the β-glucosidase polypeptide with C1 BGL1 and selecting positions corresponding to C1 338 and 339, aligning the β-glucosidase polypeptide with CelA and selecting positions corresponding to CelA 242, 372 and 373, or aligning the β-glucosidase polypeptide with TaBGL and selecting positions corresponding to TaBGL 203, 330 and 331. It will be apparent that PSPs in a target β-glucosidase polypeptide sequence can be identified by alignment of the target β-glucosidase polypeptide sequence with any BGL sequence or consensus sequence in which the PSPs that correspond to one or more of the C1BGL1, TaBGL or CelA PSPs are known.

In various embodiments the PSPs in a target β-glucosidase polypeptide can be identified by reference to positions corresponding to positions 338, and 339 of the C1 BGL1, positions 104, 116, 122, 123, 130, 160, 163, 164, 210, 484, 521, and 572 of the C1 BGL1, positions 295, 299, 350, 415, 463, and 485 of the C1 BGL1, positions 108, 221 and 157 of the C1 BGL1, positions 60, 87 and 649 of the C1 BGL1, and combinations of these positions.

Alignments may be pairwise alignments between the target β-glucosidase polypeptide sequence and a reference β-glucosidase polypeptide sequence in which PSPs corresponding to the C1 BGL1 PSPs are identified (e.g., between the β-glucosidase polypeptide sequence and the C1 BGL1 sequence). Alternatively, multisequence alignments of a plurality of BGLs (e.g., 2-52 BLGs) is used. See Table 14. In one embodiment the plurality of BGLs are BGLs from filamentous fungi. In one embodiment the plurality of BGLs comprise BGLs from thermophilic fungi.

In one embodiment the target β-glucosidase polypeptide sequence is a naturally occurring β-glucosidase polypeptide. For example, the β-glucosidase polypeptide sequence may be from a naturally occurring BGL listed in Table 5.

In one approach, for example, a first performance sensitive position in a naturally occurring target β-glucosidase polypeptide is identified and the residue at that position is replaced with a first thermoactivity enhancing residue, thereby producing a variant β-glucosidase protein, and then a second performance sensitive position in the variant β-glucosidase protein is identified and the residue at the second position is replaced with a second thermoactivity enhancing residue. In this approach, thermoactivity enhancing residues are introduced into a protein backbone sequentially. It will be understood, however, that multiple thermoactivity enhancing residues can be introduced concurrently. Thus, in one embodiment the method involves identifying two or more PSPs in the target β-glucosidase protein, and then replacing two or more of the identified PSPs with thermoactivity enhancing residues.

In one approach the target β-glucosidase protein may have at least 80% sequence identity (or in some cases at least 70%, at least 85%, at least 90%, at least 95% or at least 99% sequence identity) to a naturally occurring protein listed in Table 5. Sequence identity can be determined by carrying out multiple sequence alignments with AlignX®, supra, counting the number of identical matches in the alignment and dividing such number of identical matches by the length of the reference sequence.

In one approach, the target β-glucosidase has a GH3 domain with at least 26% identity, at least 30% identity, at least 32% identity, or at least 45% identity to the GH3 domain consensus sequence (SEQ ID NO: Similarly, GH3 β-glucosidases may have a GH3-C domain with at least 19% identity, at least 26% identity, at least 34% identity, or at least 39% identity to the GH3-C domain consensus sequence. In one embodiment the β-glucosidase has at least 26% identity to the GH3 consensus sequence and at least 19% identity to the GH3-C consensus sequence. In another embodiment the β-glucosidase has at least 32% identity to the GH3 consensus and at least 34% identity to the GH3-C consensus.

In some embodiments the target β-glucosidase protein may be a naturally occurring β-glucosidase protein from a yeast species, or a filamentous fungal cell. In some embodiments the filamentous fungal cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*. In some embodiments of the invention, the filamentous fungal cell is of the *Trichoderma* species, e.g., *T. longibrachiatum, T. viride* (e.g., ATCC 32098 and 32086), *Hypocrea jecorina* or *T. reesei, T. koningii*, and *T. harzianum*. In some embodiments of the invention, the filamentous fungal cell is of the *Aspergillus* species, e.g., *A. awamori, A. funigatus, A. japonicus, A. nidulans, A. niger, A. aculeatus, A. foetidus, A. oryzae, A. sojae*, and *A. kawachi*. In some embodiments of the invention, the filamentous fungal cell is of the *Fusarium* species, e.g., *F. bactridioides, F. cerealis, F. crookwellense, F. culmorum, F. graminearum, F. graminum. F. oxysporum, F. roseum*, and *F. venenatum*. In some embodiments of the invention, the filamentous fungal cell is of the *Myceliophthora* species, e.g., *M. thermophilia*. In some embodiments of the invention, the filamentous fungal cell is of the *Neurospora* species, e.g., *N. crassa*. In some embodiments of the invention, the filamentous fungal cell is of the *Humicola* species, e.g., *H. insolens, H. grisea*, and *H. lanuginosa*. In some embodiments of the invention, the filamentous fungal cell is of the *Mucor* species, e.g., *M. miehei* and *M. circinelloides*. In some embodiments of the invention, the filamentous fungal cell is of the *Rhizopus* species, e.g., *R. oryzae* and *R. niveus*. In some embodiments of the invention, the filamentous fungal cell is of the *Penicillum* species, e.g., *P. purpurogenum, P. chrysogenum*, and *P. verruculosum*. In some embodiments of the invention, the filamentous fungal cell is of the *Thielavia* species, e.g., *T. terrestris*. In some embodiments of the invention, the filamentous fungal cell is of the *Tolypocladium* species, e.g., *T. inflatum* and *T. geodes*. In some embodiments of the invention, the filamentous fungal cell is of the *Trametes* species, e.g., *T. villosa* and *T. versicolor*. In some embodiments of the invention, the filamentous fungal cell is of the *Chrysosporium* species, e.g., *C. lucknowense, C. keratinophilum, C. tropicum, C. merdarium, C. inops, C. pannicola*, and *C. zonatum*. In the present invention a yeast cell may be a cell of a species of, but not limited to *Candida, Hansenula, Saccharomyces, Schizosaccharomyces, Pichia, Kluyveromyces*, and *Yarrowia*. In some embodiments of the invention, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pornbe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, and *Yarrowia lipolytica*.

In some embodiments the target β-glucosidase protein may be a naturally occurring β-glucosidase protein from *Aspergillus, Azospirillum, Bacillus, Cellulomonas, Clostridium, Thermoanaerobacter, Coccidioides, Dictyostelium, Elizabethkingia, Erwinia, Escherichia, Gluconacetobacter, Hypocrea, Kuraishia, Nicotiana, Paenibacillus, Penicillium, Periconia, Phaeosphaeria, Prevotella, Rhizobium, Rhizomucor, Ruminococcus, Saccharomycopsis, Salmonella, Septoria, Streptomyces, Talaromyces, Thermotoga, Tropaeolum, Uromyces*, or *Wickerhamomyces* species. As noted above, in some embodiments the target may have at least 80% sequence identity (or in some cases at least 70%, at least 85%, at least 90%, at least 95% or at least 99% sequence identity) to a naturally occurring protein listed in Table 5 and shown in Table 14.

In some embodiments the target β-glucosidase protein may be a naturally occurring β-glucosidase protein from *Aspergillus aculeatus, Azospirillum irakense* KBC1, *Bacillus* sp. GL1, *Cellulomonas biazotea, Clostridium thermocellum, Thermoanaerobacter brockii, Coccidioides posadasii, Dictyostelium discoideum, Elizabethkingia meningoseptica, Erwinia chrysanthemi, Escherichia coli, Gluconacetobacter xylinus, Hypocrea jecorina, Kuraishia capsulata, Nicotiana tabacum, Paenibacillus* sp. C7, *Penicillium brasilianum, Periconia* sp. BCC 2871, *Phaeosphaeria avenaria, Prevotella albensis, Rhizobium leguminosarum, Rhizomucor miehei, Ruminococcus albus, Saccharomycopsis fibuligera, Salmonella typhimurium, Septoria lycopersici, Streptomyces coelicolor, Talaromyces emersonii, Thermotoga maritima, Tropaeolum majus, Uromyces viciae-fabae*, or *Wickerhamomyces anomalus*. As noted above, in some embodiments the target may have at least 80% sequence identity (or in some cases at least 70%, at least 85%, at least 90%, at least 95% or at least 99% sequence identity) to a naturally occurring protein listed in Table 5 and shown in Table 14.

In some embodiments the target β-glucosidase protein may be a naturally occurring β-glucosidase protein from a thermophilic fungus (see, e.g., Table 5).

E. Thermoactivity Enhancing Residues

Guided by the disclosure herein identifying performance sensitive positions in β-glucosidase proteins, thermoactivity enhancing residues may be identified using known mutation and screening methods.

By way of illustration, consider the hypothetical case in which residue 310 (tyrosine) of a target β-glucosidase protein ("BGL T") is identified as corresponding to C1 BLG1 performance sensitive position 338 (see Table 6). It is expected that a substitution at Y310 will result in enhanced thermoactivity. To determine which substitutions enhance thermoactivity and to what degree, 19 BGL T variants are made each containing a different non-tyrosine residue at position 310 (see Table 17 for a list of the 20 naturally occurring amino acids). The Y310 BGL T protein and 19 variants are then expressed and thermoactivity determined under appropriate conditions. Those variants with improved thermoactivity may be used for further modification or in saccharification applications or other processes in β-glucosidases are used. In some embodiments, fewer than 19 variants are tested.

Methods for introducing specific substitutions into a protein are well known. Briefly, one or more codons in a nucleic acid encoding a protein are changed by in vitro mutagenesis and the resulting variant protein is expressed. Methods for site-directed mutagenesis are well known, including oligonucleotide mismatch mutagenesis, See Mutagenesis and directed evolution methods are well known in the art. See, e.g., Ling, et al., 1999, "Approaches to DNA mutagenesis: an overview," *Anal. Biochem.*, 254(2):157-78; Dale, et al., 1996, "Oligonucleotide-directed random mutagenesis using the phosphorothioate method," *Methods Mol. Biol.*, 57:369-74; Smith, 1985, "In vitro mutagenesis," *Ann. Rev. Genet.*, 19:423-462; Botstein, et al., 1985, "Strategies and applications of in vitro mutagenesis," *Science*, 229:1193-1201; Carter, 1986, "Site-directed mutagenesis," *Biochem. J.*, 237: 1-7; Kramer, et al., 1984, "Point Mismatch Repair," *Cell*, 38:879-887; Wells, et al., 1985, "Cassette mutagenesis: an efficient method for generation of multiple mutations at defined sites," *Gene*, 34:315-323; Minshull, et al., 1999, "Protein evolution by molecular breeding," *Current Opinion in Chemical Biology*, 3:284-290. In certain preferred embodiments the methods disclosed in U.S. patent application Ser. No. 12/562,988 "Combined Automated Parallel Synthesis of Polynucleotide Variants", filed Sep. 18, 2009, incorporated herein in its entirety for all purposes, may be used

F. β-Glucosidase Thermostability and Activity ("Thermoactivity") Assays

1. β-Glucosidase Activity Assays

The term "improved activity" as used herein means a variant β-glucosidase protein displays an increase in "activity" relative to a reference protein (e.g., a wild-type β-glucosidase protein). β-glucosidase activity can be determined using methods known in the art, such as, for example, para-nitrophenyl-β-D-glucopyranoside (pNPG) assays or using a cellobiose assays.

For example, a colorimetric pNPG (p-nitrophenyl-β-D-glucopyranoside)-based assay may be used to measure β-glucosidase activity. One such assay is described in Example 3, infra. In another exemplary pNPG assay, in a total volume of 100 μL, 20 μL clear media supernatant containing β-glucosidase enzyme is added to 4 mM pNPG (Sigma-Aldrich, Inc. St. Louis, Mo.) solution in 50 mM sodium phosphate buffer at pH 5. The reactions are incubated at pH 5, 50° C. for 1.5 hours. The reaction mixture is quenched with 100 µL of 1M sodium carbonate pH 11 solution. The absorbance of the solution is measured at 405 nm to determine the conversion of pNPG to p-nitrophenol. The release of p-nitrophenol ($\epsilon$=17, 700 M-1 cm-1) is measured at 405 nm to calculate β-glucosidase activity. Detectable β-glucosidase activity is observed under high throughput screening conditions (pH 7, 50° C.). See Breves et al., 1997, *Appl. Environmental Microbiol.* 63:3902, incorporated herein by reference.

Alternatively, β-glucosidase activity may be determined using an assay in which cellobiose is the substrate. In one suitable assay 25 µL clear media supernatant containing β-glucosidase enzyme is added to 10 g/L cellobiose (Fluka Cat. No. 22150, Sigma-Aldrich, Inc., St. Louis, Mo.) in 100 mM sodium phosphate buffer (pH 6-7) or sodium acetate buffer (pH 5-5.5) in a total volume of 100 µL. The reaction is incubated at 45-70° C. for an appropriate time (25 minutes to overnight depending on the enzyme concentration) while shaking. Glucose production is determined using an enzymatic glucose assay (K-GLUC, Megazyme, Ireland). 10 µl of each reaction is added to 190 µl GOPOD reagent (supplied as part of the K-GLUC assay kit). The reaction is incubated at 45° C. for 20 minutes and the absorbance of the solution was measured at 510 nm. The GOPOD reagent contains 50 mM Potassium phosphate buffer pH 7.4, 0.011 M p-hydroxybenzoic acid, 0.008% w/v sodium azide, glucose oxidase (>12,000U/L), peroxidase (>650 U/L) and 80 mg/L 4-aminoantipyrine. The glucose oxidase enzyme in the reagent reacts with any glucose present in the sample and produces hydrogen peroxide which then reacts with the 4-aminoantipyrine to produce a quinoneimine dye in quantities proportionate with the amount of glucose present and can be measured spectrophotometrically at 510 nm.

Temperature, pH and other conditions for determining β-glucosidase activity will vary according to the particular β-glucosidase protein and the interests of the investigator. For commercial purposes, it is often desirable that the variant have improved stability or activity under low pH conditions (e.g., pH<6 or pH<5). Typically assays are conducted at pH in the range of 4-5 and temperatures of 65° C. to 80° C. Exemplary assay conditions are pH 4.5 and 65° C., pH 4.5 and 70° C., pH 4.5 and 75° C., pH 4.5 and 80° C., pH 4.0 and 65° C., and pH 5 and 75° C. for 1 hour to 25 hours.

2. Thermostability Assays

The term "improved thermostability" as used herein means a variant β-glucosidase protein displays an increase in "residual activity" relative to a reference protein (e.g., a wild-type β-glucosidase protein). Thus, in the hypothetical above a variant in which residue 310 is leucine, for example, has improved thermostability if it has greater residual activity than the Y310 BGL T form. Residual activity is determined by exposing the enzyme (variant or reference) to stress conditions of elevated temperature for a period of time and then determining β-glucosidase activity. The β-glucosidase activity of the enzyme exposed to stress conditions ("a") is compared to that of a control in which the enzyme is not exposed to the stress conditions ("b"), and residual activity is equal to the ratio a/b.

Stress conditions may vary according to the particular β-glucosidase protein and the interests of the investigator. Exemplary stress conditions, for illustration and not limitation, are a pH in the range of 4-6, temperatures of 50° C. to 80° C., and incubation times of 2-72 hours (e.g., about 2, about 3, about 4, about 5, about 6, about 10, about 15, about 20, about 24, about 48 or about 72 hrs). Exemplary assay conditions are pH 4.5 and 65° C., pH 4.5 and 70° C., pH 4.5 and 75° C., pH 4.5 and 80° C., pH 4.0 and 65° C., and pH 5 and 75° C. for 1, 2, 3, 4, 5, 6, 10, 15, 20, 24, 48 or 72 h.

G. β-Glucosidase Variants with Improved Thermoactivity

In one aspect the invention provides recombinant β-glucosidase variants, which may be produced using the methods described above.

In one embodiment, the invention provides a recombinant or non-naturally occurring β-glucosidase protein variant that has a sequence with at least 80% sequence identity to a naturally occurring β-glucosidase protein and which has amino acid substitutions, relative to the naturally occurring protein, at one or more performance sensitive positions (PSPs). For example, the variant may have substitutions at at least 1, at least 2, at least 3, at least 4, at least 5, at least 6, at least 7, at least 8, at least 9, or at least 10, at least 12 or at least 15 PSPs. The performance sensitive positions correspond to PSPs 60, 87, 104, 116, 122, 123, 130, 160, 163, 164, 210, 463, 484, 521, 572, 211, 338, 339, 295, 299, 350, 415, 463, 485, 108, 157, and 649 in SEQ ID NO:1. In specific embodiments, the variant has substitutions in at least one PSP that corresponds to a PSP in SEQ ID NO:1 within one of the following groups:

a) 338, and 339;
b) 104, 116, 122, 123, 130, 160, 163, 164, 210, 484, 521, and 572;
c) 295, 299, 350, 415, 463, 485;
d) 108, 221 and 157;
e) 60, 87, 521, and 649.

In certain embodiments the variant has substitutions at two or more PSPs within a group (e.g., at least 2, at least 3, at least 4, at least 5, at least 6, at least 7, at least 8, at least 9, or at least 10 PSPs).

In certain embodiments the naturally occurring occurring β-glucosidase protein has a sequence of one of SEQ ID NO:4-52. It will be recognized by those of skill in the art that SEQ ID NO:4-52 include signal peptide sequences that may be removed and optionally replaced with heterologous sequences in the variant protein. In certain embodiments variant has more than 80% sequence identity to a naturally occurring β-glucosidase protein, such as at least 85%, at least 90%, at least 95%, or at least 99% identical to a naturally occurring β-glucosidase protein. In certain embodiments variant has more than 80% sequence identity to a naturally occurring β-glucosidase protein, such as at least 85%, at least 90%, at least 95%, or at least 99% identical to a naturally occurring β-glucosidase protein having a sequence set forth in SEQ ID NO:4-52, where sequence identity is calculated without including a signal peptide sequence or, alternatively, without including the initiator methionine and following 19 residues (i.e., the N-terminal 20 residues). In certain embodiments the naturally occurring protein is from a thermophilic fungus.

Preferably the variant β-glucosidase protein more thermoactive than the naturally occurring β-glucosidase protein. That is, the variant will have greater β-glucosidase catalytic activity and/or residual activity than the naturally occurring protein when assayed under comparable conditions'

In one aspect the invention provides a catalytically active recombinant β-glucosidase variant protein that has GH3 and GH3-C domains and has amino acid substitutions (relative to a naturally occurring β-glucosidase protein) at one or more performance sensitive positions that correspond to one or more PSPs in SEQ ID NO: 1 (selected from residues 60, 87, 104, 116, 122, 123, 130, 160, 163, 164, 210, 484, 521, 572, 211, 338, 339, 295, 299, 350, 415, 463, 485, 108, 157, and 649), where the variant is thermostable (i.e., retains at least 60% of starting activity after incubation under challenge conditions, usually at least 70%, and sometimes at least 80% or at least 90% of the initial activity). In one embodiment, the variant β-glucosidase is thermostable and retains at least 60%, at least 70%, at least 80% or at least 90% β-glucosidase after incubation at pH 5.0, at 65° C., for 6 hours. In one embodiment, the variant β-glucosidase is thermostable and retains at least 60%, at least 70%, at least 80% or at least 90% β-glucosidase after incubation at pH 5.0, at 65° C., for 6 hours. In one embodiment, the variant β-glucosidase is thermostable and retains at least 60%, at least 70%, at least 80% or at least 90% β-glucosidase after incubation at pH 5.0, at 75° C., for at least 1, 2, 3, 4, 5, 6, 10, 15, 20, 24, 48 or 72 hours. In certain embodiments the naturally occurring β-glucosidase protein has a sequence of one of SEQ ID NOS:4-52.

The presence of GH3 and GH3-C domains is indicated by amino acid segments with sequence identity to SEQ ID NOs: 53 and 54. In some embodiments the variant a level of sequence identity described above in Section IIB. In certain embodiments, the variant has substitutions in at least one PSPs that corresponds to a PSP in SEQ ID NO:1 within one of groups (a)-(e), supra.

In a related aspect, the invention provides a recombinant β-glucosidase variant protein that has β-glucosidase activity (i.e., is catalytically active), has GH3 and GH3-C domains, and has a sequence in the GH3 domain that differs from SEQ ID NO:53 at one or more performance sensitive positions selected from positions 39, 43, 51, 57, 58, 65, 91, 94, 97, 98, 133 and 134 of SEQ ID NO:53, and has a GH3-C domain that differs from SEQ ID NO:54 at one or more performance sensitive positions selected from positions 61, 82, 83, 115 and 163 of SEQ ID NO:54. Generally the number of PSPs at which the variant protein differs from SEQ ID NOs:53 and 54 is at least 9, sometimes at least 10, and sometimes at least 15. In some embodiments has the residue at PSPs that differs from a domain consensus and also differs from the most common residues found proteins shown in Table 14, in those cases in which the domain consensus residue and the most frequently observed residue are not the same. Table 12 shows examples of residues that may be excluded from PSPs in β-glucosidase variants of the invention.

TABLE 12

| SEQ ID NO: | Specified Position | Specified Residue |
|---|---|---|
| 53 | 43 | K, R |
| 53 | 51 | K, Q |
| 53 | 57 | F, L |
| 53 | 65 | A, L |
| 53 | 94 | A, I, V |
| 53 | 98 | A, E |
| 54 | 61 | G, V |
| 54 | 82 | K, Q |
| 54 | 163 | A, I |

In a related aspect, the invention provides a catalytically active recombinant β-glucosidase variant protein that has GH3 and GH3-C domains, and which comprises no more than one, or in some embodiments, none of the following residues:
a) alanine at a position corresponding to position 104 of SEQ ID NO:1,
b) leucine at a position corresponding to position 157 of SEQ ID NO:1,
c) isoleucine at a position corresponding to position 210 of SEQ ID NO:1,
d) alanine at a position corresponding to position 485 of SEQ ID NO:1,
e) alanine at a position corresponding to position 572 of SEQ ID NO:1, and
f) tyrosine at a position corresponding to position 649 of SEQ ID NO:1.

In preferred embodiments, the recombinant β-glucosidase protein variant has greater thermoactivity than a reference β-glucosidase protein that differs only by having alanine at the position corresponding to position 104 of SEQ ID NO:1, leucine at the position corresponding to position 157 of SEQ ID NO:1, isoleucine at the position corresponding to position 210 of SEQ ID NO:1, alanine at the position corresponding to position 485 of SEQ ID NO:1, alanine at the position corresponding to position 572 of SEQ ID NO:1, and tyrosine at the position corresponding to position 649 of SEQ ID NO:1.

H. Excluded Sequences

In selected embodiments of the invention, certain sequences variants may be excluded. Thus, in some embodiments the naturally occurring occurring β-glucosidase protein is other than C1 BGL1 (SEQ ID NO:1), *T. aurantiacus* BGL (SEQ ID NO:2) or *A. irakense* CelA (SEQ ID NO:3). In some embodiments variant β-glucosidase protein has less than 90% identity with C1 BGL1 (SEQ ID NO:1), *T. aurantiacus* BGL (SEQ ID NO:2) or *A. irakense* CelA (SEQ ID NO:3). In some embodiments variant β-glucosidase protein has less than 80% identity with C1 BGL1 (SEQ ID NO:1), *T. aurantiacus* BGL (SEQ ID NO:2) or *A. irakense* CelA (SEQ ID NO:3).

I. Xylosidases

Glycoside hydrolase family 3 ("GH3") β-xylosidases ("BXLs") are enzymes, classified as E.C. 3.2.1.37). BXLs catalyse hydrolysis of 1→4)-β-D-xylans to remove successive D-xylose residues from the non-reducing termini, as well as hydrolysis of xylobiose. BXL activity can be assayed using any number of art-known assays (see, e.g., Dodd, et al., 2001 *J Bacteriol.* 192:2335-45. BXLs are expressed in nature by a variety of organisms, including filamentous fungi and cellulose-digesting bacteria. Recombinantly expressed BGLs find use in a variety of commercial applications including digestion of cellulosic feestocks for production of ethanol.

Like BGLs, BXLs are characterized by β-glucosidase activity and the presence of "GH3 domain" and "GH3-C domains." See Table 13, infra. As shown in Table 13 and Table 16, BXLs, including but not limited to those listed, may be aligned with the C1BGL1, TaBGL and CelA sequences described above.

TABLE 13

| SEQ ID NO: | Accession Number | Domain Structure | Seq Identity To: | | |
|---|---|---|---|---|---|
| | | | C1BGL1 | CelA | TABGL |
| 56 | AAK43134.1 | GH3--GH3_C | 23% | 24% | 27% |
| 57 | CAD48309.1 | GH3-- GH3_C-- CARDB | 25% | 25% | 26% |
| 58 | ACN78955.1 | GH3-- GH3_C-- PA14 | 21% | 21% | 26% |
| 59 | AAC99628.1 | GH3--GH3_C | 24% | 23% | 23% |
| 60 | AAB70867.1 | GH3--GH3_C | 24% | 24% | 23% |

TABLE 13-continued

| SEQ ID NO: | Accession Number | Domain Structure | Seq Identity To: | | |
|---|---|---|---|---|---|
| | | | C1BGL1 | CelA | TABGL |
| 61 | CAP07659.1 | GH3--GH3_C | 26% | 27% | 24% |
| 62 | BAB11424.1 | GH3--GH3_C | 21% | 22% | 22% |
| 63 | AAM53325.1 | GH3--GH3_C | 22% | 22% | 23% |
| 64 | AAK96639.1 | GH3--GH3_C | 22% | 21% | 22% |
| 65 | BAE19756.1 | GH3--GH3_C | 21% | 20% | 22% |
| 66 | ABA40420.1 | GH3--GH3_C | 22% | 22% | 23% |
| 67 | BAG82824.1 | GH3--GH3_C | 19% | 20% | 21% |
| 68 | EAA64470.1 | GH3--GH3_C | 21% | 22% | 22% |
| 69 | EAA67023.1 | GH3--GH3_C | 17% | 17% | 20% |
| 70 | BAA24107.1 | GH3--GH3_C | 22% | 23% | 25% |
| 71 | CAA73902.1 | GH3--GH3_C | 21% | 22% | 22% |
| 72 | AAS17751.2 | GH3--GH3_C | 23% | 23% | 19% |
| 73 | AAK38481.1 | GH3--GH3_C | 23% | 22% | 18% |
| 74 | AAK38482.1 | GH3--GH3_C | 23% | 23% | 19% |
| 75 | CAA93248.1 | GH3--GH3_C | 23% | 22% | 19% |
| 76 | ABQ45227.1 | GH3--GH3_C | 23% | 24% | 20% |
| 77 | CAJ41429.1 | GH3--GH3_C | 23% | 23% | 20% |
| 78 | BAE44362.1 | GH3--GH3_C | 22% | 21% | 20% |
| 79 | AAL32053.2 | GH3--GH3_C | 22% | 21% | 20% |
| 80 | ACL54109.1 | GH3--GH3_C | 22% | 22% | 22% |

In view of these particular similarities between GH3 β-xylosidases and β-glucosidases it is contemplated that the methods herein described in relation to BGLs may also be used to make and use variant BXL proteins.

Thus, in one aspect the invention provides a method of producing a variant GH3 β-xylosidase with improved thermoactivity by (a) identifying a first performance sensitive position (PSP) in a target β-xylosidases polypeptide, (b) expressing a variant β-xylosidase polypeptide in which the residue at the first performance sensitive position is replaced with a thermoactivity enhancing residue, where the variant β-xylosidase polypeptide has greater thermoactivity than the target β-xylosidase polypeptide. In some embodiments the target β-xylosidase polypeptide has the sequence of a naturally occurring xylosidase protein, such as SEQ ID NO:58-82, or is a variant of a naturally occurring protein, with at least 80% sequence identity to a naturally occurring protein.

In one approach the step of identifying a performance sensitive position involved (a) aligning the primary sequence of the target β-xylosidase polypeptide with one or more a β-glucosidase polypeptides in which performance sensitive positions ("PSP") have been defined (b) identifying a position in the target β-xylosidase polypeptide that corresponds in the alignment to a PSP in the one or more a β-glucosidase polypeptides, wherein the position so identified is a PSP.

In one embodiment the PSP corresponds to a C1 Bgl1 PSP from the group consisting of: 60, 87, 104, 116, 122, 123, 130, 160, 163, 164, 210, 484, 521, and 572, the group consisting of: 338, and 339; the group consisting of: 295, 299, 350, 415, 463, 485; the group consisting of: 108, 221 and 157; or the group consisting of: 60, 87, and 649.

In some embodiments the method of claim 1 wherein the target β-xylosidase polypeptide has a sequence from 70% to 99% identical to any one of SEQ ID NOs:56-80.

The invention further provides a non-naturally occurring β-xylosidase polypeptide produced according to the method.

J. Alignments

Table 14 shows an alignment of 52 β-glucosidase polypeptides (SEQ ID NOs:1-52).

TABLE 14

```
                                  1                                            50
CDX_CBGL1    (1) --------------------------------------------------
ABP88968.1   (1) ---------------------------------MQGSTIFLAFASWA
ABU35789.1   (1) --------------------------------------------------
BAA19913.1   (1) --------------------------------------------------
BAA10968.1   (1) --------------------------------------------------
CAD67686.1   (1) --------------------------------------------------
ACD86466.1   (1) --------------------------------------------------
AAL69548.3   (1) --------------------------------------------------
CDX_TABGL    (1) --------------------------------------------------
AAF21242.1   (1) --------------------------------------------------
ACV87737.1   (1) --------------------------------------------------
ABX84365.1   (1) -------------------------------------------MASWLAPA
CAB82861.1   (1) -------------------------------------------MALAVAFFVTQ
CDX_CelA     (1) --------------------------------------------------
CAA07070.1   (1) --------------------------------------------------
BAA33065.1   (1) --------------------------------------------------
AAA74233.1   (1) --------------------------------------------------
AAL21070.1   (1) --------------------------------------------------
AAA60495.1   (1) ----------------------------------------MLMANYGFCTI
AAB66561.1   (1) --------------------------------------------------
AAZ32298.1   (1) --------------------------------------------------
CAA91219.1   (1) --------------------------------------------------
CAB56688.1   (1) --------------------------------------------------
AAA80156.1   (1) -------------------------------------------MEKSATR
AAF21799.1   (1) ----------------------------------------------MRR
ABU68675.1   (1) ------------------------------MKRLIPFCALVLLAACGP
BAA36161.1   (1) --------------------------------------------------
AAX35883.1   (1) ----------------------------------------------MNN
EAA64969.1   (1) -------------------------------------------------M
ABI29899.1   (1) --------------------------------------------------
CAB01407.1   (1) --------------------------------------------------
AAD35119.1   (1) --------------------------------------------------
CAC07184.1   (1) --------------------------------------------------
ABE60716.1   (1) --------------------------------------------------
AAC05445.1   (1) --------------------------------------------------
CAA33665.1   (1) --------------------------------------------------
AAM93475.1   (1) --------------------------------------------------
AAC38196.1   (1) --------------------------------------------------
```

TABLE 14-continued

```
AAQ38005.1   (1)  ------------------------------------------
AAF21798.1   (1)  ------------------------------------------
CAP58431.2   (1)  ------------------------------------------
AAA34314.1   (1)  ---------------------------------MLMIVQLLVF
AAA34315.1   (1)  ---------------------------------MLLILELLVL
CAA26662.1   (1)  -----------------------------------MLLPLYG
AAB67972.1   (1)  -------------------------------MSPTIWIATLLYW
BAE57053.1   (1)  ----------------------------------MAAFPAY
CAE01320.1   (1)  ----------------------------------MKTPLGIGSTAAV
AAA18473.1   (1)  ------------------------------------------
AAA91297.1   (1)  ------------------------------------------
BAE58551.1   (1)  MLTSPTARTSVRISRPATTERPNTVLTSGSLDIAMVQVVSRTLTPPTSNM
EAL91070.1   (1)  ------------------------------------------------M
AAB08445.1   (1)  ------------------------------------------
Consensus    (1)

51                                              100
CDX_CBGL1    (1)  ------IESRKVHQKPLAR-----------------------
ABP88968.1   (15) SQVAAIAQPIQKHEPGFLHGPQ--------------------
ABU35789.1   (1)  -MRFGWLEVAALTAASVANA----------------------
BAA19913.1   (1)  -MRFTLIEAVALTAVSLASA----------------------
BAA10968.1   (1)  -MKLSWLEAAALTAASVVSA----------------------
CAD67686.1   (1)  -MKLGWIEVAALAAASVVSAK---------------------
ACD86466.1   (1)  -MKLEWLEATVLAAATVASA----------------------
AAL69548.3   (1)  -MRNGLLKVAALAAASAVNG----------------------
CDX_TABGL    (1)  -----------------K------------------------
AAF21242.1   (1)  -MWLGWLPAVFVLVAGGAAE----------------------
ACV87737.1   (1)  ------MRNSLLISLAVAALA---------------------
ABX84365.1   (9)  LLAVGLASAQAPFPNG--SSP---------------------
CAB82861.1   (12) VLAQQYPTSNTSSPAANSSSP---------------------
CDX_CelA     (1)  ------------------------------------------
CAA07070.1   (1)  -----------MGRFLLPILGW--------------------
BAA33065.1   (1)  -----------MGRMSIPMMG---------------------
AAA74233.1   (1)  MKTIKSLFLLSLLIVNLLISSTYGSSIRVSIVGGEE------
AAL21070.1   (1)  -------------MKWLCSVGV--------------------
AAA60495.1   (12) FAATSGNKGRKIHMKWLCSVGI--------------------
AAB66561.1   (1)  ------------------------------------------
AAZ32298.1   (1)  -------------MKHILNLCL--------------------
CAA91219.1   (1)  ------------------------------------------
CAB56688.1   (1)  ------------------------------------------
AAA80156.1   (8)  QKALLIALPLLFSPLASAVQQAV-------------------
AAF21799.1   (4)  LPHLSLLALMLYSGTALAAPQQP-------------------
ABU68675.1   (19) RWTETEADGYRLITQRNGATLGV-------------------
BAA36161.1   (1)  MENAARQASVRYAQNGQGPLLGY-------------------
AAX35883.1   (4)  KWVETNVKAITYVTNEGGPTLGY-------------------
EAA64969.1   (2)  RVDSTVLALVALATDCLGLAIK--------------------
ABI29899.1   (1)  ------------------------------------------
CAB01407.1   (1)  ------------------------------------------
AAD35119.1   (1)  ------------------------------------------
CAC07184.1   (1)  ------------------------------------------
ABE60716.1   (1)  -------------MSITTKLKA--------------------
AAC05445.1   (1)  ------------------------------------------
CAA33665.1   (1)  ------------------------------------------
AAM93475.1   (1)  ------------------------------------------
AAC38196.1   (1)  ------------------------------------------
AAQ38005.1   (1)  ------------------------------------------
AAF21798.1   (1)  ------MKVHQLFKAALATS----------------------
CAP58431.2   (1)  ------------------------------------------
AAA34314.1   (11) ALGLAVAVPIQNYTQSPSQ-----------------------
AAA34315.1   (11) IIGLGVALPVQTHNLTDNQGF---------------------
CAA26662.1   (8)  LASFLVLSQAALVNTSAPQASN--------------------
AAB67972.1   (14) FAFQARKSVAAPPGVGALDDR---------------------
BAE57053.1   (8)  LALLSYLVPGALSHPEAKTLT---------------------
CAE01320.1   (14) LYILSNISHVQLATTSPSENQNQSYNPQIEGLTVQPSTVANGLRINSNSL
AAA18473.1   (1)  --MRYRTAAALALATGPFARA---------------------
AAA91297.1   (1)  -MKSTIIILSVLAAATAKNIS---------------------
BAE58551.1   (51) KLSAALSTLAALQPAVGAAVQNR-------------------
EAL91070.1   (2)  HSNVGLAGLAGLLATASVCLS-A-------------------
AAB08445.1   (1)  -MVSSLFNIAALAGAVIALSH---------------------
Consensus    (51)

101                                             150
CDX_CBGL1    (14) ------------------SEPFYPSPWMN-PNADGWAEAYAQAKSFVSQ
ABP88968.1   (37) --------------AIESFSEPFYPSPWMN-PHAEGWEAAYQKAQDFVSQ
ABU35789.1   (20) --------------QELAFSPPFYPSPWAD-G-QGEWADAHRRAVEIVSQ
BAA19913.1   (20) --------------DELAYSPPYYPSPWAN-G-QGDWAQAYQRAVDIVSQ
BAA10968.1   (20) --------------DELAFSPPFYPSPWAN-G-QGEWAEAYQRAVAIVSQ
CAD67686.1   (21) --------------DDLAYSPPFYPSPWAD-G-QGEWAEVYKRAVDIVSQ
ACD86466.1   (20) --------------KDLAYSPPFYPSPWAT-G-EGEWAEAYKKAVDFVSG
AAL69548.3   (20) --------------ENLAYSPPFYPSPWAN-G-QGDWAEAYQKAVQFVSQ
```

TABLE 14-continued

```
CDX_TABGL     (2)   ---------------DDLAYSPPFYPSPWMD-G-NGEWAEAYRRAVDFVSQ
AAF21242.1   (20)   ---------------KEWAFSPPYYPSPWAS-G-QGEWSEAYNKAREFVSQ
ACV87737.1   (16)   ---------------EGKAYSPPAYPTPWAS-G-AGEWAQAHERAVEFVSQ
ABX84365.1   (28)   ---------------LNDITSPPFYPSPWMD-PSAAGWAEAYTKAQAFVRQ
CAB82861.1   (33)   ---------------LDNAVSPPFYPSPWIE-G-LGDWEAAYQKAQAFVSQ
CDX_CelA     (1)    ---------------QEGAAPAAILHPEKWPRPATQRLIDPAVEKRVDALLKQ
CAA07070.1   (12)   ---------------FLLLSCLSAFTEAEYM-RYKDPKKPLNVRIKDLMSR
BAA33065.1   (11)   ---------------FVVLCLWAVVAEGEYV-KYKDPKQPVGARIKDLMKR
AAA74233.1   (37)   AEVIEKPRTFGNKRELKLEYSQIYPKKQLNQENINFMSARDTFVDNLMSK
AAL21070.1   (10)   ---------------AVSLAMQPALAENLFG-NHPLTPEARDAFVTDLLKK
AAA60495.1   (34)   ---------------AVSLALQPALADDLFG-NHPLTPEARDAFVTELLKK
AAB66561.1   (1)    --------------------------------------------------
AAZ32298.1   (10)   ---------------LAVLCAVLSCQEQKP--STVGATAEVESRVEALLSR
CAA91219.1   (1)    ------------------MSYGIGQITRLGGASNLSPRETVRIANQIQKF
CAB56688.1   (1)    -------------------------MTLPLYRDPAAPVPDRVRDLLGR
AAA80156.1   (31)   ----LDTRGAPLITVNGLTFKDLNRDGKLN-PYEDWRLPAAERAADLVSR
AAF21799.1   (27)   ----ALPEGQPLLTVEGLSFRDLNRDGTLN-PYEDWRLSPEVRADLVAR
ABU68675.1   (42)   ----TSAP---LLDLNGHIFKDLNRNGRVD-PYEDWRLPALTRAQDLAAQ
BAA36161.1   (24)   ----DESSGVRILRVDGHAFKDLNKDGKLD-PYEDWRLPPEERARDLASK
AAX35883.1   (27)   ----ADASGVNIIFDDGYAFKDLNKDGKLD-KYEDWRLPVDIRAKDLASK
EAA64969.1   (24)   -----------------SNEPELLRRDALP-IYKNASYCVDERVRDLLSR
ABI29899.1   (1)    ------------------------------------MEKVNEILSQ
CAB01407.1   (1)    ------------------------------------MEKVNEILSQ
AAD35119.1   (1)    ------------------------------------MERIDEILSQ
CAC07184.1   (1)    -----------MKHRKLSLTLAVGLLSTTM-TAQKALQLNKKNIDEVIAA
ABE60716.1   (10)   ----VSLG----VSLALAGLLVGCNQNDSD-PLIKDDAYYRGQAEAMVAR
AAC05445.1   (1)    -------------------------MI-INLLKRRIKVMDIAHIMEI
CAA33665.1   (1)    --------------------------------MAVDIKKIIKQ
AAM93475.1   (1)    ---------------------------------MTDGTYGVRYQPDLIDG
AAC38196.1   (1)    ---------------------------------MTSQTALDPAALVAS
AAQ38005.1   (1)    ---MRLSRKIFLLSAVACGMALAQAPAFARHADDGGGDQADARARQVLAS
AAF21798.1   (15)   ---------------LCLTAFAGGAMAQAKGAWQNTSLSPDERARLLDAE
CAP58431.2   (1)    --------MFAKTALALLTAWSAMQGVAGG-INFRSWDEAHELAKAVTDQ
AAA34314.1   (30)   -----------RDESSQWVSPHYYPTPQGG-RLQDVWQEAYARAKAIVGQ
AAA34315.1   (32)   -----------DEESSQWISPHYYPTPQGG-RLQGVWQDAYTKAKALVSQ
CAA26662.1   (30)   -------------DDPFNHSPSFYPTPQGGRINDGKWQAAFYRARELVDQ
AAB67972.1   (35)   -----------AELPDGFHSPQYYPAPRG---LGAGMEEAYSKAHTVVSK
BAE57053.1   (29)   -----------SRASTEAYSPPYYPAPNG--WISEWASAYEKAHRVVSN
CAE01320.1   (64)   ISNFDFEIIQPPPGYEEWTSPVVLPAPVQS-G-LSPWSESIVRARAFVAQ
AAA18473.1   (20)   -----------DSHSTSGASAEAVVPPAG-----TPWGTAYDKAKAALAK
AAA91297.1   (21)   ----KAEMENLEHWWSYGRSDPVYPSPEIS-G-LGDWQFAYQRAREIVAL
BAE58551.1   (74)   ----ASDVADLEHYWSYGHSEPVYPTPETK-G-LGDWEEAFTKARSLVAQ
EAL91070.1   (24)   ----PADQNITSDTYFYGQSPPVYPSPEGT-G-TGSWAAAYAKAKKFVAQ
AAB08445.1   (21)   -----------EDQSKHFTTIPTFPTPDST-G-EG-WKAAFEKAADAVSR
Consensus   (101)                  S              A   RA DLVSQ
```

```
                      151                                          200
CDX_CBGL1    (44)   MTLLEKVNLTTGVGWGAEQCV----------------------------
ABP88968.1   (72)   LTILEKINLTTGVGWENGPCV----------------------------
ABU35789.1   (54)   MTLAEKVNLTTGTGWEMDRCV----------------------------
BAA19913.1   (54)   MTLAEKVNLTTGTGWELELCV----------------------------
BAA10968.1   (54)   MTLDEKVNLTTGTGWELEKCV----------------------------
CAD67686.1   (55)   MTLTEKVNLTTGTGWQLERCV----------------------------
ACD86466.1   (54)   LTLAEKVNITTGAGWEQERCV----------------------------
AAL69548.3   (54)   LTLAEKVNLTTGTGWEQDRCV----------------------------
CDX_TABGL    (36)   LTLAEKVNLTTGVGWMQEKCV----------------------------
AAF21242.1   (54)   LTLTEKVNLTTGVGWMQEACV----------------------------
ACV87737.1   (50)   LTLAEKINLTTGAGWEGGQCV----------------------------
ABX84365.1   (63)   LTLLEKVNLTTGVGWEGEACV----------------------------
CAB82861.1   (67)   LTLLEKVNLTTGTGWQSDHCV----------------------------
CDX_CelA     (39)   LSVEEKVGQVIQGDIGTITPEDLR-----------------------K
CAA07070.1   (47)   MTLAEKIGQMTQIERKEATPDVI-----------------------SK
BAA33065.1   (46)   MTLAEKIGQMTQIERKVATADVM-----------------------KQ
AAA74233.1   (87)   MSITEKIGQMTQLDITTLTSPNTITIN------------ETTLAYYAKT
AAL21070.1   (45)   MTVDEKIGQLRLISVGPDNP---------------------------K
AAA60495.1   (69)   MTVDEKIGQLRLISVGPDNP---------------------------K
AAB66561.1   (1)    MTLDEKIGQLNLPSSGDFTTGQA-----------------------QS
AAZ32298.1   (44)   MTLAEKIGQMNQVSAGGDVS---------------------------
CAA91219.1   (33)   LIENTRLGIPALIHEESCSG---------------------------
CAB56688.1   (24)   MTLAEKVGQVNQRMYGWDAYERAGDGHRLTDAFRAEVAAFDG-------M
AAA80156.1   (76)   MTLEEKAGVMMHGSAPTAGSVTGAGTQYDLN----------------AA
AAF21799.1   (72)   MTLAEKAGAVGHGTAPIQGGPMASGPAYDMT----------------AA
ABU68675.1   (84)   LSIEEIAGLMLYSAHQSVPT-----PEITER---------------QK
BAA36161.1   (69)   MTIEQIAGLMLYSSHQAIPGNMGWFPATYAGGKAFPDSGAAPSDLSDQQL
AAX35883.1   (72)   MSIEQIAGLMLYSRHQAVPASNGFFPATYNG-ESYTESGVKPYDLSDEQI
EAA64969.1   (56)   MTLEEKAGQLFHKQLSEGPLDDDS----------------------S
ABI29899.1   (11)   LTLEEKVKLVVGVGLPGLFG---------------------------
CAB01407.1   (11)   LTLEEKSETCSGGWTSGVVW---------------------------
AAD35119.1   (11)   LTLEEKVKLVVGVGLPGLFG---------------------------
CAC07184.1   (39)   MTLEEKAQLLVGVGHQDFVGS---------------------------
```

TABLE 14-continued

```
ABE60716.1   (51)  LTLGEKLDLLSGPGYGSANG------------------------
AAC05445.1   (22)  MTLEEKASLCSGADFWHTKA------------------------
CAA33665.1   (12)  MTLEEKAGLCSGLDFWHTKP------------------------
AAM93475.1   (18)  VN-DDRANLEQFLAVVNR--------------------------
AAC38196.1   (16)  LPLETKVRLLTGATAFTLAPE-----------------------
AAQ38005.1   (48)  MSLEDKMSLLFSVDGGGFNGSVAP-------------------P
AAF21798.1   (50)  LTLDERISLLHGPMPLPFPGS-----------------------
CAP58431.2   (42)  MSLEQWVNITTGTGWMKSECVG----------------------
AAA34314.1   (68)  MTIVEKVNLTTGTGWQLDPCV-----------------------
AAA34315.1   (70)  MTIVEKVNLTTGTGWQLGPCV-----------------------
CAA26662.1   (67)  MSIAEKVNLTTGVGSASGPCS-----------------------
AAB67972.1   (71)  MTLAGKVNLTTGTGFLMA-LV-----------------------
BAE57053.1   (66)  MTLAEKVNLTSGTGIYMGPCA-----------------------
CAE01320.1  (112)  LTIEEKVNLTTGAGTQGR-CVG----------------------
AAA18473.1   (54)  LNLQDKVGIVSGVGWNGGPCV-----------------------
AAA91297.1   (65)  MTNEEKTNLTFG-SSGDTGCS-----------------------
BAE58551.1  (118)  MTDKEKNNITYGYSSTANGCG----------------------- 
EAL91070.1   (68)  LTPEEKVNLTAG-TDANNGCS-----------------------
AAB08445.1   (57)  LNLTQKVALTTG-TTAGLSCN-----------------------
Consensus   (151)  MTL EKV L TG G 201                                             250
CDX_CBGL1    (65)  GQVGAIPRLGL----RS----------------LCMHD--SPLGIRGA-
ABP88968.1   (93)  GNTGSIPRLGF----KG----------------FCTQD--SPQGVRFA-
ABU35789.1   (75)  GQTGSVPRLGI----NWG---------------LCGQD--SPLGIRFS-
BAA19913.1   (75)  GQTGGVPRLGV----PG----------------MCLQD--SPLGIRFS-
BAA10968.1   (75)  GQTGGVPRLNI----GG----------------MCLQD--SPLGIRDS-
CAD67686.1   (76)  GQTGSVPRLNI----PS----------------LCLQD--SPLGIRFS-
ACD86466.1   (75)  GETGGVPRLGM----WG----------------MCMQD--SPLGVRNA-
AAL69548.3   (75)  GQVGSIPRLGF----PG----------------LCMQD--SPLGVRDT-
CDX_TABGL    (57)  GETGSIPRLGF----RG----------------LCLQD--SPLGVRFA-
AAF21242.1   (75)  GNVGSIPRLGF----RS----------------LCMQD--GPLGIRFA-
ACV87737.1   (71)  GNTGSIPRLGF----RS----------------LCMQD--SPLGVRDT-
ABX84365.1   (84)  GNTGSIPRLGF----PG----------------FCTQD--SPLGVRDS-
CAB82861.1   (88)  GNTGGVPRLNF----TG----------------ICNQD--APLGVRFA-
CDX_CelA     (64)  YPLGSILAGGNSGPNGDDRAPPKEWLDLADAFYRVSLEKRPGHTPIPVLF
CAA07070.1   (72)  YFIGSVLSGGGSVPAPKASP--EAWVDLNGMQKAALS---TRLGIPMIY
BAA33065.1   (71)  NFIGSVLSGGGSVPAPKASA--QVWTNMVDEIQKGSLS---TRLGIPMIY
AAA74233.1  (124)  YYIGSYLNSPVSGGLAGDIHHINSSVWLDMINTIQTIVIEGSPNKIPMIY
AAL21070.1   (66)  EAIREMIKDGQ---VGAIFN--TVTRQDIRQMDQVMAL--SRLKIPLFF
AAA60495.1   (90)  EAIREMIKDGQ---VGAIFN--TVTRQDIRAMDQVMEL--SRLKIPLFF
AAB66561.1   (26)  SDIGKKIEQGL---VGGLFN--IKGVNKIKAVQKVAIEK--SRLKIPMIF
AAZ32298.1   (64)  N-YAESIRKGQ---VGSILN--EVDPVKINAFQRLAVEE--SRLGIPLLV
CAA91219.1   (53)  -----------------------------------YMAKG--AT-
CAB56688.1   (67)  GALYGLQRADAWSGVGFADGLDARDGARTAAAVQRYVMD-HTRLGIPVLL
AAA80156.1  (109)  KTMIADRYVNSFITRLSGDN--PAQMAEENNKLQQLAEA--TRLGIPLTI
AAF21799.1  (105)  QAIIRDQHLNSLITRMA-IA--PADFAAENNRLQGIAAG--TRLGIPLTI
ABU68675.1  (112)  KFLEEDNLRAVLVTTVG--S--PEIAARWNNNVQAFVEA--LGHGIPANN
BAA36161.1  (119)  DFLSNDHIRHILVTRVQ--S--PEVAANWNNNVQAYAER--LGLGIPANN
AAX35883.1  (121)  EFLTKDHLRHVLLTTVE--S--PEIAACWNNNVQALAES--TLKIPMIN
EAA64969.1   (81)  GNSTETMIGKKHMTHFNLASDITNATQTAEFINLIQKRALQTRLGIPITI
ABI29899.1   (31)  ----NPHSRVA----G-AAG--ETHPVPRVGLPAFVLAD--GPAGLRIN-
CAB01407.1   (31)  ----KSHSGWR------CRG--ETHPVPRVGLPAFVLAD--GPAGLRIN-
AAD35119.1   (31)  ----NPHSRVA----G-AAG--ETHPVPRLGIPAFVLAD--GPAGLRIN-
CAC07184.1   (60)  GTMLGQHSRLV----AGAAG--QTAEISRLGIPATVVAD--GPAGVHIN-
ABE60716.1   (71)  ---AINVKQDVPGVAGYING--VLRSADGIDIPALKLAD--GPAGVRINA
AAC05445.1   (42)  -------------------------IERLDIPQIMVSD--GPHGLRKN-
CAA33665.1   (32)  -------------------------VERLGIPSIMMTD--GPHGLRKQR
AAM93475.1   (35)  --------------------------------RTEHTIEGDFSGTSP-
AAC38196.1   (37)  -------------------------ESIGLGEVRLSD--GPTGVRGLK
AAQ38005.1   (73)  GGLGSAAYLRAP--------------Q---GSGLPDLQISDAGLGVRNPA
AAF21798.1   (71)  ---PPIPEGPS---------LVPVIFPGVPRLGIPALKETDASLGVTNPM
CAP58431.2   (64)  -NTRPTKNPDFP------------------SLCLED--GPPGIRFG-
AAA34314.1   (89)  GNTGSVPRFGI----PN----------------LCLQD--GPLGVRFA-
AAA34315.1   (91)  GNTGSVPRFGI----PN----------------LCLQD--GPLGVRLT-
CAA26662.1   (88)  GNTGSVPRLNIS-------------------SICVQD--GPLSVRAA-
AAB67972.1   (91)  GQTGSALRFGI----PR----------------LCLQD--GPLGLRFN-
BAE57053.1   (87)  GQTGSVPRFGI----PN----------------LCLHD--SPLGVRNS-
CAE01320.1  (133)  -ETGTVPRLGFN-------------------QPICLQD--GPVGIRYT-
AAA18473.1   (75)  GNTSPASKISY----PS----------------LCLQD--GPLGVRYS-
AAA91297.1   (85)  GMISDVPDVDF----PG----------------LCLQD--AGNGVRLN-
BAE58551.1  (139)  GTSGGVPRLGF----PG----------------ICLQD--AGNGVRGT-
EAL91070.1   (88)  GNIAAIPRLNF----PG----------------LCVSD--AGNGLRGT-
AAB08445.1   (77)  GNIAPIPEINF----SG----------------LCLAD--GPVSVRIA-
Consensus   (201)  G  GVR                           L L D  PLGIR 251                                             300
CDX_CBGL1    (91)  ------------------DYNSAFPSGQTVAATWDRGLMYRRGYAMGQE
ABP88968.1  (119)  ------------------DYSSAFTSSQMAAATFDRSILYQRGQAMAQE
ABU35789.1  (102)  ------------------DLNSAFPAGTNVAATWDKTLAYLRGKAMGEE
```

TABLE 14-continued

```
BAA19913.1   (101) -------------------DYNSAFPSGMNVAATWDKNLAYLRGKAMGQE
BAA10968.1   (101) -------------------DYNSAFPAGVNVAATWDKNLAYLRGQAMGQE
CAD67686.1   (102) -------------------DYNSAFPAGVNVAATWDKTLAYLRGQAMGEE
ACD86466.1   (101) -------------------DYSSAFPAGVNVAATWDRRLAYQRGTAMGEE
AAL69548.3   (101) -------------------DYNSAFPAGVNVAATWDRNLAYRRGVAMGEE
CDX_TABGL     (83) -------------------DYVSAFPAGVNVAATWDKNLAYLRGKAMGEE
AAF21242.1   (101) -------------------DHVSAFPAGINVGATWSKSLAYLRGKAMGEE
ACV87737.1    (97) -------------------DYNTAFPAGVNVAATWDLDLAYRRGIAMAEE
ABX84365.1   (110) -------------------DYVSAFTAGGTIAASWDRSEFYRRGYQMGVE
CAB82861.1   (114) -------------------DYVSAFPSGGTIAAAWDRGEWYLRGYQMGSE
CDX_CelA     (114) GIDAVHG--------HGNIGSATIFPHNIALGATHDPELLRRIGEVTAVE
CAA07070.1   (117) GIDAVH---------GHNNVYNATIFPHNVGLGVTRDPALIKRIGEATALE
BAA33065.1   (116) GIDAVH---------GHNNVYGATIFPHNVGLGVTRDPDLVKRIGAATALE
AAA74233.1   (174) GLDSVHG--------ANYVHKATLFPHNTGLAATFNIEHATTAAQITSKD
AAL21070.1   (109) AYDVVH---------GQR-----TVFPISLGLASSFNLDAVRTVGRVSAYE
AAA60495.1   (133) AYDVVH---------GQR-----TVFPISLGLASSFNLDAVKTVGRVSAYE
AAB66561.1    (69) GMDVIH---------GYE-----TTFPIPLGLASSWDMDLIQRSAQIAAKE
AAZ32298.1   (106) GRDVIH---------GFH-----TVFPIPLGLAATFDPDLVEEGARVAAVE
CAA91219.1    (60) -----------------------IFPQTIGVASTWNNEIVEKMASVIREQ
CAB56688.1   (116) VEEMPHG--------HQALDGTVLPVNLAVGATWDPDLYADAVAGAAAE
AAA80156.1   (155) STDPRSSFQSLVGVSVSVGK-FSKWPETLGLAAIGDEELVRRFADIVRQE
AAF21799.1   (150) STDPRNHFQVLGGASVAASG-FSQWPETLGFGALNDPALTRRFADLVRAE
ABU68675.1   (156) SSDPRNECSATAEFNLGSGGQISLWPTPLGLAATFDPALVEQFGRIASAE
BAA36161.1   (163) SSDPRHGSDTSKEFNAGAGGAISMWPESMGLAATFDPAVAREFGEIASRE
AAX35883.1   (165) SSDPRHGSDASKEYNAGAGGSISMWPESLGLAASFDPELVQRYGEIASKE
EAA64969.1   (131) STDPRHSFTENVG-TGFQAGVFSQWPESLGLAALRDPQLVREFAEVAREE
ABI29899.1    (67) --PTRE--------NDENTYYTTAFPVEIMLASTWNRELLEEVGKAMGEE
CAB01407.1    (66) --PTRE--------NDENTYYTTAFPVEIMLASTWNRELLEEVGKAMGEE
AAD35119.1    (67) --PTRE--------NDENTYYTTAFPVEIMLASTWNRDLLEEVGKAMGEE
CAC07184.1   (101) --PTRP--------GTNQTFYATGFPIGTCLASTWNTDLVYHVGKAIGNE
ABE60716.1   (114) NRDG----------DSASYYATAWPIGSLLASSWDVKLVKAVGEAMGDE
AAC05445.1    (63) -VDGSN--------DPNEAIEAVCFPTAAALACSYDRELLKDIGKALGEE
CAA33665.1    (54) EDAEIA--------DINNSVPATCFPSAAGLACSWDRELVERVGAALGEE
AAM93475.1    (50) --------------------ATCFPNGSSFACSWDLDLAFQLGTALAAE
AAC38196.1    (58) FSGG----------------RTVALFPNATLLASAWSEESTTEVGRLLAEE
AAQ38005.1   (106) HIR-----------RNGEAVSLPSGQSTASTWDMDMARQAGVMIGRE
AAF21798.1   (109) N-------------VRPGDTATALPSGLALASTFNPKLSYDGGAAIAKE
CAP58431.2    (89) -------------------DNVTAGVSGITAAASFDKEQLLKRGQYMGKE
AAA34314.1   (115) -------------------DFVTGYPSGLATGATFNKDLFLQRGQALGHE
AAA34315.1   (117) -------------------DFSTGYPSGMATGATFNKDLFLQRGQALGHE
CAA26662.1   (114) -------------------DLTDVFPCGMAASSSFNKQLIYDRAVAIGSE
AAB67972.1   (117) -------------------DHNTAFPAGISVGATFDKKLMYERGCAMGEE
BAE57053.1   (113) -------------------DHNTAFPAGITVGATFDKDLMYERGVGLGEE
CAE01320.1   (159) -------------------DFNSVFPAAINVAATFDKQLMFKRAQAMAEE
AAA18473.1   (101) -------------------TGSTAFTPGVQAASTWDVNLIRERGQFIGEE
AAA91297.1   (111) -------------------DMVNAYASGLHVGASWNRQLAYDRAVYMGAE
BAE58551.1   (165) -------------------DMVNSYASGVHVGASWNRDLTYSRAQYMGAE
EAL91070.1   (114) -------------------DYVSSWPSGLHVGASWNKALARQRAVQMATE
AAB08445.1   (103) -------------------DLATVFPAGLTAAATWDRQLIYERARALGSE
Consensus    (251)                       TAFPAGL LAATWDKDLV   G AMG E 301                                    350
CDX_CBGL1    (122) AKGKGINVLLGPVAGPLGRMPEGGRNWEGFAPDPVLTGIGMSETIKGIQD
ABP88968.1   (150) HKAKGITIQLGPVAGPLGRIPEGGRNWEGFSPDPVLTGIAMAETIKGMQD
ABU35789.1   (133) FNDKGVDILLGPAAGPLGKYPDGGRIWEGFSPDPVLTGVLFAETIKGIQD
BAA19913.1   (132) FSDKGADIQLGPAAGPLGRSPDDGRNWEGFSPDPALSGVLFAETIKGIQD
BAA10968.1   (132) FSDKGIDVQLGPAAGPLGRSPDDGRNWEGFSPDPALTGVLFAETIKGIQD
CAD67686.1   (133) FSDKGIDVQLGPAAGPLGAHPDGGRNWEGFSPDPALTGVLFAETIKGIQD
ACD86466.1   (132) HRDKGVDVQLGPVAGPLGKNPDGGRGWEGFSPDPVLTGVMMAETIKGIQD
AAL69548.3   (132) HRGKGVDVQLGPVAGPLGRSPDAGRNWEGFAPDPVLTGNMMASTIQGIQD
CDX_TABGL    (114) HRGKGVDVQLGPVAGPLGRHPDGGRNWEGFSPDPVLTGVLMAETIKGIQD
AAF21242.1   (132) HRDKGVDVQLGPAVGPLGRSPDDGRNWEGFSPDPVLSGYLVAETIKGIQD
ACV87737.1   (128) HRGKGVDVQLGPVAGPLGRVPEGGRNWEGFAPDPVLTGQMMASTIQGMQD
ABX84365.1   (141) HRGKGVDVQLGPVVGPIGRHPKGGRNWEGFSPDPVLSGIAVAETVKGIQD
CAB82861.1   (145) HRSKGVDVQLGPVVGPLGRNPKGGRNWEGFSPDPYLSGIASAESVRGIQD
CDX_CelA     (156) MAATGIDWTFAPALSVV-RDDRWGRTYEGFSEDPEIVAAYSAAIVEGVQG
CAA07070.1   (159) CRATGIPYAFAPCIAVC-RDPRWGRCYESYSEDHTIVQAMTEIIPGLQGD
BAA33065.1   (158) VRATGIPYAFAPCIAVC-RNPRWGRCYESYSEDHRIVRSMTEIIPGLQGD
AAA74233.1   (216) TVAVGIPWVFAPVLGIG-VQPLWSRIYETFGEDPYVASMMGAAAVRGFQG
AAL21070.1   (146) AADDGLNMTWAPMVDVS-RDPRWGRASEGFGEDTYLTSIMGETMVKAMG
AAA60495.1   (170) AADDGLNMTWAPMVDVS-RDPRWGRASEGFGEDTYLTSTMGKTMVEAMQG
AAB66561.1   (106) ASADGINWTFSPMVDVS-REPRWGRVSEGSGEDPYLGSEIAKAMVYGYQG
AAZ32298.1   (143) ATSQGVRWTFSPMLDIA-RDPRWGRIAEGSGEDTYLDTRMAEAMVYGYQG
CAA91219.1    (87) MKAVGARQALAPLLDIT-RDPRWGRTEETFGEDPYLVMRMGVSYIRGLQT
CAB56688.1   (157) LRARGAHIALVSALDLV-RDPRWGREECFSEDPYLAARMTEALVEGARR
AAA80156.1   (204) YRAVGITEALSPQADLA-TEPRWPRIDGTFGEDPDLTKKMVRGYVTGMQN
AAF21799.1   (199) YRAVGIQMALSPQADLA-TEPRWSRINGTFGEDPARVSAQVKAYVQGMQG
ABU68675.1   (206) YRALGIATALSPQIDLA-TEPRWSRFNGTFGEDPELDVALARAYVDGFQT
BAA36161.1   (213) YRALGLSTALSPQVDLA-TDPRWFRFGMTFGEDPRLATDMARAYIDGFQT
AAX35883.1   (215) YRALGIATALSPQIDIA-TDPRWSRFDGTFGEDSKLSVDLTRAYIDGFQT
```

TABLE 14-continued

```
EAA64969.1   (180) YLAVGIRAALHPQVDLS-TEPRWARISGTWGENSTLTSELIVEYIKGFQG
ABI29899.1   (107) VREYGVDVLLAPAMNIH-RNPLCGRNFEYYSEDPVLSGEMASSFVKGVQS
CAB01407.1   (106) VREYGVDVLLAPAMNIH-RNPLCGRNFEYYSEDPVLSGEMASSFVKGVQS
AAD35119.1   (107) VREYGVDVLLAPAMNIH-RNPLCGRNFEYYSEDPVLSGEMASAFVKGVQS
CAC07184.1   (141) TLEYGIDVILGPGMNLH-RSPLCGRNFEYYSEDPIVTGLIGSAMVKGIQS
ABE60716.1   (153) VRQYGVDILLAPGMNIQ-RNPLNGRNFEYYSEDPLLTGKIGAAMVNGVES
AAC05445.1   (104) CQSEKVSVILGPGCNIK-RSPLCGRNFEYFSEDPYLASQMAISHIKGVQS
CAA33665.1   (96)  CQAENVSILLGPGANIK-RSPLCGRNFEYFPEDPVLSSELAASHIKGVQS
AAM93475.1   (79)  CQALGVNLLLGPGINIR-RMPLGGRGYEYYSEDPVLTGYIRPAVIWELKG
AAC38196.1   (93)  ALAQQIHVVLGPTINLH-RSVLGGRLFEAYSEDPLLTGRLAAAYVRGLQD
AAQ38005.1   (142) AWQSGFNILLGGGADLT-RDPRGGRNFEYAGEDPLQTGRMVGSTIAGVQS
AAF21798.1   (145) AASKGFNVLLAGGANLA-RDPRNGRNFEYLGEDPLLAGILAGESIRGIQS
CAP58431.2   (120) FRGKGIHFALGPCVDIM-RAPQTGRGWEGFGEDPYLAGVAGALTVEGIQS
AAA34314.1   (146) FNSKGVHIALGPAVGPLGVKARGGRNFEAFGSDPYLQGTAAAATIKGLQE
AAA34315.1   (148) FNSKGVHIALGPAVGPLGVKARGGRNFEAFGSDPYLQGIAAAATIKGLQE
CAA26662.1   (145) FKGKGADAILGPVYGPMGVKAAGGRGWEGHGPDPYLEGVIAYLQTIGIQS
AAB67972.1   (148) FRGKGANVHLGPSVGPLGRKPRGGRNWEGFGSDPSLQAIAAVETIKGVQS
BAE57053.1   (144) ARGKGINVLLGPSVGPIGRKPRGGRNWEGFGADPSLQAFGGSLTIKGMQS
CAE01320.1   (190) FRGKGANVVLAPMTNLM-RTPQAGRAWEGYGSDPYLSGVATVQSVLGIQS
AAA18473.1   (132) VKASGIHVILGPVAGPLGKTPQGGRNWEGFGVDPYLTGIAMGQTINGIQS
AAA91297.1   (142) FRHKGVNVLLGPVVGPIGRVATGGRNWEGFTNDPYLAGALVYETTKGIQE
BAE58551.1   (196) FKRKGVNVALGPVAGPIGRIARGGRNWEGFSNDPYLSGALTGDTVRGLQE
EAL91070.1   (145) FRKKGVNVLLGPVVGPLGRVAEAGRNWEGFSNDPYLSGALVYETVDGAQS
AAB08445.1   (134) FRGKGSQVHLGPASGALGRHPLGGRNWESFSPDPYLSGVAMDFSIRGIQE
Consensus    (301)      RAKGV V LGP VGIL R P GGRNWEGFSEDP LTG M A TIKGIQ
```

```
                       351                                          400
CDX_CBGL1    (172) AG---------------VIACAKHFIGNEQEHFRQVPEA------QGYGY
ABP88968.1   (200) TG---------------VIACAKHFIGNEQEHFRQVGEA------AGHGY
ABU35789.1   (183) AG---------------VIATAKHYILNEQEHFRQVGEA------QGYGY
BAA19913.1   (182) AG---------------VVATAKHYIAYEQEHFRQAPEA------QGYGF
BAA10968.1   (182) AG---------------VVATAKHYILNEQEHFRQVAEA------AGYGF
CAD67686.1   (183) AG---------------VIATAKHYIMNEQEHFRQQPEA------AGYGF
ACD86466.1   (182) AG---------------VIACAKHFIMNEQEHFRQAGEA------QGYGF
AAL69548.3   (182) AG---------------VIACAKHFILYEQEHFRQG---------AQDGY
CDX_TABGL    (164) AG---------------VIACAKHFIGNEMEHFRQASEA------VGYGF
AAF21242.1   (182) AG---------------VIACVKHFIVNEQERFRQAPEA------QGYGF
ACV87737.1   (178) TG---------------VIACAKHYIGNEQEHFRQGSQ---------ENF
ABX84365.1   (191) AG---------------VIACTKHFILNEQEHFRQPGN--------VGDF
CAB82861.1   (195) AG---------------VIACTKHYIMNEQEHFRQPGN--------FEDQ
CDX_CelA     (205) KFG-----SKDFMAPGRIVASAKHFLADGGTDQGRDQG-------------
CAA07070.1   (208) VPPDVKKGVPFVGGKTKVAACAKHFVGDGGTTKGID---------------
BAA33065.1   (207) LPAKSKNGVPYVGGKTKVAACAKHFVGDGGTLHGVD---------------
AAA74233.1   (265) GNN----SFDGPINAPSAVCTAKHYFGYSNPTSGKDR--------------
AAL21070.1   (195) KS--------PADRYSVMTSVKHFAAYGAVEGGKE----------------
AAA60495.1   (219) KS--------PADRYSVMTSVKHFAAYGAVEGGKE----------------
AAB66561.1   (155) KD---------LSLKNTILACVKHFALYGAPEGGRD---------------
AAZ32298.1   (192) R----------TADSTSMAACIKHFVGYGAAEGGRD---------------
CAA91219.1   (136) ESLKEG-----------IVATGKHFVGYGNSEGGMN---------------
CAB56688.1   (206) AG---------------VAVVLKHFAGQGATVGGRN---------------
AAA80156.1   (253) --------GKNGLNAQSVISIVKHWVGYGAAKDGWDSHNV----------
AAF21799.1   (248) --------ADTGLAPGGVATVVKHWVGYGAQIDYDGHNY----------
ABU68675.1   (255) -----TEDAPDGWGAQSVNAMVKHWPSGGPEEGGRDAHFN----------
BAA36161.1   (262) SE--GDAEIADGWGSDSVNAMVKHWPGGGSGEAGRDAHFG----------
AAX35883.1   (264) SF--GERLVTDGWGCDSVNAMVKHWPGGGSGEGGRDAHFG----------
EAA64969.1   (229) EG-------K--LGPKSVKTVTKHFPGGGPMENGEDSHFYYG--------
ABI29899.1   (156) QG---------------VGACIKHFVANNQETNRMV--------------
CAB01407.1   (155) QG---------------VGACIKHFVANNQETNRMV--------------
AAD35119.1   (156) QG---------------VGACIKHFVANNQETNRMV--------------
CAC07184.1   (190) QG---------------VGVSAKHFAANSQESDRTR--------------
ABE60716.1   (202) NG---------------VGTTIKHYFGNNSETNRNQ--------------
AAC05445.1   (153) KG---------------AGTSLKHFAANNQEHRRMS--------------
CAA33665.1   (145) QG---------------VGACLKHFAANNQEHRRMT--------------
AAM93475.1   (128) SG---------------VGASLKHFACNNSEVQRTT--------------
AAC38196.1   (142) LG---------------VGACLKHLVANESETERNT--------------
AAQ38005.1   (191) QH---------------VISTLKHYAMNDLETSRMT--------------
AAF21798.1   (145) QN---------------IISTVKHFSLNGQETNRHWG-------------
CAP58431.2   (169) QG---------------VIATAKHYIGNNQETNRKN--------------
AAA34314.1   (196) NN---------------VMACVKHFIGNEQEKYRQP--DDIN---PATNQ
AAA34315.1   (198) NN---------------VMACVKHFIGNEQDIYRQPSNSKVD---PEYDP
CAA26662.1   (195) QG---------------VVSTAKHFEHFRFAKKDKHAGKIDPGMF
AAB67972.1   (198) KG---------------VIATIKHLVGNEQEMYRMTN-------------
BAE57053.1   (194) TG---------------AIASLKHLIGNEQQHRMSS--------------
CAE01320.1   (239) TR---------------ASACVKHYIGNEQEHYRGGSG------------
AAA18473.1   (182) VG---------------VQATAKHYIGNEQELNRET--------------
AAA91297.1   (192) N----------------VIACTKHFIGNEQETNRNP----------SG
BAE58551.1   (246) S----------------VIACVKHLIGNEQETHRSTPS---------MLAN
EAL91070.1   (195) VG---------------VATCTKHYILNEQETNRNP-G---------MEDG
AAB08445.1   (184) MG---------------VQANRKHFIGNEQETQRSNTF--------TDDG
Consensus    (351) G                VIA VKHFIGNEQE  R
```

TABLE 14-continued

```
                         401                                              450
CDX_CBGL1     (201) NISETLSSNIDDKTMHELYLWPFADAVRAG---VGSVMCSYQQVNNSYAC
ABP88968.1    (229) TISDTISSNIDDRAMHELYLWPFADAVRAG---VGSFMCSYSQINNSYGC
ABU35789.1    (212) NITETISSNVDDKTMHELYLWPFADAVRAG---VGAVMCSYNQINNSYGC
BAA19913.1    (211) NISESGSANLDDKTMHELYLWPFADAIRAG---AGAVMCSYNQINNSYGC
BAA10968.1    (211) NISDTISSNVDDKTIHEMYLWPFADAVRAG---VGAIMCSYNQINNSYGC
CAD67686.1    (212) NVSDSLSSNVDDKTMHELYLWPFADAVRAG---AVAMCSYNQINNSYGC
ACD86466.1    (211) NISQSLSSNVDDKTMHELYLWPFVDSVRAG---VGSVMCSYNQINNSYGC
AAL69548.3    (208) DISDSISANADDKTMHELYLWPFADAVRAG---VGSVMCSYNQVNNSYAC
CDX_TABGL     (193) DITESVSSNIDDKTLHELYLWPFADAVRAG---VGSFMCSYNQVNNSYSC
AAF21242.1    (211) NISESSSSNVDDVTMHELYLWPFADAVRAG---VGSVMCSYNQINNSYGC
ACV87737.1    (204) TVADAISSNIDDVTLHELYLWPFADAVRAG---VGSIMCSYNQLNNSYSC
ABX84365.1    (218) GFVDAVSANLADKTLHELYLWPFADAVRAG---TGSIMCSYNKANNSQVC
CAB82861.1    (222) GFVDALSSNLDDKTLHELYLWPFADAVRAG---TGSIMCSYNKVNNSQAC
CDX_CelA      (238) ------DARISEDELIRIHNAGYPPAIDAG---VLTVMASFSSWQGIKHH
CAA07070.1    (244) ----ENNTVIDSRGLFSIHMPAYHDSIKKG---VATVMVSYSSWNGLRMH
BAA33065.1    (243) ----ESNTVISSNSLFSIHMPAYYDSLRKG---VATVMVSYSSWNGRKMH
AAA74233.1    (298) -----TAAWIPERMLRRYFLPSFAEAITGAG--AGTIMINSGEVNGVPMH
AAL21070.1    (222) ----YNTVDMSSQRLFNDYMPPYKAGLDAG---SGAVMVALNSLNGTPAT
AAA60495.1    (246) ----YNTVDMSPQRLFNDYMPPYKAGLDAG---SGAVMVALNSLNGTPAT
AAB66561.1    (182) ----YNTVDMSHIRMFNEYFPPYKAAVDAG---VGSVMASFNEVDGVPAT
AAZ32298.1    (218) ----YNSTYLTERQLRNVYLPPFEAAVKAG---AMTLMTSFNDNDGVPST
CAA91219.1    (161) ----WAPAHIPERELREVFLYPFEAAVKEAK--LSSIMPGYHELDGVPCH
CAB56688.1    (227) ----SAATELGPRELHEVHLAAARAGVAAG---AAGVMAAYNEFDGLPCV
AAA80156.1    (285) -YGKYAQFRQNNLQWHIDPFTG---AFEAH---AAGIMPTYSILRNASWH
AAF21799.1    (280) -YGRFTDFTKGGFDRHVAAFQG---AFEAG---ATGIMPTYTIQKGLSLE
ABU68675.1    (290) -YGKYAVYPGGNFATHLRPFTEGAFRLDGGTKSASAVMPYYTISYGVDPS
BAA36161.1    (300) -YGKYAVYPGNNFEEHLRPFTEGAFRLAGKTGEASAVMPYYTISVGQDPV
AAX35883.1    (302) -YGKYAVYPGNNFEEHLIPFLEGAFQLKGGTEKASAIMPYYTISYNHDQV
EAA64969.1    (262) ---KNQTYPGNNIDEHLIPFKA---ALAAG---ATEIMPYYSRPIGTNWE
ABI29899.1    (177) -----VDTIVSERALREIYLRGFEIAVKKSK--PWSVMSAYNKLNGKYCS
CAB01407.1    (176) -----VDTIVIERALREIYLKGFEIAVKKSK--PWSVMSAYNKLNGKYCS
AAD35119.1    (177) -----VDTIVSERALREIYLKGFEIAVKKAR--PWTVMSAYNKLNGKYCS
CAC07184.1    (211) -----VDERISQRALRELYLKGFEIMVRDSK--PWTLMSSYNKINGTYTQ
ABE60716.1    (223) -----INDIGEPRTFREIYLRGFQIAVDEAQ--PWAVMTSYNKVNGTYVN
AAC05445.1    (174) -----VSAEIDERTLHEIYLAAFESVIKEAK--PWTVMCSYNKINGEYSS
CAA33665.1    (166) -----VDTIVDERTLREIYFASFENAVKKAR--PWVVMCAYNKLNGEYCS
AAM93475.1    (149) -----MSSDVDERALREIYLAGFERAIRKGN--PWTVMSSYNRLNGVQAA
AAC38196.1    (163) -----MNSVVDPATLRELYLLPFEIAVDES--DPWSVMAAYNDVNGVPAT
AAQ38005.1    (212) -----MSADIDPVAMRESDLLGFEIALETG--HPGAVMCSYNRVNDLYAC
AAF21798.1    (216) -----NSVIDEAAHRESDLLAFQIAIERGQ--PGSVMCAYNLVNGAYSC
CAP58431.2    (190) -----STSNISRRALHEIWTWPYARMIEAG---IGAIMCSYNQLHGTWAC
AAA34314.1    (226) TTKEAISANIPDRAMHALYLWPFADSVRAG---VGSVMCSYNRVNNTYAC
AAA34315.1    (230) ATKESISANIPDRAMHELYLWPFADSIRAG---VGSVMCSYNRVNNTYSC
CAA26662.1    (230) NTSSSLSSEIDDRAMHEIYLWPFAEAVRGG---VSSIMCSYNKLNGSHAC
AAB67972.1    (220) IVQRAYSANIDDRTMHELWPFAESVRAG---VGAVMMAYNDVNGSASC
BAE57053.1    (216) VITQGYSSNIDDRTLHELYLWPFAESVRAG---AGSVMIAYNDVNRSACS
CAE01320.1    (262) --ATASSSNIDDRTLRELYEWPFAEAIHAG---VDYIMCSYNRVNQTYAC
AAA18473.1    (203) -----ISSNPDRTLHELYTWPFADAVQAN---VASVMCSYNKVNTTWAC
AAA91297.1    (214) TYNQSVSANIDDKTMHELYLWPFQDSVRAG---LGSIMGSYNRVNNSYAC
BAE58551.1    (272) SRNQSSSSNLDDKTMHELYLWPFQDAVKAG---AGSVMCSYNRINNSYGC
EAL91070.1    (221) VEVAAVSSNIDDKTMHELYLWPFQDAVLAG---SASIMCSYNRVNNSYGC
AAB08445.1    (211) TEIQAISSNIDDRTMHELYLWPFANAVRSG---VASVMCSYNRLNQTYAC
Consensus     (401)      ISS IDDR LHELYLWPF DAVRAG      GSVMCSYN VNGSY C 451                                              500
CDX_CBGL1     (248) Q----------NSKLLNDLLKNELGFQGFVMSDWQ---AQHTGAA-----
ABP88968.1    (276) Q----------NSQTLNKLLKSELGFQGFVMSDWG---AHHSGVS-----
ABU35789.1    (259) Q----------NSQTLNKLLKAELGFQGFVMSDWS---AHHSGVG-----
BAA19913.1    (258) Q----------NSYTLNKLLKAELGFQGFVMSDWA---AHHAGVS-----
BAA10968.1    (258) Q----------NSYTLNKLLKAELGFQGFVMSDWG---AHHSGVG-----
CAD67686.1    (259) E----------NSETLNKLLKGELGFQGFVMSDWT---AHHSGVG-----
ACD86466.1    (258) S----------NSYTLNKLLKGELGFQGFVMSDWG---AHHSGVG-----
AAL69548.3    (255) S----------NSYTMNKLLKSELGFQGFVMTDWG---GHHSGVG-----
CDX_TABGL     (240) S----------NSYLLNKLLKSELDFQGFVMSDWG---AHHSGVG-----
AAF21242.1    (258) S----------NSYTQNKLLKGELGFQGFIMSDWQ---AHHSGVG-----
ACV87737.1    (251) G----------NSYSLNHILKGELDFQGFVMTDWG---AQHSGVG-----
ABX84365.1    (265) Q----------NSYLQNYILKGELGFQGFTMSDWD---AQHSGVA-----
CAB82861.1    (269) Q----------NSYLQNYILKGELGFQGFIMSDWD---AQHSGVA-----
CDX_CelA      (279) G----------HKQLLTDVLKGQMGFNGFIVGDWNAHDQVPGCTKFN---
CAA07070.1    (287) A----------NRDLVTGYLKNKLKFRGFVISDWEGIDRITDPP------
BAA33065.1    (286) A----------NRDLVTGFLKDKLKFRGFVISDWQGIDRITDPP------
AAA74233.1    (341) T----------SYKYLTEVLRGELQFEGVAVTDWQDIEKLVYFHHTAG--
AAL21070.1    (265) S----------DSWLLKDVLRDEWGFKGITVSDHGAIKELIKHGT-----
AAA60495.1    (289) S----------DSWLLKDVLRDQWGFKGITVSDHGAIKELIKHGT-----
AAB66561.1    (225) G----------NKWLMDDVLRKQWGFNGFIVTDYTGINEMIQHG------
AAZ32298.1    (261) G----------NTFVVKDVLRGEWGFDGLVVTDWDSMGEMIAHGF-----
CAA91219.1    (205) K----------SKKLLNDILRKDWGFEGIVVSDYFAISQLYEYHHVTSDK
CAB56688.1    (270) A----------NRYLLTDLLRTEWGFEGVVMADGTAVDRLVRLTG-----
```

TABLE 14-continued

```
AAA80156.1   (328) GKPIEQVGAGFNRFLLTDLLRGQYGFDGVILSDWLITNDCKGDCLTGVKP
AAF21799.1   (323) GKPVEPVSGGYNKQMLIDLLRGTHKFKGLILSDWAITNDCNESCRTGNPP
ABU68675.1   (339) ---GKNAGNSYNEYIIGDLLRGEYGFDGVVCTDWGITADNAAVSS---FD
BAA36161.1   (349) N--GENVGNAYNAYLIRDLLRGKYGYDGVVCTDWGITADEGPDIERLFPG
AAX35883.1   (351) N--GENVGNSYNAHIIGDLLRDKYGYDGVVCTDWGITDDEGSDISRLFPG
EAA64969.1   (303) AVG-----FSFNKEIVTDLLRGELGFDGIVLTDWGLITDTYIGNQYMPAR
ABI29899.1   (220) Q----------NEWLLKKVLREEWGFEGFVMSDWY---AGDNPVE-----
CAB01407.1   (219) Q----------NEWLLKKVLREEWGFEGFVMSDWY---AGDNPVE-----
AAD35119.1   (220) Q----------NEWLLKKVLREEWGFEGFVMSDWY---AGDNPVE-----
CAC07184.1   (254) G----------SKDLLTNILRKDWGYQGIVMTDWIGERADLPVET-----
ABE60716.1   (266) E----------RRDAVTDLLRGEWKFDGLVMSDWFAGDVANNAYK-----
AAC05445.1   (217) Q----------NKSLLTDTLREKWGFDGLVMSDWG--AVDDRVK-----
CAA33665.1   (209) E----------NRYLLTEVLKNEWMHDGFVVSDWG---AVNDRVS-----
AAM93475.1   (192) E----------NKWLLTTVLRDEWHYDGVVVSDWHGIKDRAAAAK-----
AAC38196.1   (206) E----------HHHVVNEVLKGEWGYTGLVMSDWFATRTAAPAAAG----
AAQ38005.1   (255) E----------NPYLLNKTLKQDWHYPGFVMSDWG---ATHSSAR-----
AAF21798.1   (258) G----------NDHLLNKVLKGDWGYKGWVMSDWGAVPATDFALK-----
CAP58431.2   (232) E----------DEYTLNTILKQEYNFRGLIMSDWG---ATHSTAP-----
AAA34314.1   (273) E----------NSYMMNHLLKEELGFQGFVVSDWG---AQLSGVY-----
AAA34315.1   (277) E----------NSYMINHLLKEELGFQGFVVSDWA---AQMSGAY-----
CAA26662.1   (277) Q----------NSYLLNYLLKEELGFQGFVMTDWG---ALYSGID-----
AAB67972.1   (267) Q----------NSKLINGILKDELGFQGFVMTDWY---AQIGGVS-----
BAE57053.1   (263) Q----------NSKLINGILKDELGFQGFVVTDWL---AHIGGVS-----
CAE01320.1   (307) E----------NSKLINGIAKGEHKFQGVMTDWA---AAESGVR-----
AAA18473.1   (245) E----------DQYTLQTVLKDQLGFPGYVMTDWN---AQHTTVQ-----
AAA91297.1   (261) K----------NSKVLNGLLKSELGFQGFVVSDWG---GQHTGIA-----
BAE58551.1   (319) Q----------NSKAMNGLLKSELGFQGFVVSDWG---AQHTGIA-----
EAL91070.1   (268) Q----------NSKTLNGLLKTELGFQGYVMTDWG---AQHAGIA-----
AAB08445.1   (258) E----------NSKLMNGILKGELGFQGYVVSDWY---ATHSGVE-----
Consensus    (451)            NSYLLN LLK ELGFQGFVMSDWG   A   GV 501                                              550
CDX_CBGL1    (280) ----------SAVAGLDMSMPGDTQFN---------TGVSFWGANLTLA
ABP88968.1   (308) ----------SALAGLDMSMPGDTEFD---------SGLSFWGSNLTIA
ABU35789.1   (291) ----------AALAGLDMSMPGDISFD---------DGLSFWGTNLTVS
BAA19913.1   (290) ----------GALAGLDMSMPGDVDYD---------SGTSYWGTNLTVS
BAA10968.1   (290) ----------SALAGLDMSMPGDITFD---------SATSFWGTNLTIA
CAD67686.1   (291) ----------AALAGLDMSMPGDVTFD---------SGTSFWGANLTVG
ACD86466.1   (290) ----------DALAGLDMSMPGDVILG---------SPYSFWGTNLTVS
AAL69548.3   (287) ----------SALAGLDMSMPGDIAFD---------SGTSFWGTNLTVA
CDX_TABGL    (272) ----------AALAGLDMSMPGDTAFG---------TGKSFWGTNLTIA
AAF21242.1   (290) ----------DDLAGLDMSMPGDTLFL---------TGKSYWGTNLTIA
ACV87737.1   (283) ----------DALAGADMDMPGDVAFD---------SGTAFWGTNLTIA
ABX84365.1   (297) ----------STLAGLDMNMPGDTDFD---------SGFSFWGPNMTLS
CAB82861.1   (301) ----------STFAGLDMTMPGDTDFN---------SGKTFWGTNFTTS
CDX_CelA     (316) ----------CPTSLIAGLDMYMAADS-----------WKQLYENTLAQ
CAA07070.1   (321) ----------GRNYSYSVEAGVGAGIDMIM----VPEDFTKFLNELTSQ
BAA33065.1   (320) ----------HANYSYSVQAGIMAGIDMIM----VPENYREFIDTLTSQ
AAA74233.1   (379) ----------SAEEAILQALDAG---------IICLCHDLLSQLFSLEI
AAL21070.1   (300) ----------AADPEDAVRVALKAGVDMSM----ADEYYSKYLPGLIKS
AAA60495.1   (324) ----------AADPEDAVRVALKSGINMSM----SDEYYSKYLPGLIKS
AAB66561.1   (259) ----------MGDLQQVSALALNAGVDMDM----VGEGFLTTLKKSLSE
AAZ32298.1   (296) ----------GVDRKDVAEKAANAGVDMDM----MTFGFLSHLEELVKS
CAA91219.1   (245) KG-----AAKLALEAGVDVELP---------------STDYYGLPLREL
CAB56688.1   (305) ----------DPVSAGALALDAGCDLS----------LWDASFTRLGEA
AAA80156.1   (378) GEKPVPRGMPWGVEK-LTPAERFVKAVNAGV----DQFGGVTDSALLVQA
AAF21799.1   (373) -QQPKDIATPWGVED-LTQPQRFAKGMLAGI----DQFGGVNDGLPLLAA
ABU68675.1   (383) -------GKCWGMEE-LSVAERHYAVIKAGV----DQFGGNNDKGPVLEA
BAA36161.1   (397) ------GRCWGVEENHTVAQRHYKLLMAGV----DQFGGNDDAGPVIEA
AAX35883.1   (399) ------GRSWGVEEGYTVADRHYKALMAGV----DQFGGNNDGGPVLEA
EAA64969.1   (348) ----------AWGVEYLSELQRAARILDAG----CDQFGGEERPELIVQL
ABI29899.1   (252) ----------QLKAGNDLIMPGKAYQVN--------TERRDEIEEIMEA
CAB01407.1   (251) ----------QLKAGNDLIMPGKAYQVN--------TERRDEIEEIMEA
AAD35119.1   (252) ----------QLKAGNDMIMPGKAYQVN--------TERRDEIEEIMEA
CAC07184.1   (289) ----------EVEAGNDFMMPG----------------NADRAKHIVKA
ABE60716.1   (301) ----------QVLAGQDLIEPG-----------------NVKEQLQQS
AAC05445.1   (249) ----------GIEAGLDLEMPG--------------SMCKNDKMILKA
CAA33665.1   (241) ----------GLDAGLDLEMPT---------------SHGITDKKIVEA
AAM93475.1   (227) -------------AG-NDLDMPAS---------------KSRKKQLLAA
AAC38196.1   (242) --------------GL--DLVMPG--------------PDGPWGDALVAA
AAQ38005.1   (287) ----------AALAGLDQESAGDHT----------DARPYFRTLLAAD
AAF21798.1   (293) ----------GL--DQQSGQQ-----------LDEKIWFGDLLKEA
CAP58431.2   (264) ----------AINSGLDMTMPGDLEMG---------DNYTYFGVNMTKA
AAA34314.1   (305) ----------SAISGLDMSMPGEVYGGW-------NTGTSFWGQNLTKA
AAA34315.1   (309) ----------SAISGLDMSMPGELLGGW-------NTGKSYWGQNLTKA
CAA26662.1   (309) ----------AANAGLDMDMP---------------CEAQYFGGNLTTA
AAB67972.1   (299) ----------SALAGLDMSMPGDGS-VP-------LSGTSFWASELSRS
BAE57053.1   (295) ----------SALAGLDMSMPGDGA-IP-------LLGTSYWSWELSRS
CAE01320.1   (339) ----------TALAGTDMNMPGFMAYGQPSEPNPSTANGSYWGLRMIEA
AAA18473.1   (277) ----------SANSGLDMSMPGTDF----------NGNNRLWGPALTNA
```

TABLE 14-continued

```
AAA91297.1  (293) -----------SANAGLDMAMP---------------SSTYWEEG-LIEA
BAE58551.1  (351) -----------SAAAGLDMAMP---------------SSSYWENGTLALA
EAL91070.1  (300) -----------GANAGLDMVMP---------------STETWGAN-LTTA
AAB08445.1  (290) -----------SVNAGLDMTMPGPLDSPSTA----LRPPPSYLGGNLTEA
Consensus   (501)            A AGLDM MPG              FWG   L  A 551                                              600
CDX_CBGL1   (310) VLNGTVPAYR------LDDMAMRIMAALFKVTKTTDLEP----INFSFWT
ABP88968.1  (338) ILNGTVPEWR------LDDMAMRIMAAYFKVGLTIEDQPD---VNFNAWT
ABU35789.1  (321) VLNGTVPAWR------VDDMAVRIMTAYYKVGRDRLRIP----PNFSSWT
BAA19913.1  (320) VLNGTVPQWR------VDDMAVRIMAAYYKVGRDRLWTP----PNFSSWT
BAA10968.1  (320) VLNGTVPQWR------VDDMAVRIMAAYYKVGRDRLYQP----PNFSSWT
CAD67686.1  (321) VLNGTIPQWR------VDDMAVRIMAAYYKVGRDTKYTP----PNFSSWT
ACD86466.1  (320) VLNSTIPEWR------LDDMAVRIMAAYYKVGRDRHRTP----PNFSSWT
AAL69548.3  (317) VLNGSIPEWR------VDDMAVRIMSAYYKVGRDRYSVP----INFDSWT
CDX_TABGL   (302) VLNGTVPEWR------VDDMAVRIMAAFYKVGRDRYQVP----VNFDSWT
AAF21242.1  (320) VTNGTIPQWR------LDDMAVRIMAAYYKVRRDQTQVP----VNFNSWT
ACV87737.1  (313) VLNGTVPEWR------IDDMAVRIMASAFYKVGRDRTQVP----INFASWT
ABX84365.1  (327) IINGTVPEWR------LDDAATRIMAAYYLVGRDRHAVP----VNFNSWS
CAB82861.1  (331) ILNGTVPQWR------LDDAVTRIMAAFYYVGRDKARIP----VNFDSWS
CDX_CelA    (344) VKDGTIPMAR------LRVKVLAGLFEKPAPKDRPG------
CAA07070.1  (356) VKKNIIPMSR------IDDAVKRILRVKFVMGLFESPLADYSLAN-----
BAA33065.1  (355) VKANIIPMSR------IDDAVKRILRVKFVMGLFENPMSDPSLAN-----
AAA74233.1  (409) LAAGTVPESR------LDLSVRRILNLKYALGLFSNPYP--------N--
AAL21070.1  (335) GK---VTMAE------LDDATRHVLNVKYDMGLFNDPYSHLGPKESD---
AAA60495.1  (359) GK---VTMAE------LDDAARHVLNVKYDMGLFNDPYSHLGPKESD---
AAB66561.1  (294) GK---VTEQQ------ITLAARRILEAKYDLGLFDDPYRYTDEKR-----
AAZ32298.1  (331) GA---VKQNT------IDNAVRNILRVKFMLGLFENPYVNVEASQ-----
CAA91219.1  (274) IESGEIDIDF------VNEAVRKIKFELGLFENPYIN-------------
CAB56688.1  (334) VERGLVSESA------LDAAVARVLTLKFRLGLFEQPLP----P------
AAA80156.1  (423) VQDGKLTEAR------LDTSVNRILKQKFQTGLFERPYVN----------
AAF21799.1  (417) VEQKLLPEAR------LNEAVATIMTLKFEQGLFENPFVD----------
ABU68675.1  (421) YKMWVAEFGEESARARFEQSAVRLLMNSFRTGLFENPYLD----------
BAA36161.1  (436) YRIGVAEHGEPFMRARFEQSAVRLLKNMFRLGLFENPYLN----------
AAX35883.1  (438) YRIGVAEHGEAYMRQRFEQSAVRLLKNMFRVGLFENPYCQ----------
EAA64969.1  (384) VREGTISEDR------IDVSVARLLKEKFLLGLFDNPFVN----------
ABI29899.1  (283) LKEGKLSEEV------LDECVRNILKVLVNAPSFKNY-------------
CAB01407.1  (282) LKEGKLSEEV------LDECVRNILKVLVNAPSFKNY-------------
AAD35119.1  (283) LKEGKLSEEV------LDECVRNILKVLVNAPSFKGY-------------
CAC07184.1  (312) VKAGRLDIKD------VARNIKNMLEYILKTPRYKKY-------------
ABE60716.1  (322) IEQGDLDEAK------VNEAAIHILTQVMKSPSYNQLAIS----------
AAC05445.1  (273) VEDGKLSVEA------LDKCVKRILELIDKSLECR---------------
CAA33665.1  (265) VKSGKLSENI------LNRAVERILKVIIMALENKK--------------
AAM93475.1  (247) VENGTVPLAT------IDQSCLRMLQLVRRVKAGERR-------------
AAC38196.1  (262) VRSGELDESV------VDDHLRRLLVLAARVGALGDLRDYP---------
AAQ38005.1  (315) VKAGRVPEAR------INDMAERVVRALFAAGLVDHPAQ-----------
AAF21798.1  (316) AAAGTIPAER------LSDMSRRILRSMFAAGFFDGKPG-----------
CAP58431.2  (294) VRNGEVTEER------AQEMATRIIAAYYKLGQDEGFP------------
AAA34314.1  (337) IYNETVPIER------LDDMATRILAALYATNSFPTEDH---LPNFSSWT
AAA34315.1  (341) VYNETVPIER------LDDMATRILAALYATNSFPTKDR---LPNFSSFT
CAA26662.1  (333) VLNGTLPQDR------LDDMATRILSALIYSGVHNPDGP-----NYNAQT
AAB67972.1  (330) ILNGTVALDR------LNDMVTRIVATWFKFG-QDKDFP---LPNFSSYT
BAE57053.1  (326) VLNGSVPVER------LNDMVTRIVATWYKMG-QDKDYP---LPNFSSNT
CAE01320.1  (378) VKNGTVPMER------LDDMVTRVISTYYKQGQDKSDYPKLNFMSMG---
AAA18473.1  (306) VNSNQVPTSR------VDDMVTRILAAWYLTGQDQAGYP---SFNIS---
AAA91297.1  (316) VKNGTVDQSR------LDDMATRIIAAWYKYARLDDP-------------
BAE58551.1  (375) VKNESLPSTR------LDDMATRIVATWYKYAEIENP-------------
EAL91070.1  (323) ISNGTMDASR------LDDMATRIIASWYQMNQDSDFP------------
AAB08445.1  (325) VLNGTIPEAR------VDDMARRILMPYFFLGQDTDFPTVDPSTGFVFAR
Consensus   (551) V NGTVP  R      LDD A RIL    YKVG 601                                              650
CDX_CBGL1   (350) DDTYGPIHWAAKQG-YQEINSHVDVRADH-GNLIREIAAKGTVLLKN---
ABP88968.1  (379) HDTYGYKYAYSKED-YEQVNWHVDVRSDH-NKLIRETAAKGTVLLKNN--
ABU35789.1  (361) RDEYGWEHSAVSEGAWTKVNDFVNVQRSH-SQIIREIGAASTVLLKNT--
BAA19913.1  (360) RDEYGYKYYYVSEGPYEKVNHYVNVQRNH-SELIRRIGADSTVLLKND--
BAA10968.1  (360) RDEYGFKYFYPQEGPYEKVNHFVNVQRNH-SEVIRKLGADSTVLLKNN--
CAD67686.1  (361) RDEYGFAHNHVSEGAYERVNEFVDVQRDH-ADLIRRIGAQSTVLLKNK--
ACD86466.1  (360) RDEYGYEHFIVQEN-YVKLNERVNVQRDH-ANVIRKIGSDSIVMLKNN--
AAL69548.3  (357) LDTYGPEHYAVGQG-QTKINEHVDVRGNH-AEIIHEIGAASAVLLKNK--
CDX_TABGL   (342) KDEYGYEHALVGQN-YVKVNDKVDVRADH-ADIIRQIGSASVVLLKNK--
AAF21242.1  (360) RDEFGYLHAGGQEG-YGRVNQMVNVRGRH-AVIARKVASASTVLLKNR--
ACV87737.1  (353) LDTYGNEYYYAGEG-YKEINQHVDVRGDH-AEVVREIGSASIVLLKNV--
ABX84365.1  (367) KDTYGYQHAYAKVG-YGLINQHVDVRADH-FKSIRTAAAKSTVLLKNN--
CAB82861.1  (371) RDTYGFPDHYYGKAG-YSQINSHVDVRGNH-FRSIRRTAAMSTVLLKNN--
CDX_CelA    (382) ------------------LPGLETLGSPEHRAVGREAVRKSLVLLKND--
CAA07070.1  (395) ----------------------QLGSQEHRDLAREAVRKSLVLLKNGES
BAA33065.1  (394) ----------------------QLGSQEHRELAREAVRKSLVLLKNGKT
AAA74233.1  (443) ---------------PN----AAIVDTIGQVQDREAAAATAEESITLLLFKN-
AAL21070.1  (373) ------------------PVDTNAESRLHRKEAREVARESVVLLKNR--
```

TABLE 14-continued

```
AAA60495.1  (397) -------------------PVDTNAESRLHRKEAREVARESLVLLKNR--
AAB66561.1  (330) -------------------AKAEVFSKPHREEARNIAAQSMVLLKND--
AAZ32298.1  (367) ----------------------AVQYAPEHLAAAQKTAEESAILLKN---
CAA91219.1  (308) -----------------EEKAVEIFDTNEQRELAYKIAQESIVLLKNE--
CAB56688.1  (368) -------------------ARSETVELPDPAELGERIARASVTLLAHEG-
AAA80156.1  (457) -----------------ATQANDIVGRADWQQLADDTQARSLVLLQNNN-
AAF21799.1  (451) ----------------PAAAATIVGRADVVAEGRATQAKSLVMLENRLG
ABU68675.1  (461) -----------------PAAAAVVGNPEYMEAGFQAQRKSIVMLKNH--
BAA36161.1  (476) -----------------PGKSAALVGNPAFMEAGYRAQLRSVVMLKN---
AAX35883.1  (478) -----------------TEETVRIVGNAEYMAAGYEAQLKSLVLLKNK--
EAA64969.1  (418) -----------------ASAANNIVGNEHFVNLGRDAQRRSYTLLTNN--
ABI29899.1  (314) -------------------RYSNKPDLEKHAKVAYEAGAEGVVLLKNE--
CAB01407.1  (313) -------------------RYSNKPDLEKHAKVAYEAGAEGVVLLKNE--
AAD35119.1  (314) -------------------RYSNKPDLESHAEVAYEAGAEGVVLLENN--
CAC07184.1  (343) -------------------KYTNQPDLKAHAQITRQASTEGMVLLKND--
ABE60716.1  (356) --------------------NSPDLTAHSKLARQAGAESMVLLRN---
AAC05445.1  (302) -------------------TEMDWDKERHHQLAQKAAEKSAVLLKND--
CAA33665.1  (295) -------------------ENAQYEQDAHHRLARQAAAESMVLLKNE--
AAM93475.1  (278) -------------------DATWDLRENHTLARQMAAESIVLLKNE--
AAC38196.1  (297) -------------------DDLPAPDSAVRREQLTRLAAAGMTVLTN---
AAQ38005.1  (348) -------------------RGPLDVVTDTLVAQKDEEEGAVLLRNQ--
AAF21798.1  (349) -------------------KPVVDLDAHAAIAKQVADEGIVLLAND--
CAP58431.2  (326) ---------EMAIRAFQRDEAPYVPVQEDHGKLVREMGAAACTLLKN---
AAA34314.1  (378) TKEYGNKYYADNTTEIVKVNYNVDPSNDFTEDTALKVAEESIVLLKNE--
AAA34315.1  (382) TKEYGNEFFVDKTSPVVKVNHFVDPSNDFTEDTALKVAEESIVLLKNE--
CAA26662.1  (372) FLTEGHEYFKQQEGDIVVLNKHVDVRSDINRAVALRSAVEGVVLLKN---
AAB67972.1  (370) QNAKGLLYPGALFSPLGVVNQFVNVQADH-HKLARVIARESITLLKNE--
BAE57053.1  (366) EDETGPLYPGALFSPSGIVNQYVNVQGNH-NVTARAIARDAITLLKNN--
CAE01320.1  (419) ---------QGTPAEQAVSNHHVNVQKDH-YLIIRQIATASTILLKNVN-
AAA18473.1  (344) -----------RN----------VQGNH-KTNVRAIARDGIVLLKND--
AAA91297.1  (347) -----GFGMPVSLAEDHELVDARDPAA---ASTIFQGAVEGHVLVKNE--
BAE58551.1  (406) -----GHGLPYSLLAPHNLTDARDPKS---KSTILQGAVEGHVLVKNT--
EAL91070.1  (355) ---SPGAGMPSDMYAPHQRVIGRDASS---KQTLLRGAIEGHVLVKNN--
AAB08445.1  (369) TYNYPDEYLTLGGLDPYNPPPARDVRGNH-SDIVRKVAAAGTVLLKNV--
Consensus   (601)                           V     LAR IA ESIVLLKN
```

```
                        651                                    700
CDX_CBGL1   (395) --TGSLPLNKPK---FVAVIGEDAGSSPNGPNG-----------------
ABP88968.1  (425) --FHALPLKQPR---FVAVVGQDAGPNPKGPNG-----------------
ABU35789.1  (408) --G-ALPLTGKEV--KVGVLGEDAGSNPWGANG-----------------
BAA19913.1  (407) --G-ALPLTGKER--LVALIGEDAGSNPYGANG-----------------
BAA10968.1  (407) --N-ALPLTGKER--KVAILGEDAGSNSYGANG-----------------
CAD67686.1  (408) --G-ALPLSRKEK--LVALLGEDAGSNSWGANG-----------------
ACD86466.1  (406) --G-GLPLTHQER--LVAILGEDAGSNAYGANG-----------------
AAL69548.3  (403) --G-GLPLTGTER--FVGVFGKDAGSNPWGVNG-----------------
CDX_TABGL   (388) --G-GLPLTGYER--FTGVFGEDAGSNRWGADG-----------------
AAF21242.1  (406) --G-VLPLKGKEK--LTAVIGEDAGPNLWGPNG-----------------
ACV87737.1  (399) --DDALPLTGSER--FVAVFGEDAGSNPDGVNG-----------------
ABX84365.1  (413) --G-VLPLKGTEK--YTAVFGNDAGEAQYGPNG-----------------
CAB82861.1  (417) --G-ALPLTGSEK--WTAVFGDDAGEGQLGPNG-----------------
CDX_CelA    (412) --KGTLPLSPKAR--VLVAGDGADNIGK-----------------
CAA07070.1  (422) ADKPFVPLPKNAK--KILVAGSHADNLGR-------------------
BAA33065.1  (421) PSQPLLPLPKKAP--KILVAGTHADNLGY-------------------
AAA74233.1  (476) ---NILPLNTNTIK-NVLLTGPSADSIRNLNGG-----------------
AAL21070.1  (402) --LETLPLKKSG---TIAVVGPLADSQRD-------------------
AAA60495.1  (426) --LETLPLKKSA---TIAVVGPLADSKRD-------------------
AAB66561.1  (358) --KQTLPLKAGG---TVAVIGPLANNNEN-------------------
AAZ32298.1  (392) --DGVLPLKAGV---RILVTGPMADAPHD-------------------
CAA91219.1  (339) --NNLLPLKKDLK--SIAVIGPNADSIRNMIG-----------------
CAB56688.1  (398) --G-VLPLSRAVR--RIAVLGPNADSVAQQIG-----------------
AAA80156.1  (489) ----LLPLRKGS---RVWLHGIAANAAQEVG-------------------
AAF21799.1  (484) --PAPLPAGGGK---RLFIYGVDAANAKAAG-------------------
ABU68675.1  (492) --GGVLPNDS-A---RVYVPQRLYPQTPGMFGL-----------------
BAA36161.1  (506) --EGILPLPKRQ---TVYIPKRKLPADADWMGN-----------------
AAX35883.1  (509) --DQVLPLQKMK---TVYIPKRYRPAGTNWIGF-----------------
EAA64969.1  (449) --QTILPLAKPGEGTRFYIEGFDSAFMSAR-------------------
ABI29899.1  (343) --E-ALPLSENS---KIALFGTGQIETIKGGTG-----------------
CAB01407.1  (342) --E-ALPLSENS---KIALFGTGQIETIKGGTG-----------------
AAD35119.1  (343) --G-VLPFDENT---HVAVFGTGQIETIKGGTG-----------------
CAC07184.1  (372) --NNVLPVKNMK---KVALFGVNSYDFLSGGLG-----------------
ABE60716.1  (381) --EAAALPLAASS--ALASFGINQINTYKGGTG-----------------
AAC05445.1  (330) --DHILPLSKNE---KIAFIGAFAEQPRYQGGG-----------------
CAA33665.1  (323) --DDVLPLKKSG---TIALIGAFVKKPRYQGSG-----------------
AAM93475.1  (305) --GNLLPLEMMAG--RIAIIGDTAMDPIFQG-------------------
AAC38196.1  (325) -ADDTLPLARGTR--VALVGRHALETIDMGGGSATVNPPYQVSVAEGLT
AAQ38005.1  (375) --GNILPLSPTAR--IAVIGGHADAGVISGGG-----------------
AAF21798.1  (376) --KGLLPLAAGSQ--KIAVIGGFADQGVLSGAG-----------------
CAP58431.2  (364) -EDKVLPISSSVK--KIAIIGSDAGPNPDGLHD-----------------
AAA34314.1  (426) --NNTLPISPEK---AKRLLLSGIAAGPDP-IG-----------------
AAA34315.1  (430) --KNTLPISPNK---VRKLLLSGIAAGPDP-KG-----------------
```

TABLE 14-continued

```
CAA26662.1   (419) -EHETLPLGREK-VKRISILGQAAGDDSKGTS------------------
AAB67972.1   (417) --DNLLPLDPNR---AIKYSEQMPGTNPR--GI-----------------
BAE57053.1   (413) --ENVLPLKRND---TLKIFGTDAGTNSD--GI-----------------
CAE01320.1   (458) ---HTLPLKSPDKMRSVVVVGSDAGDNPQGPNS-----------------
AAA18473.1   (369) --ANILPLKKPA---SIAVVGSAAIIGNHARNS-----------------
AAA91297.1   (387) --N-ALPLKKPK---YISLFGYDGVSTDVNTVG-----------------
BAE58551.1   (446) --NNALPLKKPQ---FLSLFGYDAVAAARNTMD-----------------
EAL91070.1   (397) --HSALPLKSPQ---LLSVFGYDAKGPNALKQN-----------------
AAB08445.1   (416) --NNVLPLKEPK---SVGIFGNGAADVTEGLTF-----------------
Consensus    (651)         LPL          VAV G  A           G 701                                              750
CDX_CBGL1    (423) --------------------------------------------------
ABP88968.1   (453) --------------------------------------------------
ABU35789.1   (436) --------------------------------------------------
BAA19913.1   (435) --------------------------------------------------
BAA10968.1   (435) --------------------------------------------------
CAD67686.1   (436) --------------------------------------------------
ACD86466.1   (434) --------------------------------------------------
AAL69548.3   (431) --------------------------------------------------
CDX_TABGL    (416) --------------------------------------------------
AAF21242.1   (434) --------------------------------------------------
ACV87737.1   (428) --------------------------------------------------
ABX84365.1   (441) --------------------------------------------------
CAB82861.1   (445) --------------------------------------------------
CDX_CelA     (436) --------------------------------------------------
CAA07070.1   (449) --------------------------------------------------
BAA33065.1   (448) --------------------------------------------------
AAA74233.1   (505) --------------------------------------------------
AAL21070.1   (426) --------------------------------------------------
AAA60495.1   (450) --------------------------------------------------
AAB66561.1   (382) --------------------------------------------------
AAZ32298.1   (416) --------------------------------------------------
CAA91219.1   (367) --------------------------------------------------
CAB56688.1   (425) --------------------------------------------------
AAA80156.1   (513) --------------------------------------------------
AAF21799.1   (510) --------------------------------------------------
ABU68675.1   (519) --------------------------------------------------
BAA36161.1   (534) --------------------------------------------------
AAX35883.1   (537) --------------------------------------------------
EAA64969.1   (477) --------------------------------------------------
ABI29899.1   (370) ----------------------------------------S---------
CAB01407.1   (369) ----------------------------------------S---------
AAD35119.1   (370) ----------------------------------------S---------
CAC07184.1   (400) ----------------------------------------S---------
ABE60716.1   (410) ----------------------------------------SG--------
AAC05445.1   (358) ----------------------------------------S---------
CAA33665.1   (351) ----------------------------------------S---------
AAM93475.1   (332) --------------------------------------------------
AAC38196.1   (371) ALLGDAVDVVDGVEVRTRPVPARPGFVVDPDTGRPGLHLTLLAADGTVLD
AAQ38005.1   (403) --------------------------------------------------
AAF21798.1   (405) --------------------------------------------------
CAP58431.2   (394) ----------------------------------------P---------
AAA34314.1   (453) --------------------------------------------------
AAA34315.1   (457) --------------------------------------------------
CAA26662.1   (449) --------------------------------------------------
AAB67972.1   (443) --------------------------------------------------
BAE57053.1   (439) --------------------------------------------------
CAE01320.1   (488) --------------------------------------------------
AAA18473.1   (397) --------------------------------------------------
AAA91297.1   (414) --------------------------------------------------
BAE58551.1   (474) ----------------------------------------DLDWNMWSMG
EAL91070.1   (425) --------------------------------------------------
AAB08445.1   (444) ----------------------------------------TG--------
Consensus    (701)

751                                              800
CDX_CBGL1    (423) -------------------------CSDRGC---NEGTLAMGW-----
ABP88968.1   (453) -------------------------CADRGC---DQGTLAMGW-----
ABU35789.1   (436) -------------------------CPDRGC---DNGTLAMAW-----
BAA19913.1   (435) -------------------------CSDRGC---DNGTLAMAW-----
BAA10968.1   (435) -------------------------CSDRGC---DNGTLAMAW-----
CAD67686.1   (436) -------------------------CDDRGC---DNGTLAMAW-----
ACD86466.1   (434) -------------------------CSDRGC---DNGTLAMGW-----
AAL69548.3   (431) -------------------------CSDRGC---DNGTLAMGW-----
CDX_TABGL    (416) -------------------------CSDRGC---DNGTLAMGW-----
AAF21242.1   (434) -------------------------CPDRGC---ANGTLAMGW-----
ACV87737.1   (428) -------------------------CSDRGC---DNGTLAMGW-----
ABX84365.1   (441) -------------------------CADHGC---DNGTLAMGW-----
CAB82861.1   (445) -------------------------FPDHGG---NNGTLAMGW-----
```

TABLE 14-continued

| | | |
|---|---|---|
| CDX_CelA | (436) | ---------------------------QSGGWTISWQGTGNRNDEFPG |
| CAA07070.1 | (449) | ---------------------------QCGGWTIEWQGVNGND--LTT |
| BAA33065.1 | (448) | ---------------------------QCGGWTIEWQGVAGND--LTI |
| AAA74233.1 | (505) | ---------------------------WSVHWQGAYEDSEFPFG---- |
| AAL21070.1 | (426) | ---------------------------VMGSWSAAGVANQS------ |
| AAA60495.1 | (450) | ---------------------------VMGSWSAAGVADQS------ |
| AAB66561.1 | (382) | ---------------------------MTGTWSVASRMKDA------ |
| AAZ32298.1 | (416) | ---------------------------QLGTWAFDGQKAHT------ |
| CAA91219.1 | (367) | -----------------------DYAYPCHIESLLEMRETDNVFNTPLP |
| CAB56688.1 | (425) | ----------------------------DYTAPQRPGGG----- |
| AAA80156.1 | (513) | ------------------------------------------------ |
| AAF21799.1 | (510) | ------------------------------------------------ |
| ABU68675.1 | (519) | -------------------------SMGPAAHWDYPIDKEL----- |
| BAA36161.1 | (534) | -------------------------PVPPSE--TYPINLDV----- |
| AAX35883.1 | (537) | -------------------------PTPEVD--GYPVNMDV----- |
| EAA64969.1 | (477) | ----------------------------------------N----- |
| ABI29899.1 | (371) | -----------------------GDTHPRYAISILEGIKERG---LNF |
| CAB01407.1 | (370) | -----------------------GDTHPRYAISILEGIKERG---LNF |
| AAD35119.1 | (371) | -----------------------GDTHPRYTISILEGIKERN---MKF |
| CAC07184.1 | (401) | -----------------------GCVNVPYVVDMVHGLQNAG---IAT |
| ABE60716.1 | (412) | -----------------------DVNAASTATIAQGLAARFPVN--- |
| AAC05445.1 | (359) | ------------------------SHINSFRTVSALEAVDG----WENI |
| CAA33665.1 | (352) | ------------------------SHITPTRLDDIYEEIKKAGADKVNL |
| AAM93475.1 | (332) | -----------------------------------WG------ |
| AAC38196.1 | (421) | ERHDAPSTVMVGFDDDFPQAVARVRFRARVAGEGALEVGAIGVGRWQVTA |
| AAQ38005.1 | (403) | --------------------------SSQVDPIGGEAVKGPGK--- |
| AAF21798.1 | (405) | -------------------------SSQVTSVGGNPVVIPVGG---EG |
| CAP58431.2 | (395) | -------------------------DCVDQGC---AKGTTAMGWG---- |
| AAA34314.1 | (453) | -------------------------YQCEDQSC---TNGALFQGW----- |
| AAA34315.1 | (457) | -------------------------YECSDQSC---VDGALFEGW----- |
| CAA26662.1 | (449) | -------------------------CSLRGCG---SGAIGTGY----- |
| AAB67972.1 | (443) | -------------------------NACPDKGC---NKGVLTMGW----- |
| BAE57053.1 | (439) | -------------------------NSCTDKGC---NKGVLTMGW----- |
| CAE01320.1 | (488) | -------------------------CVDRGCN---RGILAIGWG---- |
| AAA18473.1 | (397) | -------------------------PSCNDKGC---DDGALGMGW----- |
| AAA91297.1 | (414) | -----------------------GGFSFFSFDVKAIENKTLISGG----- |
| BAE58551.1 | (484) | YDNSLTYPNGSAVDAMMLKYIFLSSANPSAFGPGVALNATTITGG----- |
| EAL91070.1 | (425) | -------------------------FNWLSYSPAIQENHTLWVGG----- |
| AAB08445.1 | (446) | -------------------------DDSGPWGA---DIGALSVGG---- |
| Consensus | (751) |                             G        G L   G |

| | | 801                                              850 |
|---|---|---|
| CDX_CBGL1 | (438) | ---------GSGTANYP-YLVSPDAALQARAIQDGT---------RYES |
| ABP88968.1 | (468) | ---------GSGSTEFP-YLVTPDTAIQSKVLEYGG---------RYES |
| ABU35789.1 | (451) | ---------GSGTANFP-YLVTPEQAIQREVISNGG---------NVFA |
| BAA19913.1 | (450) | ---------GSGTANFP-YLVTPEQAISNEVLKNKN---------GVFT |
| BAA10968.1 | (450) | ---------GSGTAEFP-YLVTPEQAIQAEVLKHKG---------SVYA |
| CAD67686.1 | (451) | ---------GSGTANFP-YLVTPEQAIQNEVLQGRG---------NVFA |
| ACD86466.1 | (449) | ---------GSGTANFP-YLITPEQAIQNEVLNYGNGD------TNVFA |
| AAL69548.3 | (446) | ---------GSGTANFP-YLVTPEQAIQREVLSRN---------GTFTG |
| CDX_TABGL | (431) | ---------GSGTADFP-YLVTPEQAIQNEILSKGK---------GLVSA |
| AAF21242.1 | (449) | ---------GSGTADFP-YLVTPAQAIENEVITKGVG--------EAMS |
| ACV87737.1 | (443) | ---------GSGTANFP-YLVTPEQAIQAEVVKNGG---------MFTA |
| ABX84365.1 | (456) | ---------GSGTADYP-YLVTPLEAIKRTVGDHGG---------VIAS |
| CAB82861.1 | (460) | ---------GSGTSDYP-YLVTPLESIKATVAQNGG---------IVTS |
| CDX_CelA | (457) | ---------ATSILGGIRDAVADAGGSVEFDVAG---------------- |
| CAA07070.1 | (468) | ---------GTTILNAIKKTVDPTTQVIYNENP--------------D- |
| BAA33065.1 | (467) | ---------GTTILTAIKKTVDPSTQVVYQQNP--------------D- |
| AAA74233.1 | (522) | ---------TSILTGLREITNDTADFNIQYTIG--------------HE |
| AAL21070.1 | (440) | ---------VTVLAGIQNAVGDGAKILYAKGANITNDKGIVDFLNLYEE |
| AAA60495.1 | (464) | ---------VTVLTGIKNAVGENGKVLYAKGANVTSDKGIIDFLNQYEE |
| AAB66561.1 | (396) | ---------VSIMTGLKETVKG-VNFIYAKGSNVFYDAKMEEKATMFGK |
| AAZ32298.1 | (430) | ---------VTPLKALQARFPG--LVDYVPG---------LT--YS- |
| CAA91219.1 | (393) | ---------ESLEAKDIYVPIVTVLQGIKAKVSSN---------TEVLYA |
| CAB56688.1 | (436) | ---------ITVLEGIRAAVAAGTEVVHDRGCALVGDDVSGVPAAVALA |
| AAA80156.1 | (513) | -----------------FIVVNTPEQADVALIRTHTP----------- |
| AAF21799.1 | (510) | -----------------FTIAASLDEADIALIRLKAP------------- |
| ABU68675.1 | (535) | -------------VGKYFQWTEDPEAADFALVMIQEPFP------GAGYD |
| BAA36161.1 | (548) | -------------VRKYFDVTDRPADADFALVCIESPRS------TKGYS |
| AAX35883.1 | (551) | -------------IRKYFNFTDEPETADFAIVFITGADS------GSGYS |
| EAA64969.1 | (478) | -------------YTVVNTTEEADFALLRYNAPYE------------- |
| ABI29899.1 | (393) | ---------DEELAKTYEDYIKKMRETEEYKPRRDSWGT------IIK-P |
| CAB01407.1 | (392) | ---------DEELAKIYEDYIKKMRETEEYKPRRDSWGT------IIK-P |
| AAD35119.1 | (393) | ---------DEELASTYEEYIKKMRETEEYKPRTDSWGT------VIK-P |
| CAC07184.1 | (423) | ---------TKQLTEIYENYVKYAKAKLQADKPEMWFL------DQGQP |
| ABE60716.1 | (433) | ---------EALQSYYRDFYENNKVYHEGQFGAKG---------YYTCA |
| AAC05445.1 | (380) | ---------TYAKGFSLDNDEINTELEQQAVEAAMNADK------VVVFA |
| CAA33665.1 | (377) | ---------VYSEGYRLENDGIDEELINEAKKAASSSDV------AVVFA |
| AAM93475.1 | (334) | -------------CATTHPSMVDIPLDEIRAFAAPG---------VEVQHF |
| AAC38196.1 | (471) | GGTELAWTLATSGTGFAEEMLAPPTRTDQVHVGSDAVVDATVVLRSSTRS |

TABLE 14-continued

```
AAQ38005.1   (420) ----------KEWPGDPVYFPSSPLKAMQAEAPG--------------AR
AAF21798.1   (425) ---------MLAAFLRQAYHNSSPLKALKERLPN--------------AT
CAP58431.2   (412) -----------SGTVDFP-YLVTPLDGITARAG-----------DDVEV
AAA34314.1   (470) ----------GSGSVGSPKYQVTPFEEISYLARKNKMQF------DYIRE
AAA34315.1   (474) ----------GSGSVGYPKYQVTPFEEISANARKNKMQF------DYIRE
CAA26662.1   (464) ----------GSGAGTFS-YFVTPADGIGARAQQEK-----------ISY
AAB67972.1   (460) ----------GSGTSNLP-YLVTPEDAIRNISKN-----------TEFH
BAE57053.1   (456) ----------GSGTSRLP-YLITPQEAIANISSN-----------AEFH
CAE01320.1   (504) ----------SGTANFA-HLTAPATSIQNYLLQSNP-------TITYRS
AAA18473.1   (414) ----------GSGAVNYP-YFVAPYDAINTRASSQG-TQ------VTLSN
AAA91297.1   (436) ----------GSGTNTPS-YVDAPFNAFVAKAREDNT--------FLSWD
BAE58551.1   (529) ----------GSGASTAS-YIDAPFNAFQRQAYDDDT--------FLAWD
EAL91070.1   (445) ----------GSGANNAA-YIDAPIDRQAYEDGT---------SVLYD
AAB08445.1   (463) ----------GSGAGRHT-HLVSPLAAIRKRTESVGG--------RVQYL
Consensus    (801)           SG    F  YL TP  AI 851                                            900
CDX_CBGL1    (468) VLSNYAEEKTKA-LVSQANA--------------------TAIVFVNA
ABP88968.1   (498) IFDNYDDNAILS-LVSQPDA--------------------TCIVFANA
ABU35789.1   (481) VTDNGALSQMA--DVASQSS--------------------VSLVFVNA
BAA19913.1   (480) ATDNWAIDQIE--ALAKTAS--------------------VSLVFVNA
BAA10968.1   (480) ITDNWALSQVE--TLAKQAS--------------------VSLVFVNS
CAD67686.1   (481) VTDSWALDKIA--AARQAS---------------------VSLVFVNS
ACD86466.1   (482) VTDNGALGQMA--ALASTAS--------------------VALVFVNA
AAL69548.3   (476) ITDNGALAEMA--AAASQAD--------------------TCLVFANA
CDX_TABGL    (462) VTDNGALDQME--QVASQAS--------------------VSIVFVNA
AAF21242.1   (480) VFDNYATSQIE--SVVSQAT--------------------VSLVFVNA
ACV87737.1   (473) ITDSGATNTTAN-TVAAQAS--------------------ACLVFANA
ABX84365.1   (486) VTDNYAFSQIM--ALAKQAT--------------------HAIVFVNA
CAB82861.1   (490) VTDNWAYTQIQ--TLAKQAS--------------------VAIVFVNA
CDX_CelA     (482) -----------------QYK--------------------TKPDVAIV
CAA07070.1   (493) -------SN-------YVKT--------------------NSFDYAIV
BAA33065.1   (492) -------AN-------FVKS--------------------NKFSYAIV
AAA74233.1   (548) IGVPTNQTSIDEAVELAQSS--------------------DVVVV
AAL21070.1   (480) AVKIDPRSPQAMIDEAVQAA--------------------KQADVVVA
AAA60495.1   (504) AVKVDPRSPQEMIDEAVQTA--------------------KQSDVVVA
AAB66561.1   (435) TANRDSRSKEELLKEAVATA--------------------NKADVVVL
AAZ32298.1   (454) ------REKRSGFSDVVAAA--------------------RSADVVLA
CAA91219.1   (425) KGCDVLNNSKDGFKEAVEIA--------------------KQADVAVV
CAB56688.1   (476) AGSDVAVLVLGG--SSARSP--------------------DTVFDANG
AAA80156.1   (533) -------------------------------------------YEQPHK
AAF21799.1   (530) -------------------------------------------FQTLHP
ABU68675.1   (566) VNDRKRGGNGYVPISLQYRP--------------------YKAEYARP
BAA36161.1   (579) KADAEAGGNGYVPISLQYRP--------------------YTADHARE
AAX35883.1   (582) KGDVEAGGNGYVPISLQYAP--------------------YTAEHARE
EAA64969.1   (500) ---------------PRNG---------------------TFEA
ABI29899.1   (427) KLPENFLSEKEIHKLAKKND--------------------VAVIVISR
CAB01407.1   (426) KLSENFLSEKEVHKLAKKND--------------------VAVIVISR
AAD35119.1   (427) KLPENFLSEKEIKKAAKKND--------------------VAVVVISR
CAC07184.1   (458) KLDEIEITQRCVEHEVGDAD--------------------AAIITIAR
ABE60716.1   (464) EAPISGELAALIANAAATQQ--------------------AAVISIGR
AAC05445.1   (415) GLPDSFES-----------------------------------
CAA33665.1   (412) GLPDEYES-----------------------------------
AAM93475.1   (363) PLGGGDKLKLAEAAIAGAAS--------------------ADVVLFFA
AAC38196.1   (521) VTVGDADPGTDAGAAAEPLAGVGLFGLVARPAPEAEDDVITRAAAAAQA
AAQ38005.1   (446) ITYDPGTSIASAVRAARAAD--------------------VVVVYATQ
AAF21798.1   (452) IRFNDGRYSAAAAALARQSD--------------------IVILFANQ
CAP58431.2   (438) VHTFDDWDEEGAAELAKDAD--------------------IAFVFSMT
AAA34314.1   (504) SYDLAQVTKVA-----SDAH--------------------LSIVVVSA
AAA34315.1   (508) SFDLTQVSTVA-----SDAH--------------------MSIVVVSA
CAA26662.1   (492) EFIGDSWNQAAAMDSALYAD--------------------AAIEVANS
AAB67972.1   (487) ITDKFPNNVQP-----GPDD--------------------VAIVFVNA
BAE57053.1   (483) ITDTFPLGVTA-----GPDD--------------------IAIVFINS
CAE01320.1   (535) IFDDYAYDEIAK--AASTAD--------------------VSIVHVSS
AAA18473.1   (446) TDNTSSGASAA-----RGKD--------------------VAIVFITA
AAA91297.1   (467) FTSA------EP-VANPASD--------------------ACIDFINA
BAE58551.1   (560) FASQ------NP-LVNPASD--------------------ACIVFINE
EAL91070.1   (476) ISSE------DP-EVDPTTD--------------------ACLVFINS
AAB08445.1   (494) LSNSRIVNDDFT-SIYPTPE--------------------VCLVFLKT
Consensus    (851)                 A  A                        AIVFV A 901                                            950
CDX_CBGL1    (495) DSGEGYINVDGNEGDRK----NLTLWNNGDTLVKNVSSWCSN-----TIV
ABP88968.1   (525) DSGEGYITVDNNWGDRN----NLTLWQNADQVISTVSSRCNN-----TIV
ABU35789.1   (507) DSGEGYISVDGNEGDRK----NLTLWKNGEAVIDTVVSHCNN-----TIV
BAA19913.1   (506) DSGEGYINVDGNLGDRK----NLTLWRNGDNVIKAAASNCNN-----TIV
BAA10968.1   (506) DAGEGYISVDGNEGDRN----NLTLWKNGDNLIKAAANNCNN-----TIV
CAD67686.1   (507) DSGESYLSVDGNEGDRN----NITLWKNGDNVVKTAANNCNN-----TVV
ACD86466.1   (508) DSGEGYISVDGNEGDRK----NMTLWKNGEELIKTATANCNN-----TIV
AAL69548.3   (502) DSGEGYITVDGNEGDRK----NLTLWQGADQVIHNVSANCNN-----TVV
```

TABLE 14-continued

```
CDX_TABGL    (488) DSGEGYINVDGNEGDRK----NLTLWKGGEEVIKTVAANCNN-----TIV
AAF21242.1   (506) GAGEGFISVDGNEGDRK----NLTLWKNGDELIKTVASMCNN-----TVV
ACV87737.1   (500) DSGEGYITVDGNVGDRK----NLTLWQNGEAMISAVAGNCNN-----TIV
ABX84365.1   (512) DSGEGYITVDGNEGDRN----NLTLWQNGEELVRNVSGYCNN-----TIV
CAB82861.1   (516) DSGEGYITVDGNAGDRN----NLTLWQDGDTLIKNVSSLCNN-----TIV
CDX_CelA     (493) VFGEEP------YAEFQGDVETLEYQPDQKQDLALLKKLKDQG--IPVVA
CAA07070.1   (507) VVGEPP------YAEMQGDSFNLTIPEPGPTTISSVCGAVK-----CVVV
BAA33065.1   (506) VVGEVP------YAEMFGDSSNLTIAEPGPSTISNICGSVK-----CVVV
AAA74233.1   (573) VIGELP------EAETPGDIYDLSMDPNEVLLLQQLVDTGKP----VVL
AAL21070.1   (508) VVGESQG-----MAHEASSRTNITIPQSQRDLITALKATGK-----PLVL
AAA60495.1   (532) VVGEAQG-----MAHEASSRTDITIPQSQRDLIAALKATGK-----PLVL
AAB66561.1   (463) AIGETAE-----LSGESSSRANIEIPQAQKDLLTELKKTGK-----PIVM
AAZ32298.1   (476) FLGEEAI-----LSGEAHSLADLNLMGSQSELLEALKTAGK-----PVVA
CAA91219.1   (453) VVGDKSGLTDGCTSGESRDRADLNLPGVQEELIKAIYETGTP-----VIV
CAB56688.1   (502) AAVTGTGTPSGMTCGEGVDLADLALPPGQRALLTAVSATGTP-----VVV
AAA80156.1   (539) NFFFG-------S-RHHEGSLAFRNDNPDYQAIVRASAKV------PTLV
AAF21799.1   (536) GFFFG-------R-MQHEGDLDFKEGDAGLTLVRQAAAKV------PVIL
ABU68675.1   (594) VSIAGGDPKETFTNRSYRGKKVTTYNESDLDLVIETKRRMGD---KPVVV
BAA36161.1   (607) TSLAG--DPRDVLNRSYKGKTAAVANEGDLDAVLETKRLMNG---KPVVV
AAX35883.1   (610) KSIAG--DERDIVNRSYKGKMISATNASDLDAVLKAKALMKG---KPVIV
EAA64969.1   (508) NFHAG----------------SLAFNATEKARQAKIYSSLP------TIV
ABI29899.1   (455) ISGEG--------YDRKPVKGDFYLSDDETDLIKTVSREFHEQGKK-VIV
CAB01407.1   (454) ISGEG--------YDRKPVKGDFYLSDDETDLIKTVSREFHEQGKK-VIV
AAD35119.1   (455) ISGEG--------YDRKPVKGDFYLSDDELELIKTVSKEFHDQGKK-VVV
CAC07184.1   (486) QAGEG--------MDRS-IEGEFNLTDHEKAMISRVSDVFHANNKP-VIV
ABE60716.1   (492) QAGEG--------ADRSSGKGDYLLGDDERALIDAVSSAFHTQG-KKVVV
AAC05445.1   (423) ---EG---------FDRK----HMQLPQCQIDLIDKLSEVNP--N---IVV
CAA33665.1   (420) ---EG---------FDRT----HMSIPENQNRLIEAVAEVQS--N---IVV
AAM93475.1   (391) NTENGYDG------E-GSDRLHLGLADGQDALIARIATANPR-----TIV
AAC38196.1   (571) DVAVVVVGLTEEEETESVDKSTIALPGAQDALVRAVAAAARR-----TVV
AAQ38005.1   (474) FTFEG------------MDAPSMHLDDNADALITAVAAANPR-----TVV
AAF21798.1   (480) WMSEG------------MDAYDLKLPQGQDALIEAVAEANPN-----AVI
CAP58431.2   (466) KAGEEYIVVDGNHDRKN-----LSLWNNGDNLIRAVADANEN-----TVV
AAA34314.1   (527) ASGEGYITVDGNQGDR----KNLTLWNNGDKLIETVAENCAN-----TVV
AAA34315.1   (531) VSGEGYLIIDGNRGDK----NNVTLWHNSDNLIKAVAENCAN-----TVV
CAA26662.1   (520) VAGEEIGDVDGNYGDLN----NLTLWHNAVPLIKNISSINNN-----TIV
AAB67972.1   (510) DSGENYIIVESNPGDRTV--AQMKLWHNGDELIESAAKKFSN----VVVV
BAE57053.1   (506) DSGENYITVDGNPGDRTL--AGLHAWHNGDNLVKAAAEKFSN-----VVV
CAE01320.1   (561) DSGEGYLTVEGNQGDRS----NTSLWNKGDELILKAAEACNN-----VVV
AAA18473.1   (469) DSGEGYITVEGNAGDR----NNLDPWHNGNALVQAVAGANSN-----VIV
AAA91297.1   (488) AASE--------GYDRP----NLADKY-SDKLVEAVASQCSN-----TIV
BAE58551.1   (581) QSSE--------GWDRP----SLADPY-SDTLVQNVASQCSN-----TMV
EAL91070.1   (497) YATE--------GWDRP----GLADNS-SDTLVKNVARKCAN-----TIV
AAB08445.1   (521) WARE--------GTDRL----SYENDWNSTAVVNNVARRCPN-----TIV
Consensus    (901)      SGEG        GDR      L L    D LI  VA   N       TVV 951                                          1000
CDX_CBGL1    (536) VIHSVGPVLLTDWYDNP---NITAILWAGLPGQESGNSITDVLYGK----
ABP88968.1   (566) VLHSVGPVLLNGIYEHP---NITAIVWAGMPGEESGNALVDILWGN----
ABU35789.1   (548) VIHSVGPVLIDRWYDNP---NVTAIIWAGLPGQESGNSLVDVLYGR----
BAA19913.1   (547) IIHSVGPVLVNEWYDNP---NVTAILWGGLPGQESGNSLADVLYGR----
BAA10968.1   (547) VIHSVGPVLVDEWYDHP---NVTAILWAGLPGQESGNSLADVLYGR----
CAD67686.1   (548) IIHSVGPVLIDEWYDHP---NVTGILWAGLPGQESGNSIADVLYGR----
ACD86466.1   (549) IMHTPNAVLVDSWYDNE---NITAILWAGMPGQESGRSLVDVLYGR----
AAL69548.3   (543) VLHTVGPVLIDDWYDHP---NVTAILWAGLPGQESGNSLVDVLYGR----
CDX_TABGL    (529) VMHTVGPVLIDEWYDNP---NVTAIVWAGLPGQESGNSLVDVLYGR----
AAF21242.1   (547) VMHTAGPVLNKWYDHP----NVTAILWAGLPGQESGNALGDVIYGR----
ACV87737.1   (541) ILHTVGPVLIEDWVNHP---NITAVLWAGLPGEQSGNSLVDVLYGS----
ABX84365.1   (553) VIHSVGPVLVDSFNNSP---NVSAILWAGLPGQESGNAITDVLYGR----
CAB82861.1   (557) VIHSVGPVLVNSFYDSE---NVTAILWAGLPGQESGNAIADILYGR----
CDX_CelA     (535) VFLSGRPMWVNPELN-----ASDAFVAAWLPGTE-GGGVADVLFTDKAGK
CAA07070.1   (546) VIS-GRPVVLQPYVS-----YMDALVAAWLPGTE-GQGVTDVLFGD----
BAA33065.1   (545) VVS-GRPVVLEPYVS-----KMDALVAAWLPGTE-GQGVADALFGD----
AAA74233.1   (612) ILVEARPRILPPDLVYS----CAAVLMAYLPGSEGGKPIANILMGN----
AAL21070.1   (548) VLMNGRPLALVKEDQ-----QADAILETWFAGTEGGNAIADVLFGD----
AAA60495.1   (572) VLMNGRPLALVKEDQ-----QADAILETWFAGTEGGNAIADVLFGD----
AAB66561.1   (503) VLFTGRPLVLNDENK-----QADAIVNAWFAGSEAGYAIADVLFGD----
AAZ32298.1   (516) TVMAGRPLTIERDLP-----NVNAMLYSFHPGTMGGPALANLLFGD----
CAA91219.1   (498) VLINGRPMSISWIAEK-----IPAIIEAWLPGEEGGRAVADVIFGD----
CAB56688.1   (547) VLVQGRPHALTELDAP-----AAAVLSAWYPGPRGGRAVAEVLFGDAE--
AAA80156.1   (575) TVYMERPAILTNVVD--------KTRAVVANFGVSDSVLLNRLMSG----
AAF21799.1   (572) TIYLDRPAILTNIKP--------HAATLIGEFGITDAALFDALTGK----
ABU68675.1   (641) VIGVSRPLVLAELEP--------YADAILLTFGVQNQAVLDILSGA----
BAA36161.1   (652) SIALSNPAVAAEFEP--------AADAILAHFGVQDQAILDILTGA----
AAX35883.1   (655) SLQLSKPSIVAEFEA--------AADAVATFGVQDQAFLDILIGE----
EAA64969.1   (536) DIILDRPAVIPEVVEQ--------AQAVLASYGSDSEAFLDVVFGVS---
ABI29899.1   (496) LLNIGSPVEVVSWR-----DLVDGILLVWQAGQETGRIVADVLTGR----
CAB01407.1   (495) LLNIGSPVEVVSWR-----DLVDGILLVWQAGQETGRIVADVLTGR----
AAD35119.1   (496) LLNIGSPIEVASWR-----DLVDGILLVWQAGQEMGRIVADVLVGK----
CAC07184.1   (526) IINSGSVMETASWR-----DRVDAILVAWQPGEEGGNSVADVLIGK----
```

TABLE 14-continued

```
ABE60716.1  (533) VLNVNGVIDTAQWGD-----KVDGILLAYMAGQETGHAVADVLSGA----
AAC05445.1  (453) VLHNGAPVEMPFANGDEDSNSVKAILEMYLSGQAAGEAVVRILFGE----
CAA33665.1  (450) VLLNGSPVEMPWID------KVKSVLEAYLGGQALGG-RWRMCYSV----
AAM93475.1  (429) IVASPDAVEMPWLAEVP------SVLATFFAGQGMGHAVASILFGR----
AAC38196.1  (616) VVNAATPVLMPWLDD------VDAVLWAGLPGQEGGHAVAAALLGD----
AAQ38005.1  (507) VMETGDPVLMPWNSS------VAGVLEAWFPGSGGGPAIARLLFGK----
AAF21798.1  (513) VLQTGGPVLMP-WKDKVG-----AIVSAWYSGQKGGEAIADILVGK----
CAP58431.2  (506) VIHSVGPVDMP-WIDHP---NIKAVVWPHLPGQETGNSLADVLFGD----
AAA34314.1  (568) VVTSTGQINFEGFADHP---NVTAIVWAGPLGDRSGTAIANILFGK----
AAA34315.1  (572) VITSTGQVDVESFADHP---NVTAIVWAGPLGDRSGTAIANILFGN----
CAA26662.1  (561) IVTSGQQIDLEPFIDN---ENVTAVIYSSYLGQDFGTVLAKVLFGD----
AAB67972.1  (554) VVHTVGPIIMEKWIDLL---RSRVSCLPDFQDK-KLEILLLISCSE----
BAE57053.1  (549) VVHTVGPILMEEWIDLD---SVKAVLVAHLPGQEAGWSLTDILFGD----
CAE01320.1  (602) VIHSVGPVDMEAWINHP---NVTAVLLAGLPGQEAGSAEVDVLWGS----
AAA18473.1  (510) VVHSVGAIILEQILALP---QVKAVVWAGLPSQESGNALVDVLWGD----
AAA91297.1  (520) VIHNAGIRLVDNWIEHE---NVTGVILAHLPGQDTGTSLIEVLYGN----
BAE58551.1  (613) VIHNAGVRLVDRWIEND---NITAVIAHLPGQDSGRALVEVMYGK----
EAL91070.1  (529) TIHNAGIRVVGEWIDHE---NVTAVIFAHLPGQDSGRALVELLYGR----
AAB08445.1  (554) VTHSGGINTMP-WADNA---NVTAILAAHYPGQENGNSIMDILYGD----
Consensus   (951) VI S GPVLV  W D     NV AIL A LPGQE G ALADVLYG 1001                                          1050
CDX_CBGL1   (579) --VNPAARSPFTWGKTRESYGADVLYKPN-------------NGNGAPQQ
ABP88968.1  (609) --VNPAGRTPFTWAKSREDYGTDIMYEPN-------------NGGQRAPQQ
ABU35789.1  (591) --VNPSAKTPFTWGKTRESYGAPLLTEPN-------------NGNGAPQQ
BAA19913.1  (590) --VNPGAKSPFTWGKTREAYQDYLVTEPN-------------NGNGAPQE
BAA10968.1  (590) --VNPGAKSPFTWGKTREAYGDYLVRELN-------------NGNGAPQD
CAD67686.1  (591) --VNPGAKSPFTWGKTRESYGSPLVKDAN-------------NGNGAPQS
ACD86466.1  (592) --TNPGGKTPFTWGKERKDWGSPLLTKPN-------------NGHGAPQQ
AAL69548.3  (586) --VNPG-KTPFTWGRARDDYGAPLIVKPN-------------NGKGAPQQ
CDX_TABGL   (572) --VSPGGKTPFTWGKTRESYGAPLLTKPN-------------NGKGAPQD
AAF21242.1  (590) --VNPGAKSPFTWAATSEDYGVSILKEPN-------------AATKAPQI
ACV87737.1  (584) --VNPGGKTPFTWGKQRSDWGVDVIYEPS-------------NGDGAPQQ
ABX84365.1  (596) --VNPGGKLPFTIGKSAEEYGPDIIYEPT-------------AGHGSPQA
CAB82861.1  (600) --HNPGGKLPFTIGSDAAEYGPDLIYEPT-------------NNSSSPQD
CDX_CelA    (579) VQHDFAGKLSYSWPRTAAQTTVNRG------------------------
CAA07070.1  (585) --YGFTGKLARTWFKTVDQLPMNVG------------------------
BAA33065.1  (584) --YGFTGKLARTWFKRVDQLPMNFD------------------------
AAA74233.1  (654) --VNPGGRLPLTYPGTTGDIGVPYYHKYS--------------------
AAL21070.1  (589) --YNPGGKLPISFPRSVGQIPVYYSHLNT-------------GRPYNPE
AAA60495.1  (613) --YNPSGKLPMSFPRSVGQIPVYYSHLNT-------------GRPYNAD
AAB66561.1  (544) --VNPGGKLPMTFPRSVGQVPIYYNAKNT-------------GRPLSDE
AAZ32298.1  (557) --VNPSGKTPITFLRTVGQAPLYYSHNMT-------------GRPYKGE
CAA91219.1  (539) --YNPGGKLPISIPQSVGQLPVYYYHKPSG-------------------
CAB56688.1  (590) ----PRGRLPVSVPRSAAQLPVYYNGKDHR-------------------
AAA80156.1  (613) --AAYTAKLPFELPSSMSAVRNQQP------------------------
AAF21799.1  (610) --VAPMGKLPFELPATMAAVRAQSP------------------------
ABU68675.1  (679) --AEPSGLLPMQLPADMRTVEEQAE------------------------
BAA36161.1  (690) --FEPQALLPFRMPADMTTVEKQLE------------------------
AAX35883.1  (693) --AEPSGLLPMQIPANMKTVEEQLE------------------------
EAA64969.1  (575) ---KPEGKLPFDLPRSMDAVEAQAED-----------------------
ABI29899.1  (537) --INPSGKLPTTFPRDYSDVPSWTFPGEP----------KDNPQK----V
CAB01407.1  (536) --INPSGKLPTTFPRDYSDVPSWTFPGEP----------KDNPQK----V
AAD35119.1  (537) --INPSGKLPTTFPRDYSDVPSWTFPGEP----------KDNPQR----V
CAC07184.1  (567) --ANPSGHLTSWPISAADVPSTKNFPQQPAYYNLSDKLYSNNMKGVNYT
ABE60716.1  (574) --VNPSGKLAQSFPHSYASVPSAGTFPGEDTDG---------DGEPDDL
AAC05445.1  (499) --VNPSGKLAETFPLRLEDNPSYLNFPGEA----------D--I----V
CAA33665.1  (489) --KSIVGKLAETFPVKLSHNPSYLNFPGED----------D--R----V
AAM93475.1  (469) --TNPSGKLTVTFPKRLQDVAAYLHYPGE-----------N---DRH
AAC38196.1  (656) --QEPTGRLVTTFPAADGAAPAWSVTPVDG-----------------DL
AAQ38005.1  (547) --VAPSGHLTMTFPQAESQLAHPDIAGVTADN------VFEMQFHTDQEL
AAF21798.1  (553) --TNPSGRLPSTFPASADQYPHPEVPGWNLP-----------EKQQFDV
CAP58431.2  (548) --VNPSGPSSIAPLAGLQRTTLLIEYTEELN-------------------
AAA34314.1  (611) --ANPSGHLPFTIAKTDDDYIPIETYSPS-------------SGEPEDNH
AAA34315.1  (615) --ANPSGHLPFTVAKSNDDYIPIVTYNPP-------------NGEPEDNT
CAA26662.1  (604) --ENPSGKLPFTIAKDVNDYIPVIEKVDVP----------------DPVD
AAB67972.1  (596) --TSVRVAASIYDTESRIGLSDSVSLINQ-------------RFG-QIQD
BAE57053.1  (592) --YSPSGHLPYTIPHSESDYPESVGLIAQ-------------PFG-QIQD
CAE01320.1  (645) --TNPSGRLPYTIAKKPSDYPAELLYESN-------------MTVPQI
AAA18473.1  (553) --VSPSGKLVYTIAKSPNDYNTRIVS--------------GGS----D
AAA91297.1  (563) --QSPSGRLPYTVAKKASDYGGLLWPTEPE------------GDLDLYFPQS
BAE58551.1  (656) --QSPSGRLPYTVAKNESDYGSLLNPVIQS----------GTDDIYYPQD
EAL91070.1  (572) --ANPSGKLPYTVAKKVEDYGSLLHPSLP----------ETPYGLFPQS
AAB08445.1  (596) --VNPSGRLPYTIPKLATDYDFPVVNITN----------EAQDPYVWQA
Consensus   (1001)   NPSGKLPFTWPKS           L 1051                                          1100
CDX_CBGL1   (614) DFTEG-------VFIDYRYFDKVDDDSVIYEFGHGLSYTTFEYSNIRVVK
ABP88968.1  (644) DFTES-------IYLDYRHFDKAG-IEPIYEFGFGLSYTTFEYSDLRVVK
ABU35789.1  (626) DFNEG-------VFIDYRHFDKRN-ETPIYEFGHGLSYTTFGYSHLRVQA
```

TABLE 14-continued

```
BAA19913.1   (625) DFVEG-------VFIDYRGFDKRN-ETPIYEFGYGLSYTTFNYSNLEVQV
BAA10968.1   (625) DFSEG-------VFIDYRGFDKRN-ETPIYEFGHGLSYTTFNYSGLHIQV
CAD67686.1   (626) DFTQG-------VFIDYRHFDKFN-ETPIYEFGYGLSYTTFELSDLHVQP
ACD86466.1   (627) DFTD--------VLIDYRRFDKDN-VEPIFEFGFGLSYTKFEFSDIQVKA
AAL69548.3   (620) DFTEG-------IFIDYRRFDKYN-ITPIYEFGFGLSYTTFEFSQLNVQP
CDX_TABGL    (607) DFTEG-------VFIDYRRFDKYN-ETPIYEFGFGLSYTTFEYSDIYVQP
AAF21242.1   (625) DFEEG-------IFIDYRAFDKSN-TKPIYEFGFGLSYTTFTFSDLEVQP
ACV87737.1   (619) DFTEG-------IFIDYRHFDKYN-ITPTYEFGYGLSYSTFSFSDLKVTP
ABX84365.1   (631) NFEEG-------VFIDYRSFDKKN-ITPVYEFGFGLSYTNFSYSNLVVTR
CAB82861.1   (635) NFEEG-------VFIDYRAFDKQN-VTPIYEFGFGLSYTKFSYSNLTVKK
CDX_CelA     (604) ---------------------DADYNPLFAYGYGLTYKDKSKVGTLPEE
CAA07070.1   (608) ---------------------DKHYDPLPFGFGLTTKPSNRTEFIG--
BAA33065.1   (607) ---------------------DAHVDPLFPFGFGITTKPVKGY------
AAA74233.1   (681) ---------------------ENGVTTPLFQFGDGLSYTTFNYTNLACSN
AAL21070.1   (623) KPN------------KYTSRYFDEANGPLYPFGYGLSYTTFTVSDVTLSS
AAA60495.1   (647) KPN------------KYTSRYFDEANGALYPFGYGLSYTTFTVSDVKLSA
AAB66561.1   (578) RSDKCE-------FEKFRSNYIDECNTPLFPFGYGLSYTTFNYSDIQLNK
AAZ32298.1   (591) TLLDDIPAEAGQTSLGNTSYYLDYGAYPLFPFGFGLSYTSFAYSDIALDK
CAA91219.1   (567) ------------GRSHWKGDYVELSTKPLYPFGYGLSYTEFSYTNLNISN
CAB56688.1   (616) -----------------YRGYADQSAGPLHAFGHGLSYTSVVYGAPRLSQ
AAA80156.1   (636) -------------------DLPYDSAKPLFPFGYGLPH-----------
AAF21799.1   (633) -------------------ALPHDSADPLYPVGFGR-------------
ABU68675.1   (702) ------------------DVPRDMRVYVDADGHAYDFAYGLGWDGVIND
BAA36161.1   (713) ------------------DVPHDMDVYVDSAGHAYDFAFGLNWSGVIAD
AAX35883.1   (716) ------------------DVPHDMEVHVDSEGNAYDFAYGLNWSGVISD
EAA64969.1   (598) -------------------LPFDTENPVFRYGHGLEYEDN---------
ABI29899.1   (571) VYEED-------IYVGYRYYDTFG-VEPAYEFGYGLSYTTFEYSDLNVS-
CAB01407.1   (570) VYEED-------IYVGYRYYDTFG-VEPAYEFGYGLSYTTFEYSDLNVS-
AAD35119.1   (571) VYEED-------IYVGYRYYDTFG-VEPAYEFGYGLSYTKFEYKDLKIA-
CAC07184.1   (615) NHEED-------IYVGYRYFDTFN-KKVAYPFGYGLSYTTFEFGKPSVS-
ABE60716.1   (612) YYNEG-------IYVGYRYYSTFE-QAVSYPFGFGLSYTSFSYTSPAIAS
AAC05445.1   (530) KYSEG-------IFVGYRYYEKKN-MEVLYPFGHGLSYTEFEYSDIKISS
CAA33665.1   (520) EYKEG-------LFVGYRYYDTKG-IEPLFPFGHGLSYTKFEYSDISVDK
AAM93475.1   (500) AYSEA-------IYVGYRYYDRRE-LSPLFPFRFGLSFTEFRYSDLELDR
AAC38196.1   (686) EYTEG-------RFVGYRGHWADRAPAPAFWLGHGLGYATWEYADATLDT
AAQ38005.1   (589) VYDEG-------SDVGYRWFDRNH-FKPLYPFGYGLTYTTFSTDGLKVTE
AAF21798.1   (589) VYEEG-------SDVGYRRFAAKG-MKPLFPFGHGLSYTTFAYDKLKVK-
CAP58431.2   (577) --------------VGYRHDANN-IEPLFPFGHGLSYTTFEYNKLKVKK
AAA34314.1   (646) LVEND-------LLVDYRYFEEKN-IEPRYAFGYGLSYNEYEVSNAKVSA
AAA34315.1   (650) LAEHD-------LLVDYRYFEEKN-IEPRYAFGYGLSYNEYKVSNAKVSA
CAA26662.1   (636) KFTES-------IYVDYRYFDKYN-KPVRYEFGYGLSYSNFSLSDIEIQT
AAB67972.1   (630) TFTEG-------LFIDYRHFQKEN-ITPRYHFGYGLSYTTFNFTEPRLES
BAE57053.1   (626) DYTEG-------LYIDYRHFLKAN-ITPRYPFGHGLSYTTFNFTEPNLSI
CAE01320.1   (678) NYSER-------LNIDYRHFDTYN-IEPRFEFGFGLSYTTFAWNSLKFSS
AAA18473.1   (581) SFSEG-------LFIDYKHFDDAN-ITPRYEFGYGLSYTKFNYSRLSVLS
AAA91297.1   (601) NFTEG-------VYIDYKYFIQKN-ITPRYEFGYGLTYTTFDYSELEVDA
BAE58551.1   (694) NFTEG-------VYIDYKAFVAAN-ITPRYEFGYGLTYSFTFDYSDLKVST
EAL91070.1   (609) DFDEG-------VYIDYRAFDRAN-ITAQFEFGFGLSYTSFDYSGLQISN
AAB08445.1   (633) DFTEG-------LLIDYRHFDARN-ITPLYEFGYGLSYTTFEIEGVANLV
Consensus  (1051)  F E         IFI YR FD  N    PLY FGYGLSYTTF YS L V 1101                                          1150
CDX_CBGL1    (657) SN--VSEYRPTTGTTAQAPTFGNFSTDLEDYLFPKDEFPYIYQYIYPYLN
ABP88968.1   (686) KY--VQPYSPTTGTGAQAPSIGQPPSQNLDTYKFPATYKYIKTFIYPYLN
ABU35789.1   (668) LNSSSSAYVPTSGETKPAPTYGEIG--SAADYLYPEGLKRITKFIYPWLN
BAA19913.1   (667) LS--APAYEPASGETEAAPTFGEVG--NASNYLYPDGLQKITKFIYPWLN
BAA10968.1   (667) LN--ASSNAQVATETGAAPTFGQVG--NASDYVYPEGLTRISKFIYPWLN
CAD67686.1   (668) LN--ASRYTPTSGMTEAAKNFGEIG--DASEYVYPEGLERIHEFIYPWIN
ACD86466.1   (668) LN--HGEYNATVGKTKPAPSLGKPG--NASDHLFPSNINRVRQYLYPYLN
AAL69548.3   (662) IN--APPYTPASGFTKAAQSFGQPS--NASDNLYPSDIERVPLYIYPWLN
CDX_TABGL    (649) LN--ARPYTPASGSTKAAPTFGNIST-DYADYLYPEDIHKVPLYIYPWLN
AAF21242.1   (667) LR--ANPYVPTSGFTDSAPVFGNST----DHLQFPAGFDPVHLYIYPWLN
ACV87737.1   (661) LA--ASPYQPAKGQSGPAPVLGKVL--NATAYLFPDYIKRIEAFIYPWLN
ABX84365.1   (673) VN--APAYVPTTGNTTAAPTLGNSSK-DASDYQWPANLTYVNKYIYPYLN
CAB82861.1   (677) AN--AGAYTPATGQSKAAPTLGNFST-DASQYQWPSDFTYIDTFIYPYLN
CDX_CelA     (632) SG-----------------------------------------------
CAA07070.1   (634) -------------------------------------------------
BAA33065.1   (629) -------------------------------------------------
AAA74233.1   (710) CKPISGQ------------------------------------------
AAL21070.1   (661) PT-----------------------------------------------
AAA60495.1   (685) PT-----------------------------------------------
AAB66561.1   (621) TQ-----------------------------------------------
AAZ32298.1   (641) ES-----------------------------------------------
CAA91219.1   (605) RK-----------------------------------------------
CAB56688.1   (649) AR-----------------------------------------------
AAA80156.1   (655) -------------------------------------------------
AAF21799.1   (650) -------------------------------------------------
ABU68675.1   (733) ARVSIYRR-----------------------------------------
BAA36161.1   (744) ARTSRYANKRRTL------------------------------------
AAX35883.1   (747) ERTKRYGKKK---------------------------------------
```

TABLE 14-continued

```
EAA64969.1  (619) ------------------------------------------------
ABI29899.1  (612) ------------------------------------------------
CAB01407.1  (611) ------------------------------------------------
AAD35119.1  (612) ------------------------------------------------
CAC07184.1  (656) ------------------------------------------------
ABE60716.1  (654) NTLEG-------------------------------------------
AAC05445.1  (572) YE----------------------------------------------
CAA33665.1  (562) KD----------------------------------------------
AAM93475.1  (542) ------------------------------------------------
AAC38196.1  (729) DG----------------------------------------------
AAQ38005.1  (631) R-----------------------------------------------
AAF21798.1  (630) ------------------------------------------------
CAP58431.2  (612) GR----------------------------------------------
AAA34314.1  (688) AKKVDEELPEPATYLSEFSYQNAKDSKNPSDAFAPADLNRVNEYLYPYLD
AAA34315.1  (692) AKKVDEELPQPKLYLAEYSYNKTEEINNPEDAFFPSNARRIQEFLYPYLD
CAA26662.1  (678) LQPFSENAEPAANYSETYQYK---------------------------
AAB67972.1  (672) VTTLS-EYPPARKPKAGDRHTPTIS-HLLQKWPGPKTLTGSGAYLYPYLD
BAE57053.1  (668) IKALDTAYPAARPPKGSTPTYPTAK-PDASEVAWPKNFNRIWRYLYPYLD
CAE01320.1  (720) SFQLQKTSP---------------------------------------
AAA18473.1  (623) TAKSG-------------------------------------------
AAA91297.1  (643) ITNQS-------------------------------------------
BAE58551.1  (736) SSNVST------------------------------------------
EAL91070.1  (651) PKQSP-------------------------------------------
AAB08445.1  (675) AKSAKL------------------------------------------
Consensus  (1101)

1151                                         1200
CDX_CBGL1   (705) -TTDPRRASADPHYGQTAEEFLPPHATDDDPQPLLRSSGGNSPGGNRQLY
ABP88968.1  (734) STVSLRAASKDPEYGRT--DFIPPHARDSPQPLNPAGDPVASGGNNMLY
ABU35789.1  (716) -STDLEDSSDDPNYGWEDSEYIPEGARDGSPQPLLKAGG--APGGNPTLY
BAA19913.1  (713) -STDLEASSGDASYGQDSSDYLPEGATDGSAQPILPAGG--GPGGNPRLY
BAA10968.1  (713) -STDLKASSGDPYYGVDTAEHVPEGATDGSPQPVLPAGG--GSGGNPRLY
CAD67686.1  (714) -STDLKASSDDSNYGWEDSKYIPEGATDGSAQPRLPASG--GAGGNPGLY
ACD86466.1  (714) -STDLKASANDPDYGMNASAYIPPHATDSDPQDLLPASG--PSGGNPGLF
AAL69548.3  (708) -STDLKASANDPDYGLPTEKYVPPNATNGDPQPIDPAGG--APGGNPSLY
CDX_TABGL   (696) -TTDPKKSSGDPDYGMKAEDYIPSGATDGSPQPILPAGG--APGGNPGLY
AAF21242.1  (711) -STDLKESSMDRDYGLPTEKYVPPGATDGGPQALLPAGG--GPGGNPGLY
ACV87737.1  (707) -STDLKTSSGDPNYGWSTSKYVPDGAQDGSPQPVNPAGG--APGGNPALY
ABX84365.1  (720) -STDLKEASNDPEYGIE--HEYPEGATDGSPQPRIAAGG--GPGGNPQLW
CAB82861.1  (724) -STDLKTASQDPEYGLN--YTWPAGATDGTPQARIPAGG--APGGNPQLW
CDX_CelA    (634) ------------------------------------------------VP
CAA07070.1  (634) ------------------------------------------------LI
BAA33065.1  (629) ------------------------------------------------
AAA74233.1  (717) ----------------------------------------SGNYTGLGQ
AAL21070.1  (663) ---------------------------------------------MQR
AAA60495.1  (687) ---------------------------------------------MKR
AAB66561.1  (623) ---------------------------------------------LSG
AAZ32298.1  (643) ---------------------------------------------YAA
CAA91219.1  (607) --------------------------------------------VSLR
CAB56688.1  (651) --------------------------------------------VGTR
AAA80156.1  (655) ------------------------------------------------
AAF21799.1  (650) ------------------------------------------------
ABU68675.1  (741) ------------------------------------------------
BAA36161.1  (757) ------------------------------------------------
AAX35883.1  (757) ------------------------------------------------
EAA64969.1  (619) ------------------------------------------------
ABI29899.1  (612) ----------------------------------------------FD
CAB01407.1  (611) ----------------------------------------------FD
AAD35119.1  (612) ----------------------------------------------ID
CAC07184.1  (656) ----------------------------------------------LN
ABE60716.1  (659) ----------------------------------------------GS
AAC05445.1  (574) ---------------------------------------I--------SD
CAA33665.1  (564) ---------------------------------------V--------SD
AAM93475.1  (542) --------------------------------------------VVLKD
AAC38196.1  (731) ------------------------------------------------
AAQ38005.1  (632) ------------------------------------------------
AAF21798.1  (630) -----------------------------------------------G
CAP58431.2  (614) ---------------------------------------------KKD
AAA34314.1  (738) SN--VTLKDG----------NYEYPDGYSTEQRTTPNQPGGGLGGNDALW
AAA34315.1  (742) SN--VTLKDG----------NYEYPDGYSTEQRTTPIQPGGGLGGNDALW
CAA26662.1  (699) --------Q--------------SN-------MDPSEYTVPEGFKELA
AAB67972.1  (720) NPSAIKPKPG----------YPYPEAIQPNLNLNP-RAGGSEAVTRRYG
BAE57053.1  (717) NPEGAAANSSK---------TYPYPDGYTTEPKPAP-RAGGAEGGNPALW
CAE01320.1  (729) --------VIVPP---------------------------NLDLY
AAA18473.1  (628) --------------------P----------ATGAVVPGGPSDLF
AAA91297.1  (648) --------------------YLPPDCTIEE------------GGAKSLW
BAE58551.1  (742) -------------S------YLAPGTTVAE-------------GGLPSVW
EAL91070.1  (656) --------------------QYPPSAAIQQ-------------GGNPHLW
AAB08445.1  (681) -------------S------AFPASTDISHP------------GGNPDLW
Consensus  (1151)                                                    L
```

TABLE 14-continued

```
                    1201                                              1250
CDX_CBGL1    (754)  DIVYTITADITNTGSVVGEEVPQLYVSLGGP----EDPKVQLRDFDRMRI
ABP88968.1   (782)  DELYEVTAQIKNTGDVAGDEVVQLYVDLGG-----DNPPRQLRNFDRFYL
ABU35789.1   (763)  QDLVRVSATITNTGNVAGYEVPQLYVSLGGP----NEPRVVLRKFDRIFL
BAA19913.1   (760)  DELIRVSVTIKNTGKVAGDEVPQLYVSLGGP----NEPKIVLRQFERITL
BAA10968.1   (760)  DELIRVSVTVKNTGRVAGDAVPQLYVSLGGP----NEPKVVLRKFDRLTL
CAD67686.1   (761)  EDLFRVSVKVKNTGNVAGDEVPQLYVSLGGP----NEPKVVLRKFERIHL
ACD86466.1   (761)  EDLIEVTATVTNTGSVTGDEVPQLYVSLGGA----DDPVKVLRAFDRVTI
AAL69548.3   (755)  EPVARVTTIITNTGKVTGDEVPQLYVSLGGP----DDAPKVLRGFDRITL
CDX_TABGL    (743)  DEMYRVSAIITNTGNVVGDEVPQLYVSLGGP----DDPKVVLRNFDRITL
AAF21242.1   (758)  EELYRVSVTITNTGSVTGDEVPQLYLSLGGP----NDAKIVLRGFDRVTL
ACV87737.1   (754)  DPVAEITVTVKNTGEVAGVEVPQLYVSLGGP----SDAPKVLRGFGRLPL
ABX84365.1   (765)  DVLYKVTATVTNNGAVAGDEVAQLYVSLGGP----EDPVVLRNFDRLTI
CAB82861.1   (769)  DVLFSVEATITNNGTVPGDEVVQLYVSLGNP----DDPKIVLRGFDRLSI
CDX_CelA     (636)  AEARQNAGIYFR------AGALRLPGRFL---------------------
CAA07070.1   (636)  FGDLEMFSRYYVEGCKDGV-------------------------------
BAA33065.1   (629)  --------------------------------------------------
AAA74233.1   (726)  SYTFTVTVTVTNNGNVQGKDSVLLYLSDLWAQ--VTPEVKMLRGFQKVDL
AAL21070.1   (666)  DGKVTASVEVTNTGKREGATVIQMYLQDVTAS--MSRPVKQLKGFEKITL
AAA60495.1   (690)  DGKVTASVQVTNTGKREGATVVQMYLQDVTAS--MSRPVKQLKGFEKITL
AAB66561.1   (626)  NDQLTASVTLTNNGKYDGNEVVQLYIRDMVGS--VTRPVKELKGFQKVFL
AAZ32298.1   (646)  DDVLHVSFNLANTGTFDGTEVAQVYIRDLVGS--VTRPVKELKAFRRVSL
CAA91219.1   (611)  DRMVEISVDIKNTGTLKGDEVVQLYIHQEALS--VTRPVKELKGFKRITL
CAB56688.1   (655)  APRLTCRVTVRNTGSRPAEETVQLYVRRLSGGS-SWPRVRELRGFVRLTI
AAA80156.1   (655)  --------------------------------------------------
AAF21799.1   (650)  --------------------------------------------------
ABU68675.1   (741)  --------------------------------------------------
BAA36161.1   (757)  --------------------------------------------------
AAX35883.1   (757)  --------------------------------------------------
EAA64969.1   (619)  --------------------------------------------------
ABI29899.1   (614)  GETLRVQYRIENTGGRAGKEVSQVYIKAPKGK--IDKPFQELKAFHKTRL
CAB01407.1   (613)  GETLRVQYRIENTGGRAGKEVSQVYIKAPKGK--IDKPFQELKAFHKTRL
AAD35119.1   (614)  GETLRVSYTITNTGDRAGKEVSQVYIKAPKGK--IDKPFQELKAFHKTKL
CAC07184.1   (658)  GDKITVTVSVKNIGKVAGKQVAQVYVKAPKGA--YEKPSCELKAFAKTKN
ABE60716.1   (661)  AGNLVLTATITNTGAVAGKEAAQVYVTAPEVK--LKKPLIELKAFAKTAQ
AAC05445.1   (577)  KKAFTVEMTVTNSGSRDGEEIIQLYIEPLTPT--VIRPIKELKGFEKVFL
CAA33665.1   (567)  NSIINVSVKVKNVGKMAGKEIVQLYVKDVKSS--VRRPEKELKGFEKVTL
AAM93475.1   (547)  GETLTATFSLTNTGRMTGKEICQLYGRPVKTR--LHRPVRELKGFTKVGL
AAC38196.1   (731)  -DAPAVTVTVTNTGARTSREVVQVYLEPASS-----DEPVRLVGWADATV
AAQ38005.1   (632)  HGQVTATFNVHNTGTRAGVDVPQVYVGLPDGG------ARRLAGWQRISL
AAF21798.1   (631)  GETLEVSFQVTNTGKLQGKDAPQIYLAGANG---QKLQRLIGFEKIDL
CAP58431.2   (617)  NSLIRATIYIRNTGEVDGAEIPQAYISFPACE-----PPKVLRGFEKVFL
AAA34314.1   (776)  EVAYNSTDKFVPQGNSTDKFVPQLYLKHPE-DGKFETP-IQLRGFEKVEL
AAA34315.1   (780)  EVAYKVEVDVQNLGNSTDKFVPQLYLKHPE-DGKFETP-VQLRGFEKVEL
CAA26662.1   (718)  NYTYPYIHDASSIKANSSYDYPEGYSTEQLDG------PKSLAAGGLGGN
AAB67972.1   (758)  MLRSRFPLKLLILERNPVRAVAQLYVELPT-DDEHPTPKLQLRQFEKTAT
BAE57053.1   (757)  DVTFSVQVKVTNTGSRDGRAVAQLYVELPS-SLGLDTPSRQLRQFEKTKI
CAE01320.1   (739)  QDVIEFEFQVTNSGPFDGSEVAQLYVDFPNQVN---EPPKVLRGFERAYI
AAA18473.1   (643)  QNVATVTVDIANSGQVTGAEVAQLYITYPS-SAPRTPP-KQLRGFAKLNL
AAA91297.1   (665)  DIVATVKFTVTNTGDVAAAEVPQLYVGIPNG------PPKVLRGFDKKLI
BAE58551.1   (760)  DIIATVTCTVSNTGSVAAAEVAQLYIGIPGG------PAKVLRGFEKQLI
EAL91070.1   (673)  DNIVTVSAEIKNTGRVAGAEVAQLYIGIPNG------PVRQLRGFEKVDV
AAB08445.1   (700)  EEVVSVTAAVKNTGSVSGSQVVQLYISLPADGIPENSPMQVLRGFEKVDL
Consensus   (1201)       VT  V NTG V G EV QLYV            P   LRGFEKV L 1251                                              1300
CDX_CBGL1    (800)  E-PGETRQFTGRLTRRDLSNWDVTVQDWVISRY--PKTAYVGRSSRKLDL
ABP88968.1   (827)  L-PGQSSTFRATLTRRDLSNWDIEAQNWRVTES--PKRVYVGRSSRDLPL
ABU35789.1   (809)  A-PGEQKVWTTTLNRRDLANWDVEAQDWVITKY--PKKVHVGSSSRKLPL
BAA19913.1   (806)  Q-PSEETKWSTTLTRRDLNWNVEKQDWEITSY--PKMVFVGSSSRKPPL
BAA10968.1   (806)  K-PSEETVWTTTLTRRDLSNWDVAAQDWVITSY--PKKVVGSSSRQLPL
CAD67686.1   (807)  A-PSQEAVWTTTLTRRDLANWDVSAQDWTVTPY--PKTIYVGNSSRKLPL
ACD86466.1   (807)  A-PGQKLRWTATLNRRDLSNWDVPSQNWIISDA--PKKVWVGNSSRKLPL
AAL69548.3   (801)  A-PGQQYLWTTTLTRRDISNWDPVTQNWVVTNY--TKTIYVGNSSRNLPL
CDX_TABGL    (789)  H-PGQQTMWTTTLTRRDISNWDPASQNWVVTKY--PKTVYIGSSRKLHL
AAF21242.1   (804)  R-PGENTVWQTTLTRRDISNWDPVTQNWVVTSH--PKMIYVGNSSRNQPL
ACV87737.1   (800)  A-PVNETQWTATLTRRDVSNWDTVSQNWVVTDY--TKTVYVGNSSRNLPL
ABX84365.1   (811)  A-PGQSVEFTADITRRDVSNWDTVSQNWVISNS--TKTVYVGASSRKLPL
CAB82861.1   (815)  Q-PGKTATFHADITRRDVSNWDVASQNWVITSA--PKTVYVGASSRKLPL
CDX_CelA     (659)  --------------------------------------------------
CAA07070.1   (655)  --------------------------------------------------
BAA33065.1   (629)  --------------------------------------------------
AAA74233.1   (774)  M-PAKSQQISFTLNAYEFSFIGVDNKITLESGP---FIIMVGNQQLGLYL
AAL21070.1   (714)  K-PGERKTVSFPIDIEALKFWNQQMKYDAEPGK---FNVFIGVDSARVKQ
AAA60495.1   (738)  K-PGETQTVSFPIDIEALKFWNQQMKYDAEPGK---FNVFIGTDSARVKK
AAB66561.1   (674)  K-AGESKIVTFNITPEDLKFYNSALKYDWEPGE---FDIMIGTNSHDVKH
AAZ32298.1   (694)  K-AGESRRLTLDIPVSELAFYGLDMQKKVEPGQ---FQLWVAGDSSSGEA
CAA91219.1   (659)  D-AGEEKTVIFKLSIEQLGFYDENMEYVVEPGR---VDVMIGSSSEDIRL
CAB56688.1   (704)  A-PGEEAEAVFEVDRDTLASVGRDLRLAVEPGLVELETGPASDRTTGVRL
```

TABLE 14-continued

```
AAA80156.1  (655) ------------------------------------------
AAF21799.1  (650) ------------------------------------------
ABU68675.1  (741) ------------------------------------------
BAA36161.1  (757) ------------------------------------------
AAX35883.1  (757) ------------------------------------------
EAA64969.1  (619) ------------------------------------------
ABI29899.1  (662) LNPGESEEVVLEIPVRDLASFNGE--EWVVEAG--EYEVRVGASSRNIKL
CAB01407.1  (661) LNPGESEEVVLEIPVRDLASFNGE--EWVVEAG--EYEVRVGASSRNIKL
AAD35119.1  (662) LNPGESEEISLEIPLRDLASFDGK--EWVVESG--EYEVRVGASSRDIRL
CAC07184.1  (706) LKPGQSETLKMIIAKRDLASFDEANSQWKVDAG--KYEFCVGDNVESIKG
ABE60716.1  (709) LAPGASEQLSFTIPASILASFDEASNQWIVEPG--RYSAYISPSS-DVSA
AAC05445.1  (625) K-AGESKRVVFRLDSSAFAYYSDKIHDWLSESG--YYNILIGKSSADICL
CAA33665.1  (615) N-PGEEKTVTFTLDKRAFAYYNTQIKDWHVESG--EFLILIGRSSRDIVL
AAM93475.1  (595) K-PGETKRVSIVFEARDTRYFDPELGQWLTDGG--AYGIDVGASSRDIRL
AAC38196.1  (775) D-AGASARVTVTADARMWRRWDEAAGGWSRLADG--GRLLVARGLGDVRA
AAQ38005.1  (676) A-PGESRQVSVQLEPRLLAHFDGKHDRWSVPSG--TFRVWLASCATDDSQ
AAF21798.1  (676) K-PGERRTVTIKADPRLLARFDEQGHQWRIDGG--DYDVVVGSSATMTVL
CAP58431.2  (662) K-AGKHAKVEFNFGETELSIWDPETEEWVTPSG--EYTLHIGASSRDIRQ
AAA34314.1  (824) S-PGEKKTVDLRLLRRDLSVWDTTRQSWIVESG--TYEALIGVAVNDIKT
AAA34315.1  (828) S-PGEKKTVEFELLRRDLSVWDTTRQSWIVESG--TYEALIGVAVNDIKT
CAA26662.1  (762) HTCGMLVTLSLLKSQIKVLMLVGLHLNCMLDIQIMMNSQHLQCNYVDLKR
AAB67972.1  (807) LEPGQSEVLKMEITRKDVSIWDTMVQDWKVPATGKGIKLWIGASVGDLKA
BAE57053.1  (806) LAAGESEVLTLDVTRKDLSVWDVVVQDWKAPVNGEGVKIWVGESVADLRV
CAE01320.1  (786) P-SKQSKTIEIKLRVKDLSFWDVITQSWQIPDG--KFNFMIGSSSRKIIF
AAA18473.1  (691) T-PGQSGTATFNIRRRDLSYWDTASQKWVVPSG--SFGISVGASSRDILL
AAA91297.1  (709) H-PGQSEEFVFELTRRDLSTWDVVAQNWGLQAG--TYQFYVGRSVFDVPL
BAE58551.1  (804) E-PGQQVQVFDLTRRDLSTWDTEKQNWGLQAG--SYALYVGKSVLDIQL
EAL91070.1  (717) S-AGETTQVQFALNRRDLSTWDVEAQQWSLQRG--TYRVYVGRSSRDLPL
AAB08445.1  (750) Q-PGQSKSVEFSIMRRDLSFWNTTAQDWEIPNG--QIEFRVGFSSRDIKS
Consensus  (1251)       PG     VT  L  RDLS WD       W V         V VG SS   L L 1301                                           1350
CDX_CBGL1   (847) KIELP---------------------------------------
ABP88968.1  (874) SSQLE---------------------------------------
ABU35789.1  (856) RAPLPRVY------------------------------------
BAA19913.1  (853) RASLPTVH------------------------------------
BAA10968.1  (853) HAALPKVQ------------------------------------
CAD67686.1  (854) QASLPKAQ------------------------------------
ACD86466.1  (854) SADLPKVQ------------------------------------
AAL69548.3  (848) QAPLKPYPGI----------------------------------
CDX_TABGL   (836) QAPLPPY-------------------------------------
AAF21242.1  (851) SAPLAPSS------------------------------------
ACV87737.1  (847) QQTLALNIGK----------------------------------
ABX84365.1  (858) KATLPSSSY-----------------------------------
CAB82861.1  (862) TATLDTSDFQ----------------------------------
CDX_CelA    (659) --------------------------------------------
CAA07070.1  (655) --------------------------------------------
BAA33065.1  (629) --------------------------------------------
AAA74233.1  (820) Q-------------------------------------------
AAL21070.1  (760) GSFELL--------------------------------------
AAA60495.1  (784) GEFELL--------------------------------------
AAB66561.1  (720) AKINWNK-------------------------------------
AAZ32298.1  (740) LTFSVR--------------------------------------
CAA91219.1  (705) RDYFEIVGEKEKVAKKFITEVRVENK------------------
CAB56688.1  (753) EITDSESNAT----------------------------------
AAA80156.1  (655) --------------------------------------------
AAF21799.1  (650) --------------------------------------------
ABU68675.1  (741) --------------------------------------------
BAA36161.1  (757) --------------------------------------------
AAX35883.1  (757) --------------------------------------------
EAA64969.1  (619) --------------------------------------------
ABI29899.1  (708) KGTFSVGEERRFKP------------------------------
CAB01407.1  (707) KGTFSVGEERRFKP------------------------------
AAD35119.1  (708) RDIFLVEGEKRFKP------------------------------
CAC07184.1  (754) TASLNLSEYTEKTTNSLPLNTKMNLLHQ----------------
ABE60716.1  (756) ITPVSFTVSKEIVVSNTTPGALALPAGVDPASVTTITR------
AAC05445.1  (672) EEQVHFNSSVRIPILFTLDNTVSDINSTAEGKKLFKDMMSSVFATANGGA
CAA33665.1  (662) KESVRVNSTVKIRKRFTVNSAVEDVMSDSS----AAAVLGPVLKEITDAL
AAM93475.1  (642) SAEVTCETPQLTPRRLTLETQPFLLFETPVGRERLAAFFRERLGLDV--
AAC38196.1  (822) TLALPTA-------------------------------------
AAQ38005.1  (723) QTTMHLHGRTMAP-------------------------------
AAF21798.1  (723) SGKAASASVP----------------------------------
CAP58431.2  (709) TAKFRLYLY-----------------------------------
AAA34314.1  (871) SVLFTI--------------------------------------
AAA34315.1  (875) SVLFTI--------------------------------------
CAA26662.1  (812) CFWIKIILKLFLLN------------------------------
AAB67972.1  (857) VCETGKGKSCHVLN------------------------------
BAE57053.1  (856) GCVVGEG--CSTL-------------------------------
CAE01320.1  (833) TQEISLQHSHM---------------------------------
AAA18473.1  (738) TSTLSVA-------------------------------------
```

TABLE 14-continued

```
AAA91297.1  (756) TSALVFTN--------------------------------------
BAE58551.1  (851) TGSLSL----------------------------------------
EAL91070.1  (764) TGSFTL----------------------------------------
AAB08445.1  (797) IVSRSFL---------------------------------------
Consensus  (1301)      L 1351                                          1400
CDX_CBGL1   (852) ----------------------------------------------
ABP88968.1  (879) ----------------------------------------------
ABU35789.1  (864) ----------------------------------------------
BAA19913.1  (861) ----------------------------------------------
BAA10968.1  (861) ----------------------------------------------
CAD67686.1  (862) ----------------------------------------------
ACD86466.1  (862) ----------------------------------------------
AAL69548.3  (858) ----------------------------------------------
CDX_TABGL   (843) ----------------------------------------------
AAF21242.1  (859) ----------------------------------------------
ACV87737.1  (857) ----------------------------------------------
ABX84365.1  (867) ----------------------------------------------
CAB82861.1  (872) ----------------------------------------------
CDX_CelA    (659) ----------------------------------------------
CAA07070.1  (655) ----------------------------------------------
BAA33065.1  (629) ----------------------------------------------
AAA74233.1  (821) ----------------------------------------------
AAL21070.1  (766) ----------------------------------------------
AAA60495.1  (790) ----------------------------------------------
AAB66561.1  (727) ----------------------------------------------
AAZ32298.1  (746) ----------------------------------------------
CAA91219.1  (731) ----------------------------------------------
CAB56688.1  (763) ----------------------------------------------
AAA80156.1  (655) ----------------------------------------------
AAF21799.1  (650) ----------------------------------------------
ABU68675.1  (741) ----------------------------------------------
BAA36161.1  (757) ----------------------------------------------
AAX35883.1  (757) ----------------------------------------------
EAA64969.1  (619) ----------------------------------------------
ABI29899.1  (722) ----------------------------------------------
CAB01407.1  (721) ----------------------------------------------
AAD35119.1  (722) ----------------------------------------------
CAC07184.1  (782) ----------------------------------------------
ABE60716.1  (794) ----------------------------------------------
AAC05445.1  (722) DQLGDSAREMEMAIANDLPLHAMVSFTDNPDITREKLQMMLDKLNVIINS
CAA33665.1  (708) QIDMDNAHDMMAANIKNMPLRSLVGYSQG-RLSEEMLEELVDKINNVE--
AAM93475.1  (690) ----------------------------------------------
AAC38196.1  (829) ----------------------------------------------
AAQ38005.1  (736) ----------------------------------------------
AAF21798.1  (733) ----------------------------------------------
CAP58431.2  (718) ----------------------------------------------
AAA34314.1  (877) ----------------------------------------------
AAA34315.1  (881) ----------------------------------------------
CAA26662.1  (826) ----------------------------------------------
AAB67972.1  (871) ----------------------------------------------
BAE57053.1  (867) ----------------------------------------------
CAE01320.1  (844) ----------------------------------------------
AAA18473.1  (745) ----------------------------------------------
AAA91297.1  (764) ----------------------------------------------
BAE58551.1  (857) ----------------------------------------------
EAL91070.1  (770) ----------------------------------------------
AAB08445.1  (804) ----------------------------------------------
Consensus  (1351)

1401
CDX_CBGL1   (852) -
ABP88968.1  (879) -
ABU35789.1  (864) -
BAA19913.1  (861) -
BAA10968.1  (861) -
CAD67686.1  (862) -
ACD86466.1  (862) -
AAL69548.3  (858) -
CDX_TABGL   (843) -
AAF21242.1  (859) -
ACV87737.1  (857) -
ABX84365.1  (867) -
CAB82861.1  (872) -
CDX_CelA    (659) -
CAA07070.1  (655) -
BAA33065.1  (629) -
AAA74233.1  (821) -
AAL21070.1  (766) -
```

TABLE 14-continued

| | | |
|---|---|---|
| AAA60495.1 | (790) | - |
| AAB66561.1 | (727) | - |
| AAZ32298.1 | (746) | - |
| CAA91219.1 | (731) | - |
| CAB56688.1 | (763) | - |
| AAA80156.1 | (655) | - |
| AAF21799.1 | (650) | - |
| ABU68675.1 | (741) | - |
| BAA36161.1 | (757) | - |
| AAX35883.1 | (757) | - |
| EAA64969.1 | (619) | - |
| ABI29899.1 | (722) | - |
| CAB01407.1 | (721) | - |
| AAD35119.1 | (722) | - |
| CAC07184.1 | (782) | - |
| ABE60716.1 | (794) | - |
| AAC05445.1 | (772) | K |
| CAA33665.1 | (755) | - |
| AAM93475.1 | (690) | - |
| AAC38196.1 | (829) | - |
| AAQ38005.1 | (736) | - |
| AAF21798.1 | (733) | - |
| CAP58431.2 | (718) | - |
| AAA34314.1 | (877) | - |
| AAA34315.1 | (881) | - |
| CAA26662.1 | (826) | - |
| AAB67972.1 | (871) | - |
| BAE57053.1 | (867) | - |
| CAE01320.1 | (844) | - |
| AAA18473.1 | (745) | - |
| AAA91297.1 | (764) | - |
| BAE58551.1 | (857) | - |
| EAL91070.1 | (770) | - |
| AAB08445.1 | (804) | - |
| Consensus | (1401) | |

Table 15 shows an alignment of the C1 β-glucosidase protein (SEQ ID NO:1) and GH3 and GH3-C domain consensus sequences (SEQ ID NOs:53-54).

TABLE 15

(SEQ ID NOS: 1, 53 and 54)

```
                     1                             30
C1 CBGL1      (1)    IESRKVHQKPLARSEPFYPSPWMNPNADGW 31                             60
C1 CBGL1     (31)    AEAYAQAKSFVSQMTLLEKVNLTTGVGWGA 61                             90
C1 CBGL1     (61)    EQCVGQVGAIPRLGLRSLCMHDSPLGIRG-
GH3-PFAM      (1)    -------AEKPRLGIPLLVVVDAEHGVRQR 91                            120
C1 CBGL1     (90)    -ADYNSAFPSGQTVAATWDRGLMYRRGYAM
GH3-PFAM     (24)    DKEEATAFPSALALAATWDKELIKEVGKAI 121                            150
C1 CBGL1    (119)    GQEAKGKGINVLLGPVAGPLGRMPEGGRNW
GH3-PFAM     (54)    GEELRAKGIDVLLAPVVDLK-RSPRWGRNF 151                            180
C1 CBGL1    (149)    EGFAPDPVLTGIGMSETIKGIQDAGVIACA
GH3-PFAM     (83)    ESFSEDPYLVGALAAATIKGLQSAGVAATA 181                            210
C1 CBGL1    (179)    KHFIGNEQEHFRQVPEAQGYGYNISETLSS
GH3-PFAM    (113)    KHFAGNGQETARSK-------E----TVSA 211                            240
C1 CBGL1    (209)    NIDDKTMHELYLWPFADAVRAG-VGSVMCS
GH3-PFAM    (132)    EIDERALREIYLLPFEAAVKEAGVGSVMCS 241                            270
C1 CBGL1    (238)    YQQVNNSYACQNSKLLNDLLKNELGFQGFV
GH3-PFAM    (162)    YNKVNGLPATENSKLLTKLLREELGFQGFV
```

TABLE 15-continued

```
                   271                            300
C1 CBGL1    (268)    MSDWQAQHTGAASAVAGLDMSMPGDTQFNT
GH3-PFAM    (192)    VSDWLAVKSGVASDAANESEAAAAALKAGL 301                            330
C1 CBGL1    (298)    GVSFWGANLTLAVLNGTVPAYRLDDMAMRI
GH3-PFAM    (222)    DIEMP-------------------------

331                            360
C1 CBGL1    (328)    MAALFKVTKTTDLEPINFSFWTDDTYGPIH 361                            390
C1 CBGL1    (358)    WAAKQGYQEINSHVDVRADHGNLIREIAAK 391                            420
C1 CBGL1    (388)    GTVLLKNTG-SLPLNKPK-FVAVIGEDAGS
GH3C-PFAM     (1)    -IVLLKNEGNLLPLKKKKKKIAVIGPNA--

421                            450
C1 CBGL1    (416)    SPNGPNGCSDRGCNEGTLAMGWGSGTANYP
GH3C-PFAM    (28)    ----------DGTVK--S--GGGSGAVNPS 451                            480
C1 CBGL1    (446)    YLVSPDAALQARAIQDGTRYESVLSNYABEE
GH3C-PFAM    (44)    YLVSPLEGIRKRLSKAKVVEEGSEDDEEI 481                            510
C1 CBGL1    (476)    KTKALVSQANATAIVFVNADSGEGYINVDG
GH3C-PFAM    (74)    AEAVAAAKKADVAVVVVGEWEGEG----ES 511                            540
C1 CBGL1    (506)    NEGDRKNLTLWNNGDTLVKNVSSWCSNTIV
GH3C-PFAM   (100)    EEGDRTDLALPENQDELIEAVAAANKPVVV 541                            570
C1 CBGL1    (536)    VIHSVGPVLLTDWYDNPNITAILWAGLPGQ
GH3C-PFAM   (130)    VLHSGGPVDMEPWAEK--VKAILAAWYPGQ
```

TABLE 15-continued

```
                  571                           600
C1 CBGL1   (566)  ESGNSITDVLYGKVNPAARSPFTWGKTRES
GH3C-PFAM  (158)  EGGNAIADVLFGDVNPSGKLPVTFPKSLED 601                           630
C1 CBGL1   (596)  YGADVLYKPNNGNGAPQQDFTEGVFIDYRY
GH3C-PFAM  (188)  LPAYYRYKSED----PLYPFGEGLSVGY--

631                           660
C1 CBGL1   (626)  FDKVDDDSVIYEFGHGLSYTTFEYSNIRVV 661                           690
C1 CBGL1   (656)  KSNVSEYRPTTGTTAQAPTFGNFSTDLEDY 691                           720
C1 CBGL1   (686)  LFPKDEFPYIYQYIYPYLNTTDPRRASADP 721                           750
C1 CBGL1   (716)  HYGQTAEEFLPPHATDDDPQPLLRSSGGNS 751                           780
C1 CBGL1   (746)  PGGNRQLYDIVYTITADITNTGSVVGEEVP 781                           810
C1 CBGL1   (776)  QLYVSLGGPEDPKVQLRDFDRMRIEPGETR 811                           840
C1 CBGL1   (806)  QFTGRLTRRDLSNWDVTVQDWVISRYPKTA 841           856
C1 CBGL1   (836)  YVGRSSRKLDLKIELP
```

Table 16 shows an alignment of the C1 BGL1 (SEQ ID NO:1), TaBGL (SEQ ID NO:2), CelA (SEQ ID NO:3) and twenty-five xylosidases (SEQ ID NOs:58-82).

TABLE 16

```
(SEQ ID NOS1-3 and 58-82)
                    1                                                50
C1 BGL1      (1)    ----------------------------------IESRKVHQKPLARSEP
TaBGL        (1)    ----------------------------------------KDDLAYSPP
CelA         (1)    QEGAAPAAILHPEKWPRPATQRLIDPAVEKRVDALLKQLSVEEKVGQVIQ
AAK43134.1   (1)    --------------------------MTAIKSLLNQMSIEEKIAQLQA-
AAB70867.1   (1)    ----------------MELYRDPSQPVEVRVKDLLSRMTLEEKIAQLGS
AAC99628.1   (1)    -----MTADVAVETTPEIPLWNDPNHPVASRVDALVAAMTLEEKIAQLYG
CAP07659.1   (1)    ------------------MMNLRLCFRAALAAACMMAAFAS---
ACN78955.1   (1)    -----------------------MKYQLFLSLALCVGLG---
CAD48309.1   (1)    --------------------------------------------------
BAB11424.1   (1)    ----------MGSSSPLTRRNRAPPSSVSSVYLIFLCFFLYFLNFSNAQS
BAE44362.1   (1)    ----------MGSSSPPTRRNRAP-SSVFSLSLIFLC----LLDSSNAQS
AAK96639.1   (1)    ----------------MASRN--R--ALFSVSTLFLCFIVCISEQSNNQS
ABQ45227.1   (1)    ---------------ANTKNREPKVSSVFLCFSIFYVTVLLNCNHVYGQT
AAK38481.1   (1)    ----------------MATAARPPFLAMAAAALLVAAWWGGNAGAAEAQA
AAM53325.1   (1)    ----------------MSCYNKALLIGNKVVVILVFLLCLVHSSESL
AAS17751.2   (1)    ----------------MASGYNNKLSLIALVLCVSALLFNLVHA----
CAJ41429.1   (1)    ------------------MPTSFIITLSVLFLGVSLQTSKA
AAK38482.1   (1)    -----------------MGRRTHVVLAAAVPALLLVLLLRLHAAVAAD
ACL54109.1   (1)    ---------MPLAAMASASSSPCSRHPLILVVLLCAIAAISFSSSVAAGTV
BAG82824.1   (1)    --------------------------MAVAALALLALLPQALGQHNS
BAE19756.1   (1)    ------------------MAHSMSRPVAATAAALLALALPQALAQANT
BAA24107.1   (1)    ------------------------MPGAASIVAVLAALLPTALGQANQ
ABA40420.1   (1)    ------------------------MAVAKSIAAVLVALLPGALAQANT
CAA73902.1   (1)    -------------------------MRSLISVAVLSAL--AAFSQANT
EAA64470.1   (1)    -------------------------MRSLISVAVLSALP-TAFSQANT
AAL32053.2   (1)    ------------------------MMTRTAILTALAALLPTATWAQDNQ
CAA93248.1   (1)    ------------------------MVNNAALLAALSALLPTA-LAQNNQ
EAA67023.1   (1)    -------------------------MAVFKSWNLALLSSLFIPALCQSN-
Consensus    (1)                                         V   L  L   LAQ N 51                                               100
C1 BGL1      (17)   ----------------------------FYPSPWMNPNADGWAEAYAQAK
TaBGL        (10)   ----------------------------FYPSPWMDGNGE-WAEAYRRAV
CelA         (51)   G--------------DIGTITPEDLRKYPLGSILAGGNSGPNGDDRAP
AAK43134.1   (23)   --------------IPIDALMEGK-EFSEEKARKYLKLGIGQITRVAGSR
AAB70867.1   (34)   --------------VWGYELIDERGKFKREKAKDLLKNGIGQITRPGGS-
AAC99628.1   (46)   VWVGASDQ-------GGE--VAPISTTWRRPSTSTRSCPPGSVSSPGPSA
CAP07659.1   (24)   ----------------------------CAPQEISYTDKSQPAELRAK
ACN78955.1   (17)   ----------------------------ASAQTLPYQNPNLSAKERAV
CAD48309.1   (1)    -----------------------------MENKPVYLDPSYSFEERAK
BAB11424.1   (41)   --------------SPVFACDVAA----NPSLAAYGFCNTVLKIEYRVA
BAE44362.1   (36)   --------------TPVFACDVAG----NPSLAAYGFCNTAIKIEYRVA
AAK96639.1   (31)   --------------SPVFACDVTG----NPSLAGLRFCNAGLSIKARVT
ABQ45227.1   (36)   --------------STVFACDVAK----NTNVSSYGFCDNSLSVEDRVS
AAK38481.1   (35)   Q-------------APVFACDAS-----NATLAAYGFCNRKATASARAR
AAM53325.1   (32)   --------------RPLFACDPA-----NGLTRTLRFCRANVPIHVRVQ
AAS17751.2   (29)   --------------RPPFACDPR-----NPLTRGFKFCRTRVPVHVRVQ
CAJ41429.1   (24)   --------------LDPFACDPK-----DGTNRDLPFCQVNLPIHTRVN
AAK38482.1   (32)   --------------PPFSCGAP------SSAAFCDRRLPIEQRAA
ACL54109.1   (43)   GGGTGGLGPISTNGKNYTKVCDPARFVALGLDMSFRYCDASLPYADRVR
BAG82824.1   (22)   SYVDYNVEANPDLFPQCLDTISLSFPDCQSGPLSKNLVCDSTASPYDRAA
BAE19756.1   (31)   SYVDYNIEANPDLYPLCIETIPLSFPDCQNGPLRSHLICDETATPYDRAA
BAA24107.1   (25)   SYVDYNSEANPDLFSECLETGGTSFPDCESGPLSKTLVCDTSAKPHDRAA
ABA40420.1   (25)   SYVDYNVEANPDLTPQSVATIDLSFPDCENGPLSKTLVCDTSARPHDRAA
CAA73902.1   (22)   SYTDYNVEANPDLFPLCLQHLNASFPDCATGPLSLTPVCDRSLSPKDRAT
```

TABLE 16-continued

```
EAA64470.1    (23) SYTDYNVEANPDLFPLCLQHLNASFPDCASGPLSLTPVCDRSLSPKDRAT
AAL32053.2    (26) TYANYSSQSQPDLFPRTVATIDLSFPDCENGPLSTNLVCNTSADPWARAE
CAA93248.1    (25) TYANYSAQGQPDLYPETLATLTLSFPDCEHGPLKNNLVCDSSAGYVERAQ
EAA67023.1    (25) -----------------------YPDCTTGPLSELPICDTSLSPLERAK
Consensus     (51)                     V  S        LS  CD SL    RA 101                                               150
C1 BGL1       (39) -SFVSQMTLLEKVNLTTGVGWGAEQCVGQVGAIPRLGLRSLCMHDSPLGI
TaBGL         (31) -DFVSQLTLAEKVNLTTGVGWMQEKCVGETGSIPRLGFRGLCLQDSPLGV
CelA          (85) --PKEWLDLADAFYRVSLEK-RPGHTPIP-VLFGIDAVHGHGNIG-----
AAK43134.1    (58) -LGLKPKEVVKLVNKVQKFLVENTRLKIP-AIIHEECLSGLMG-------
AAB70867.1    (69) -TNLEPQEAAELVNEIQRFLVEETRLGIP-AMIHEECLTGYMG-------
AAC99628.1    (87) PSRSTPRSAPSRSCARRPRITSAGRFGIP-AVAHEECLAGFAPWG-----
CAP07659.1    (44) -ALLPKLSLEEKAGLVQYNSPAVERLGIKAYNWWSEALHGVARNG--S--
ACN78955.1    (37) -DLCSRLTLEEKAMLMLDESPAIPRLGIKKFFWWSEALHGAANMG--N--
CAD48309.1    (20) -DLVSRMTIEEKVSQMLYNSPAIERLGIPAYNWWNEALHGVARAG-----
BAB11424.1    (72) -DLVARLTLQEKIGFLVSKANGVTRLGIPTYEWWSEALHGVSYIG-PG-T
BAE44362.1    (67) -DLVARLTLQEKIGVLTSKLHGVARLGIPTYEWWSEALHGVSYVG-PG-T
AAK96639.1    (62) -DLVGRLTEEKIGFLTSKAIGVSRLGIPSYKWWSEALHGVSNVG-GG-S
ABQ45227.1    (67) -DLVKRLTLQEKIGNLGNSAVEVSRLGIPKYEWWSEALHGVSNIG-PG-T
AAK38481.1    (66) -DLVSRLTLAEKVGFLVNKQPALGRLGIPAYEWWSEALHGVSYVG-PG-T
AAM53325.1    (62) -DLLGRLTLQEKIRNLVNNAAAVPRLGIGGYEWWSEALHGISDVG-PG-A
AAS17751.2    (59) -DLIGRLTLQEKIRLLVNNAIAVPRLGIQGYEWWSEALHGVSNVG-PG-T
CAJ41429.1    (54) -DLIGRMTLQEKVGLLVNNAAAVPRLGIKGYEWWSEALHGVSNVG-PG-T
AAK38482.1    (57) -DLVSKLTLEEKISQLGDESPAVDRLGVPAYKWWSEALHGVANAG-RG-V
ACL54109.1    (93) -DLVGRLALEEKVRNLGDQAEGAPRVGLPPYKWWEALHGVSDVG-PGGT
BAG82824.1    (72) -ALVSLFTLEELIANTGNTSPGVPRLGLPPYQVWSEALHGLAR---ANFT
BAE19756.1    (81) -SLISLFTLDELIANTGNTGLGVSRLGLPAYQVWSEALHGLDR---ANFS
BAA24107.1    (75) -ALVSLLTFEELVNNTANTGHPRIGLPAYQVWNEALHGVAH---ADFS
ABA40420.1    (75) -ALVSMFTFEELVNNTGNTSPGVPRLGLPPYQVWSEALHGLDR---ANFT
CAA73902.1    (72) -ALVSLFTFDELVNNTGNTGLGVSRLGLPNYQVWGEALHGVGR---ANFV
EAA64470.1    (73) -ALVSLFTFDELVNNTGNTGLGVSRLGLPNYQVWGEALHGVGR---ANFV
AAL32053.2    (76) -ALVSLFTLEELINNTQNTAPGVPRLGLPQYQVWNEALHGLDR---ANFS
CAA93248.1    (75) -ALISLFTLEELILNTNSGPGVPRLGLPNYQVWNEALHGLDR---ANFA
EAA67023.1    (51) -SLVSALTLEEKINNTGHEAAGSSRLGLPAYNWWNEALHGVAEKHGVSFE
Consensus    (101)     LVS LTLEEKI NL    A GV RLGIP Y WWSEALHGVS  G 151                                               200
C1 BGL1       (88) R---GADYNSAFPSGQTVAATWDRGLMYRRGYAMGQEAKGKG--------
TaBGL         (80) R---FADYVSAFPAGVNVAATWDKNLAYLRGKAMGEEHRGKG--------
CelA         (126) -------SATIFPHNIALGATHDPELLRRIGEVTAVEMAATG--------
AAK43134.1    (99) ---YS---STAFPQAIGLASTWNPELLTNVASTIRSQGRLIG--------
AAB70867.1   (110) ---LG---GTNFPQAIAMASTWDPDLIEKMTAAIREDMRKLG--------
AAC99628.1   (131) --------ATAYPVPLSWGATFDPDAVRRMAAAIGRDMRSVG--------
CAP07659.1    (89) --------ATVFPQPIGMAASFDVEKIETVFTAVSDEARVKN--RIAAED
ACN78955.1    (82) --------VTNFPEPVGMAASFNPHLLFKVFDIASTEFRAQYNHRMYDLN
CAD48309.1    (64) --------TATMFPQAIGMAATFDEELIYKVADVISTEGRAKYHAS--SKK
BAB11424.1   (119) HFSSQVPGATSFPQVILTAASFNVSLFQAIGKVVSTEARAMYN-------
BAE44362.1   (114) RFSGQVPGATSFPQVILTAASFNVSLFQAIGKVVSTEARAMYN-------
AAK96639.1   (109) RFTGQVPGATSFPQVILTAASFNVSLFQAIGKVVSTEARAMYN-------
ABQ45227.1   (114) HFSSLVPGATNFPMPILTAASFNTSLFQAIGSVVSNEARAMYN-------
AAK38481.1   (113) RFSPLVPGATSFPQPILTAASFNASLFRAIGEVVSTEARAMHN-------
AAM53325.1   (109) KFGGAFPGATSFPQVITTAASFNQSLWEEIGRVVSDEARAMYN-------
AAS17751.2   (106) KFGGAFPGATSFPQVITTAASFNQSLWQEIGQVVSDEARAMYN-------
CAJ41429.1   (101) KFGGAFPVATSFPQVITTAASFNATLWEAIGRVVSDEARAMFN-------
AAK38482.1   (104) HLDGPLRAATSFPQVILTAASFNPHLWYRIGQVIGTEARGVYN-------
ACL54109.1   (141) WFGDVVPGATSFPLVINSAAAFNESLWRAIGGVVSTEIRAMYN-------
BAG82824.1   (118) DNG-AYSWATSFPSPILSAAAFNRTLINQIASIISTQGRAFNN-------
BAE19756.1   (127) DSG-AYNWATSFPQPILTTAALNRTLIHQIASIISTQGRAFNN-------
BAA24107.1   (121) DAG-DFSWSTSFPQPISTMAALNRTLIHQIATIISTQGRAFMN-------
ABA40420.1   (121) DEG-EYSWATSFPMPILTMSALNRTLINQIATIIATQGRAFNN-------
CAA73902.1   (118) ESG-NFSWATSFPMPITMMAALNRTLIHQIGTIVSTQLRAFSN-------
EAA64470.1   (119) ESG-NFSWATSFPMPITMMAALNKTLIHQIGTIVSTQLRAFSN-------
AAL32053.2   (122) DSG-EYSWATSFPMPILSMASFNRTLINQIASIIATQARAFNN-------
CAA93248.1   (121) TKGGQFEWATSFPMPILTTAALNRTLIHQIADIISTQARAFSN-------
EAA67023.1   (100) ESG-DFSYATSFPAPIVLGAAFNDALIRRVAEIISTEARAFSN-------
Consensus    (151)         ATSFPQPI TAASFN TLI  IG VISTEARA  N 201                                               250
C1 BGL1      (127) ------INVLLGPVAGPLGRMPEGGRNWEGFAPDPVLTG-IGMSETIKGI
TaBGL        (119) ------VDVQLGPVAGPLGRHPDGGRNWEGFSPDPVLTG-VLMAETIKGI
CelA         (161) -------IDWTFAPALSVVRDDRWGRTYEGFSEDPEIVA-AYSAAIVEGV
AAK43134.1   (135) ------VNQCLSP-VLDVCRDPRWGRCEETYGEDPYLVA-SMGLAYITGL
AAB70867.1   (146) ------AHQGLAP-VLDVARDPRWGRTEETFGESPYLVA-RMGVSYVKGL
AAC99628.1   (165) -------IHQGLAPVLDVVRDGARWEETIGEDPYLVG-TIGTAYVQGL
CAP07659.1   (129) GRVYQYAGLSFWTPNINIFRDPRWGRGMETYGEDPYLMG-QLGMAVVRGL
ACN78955.1   (124) GEDMKMRSLSVWTPNVNIFRDPRWGRGQETYGEDPYLTS-VMGVQVVKGL
CAD48309.1   (105) GDRGIYKGLTFWSPNINIFRDPRWGRGQETYGEDPYLTA-RLGVAFVKGL
BAB11424.1   (162) --VG-LAGLTYWSPNVNIFRDPRWGRGQETPGEDPLLAS-KYASGYVKGL
BAE44362.1   (157) --VG-LAGLTYWSPNVNIFRDPRWGRGQETPGEDPLLSS-KYASGYVKGL
```

TABLE 16-continued

```
AAK96639.1  (152) --VG-SAGLTFWSPNVNIFRDPRWGRGQETPGEDPTLSS-KYAVAYVKGL
ABQ45227.1  (157) --VG-LAGLTFWSPNINIFRDPRWGRGQETPGEDPLLSS-KYAAGYVKGL
AAK38481.1  (156) --VG-LAGLTFWSPNINIFRDPRWGRGQETPGEDPLLAS-KYAVGYVTGL
AAM53325.1  (152) --GG-VAGLTFWSPNVNILRDPRWGRGQETPGEDPIVAA-KYAASYVRGL
AAS17751.2  (149) --GG-QAGLTFWSPNVNIFRDPRWGRGQETPGEDPVLSA-KYAASYVKGL
CAJ41429.1  (144) --GG-VAGLTFWSPNVTYSVYPRWGRGQETPGEDPVVVG-KYAASYVRGL
AAK38482.1  (147) --NGQAEGLTFWAPNINVERDPRWGRGQETPGEDPTMTG-KYAAVEVRGV
ACL54109.1  (184) --LG-HAELTYWSPNINVVRDPRWGRASETPGEDPFVVG-RYAVNFVRGM
BAG82824.1  (160) --AG-RFGLDVYSPNINTFRHPVWGRGQETPGEDAYTLTAAYAYEYITGI
BAE19756.1  (169) --AG-RYGLDVYAPNINTFRHPVWGRGQETPGEDVSLAA-VYAYEYITGI
BAA24107.1  (163) --AG-RYGLDVYSPNINTFRHPVWGRGQETPGEDAYCLASTYAYEYITGI
ABA40420.1  (163) --VG-RYGLDVYAPNINAFRSAMWGRGQETPGEDAYCLASAYAYEYITGI
CAA73902.1  (160) --AG-LGGVDVYSPNINTFRHPVWGRGQETPGEDAFLTS-VYGYEYITAL
EAA64470.1  (161) --AG-LGGVDVYSPNINTFRHPVWGRGQETPGEDAFLTS-VYGYEYITAL
AAL32053.2  (164) --AG-RYGLDSYAPNINGFRSPLWGRGQETPGEDAFFLSSAYAYEYITGL
CAA93248.1  (164) --SG-RYGLDVYAPNVNGFRSPLWGRGQETPGEDAFFLSSAYTYEYITGI
EAA67023.1  (142) --SD-HAGIDYWTPNVNPFKDPRWGRGQETPGEDPLHCS-RYVKEFVGGL
Consensus   (201)       G  AGL  WSPNINIFRDPRWGRGQETPGEDPYL S  YA  YVKGL 251                                             300
C1 BGL1     (170) QDAG----------------VIACAKHFIGNEQEHFRQVPEAQGYGYNIS
TaBGL       (162) QDAG----------------VIACAKHFIGNEMEHFRQASEAVGYGFDIT
CelA        (203) QGKFGS------KDFMAPGRIVASAKHFLADGGTDQG-----------R
AAK43134.1  (177) QG--------------ETQLVATAKHFAAHGFPEG------------GR
AAB70867.1  (188) QGE--NI----------KEGVVATVKHFAGYSASEG------------GK
AAC99628.1  (207) ESAG------------IVATLKHFVGYSASRAG-------------R
CAP07659.1  (178) QGDPDAD---------VLKTHACAKHYAVHSGLES--N---------RH
ACN78955.1  (173) QGPEDAR---------YRKLWACAKHYAVHSGPEY--T---------RH
CAD48309.1  (154) QGNHPK----------YLKAGGMCKNILPFTVVPES-----------LR
BAB11424.1  (208) QETDGG--------DSNRLKVAACCKHYTAYDVDNWKGV---------ER
BAE44362.1  (203) QETDSS--------DANRLKVAACCKHYTAYDVDNWKGV---------ER
AAK96639.1  (198) QETDGG--------DPNRLKVAACCKHYTAYDIDNWRNV---------NR
ABQ45227.1  (203) QQTDDG--------DSDKLKVAACCKHYTAYDVDNWKGV---------QR
AAK38481.1  (202) QDAGAGG-------VTDGALKVAACCKHYTAYDVDNWKGV---------ER
AAM53325.1  (198) QGTAAG---------NRLKVAACCKHYTAYDLDNWNGV---------DR
AAS17751.2  (195) QGDGAG---------NRLKVAACCKHYTAYDLDNWNGV---------DR
CAJ41429.1  (190) QG-SDG---------IRLKVAACCKHFTAYDLDNWNGV---------DR
AAK38482.1  (194) QGYGMSG-----AINSSDLEASACCKHYTAYDLENWKGV---------TR
ACL54109.1  (230) QDVDDRPYAAAADPFSRPIKVSSCCKHFAAYDVDAWFKA---------DR
BAG82824.1  (207) QGGVNP---------EHLKAATAKHFAGYDIENWDNH---------SR
BAE19756.1  (215) QGPDPE---------SNLKLAATAKHYAGYDIENWHNH---------SR
BAA24107.1  (210) QGGVDA---------NPLKLIATAKHYAGYDIENWDNH---------SR
ABA40420.1  (210) QGGVDP---------EHLKLVATAKHYAGYDLENWDGH---------SR
CAA73902.1  (206) QGAVDP---------ETSKIIATAKHYAGYDIESWNNH---------SR
EAA64470.1  (207) QGGVDP---------ETLKIIATAKHYAGYDIESWNNH---------SR
AAL32053.2  (211) QGGVDP---------EHVKIVATAKHYAGYDLENWGNV---------SR
CAA93248.1  (211) QGGVDP---------EHLKVAATVKHFAGYDLENWNNQ---------SR
EAA67023.1  (188) QG-DDP---------EKPKVVATCKHLAAYDLEEWGGV---------SR
Consensus   (251) QG              LKV AC KHYAAYDLENW              R 301                                             350
C1 BGL1     (204) ETLSSNIDDKTMHELYLWPFADAVRAG-VGSVMCSYQQVNNSYACQNSKL
TaBGL       (196) ESVSSNIDDKTLHELYLWPFADAVRAG-VGSFMCSYNQVNNSYSCSNSYL
CelA        (235) DQGDARISEDELIRIHNAGYPAIDAG-VLTVMASFSSWQGIKHHGHKQL
AAK43134.1  (200) NIAQVHVGNRELRETFLFPPFEVAVKIGKVMSIMPAYHEIDGVPCHGNPQL
AAB70867.1  (214) NWAPTNIPEREFREVFLFPPFEAAVKEARVLSVMNSYSEIDGVPCAANRRL
AAC99628.1  (229) NLGPSSVGTRERTDVLLPPFEMAVREGGSRSVMSAYTDIDGVPAAADEAL
CAP07659.1  (207) RFDA-QVSERDLRETYLPAFKDLYTKAGVKEVMTAYNRFRGYPCAASEYL
ACN78955.1  (202) TANLTDVSARDFWETYMPAFKTLVKDAKVREVMCAYQRLDDDPCCGSTRL
CAD48309.1  (182) HEFNAVVSKKDLYETYLPAFKALVQEAKVESVMGAYNRTNGEPCCGSKTL
BAB11424.1  (241) YSFNAVVTQQDMDDTYQPPPFKSCVVDGNVASVMCSYNQVNGKPTCADPDL
BAE44362.1  (236) YSFNAVVNQQDLDDTYQPPPFKSCVVDGNVASVMCSYNKVNGKPTCADPDL
AAK96639.1  (231) LTFNAVVNQQDLADTFQPPPFKSCVVDGHVASVMCSYNQVNGKPTCADPDL
ABQ45227.1  (236) YTFDAVVSQQDLDDTFQPPPFKSCVIDGNVASVMCSYNKVNGKPTCADPDL
AAK38481.1  (237) YTFDAKVSQQDLDDTFQPPPFKSCVLDGNVASVMCSYNKVNGKPTCADKDL
AAM53325.1  (229) FHFNAKVTQQDLEDTYNVPPFKSCVYEGKVASVMCSYNQVNGKPTCADENL
AAS17751.2  (226) FHFNARVSKQDLADTYDVPFRGCVLEGKVASVMCSYNQVNGKPTCADENL
CAJ41429.1  (220) FHFNAKVSKQDMVDTFDVPFRMCVKEGKVASVMCSYNQVNGIPTCADPNL
AAK38482.1  (230) FAFDAKVTEQDLADTYNPPPFKSCVEDGGASGIMCSYNRVNGVPTCADHNL
ACL54109.1  (271) LTFDAQVEERDMVETFERPPFEMCIRDGDASCVMCSYNRINGIPACADARL
BAG82824.1  (238) LGNDVNITQQDLAEYYTPQFLVAARDAVHSFMCSYNAVNGVPSCSNTFF
BAE19756.1  (246) LGNDMNITQQDLSEYYTPQFHVAARDAKVQSVMCAYNAVNGVPSCADSYF
BAA24107.1  (241) LGNDMQITQQDLAEYYTPQFVASRDAKVHSVMCSYNAVNGVPSCSNSFF
ABA40420.1  (241) LGNDMNITQQELSEYYTPQFLVAARDAKVHSVMCSYNAVNGVPSCANSFF
CAA73902.1  (237) LGNDMQITQQELSEYYTPPFIVASRDAKVRSVMCSYNAVNGVPSCANKFF
EAA64470.1  (238) LGNDMQITQQELSEYYTPPFIVASRDAKVRSVMCSYNAVNGVPSCANKFF
AAL32053.2  (242) LGSNAIITQQDLSEYYTPQFLASARYAKTRSLMCSYNAVNGVPSCSNSFF
CAA93248.1  (242) LGFDAIITQQDLSEYYTPQFLAAARYAKSRSLMCAYNSVNGVPSCANSFF
EAA67023.1  (218) FEFDAKVSAVDLLEYYLPPFKTCAVDASVGAFMCSYNALNGVPACADRYL
Consensus   (301)     A VTQQDL ETY PPF AVRDGKV SVMCSYN VNGVPTCA    L
```

TABLE 16-continued

```
                  351                                              400
C1 BGL1      (253) LNDLLKNELGFQG---FVMSDWQAQHTGAAS--------AVAGLDMSMPG
TaBGL        (245) LNKLLKSELDFQG---FVMSDWGAHHSGVGA--------ALAGLDMSMPG
CelA         (284) LTDVLKGQMGFNG---FIVGDWNAHDQVPGCTKFN--------CPTSLIA
AAK43134.1   (250) LTNILRQEWGFDG---IVVSDYDGIRQLEAIHKVASNK--MEAAILALES
AAB70867.1   (264) LTDILRKDWGFEG---IVVSDYFAVNMLGEYHRIAKDK--SESARLALEA
AAC99628.1   (279) LTGAVRDTWGFEG---TVVADYFGIAFLKTLHGITAD--WADAAGAALKA
CAP07659.1   (256) VQKILREEWGYKG---LVVSDCWAIPDFFEPGRHGFVATGEEAAALAVAN
ACN78955.1   (252) LQQILRDEWGFEY---LVVSDCGAVSDFYEN--HKSSSDAVHGTSKAVLA
CAD48309.1   (232) LSDILRGEWGFKG---HVVSDCWAIRDFHMHHHVTAT--APESAALAVRN
BAB11424.1   (291) LSGVIRGEWKLNG---YIVSDCDSVDVLYKNQHYTKT--PAEAAAISILA
BAE44362.1   (286) LSGVIRGEWKLNG---YIVSDCDSVDVLYKNQHYTKT--PEEAAAISINA
AAK96639.1   (281) LSGVIRGQWQLNG---YIVSDCDSVDVLFRKQHYAKT--PEEAVAKSLLA
ABQ45227.1   (286) LKGVIRGKWKLNG---YIVSDCDSVEVLYKDQHYTKT--PEEAAAKTILS
AAK38481.1   (287) LEGVIRGDWKLNG---YIVSDCDSVDVLYTQQHYTKT--PEEAAAITIKS
AAM53325.1   (279) LKNTIRGQWRLNG---YIVSDCDSVDVFNQQHYTST--PEEAAARSIKA
AAS17751.2   (276) LKNTIRGEWKLNG---YIVSDCDSVGVFYDQQHYTRT--PEEAAAEAIKA
CAJ41429.1   (270) LKKTVRGQWRLNG---YIVSDCDSFGVYYGQQHFTS---PRRSSLGCYKA
AAK38482.1   (280) LSKTARGDWSFNG---YITSDCDAVAIIHDVQGYAKA--PEDAVADVLKA
ACL54109.1   (321) LSETVRSQWQLHG---YIVSDCSVRVMVRDAKWLNY-TGVEATAAAMKA
BAG82824.1   (288) LQTLLRDTFSFVDHG-YVSGDCGAVYGVFNPHGYAAN--EPSAADAILA
BAE19756.1   (296) LQTLLRDTFGFVDHG-YVSSDCDAAYNIYNPHGYASS--QAAAAAEAILA
BAA24107.1   (291) LQTLLRDTFDFVEDG-YVSGDCGAVYNVFNPHGYATN--ESSAAADSIRA
ABA40420.1   (291) LQTLLRDTFGFVEDG-YVSSDCSAYNVWNPHEFAAN--ITGAAASDSIRA
CAA73902.1   (287) LQTLLRDTFEFSEDG-YVSGDCGAVYNVWNPHGYASN--EAAASADSILA
EAA64470.1   (288) LQTLLRDTFEFSEDG-YVSGDCGAVYNVWNPHGYASN--EAAASADSILA
AAL32053.2   (292) LQTLLRESFNFVDDG-YVSSDCDAVYNVFNPHGYALN--QSGAAADSLLA
CAA93248.1   (292) LQTLLRESWGFPEWG-YVSSDCASVNVFNPHDYASN--QSSAAASSLRA
EAA67023.1   (268) LQTVLREHWGWEGPGHWVTGDCGAVERIQTYHHYVES--GPEAAAALNA
Consensus    (351) L  LLR  W F G   YVVSDCDAV  LY    Y      EAAA SI A 401                                              450
C1 BGL1      (292) DTQFNTGVSFWG------ANLTLAVLNGTVPAYRLDDMAMR----IMAAL
TaBGL        (284) DTAFGTGKSFWG------TNLTIAVLNGTVPEWRVDDMAVR----IMAAF
CelA         (323) GLDMYMAADSWK---QLYENTLAQVKDGTIPMARLDDAVRR----ILRVK
AAK43134.1   (295) GVDIEFPTIDCYG-----EPLVTAIKEGLVSEAIIDRAVER----VLRIK
AAB70867.1   (309) GIDVELPKTDCY------QHLKDLVEKGIVPESLIDEAVSR----VLKIK
AAC99628.1   (324) GLDVELPTVQDFG-----TPLVDAVTDGRVPEALIDRAAPRPGTEGGART
CAP07659.1   (303) GLDVECGS--TFSKIP------AAIDQGLLKEEDLDRNLLR----VLTER
ACN78955.1   (297) GTDVECGFNYAYKSLP------EAVRKGLLSEKEVDKHVIR----LLEGR
CAD48309.1   (277) GCDLNCGNMFG--------NLLIALKEGLITEEEIDRAVTR----LMITR
BAB11424.1   (336) GLDLNCGSFLG-------QHTEEAVKSGLVNEAAIDKAISN----NFLTL
BAE44362.1   (331) GLDLNCGYFLG-------DHTEAAVKAGLVKEAAIDKAITN----NFLTL
AAK96639.1   (326) GLDLNCDHFNG-------QHAMGAVKAGLVNETAIDKAISN----NFATL
ABQ45227.1   (331) GLDLDCGSYLG-------QYTGGAVKQGLVDEASITNAVSN----NFATL
AAK38481.1   (332) GVDLNCGNFLA-------QHTVAAVQAGELSEEDVDRAITN----NFIML
AAM53325.1   (324) GLDLDCGPFLA-------IFTEGAVKKGLLTENDINLALAN----TLTVQ
AAS17751.2   (321) GLDLDCGPFLA-------IHTEGAIKAGLLPEIDVDYALAN----TLTVQ
CAJ41429.1   (314) GLDLDCGPFLV-------THRDAVKKA--AEEAEINNAWLK----TLTFQ
AAK38482.1   (325) GMDVNCGGYIQ-------THGVSAYQQGKITGEDIDRALRN----LFAIR
ACL54109.1   (367) GLDLDCGMFWEGARDFFTTYGVDAVRQGKIKEGDVDNALSN----VYTTL
BAG82824.1   (335) GTDIDCGTSYQ-------YHFNESITTGAVARDDIERGFIR----LYANL
BAE19756.1   (343) GTDIDCGTTYQ-------WHLNESITAGDLSRDDIEQGVIR----LYTTL
BAA24107.1   (338) GTDIDCGVSYP-------RHFQESFHDQEVSRQDLERGVIR----LYASL
ABA40420.1   (338) GTDIDCGTTYQ-------YYFGEAFDEQEVTRAEIERGVIR----LYSNL
CAA73902.1   (334) GTDIDCGTSYQ-------WHSEDAFEDSLVSRSDIERGVIR----LYSNL
EAA64470.1   (335) GTDIDCGTSYQ-------WHSEDAFEDSLVSRSDIERGVIR----LYSNL
AAL32053.2   (339) GTDIDCGQTMP-------WHLNESFYERYVSRGDIEKSLTR----LYANL
CAA93248.1   (339) GTDIDCGQTYP-------WHLNESFVAGEVSRGEIERSVTR----LYANL
EAA67023.1   (316) GVDLDCGTWLP-------SYLGEAERQGLISNETLDAALTR----LYTSL
Consensus    (401) GLDLDCG            H EAV  GLVSE DIDRAV R      LY L 451                                              500
C1 BGL1      (332) FKVTKTTDLEPINFSFWTDDTYGPIHWAAKQGYQEINSHVDVRADHGNLI
TaBGL        (324) YKVGRDRYQVPVNFDSWTKDEYGYEHALVGQNYVKVNDKVDVRADHADII
CelA         (366) VLAGLFEKPAP-----------------KDRPGLPGLETLGSPEHRAVG
AAK43134.1   (336) ERLGLLDNPFVD----------------ES-----AVPERLDDRKSRELA
AAB70867.1   (349) FMLGLFENPYVD----------------V---------EKAKIESHRDLA
AAC99628.1   (369) ARPGLEPGPAALDG-----------VDLSHPEALRGRIDLDRPENRELA
CAP07659.1   (341) FRLGEMDGES-------------------PWDDLDPAIVEGPEHRALS
ACN78955.1   (337) FDLGEMDDPSL-------------------VEWSKIPYSAMSTKASANVA
CAD48309.1   (315) MKLGMFDPEDQ------------------VPYASIS-SFVDCKEHRELA
BAB11424.1   (375) MRLGFFDGNPK----------------NQIYGGLGPTDVCTSANQELA
BAE44362.1   (370) MRLGFFDGDPK----------------KQIYGGLGPKDVCTPANQELA
AAK96639.1   (365) MRLGFFDGPK-----------------KQLYGGLGPKDVCTADNQELA
ABQ45227.1   (370) MRLGFFDGDPS----------------KQPYGNLGPKDVCTPENQELA
AAK38481.1   (371) MRLGFFDGDPR----------------QLAFGSLGPKDVCTSSNRELA
AAM53325.1   (363) MRLGMFDG--N----------------LGPYANLGPRDVCTPAHKHLA
AAS17751.2   (360) MRLGMFDGEPS----------------AQQYGNLGPRDVCTPAHQELA
```

TABLE 16-continued

```
CAJ41429.1   (351) ISLGIFDG-SP------------------LQAVGDVVP-TMGPPTNQDLA
AAK38482.1   (364) MRLGLFDGNPK-----------------YNRYGNIGADQVCSKEHQDLA
ACL54109.1   (413) MRLGFFDG--------------------MPEFESLGASNVCTDGHKELA
BAG82824.1   (374) VELGYFDGNSSS----------------SN-PYRSLGWPDVQKTDAWNIS
BAE19756.1   (382) VQAGYFDSNTTK----------------ANNPYRDLSWSDVLETDAWNIS
BAA24107.1   (377) IRAGYFDGKTS-----------------PYRNITWSDVVSTNAQNLS
ABA40420.1   (377) VRLGYFDGNGS-----------------VYRDLTWNDVVTTDAWNIS
CAA73902.1   (373) VQAGYFDGEDA-----------------PYRDITWDDVLSTDAWNIA
EAA64470.1   (374) VQAGYFDGEDA-----------------PYRDITWDDVLSTDAWNIA
AAL32053.2   (378) VRLGYFDGNNS-----------------VYRNLNWNDVVTTDAWNIS
CAA93248.1   (378) VRLGYFDKKN------------------QYRSLGWKDVVKTDAWNIS
EAA67023.1   (355) VQLGYFDPAEGQ----------------PLRSLGWDDVATSEAEELA
Consensus    (451) MRLGYFDG                   Y  LG DV T D  ELA 501                                               550
C1 BGL1      (382) REIAAKGTVLLKN-TGSLPLN------KPKFVAVIGEDAGSSPNGPNGCS
TaBGL        (374) RQIGSASVVLLKN-DGGLPLTG-----YEKFTGVFGEDAGSNRWGADGCS
CelA         (398) REAVRKSLVLLKNDKGTLPLSPK------ARVLVAGDGADNIG-------
AAK43134.1   (365) LKAARESIVLLKNENNMLPLSKNIN-----KIAVIGPNAN----------
AAB70867.1   (374) LEIARKSIILLKNDG-TLPLQKNK------KVALIGPNAG----------
AAC99628.1   (407) REIAEKAVVLLTN-DGTLPLARP------RRIALIGPNAA----------
CAP07659.1   (370) LDIARETMVLLRN-NGVLPLKAG------EKIALIGPNADD---------
ACN78955.1   (368) LDMARQTIVLLQNKNNILPLKKNA-----EKIAIIGPNAHN---------
CAD48309.1   (345) LDVAKKSIVLLKN-DGLLPLDRK----KIRSIAVIGPNADS---------
BAB11424.1   (407) ADAARQGIVLLKN-TGCLPLSPK----SIKTLAVIGPNANV---------
BAE44362.1   (402) AEAARQGIVLLKN-TGALPLSPK----TIKTLAVIGPNANV---------
AAK96639.1   (397) RDGARQGIVLLKNSAGSLPLSPS----AIKTLAVIGPNANA---------
ABQ45227.1   (402) REAARQGIVLLKNSPRSLPLSSK----AIKSLAVIGPNANA---------
AAK38481.1   (403) RETARQGIVLLKN-SGALPLSAK----SIKSMAVIGPNANA---------
AAM53325.1   (393) LEAAHQGIVLLKNSARSLPLSPR----RHRTVAVIGPNSDV---------
AAS17751.2   (392) LEASRQGIVLLQNNGHTLPLSTV----RHRTVAVVGPNSDV---------
CAJ41429.1   (381) VNAPKR-LFIFKNRAFLLYSPRH----IFGPVALFKS-------------
AAK38482.1   (396) LQAARDGIVLLKNDGAALPLSKS----KVSSLAVIGPNGNN---------
ACL54109.1   (442) ADAARQGMVLLKNDARRLPLDPN----KINSVSLVGLLEHIN--------
BAG82824.1   (407) YEAAVEGIVLLKN-DGTLPLASPSE-GKNKSIALIGPWAN----------
BAE19756.1   (416) YQAATQGIVLLKNSNNVLPLTEKAYPPSNTTVALIGPWAN----------
BAA24107.1   (407) YEAAQSIVLLKN-DGILPLTSTS--SSTKTIALIGPWAN-----------
ABA40420.1   (407) YEAAVEGIVLLKN-DGTLPLA-----KSVRSVALIGPWMN----------
CAA73902.1   (403) YEAAVEGIVLLKN-DETLPLS-----KDIKSVAVIGPWAN----------
EAA64470.1   (404) YEAAVEGIVLLKN-DETLPLS-----KDIKSVAVIGPWAN----------
AAL32053.2   (408) YEAAVEGITLLKN-DGTLPLS-----KKVRSIALIGPWAN----------
CAA93248.1   (407) YEAAVEGIVLLKN-DGTLPLS-----KKVRSIALIGPWAN----------
EAA67023.1   (386) KTVAIQGTVLLKNIDWTLPLK-----ANG-TLALIGPFIN----------
Consensus    (501)  EAAR GIVLLKN  GTLPLS         KSVAVIGPNAN 551                                               600
C1 BGL1      (425) DRGCNEGTLAMGWGSGTANYP---------------------
TaBGL        (418) DRGCDNGTLAMGWGSGTADFP---------------------
CelA         (435) ----KQSGGWTISWQGTGNRN---------------------
AAK43134.1   (400) -----DPRNMLGDYTYTGHLN---------------------
AAB70867.1   (407) -----EVRNLLGDYMYLAHIRALLDNIDDVFGNPQIPRENYERLKKSIEE
AAC99628.1   (440) -----EATAVLGCYSFPRHVG---------------------VQHPEVP
CAP07659.1   (404) ------AQMQWGNYNPVPKST---------------------
ACN78955.1   (404) -----EPMMWGNYNGTPNHT----------------------
CAD48309.1   (381) ------RQALIGNYEGTASEY---------------------
BAB11424.1   (443) ------TKTMIGNYEGTPCKY---------------------
BAE44362.1   (438) ------TKTMIGNYEGTPCKY---------------------
AAK96639.1   (434) ------TETMIGNYHGVPCKY---------------------
ABQ45227.1   (439) ------TRVMIGNYEGIPCKY---------------------
AAK38481.1   (439) ------SFTMIGNYEGTPCKY---------------------
AAM53325.1   (430) ------TETMIGNYAGKACAY---------------------
AAS17751.2   (429) ------TETMIGNYAGVACGY---------------------
CAJ41429.1   (413) ------LPFMLGNYEGLPCKY---------------------
AAK38482.1   (433) ------ASLLLGNYFGPPCIS---------------------
ACL54109.1   (480) -----ATDVMLGDYRGKPCRI---------------------
BAG82824.1   (445) -----ATTQLQGNYYGDAPYL---------------------
BAE19756.1   (456) -----ATTQLLGNYYGNAPYM---------------------
BAA24107.1   (444) -----ATTQMLGNYYGPAPYL---------------------
ABA40420.1   (441) -----VTTQLQGNYFGPAPYL---------------------
CAA73902.1   (437) -----VTEELQGNYFGPAPYL---------------------
EAA64470.1   (438) -----VTEELQGNYFGPAPYL---------------------
AAL32053.2   (442) -----ATVQMQGNYYGTPPYL---------------------
CAA93248.1   (441) -----ATTQMQGNYYGPAPYL---------------------
EAA67023.1   (420) -----FTTELQSNYAGPAKHI---------------------
Consensus    (551)        T  MIGNY G A 601                                               650
C1 BGL1      (446) --YLVSPDAALQARAIQ-------DGTR------------YESVLSNYA-
TaBGL        (439) --YLVTPEQAIQNEILS-------KGKG------------LVSAVTDNG-
CelA         (452) -----DEFPGATSILGGIRDAVADAGGS---------------VEFDVAG
```

TABLE 16-continued

```
AAK43134.1  (419) GIEIVTVLQGIAKKVGEGK-VLYAKGCDIAG------------ESKEG--
AAB70867.1  (452) HMKSIPSVLDAFKEEG-ID-FEYAKGCEVTG------------EDRSG--
AAC99628.1  (463) VGLDLPTLYDTLTAEFPDADIALARGTG--------------VDDGEVSG
CAP07659.1  (419) ----ITLLQAMQARVP--G-LVYDR---------ACGILDAEYAPQGS-
ACN78955.1  (419) ----VTILDGVKAKQK--K-LVYIPGCDLTNDKVMECHLATDCVTPDGKK
CAD48309.1  (396) ----VTVLDGIREMAGDDVRIYYSVGCHLYKDR--------VENLGEPG-
BAB11424.1  (458) ----TTPLQGLAGTVS----TTYLPGCSN-----------VACAVADVA-
BAE44362.1  (453) ----TTPLQGLAGTVH----TTYLPGCSN-----------VACAVADVA-
AAK96639.1  (449) ----TTPLQGLAETVS----STYQLGCN------------VACVDADIG-
ABQ45227.1  (454) ----TSPLQGLTAFVP----TSYAPGCPD-----------VQCANAQID-
AAK38481.1  (454) ----TTPLQGLGAKVN----TVYQPGCTN-----------VGCSGNSLQ-
AAM53325.1  (445) ----TSPLQGISRYAR----TLHQAGCAG-----------VACKGNQGF-
AAS17751.2  (444) ----TTPLQGIGRYTK----TIHQQGCTN-----------VACTTNQLF-
CAJ41429.1  (428) ----LFPLQGLAGFVS----LLYLPGCSN-----------VICAVAD-V-
AAK38482.1  (448) ----VTPLQALQGYVK--D-ARFVQGCNA-----------AVCNVSN-I-
ACL54109.1  (496) ----VTPYNAIRNMVN----ATYVHACDS-----------GACNTAEGM-
BAG82824.1  (461) ----ISPVDAFTAAGY--T-VHYAPGTE-----------ISTNSTAN--
BAE19756.1  (472) ----ISPRAAFEEAGY--K-VNFAEGTG-----------ISSTSTSG--
BAA24107.1  (460) ----ISPLQAFQDSEY--K-ITYTIGTN-----------TTTDPDSTS-
ABA40420.1  (457) ----ISPLNAFQNSDF--D-VNYAFGTN-----------ISSHSTDG--
CAA73902.1  (453) ----ISPLTGFRDSGL--D-VHYALGTN-----------LTSHSTSG--
EAA64470.1  (454) ----ISPLTGFRDSGL--D-VHYALGTN-----------LTSHSTSG--
AAL32053.2  (458) ----ISPLEAAKASGF--T-VNYAFGTN-----------ISTDSTQW--
CAA93248.1  (457) ----ISPLEAAKKAGY--H-VNFELGTE-----------IAGNSTTG--
EAA67023.1  (436) ----PTMIEAAERLGY--N-VLTAPGTE-----------VNSTSTDG--
Consensus   (601)     ITPLQGL       V Y  GC              V 651                                              700
C1 BGL1     (474) --------------------------------------------------
TaBGL       (467) --------------------------------------------------
CelA        (482) --------------------------------------------------
AAK43134.1  (454) --------------------------------------------------
AAB70867.1  (486) --------------------------------------------------
AAC99628.1  (499) --------------------------------------------------
CAP07659.1  (451) --------------------AYANLIGASEAQLEAAAR------------
ACN78955.1  (462) GLKGTFWNNTEMAGKPFTTEYYTKPVNVTTAGMHVFAPNLPIEDFSAKYE
CAD48309.1  (433) --------------------------------------------------
BAB11424.1  (488) --------------------------------------------------
BAE44362.1  (483) --------------------------------------------------
AAK96639.1  (478) --------------------------------------------------
ABQ45227.1  (484) --------------------------------------------------
AAK38481.1  (484) --------------------------------------------------
AAM53325.1  (475) --------------------------------------------------
AAS17751.2  (474) --------------------------------------------------
CAJ41429.1  (457) --------------------------------------------------
AAK38482.1  (478) --------------------------------------------------
ACL54109.1  (526) --------------------------------------------------
BAG82824.1  (490) --------------------------------------------------
BAE19756.1  (501) --------------------------------------------------
BAA24107.1  (490) --------------------------------------------------
ABA40420.1  (486) --------------------------------------------------
CAA73902.1  (482) --------------------------------------------------
EAA64470.1  (483) --------------------------------------------------
AAL32053.2  (487) --------------------------------------------------
CAA93248.1  (486) --------------------------------------------------
EAA67023.1  (465) --------------------------------------------------
Consensus   (651)

701                                              750
C1 BGL1     (474) --------------------------------------------------
TaBGL       (467) --------------------------------------------------
CelA        (482) --------------------------------------------------
AAK43134.1  (454) --------------------------------------------------
AAB70867.1  (486) --------------------------------------------------
AAC99628.1  (499) --------------------------------------------------
CAP07659.1  (469) ------------------RYAVSVNDIKNYIRRDEEQRRSFMP---
ACN78955.1  (512) TTFTAKEAGEYVVNVESTGHFELYVNGKQQFVNHIWRATPTRTVLKAEKG
CAD48309.1  (433) --------------------------------------------------
BAB11424.1  (488) --------------------------------------------------
BAE44362.1  (483) --------------------------------------------------
AAK96639.1  (478) --------------------------------------------------
ABQ45227.1  (484) --------------------------------------------------
AAK38481.1  (484) --------------------------------------------------
AAM53325.1  (475) --------------------------------------------------
AAS17751.2  (474) --------------------------------------------------
CAJ41429.1  (457) --------------------------------------------------
AAK38482.1  (478) --------------------------------------------------
ACL54109.1  (526) --------------------------------------------------
BAG82824.1  (490) --------------------------------------------------
BAE19756.1  (501) --------------------------------------------------
```

TABLE 16-continued

```
BAA24107.1   (490) --------------------------------------------------
ABA40420.1   (486) --------------------------------------------------
CAA73902.1   (482) --------------------------------------------------
EAA64470.1   (483) --------------------------------------------------
AAL32053.2   (487) --------------------------------------------------
CAA93248.1   (486) --------------------------------------------------
EAA67023.1   (465) --------------------------------------------------
Consensus    (701)

751                                              800
C1 BGL1      (474) ---------------------------EEKTKALVSQANATAIVFVNA
TaBGL        (467) ---------------------------ALDQMEQVASQASVSIVFVNA
CelA               ---------------------------QYKTKP--DVAIVVFGE
AAK43134.1   (454) ---------------------------FSEAIEIAKQADVIIAVMGE
AAB70867.1   (486) ---------------------------FKEAIEVAKRSDVAIVVVGD
AAC99628.1   (499) ---------------------------IGEAVDAARAADVVVAVLGD
CAP07659.1   (494) ---------------------------ALDEAAVLKKLEGVDVVVFAGGI
ACN78955.1   (562) QKFDIEVRFQTVKTWGASMKIDVARELNIDYQETIAQLKGINKVIFCGGI
CAD48309.1   (433) ---------------------------DRIAEAVTCAEHADVVIMCLGL
BAB11424.1   (488) ---------------------------G--ATKLAATADVSVLVIGA
BAE44362.1   (483) ---------------------------G--STKLAAASDATVLVIGA
AAK96639.1   (478) ---------------------------S--AVDLAASADAVVLVVGA
ABQ45227.1   (484) ---------------------------D--AAKIAASADATIIVVGA
AAK38481.1   (484) ---------------------------LSTAVAAAASADVTVLVVGA
AAM53325.1   (475) ---------------------------G--AAEAAAREADATVLVMGL
AAS17751.2   (474) ---------------------------G--AAEEAAARQADATVLVMGL
CAJ41429.1   (457) ---------------------------G--SAVDLAASADAVVLVVGA
AAK38482.1   (478) ---------------------------G--EAVHAAGSADYVVLFMGL
ACL54109.1   (526) ---------------------------G--RASSTAKIADATIVIAGL
BAG82824.1   (490) ---------------------------FSAALSAARAADTIVFLGGI
BAE19756.1   (501) ---------------------------FAAALSAAQSADVIIYAGGI
BAA24107.1   (490) ---------------------------QSTALTTAKEADLIIFAGGI
ABA40420.1   (486) ---------------------------FSEALSAAKKSDVIIFAGGI
CAA73902.1   (482) ---------------------------FEEALTAAKQADAIIFAGGI
EAA64470.1   (483) ---------------------------FEEALTAAKQADAIIFAGGI
AAL32053.2   (487) ---------------------------FAEAISAAKKSDVIIYAGGI
CAA93248.1   (486) ---------------------------FAKAIAAAKKSDAIIYLGGI
EAA67023.1   (465) ---------------------------FDDALAIAAEADALIFFGGI
Consensus    (751)                            AL  AK AD IILVVGI 801                                              850
C1 BGL1      (495) DSGEGYINVDG-----------N---EGDRKNLTLWNNGDTLVKNVSSWC
TaBGL        (488) DSGEGYINVDG-----------N---EGDRKNLTLWKGGEEVIKTVAANC
CelA         (497) EPYAEFQG-------------------DVETLEYQPDQKQDLALLKKLK
AAK43134.1   (474) KSGLPLSWTDIPSEEEFKKYQAVTGEGNDRASLRLLGVQEELLKELYKTG
AAB70867.1   (506) RSGLTLDCTTG-----------ES---RDMANLKLPGVQEELVLEIAKTG
AAC99628.1   (519) RAGLFGRGTSG-----------EGCDAESLTLPGAQQRLLDALLDSG
CAP07659.1   (517) SPRLEGEEMRV---------QVPGFSGGDRTDIELPGVQRRLLKALHDAG
ACN78955.1   (612) APSLEGEEMPV---------NIEGFKGGDRTSIELPKVQREFLKALKAAG
CAD48309.1   (455) DSTIEGEE----------MHESNIYGSGDKPDLNLPGQQQELLEAVYATG
BAB11424.1   (506) DQSIEAE------------------SRDRVDLHLPGQQQELVIQVAKAA
BAE44362.1   (501) DQSIEAE------------------SRDRVDLNLPGQQQELVTQVAKAA
AAK96639.1   (496) DQSIERE------------------GHDRVDLYLPGKQQELVTRVAMAA
ABQ45227.1   (502) NLAIEAE------------------SLDRVNILLPGQQQQLVNEVANVS
AAK38481.1   (504) DQSIERE------------------SLDRTSLLLPGQQTQLVSAVANAS
AAM53325.1   (494) DQSIEAE------------------TRDRTGLLLPGYQQDLVTRVAQAS
AAS17751.2   (493) DQSIEAE------------------FRDRTDLVMPGHQQELVSRVARAS
CAJ41429.1   (476) DQSIERE------------------GHDRVDFYLPGKQQELVTRVAMAA
AAK38482.1   (497) DQNQERE------------------EVDRLELGLPGMQESLVNSVADAA
ACL54109.1   (545) NMSVERE------------------SNDREDLLLPWNQSSWINAVAMAS
BAG82824.1   (510) DNTIEAE------------------AQDRSSIAWPGNQLELISQLAAQK
BAE19756.1   (521) DNTLEAE------------------ALDRESIAWPGNQLDLIQKLASAA
BAA24107.1   (510) DNTLETE------------------AQDRSNITWPSNQLSLITKLADLG
ABA40420.1   (506) DNTLEAE------------------AMDRMNITWPGNQLQLIDQLSQLG
CAA73902.1   (502) DNTIEAE------------------AMDRENITWPGNQLDLISKLSELG
EAA64470.1   (503) DNTIEAE------------------AMDRENITWPGNQLDLISKLSELG
AAL32053.2   (507) DNTIEAE------------------GQDRTDLKWPGNQLDLIEQLSKVG
CAA93248.1   (506) DNTIEQE------------------GADRTDIAWPGNQLDLIKQLSEVG
EAA67023.1   (485) DNTVEEE------------------SLDRTRIDWPGNQEELILELAELG
Consensus    (801) DNTIEAE                   S DR  L LPGNQ ELI  LA  G 851                                              900
C1 BGL1      (531) S---NTIVVIHSVGPVLLTDWYDNPNITAILWAGLPGQESGNSITDVLYG
TaBGL        (524) N---NTIVVMHTVGPVLIDEWYDNPNVTAIVWAGLPGQESGNSLVDVLYG
CelA         (527) DQGIPVVAVFLSGRP--MWVNPELNASDAFVAAWLPGTEGG-GVADVLFT
AAK43134.1   (524) ---KPIILVLINGRP--LVLSPIINYVKAIIEAWFPGEEGGNAIADIIFG
AAB70867.1   (542) ---KPVVLVLITGRP--YSLKNLVDRVNAILQVWLPGEAGGRAIVDVIYG
AAC99628.1   (555) ---TPVVTVLLAGRPYALG---RARQSAAIVQSFFPGEEGTAALAGVLSG
CAP07659.1   (558) ---KKVVLVNFSG--CAIGLVPETESCDAILQAWYPGQEGGTAIADVLFG
ACN78955.1   (653) ---KQVIYVNCSG--SAIALQPETESCDAIVQAWYPGQEGGTAVADVLFG
```

TABLE 16-continued

```
CAD48309.1   (495)  ---KPIVLVLLTG--SALAVTWADEHIPAILNAWYPGALGGRAIASVLFG
BAB11424.1   (537)  K--GPVLLVIMSGGGFDITFAKNDPKIAGILWVGYPGEAGGIAIADIIFG
BAE44362.1   (532)  K--GPVFLVIMSGGGFDITFAKNDAKIAGILWVGYPGEAGGIATADVIFG
AAK96639.1   (527)  R--GPVVLVIMSGGGFDITFAKNDKKITSIMWVGYPGEAGGLAIADVIFG
ABQ45227.1   (533)  K--GPVILVIMSGGGMDVSFAKTNDKITSILWVGYPGEAGGAAIADVIFG
AAK38481.1   (535)  S--GPVILVVMSGGPFDISFAKASDKIAATLWVGYPGEAGGAALDDTLFG
AAM53325.1   (525)  R--GPVILVLMSGGPIDVTFAKNDPRVAAIIWAGYPGQAGGAAIANIIFG
AAS17751.2   (524)  R--GPTVLVLMSGGPIDVSFAKNDPKIGAIIWVGYPGQAGGTAMADVLFG
CAJ41429.1   (507)  K--GPVLLVIMD--------------LAISGGGCSYNQVNGIPISDVCEG
AAK38482.1   (528)  K--KPVILVLLCGGPVDVTFAKNNPKIGAIVWAGYPGQAGGIAIAQVLFG
ACL54109.1   (576)  P--TPIVLVIMSAGGVDVSFAHNNTKIGAIVWAGYPGEEGGTAIADVLFG
BAG82824.1   (541)  SDDQPLVVYQMGGGQVDSSALKSNAKVNALLWGGYPGQSGGLALRDILTG
BAE19756.1   (552)  GK-KPLIVLQMGGGQVDSSSLKNNTKVSALLWGGYPGQSGGFALRDIITG
BAA24107.1   (541)  ---KPLIVLQMGGGQVDSSALKNNKNVNALIWGGYPGQSGGQALADIITG
ABA40420.1   (537)  ---KPLIVLQMGGGQVDSSSLKSNKNVNSLIWGGYPGQSGGQALLDIITG
CAA73902.1   (533)  ---KPLVVLQMGGGQVDSSSLKDNDNVNALIWGGYPGQSGGHALADIITG
EAA64470.1   (534)  ---KPLVVLQMGGGQVDSSSLKDNDNVNALIWGGYPGQSGGHALADIITG
AAL32053.2   (538)  ---KPLVVLQMGGGQVDSSSLKANKNVNALVWGGYPGQSGGAALFDILTG
CAA93248.1   (537)  ---KPLVVLQMGGGQVDSSSLKSNKKVNSLVWGGYPGQSGGVALFDILSG
EAA67023.1   (516)  ---RPLTVVQFGGGQVDDSALLASAGVGAIVWAGYPSQAGGAGVFDVLTG
Consensus    (851)       KPVVLVIMSGG VDIS  K     V AILWAGYPGQAGG AIADVLFG 901                                             950
C1 BGL1      (578)  KVNPAARSPFTWGKTRESYGADVLYKPNNGNGAPQQDFTEGVFIDYRYFD
TaBGL        (571)  RVSPGGKTPFTWGKTRESYGAPLLTKPNNGKGAPQDDFTEGVFIDYRRFD
CelA         (574)  DKAGKVQHDFAGKLSYSWPRTAAQTTVNRGD-------------------
AAK43134.1   (569)  DYNPSGRLPITFPMDTG--QIPLYYSRKPSS--------------FRPYV
AAB70867.1   (587)  KVNPSGKLPISFPRSAG--QIPVFHYVKPSG--------G-RSHWHGDYV
AAC99628.1   (599)  RTSPTGRLPVSVPGSAAQPTTYLGARLAQAS---------------EVS
CAP07659.1   (603)  DVNPSGKLPVTFYKN---------VDQLPDV--------EDYNMEGHTYR
ACN78955.1   (698)  DYNPGGKLSVTFYKN---------DQQLPDY--------EDYSMKGRTYR
CAD48309.1   (540)  ETNPSGKLPVTFYRTT--EELPDFTDYSMEN---------------RTYR
BAB11424.1   (585)  RYNPSGKLPMTWYPQSYVEKVPMTIMNMRPD---------KASGYPGRTYR
BAE44362.1   (580)  RYNPSGRLPMTWYPQSYVEKVPMTNMNMRPD---------KSNGYPGRTYR
AAK96639.1   (575)  RHNPSGNLPMTWYPQSYVEKVPMSNMNMRPD---------KSKGYPGRSYR
ABQ45227.1   (581)  SYNPSGRLPMTWYPQSYVEKVPMTNMNMRAD---------PATGYPGRTYR
AAK38481.1   (583)  SHNPSGRLPVTWYPASYADTVTMTDMRRPD----------TSTGYPGRTYR
AAM53325.1   (573)  AANPGGKLPMTWYPQDYVAKVPMTVMAMRAS----------GNYPGRTYR
AAS17751.2   (572)  TTNPSGKLPMTWYPQDYVSKVPMTNMAMRAG----------RGYPGRTYR
CAJ41429.1   (541)  SS---YRWPSFSNCHGYMPWISYS-----R-----------AIW--ETLR
AAK38482.1   (576)  DHNPGGRLPVTWYPK-EFTAVPMTDMRMRAD---------PSTGYPGRTYR
ACL54109.1   (624)  KYNPGGRLPLTWFKNEYVNQIPMTSMALRPD---------AALGYPGRTYK
BAG82824.1   (591)  ARAPAGRLTTTQYPAAYAESFSALDMNLRPN---------ETTQNPGQTYM
BAE19756.1   (601)  KKNPAGRLVTTQYPASYAEEFPATDMNLRPE---------G--DNPGQTYK
BAA24107.1   (588)  KRAPAARLVTTQYPAEYAEVFPAIDMNLRPN----------GSNPGQTYM
ABA40420.1   (584)  KRAPAGRLVTTQYPAEYATQFPATDMSLRPH---------G--NNPGQTYM
CAA73902.1   (580)  KRAPAGRLVTTQYPAEYAEVFPATDMNLRPN---------ETSGNPGQTYM
EAA64470.1   (581)  KRAPAGRLVTTQYPAEYAEVFPAIDMNLRPN---------ETSGNPGQTYM
AAL32053.2   (585)  KRAPAGRLVSTQYPAEYATQFPANDMNLRPN---------G--SNPGQTYI
CAA93248.1   (584)  KRAPAGRLVTTQYPAEYVHQFPQNDMNLRPD---------GK-SNPGQTYI
EAA67023.1   (563)  KAAPAGRLPITQYPKSYVDEVPMTDMNLQPG----------TDNPGRTYR
Consensus    (901)  K NPAGRLPVTWYP   Y     VPM  MNLRP              PGRTYR 951                                            1000
C1 BGL1      (628)  KVDDDSVIYEFGHGLSYTTFEYSNIRVVKSNVSEYRPTTGTTAQAPTFGN
TaBGL        (621)  KYN-ETPIYEFGFGLSYTTFEYSDIYVQPLNARPYTPASGSTKAAPTFGN
CelA         (605)  -ADYNPLFA-YGYGLTYKDKSKVG--------------------------
AAK43134.1   (603)  MLHSSPLFT-FGYGLSYTQFEYSN---------LEVTPKEVGPLS-----
AAB70867.1   (626)  DESTKPLFP-FGHGLSYTRFEYSN---------LRIEPKEVPSAG-----
AAC99628.1   (633)  NIDPTPAFG-FGHGLTYTTFAWSD---------LVAHTKEAPTDG-----
CAP07659.1   (636)  YFRGEPLYP-FGYGLSYTSFAFGE--------------PKVKGK------
ACN78955.1   (731)  YFD-DALFP-FGYGLSYTTFEVGE--------------AKVEAATDGAL-
CAD48309.1   (573)  FMKNEALYP-FGFGLSYTFFDYSD--------LKLSKDTIRAGEG-----
BAB11424.1   (627)  FYTGETVYA-FGDGLSYTKFSHTLVKAP-SLVSLGLEENHVCRSSECQS-
BAE44362.1   (622)  FYTGETVYA-FGDGLSYTKFSHSLVKAP-RLVSLSLEENHVCRSSECQS-
AAK96639.1   (617)  FYTGETVYA-FADALTYTKFDHQLIKAP-RLVSLSLDENHPCRSSECQS-
ABQ45227.1   (623)  FYKGETVFS-FGDGMSFGTVEHKIVKAP-QLVSVPLAEDHECRSLECKS-
AAK38481.1   (625)  FYTGDTVFA-FGDGLSYTKMSHSLVSAPPSYVSMRLAEDHLCRAEECAS-
AAM53325.1   (613)  FYKGPVVFP-FGFGLSTTFTHSLAKSPLAQLSVSLSNLNSANTILNSSS
AAS17751.2   (612)  FYKGPVVFP-FGLGLSYTTFAHSLAQVPTSVSVPLTSLSATTNSTMLSS-
CAJ41429.1   (570)  FTKVNWVPT-WSWNKLHKFGSHHSKCTDDGFGTPRRPPPWLRKCNHFQG-
AAK38482.1   (617)  FYKGKTVYN-FGYGLSYKYSHRFASKGTKPPSMSGIEGLKATARASAAG
ACL54109.1   (666)  FYGGPAVLYPPGHGLSYTNFSYASGTTGATVTIHIGAWEHCKMLTYKMGA
BAG82824.1   (633)  WYTGEPVYA-FGHGLFYTTFNASS--AQAAKTKYTFNITDLTSAAHPDT-
BAE19756.1   (641)  WYTGEAVYE-FGHGLFYTTFAESS--SNTTTKEVKLNIQDILSRTHEEL-
BAA24107.1   (628)  WYTGTPVYE-FGHGLYTNFTASASAGSGTKNRTSFNIDEVLGRPHPGY-
ABA40420.1   (624)  WYTGTPVYE-FGHGLFYTTFHASLPG--TGKDKTSFNIQDLLTQPHPGF-
CAA73902.1   (622)  WYTGTPVYE-FGHGLFYTTFEEST----ETTDAGSFNIQTVLTTPHSGY-
EAA64470.1   (623)  WYTGTPVYE-FGHGLFYTTFEEST----ETTDAGSFNIQTVLTTPHSGY-
AAL32053.2   (625)  WYTGTPVYE-FGHGLFYTEFQESA--AAGTNKTSTLDILDLVPTPHPGY-
```

TABLE 16-continued

```
CAA93248.1   (625) WYTGKPVYE-FGSGLFYTTFKETL--ASHP-KSLKFNTSSILSAPHPGY-
EAA67023.1   (603) WYE-DAVLP-FGFGLHYTTFNVSW----AKKAFGPYDAATLARGKNP---
Consensus    (951) FY G   VY  FGHGLSYTTF HS                       V 1001                                              1050
C1 BGL1      (678) FSTDLEDYLFPKDEFPYIYQYIYPYLNTTDPRRASADPHYGQTAEEFLPP
TaBGL        (670) ISTDYADYLYPEDIH-KVPLYIYPWLNTTDPKKSSGDPDYGMKAEDYIPS
CelA         (627) --------------------------------------------------
AAK43134.1   (638) --------------------------------------------------
AAB70867.1   (661) --------------------------------------------------
AAC99628.1   (668) --------------------------------------------------
CAP07659.1   (665) --------------------------------------------------
ACN78955.1   (764) --------------------------------------------------
CAD48309.1   (609) --------------------------------------------------
BAB11424.1   (674) -LDAIGPHCENAVSG-----------------------------------
BAE44362.1   (669) -LNAIGPHCDNAVSG-----------------------------------
AAK96639.1   (664) -LDAIGPHCENAVEG-----------------------------------
ABQ45227.1   (670) -LDVADKHCQNLAFD-----------------------------------
AAK38481.1   (673) -VEAAGDHCDDLALD-----------------------------------
AAM53325.1   (662) -HSIKVSHTNCNSFP-----------------------------------
AAS17751.2   (660) --AVRVSHTNCNPLS-----------------------------------
CAJ41429.1   (618) --RQSELHMLDVIDS-----------------------------------
AAK38482.1   (666) TVSYDVEEMGAEACD-----------------------------------
ACL54109.1   (716) PSPSPACPALNVASH-----------------------------------
BAG82824.1   (679) ----------TTVGQ-----------------------------------
BAE19756.1   (687) ----------ASITQ-----------------------------------
BAA24107.1   (676) ----------KLVEQ-----------------------------------
ABA40420.1   (670) ----------ANVEQ-----------------------------------
CAA73902.1   (666) ----------EHAQQ-----------------------------------
EAA64470.1   (667) ----------EHAQQ-----------------------------------
AAL32053.2   (671) ----------EYIEL-----------------------------------
CAA93248.1   (670) ----------TYSEQ-----------------------------------
EAA67023.1   (644) ----------SS--------------------------------------
Consensus   (1001)

1051                                              1100
C1 BGL1      (728) HATDDDPQPLLRSSGGNSPGGNRQLYDIVYTITADITNTGSVVGEEVPQL
TaBGL        (719) GATDGSPQPILPAGG--APGGNPGLYDEMYRVSAIITNTGNVVGDEVPQL
CelA         (627) ------------------------------TLPEESGVP-AEARQNAGI
AAK43134.1   (638) ---------------------------YITILLDVKNVGNMEGDEVVQL
AAB70867.1   (661) ---------------------------EVVIKVDVENVGDMDGDEVVQL
AAC99628.1   (668) ---------------------------AFSLELTVRNTGERHGTEVVQL
CAP07659.1   (665) -----------------------------NLEIDVTNTGSVAGTEVVQL
ACN78955.1   (764) ---------------------------YNVQIPVTNTGTKNGSETIQL
CAD48309.1   (609) ---------------------------FNVSVKVTNTGKMAGEEVVQV
BAB11424.1   (688) -------------------------GGSAFEVHIKVRNGGDREGIHTVFL
BAE44362.1   (683) -------------------------TGGKAFEVHIKVQNGGDREGIHTVFL
AAK96639.1   (678) -------------------------GSDFEVHLNVKNTGDRAGSHTVFL
ABQ45227.1   (684) ---------------------------IHLSVKNMGKMSSSHSVLL
AAK38481.1   (687) ---------------------------VKLQVRNAGEVAGAHSVLL
AAM53325.1   (676) ----------------------------K----MPLHVEVSNTGEFDGTHTVFV
AAS17751.2   (673) ---------------------------LALHVVVKNTGARDGTHTLLV
CAJ41429.1   (631) ----------------------------L----LGMQVDVKNTGSMDGTHTLLV
AAK38482.1   (681) ----------------------------R--LRFPAVVRVQNHGPMDGGHLVLL
ACL54109.1   (731) ---------------------------MCSEVVSFSLRVANTGGVGGDHVVPV
BAG82824.1   (684) -------------------------RTLFNFTASITNSGQRDSDYTALV
BAE19756.1   (692) -------------------------LPVLNFTANIRNTGKLESDYTAMV
BAA24107.1   (681) -------------------------MPLLNFTVDVKNTGDRVSDYTAMA
ABA40420.1   (675) -------------------------MPLLNFTVTITNTGKVASDYTAML
CAA73902.1   (671) -------------------------KTLLNFTATVKNTGERESDYTALV
EAA64470.1   (672) -------------------------KTLLNFTATVKNTGERESDYTALV
AAL32053.2   (676) -------------------------VPFLNVTVDVKNVGHTPSPYTGLL
CAA93248.1   (675) -------------------------IPVFTFEANIKNSGKTESPYTAML
EAA67023.1   (646) -------------------------NIVDTFSLAVTNTGDVASDYVALV
Consensus   (1051)                            V V VKNTG VEG HTVLL 1101                                              1150
C1 BGL1      (778) YVSLGGPE----DPKVQLRDFDRMRIEPG-ETRQFTGRLTRRDLSNWDVT
TaBGL        (767) YVSLGGPD----DPKVVLRNFDRITLHPG-QQTMWTTTLTRRDISNWDPA
CelA         (645) YFRAG-ALR---LPGRFL--------------------------------
AAK43134.1   (660) YISKSFSSVAR--PVKELKGFAKVHLKPG--EKRRVKFALPMEALAFYDN
AAB70867.1   (683) YIGREFASVTR--PVKELKGFKRVSLKAK--EKKTVVFRLHTDVLAYYDR
AAC99628.1   (690) YLHDPVASVVQ--PVQRLIGYTRVPLRPG--EARRVRVEVPADLASFNRR
CAP07659.1   (685) YVRKPDDTAG---PVKTLRAFRRVSVPAG-QTVKVSIPLDKETFLWWSEK
ACN78955.1   (785) YIRNLQDPDG---PLKSLRGFERLDIKAG--KTATANLKLTKESLEFWDAE
CAD48309.1   (630) YIKDLEASWR--VPNWQLSGMKRVRLESG--ETAEITFEIRPEQLAVVTD
BAB11424.1   (713) FTTPPAIHG---SPRKHLVGFEKIRLGKR--EEAVVRFKVEICKDLSVVDE
BAE44362.1   (709) FTTPPAVHG---SPRKHLLGFEKIRLGKM--EEAVKFKVDVCKDLSVVDE
AAK96639.1   (702) FTTSPQVHG---SPIKQLLGFEKIRLGKS--EEAVVRFNVNVCKDLSVVDE
ABQ45227.1   (703) FFTPPNVHN---APQKHLLGFEKVQLAGK--SEGMVRFKVDVCNDLSVVDE
```

TABLE 16-continued

```
AAK38481.1   (706) FSSPPPAHN---APAKHLVGFEKVSLAPG-EAGTVAFRVDVCRDLSVVDE
AAM53325.1   (698) FAEPPINGIKGLGVNKQLIAFEKVHVMAG-AKQTVQVDVDACKHLGVVDE
AAS17751.2   (694) FSSPPSG---KWAANKQLVGFHKVHIVAG-SHKRVKVDVHVCKHLSVVDQ
CAJ41429.1   (653) YFRPPAR---HWAPHKQLVAFEKVHVEAG-TQQRVGINIHVCKSLSVVDG
AAK38482.1   (705) FLRWPNATDG--RPASQLIGFQSVHLRAD-EAAHVEFEVSPCKHLSRAAE
ACL54109.1   (757) YTAPPPEVG--DAPLKQLVAFRRVFVPAG-AAVDVPFALNVCKTFAIVEE
BAG82824.1   (708) YANTSTAGPSP-YPNKWLVGFDRLAAVAKEGGTAELNVPVAVDRLARVDE
BAE19756.1   (716) FANTSDAGPAP-YPKKWLVGVDRLGEVKV-GETRELRVPVEVGSPARVNE
BAA24107.1   (705) FVNTT-AGPAP-HPNKWLVGFDRLSAVEP-GSAKTMVIPVTVDSLARTDE
ABA40420.1   (699) FANTT-AGPAP-YPNKWLVGFDRLASLEP-HRSQTMTIPVTIDSVARTDE
CAA73902.1   (695) YVNTT-AGPAP-YPKKWVVGFDRLGGLEP-GDSQTLTVPVTVESVARTDE
EAA64470.1   (696) YVNTT-AGPAP-YPKKWVVGFDRLGGLEP-GDSQTLTVPVTVESVARTDE
AAL32053.2   (700) FANTT-AGPKP-YPNKWLVGFDRLATIHP-AKTAQVTFPVPLGAIARADE
CAA93248.1   (699) FVRTSNAGPAP-YPNKWLVGFDRLADIKP-GHSSKLSIPIPVSALARVDS
EAA67023.1   (670) FASAPELGAQP-APIKTLVGYSRASLIKP-GETRKVDVEVTVAPLTRATE
Consensus   (1101) F      A      P K LVGFDRV L              V    LA DE 1151                                            1200
C1 BGL1      (823) VQDWVISRYPKTAYVGRS---SRKLDLKIELP------------------
TaBGL        (812) SQNWVVTKYPKTVYIGSS---SRKLHLQAPLPPY----------------
CelA         (659) --------------------------------------------------
AAK43134.1   (706) FMRLVVEKGEYQILIGNS---SENIILKDTFRIKETKP-IMERRIFLSNV
AAB70867.1   (729) DMKLVVEPGEFRVMVGSS---SEDIRLTGSFSVTGSKREVVGKRKFFTEV
AAC99628.1   (736) DGRRIVEPGDLELRFAAS---STEPRLTATVALTGPERRVDQHPATARRL
CAP07659.1   (731) DQDMVPVRGRYELLCGGS---SAASDLKSVSYKF----------------
ACN78955.1   (831) TNTMRTKPGKYEILYGTS---SLDKDLKKLTITL----------------
CAD48309.1   (676) EGKSVIEPGEFEIYVGGSQPDARSVRLMGKAPLKAVLRVQ----------
BAB11424.1   (759) IGKRKIGLGKHLLHVGDL---KHSLSIRI---------------------
BAE44362.1   (755) VGKRKIGLGQHLLHVGDV---KHSLSIRI---------------------
AAK96639.1   (748) TGKRKIALGHHLLHVGSL---KHSLNISV---------------------
ABQ45227.1   (749) LGNRKVPLGDHMLHVGNL---KHSLSVRI---------------------
AAK38481.1   (752) LGGRKVALGGHTLHDGDL---KHTVELRV---------------------
AAM53325.1   (747) YGKRRIPMGEHKLHIGDL---KHTILVQPQL-------------------
AAS17751.2   (740) FGIRRIPIGEHKLQIGDL---EHHISVEANVGEIRS--------------
CAJ41429.1   (699) SGIRRIPMGEHSLHIGDV---KHSVSLQASILGVVES-------------
AAK38482.1   (752) DGRKVIDQGSHFVRVGDD---EFELSFMA---------------------
ACL54109.1   (804) TAYTVVPSGVSTVVVGDD---ALVLSFPVTINLAV---------------
BAG82824.1   (757) AGNTVLFPGRYEVALNN----EREVVELVGEQVVLLKWPEEVQGVAG
BAE19756.1   (764) DGDWVLFPGTFELALNL----ERKVRVKVVLEGEEEVVLKWPGKE-----
BAA24107.1   (752) EGNRVLYPGRYEVALNN----EREVVLGFTLTGEKAVLFKWPKEEQLIAP
ABA40420.1   (746) AGNRVLYPGKYELALNN----ERSVVLQFVLTGREAVVFKWPVEQQQISS
CAA73902.1   (742) QGNRVLYPGSYDVALNN----ERSVVVKFELKGEEAVILSWPEDTTSDFV
EAA64470.1   (743) QGNRVLYPGSYELALNN----ERSVVVKFELKGEEAVILSWPEDTTSDFV
AAL32053.2   (747) NGNKVIFPGEYELALNN----ERSVVVSFSLTGNAATLENWPVWEQAVPG
CAA93248.1   (747) HGNRIVYPGKYELALNT----DESVKLEFELVGEEVTIENWPLEEQQIKD
EAA67023.1   (718) DGRVVLYPGEYTLLVDVN---DEYPTAKFEIKGDVQVLEKFPLSGNDSD-
Consensus   (1151)   G RVI   G Y L VG         V L    L 1201                                            1250
C1 BGL1      (852) --------------------------------------------------
TaBGL        (843) --------------------------------------------------
CelA         (659) --------------------------------------------------
AAK43134.1   (752) QIE-----------------------------------------------
AAB70867.1   (776) YEE-----------------------------------------------
AAC99628.1   (783) RAGDRGRRGRGRLSGPWEAPVVPATTARRAVQRTTSKTFFWMPLAYTSCS
CAP07659.1   (762) --------------------------------------------------
ACN78955.1   (862) --------------------------------------------------
CAD48309.1   (716) --------------------------------------------------
BAB11424.1   (785) --------------------------------------------------
BAE44362.1   (781) --------------------------------------------------
AAK96639.1   (774) --------------------------------------------------
ABQ45227.1   (775) --------------------------------------------------
AAK38481.1   (778) --------------------------------------------------
AAM53325.1   (775) --------------------------------------------------
AAS17751.2   (773) --------------------------------------------------
CAJ41429.1   (733) --------------------------------------------------
AAK38482.1   (778) --------------------------------------------------
ACL54109.1   (836) --------------------------------------------------
BAG82824.1   (803) DE------------------------------------------------
BAE19756.1   (805) --------------------------------------------------
BAA24107.1   (798) Q-------------------------------------------------
ABA40420.1   (792) A-------------------------------------------------
CAA73902.1   (788) SSIDGGLDRKQDVIA-----------------------------------
EAA64470.1   (789) SSIDGGLDRKQDVIA-----------------------------------
AAL32053.2   (793) VLQQ----------------------------------------------
CAA93248.1   (793) ATPDA---------------------------------------------
EAA67023.1   (764) --------------------------------------------------
Consensus   (1201)
```

TABLE 16-continued

```
                 1251                           1279
C1 BGL1    (852) ----------------------------
TaBGL      (843) ----------------------------
CelA       (659) ----------------------------
AAK43134.1 (755) ----------------------------
AAB70867.1 (779) ----------------------------
AAC99628.1 (833) TSLSFRASLSVSLNSRLPAPSSSGKTSRW
CAP07659.1 (762) ----------------------------
ACN78955.1 (862) ----------------------------
CAD48309.1 (716) ----------------------------
BAB11424.1 (785) ----------------------------
BAE44362.1 (781) ----------------------------
AAK96639.1 (774) ----------------------------
ABQ45227.1 (775) ----------------------------
AAK38481.1 (778) ----------------------------
AAM53325.1 (775) ----------------------------
AAS17751.2 (773) ----------------------------
CAJ41429.1 (733) ----------------------------
AAK38482.1 (778) ----------------------------
ACL54109.1 (836) ----------------------------
BAG82824.1 (805) ----------------------------
BAE19756.1 (805) ----------------------------
BAA24107.1 (799) ----------------------------
ABA40420.1 (793) ----------------------------
CAA73902.1 (803) ----------------------------
EAA64470.1 (804) ----------------------------
AAL32053.2 (797) ----------------------------
CAA93248.1 (798) ----------------------------
EAA67023.1 (764) ----------------------------
Consensus  (1251)
```

III. Polynucleotides, Expression Systems and Related Aspects

In related aspects, the invention provides recombinant polynucleotides encoding a variant β-glucosidase polypeptide, a host cell containing a recombinant nucleic acid sequence encoding a variant β-glucosidase polypeptide, methods for expressing a variant β-glucosidase by maintaining the cell under conditions in which the β-glucosidases protein is expressed and, preferably, secreted. As described below, recombinant host cells expressing β-glucosidase variants of the invention may be combined with a cellulosic biomass or other β-glucosidases substrates under conditions in which the β-glucosidase is expressed, and preferably secreted, by the cells as part of a saccharification process.

The present invention provides polynucleotide sequences that encode the β-glucosidase variants of the invention. Those having ordinary skill in the art will understand that provided with an amino acid sequence of a protein, the genetic code (Table 17) can be used to design a polynucleotide sequence encoding the protein. Polynucleotides encoding a β-glucosidase can be referred to, for convenience, as "β-glucosidase polynucleotides."

A DNA sequence may also be designed for high codon usage bias codons (codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available See e.g., Henaut and Danchin in "*Escherichia Salmonella*," Neidhardt, et al. Eds., ASM Press, Washington D.C. (1996), pp. 2047-2066, which is incorporated herein by reference.

TABLE 17

GENETIC CODE

| Amino acid | | | Codon | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

A. Expression Vectors

The present invention makes use of recombinant constructs comprising a sequence encoding a β-glucosidase variant as described above. In a particular aspect the present invention provides an expression vector comprising a β-glucosidase polynucleotide operably linked to a heterologous promoter. Expression vectors of the present invention may be used to transform an appropriate host cell to permit the host to express β-glucosidase protein. Methods for recombinant expression of proteins in fungi and other organisms are well known in the art, and a number expression vectors are available or can be constructed using routine methods. See, e.g., Tkacz and Lange, 2004, ADVANCES IN FUNGAL BIOTECHNOLOGY FOR INDUSTRY, AGRICULTURE, AND MEDICINE, KLUWER ACADEMIC/PLENUM PUBLISHERS. New York; Zhu et al., 2009, Construction of two Gateway vectors for gene expression in fungi *Plasmid* 6:128-33; Kavanagh, K. 2005, FUNGI: BIOLOGY AND APPLICATIONS Wiley, all of which are incorporated herein by reference.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

In a preferred aspect of this embodiment, the construct further comprises regulatory sequences, including, for example, a promoter, operably linked to the protein encoding sequence. Large numbers of suitable vectors and promoters are known to those of skill in the art.

B. Promoter/Gene Constructs

To obtain high levels of expression in a particular host it is often useful to express a β-glucosidase under control of a promoter other than the naturally occurring promoter. A promoter sequence can be operably linked to the 5' region of a β-glucosidase coding sequence using routine methods.

Examples of useful promoters include promoters from fungi such as promoters obtained from the genes for *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral α-amylase and *Aspergillus oryzae* triose phosphate isomerase), promoters such as cbh1, cbh2, egl1, egl2, pepA, hfb1, hfb2, xyn1, amy, and glaA (Nunberg et al., 1984, *Mol. Cell Biol.,* 4:2306-2315, Boel et al., 1984, *EMBO J.* 3:1581-85 and EPA 137280, all of which are incorporated herein by reference), and mutant, truncated, and hybrid promoters thereof. In a yeast host, useful promoters can be from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are described by Romanos et al., 1992, *Yeast* 8:423-488, incorporated herein by reference. Promoters associated with chitinase production in fungi may be used. See, e.g., Blaiseau and Lafay, 1992, *Gene* 120243-248 (filamentous fungus *Aphanocladium album*); Limon et al., 1995, *Curr. Genet,* 28:478-83 (*Trichoderma harzianum*), both of which are incorporated herein by reference.

Promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. In bacterial host cells, suitable promoters include the promoters obtained from the *E. coli* lac operon, *Streptomyces coelicolor* agarase gene (dagA), *Bacillus subtilis* levansucranse gene (sacB), *Bacillus licheniformis* α-amylase gene (amyL), *Bacillus stearothermophilus* maltogenic amylase gene (amyM), *Bacillus amyloliquefaciens* α-amylase gene (amyQ), *Bacillus subtilis* xylA and xylB genes and prokaryotic β-lactamase gene.

Any other promoter sequence that drives expression in a suitable host cell may be used. Suitable promoter sequences can be identified using well known methods. In one approach, a putative promoter sequence is linked 5' to a sequence encoding a reporter protein, the construct is transfected into the host cell (e.g., C1) and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (Henriksen et al, 1999, *Microbiology* 145:729-34, incorporated herein by reference) or a lacZ reporter gene (Punt et al, 1997, *Gene,* 197:189-93, incorporated herein by reference). Functional promoters may be derived from naturally occurring promoter sequences by directed evolution methods. See, e.g. Wright et al., 2005, *Human Gene Therapy,* 16:881-892, incorporated herein by reference.

An expression vector optionally contains a ribosome binding site for translation initiation, and a transcription terminator, such as PinII. The vector also optionally includes appropriate sequences for amplifying expression, e.g., an enhancer.

In addition, expression vectors of the present invention optionally contain one or more selectable marker genes to provide a phenotypic trait for selection of transformed host cells. Suitable marker genes include those coding for antibiotic resistance such as, ampicillin (ampR), kanamycin, chloramphenicol, or tetracycline resistance. Further examples include the antibiotic streptomycin or spectinomycin (e.g., the aada gene), the streptomycin phosphotransferase (spt) gene coding for streptomycin resistance, the neomycin phosphotransferase (nptII) gene encoding kanamycin or geneticin resistance, the hygromycin phosphotransferase (hpt) gene coding for hygromycin resistance. Additional selectable marker genes include dihydrofolate reductase or neomycin resistance for eukaryotic cell culture, and tetracycline or ampicillin resistance in *E. coli.*

C. Synthesis and Manipulation of β-Glucosidase Polynucleotides

Polynucleotides encoding β-glucosidases can be prepared using methods that are well known in the art. For example, oligonucleotides of up to about 40 bases are individually synthesized, then joined (e.g., by enzymatic or chemical ligation methods, or polymerase-mediated methods) to form essentially any desired continuous sequence. For example, polynucleotides of the present invention can be prepared by chemical synthesis using, for example, the classical phosphoramidite method described by Beaucage, et al., 1981, *Tetrahedron Letters,* 22:1859-69, or the method described by Matthes, et al., 1984, *EMBO J.* 3:801-05, both of which are incorporated herein by reference. These methods are typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (Midland, Tex.), The Great American Gene Company (Ramona, Calif.), ExpressGen Inc. (Chicago, Ill.), Operon Technologies Inc. (Alameda, Calif.), and many others.

Polynucleotides may also be synthesized by well-known techniques as described in the technical literature. See, e.g., Carruthers, et al., 1982, *Cold Spring Harbor Symp. Quant. Biol.*, 47:411-18 and Adams et al., 1983, *J. Am. Chem. Soc.* 105:661, both of which are incorporated herein by reference. Double stranded DNA fragments may then be obtained either by synthesizing the complementary strand and annealing the strands together under appropriate conditions, or by adding the complementary strand using DNA polymerase with an appropriate primer sequence.

General texts that describe molecular biological techniques which are useful herein, including the use of vectors, promoters, protocols sufficient to direct persons of skill through in vitro amplification methods, including the polymerase chain reaction (PCR) and the ligase chain reaction (LCR), and many other relevant methods, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 and *Current Protocols in Molecular Biology*, F. M. Ausubel et al., eds., Current Protocols, a joint venture between Greene Publishing Associates, Inc. and John Wiley & Sons, Inc., (supplemented through 2009) ("Ausubel"), all of which are incorporated herein by reference; Mullis et al., 1987, U.S. Pat. No. 4,683, 202; *PCR Protocols A Guide to Methods and Applications* (Innis et al. eds) Academic Press Inc. San Diego, Calif. (1990); Arnheim & Levinson, 1990, *C&EN* 36-47; *The Journal Of NIH Research* (1991) 3, 81-94; Kwoh et al., 1989, *Proc. Natl. Acad. Sci. USA* 86, 1173; Guatelli et al., 1990, *Proc. Natl. Acad. Sci. USA* 87, 1874; Lomell et al., 1989, *J. Clin. Chem.* 35, 1826; Landegren et al., 1988, *Science* 241, 1077-1080; Van Brunt, 1990, *Biotechnology* 8, 291-294; Wu and Wallace, 1989, *Gene* 4, 560; Barringer et al., 1990, *Gene* 89, 117, and Sooknanan and Malek, 1995, *Biotechnology* 13: 563-564, all of which are incorporated herein by reference. Methods for cloning in vitro amplified nucleic acids are described in Wallace et al., U.S. Pat. No. 5,426,039, which is incorporated herein by reference.

D. Expression Hosts

The present invention also provides engineered (recombinant) host cells that are transformed with an expression vector or DNA construct encoding β-glucosidase. Optionally, β-glucosidase expression in the cell is under the control of a heterologous promoter. Host cells of the invention may be used to produce β-glucosidase polypeptides. Thus, the present invention is directed to a host cell comprising any β-glucosidase polynucleotide of the present invention that is described hereinabove. As used herein, a genetically modified or recombinant host cell includes the progeny of said host cell that comprises a β-glucosidase polynucleotide which encodes a recombinant polypeptide of the invention. Often, the genetically modified or recombinant host cell is a microorganism. In some embodiments, the genetically modified or recombinant host cell is a prokaryote. In some embodiments, the genetically modified or recombinant host cell is a eukaryotic cell. Generally the eukaryotic host cell is a non-human cell. Suitable eukaryotic host cells include, but are not limited to, fungal cells, algal cells, insect cells, and plant cells. In some cases host cells may be modified to increase protein expression, secretion or stability, or to confer other desired characteristics. Cells (e.g., fungi) that have been mutated or selected to have low protease activity are particularly useful for expression. For example, protease deficient strains of C1 (e.g., in which the alkaline protease locus has been deleted or disrupted) may be used.

Suitable fungal host cells include, but are not limited to, *Ascomycota, Basidiomycota, Deuteromycota, Zygomycota, Fungi imperfecti*. Particularly preferred fungal host cells are yeast cells and filamentous fungal cells. The filamentous fungal host cells of the present invention include all filamentous forms of the subdivision *Eumycotina* and *Oomycota*. (see, for example, Hawksworth et al., In Ainsworth and Bisby's Dictionary of The Fungi, 8$^{th}$ edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungal host cells of the present invention are morphologically distinct from yeast.

In some embodiments the filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella*, or teleomorphs, or anamorphs, and synonyms or taxonomic equivalents thereof.

In some embodiments of the invention, the filamentous fungal host cell is of the *Aspergillus* species, *Ceriporiopsis* species, *Chrysosporium* species, *Corynascus* species, *Fusarium* species, *Humicola* species, *Neurospora* species, *Penicillium* species, *Tolypocladium* species, *Tramates* species, or *Trichoderma* species.

In some embodiments of the invention, the filamentous fungal host cell is of the *Trichoderma* species, e.g., *T. longibrachiatum, T. viride* (e.g., ATCC 32098 and 32086), *Hypocrea jecorina* or *T. reesei* (NRRL 15709, ATTC 13631, 56764, 56765, 56466, 56767 and RL-P37 and derivatives thereof—See Sheir-Neiss et al., 1984, *Appl. Microbiol. Biotechnology*, 20:46-53, which is incorporated herein by reference), *T. koningii*, and *T. harzianum*. In addition, the term "*Trichoderma*" refers to any fungal strain that was previously classified as *Trichoderma* or currently classified as *Trichoderma*.

In some embodiments of the invention, the filamentous fungal host cell is of the *Aspergillus* species, e.g., *A. awamori, A. funigatus, A. japonicus, A. nidulans, A. niger, A. aculeatus, A. foetidus, A. oryzae, A. sojae*, and *A. kawachi*. (Reference is made to Kelly and Hynes, 1985, *EMBO J.* 4,475479; NRRL 3112, ATCC 11490, 22342, 44733, and 14331; Yelton et al., 1984, *Proc. Natl. Acad. Sci. USA*, 81, 1470-1474; Tilburn et al., 1982, *Gene* 26, 205-221; and Johnston et al., 1985, *EMBO J.* 4, 1307-1311, all of which are incorporated herein by reference).

In some embodiments of the invention, the filamentous fungal host cell is of the *Fusarium* species, e.g., *F. bactridioides, F. cerealis, F. crookwellense, F. culmorum, F. graminearum, F. graminum. F. oxysporum, F. roseum*, and *F. venenatum*.

In some embodiments of the invention, the filamentous fungal host cell is of the *Myceliophthora* species, e.g., *M. thermophilia*.

In some embodiments of the invention, the filamentous fungal host cell is of the *Neurospora* species, e.g., *N. crassa*. Reference is made to Case, M. E. et al., 1979, *Proc. Natl. Acad. Sci. USA*, 76, 5259-5263; U.S. Pat. No. 4,486,553; and Kinsey, J. A. and Rambosek, 1984, *Molecular and Cellular Biology* 4:117-22, all of which are incorporated herein by reference. In some embodiments of the invention, the filamentous fungal host cell is of the *Humicola* species, e.g., *H. insolens*, *H. grisea*, and *H. lanuginosa*. In some embodiments of the invention, the filamentous fungal host cell is of the *Mucor* species, e.g., *M. miehei* and *M. circinelloides*. In some embodiments of the invention, the filamentous fungal host cell is of the *Rhizopus* species, e.g., *R. oryzae* and *R. niveus*. In some embodiments of the invention, the filamentous fungal host cell is of the *Penicillum* species, e.g., *P. purpurogenum*, *P. chrysogenum*, and *P. verruculosum*. In some embodiments of the invention, the filamentous fungal host cell is of the *Thielavia* species, e.g., *T. terrestris*. In some embodiments of the invention, the filamentous fungal host cell is of the *Tolypocladium* species, e.g., *T. inflatum* and *T. geodes*. In some embodiments of the invention, the filamentous fungal host cell is of the *Trametes* species, e.g., *T. villosa* and *T. versicolor*.

In some embodiments of the invention, the filamentous fungal host cell is of the *Chrysosporium* species, e.g., *C. lucknowense*, *C. keratinophilum*, *C. tropicum*, *C. merdarium*, *C. inops*, *C. pannicola*, and *C. zonatum*. In a particular embodiment the host is *C. lucknowense*.

In the present invention a yeast host cell may be a cell of a species of, but not limited to *Candida*, *Hansenula*, *Saccharomyces*, *Schizosaccharomyces*, *Pichia*, *Kluyveromyces*, and *Yarrowia*. In some embodiments of the invention, the yeast cell is *Hansenula polymorpha*, *Saccharomyces cerevisiae*, *Saccharomyces carlsbergensis*, *Saccharomyces diastaticus*, *Saccharomyces norbensis*, *Saccharomyces kluyveri*, *Schizosaccharomyces pornbe*, *Pichia pastoris*, *Pichia finlandica*, *Pichia trehalophila*, *Pichia kodamae*, *Pichia membranaefaciens*, *Pichia opuntiae*, *Pichia thermotolerans*, *Pichia salictaria*, *Pichia quercuum*, *Pichia pijperi*, *Pichia stipitis*, *Pichia methanolica*, *Pichia angusta*, *Kluyveromyces lactis*, *Candida albicans*, and *Yarrowia lipolytica*.

In some embodiments on the invention, the host cell is an algae such as, *Chlamydomonas* (e.g., *C. Reinhardtii*) and *Phormidium* (P. sp. ATCC29409).

In other embodiments, the host cell is a prokaryotic cell. Suitable prokaryotic cells include gram positive, gram negative and gram-variable bacterial cells. Examples of bacterial host cells include, but are not limited to *Bacillus* (e.g., *subtilis*, *B. licheniformis*, *B. megaterium*, *B. stearothermophilus* and *B. amyloliquefaciens*), *Streptomyces* (*S. ambofaciens*, *S. achromogenes*, *S. avermitilis*, *S. coelicolor*, *S. aureofaciens*, *S. aureus*, *S. fungicidicus*, *S. griseus*, and *S. lividans*), and *Streptococcus* (e.g., *S. equisimiles*, *S. pyogenes*, and *S. uberis*) species.

Strains that may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Host cells may be genetically modified to have characteristics that improve protein secretion, protein stability or other properties desirable for expression and/or secretion of a protein. For example, knock out of Alp1 function results in a cell that is protease deficient. Knock out of pyr5 function results in a cell with a pyrimidine deficient phenotype. In particular embodiments host cells are modified to delete endogenous cellulase protein-encoding sequences or otherwise eliminate expression of one or more endogenous cellulases. In one embodiment expression of one or more endogenous cellulases is inhibited to increase production of cellulases of interest. Genetic modification can be achieved by genetic engineering techniques or using classical microbiological techniques, such as chemical or UV mutagenesis and subsequent selection. In one genetic engineering approach, homologous recombination can be used to induce targeted gene modifications by specifically targeting a gene in vivo to suppress expression of the encoded protein. In an alternative approach, siRNA, antisense, or ribozyme technology can be used to inhibit gene expression.

E. Transformation and Culture

Introduction of a vector or DNA construct into a host cell can be effected by calcium phosphate transfection, DEAE-Dextran mediated transfection, electroporation, or other common techniques (See Davis et al., 1986, *Basic Methods in Molecular Biology*, which is incorporated herein by reference).

The engineered host cells can be cultured in conventional nutrient media modified as appropriate for activating promoters, selecting transformants, or amplifying the β-glucosidase polynucleotide. Culture conditions, such as temperature, pH and the like, are those previously used with the host cell selected for expression, and will be apparent to those skilled in the art. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths, 1997, *Mammalian Cell Culture: Essential Techniques* John Wiley and Sons, NY; Humason, 1979, *Animal Tissue Techniques*, fourth edition W.H. Freeman and Company; and Ricciardelli, et al., 1989, *In Vitro Cell Dev. Biol.* 25:1016-1024, all of which are incorporated herein by reference. For plant cell culture and regeneration, Payne et al., 1992, *Plant Cell and Tissue Culture in Liquid Systems* John Wiley & Sons, Inc. New York, N.Y.; Gamborg and Phillips (eds), 1995, *Plant Cell, Tissue and Organ Culture*; Fundamental Methods Springer Lab Manual, Springer-Verlag (Berlin Heidelberg New York); Jones, ed., 1984, *Plant Gene Transfer and Expression Protocols*, Humana Press, Totowa, N.J. and *Plant Molecular Biology*, 1993, R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media*, 1993, CRC Press, Boca Raton, Fla., which is incorporated herein by reference. Additional information for cell culture is found in available commercial literature such as the *Life Science Research Cell Culture Catalogue*, 1998, from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference.

In some embodiments, cells expressing the β-glucosidase polypeptides of the invention are grown under batch or continuous fermentations conditions. Classical batch fermentation is a closed system, where the compositions of the medium is set at the beginning of the fermentation and is not subject to artificial alternations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

Cell-free transcription/translation systems can also be employed to produce β-glucosidase polypeptides using the polynucleotides of the present invention. Several such systems are commercially available. A general guide to in vitro transcription and translation protocols is found in Tymms, 1995, *In vitro Transcription and Translation Protocols: Methods in Molecular Biology*, Volume 37, Garland Publishing, NY, which is incorporated herein by reference.

F. Signal Peptides, Fusion Polypeptides and Additional Modifications and Sequence Elements In general, the β-Glucosidase polypeptides are secreted from the host cell in which they are expressed (e.g., a fungal cell) and are expressed as a pre-protein including a signal peptide, i.e., an amino acid sequence linked to the amino terminus of a polypeptide and which directs the encoded polypeptide into the cell secretory pathway. Various signal peptides may be used, depending on the host cell and other factors. Effective signal peptide coding regions for filamentous fungal host cells include, but are not limited to, the signal peptide coding regions obtained from *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola lanuginosa* lipase, and *T. reesei* cellobiohydrolase II (TrCBH2).

Effective signal peptide coding regions for bacterial host cells are the signal peptide coding regions obtained from the genes for *Bacillus* NClB 11837 maltogenic amylase, *Bacillus stearothermophilus* α-amylase, *Bacillus licheniformis* subtilisin, *Bacillus licheniformis* β-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57:109-137 (incorporated herein by reference).

Useful signal peptides for yeast host cells also include those from the genes for *Saccharomyces cerevisiae* alpha-factor, *Saccharomyces cerevisiae* SUC2 invertase (see Taussig and Carlson, 1983, *Nucleic Acids Res* 11:1943-54; SwissProt Accession No. P00724), and others. See, e.g., Romanos et al., 1992, *Yeast* 8:423-488. Variants of these signal peptides and other signal peptides are suitable.

The present invention also provides β-glucosidase variant fusion polypeptides, where the fusion polypeptide comprises an amino acid sequence encoding a β-glucosidase variant polypeptide of the present invention or fragment thereof, linked either directly or indirectly through the N- or C-terminus of the β-glucosidase variant polypeptide to an amino acid sequence encoding at least a second (additional) polypeptide. The β-glucosidase variant fusion polypeptide may further include amino acid sequence encoding a third, fourth, fifth, or additional polypeptides. In some embodiments, each additional polypeptide has a biological activity, or alternatively, is a portion of a polypeptide that has a biological activity, where the portion has the effect of improving expression and/or secretion of the fusion polypeptide from the desired expression host. These sequences may be fused, either directly or indirectly, to the N- or C-terminus of the β-glucosidase variant polypeptide or fragment thereof, or alternatively, to the N- or C-terminus of the additional polypeptides having biological activity.

The polypeptide components of the fusion polypeptide may be linked to each other indirectly via a linker. Linkers suitable for use in the practice of the present invention are described in WO 2007/075899, which is incorporated herein by reference. Exemplary linkers include peptide linkers of from 1 to about 40 amino acid residues in length, including those from about 1 to about 20 amino acid residues in length, and those from about 1 to about 10 amino acid residues in length. In some embodiments, the linkers may be made up of a single amino acid residue, such as, for example, a Gly, Ser, Ala, or Thr residue or combinations thereof, particularly Gly and Ser. Linkers employed in the practice of the present invention may be cleavable. Suitable cleavable linkers may contain a cleavage site, such as a protease recognition site. Exemplary protease recognition sites are well known in the art and include, for example, Lys-Arg (the KEX2 protease recognition site, which can be cleaved by a native *Aspergillus* KEX2-like protease), Lys and Arg (the trypsin protease recognition sites). See, for example, WO 2007/075899, which is incorporated herein by reference.

In addition, It will be appreciated that β-glucosidase variants of the invention may be less-than-full length compared to naturally occurring proteins. Thus, variants of the invention may comprise insertions or deletions (e.g., truncation at the amino- and/or carboxy-termini) In some embodiments the variant may be longer or shorter by up to 10% of the wild-type length, sometimes up to 5%, sometimes up to 4%, sometimes up to 3%, sometimes up to 2%, sometimes up to 1%.

In some embodiments the variant differs from the reference sequence by internal deletions. Often such deletions are not more than 10 residues in length, sometimes not more than 5, not more than 4, not more than 3, not more than 2 or not more than 1 residue in length. In some embodiments internal deletions relative to the reference sequence comprise no more than 50 residues, sometimes not more than 40 residues, sometimes not more than 30 residues, sometimes not more than 20 residues, and sometimes not more than 10 residues.

In some embodiments, a β-glucosidase polypeptide variant of the invention includes additional sequences which do not alter the encoded activity of a β-glucosidase. For example, the β-glucosidase may be linked to an epitope tag or to other sequence useful in β-glucosidase purification.

IV. Production and Recovery of β-Glucosidase Polypeptides

In one aspect, the present invention is directed to a method of making a polypeptide having β-glucosidase activity, the method comprising providing a host cell transformed with any one of the described β-glucosidase polynucleotides of the present invention; culturing the transformed host cell in a culture medium under conditions in which the host cell expresses the encoded β-glucosidase polypeptide; and optionally recovering or isolating the expressed β-glucosidase polypeptide, or recovering or isolating the culture medium containing the expressed β-glucosidase polypeptide. The method further provides optionally lysing the transformed host cells after expressing the encoded β-glucosidase polypeptide and optionally recovering or isolating the expressed β-glucosidase polypeptide from the cell lysate. The present invention further provides a method of making a β-glucosidase polypeptide, said method comprising cultivating a host cell transformed with a β-glucosidase polynucleotide under conditions suitable for the production of the β-glucosidase polypeptide and recovering the β-glucosidase polypeptide.

Typically, recovery or isolation of the β-glucosidase polypeptide is from the host cell culture medium, the host cell or both, using protein recovery techniques that are well known in the art, including those described herein. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

The resulting polypeptide may be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic interaction, chromatofocusing, and size exclusion), or precipitation. Protein refolding steps can be used, as desired, in completing the configuration of the mature protein. Finally, high performance liquid chromatography (HPLC) can be employed in the final purification steps. In addition to the references noted supra, a variety of purification methods are well known in the art, including, for example, those set forth in Sandana, 1997, Bioseparation of Proteins, Academic Press, Inc.; Bollag et al., 1996, Protein Methods, 2nd Edition, Wiley-Liss, NY; Walker, 1996, The Protein Protocols Handbook Humana Press, NJ; Harris and Angal, 1990, Protein Purification Applications: A Practical Approach, IRL Press at Oxford, Oxford, England; Harris and Angal Protein Purification Methods: A Practical Approach, IRL Press at Oxford, Oxford, England; Scopes, 1993, Protein Purification: Principles and Practice 3$^{rd}$ Edition, Springer Verlag, NY; Janson and Ryden, 1998, Protein Purification: Principles, High Resolution Methods and Applications, Second Edition, Wiley-VCH, NY; and Walker, 1998, Protein Protocols on CD-ROM, Humana Press, NJ, all of which are incorporated herein by reference.

As noted, in some embodiments the β-glucosidase is expressed as a fusion protein including a non-enzyme portion. In some embodiments the β-glucosidase sequence is fused to a purification facilitating domain.

V. Methods of Using B-Glucosidase Polypeptides And Cells Expressing β-Glucosidase Polypeptides As described supra, β-glucosidase polypeptides of the present invention can be used in conjunction with other enzymatic activities to catalyze the progressive hydrolysis of a cellulosic substrate to produce soluble sugars.

The β-glucosidase polypeptide may be used in such methods in either isolated form or as part of a composition, such as any of those described herein. The β-glucosidase polypeptide may also be provided in cell culturing media or in a cell lysate. For example, after producing the β-glucosidase polypeptide by culturing a host cell transformed with a β-glucosidase polynucleotide or vector of the present invention, the β-glucosidase need not be isolated from the culture medium (i.e., if the β-glucosidase is secreted into the culture medium) or cell lysate (i.e., if the β-glucosidase is not secreted into the culture medium) or used in purified form to be useful in further methods of using the β-glucosidase polypeptide. Any composition, cell culture medium, or cell lysate containing a β-glucosidase polypeptide of the present invention may be suitable in methods that use a β-glucosidase. Therefore, the present invention further provides a method for producing cellobiose, by: (a) providing a cellulosic substrate; and (b) contacting the substrate with a culture medium or cell lysate or composition comprising a β-glucosidase polypeptide of the present invention under conditions sufficient to form a reaction mixture for converting the substrate to cellobiose.

The present invention further provides compositions that are useful for the enzymatic generation of sugars from a cellulosic substrate. For example, one or more β-glucosidase polypeptides of the present invention may be combined with another enzyme and/or an agent that alters the bulk material handling properties or further processability of the β-glucosidase(s) (e.g., a flow-aid agent, water, buffer, a surfactant, and the like) or that improves the efficiency of the generation of sugar from a substrate, as described in more detail hereinbelow. The other enzyme may be a different β-glucosidase or another cellulase enzyme.

A. Cellulase Mixtures

For example, in some embodiments, the β-glucosidase is combined with other enzymes to produce an enzyme mixture. The enzyme mixture may include β-glucosidases and one or more other enzymes, including other cellulases, that can act in concert to break down a cellulosic biomass, including xylanases hemicellulases, amylases, esterases, and cellulases (e.g., type 1 and type 2 cellobiohydrolases, endoglucanses, and β-glucosidases), α-glucosidases, aminopeptidases, carbohydrases, carboxypeptidases, catalases, chitinases, cutinases, cyclodextrin glycosyltransferases, deoxyribonucleases, α-galactosidases, β-galactosidases, glucoamylases, glucocerebrosidases, invertases, laccases, lipases, mannosidases, mutanases, oxidases, pectinolytic enzymes, peroxidases, phospholipases, phytases, polyphenoloxidases, ribonucleases, and trans-glutaminases. The enzyme mixture may include cellulases selected from CBH, EG and BG cellulases, for example, cellulases from *Acidothermus cellulolyticus, Thermobifida fusca, Humicola grisea, Chrysosporium* sp., *Trichoderma reesei* (e.g., C2730 Cellulase from *Trichoderma reesei* ATCC No. 25921, Sigma-Aldrich, Inc., *T. reesei* CBH1, CBH2, and/or EG1 or variants thereof, and/or *T. reesei* broth), C1 (see U.S. Pat. Nos. 6,015,707, 5,811,381 and 6,573,086; US Pat. Pub. Nos. 2007/0238155, US 2008/0194005, US 2009/0099079; International Pat. Pub. Nos. WO 2008/073914 and WO 98/15633, each of which is incorporated herein by reference), and other fungal and non-fungal species. The enzymes of the cellulase mixture work together resulting in decrystallization and hydrolysis of the cellulose from a biomass substrate to yield soluble sugars, such as but not limited to glucose (See Brigham et al., 1995, in Handbook on Bioethanol, C. Wyman ed., pp 119-141, Taylor and Francis, Washington D.C., which is incorporated herein by reference).

Cellulase mixtures for efficient enzymatic hydrolysis of cellulose are known (see, e.g., Viikari et al., 2007, "Thermostable enzymes in lignocellulose hydrolysis" *Adv Biochem Eng Biotechnol* 108:121-45, and US Pat. publications US 2009/0061484; US 2008/0057541; and US 2009/0209009 to Iogen Energy Corp., each of which is incorporated herein by reference for all purposes). In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulases, may be combined with cellulosic feedstock or a product of cellulose hydrolysis.

B. Other Components of β-glucosidase Compositions

β-glucosidase polypeptides of the present invention may be used in combination with other optional ingredients such as a buffer, a surfactant, and/or a scouring agent. Suitable buffers, surfactants and scouring agents are well known in the art, and include any compatible with the β-glucosidase and, optionally, with any other cellulases being used.

Exemplary surfactants include an anionic, a non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants can also be employed as is known in the art.

C. Production of Soluble Sugars From Cellulosic Biomass

β-glucosidase polypeptides of the present invention, as well as any composition, culture medium, or cell lysate comprising such β-glucosidase polypeptides, may be used in the production of soluble sugars from biomass. As used herein, the term "biomass" refers to living or dead biological material that contains a polysaccharide substrate, such as, for example, cellulose, starch, and the like. Therefore, the present invention provides a method of converting a biomass substrate to a cellobiose and using a β-glucosidase variant of the invention to convert the cellobiose to glucose.

The present invention further provides a method of converting a biomass substrate to a soluble sugar by (a) pretreating a cellulose substrate to increase its susceptibility to hydrolysis; (b) contacting the pretreated cellulose substrate of step with a composition, culture medium or cell lysate containing cellulases under conditions suitable for the production of cellobiose. And (c) contacting the pretreated cellulose substrate of step (a) with a composition, culture medium or cell lysate containing a β-glucosidase polypeptide of the present invention under conditions suitable for the production of glucose. It will be recognized that steps (b) and (c) may be simultaneous.

In some embodiments, the biomass includes cellulosic substrates including but not limited to, wood, wood pulp, paper pulp, corn stover, corn fiber, rice, paper and pulp processing waste, woody or herbaceous plants, fruit or vegetable pulp, distillers grain, grasses, rice hulls, wheat straw, cotton, hemp, flax, sisal, corn cobs, sugar cane bagasse, switch grass and mixtures thereof. The biomass may optionally be pretreated to increase the susceptibility of cellulose to hydrolysis using methods known in the art such as chemical, physical and biological pretreatments (e.g., steam explosion, pulping, grinding, acid hydrolysis, solvent exposure, and the like, as well as combinations thereof). In some embodiments, the biomass comprises transgenic plants that express ligninase and/or cellulase enzymes which degrade lignin and cellulose. See, e.g., US 20080104724, which is incorporated herein by reference.

In some embodiments, the β-glucosidase polypeptide and β-glucosidase polypeptide-containing compositions, cell culture media, and cell lysates may be reacted with the substrate at a temperature in the range of about 25° C. to about 100° C., about 30° C. to about 90° C., about 30° C. to about 80° C., about 40° C. to about 80° C., about 35° C. to about 75° C., about 55° C. to about 90° C. In some embodiments, the β-glucosidase polypeptide, β-glucosidase polypeptide-containing compositions, cell culture media, and cell lysates may be reacted with the substrate at a temperature in the range of about 55° C. to about 100° C., about 60° C. to about 90° C. Also, the biomass may be reacted with the β-glucosidase polypeptides and β-glucosidase polypeptide-containing compositions, cell culture media, and cell lysates at a temperature about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. at about 100° C., and at about 110° C. The process may be carried out at a pH in a range from about pH 3.0 to about 8.5, about pH 3.5 to about 8.5, about pH 4.0 to about 7.5, about pH 4.0 to about 7.0 and about pH 4.0 to about 6.5. In some embodiments the pH is in a range from about pH 3.5 to about pH 6.0, such as about pH 4.0 to about pH 6.0, or about pH 4.0 to about pH 5.0. Those having ordinary skill in the art will appreciate that the reaction times for converting a particular biomass substrate to a soluble sugar may vary but the optimal reaction time can be readily determined. Exemplary reaction times may be in the range of from about 1 to about 240 hours, from about 5 to about 180 hrs and from about 10 to about 150 hrs. For example, the incubation time may be at least 1 hr, at least 5 hrs, at least 10 hrs, at least 15 hrs, at least 25 hrs, at least 50 hr, at least 100 hrs, at least 180 and the like.

Sugars produced using methods of the present invention may be used to produce an end product such as an alcohol (e.g., ethanol, butanol, and the like). In other embodiments other end-products, such as, for example, acetone, an amino acid (e.g., glycine, lysine, and the like), an organic acid (e.g., lactic acid, acetic acid, formic acid, citric acid, oxalic acid, uric acid), glycerol, a diol (e.g., 1,3 propanediol, butanediol, and the like) or a hydrocarbon with 1-20 carbon atoms, may be produced. In one embodiment, a cellulosic biomass or a pre-treated cellulosic biomass may be treated with a β-glucosidase of the invention (optionally along with other cellulases) to prepare an animal feed.

In some embodiments, the β-glucosidase polypeptide of the present invention, or composition, cell culture medium, or cell lysate containing the β-glucosidase polypeptide may be used to catalyze the hydrolysis of cellobiose in the presence of a fermenting microorganism such as a yeast (e.g., *Saccharomyces* sp., such as, for example, *S. cerevisiae*, *Pichia* sp., and the like) or other C5 or C6 fermenting microorganisms that are well known in the art (e.g., *Zymomonas* sp., *E. coli*), to produce an end-product such as ethanol. In one embodiment a simultaneous saccharification and fermentation (SSF) process is used.

One of skill in the art will readily appreciate that the β-glucosidase polypeptide compositions of the present invention may be used in the form of an aqueous solution or a solid concentrate. When aqueous solutions are employed, the β-glucosidase solution can easily be diluted to allow accurate concentrations. A concentrate can be in any form recognized in the art including, for example, liquids, emulsions, suspensions, gel, pastes, granules, powders, an agglomerate, a solid disk, as well as other forms that are well known in the art. Other materials can also be used with or included in the β-glucosidase composition of the present invention as desired, including stones, pumice, fillers, solvents, enzyme activators, and anti-redeposition agents depending on the intended use of the composition. β-glucosidase polypeptides of the present invention may also be employed in detergent compositions for improved cleaning performance.

VI: Identification of BGL Variants With Performance Sensitive Residues

A. Identification of Performance Sensitive Residues in C1 β-Glucosidase

The amino acid sequence of wild-type C1 β-Glucosidase 1 (Bgl1) preprotein is shown below, with the residues of the signal peptide underlined and in bold font.

```
                                       (SEQ ID NO: 55)
MKAAALSCLF GSTLAVAGAI ESRKVHQKPL ARSEPFYPSP        60
WMNPNADGWA EAYAQAKSFV

SQMTLLEKVN LTTGVGWGAE QCVGQVGAIP RLGLRSLCMH       120
DSPLGIRGAD YNSAFPSGQT

VAATWDRGLM YRRGYAMGQE AKGKGINVLL GPVAGPLGRM       180
PEGGRNWEGF APDPVLTGIG

MSETIKGIQD AGVIACAKHF IGNEQEHFRQ VPEAQGYGYN       240
ISETLSSNID DKTMHELYLW

PFADAVRAGV GSVMCSYQQV NNSYACQNSK LLNDLLKNEL       300
GFQGFVMSDW QAQHTGAASA

VAGLDMSMPG DTQFNTGVSF WGANLTLAVL NGTVPAYRLD       360
DMAMRIMAAL FKVTKTTDLE

PINFSFWTDD TYGPIHWAAK QGYQEINSHV DVRADHGNLI       420
REIAAKGTVL LKNTGSLPLN

KPKFVAVIGE DAGSSPNGPN GCSDRGCNEG TLAMGWGSGT       480
ANYPYLVSPD AALQARAIQD

GTRYESVLSN YAEEKTKALV SQANATAIVF VNADSGEGYI       540
NVDGNEGDRK NLTLWNNGDT

LVKNVSSWCS NTIVVIHSVG PVLLTDWYDN PNITAILWAG       600
LPGQESGNSI TDVLYGKVNP

AARSPFTWGK TRESYGADVL YKPNNGNGAP QQDFTEGVFI       660
DYRYFDKVDD DSVIYEFGHG

LSYTTFEYSN IRVVKSNVSE YRPTTGTTAQ APTFGNFSTD       720
LEDYLFPKDE FPYIYQYIYP

YLNTTDPRRA SADPHYGQTA EEFLPPHATD DDPQPLLRSS       780
GGNSPGGNRQ LYDIVYTITA

DITNTGSVVG EEVPQLYVSL GGPEDPKVQL RDFDRMRIEP       840
GETRQFTGRL TRRDLSNWDV

TVQDWVISRY PKTAYVGRSS RKLDLKIELP                  870
```

A polynucleotide encoding the wild-type (WT) C1 Bgl1 protein including the C1Bgl1 signal peptide (SEQ ID NO:55) was prepared. The polynucleotide was inserted into an expression vector and libraries of polynucleotides encoding variant Bgl1 proteins were prepared by mutagenesis and directed evolution, and the properties (β-glucosidase activity and thermostability) of individual Bgl1 variants were assessed using highthroughput assays. Activity was assayed using a cellobiose assay at at pH 4.5-5, 65-70° C. for 21 h. Thermostability was assayed by challenging the proteins at pH 4.5-5, 65-70° C. for 2-48 hours before assaying for activity in a pNPG assay (pH 5, 50° C., 1.5 h). A number of amino acid substitutions and combinations of substitutions were identified in variants with greater than wild-type activity and/ or greater than wild-type thermostability. A variant was selected and subjected to further mutagenesis and selection, and the process was repeated twice more (4 rounds of selection).

Table 18 shows a selection of variants identified as having superior activity and thermostability than the wild-type. Numbering is relative to SEQ ID NO:55. Subtracting "19" from each position will conform the numbering the SEQ ID NO:1 (e.g., V318E=V299E). The mutation/selection process commonly identifies variants with multiple substitutions so that in several of the variants shown below include substitutions at PSPs and other positions.

TABLE 18

V318E
D369P
S434P
I106V + D369L
Q291W + T540K
K142R + Y219V
I179M + R682W
A123N + T482A
T120M + L149Q + Q313M
S182W + T354Q + E385L
M234I + E360D + T482A
D369L + S434P + T540K
N220Y + Q258N + T357L
D358K + D369L + S388W
Y135I + Q258N + Q474I
Q119L + A141F + G202M + A394Q
Q291W + F314V + D369L + E402N
E183G + E360A + D369L + I428V
Y135Q + I229M + F242L + D369L + K530M
Q291W + D369L + E402N + E493V + N504Y
Q291W + D369L + E402N + N536K + T591A
Q291W + D369L + E402N + K495V + S501R + A503E + K530N + T611H
Q119L + I229M + D230N + A245S + V246L + E360A + A378K
A79E + Q258N + Q291W + Q313M + D369R + E402N + S434P + A475L + K495N + G628W

B: Identification of Performance Sensitive Residues in T. aurantiacus β-Glucosidase The secreted form of the *T. aurantiacus* Bgl protein ("TaBgl" SEQ ID NO:2) was used to design a synthetic nucleotide sequence based on codon selection from a merged *S. cerevisiae* and *P. pastoris* codon bias table. In addition, an amino terminal methionine residue was added ("TaBgl WT$^M$"; SEQ ID NO:56). Expression constructs were prepared in which the TaBgl WT$^M$ sequence was linked to a yeast or fungal signal peptide appropriate for secretion in *S. cerevisiae*.

```
                                            (SEQ ID NO: 56)
MKDDLAYSPPFYPSPWMDGNGEWAEAYRRAVDFVSQLTLAEKVNLTTGV

GWMQEKCVGETGSIPRLGFRGLCLQDSPLGVRFADYVSAFPAGVNVAAT

WDKNLAYLRGKAMGEEHRGKGVDVQLGPVAGPLGRHPDGGRNWEGFSPD

PVLTGVLMAETIKGIQDAGVIACAKHFIGNEMEHFRQASEAVGYGFDIT

ESVSSNIDDKTLHELYLWPFADAVRAGVGSFMCSYNQVNNSYSCSNSYL
```

-continued
LNKLLKSELDFQGFVMSDWGAHHSGVGAALAGLDMSMPGDTAFGTGKSF

WGTNLTIAVLNGTVPEWRVDDMAVRIMAAFYKVGRDRYQVPVNFDSWTK

DEYGYEHALVGQNYVKVNDKVDVRADHADIIRQIGSASVVLLKNDGGLP

LTGYEKFTGVFGEDAGSNRWGADGCSDRGCDNGTLAMGWGSGTADFPYL

VTPEQAIQNEILSKGKGLVSAVTDNGALDQMEQVASQASVSIVFVNADS

GEGYINVDGNEGDRKNLTLWKGGEEVIKTVAANCNNTIVVMHTVGPVLI

DEWYDNPNVTAIVWAGLPGQESGNSLVDVLYGRVSPGGKTPFTWGKTRE

SYGAPLLTKPNNGKGAPQDDFTEGVFIDYRRFDKYNETPIYEFGFGLSY

TTFEYSDIYVQPLNARPYTPASGSTKAAPTFGNISTDYADYLYPEDIHK

VPLYIYPWLNTTDPKKSSGDPDYGMKAEDYIPSGATDGSPQPILPAGGA

PGGNPGLYDEMYRVSAIITNTGNVVGDEVPQLYVSLGGPDDPKVVLRNF

DRITLHPGQQTMWTTTLTRRDISNWDPASQNWVVTKYPKTVYIGSSSRK

LHLQAPLPPY

Libraries of polynucleotides encoding variant TaBgl proteins were prepared by mutagenesis and directed evolution, and the properties (e.g., β-glucosidase activity) of individual Bgl1 variants were assessed using highthroughput assays. A number of amino acid substitutions and combinations of substitutions were identified in variants with greater than wild-type activity.

Table 19 provides examples of combinations of substitutions in variants with high catalytic activity in assays carried out at pH 5 and 60° C. Numbering is relative to SEQ ID NO:56.

TABLE 19

D204G, K292I, E345V, Y747C
M1T, K55R, K101R, T151S, R331K, Y332C, K343R, N356S, S409N, Y642N
M1T, K55R, K101R, T151S, R331K, Y332C, K343R, N356S, S409N, Y642N
S87N, T151S, F288Y, Y642N, N651K
L150V, T151S, K343R, S409N, K457N, Y642N, N651K
M1T, T151S, K343R, S409N, A479V, Y642N, Y680F

C: Identification of Performance Sensitive Residues in *Azospirillum irakense* β-Glucosidase (CelA)

A gene coding for *Azospirillum irakense* CelA was codon optimized for expression in *B. megaterium* and *E. coli* based on the reported amino acid sequence (AAG43575.1) and a codon optimization algorithm incorporated as described in Example 1 of PCT publication WO2008/042876, which is incorporated herein by reference. The gene was cloned behind a nucleotide sequence encoding the *Bacillus megaterium* penicillin G acylase signal peptide plus a spacer region. The amino acid sequence of the encoded polypeptide is shown below in SEQ ID NO:57:

```
STAIAQEGAAPAAILHPEKWPRPATQRLIDPAVEKRVDALLKQLSVEEKVG
1                                                 51

QVIQGDIGTITPEDLRKYPLGSILAGGNSGPNGDDRAPPKEWLDLADAFYR
52                                                102

VSLEKRPGHTPIPVLFGIDAVHGHGNIGSATIFPHNIALGATHDPELLRRI
103                                               153

GEVTAVEMAATGIDWTFAPALSVVRDDRWGRTYEGFSEDPEIVAAYSAAIV
154                                               204

EGVQGKFGSKDFMAPGRIVASAKHFLADGGTDQGRDQGDARISEDELIRIH
205                                               255

NAGYPPAIDAGVLTVMASFSSWQGIKHHGHKQLLTDVLKGQMGFNGFIVGD
256                                               306

WNAHDQVPGCTKFNCPTSLIAGLDMYMAADSWKQLYENTLAQVKDGTIPMA
307                                               357

RLDDAVRRILRVKVLAGLFEKPAPKDRPGLPGLETLGSPEHRAVGREAVRK
358                                               408

SLVLLKNDKGTLPLSPKARVLVAGDGADNIGKQSGGWTISWQGTGNRNDEF
409                                               459

PGATSILGGIRDAVADAGGSVEFDVAGQYKTKPDVAIVVFGEEPYAEFQGD
460                                               510

VETLEYQPDQKQDLALLKKLKDQGIPVVAVFLSGRPMWVNPELNASDAFVA
511                                               561

AWLPGTEGGGVADVLFTDKAGKVQHDFAGKLSYSWPRTAAQTTVNRGDADY
562                                               612

NPLFAYGYGLTYKDKSKVGTLPEESGVPAEARQNAGIYFRAGALRLPGRFL
613                                               663
```

Libraries of polynucleotides encoding variant CelA proteins were prepared by mutagenesis and directed evolution, and the properties (e.g., β-glucosidase activity) of individual CelA variants were assessed using highthroughput assays. A number of amino acid substitutions and combinations of substitutions were identified in variants with greater than wild-type activity. The CelA libraries were screened in high throughput using a cellobiose assay at pH: 5-7; 45-65° C.; for 2-24 hrs to identify improved variants.

Residual activity was determined for some CelA variants using incubation at pH 5.0, 55° C. for 48 hours or pH 5.0, 65° C. for 5 hours. The residual enzyme activity after the thermal challenge was measured using pNPG as substrate at pH 7, 30° C. for approximately 1 hour.

Table 20 provides examples of combinations of substitutions in variants with improved thermoactivity as measured in assays carried out at pH 5 and 60° C. Numbering is relative to SEQ ID NO:57, below. A truncation is designated by "des". The designation "des-[A647-L663]" refers to a carboxy (C)-terminal truncation of the amino acid residues from the alanine at position 647 to the leucine at position 663. Subtracting "5" from each position will conform the numbering of SEQ ID NO: 3 (e.g., E377D=E372D).

TABLE 20

T2A + I14M + N79D + A143M + H145R + V159E + A198S + F211Y + I222A + S225C + E377D + Q508R + A525T
N79D + A143M + H145R + V159Q + A201P + S225C + K378R
A143M + H145R + A198S + P219M
T2A + A5T + I14M + N79D + G127N + A143M + H145R + V159E + A198S + V207F + F211Y + I222A + S225C + Q508R + A525T + E155G-des[A647-L663]
[397-S03692170] T2A + A5T + I14M + N79D + G127N + A143M + H145R + V159E + A198S + V207F + F211Y + I222A + S225C + Q508R + A525T + A3R + M161V + I203Y + A222I +

TABLE 20-continued

| |
|---|
| D383G-des[A647-L663] |
| H145R + A162T + I222A + S225C |
| T2A + A5T + I14M + N79D + G127N + A143M + H145R + V159E + A198S + V207F + F211Y + I222A + S225C + Q508R + A525T + T169N-des[A647-L663] |
| A193 = A143M + H145R + A198S + P219M |
| A196 = T2A + H145R + A162T + A201P + I222A |
| T2A + A5T + I14M + N79D + G127N + A143M + H145R + V159E + A198S + V207F + F211Y + I222A + S225C + Q508R + A525T + T169N + A202P + A272L + Q287R + D311G + E512G-des[A647-L663] |
| N79D + A143M + H145R + V159E + A198S + F211Y + I246C |
| N79D + N128K + H145R + A201P + P219V + K491R [142] |
| A568 = H145R + A162T + S225C + A573S |
| T2A + A5T + I14M + N79D + G127N + A143M + H145R + V159E + A198S + V207F + F211Y + I222A + S225C + Q508R + A525T + T60H + H285N-des[A647-L663] |
| N79D + I114V + N128K + H145R + A162T + A198S + F211Y + S225C |
| I14M + N79D + K91Q + H145R + G154V + V159E + A198S + A201P + F211Y + S225C + A525T + K627R |
| T2A + I14M + N79D + A143M + H145R + P147K + V159E + A198S + F211Y + I222A + S225C + Q508R + A525T |
| I195L |
| F211Y + S225C + S247P + Q508R + A525S |
| K629C |

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

We claim:

1. A method of producing a variant β-xylosidase polypeptide with improved thermoactivity, comprising:
    a) identifying a first performance sensitive position (PSP) in a target β-xylosidase polypeptide, comprising the steps of:
        i) aligning the primary sequence of the target β-xylosidase polypeptide with one or both of a GH3 consensus sequence SEQ ID NO:53 or portion thereof and a GH3-C consensus sequence SEQ ID NO:54 or portion thereof; and
        ii) identifying a position in the target β-xylosidase polypeptide that corresponds in the alignment to a PSP in the one or more a β-glucosidase polypeptides, wherein the position so identified is a PSP; and
    b) expressing a variant β-xylosidase polypeptide in which the residue at the first performance sensitive position is replaced with a thermoactivity enhancing residue, wherein the variant β-xylosidase polypeptide has greater thermoactivity than the target β-xylosidase polypeptide.

2. The method of claim 1, wherein the target β-xylosidase polypeptide has the sequence of a naturally occurring protein.

3. The method of claim 1, wherein the target β-xylosidase polypeptide is a variant of a naturally occurring protein, wherein said variant has at least 80% sequence identity to a naturally occurring protein.

4. The method of claim 1, further comprising:
    c) identifying a second performance sensitive position in the target β-xylosidase polypeptide; and
    d) expressing a polypeptide in which the residues at both the first and second performance sensitive positions are replaced with thermoactivity enhancing residues.

5. The method of claim 4, wherein steps (c) and (d) are carried out simultaneously with steps (a) and (b).

6. The method of claim 1, further comprising:
    c) identifying a second performance sensitive position in the variant β-xylosidase polypeptide; and
    d) expressing a second variant polypeptide, in which the residues at both the first and second performance sensitive positions are replaced with thermoactivity enhancing residues.

7. The method of claim 1, wherein the step of identifying a performance sensitive position comprises:
    a) aligning the primary sequence of the target β-xylosidase polypeptide with one or more a β-glucosidase polypeptides in which performance sensitive positions ("PSP") have been defined; and
    b) identifying a position in the target β-xylosidase polypeptide that corresponds in the alignment to a PSP in the one or more β-glucosidase polypeptides, wherein the position so identified is a PSP.

8. The method of claim 7, wherein the step of identifying a performance sensitive position comprises aligning the primary sequence of the target β-xylosidase polypeptide with at least a portion of C1 BGL1 SEQ ID NO:1, *T. aurantiacus* BGL SEQ ID NO:2, or *A. irakense* CelA SEQ ID NO:3.

9. The method of claim 7, comprising aligning the target β-xylosidase polypeptide with a plurality of naturally occurring β-glucosidase polypeptides in at least one of which performance sensitive positions have been defined.

10. The method of claim 1, wherein the target β-xylosidase polypeptide has a sequence from 70% to 99% identical to any one of SEQ ID NOS:58-82.

11. A non-naturally occurring β-xylosidase polypeptide produced according to the method of claim 1.

* * * * *